US011981661B2

(12) United States Patent
Benz et al.

(10) Patent No.: US 11,981,661 B2
(45) Date of Patent: May 14, 2024

(54) HETEROCYCLIC COMPOUNDS

(71) Applicant: Hoffmann-La Roche Inc., Little Falls, NJ (US)

(72) Inventors: Joerg Benz, Basel (CH); Uwe Grether, Basel (CH); Benoit Hornsperger, Basel (CH); Carsten Kroll, Basel (CH); Bernd Kuhn, Basel (CH); Rainer E. Martin, Basel (CH); Fionn O'Hara, Basel (CH); Bernd Puellmann, Basel (CH); Hans Richter, Basel (CH); Martin Ritter, Basel (CH)

(73) Assignee: Hoffmann-La Roche Inc., Little Falls, NJ (US)

( * ) Notice: Subject to any disclaimer, the term of this patent is extended or adjusted under 35 U.S.C. 154(b) by 41 days.

(21) Appl. No.: 17/465,536

(22) Filed: Sep. 2, 2021

(65) Prior Publication Data
US 2022/0098176 A1    Mar. 31, 2022

(30) Foreign Application Priority Data
Sep. 3, 2020 (EP) .................... 20194318

(51) Int. Cl.
| C07D 401/14 | (2006.01) |
| A61K 9/00 | (2006.01) |
| A61K 9/20 | (2006.01) |
| A61K 9/48 | (2006.01) |
| C07D 403/06 | (2006.01) |
| C07D 413/06 | (2006.01) |
| C07D 413/14 | (2006.01) |
| C07D 487/04 | (2006.01) |

(52) U.S. Cl.
CPC .......... C07D 403/06 (2013.01); A61K 9/2009 (2013.01); A61K 9/2054 (2013.01); A61K 9/2059 (2013.01); A61K 9/485 (2013.01); A61K 9/4858 (2013.01); A61K 9/4866 (2013.01); C07D 401/14 (2013.01); C07D 413/06 (2013.01); C07D 413/14 (2013.01); C07D 487/04 (2013.01)

(58) Field of Classification Search
CPC .. C07D 401/14; C07D 403/06; C07D 413/06; C07D 413/14
See application file for complete search history.

(56) References Cited

U.S. PATENT DOCUMENTS

| 4,454,130 A | 6/1984 | Tominaga et al. |
| 4,632,925 A | 12/1986 | Mullin, Jr. et al. |
| 4,956,359 A | 9/1990 | Taylor, Jr. et al. |
| 10,106,556 B2 | 10/2018 | Ikeda et al. |
| 10,610,520 B2 | 4/2020 | Ikeda et al. |
| 11,390,610 B2 | 7/2022 | Benz et al. |
| 11,420,961 B2 | 8/2022 | Benz et al. |
| 11,608,347 B2 | 3/2023 | Petersen et al. |
| 2015/0018335 A1 | 1/2015 | Cisar et al. |
| 2020/0255439 A1 | 8/2020 | Kamata et al. |
| 2020/0299277 A1 | 9/2020 | Benz et al. |
| 2020/0308158 A1 | 10/2020 | Bell et al. |
| 2020/0308190 A1 | 10/2020 | Bell et al. |
| 2020/0392125 A1 | 12/2020 | Benz et al. |
| 2021/0024546 A1 | 1/2021 | Petersen et al. |
| 2021/0094943 A1 | 4/2021 | Benz et al. |
| 2021/0094971 A1 | 4/2021 | Grether et al. |
| 2021/0094972 A1 | 4/2021 | Benz et al. |
| 2021/0094973 A1 | 4/2021 | Gobbi et al. |
| 2021/0107920 A1 | 4/2021 | Bell et al. |
| 2021/0107921 A1 | 4/2021 | Benz et al. |
| 2021/0277020 A1 | 9/2021 | Anselm et al. |
| 2021/0387999 A1 | 12/2021 | Kuhn et al. |
| 2022/0106328 A1 | 4/2022 | Benz et al. |
| 2022/0135591 A1 | 5/2022 | Benz et al. |
| 2022/0202963 A1 | 6/2022 | Collin et al. |
| 2022/0213093 A1 | 7/2022 | Benz et al. |
| 2022/0220373 A1 | 7/2022 | Benz et al. |
| 2022/0242678 A1 | 8/2022 | Kroll et al. |
| 2022/0267349 A1 | 8/2022 | Benz et al. |
| 2022/0275005 A1 | 9/2022 | Grether et al. |
| 2023/0050901 A1 | 2/2023 | Bell et al. |
| 2023/0117324 A1 | 4/2023 | Bell et al. |

(Continued)

FOREIGN PATENT DOCUMENTS

| CN | 111793064 A | 10/2020 |
| EP | 3279191 A1 | 2/2018 |

(Continued)

OTHER PUBLICATIONS

Chemical Library for CAS RN # 2431092-79-2 (Year: 2020).*
"International Search Report—PCT/EP2021/074150" (w/Written Opinion),:pp. 1-13 (dated Dec. 8, 2021).
"U.S. Appl. No. 17/818,459, filed Aug. 9, 2022" (unpublished application).
"U.S. Appl. No. 18/057,861, filed Nov. 22, 2022" (unpublished application).
"U.S. Appl. No. 18/172,506, filed Feb. 22, 2023" (unpublished application).

(Continued)

Primary Examiner — Sikarl A Witherspoon
(74) Attorney, Agent, or Firm — Katherine J. Mackenzie

(57) ABSTRACT

The invention provides new heterocyclic compounds having the general formula (I)

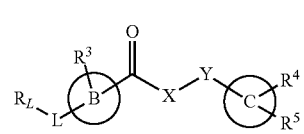

(I)

wherein B, C, L, X, Y, $R_L$ and $R^3$ to $R^5$ are as described herein, compositions including the compounds, processes of manufacturing the compounds and methods of using the compounds.

17 Claims, No Drawings

(56) References Cited

U.S. PATENT DOCUMENTS

| | | | |
|---|---|---|---|
| 2023/0183224 | A1 | 6/2023 | Bell et al. |
| 2023/0203056 | A1 | 6/2023 | Benz et al. |

FOREIGN PATENT DOCUMENTS

| | | | |
|---|---|---|---|
| EP | 3312177 | A2 | 4/2018 |
| EP | 3679043 | B1 | 5/2023 |
| WO | 01/07043 | A1 | 2/2001 |
| WO | 2004/096763 | A1 | 11/2004 |
| WO | 2005/066187 | A1 | 7/2005 |
| WO | 2006/051410 | A1 | 5/2006 |
| WO | 2007/002057 | A1 | 1/2007 |
| WO | 2007/098418 | A1 | 8/2007 |
| WO | 2007/117557 | A2 | 10/2007 |
| WO | 2009/058347 | A1 | 5/2009 |
| WO | 2010/106333 | A1 | 9/2010 |
| WO | 2011/059118 | A1 | 5/2011 |
| WO | 2012/155199 | A1 | 11/2012 |
| WO | 2013/059118 | A1 | 4/2013 |
| WO | 2013/179024 | A1 | 12/2013 |
| WO | 2015/179559 | A2 | 11/2015 |
| WO | 2016/014975 | A2 | 1/2016 |
| WO | 2016/109501 | A1 | 7/2016 |
| WO | 2016/180536 | A1 | 11/2016 |
| WO | 2016/185279 | A1 | 11/2016 |
| WO | 2016/205590 | A1 | 12/2016 |
| WO | 2017/087858 | A1 | 5/2017 |
| WO | 2017/087863 | A1 | 5/2017 |
| WO | 2017/171100 | A1 | 10/2017 |
| WO | 2019/072785 | A1 | 4/2019 |
| WO | 2019/105915 | A1 | 6/2019 |
| WO | 2019/115660 | A1 | 6/2019 |
| WO | 2019/134985 | A1 | 7/2019 |
| WO | 2019/169156 | A1 | 9/2019 |
| WO | 2019/180185 | A1 | 9/2019 |
| WO | 2019/180185 | A8 | 9/2019 |
| WO | 2019/209962 | A1 | 10/2019 |
| WO | 2020/198526 | A2 | 1/2020 |
| WO | 2020/035424 | A1 | 2/2020 |
| WO | 2020/035425 | A1 | 2/2020 |
| WO | 2020/104494 | A1 | 5/2020 |
| WO | 2020/207941 | A1 | 10/2020 |
| WO | 2021/048036 | A1 | 3/2021 |
| WO | 2021/048242 | A1 | 3/2021 |
| WO | 2021/058416 | A1 | 4/2021 |
| WO | 2021/058444 | S2 | 4/2021 |
| WO | 2021/058445 | A1 | 4/2021 |
| WO | 2021/001330 | A1 | 7/2021 |

OTHER PUBLICATIONS

Alpar, A., et al., "Endocannabinoids modulate cortical development by configuring Slit2/Robo1 signaling" Nat Commun 5(4421):1-13 (Jul. 17, 2014).
Ashton, K., et al., "Design and synthesis of novel amide AKT1 inhibitors with selectivity over CDK2" Bioorg Med Chem Lett 21(18):5191-5196 (Sep. 15, 2011).
Aurora Fine Chemicals, Other Database, 1907579-56-9, (C26 H25 N3 O3), pp. 1 Creation Date May 10, 2016.
Barney, C., et al., "A convenient synthesis of hindered amines and α-trifluoromethylamines from ketones" Tetrahedron Lett 31(39):5547-5550 ( 1990).
Bernal-Chico, A., et al., "Blockade of Monoacylglycerol Lipase Inhibits Oligodendrocyte Excitotoxicity and Prevents Demyelination In Vivo" GLIA 63(1):163-176 (Jan. 1, 2015).
Chanda, P.K., et al., "Monoacylglycerol Lipase Activity Is a Critical Modulator of the Tone and Integrity of the Endocannabinoid System" Mol Pharmacol 78(6):996-1003 (Dec. 1, 2010).
Chang, J. et al., "Highly Selective Inhibitors of Monoacylglycerol Lipase Bearing a Reactive Group that Is Bioisosteric with Endocannabinoid Substrates" Chem Biol 19(5):579-588 (May 1, 2012).
Dugar, S. et al., "A Concise and Efficient Synthesis of Substituted Morpholines" Synthesis 47(5):712-720 (Mar. 1, 2015).
Duncan, M., et al., "Review article: endocannabinoids and their receptors in the enteric nervous system" Aliment Pharmacol Ther 22(8):667-683 (Oct. 15, 2005).
Enamine, et al., CAS Registry Database, 931085-56-2, pp. 1-2; Creation Date Apr. 20, 2007.
Evano, G., et al., "Copper-Mediated Coupling Reactions and Their Applications in Natural Products and Designed Biomolecules Synthesis" Chem Rev 108(8):3054-3131 (Aug. 13, 2008).
Feliu, A., et al., "2-Arachidonoylglycerol Reduces Proteoglycans and Enhances Remyelination in a Progressive Model of Demyelination" J Neurosci 37(35):8385-8398 (Aug. 30, 2017).
Fray, M., et al., "Second generation N-(1,2-diphenylethyl)piperazines as dual serotonin and noradrenaline reuptake inhibitors: improving metabolic stability and reducing ion channel activity" Bioorg Med Chem Lett 20(12):3788-3792 (Jun. 15, 2010).
Fray, M., et al., "Structure-activity relationships of N-substituted piperazine amine reuptake inhibitors" Bioorg Med Chem Lett 16(16):4349-4353 (Aug. 15, 2006).
Granchi, C., et al., "A patent review of monoacylglycerol lipase (MAGL) inhibitors" Expert Opin Ther Pat 27(12):1341-1351 (Dec. 1, 2017).
Grill, M., et al., "Members of the endocannabinoid system are distinctly regulated in inflammatory bowel disease and colorectal cancer" Sci Rep 9(2358):1-13 (Feb. 20, 2019).
He, S., et al., "High-Affinity Small-Molecule Inhibitors of the Menin-Mixed Lineage Leukemia (MLL) Interaction Closely Mimic a Natural Protein-Protein Interaction" J Med Chem 57(4):1543-1556 (Feb. 27, 2014).
Iannotti, F. A., et al., "Endocannabinoids and endocannabinoid-related mediators: Targets, metabolism and role in neurological disorders" Prog Lipid Res 62:107-128 (Apr. 1, 2016).
Ignatowska-Jankowska, B., et al., "Selective Monoacylglycerol Lipase Inhibitors: Antinociceptive versus Cannabimimetic Effects in Mice" J Pharmacol Exp Ther 353(2):424-432 (May 1, 2015).
"International Preliminary Report on Patentability—PCT/EP2019/071520" (dated Feb. 16, 2021, Chapter I),:pp. 1-8 (Feb. 25, 2021).
"International Preliminary Report on Patentability—PCT/EP2019/081870" (dated May 25, 2021; Chapter I),:pp. 1-8 (Jun. 3, 2021).
"International Preliminary Report on Patentability—PCT/EP2019/071522" (dated Feb. 16, 2021, Chapter I),:pp. 1-9 (Feb. 25, 2021).
"International Preliminary Report on Patentability—PCT/EP2019/057174" (dated Sep. 22, 2020—Chapter I),:pp. 1-9 (Oct. 1, 2020).
"International Preliminary Report on Patentability—PCT/EP2020/059709" (dated Sep. 28, 2021; Chapter I),:pp. 1-10 (Oct. 21, 2021).
"International Search Report—PCT/EP2019/057174" (w/Written Opinion),:pp. 1-14 (dated Jul. 3, 2019).
"International Search Report—PCT/EP2019/071520" (w/Written Opinion),:pp. 1-14 (dated Sep. 17, 2019).
"International Search Report—PCT/EP2019/071522" (w/Written Opinion),:pp. 1-15 (dated Sep. 17, 2019).
"International Search Report—PCT/EP2019/081870" (w/Written Opinion),:pp. 1-12 (dated Jan. 14, 2020).
"International Search Report—PCT/EP2020/059709" (w/Written Opinion),:1-17 (dated Jun. 8, 2020).
"International Search Report—PCT/EP2020/074897" (w/Written Opinion),:pp. 1-15 (dated Nov. 18, 2020).
"International Search Report—PCT/EP2020/075260" (w/Written Opinion),:pp. 1-14 (dated Nov. 18, 2020).
"International Search Report—PCT/EP2020/076228" (w/Written Opinion),:pp. 1-14 (dated Nov. 12, 2020).
"International Search Report—PCT/EP2020/076346" (w/Written Opinion),:pp. 1-16 (dated Nov. 13, 2020).
"International Search Report—PCT/EP2020/076347" (w/Written Opinion),:pp. 1-16 (dated Nov. 30, 2020).
Ishichi, Y., et al., "Novel triple reuptake inhibitors with low risk of CAD associated liabilities: design, synthesis and biological activities of 4-[(1S)-1-(3,4-dichlorophenyl)-2-methoxyethyl]piperidine and related compounds" Bioorg Med Chem 21(15):4600-4613 (Aug. 1, 2013).

(56) References Cited

OTHER PUBLICATIONS

Keenan, M., et al., "Design, structure-activity relationship and in vivo efficacy of piperazine analogues of fenarimol as inhibitors of Trypanosoma cruzi" Bioorg Med Chem 21(7):1756-1763 (Apr. 1, 2013).

Kitbunnadaj, R., et al., "Synthesis and structure-activity relationships of conformationally constrained histamine H(3) receptor agonists" J Med Chem 46(25):5445-5457 (Dec. 4, 2003).

Liu, F., et al., "Structure-Based Optimization of Pyridoxal 5'-Phosphate-Dependent Transaminase Enzyme (BioA) Inhibitors that Target Biotin Biosynthesis in *Mycobacterium* tuberculosis" J Med Chem 60(13):5507-5520 (Jul. 13, 2017).

Liu, Y. et al., "Discovery of 4-benzoylpiperidine and 3-(piperidin-4-yl)benzo[d]isoxazole derivatives as potential and selective GlyT1 inhibitors" RSC ADV 5(51):40964-40977 (Apr. 30, 2015).

Lleo, A., et al., "Molecular targets of non-steroidal anti-inflammatory drugs in neurodegenerative diseases" Cell Mol Life Sci 64(11):1403-1418 (Apr. 20, 2007).

Long, J.Z., et al., "Selective blockade of 2-arachidonoylglycerol hydrolysis produces cannabinoid behavioral effects" Nat Chem Biol 5(1):37-44 (Jan. 1, 2009).

Marquez, L., et al., "Ulcerative Colitis Induces Changes on the Expression of the Endocannabinoid System in the Human Colonic Tissue" PLOS ONE 4(9):(e6893) 1-13 (Sep. 4, 2009).

McAllister, L., et al., "Discovery of Trifluoromethyl Glycol Carbamates as Potent and Selective Covalent Monoacylglycerol Lipase (MAGL) Inhibitors for Treatment of Neuroinflammation" J Med Chem 61(7):3008-3026 (Apr. 12, 2018).

Muccioli, G., et al., "CAY10499, a Novel Monoglyceride Lipase Inhibitor Evidenced by an Expeditious MGL Assay" Chem Bio Chem 9(16):2704-2710 (Nov. 3, 2008).

Mulvihill, M., et al., "Therapeutic Potential of Monoacylglycerol Lipase Inhibitors" Life Sci 92(8-9):492-497 (Nov. 8, 2013).

Negishi, E., "Palladium- or Nickel-Catalyzed Cross Coupling. A New Selective Method for Carbon-Carbon Bond Formation" ACC Chem Res 15(11):340-348 (Nov. 1, 1982).

Nomura, D.K., et al., "Endocannabinoid Hydrolysis Generates Brain Prostaglandins That Promote Neuroinflammation" Science 334(6057):809-813 (Nov. 11, 2011).

Nomura, D.K., et al., "Monoacylglycerol Lipase Exerts Dual Control over Endocannabinoid and Fatty Acid Pathways to Support Prostate Cancer" Chem Biol 18(7):846-856 (Jul. 29, 2011).

Nomura, D.K., et al., "Monoacylglycerol Lipase Regulates a Fatty Acid Network that Promotes Cancer Pathogenesis" Cell 140(1):49-61 (Jan. 8, 2010).

Patel, J. et al., "Loratadine analogues as MAGL inhibitors" Bioorg Med Chem Lett 25(7):1436-1442 (Feb. 24, 2015).

Perisetti, A., et al., "Role of cannabis in inflammatory bowel diseases" Ann Gastroenterol 33(2):134-144 (Feb. 12, 2020).

Qin, H., et al., "The role of monoacylglycerol lipase (MAGL) in the cancer progress" Cell Biochem Biophys 70:33-36 (Mar. 16, 2014).

Rafinski, Z. et al., "Enantioselective Synthesis of Chromanones Bearing Quaternary Substituted Stereocenters Catalyzed by (1R)-Camphor-Derived N-Heterocyclic Carbenes" J Org Chem 80(15):7468-7476 (Aug. 7, 2015).

Scalvini, L., et al., "Monoglyceride lipase: Structure and inhibitors" Chem Phys Lipids 197:13-24 (Jul. 26, 2015).

Senter, T., et al., "Progress towards small molecule menin-mixed lineage leukemia (MLL) interaction inhibitors with in vivo utility" Bioorg Med Chem Lett 25(13):2720-2725 (Jul. 1, 2015).

Surry, D., et al., "Biaryl Phosphane Ligands in Palladium-Catalyzed Amination" Angew Chem Int Ed Engl 47(34):6338-6361 (Aug. 11, 2008).

Ukrorgsyntez, Ltd., CAS Registry Database, 1941372-36-6, (Stereosearch—C20 H27 N3 O3), pp. 1; Creation Date Jun. 29, 2016.

USPTO, "U.S. Appl. No. 17/325,934, filed May 20, 2021".

USPTO, "U.S. Appl. No. 17/497,633, filed Oct. 8, 2021".

Venkatesh, R., et al., "Novel benzothiazine-piperazine derivatives by peptide-coupling as potential anti-proliferative agents" Bioorg Med Chem Lett 27(2):354-359 (Jan. 15, 2017).

Viader, A., et al., "Metabolic Interplay between Astrocytes and Neurons Regulates Endocannabinoid Action" Cell Rep 12(5):798-808 (Aug. 4, 2015).

Walsh, D., et al., "Synthesis and antiallergy activity of 4-(diarylhydroxymethyl)-1-[3-(aryloxy)propyl]piperidines and structurally related compounds" J Med Chem 32(1):105-118 (Jan. 1, 1989).

Wang, J., et al., "Effect of monoacylglycerol lipase inhibition on intestinal permeability in chronic stress model" Biochem Biophys Res Commun 525(4):962-967 (May 14, 2020).

Wright, K., et al., "Differential expression of cannabinoid receptors in the human colon: cannabinoids promote epithelial wound healing" Gastroenterology 129(2):437-453 (Aug. 1, 2005).

Wu, W., et al., "Synthesis and structure-activity relationships of piperidine-based melanin-concentrating hormone receptor 1 antagonists" Bioorg Med Chem Lett 16(14):3668-3673 (Jul. 15, 2006).

Yin, J., et al., "ARS2/MAGL signaling in glioblastoma stem cells promotes self-renewal and M2-like polarization of tumor-associated macrophages" Nat Commun 11(1):2978(1-15) (Jun. 12, 2020).

Zhang, P., et al., "Silyl Radical Activation of Alkyl Halides in Metallaphotoredox Catalysis: A Unique Pathway for Cross-Electrophile Coupling" J Am Chem Soc 138(26):8084-8087 (Jul. 6, 2016).

Zhang, X., et al., "Direct Aldehyde C-H Arylation and Alkylation via the Combination of Nickel, Hydrogen Atom Transfer, and Photoredox Catalysis" J Am Chem Soc 139(33):11353-11356 (Aug. 23, 2017).

Zhong, P., et al., "Monoacylglycerol Lipase Inhibition Blocks Chronic Stress-Induced Depressive-Like Behaviors via Activation of mTOR Signaling" Neuropsychopharmacology 39(7):1763-1776 (Feb. 19, 2014).

Gavryushin, A., et al., "Efficient Cross-Coupling of Functionalized Arylzinc Halides Catalyzed by a Nickel Chloride-Diethyl Phosphite System" Org Lett 7(22):4871-4874 (Oct. 7, 2005).

Haas, D., et al., "Recent Developments in Negishi Cross-Coupling Reactions" ACS CATAL 6(3):1540-1552 (Feb. 3, 2016).

Heravi, M., et al., "Buchwald-Hartwig reaction: An overview" J Organometallic Chem 861:17-104 (Apr. 15, 2018).

Hutchings, K., et al., "Synthesis and antibacterial activity of the C-7 side chain of 3-aminoquinazolinediones" Bioorg Med Chem Lett 18(18):5087-5090 (Sep. 15, 2008).

"International Search Report—PCT/EP2022/060644" (w/Written Opinion),:pp. 1-44 (dated Sep. 1, 2022).

Liu, Y., et al., "Discovery of 3-Pyridyl Isoindolin-1-one Derivatives as Potent, Selective, and Orally Active Aldosterone Synthase (CYP11B2) Inhibitors" J Med Chem 63(13):6875-6897 (Jun. 12, 2020).

Xu, G., et al., "Synthesis and biological evaluation of 4-(pyridin-4-oxy)-3-(3,3-difluorocyclobutyl)-pyrazole derivatives as novel potent transforming growth factor-β type 1 receptor inhibitors" Eur J Med Chem 198:112354 (1-12) (Jul. 15, 2020).

\* cited by examiner

HETEROCYCLIC COMPOUNDS

CROSS-REFERENCE TO RELATED APPLICATIONS

This application claims priority to EP Application No. 20194318.0, filed Sep. 3, 2020, which is incorporated herein by reference in its entirety.

FIELD OF THE INVENTION

The present invention relates to organic compounds useful for therapy or prophylaxis in a mammal, and in particular to monoacylglycerol lipase (MAGL) inhibitors for the treatment or prophylaxis of neuroinflammation, neurodegenerative diseases, pain, cancer, mental disorders, multiple sclerosis, Alzheimer's disease, Parkinson's disease, amyotrophic lateral sclerosis, traumatic brain injury, neurotoxicity, stroke, epilepsy, anxiety, migraine, depression, inflammatory bowel disease, abdominal pain, abdominal pain associated with irritable bowel syndrome and/or visceral pain in a mammal.

BACKGROUND OF THE INVENTION

Endocannabinoids (ECs) are signaling lipids that exert their biological actions by interacting with cannabinoid receptors (CBRs), CB1 and CB2. They modulate multiple physiological processes including neuroinflammation, neurodegeneration and tissue regeneration (Iannotti, F. A. et al., *Prog. in Lipid Res.* 2016, 62, 107). In the brain, the main endocannabinoid, 2-arachidonoylglycerol (2-AG), is produced by diacyglycerol lipases (DAGL) and hydrolyzed by the monoacylglycerol lipase, MAGL. MAGL hydrolyses 85% of 2-AG; the remaining 15% being hydrolysed by ABHD6 and ABDH12 (Nomura, D. K. et al., *Science* 2011, 334, 809). MAGL is expressed throughout the brain and in most brain cell types, including neurons, astrocytes, oligodendrocytes and microglia cells (Chanda, P. K. et al., *Mol. Pharmacol.* 2010, 78, 996; Viader, A. et al., *Cell. Rep.* 2015, 12, 798). 2-AG hydrolysis results in the formation of arachidonic acid (AA), the precursor of prostaglandins (PGs) and leukotrienes (LTs). Oxidative metabolism of AA is increased in inflamed tissues. There are two principal enzyme pathways of arachidonic acid oxygenation involved in inflammatory processes, the cyclooxygenase which produces PGs and the 5-lipoxygenase which produces LTs. Of the various cyclooxygenase products formed during inflammation, PGE2 is one of the most important. These products have been detected at sites of inflammation, e.g., in the cerebrospinal fluid of patients suffering from neurodegenerative disorders and are believed to contribute to inflammatory response and disease progression. Mice lacking MAGL (Mgll−/−) exhibit dramatically reduced 2-AG hydrolase activity and elevated 2-AG levels in the nervous system while other arachidonoyl-containing phospho- and neutral lipid species including anandamide (AEA), as well as other free fatty acids, are unaltered. Conversely, levels of AA and AA-derived prostaglandins and other eicosanoids, including prostaglandin E2 (PGE2), D2 (PGD2), F2 (PGF2), and thromboxane B2 (TXB2), are strongly decreased. Phospholipase $A_2$ ($PLA_2$) enzymes have been viewed as the principal source of AA, but $cPLA_2$-deficient mice have unaltered AA levels in their brain, reinforcing the key role of MAGL in the brain for AA production and regulation of the brain inflammatory process.

Neuroinflammation is a common pathological change characteristic of diseases of the brain including, but not restricted to, neurodegenerative diseases (e.g., multiple sclerosis, Alzheimer's disease, Parkinson disease, amyotrophic lateral sclerosis, traumatic brain injury, neurotoxicity, stroke, epilepsy and mental disorders such as anxiety and migraine). In the brain, production of eicosanoids and prostaglandins controls the neuroinflammation process. The pro-inflammatory agent lipopolysaccharide (LPS) produces a robust, time-dependent increase in brain eicosanoids that is markedly blunted in Mgll−/− mice. LPS treatment also induces a widespread elevation in pro-inflammatory cytokines including interleukin-1-a (IL-1-a), IL-1b, IL-6, and tumor necrosis factor-a (TNF-a) that is prevented in Mgll−/− mice.

Neuroinflammation is characterized by the activation of the innate immune cells of the central nervous system, the microglia and the astrocytes. It has been reported that anti-inflammatory drugs can suppress in preclinical models the activation of glia cells and the progression of disease including Alzheimer's disease and multiple sclerosis (Lleo, A., *Cell. Mol. Life Sci.* 2007, 64, 1403). Importantly, genetic and/or pharmacological disruption of MAGL activity also blocks LPS-induced activation of microglial cells in the brain (Nomura, D. K. et al., *Science* 2011, 334, 809).

In addition, genetic and/or pharmacological disruption of MAGL activity was shown to be protective in several animal models of neurodegeneration including, but not restricted to, Alzheimer's disease, Parkinson's disease and multiple sclerosis. For example, an irreversible MAGL inhibitor has been widely used in preclinical models of neuroinflammation and neurodegeneration (Long, J. Z. et al., *Nat. Chem. Biol.* 2009, 5, 37). Systemic injection of such inhibitor recapitulates the Mgll−/− mice phenotype in the brain, including an increase in 2-AG levels, a reduction in AA levels and related eicosanoids production, as well as the prevention of cytokines production and microglia activation following LPS-induced neuroinflammation (Nomura, D. K. et al., *Science* 2011, 334, 809), altogether confirming that MAGL is a druggable target.

Consecutive to the genetic and/or pharmacological disruption of MAGL activity, the endogenous levels of the MAGL natural substrate in the brain, 2-AG, are increased. 2-AG has been reported to show beneficial effects on pain with, for example, anti-nociceptive effects in mice (Ignatowska-Jankowska, B. et al., *J. Pharmacol. Exp. Ther.* 2015, 353, 424) and on mental disorders, such as depression in chronic stress models (Zhong, P. et al., *Neuropsychopharmacology* 2014, 39, 1763).

Furthermore, oligodendrocytes (OLs), the myelinating cells of the central nervous system, and their precursors (OPCs) express the cannabinoid receptor 2 (CB2) on their membrane. 2-AG is the endogenous ligand of CB1 and CB2 receptors. It has been reported that both cannabinoids and pharmacological inhibition of MAGL attenuate OLs's and OPCs's vulnerability to excitotoxic insults and therefore may be neuroprotective (Bernal-Chico, A. et al., *Glia* 2015, 63, 163). Additionally, pharmacological inhibition of MAGL increases the number of myelinating OLs in the brain of mice, suggesting that MAGL inhibition may promote differentiation of OPCs in myelinating OLs in vivo (Alpar, A. et al., *Nat. Commun.* 2014, 5, 4421). Inhibition of MAGL was also shown to promote remyelination and functional recovery in a mouse model of progressive multiple sclerosis (Feliu, A. et al., *J. Neurosci.* 2017, 37, 8385).

In addition, in recent years, metabolism is talked highly important in cancer research, especially the lipid metabolism. Researchers believe that the de novo fatty acid synthesis plays an important role in tumor development. Many studies illustrated that endocannabinoids have anti-tumorigenic actions, including anti-proliferation, apoptosis induction and anti-metastatic effects. MAGL as an important decomposing enzyme for both lipid metabolism and the endocannabinoids system, additionally as a part of a gene expression signature, contributes to different aspects of tumourigenesis, including in glioblastoma (Qin, H. et al., *Cell Biochem. Biophys.* 2014, 70, 33; Nomura, D. K. et al., *Cell* 2009, 140, 49; Nomura, D. K. et al., *Chem. Biol.* 2011, 18, 846; Jinlong, Y. et al., *Nat. Commun.* 2020, 11, 2978).

The endocannabinoid system is also involved in many gastrointestinal physiological and physiopathological actions (Marquez, L. et al., *PLoS One* 2009, 4, e6893). All these effects are driven mainly via cannabinoid receptors (CBRs), CB1 and CB2. CB1 receptors are present throughout the GI tract of animals and healthy humans, especially in the enteric nervous system (ENS) and the epithelial lining, as well as smooth muscle cells of blood vessels in the colonic wall (Wright, K. et al., *Gastroenterology* 2005, 129, 437; Duncan, M. et al., *Aliment. Pharmacol. Ther.* 2005, 22, 667). Activation of CB1 produces anti-emetic, anti-motility, and anti-inflammatory effect, and help to modulate pain (Perisetti, A. et al., *Ann. Gastroenterol.* 2020, 33, 134). CB2 receptors are expressed in immune cells such as plasma cells and macrophages, in the lamina propria of the GI tract (Wright, K. et al., *Gastroenterology* 2005, 129, 437), and primarily on the epithelium of human colonic tissue associated with inflammatory bowel disease (IBD). Activation of CB2 exerts anti-inflammatory effect by reducing pro-inflammatory cytokines. Expression of MAGL is increased in colonic tissue in UC patients (Marquez, L. et al., *PLoS One* 2009, 4, e6893) and 2-AG levels are increased in plasma of IBD patients (Grill, M. et al., *Sci. Rep.* 2019, 9, 2358). Several animal studies have demonstrated the potential of MAGL inhibitors for symptomatic treatment of IBD. MAGL inhibition prevents TNBS-induced mouse colitis and decreases local and circulating inflammatory markers via a CB1/CB2 MoA (Marquez, L. et al., *PLoS One* 2009, 4, e6893). Furthermore, MAGL inhibition improves gut wall integrity and intestinal permeability via a CB1 driven MoA (Wang, J. et al., *Biochem. Biophys. Res. Commun.* 2020, 525, 962).

In conclusion, suppressing the action and/or the activation of MAGL is a promising new therapeutic strategy for the treatment or prevention of neuroinflammation, neurodegenerative diseases, pain, cancer, mental disorders, inflammatory bowel disease, abdominal pain and abdominal pain associated with irritable bowel syndrome. Furthermore, suppressing the action and/or the activation of MAGL is a promising new therapeutic strategy for providing neuroprotection and myelin regeneration. Accordingly, there is a high unmet medical need for new MAGL inhibitors.

SUMMARY OF THE INVENTION

In a first aspect, the present invention provides a compound of formula (I), or a pharmaceutically acceptable salt thereof,

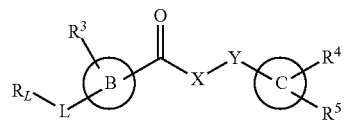

(I)

wherein B, C, L, X, Y, $R_L$ and $R^3$ to $R^5$ are as described herein.

In one aspect, the present invention provides processes of manufacturing the compounds of formula (I), or pharmaceutically acceptable salts thereof, described herein.

In a further aspect, the present invention provides a compound of formula (I) as described herein, or a pharmaceutically acceptable salt thereof, when manufactured according to the processes described herein.

In a further aspect, the present invention provides a compound of formula (I) as described herein, or a pharmaceutically acceptable salt thereof, for use as therapeutically active substance.

In a further aspect, the present invention provides a pharmaceutical composition comprising a compound of formula (I) as described herein, or a pharmaceutically acceptable salt thereof, and a therapeutically inert carrier.

In a further aspect, the present invention provides the use of a compound of formula (I) as described herein, or a pharmaceutically acceptable salt thereof, or of a pharmaceutical composition described herein for inhibiting monoacylglycerol lipase (MAGL) in a mammal.

In a further aspect, the present invention provides the use of a compound of formula (I) as described herein, or a pharmaceutically acceptable salt thereof, or of a pharmaceutical composition described herein for the treatment or prophylaxis of neuroinflammation, neurodegenerative diseases, pain, cancer, mental disorders and/or inflammatory bowel disease in a mammal.

In a further aspect, the present invention provides the use of a compound of formula (I) as described herein, or a pharmaceutically acceptable salt thereof, or of a pharmaceutical composition described herein for the treatment or prophylaxis of multiple sclerosis, Alzheimer's disease, Parkinson's disease, amyotrophic lateral sclerosis, traumatic brain injury, neurotoxicity, stroke, epilepsy, anxiety, migraine, depression, hepatocellular carcinoma, colon carcinogenesis, ovarian cancer, neuropathic pain, chemotherapy induced neuropathy, acute pain, chronic pain, spasticity associated with pain, abdominal pain, abdominal pain associated with irritable bowel syndrome and/or visceral pain in a mammal.

DETAILED DESCRIPTION OF THE INVENTION

Definitions

Features, integers, characteristics, compounds, chemical moieties or groups described in conjunction with a particular aspect, embodiment or example of the invention are to be understood to be applicable to any other aspect, embodiment or example described herein, unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

The term "alkyl" refers to a mono- or multivalent, e.g., a mono- or bivalent, linear or branched saturated hydrocarbon group of 1 to 12 carbon atoms. In some preferred embodiments, the alkyl group contains 1 to 6 carbon atoms ("$C_{1-6}$-alkyl"), e.g., 1, 2, 3, 4, 5, or 6 carbon atoms. In other embodiments, the alkyl group contains 1 to 3 carbon atoms, e.g., 1, 2 or 3 carbon atoms. Some non-limiting examples of alkyl include methyl, ethyl, propyl, 2-propyl (isopropyl), n-butyl, iso-butyl, sec-butyl, tert-butyl, and 2,2-dimethylpropyl. A particularly preferred, yet non-limiting example of alkyl is methyl.

The term "alkoxy" refers to an alkyl group, as previously defined, attached to the parent molecular moiety via an oxygen atom. Unless otherwise specified, the alkoxy group contains 1 to 12 carbon atoms. In some preferred embodiments, the alkoxy group contains 1 to 6 carbon atoms ("$C_{1-6}$-alkoxy"). In other embodiments, the alkoxy group contains 1 to 4 carbon atoms. In still other embodiments, the alkoxy group contains 1 to 3 carbon atoms. Some non-limiting examples of alkoxy groups include methoxy, ethoxy, n-propoxy, isopropoxy, n-butoxy, isobutoxy and tert-butoxy. A particularly preferred, yet non-limiting example of alkoxy is methoxy.

The term "halogen" or "halo" refers to fluoro (F), chloro (Cl), bromo (Br), or iodo (I). Preferably, the term "halogen" or "halo" refers to fluoro (F), chloro (Cl) or bromo (Br). Particularly preferred, yet non-limiting examples of "halogen" or "halo" are fluoro (F) and chloro (Cl).

The term "cycloalkyl" as used herein refers to a saturated or partly unsaturated monocyclic or bicyclic hydrocarbon group of 3 to 10 ring carbon atoms ("$C_3$-$C_{10}$-cycloalkyl"). In some preferred embodiments, the cycloalkyl group is a saturated monocyclic hydrocarbon group of 3 to 8 ring carbon atoms. "Bicyclic cycloalkyl" refers to cycloalkyl moieties consisting of two saturated carbocycles having two carbon atoms in common, i.e., the bridge separating the two rings is either a single bond or a chain of one or two ring atoms, and to spirocyclic moieties, i.e., the two rings are connected via one common ring atom. Preferably, the cycloalkyl group is a saturated monocyclic hydrocarbon group of 3 to 6 ring carbon atoms, e.g., of 3, 4, 5 or 6 carbon atoms. Some non-limiting examples of cycloalkyl include cyclopropyl, cyclobutyl, cyclopentyl, cyclohexyl and cycloheptyl. A particularly preferred example of cycloalkyl is cyclopropyl.

The terms "heterocyclyl" and "heterocycloalkyl" are used herein interchangeably and refer to a saturated or partly unsaturated mono- or bicyclic, preferably monocyclic ring system of 3 to 14 ring atoms, preferably 3 to 10 ring atoms, more preferably 3 to 8 ring atoms, wherein 1, 2, or 3 of said ring atoms are heteroatoms selected from N, O and S, the remaining ring atoms being carbon. Preferably, 1 to 2 of said ring atoms are selected from N and O, the remaining ring atoms being carbon. "Bicyclic heterocyclyl" refers to heterocyclic moieties consisting of two cycles having two ring atoms in common, i.e., the bridge separating the two rings is either a single bond or a chain of one or two ring atoms, and to spirocyclic moieties, i.e., the two rings are connected via one common ring atom. Some non-limiting examples of heterocyclyl groups include azetidin-3-yl, azetidin-2-yl, 2,3,3a,4,6,6a-hexahydro-1H-pyrrolo[3,4-c]pyrrol-5-yl, 2-azaspiro[3.3]heptan-2-yl, oxetan-3-yl, oxetan-2-yl, 1-piperidyl, 2-piperidyl, 3-piperidyl, 4-piperidyl, morpholin-2-yl, morpholin-3-yl, pyrrolidinyl and oxazolidinyl. Some preferred, yet non-limiting examples of heterocyclyl groups include azetidinyl, 2,3,3a,4,6,6a-hexahydro-1H-pyrrolo[3,4-c]pyrrol-5-yl, 2-azaspiro[3.3]heptan-2-yl, pyrrolidinyl and oxazolidinyl.

The term "aryl" refers to a monocyclic, bicyclic, or tricyclic carbocyclic ring system having a total of 6 to 14 ring members ("$C_6$-$C_{14}$-aryl"), preferably, 6 to 12 ring members, and more preferably 6 to 10 ring members, and wherein at least one ring in the system is aromatic. Some non-limiting examples of aryl include phenyl and 9H-fluorenyl (e.g., 9H-fluoren-9-yl). A particularly preferred, yet non-limiting example of aryl is phenyl.

The term "heteroaryl" refers to a mono- or multivalent, monocyclic or bicyclic ring system having a total of 5 to 14 ring members, preferably, 5 to 12 ring members, and more preferably 5 to 10 ring members, wherein at least one ring in the system is aromatic, and at least one ring in the system contains one or more heteroatoms. Preferably, "heteroaryl" refers to a 5-10 membered heteroaryl comprising 1, 2, 3 or 4 heteroatoms independently selected from O, S and N. Most preferably, "heteroaryl" refers to a 5-10 membered heteroaryl comprising 1 to 2 heteroatoms independently selected from O, S and N. Some preferred, yet non-limiting examples of heteroaryl include thiazolyl (e.g., thiazol-2-yl); oxazolyl (e.g., oxazol-2-yl); 5,6-dihydro-4H-cyclopenta[d]thiazol-2-yl; 1,2,4-oxadiazol-5-yl; pyridyl (e.g., 2-pyridyl); pyrimidinyl (e.g., pyrimidin-2-yl); pyrazolyl (e.g., pyrazol-1-yl); pyrazinyl; triazolyl; imidazolyl (e.g., imidazole-1-yl); benzoxazolyl (e.g., benzoxazol-2-yl) and oxazolo[5,4-c]pyridin-2-yl. Some preferred, yet non-limiting examples of heteroaryl include pyridyl, pyrimidinyl, pyrazinyl and triazolyl.

It is to be understood that a heterocyclic or heteroaromatic ring can be attached to its pendant group at any heteroatom or carbon atom that results in a stable structure and any of the ring atoms can be optionally substituted.

The term "hydroxy" refers to an —OH group.

The term "cyano" refers to a —CN (nitrile) group.

The term "oxo" refers to a group =O.

The term "carbamoyl" refers to a group —C(O)NH$_2$.

The term "haloalkyl" refers to an alkyl group, wherein at least one of the hydrogen atoms of the alkyl group has been replaced by a halogen atom, preferably fluoro. Preferably, "haloalkyl" refers to an alkyl group wherein 1, 2 or 3 hydrogen atoms of the alkyl group have been replaced by a halogen atom, most preferably fluoro. Particularly preferred, yet non-limiting examples of haloalkyl are trifluoromethyl (CF$_3$), difluoromethyl (CHF$_2$) and trifluoroethyl (e.g., 2,2,2-trifluoroethyl).

The term "haloalkoxy" refers to an alkoxy group, wherein at least one of the hydrogen atoms of the alkoxy group has been replaced by a halogen atom, preferably fluoro. Preferably, "haloalkoxy" refers to an alkoxy group wherein 1, 2 or 3 hydrogen atoms of the alkoxy group have been replaced by a halogen atom, most preferably fluoro. Particularly preferred, yet non-limiting examples of haloalkoxy include trifluoromethoxy (OCF$_3$), 2,2,2-trifluoroethoxy and 2,2,2-trifluoro-1,1-dimethyl-ethoxy.

The term "aryloxy" refers to an aryl group, as previously defined, attached to the parent molecular moiety via an oxygen atom. A preferred, yet non-limiting example of aryloxy is phenoxy.

The term "cycloalkyloxy" refers to a cycloalkyl group, as previously defined, attached to the parent molecular moiety via an oxygen atom. A preferred, yet non-limiting example of cycloalkyloxy is cyclopropoxy.

The term "heteroaryloxy" refers to a heteroaryl group, as previously defined, attached to the parent molecular moiety via an oxygen atom. A preferred, yet non-limiting example of heteroaryloxy is pyridyloxy (e.g., 2-pyridyloxy, 3-pyridyloxy or 4-pyridyloxy).

The term "heterocyclyloxy" refers to a heterocyclyl group, as previously defined, attached to the parent molecular moiety via an oxygen atom. Preferred, yet non-limiting examples of heterocyclyloxy are oxazolidinyloxy, pyrrolidinyloxy and azetidinyloxy.

The term "pharmaceutically acceptable salt" refers to those salts which retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid and the like, in particular hydrochloric acid, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcystein and the like. In addition these salts may be prepared by addition of an inorganic base or an organic base to the free acid. Salts derived from an inorganic base include, but are not limited to, the sodium, potassium, lithium, ammonium, calcium, magnesium salts and the like. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polyimine resins and the like. Particular pharmaceutically acceptable salts of compounds of formula (I) are hydrochloride salts.

The term "protective group" (PG) denotes the group which selectively blocks a reactive site in a multifunctional compound such that a chemical reaction can be carried out selectively at another unprotected reactive site in the meaning conventionally associated with it in synthetic chemistry. Protective groups can be removed at the appropriate point. Exemplary protective groups are amino-protective groups, carboxy-protective groups or hydroxy-protective groups. Particular protective groups are the tert-butoxycarbonyl (Boc), benzyloxycarbonyl (Cbz), fluorenylmethoxycarbonyl (Fmoc) and benzyl (Bn). Further particular protective groups are the tert-butoxycarbonyl (Boc) and the fluorenylmethoxycarbonyl (Fmoc). More particular protective group is the tert-butoxycarbonyl (Boc). Exemplary protective groups and their application in organic synthesis are described, for example, in "Protective Groups in Organic Chemistry" by T. W. Greene and P. G. M. Wutts, 5th Ed., 2014, John Wiley & Sons, New York.

The term "urea forming reagent" refers to a chemical compound that is able to render a first amine to a species that will react with a second amine, thereby forming an urea derivative. Non-limiting examples of urea forming reagents include bis(trichloromethyl) carbonate, phosgene, trichloromethyl chloroformate, (4-nitrophenyl)carbonate and 1,1'-carbonyldiimidazole (CDI). The urea forming reagents described in Sartori, G. et al., *Green Chem.* 2000, 2, 140 are incorporated herein by reference.

The compounds of formula (I) can contain several asymmetric centers and can be present in the form of optically pure enantiomers, mixtures of enantiomers such as, for example, racemates, optically pure diastereoisomers, mixtures of diastereoisomers, diastereoisomeric racemates or mixtures of diastereoisomeric racemates. In a preferred embodiment, the compound of formula (I) according to the invention is a cis-enantiomer of formula (Ia) or (Ib), respectively, as described herein.

According to the Cahn-Ingold-Prelog Convention, the asymmetric carbon atom can be of the "R" or "S" configuration.

The abbreviation "MAGL" refers to the enzyme monoacylglycerol lipase. The terms "MAGL" and "monoacylglycerol lipase" are used herein interchangeably.

The term "treatment" as used herein includes: (1) inhibiting the state, disorder or condition (e.g., arresting, reducing or delaying the development of the disease, or a relapse thereof in case of maintenance treatment, of at least one clinical or subclinical symptom thereof); and/or (2) relieving the condition (i.e., causing regression of the state, disorder or condition or at least one of its clinical or subclinical symptoms). The benefit to a patient to be treated is either statistically significant or at least perceptible to the patient or to the physician. However, it will be appreciated that when a medicament is administered to a patient to treat a disease, the outcome may not always be effective treatment.

The term "prophylaxis" as used herein includes: preventing or delaying the appearance of clinical symptoms of the state, disorder or condition developing in a mammal and especially a human that may be afflicted with or predisposed to the state, disorder or condition but does not yet experience or display clinical or subclinical symptoms of the state, disorder or condition.

The term "neuroinflammation" as used herein relates to acute and chronic inflammation of the nervous tissue, which is the main tissue component of the two parts of the nervous system; the brain and spinal cord of the central nervous system (CNS), and the branching peripheral nerves of the peripheral nervous system (PNS). Chronic neuroinflammation is associated with neurodegenerative diseases such as Alzheimer's disease, Parkinson's disease and multiple sclerosis. Acute neuroinflammation usually follows injury to the central nervous system immediately, e.g., as a result of traumatic brain injury (TBI).

The term "traumatic brain injury" ("TBI", also known as "intracranial injury"), relates to damage to the brain resulting from external mechanical force, such as rapid acceleration or deceleration, impact, blast waves, or penetration by a projectile.

The term "neurodegenerative diseases" relates to diseases that are related to the progressive loss of structure or function of neurons, including death of neurons. Examples of neurodegenerative diseases include, but are not limited to, multiple sclerosis, Alzheimer's disease, Parkinson's disease and amyotrophic lateral sclerosis.

The term "mental disorders" (also called mental illnesses or psychiatric disorders) relates to behavioral or mental patterns that may cause suffering or a poor ability to function in life. Such features may be persistent, relapsing and remitting, or occur as a single episode. Examples of mental disorders include, but are not limited to, anxiety and depression.

The term "pain" relates to an unpleasant sensory and emotional experience associated with actual or potential tissue damage. Examples of pain include, but are not limited to, nociceptive pain, chronic pain (including idiopathic pain), neuropathic pain including chemotherapy induced neuropathy, phantom pain and phsychogenic pain. A particular example of pain is neuropathic pain, which is caused by damage or disease affecting any part of the nervous system involved in bodily feelings (i.e., the somatosensory system). In one embodiment, "pain" is neuropathic pain resulting from amputation or thoracotomy. In one embodiment, "pain" is chemotherapy induced neuropathy.

The term "neurotoxicity" relates to toxicity in the nervous system. It occurs when exposure to natural or artificial toxic substances (neurotoxins) alter the normal activity of the nervous system in such a way as to cause damage to nervous tissue. Examples of neurotoxicity include, but are not limited to, neurotoxicity resulting from exposure to substances used in chemotherapy, radiation treatment, drug therapies, drug abuse, and organ transplants, as well as exposure to heavy metals, certain foods and food additives, pesticides, industrial and/or cleaning solvents, cosmetics, and some naturally occurring substances.

The term "cancer" refers to a disease characterized by the presence of a neoplasm or tumor resulting from abnormal uncontrolled growth of cells (such cells being "cancer cells"). As used herein, the term cancer explicitly includes, but is not limited to, hepatocellular carcinoma, colon carcinogenesis and ovarian cancer.

The term "mammal" as used herein includes both humans and non-humans and includes but is not limited to humans, non-human primates, canines, felines, murines, bovines, equines, and porcines. In a particularly preferred embodiment, the term "mammal" refers to humans.

Compounds of the Invention

In a first aspect, the present invention provides a compound of formula (I)

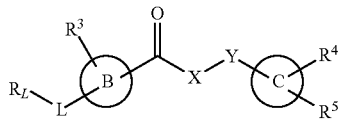

(I)

or a pharmaceutically acceptable salt thereof, wherein:
X is selected from O, NH, N($C_{1-6}$-alkyl) and $(CH_2)_m$CHR$^6$; and Y is $(CH_2)_n$CHR$^7$; or
X and Y together form a group —CR$^6$=CR$^7$—;
m and n are each independently an integer selected from 0 and 1;
$R_L$ is selected from $C_{1-6}$-alkyl and a group

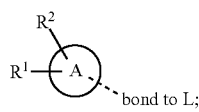

L is selected from a covalent bond, SO$_2$, —SO$_2$NH—, —NHSO$_2$—, —SO$_2$NH—$C_{1-6}$-alkyl-, —$C_{1-6}$-alkyl-NHSO$_2$—, —CHR$^8$—, —O—, —NH—, —OCH$_2$—, —CH$_2$O—, —CH$_2$NH—, —NHCH$_2$—, —CH$_2$N($C_{1-6}$-alkyl)-, —N($C_{1-6}$-alkyl)CH$_2$—, —CH$_2$OCH$_2$—, —CF$_2$CH$_2$—, —CH$_2$CF$_2$—, —CH$_2$CH$_2$—, —CH=CH— and —C≡C—;
L$^D$ is selected from a covalent bond, SO$_2$, —O—, —NR$^{11}$—, —CH$_2$NH—;
A is selected from $C_6$-$C_{14}$-aryl, 5- to 14-membered heteroaryl, $C_3$-$C_{10}$-cycloalkyl, and 3- to 14-membered heterocyclyl;
B is a 4- to 10-membered heterocycle comprising 1-2 nitrogen atoms;
C is
(i) a 5- to 6-membered heterocycle comprising 1-3 heteroatoms independently selected from N, S and O;
(ii) a 5- to 6-membered heteroaryl comprising 1-3 heteroatoms independently selected from N, S and O; or
(iii) $C_3$-$C_{10}$-cycloalkyl;
D is selected from $C_6$-$C_{14}$-aryl, $C_3$-$C_{10}$-cycloalkyl, 5-14-membered heteroaryl, and 3- to 14-membered heterocyclyl;
R$^1$ and R$^2$ are each independently selected from hydrogen, halogen, SF$_5$, cyano, carbamoyl, sulfamoyl, $C_{1-6}$-alkyl, $C_{1-6}$-alkoxy, halo-$C_{1-6}$-alkyl, halo-$C_{1-6}$-alkoxy, $C_{1-6}$-alkyl-SO$_2$—, halo-$C_{1-6}$-alkyl-SO$_2$—, cyano-$C_{1-6}$-alkyl-SO$_2$—, and a group

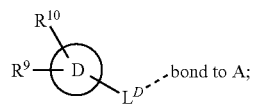

R$^3$ is selected from hydrogen, halogen, hydroxy, cyano, $C_{1-6}$-alkyl, halo-$C_{1-6}$-alkyl, $C_{1-6}$-alkoxy and halo-$C_{1-6}$-alkoxy;
R$^4$ independently selected from hydrogen, halogen, cyano, hydroxy, amino, $C_{1-6}$-alkyl, halo-$C_{1-6}$-alkyl, $C_{1-6}$-alkoxy, halo-$C_{1-6}$-alkoxy and oxo;
R$^5$ is hydrogen;
R$^6$ and R$^7$ are independently selected from hydrogen, halogen, hydroxy and $C_{1-6}$-alkyl; or
R$^6$ and R$^7$, taken together with the carbon atoms to which they are attached, form a $C_3$-$C_{10}$-cycloalkyl ring;
R$^8$ is selected from hydrogen, $C_6$-$C_{14}$-aryl and halo-$C_6$-$C_{14}$-aryl;
R$^9$ is selected from hydrogen, hydroxy, oxo, halogen, cyano, carbamoyl, $C_{1-6}$-alkyl, $C_3$-$C_{10}$-cycloalkyl, $C_{1-6}$-alkoxy, halo-$C_{1-6}$-alkyl, hydroxy-$C_{1-6}$-alkyl, halo-$C_{1-6}$-alkoxy, cyano-$C_{1-6}$-alkyl, cyano-$C_{1-6}$-alkoxy, $C_{1-6}$-alkyl-SO$_2$—$C_{1-6}$-alkyl-, $C_{1-6}$-alkyl-SO$_2$—, $C_{1-6}$-alkoxycarbonyl, halo-$C_{1-6}$-alkyl-SO$_2$—, cyano-$C_{1-6}$-alkyl-SO$_2$—, $C_{1-6}$-alkyl-SO— and $C_{1-6}$-alkyl-S—, wherein said $C_3$-$C_{10}$-cycloalkyl is optionally substituted with one halo-$C_1$-$C_6$-alkyl;
R$^{10}$ is selected from hydrogen, halogen, hydroxy, $C_{1-6}$-alkyl, and halo-$C_{1-6}$-alkyl; and
R$^{11}$ is selected from hydrogen, $C_{1-6}$-alkyl, $C_{1-6}$-alkoxy-$C_{1-6}$-alkyl, and $C_{3-10}$-cycloalkyl-$C_{1-6}$-alkyl-, $C_6$-$C_{14}$-aryl.

In one embodiment, the present invention provides a compound of formula (I) as described herein, or a pharmaceutically acceptable salt thereof, wherein:
X is selected from O, NH, N($C_{1-6}$-alkyl) and $(CH_2)_m$CHR$^6$; and Y is $(CH_2)_n$CHR$^7$; or
X and Y together form a group —CR$^6$=CR$^7$—;
m and n are each independently an integer selected from 0 and 1;
L is selected from a covalent bond, SO$_2$, —SO$_2$NH—, —NHSO$_2$—, —SO$_2$NH—$C_{1-6}$-alkyl-, —$C_{1-6}$-alkyl-NHSO$_2$—, —CHR$^8$—, —O—, —NH—, —OCH$_2$—, —CH$_2$O—, —CH$_2$NH—, —NHCH$_2$—, —CH$_2$N($C_{1-6}$-alkyl)-, —N($C_{1-6}$-alkyl)CH$_2$—, —CH$_2$OCH$_2$—, —CF$_2$CH$_2$—, —CH$_2$CF$_2$—, —CH$_2$CH$_2$—, —CH=CH— and —C≡C—;
L$^D$ is selected from a covalent bond, SO$_2$, —O—, —NR$^{11}$—, —CH$_2$NH—;

A is selected from

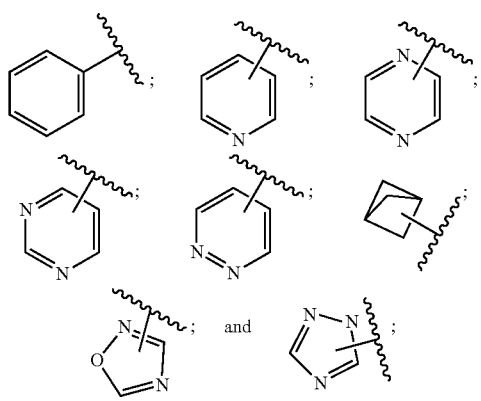

B is selected from

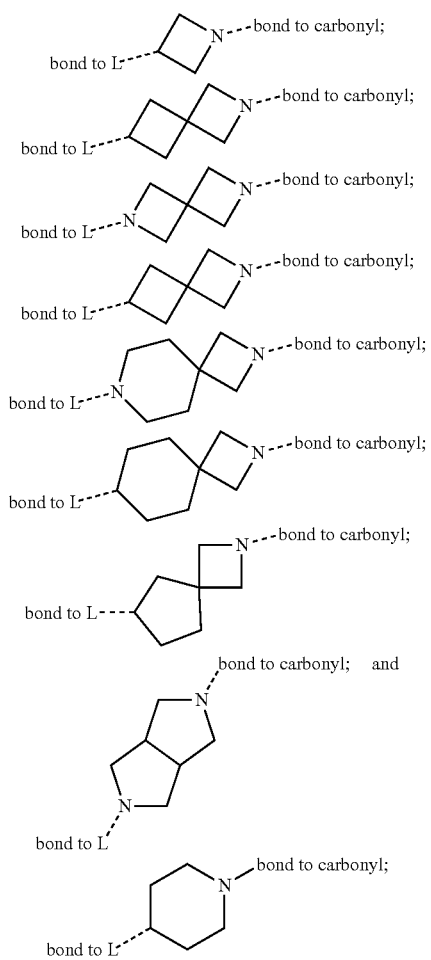

C is selected from

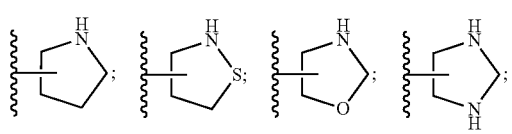

-continued

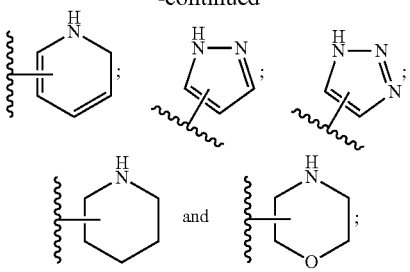

D is selected from $C_6$-$C_{14}$-aryl, $C_3$-$C_{10}$-cycloalkyl, 5-14-membered heteroaryl, and 3- to 14-membered heterocyclyl;

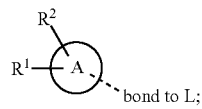

$R_L$ is selected from $C_{1-6}$-alkyl and a group
$R^1$ and $R^2$ are independently selected from hydrogen, halogen, $SF_5$, cyano, carbamoyl, sulfamoyl, $C_{1-6}$-alkyl, $C_{1-6}$-alkoxy, halo-$C_{1-6}$-alkyl, halo-$C_{1-6}$-alkoxy, $C_{1-6}$-alkyl-$SO_2$-halo-$C_{1-6}$-alkyl-$SO_2$—, cyano-$C_{1-6}$-alkyl-$SO_2$—, and a group

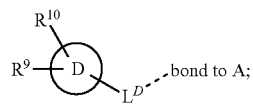

$R^3$ is selected from hydrogen, halogen, hydroxy, cyano, $C_{1-6}$-alkyl, halo-$C_{1-6}$-alkyl, $C_{1-6}$-alkoxy and halo-$C_{1-6}$-alkoxy;
$R^4$ and $R^5$ are independently selected from hydrogen, halogen, cyano, hydroxy, amino, $C_{1-6}$-alkyl, halo-$C_{1-6}$-alkyl, $C_{-6}$-alkoxy, halo-$C_{1-6}$-alkoxy and oxo;
$R^6$ and $R^7$ are independently selected from hydrogen, halogen, hydroxy and $C_{1-6}$-alkyl; or
$R^6$ and $R^7$, taken together with the carbon atoms to which they are attached, form a $C_3$-$C_{10}$-cycloalkyl ring;
$R^8$ is selected from hydrogen, $C_6$-$C_{14}$-aryl and halo-$C_6$-$C_{14}$-aryl;
$R^9$ is selected from hydrogen, hydroxy, oxo, halogen, cyano, carbamoyl, $C_{1-6}$-alkyl, $C_3$-$C_{10}$-cycloalkyl, $C_{1-6}$-alkoxy, halo-$C_{1-6}$-alkyl, hydroxy-$C_{1-6}$-alkyl, halo-$C_{1-6}$-alkoxy, cyano-$C_{1-6}$-alkyl, cyano-$C_{1-6}$-alkoxy, $C_{1-6}$-alkyl-$SO_2$—$C_{1-6}$-alkyl-, $C_{1-6}$-alkyl-$SO_2$—, $C_{1-6}$-alkoxycarbonyl, halo-$C_{1-6}$-alkyl-$SO_2$—, cyano-$C_{1-6}$-alkyl-$SO_2$—, $C_{1-6}$-alkyl-SO— and $C_{1-6}$-alkyl-S—, wherein said $C_3$-$C_{10}$-cycloalkyl is optionally substituted with one halo-$C_1$-$C_6$-alkyl;
$R^{10}$ is selected from hydrogen, halogen, hydroxy, oxo, $C_{1-6}$-alkyl, and halo-$C_{1-6}$-alkyl; and
$R^{11}$ is selected from hydrogen, $C_{1-6}$-alkyl, $C_{1-6}$-alkoxy-$C_{1-6}$-alkyl, and $C_{3-10}$-cycloalkyl-$C_{1-6}$-alkyl-, $C_6$-$C_{14}$-aryl.

In one embodiment, the present invention provides a compound of formula (I) as described herein, or a pharmaceutically acceptable salt thereof, wherein:

$R_L$ is a group

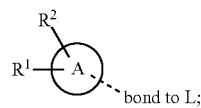

bond to L;

X is selected from O, NH, N($C_{1-6}$-alkyl) and $(CH_2)_m$ $CHR^6$; and Y is $(CH_2)_n CHR^7$; or X and Y together form a group —$CR^6$=$CR^7$—;

m and n are each independently an integer selected from 0 and 1;

L is selected from a covalent bond, —$CHR^8$—, —O—, —$OCH_2$—, —$CH_2O$—, —$CH_2OCH_2$—, —$CF_2CH_2$—, —$CH_2CF_2$—, —$CH_2CH_2$—, —CH=CH— and —C≡C—;

A is selected from $C_6$-$C_{14}$-aryl, 5- to 14-membered heteroaryl, and 3- to 14-membered heterocyclyl;

B is a 4- to 10-membered heterocycle comprising 1-2 nitrogen atoms;

C is
   (i) a 5- to 6-membered heterocyclyle comprising 1-3 heteroatoms independently selected from N, S and O;
   (ii) a 5- to 6-membered heteroaryl comprising 1-3 heteroatoms independently selected from N, S and O; or
   (iii) $C_3$-$C_{10}$-cycloalkyl;

$R^1$ and $R^2$ are independently selected from hydrogen, halogen, $SF_5$, cyano, carbamoyl, $C_{1-6}$-alkyl, $C_{1-6}$-alkoxy, halo-$C_{1-6}$-alkyl, halo-$C_{1-6}$-alkoxy, $C_{1-6}$-alkyl-$SO_2$—, halo-$C_{1-6}$-alkyl-$SO_2$—, cyano-$C_{1-6}$-alkyl-$SO_2$—, $C_6$-$C_{14}$-aryl, $C_3$-$C_{10}$-cycloalkyl, $C_3$-$C_{10}$-cycloalkyl-$SO_2$—, 5-14-membered heteroaryl, 3- to 14-membered heterocyclyl, 3- to 14-membered heterocyclyloxy, $C_6$-$C_{14}$-aryloxy, $C_6$-$C_{14}$-aryl-$SO_2$—, $C_3$-$C_{10}$-cycloalkyloxy, 5-14-membered heteroaryloxy, $C_6$-$C_{14}$-aryl-NH— and $C_6$-$C_{14}$-aryl-N($C_{1-6}$-alkyl)-, wherein said $C_6$-$C_{14}$-aryl, $C_3$-$C_{10}$-cycloalkyl, 5-14-membered heteroaryl, 3- to 14-membered heterocyclyl, 3- to 14-membered heterocyclyloxy, $C_6$-$C_{14}$-aryloxy, $C_3$-$C_{10}$-cycloalkyloxy, 5-14-membered heteroaryloxy, $C_6$-$C_{14}$-aryl-NH— and $C_6$-$C_{14}$-aryl-N($C_{1-6}$-alkyl)- are optionally substituted with 1-2 substituents selected from halogen, cyano, carbamoyl, $C_{1-6}$-alkyl, $C_3$-$C_{10}$-cycloalkyl, $C_{1-6}$-alkoxy, halo-$C_{1-6}$-alkyl, halo-$C_{1-6}$-alkoxy, cyano-$C_{1-6}$-alkyl, cyano-$C_{1-6}$-alkoxy, $C_{1-6}$-alkyl-$SO_2$—, halo-$C_{1-6}$-alkyl-$SO_2$—, cyano-$C_{1-6}$-alkyl-$SO_2$—, $C_{1-6}$-alkyl-SO— and $C_{1-6}$-alkyl-S—;

$R^3$ is selected from hydrogen, halogen, hydroxy, cyano, $C_{1-6}$-alkyl, halo-$C_{1-6}$-alkyl, $C_{1-6}$-alkoxy and halo-$C_{1-6}$-alkoxy;

$R^4$ and $R^5$ are independently selected from hydrogen, halogen, cyano, hydroxy, amino, $C_{1-6}$-alkyl, halo-$C_{1-6}$-alkyl, $C_{1-6}$-alkoxy, halo-$C_{1-6}$-alkoxy and oxo;

$R^6$ and $R^7$ are independently selected from hydrogen, halogen, hydroxy and $C_{1-6}$-alkyl; or $R^6$ and $R^7$, taken together with the carbon atoms to which they are attached, form a $C_3$-$C_{10}$-cycloalkyl ring; and $R^8$ is selected from hydrogen, $C_6$-$C_{14}$-aryl and halo-$C_6$-$C_{14}$-aryl.

In one embodiment, the present invention provides a compound of formula (I) as defined herein, or a pharmaceutically acceptable salt thereof, wherein ring B is selected from:

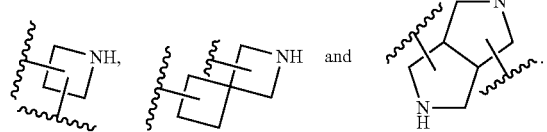

In a preferred embodiment, the present invention provides a compound of formula (I) as defined herein, or a pharmaceutically acceptable salt thereof, wherein ring B is selected from:

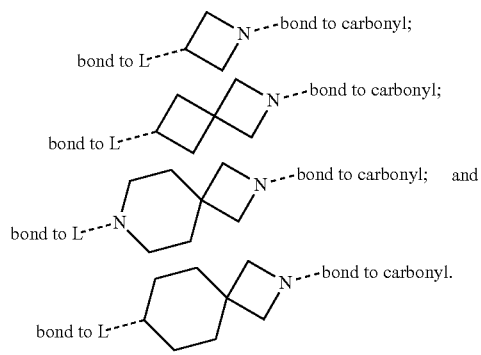

In a particularly preferred embodiment, the present invention provides a compound of formula (I) as defined herein, or a pharmaceutically acceptable salt thereof, wherein ring B is

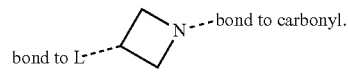

In one embodiment, the present invention provides a compound of formula (I) as defined herein, or a pharmaceutically acceptable salt thereof, wherein ring C is selected from:

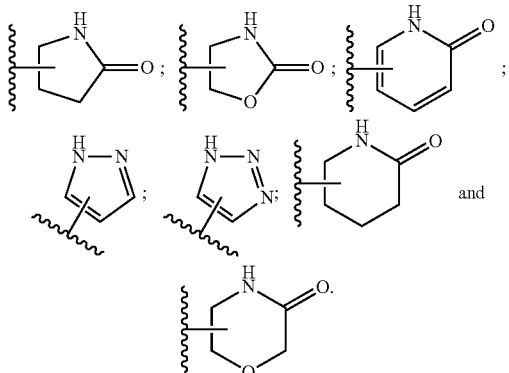

In one embodiment, the present invention provides a compound of formula (I) as defined herein, or a pharmaceutically acceptable salt thereof, wherein ring C is selected from:

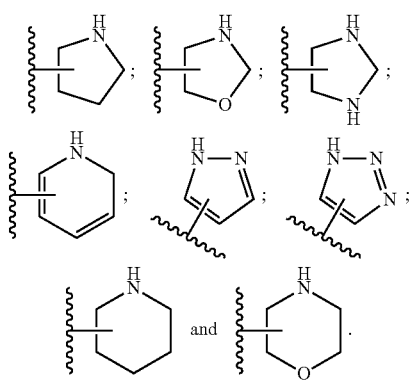

In a preferred embodiment, the present invention provides a compound of formula (I) as defined herein, or a pharmaceutically acceptable salt thereof, wherein ring C is

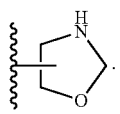

In one embodiment, the present invention provides a compound of formula (I) as defined herein, or a pharmaceutically acceptable salt thereof, wherein said compound of formula (I) is a compound of formula (II)

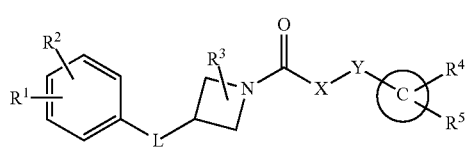

(II)

wherein C, L and $R^1$ to $R^5$ are as defined herein.

In one embodiment, the present invention provides a compound of formula (I) as defined herein, or a pharmaceutically acceptable salt thereof, wherein:

$R_L$ is a group

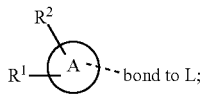

X is selected from O, NH, N($C_{1-6}$-alkyl) and $(CH_2)_m CHR^6$;
Y is $(CH_2)_n CHR^7$;
m and n are each independently an integer selected from 0 and 1;
$R^6$ is selected from hydrogen, halogen, hydroxy and $C_{1-6}$-alkyl; and
$R^7$ is hydrogen.

In a preferred embodiment, the present invention provides a compound of formula (I) as defined herein, or a pharmaceutically acceptable salt thereof, wherein:

$R_L$ is a group

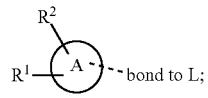

X is selected from N($C_{1-6}$-alkyl) and $(CH_2)_m CHR^6$;
Y is $(CH_2)_n CHR^7$;
m is 0;
n is an integer selected from 0 and 1; and
$R^6$ and $R^7$ are both hydrogen.

In a particularly preferred embodiment, the present invention provides a compound of formula (I) as defined herein, or a pharmaceutically acceptable salt thereof, wherein:

$R_L$ is a group

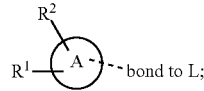

X is selected from N-methyl and $(CH_2)_m CHR^6$;
Y is $(CH_2)_n CHR^7$;
m is 0;
n is an integer selected from 0 and 1; and
$R^6$ and $R^7$ are both hydrogen.

In a further particularly preferred embodiment, the present invention provides a compound of formula (I) as defined herein, or a pharmaceutically acceptable salt thereof, wherein:

$R_L$ is a group

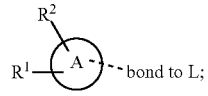

X is $(CH_2)_m CHR^6$;
Y is $(CH_2)_n CHR^7$;
m and n are both 0; and
$R^6$ and $R^7$ are both hydrogen.

In one embodiment, the present invention provides a compound of formula (I) as defined herein, or a pharmaceutically acceptable salt thereof, wherein:

L is selected from a covalent bond, —$CHR^8$—, —$CH_2O$—, $SO_2$, —$SO_2NH$—, —$SO_2NH$—$C_{1-6}$-alkyl-, —O—, —NH—, —$CH_2NH$—, —$CH_2N(C_{1-6}$-alkyl)-, and —C≡C—;
$L^D$ is selected from a covalent bond, $SO_2$, —O—, —$NR^{11}$—, and —$CH_2NH$—;
A is selected from $C_6$-$C_{14}$-aryl, $C_3$-$C_{10}$-cycloalkyl, and 5- to 14-membered heteroaryl;
D is selected from $C_6$-$C_{14}$-aryl, $C_3$-$C_{10}$-cycloalkyl, 5-14-membered heteroaryl, and 3- to 14-membered heterocyclyl;
$R^1$ is selected from halogen, $SF_5$, sulfamoyl, $C_{1-6}$-alkyl, halo-$C_{1-6}$-alkyl, $C_{1-6}$-alkyl-$SO_2$—, halo-$C_{1-6}$-alkyl-$SO_2$—, cyano-$C_{1-6}$-alkyl-$SO_2$—, $C_3$-$C_{10}$-cycloalkyl-$SO_2$—, $C_6$-$C_{14}$-aryl-$SO_2$—, halo-$C_{1-6}$-alkoxy, and a group

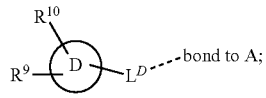

R² is selected from hydrogen, C₁₋₆-alkyl-SO₂— and halogen;

R⁸ is selected from hydrogen and C₆-C₁₄-aryl;

R⁹ is selected from hydrogen, hydroxy, oxo, halogen, cyano, carbamoyl, C₁₋₆-alkyl, C₃-C₁₀-cycloalkyl, C₁₋₆-alkoxy, halo-C₁₋₆-alkyl, hydroxy-C₁₋₆-alkyl, halo-C₁₋₆-alkoxy, C₁₋₆-alkyl-SO₂—C₁₋₆-alkyl-, C₁₋₆-alkyl-SO₂—, C₁₋₆-alkoxy-carbonyl, wherein said C₃-C₁₀-cycloalkyl is optionally substituted with one halo-C₁-C₆-alkyl;

R¹⁰ is selected from hydrogen, halogen, hydroxy, oxo, C₁₋₆-alkyl, and halo-C₁₋₆-alkyl; and R¹¹ is selected from hydrogen, C₁₋₆-alkyl, C₁₋₆-alkoxy-C₁₋₆-alkyl, and C₃₋₁₀-cycloalkyl-C₁₋₆-alkyl-, C₆-C₁₄-aryl.

In one embodiment, the present invention provides a compound of formula (I) as defined herein, or a pharmaceutically acceptable salt thereof, wherein:

L is selected from a covalent bond, —CHR⁸—, —CH₂O—, SO₂, —SO₂NH—, —SO₂NH—C₁₋₆-alkyl-, —O—, —NH—, —CH₂NH—, —CH₂N(C₁₋₆-alkyl)-, and —C≡C—;

L^D is selected from a covalent bond, SO₂, —O—, —NR¹¹—, and —CH₂NH—;

D is selected from C₆-C₁₄-aryl, C₃-C₁₀-cycloalkyl, 5-14-membered heteroaryl, and 3- to 14-membered heterocyclyl;

R¹ is selected from halogen, SF₅, sulfamoyl, C₁₋₆-alkyl, halo-C₁₋₆-alkyl, C₁₋₆-alkyl-SO₂—, halo-C₁₋₆-alkyl-SO₂—, cyano-C₁₋₆-alkyl-SO₂—, C₃-C₁₀-cycloalkyl-SO₂—, C₆-C₁₄-aryl-SO₂—, halo-C₁₋₆-alkoxy, and a group

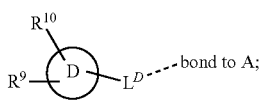

R² is selected from hydrogen, C₁₋₆-alkyl-SO₂— and halogen;

R⁸ is selected from hydrogen and C₆-C₁₄-aryl;

R⁹ is selected from hydrogen, hydroxy, oxo, halogen, cyano, carbamoyl, C₁₋₆-alkyl, C₃-C₁₀-cycloalkyl, C₁₋₆-alkoxy, halo-C₁₋₆-alkyl, hydroxy-C₁₋₆-alkyl, halo-C₁₋₆-alkoxy, C₁₋₆-alkyl-SO₂—C₁₋₆-alkyl-, C₁₋₆-alkyl-SO₂—, C₁₋₆-alkoxy-carbonyl, wherein said C₃-C₁₀-cycloalkyl is optionally substituted with one halo-C₁-C₆-alkyl;

R¹⁰ is selected from hydrogen, halogen, hydroxy, oxo, C₁₋₆-alkyl, and halo-C₁₋₆-alkyl; and R¹¹ is selected from hydrogen, C₁₋₆-alkyl, C₁₋₆-alkoxy-C₁₋₆-alkyl, and C₃₋₁₀-cycloalkyl-C₁₋₆-alkyl-, C₆-C₁₄-aryl.

In one embodiment, the present invention provides a compound of formula (I) as defined herein, or a pharmaceutically acceptable salt thereof, wherein:

L is selected from a covalent bond, —CHR⁸—, —CH₂O—, SO₂, —SO₂NH—, —SO₂NH—C₁₋₆-alkyl-, —O—, —NH—, —CH₂NH—, —CH₂N(C₁₋₆-alkyl)-, and —C≡C—;

L^D is selected from a covalent bond, SO₂, —O—, —NR¹¹—, and —CH₂NH—;

D is selected from:

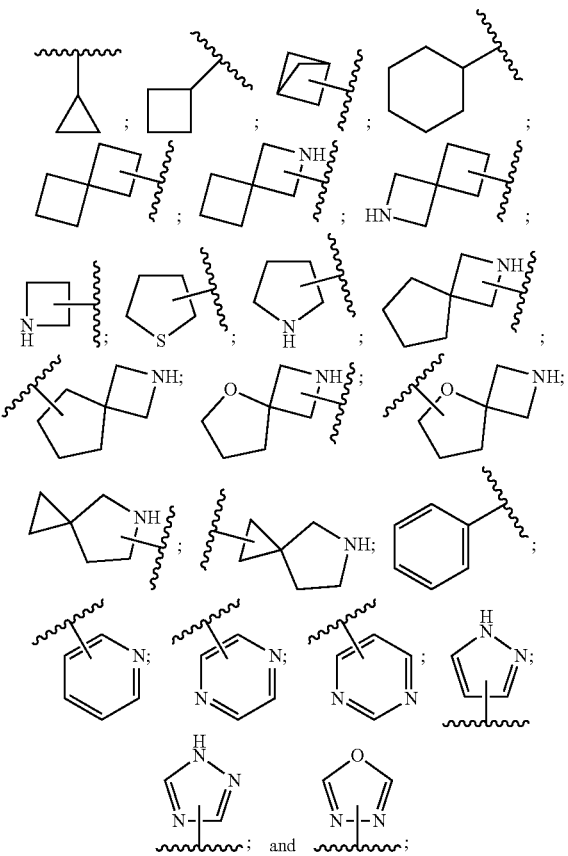

R¹ is selected from halogen, SF₅, sulfamoyl, C₁₋₆-alkyl, halo-C₁₋₆-alkyl, C₁₋₆-alkyl-SO₂—, halo-C₁₋₆-alkyl-SO₂—, cyano-C₁₋₆-alkyl-SO₂—, C₃-C₁₀-cycloalkyl-SO₂—, C₆-C₁₄-aryl-SO₂—, halo-C₁₋₆-alkoxy, and a group

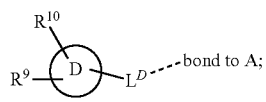

R² is selected from hydrogen, C₁₋₆-alkyl-SO₂— and halogen;

R⁸ is selected from hydrogen and C₆-C₁₄-aryl;

R⁹ is selected from hydrogen, hydroxy, oxo, halogen, cyano, carbamoyl, C₁₋₆-alkyl, C₃-C₁₀-cycloalkyl, C₁₋₆-alkoxy, halo-C₁₋₆-alkyl, hydroxy-C₁₋₆-alkyl, halo-C₁₋₆-alkoxy, C₁₋₆-alkyl-SO₂—C₁₋₆-alkyl-, C₁₋₆-alkyl-SO₂—, C₁₋₆-alkoxy-carbonyl, wherein said C₃-C₁₀-cycloalkyl is optionally substituted with one halo-C₁-C₆-alkyl;

R¹⁰ is selected from hydrogen, halogen, hydroxy, oxo, C₁₋₆-alkyl, and halo-C₁₋₆-alkyl; and R¹¹ is selected from hydrogen, C₁₋₆-alkyl, C₁₋₆-alkoxy-C₁₋₆-alkyl, and C₃₋₁₀-cycloalkyl-C₁₋₆-alkyl-, C₆-C₁₄-aryl.

In one embodiment, the present invention provides a compound of formula (I) as defined herein, or a pharmaceutically acceptable salt thereof, wherein:

$R_L$ is a group

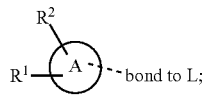

L is selected from a covalent bond, —CHR$^8$—, —CH$_2$O—, and —C≡C—;
A is selected from C$_6$-C$_{14}$-aryl and 5- to 14-membered heteroaryl;
R$^1$ is selected from halogen, SF$_5$, C$_{1-6}$-alkyl, halo-C$_{1-6}$-alkyl, halo-C$_{1-6}$-alkyl-SO$_2$—, cyano-C$_{1-6}$-alkyl-SO$_2$—, C$_3$-C$_{10}$-cycloalkyl-SO$_2$—, C$_6$-C$_{14}$-aryl-SO$_2$—, halo-C$_{1-6}$-alkoxy, C$_6$-C$_{14}$-aryl, C$_3$-C$_{10}$-cycloalkyl, 3- to 14-membered heterocyclyl, C$_6$-C$_{14}$-aryloxy and C$_6$-C$_{14}$-aryl-N(C$_{1-6}$-alkyl)-, wherein said C$_6$-C$_{14}$-aryl, C$_3$-C$_{10}$-cycloalkyl, 3- to 14-membered heterocyclyl, 5-14-membered heteroaryl, C$_6$-C$_{14}$-aryloxy and 5-14-membered heteroaryloxy are substituted with 1-2 substituents selected from halogen, cyano, carbamoyl, C$_{1-6}$-alkyl, C$_3$-C$_{10}$-cycloalkyl, halo-C$_{1-6}$-alkyl, C$_{1-6}$-alkyl-SO$_2$— and halo-C$_{1-6}$-alkoxy;
R$^2$ is selected from hydrogen and halogen; and
R$^8$ is selected from hydrogen and C$_6$-C$_{14}$-aryl.

In a preferred embodiment, the present invention provides a compound of formula (I) as defined herein, or a pharmaceutically acceptable salt thereof, wherein:
$R_L$ is a group

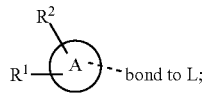

L is selected from a covalent bond, —CHR$^8$—, and —CH$_2$O—;
L$^D$ is selected from a covalent bond, —O—, and —NR$^{11}$—;
A is selected from C$_6$-C$_{14}$-aryl and 5- to 14-membered heteroaryl;
D is selected from C$_6$-C$_{14}$-aryl, C$_3$-C$_{10}$-cycloalkyl, and 3- to 14-membered heterocyclyl;
R$^1$ is selected from halo-C$_{1-6}$-alkyl and a group

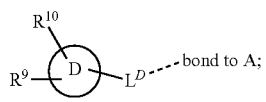

R$^2$ is selected from hydrogen and halogen;
R$^8$ is hydrogen;
R$^9$ is selected from hydrogen, halogen, halo-C$_{1-6}$-alkyl, halo-C$_{1-6}$-alkoxy, and C$_{1-6}$-alkyl-SO$_2$—;
R$^{10}$ is selected from hydrogen, halogen, and halo-C$_{1-6}$-alkyl; and
R$^{11}$ is selected from C$_{1-6}$-alkyl and C$_{3-10}$-cycloalkyl-C$_{1-6}$-alkyl-.

In a preferred embodiment, the present invention provides a compound of formula (I) as defined herein, or a pharmaceutically acceptable salt thereof, wherein:

$R_L$ is a group

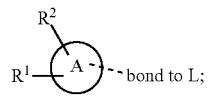

L is selected from a covalent bond, —CHR$^8$—, and —CH$_2$O—;
L$^D$ is selected from a covalent bond, —O—, and —NR$^{11}$—;
A is selected from

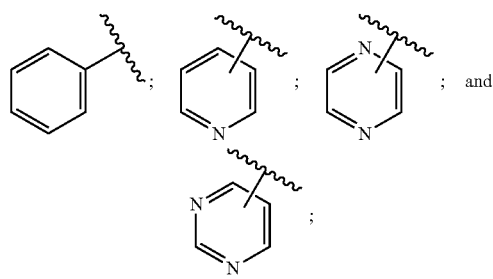

D is selected from:

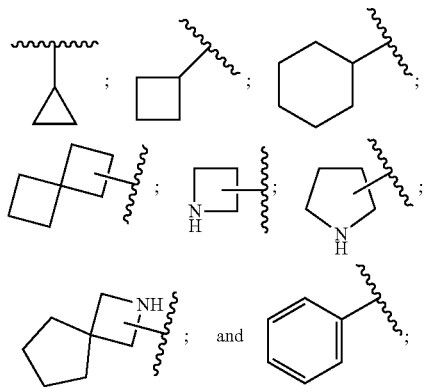

R$^1$ is selected from halo-C$_{1-6}$-alkyl and a group

R$^2$ is selected from hydrogen and halogen;
R$^8$ is hydrogen;
R$^9$ is selected from hydrogen, halogen, halo-C$_{1-6}$-alkyl, halo-C$_{1-6}$-alkoxy, and C$_{1-6}$-alkyl-SO$_2$—;
R$^{10}$ is selected from hydrogen, halogen, and halo-C$_{1-6}$-alkyl; and
R$^{11}$ is selected from C$_{1-6}$-alkyl and C$_{3-10}$-cycloalkyl-C$_{1-6}$-alkyl-.

In a preferred embodiment, the present invention provides a compound of formula (I) as defined herein, or a pharmaceutically acceptable salt thereof, wherein:
L is selected from a covalent bond and —CH$_2$O—;
A is C$_6$-C$_{14}$-aryl;
R$^1$ is selected from halo-C$_{1-6}$-alkyl, C$_6$-C$_{14}$-aryl, C$_3$-C$_{10}$-cycloalkyl and C$_6$-C$_{14}$-aryl-N(C$_{1-6}$-alkyl)-, wherein said $C_6$-$C_{14}$-aryl and $C_3$-$C_{10}$-cycloalkyl are substituted with 1-2 substituents selected from halogen, $C_{1-6}$-alkyl-$SO_2$— and halo-$C_{1-6}$-alkyl;
$R^2$ is selected from hydrogen and halogen; and
$R^8$ is hydrogen.

In a particularly preferred embodiment, the present invention provides a compound of formula (I) as defined herein, or a pharmaceutically acceptable salt thereof, wherein:
$R_L$ is a group

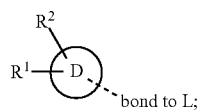
bond to L;

L is selected from a covalent bond, —$CHR^8$—, and —$CH_2O$—;
$L^D$ is selected from a covalent bond, —O—, and —$NR^{11}$—;
A is selected from

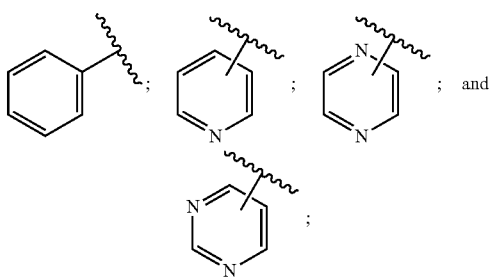

D is selected from:

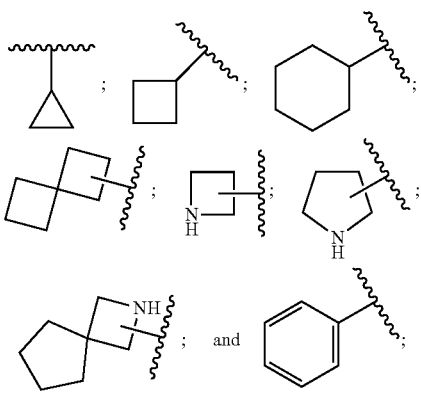

$R^1$ is selected from $CF_3$ and a group

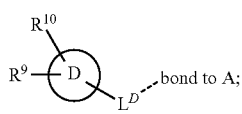

$R^2$ is selected from hydrogen and fluoro;
$R^8$ is hydrogen;
$R^9$ is selected from hydrogen, fluoro, chloro, $CF_3$, 2,2,2-trifluoroethoxy, and methylsulfonyl;

$R^{10}$ is selected from hydrogen, chloro, and $CF_3$; and
$R^{11}$ is selected from methyl and cyclopropylmethyl.

In a particularly preferred embodiment, the present invention provides a compound of formula (I) as defined herein, or a pharmaceutically acceptable salt thereof, wherein:
L is selected from a covalent bond and —$CH_2O$—;
A is phenyl;
$R^1$ is selected from $CF_3$, phenyl, cyclopropyl and phenyl-N(methyl)-, wherein said phenyl and cyclopropyl are substituted with 1-2 substituents selected from fluoro, chloro, methylsulfonyl and $CF_3$;
$R^2$ is selected from hydrogen and fluoro; and
$R^8$ is hydrogen.

In one embodiment, the present invention provides a compound of formula (I) as defined herein, or a pharmaceutically acceptable salt thereof, wherein:
B is a 4- to 9-membered heterocycle comprising 1-2 nitrogen atoms; and
$R^3$ is hydrogen.

In one embodiment, the present invention provides a compound of formula (I) as defined herein, or a pharmaceutically acceptable salt thereof, wherein:
B is a 4- to 8-membered heterocycle comprising 1-2 nitrogen atoms; and
$R^3$ is hydrogen.

In a preferred embodiment, the present invention provides a compound of formula (I) as defined herein, or a pharmaceutically acceptable salt thereof, wherein:
B is selected from

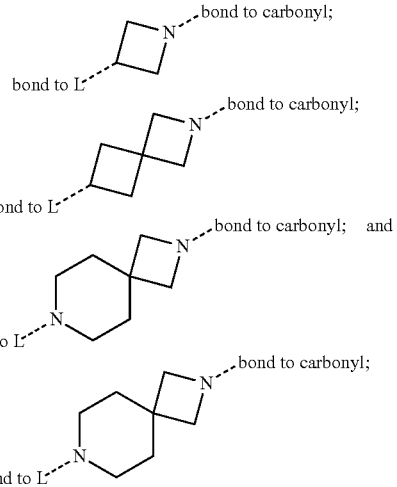

and
$R^3$ is hydrogen.

In a preferred embodiment, the present invention provides a compound of formula (I) as defined herein, or a pharmaceutically acceptable salt thereof, wherein:
B is azetidinyl; and
$R^3$ is hydrogen.

In one embodiment, the present invention provides a compound of formula (I) as defined herein, or a pharmaceutically acceptable salt thereof, wherein:
C is
(i) a 5- to 6-membered heterocyclyle comprising 1-2 heteroatoms independently selected from N, S and O; or
(ii) a 5- to 6-membered heteroaryl comprising 1-3 nitrogen atoms;

R⁴ is selected from hydrogen and oxo; and
R⁵ is selected from hydrogen and $C_{1-6}$-alkyl.

In one embodiment, the present invention provides a compound of formula (I) as defined herein, or a pharmaceutically acceptable salt thereof, wherein:
C is selected from

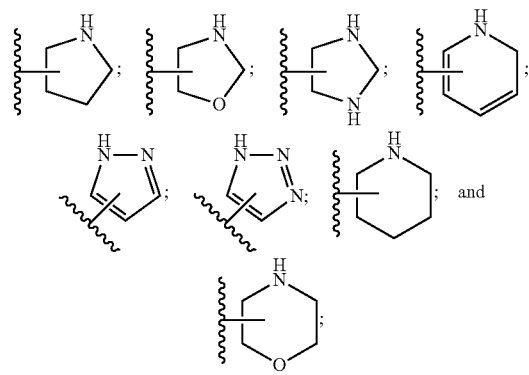

R⁴ is selected from hydrogen and oxo; and
R⁵ is selected from hydrogen and $C_{1-6}$-alkyl.

In a preferred embodiment, the present invention provides a compound of formula (I) as defined herein, or a pharmaceutically acceptable salt thereof, wherein:
C is
(i) a 5-membered heterocyclyle comprising 1-2 heteroatoms independently selected from N and O; or
(ii) a 5-membered heteroaryl comprising 3 nitrogen atoms;
R⁴ is selected from hydrogen and oxo; and
R⁵ is hydrogen.

In a particularly preferred embodiment, the present invention provides a compound of formula (I) as defined herein, or a pharmaceutically acceptable salt thereof, wherein:
C is selected from pyrrolidinyl, oxazolidinyl and triazolyl;
R⁴ is selected from hydrogen and oxo; and
R⁵ is hydrogen.

In a further particularly preferred embodiment, the present invention provides a compound of formula (I) as defined herein, or a pharmaceutically acceptable salt thereof, wherein:
C is selected from

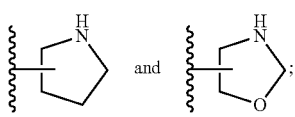

R⁴ is oxo; and
R⁵ is hydrogen.

In one embodiment, the present invention provides a compound of formula (I) as defined herein, or a pharmaceutically acceptable salt thereof, wherein:
X is selected from O, NH, N($C_{1-6}$-alkyl) and $(CH_2)_m CHR^6$;
Y is $(CH_2)_n CHR^7$;
m and n are each independently an integer selected from 0 and 1;
C is
(i) a 5- to 6-membered heterocyclyle comprising 1-2 heteroatoms independently selected from N, S and O; or
(ii) a 5- to 6-membered heteroaryl comprising 1-3 nitrogen atoms;
R⁴ is selected from hydrogen and oxo;
R⁵ is selected from hydrogen and $C_{1-6}$-alkyl;
R⁶ is selected from hydrogen, hydroxy and $C_{1-6}$-alkyl; and
R⁷ is selected from hydrogen.

In a preferred embodiment, the present invention provides a compound of formula (I) as defined herein, or a pharmaceutically acceptable salt thereof, wherein:
X is selected from N($C_{1-6}$-alkyl) and $(CH_2)_m CHR^6$;
Y is $(CH_2)_n CHR^7$;
m is 0;
n is an integer selected from 0 and 1;
C is
(i) a 5-membered heterocyclyle comprising 1-2 heteroatoms independently selected from N and O; or
(ii) a 5-membered heteroaryl comprising 3 nitrogen atoms;
R⁴ is selected from hydrogen and oxo; and
R⁵, R⁶ and R⁷ are all hydrogen.

In a particularly preferred embodiment, the present invention provides a compound of formula (I) as defined herein, or a pharmaceutically acceptable salt thereof, wherein:
X is selected from N(methyl) and $(CH_2)_m CHR^6$;
Y is $(CH_2)_n CHR^7$;
m is 0;
n is an integer selected from 0 and 1;
C is selected from pyrrolidinyl, oxazolidinyl and triazolyl;
R⁴ is selected from hydrogen and oxo; and
R⁵, R⁶ and R⁷ are all hydrogen.

In one embodiment, the present invention provides a compound of formula (I) as defined herein, or a pharmaceutically acceptable salt thereof, wherein:
X is selected from O, NH, N($C_{1-6}$-alkyl) and $(CH_2)_m CHR^6$;
Y is $(CH_2)_n CHR^7$;
m and n are each independently an integer selected from 0 and 1;
L is selected from a covalent bond, —CHR⁸—, —CH₂O—, SO₂, —SO₂NH—, —SO₂NH—$C_{1-6}$-alkyl-, —O—, —NH—, —CH₂NH—, —CH₂N($C_{1-6}$-alkyl)-, and —C≡C—;
$L^D$ is selected from a covalent bond, SO₂, —O—, —NR¹¹—, and —CH₂NH—;
A is selected from $C_6$-$C_{14}$-aryl, $C_3$-$C_{10}$-cycloalkyl, and 5- to 14-membered heteroaryl;
B is a 4- to 9-membered heterocycle comprising 1-2 nitrogen atoms;
C is
(i) a 5- to 6-membered heterocyclyle comprising 1-2 heteroatoms independently selected from N, S and O; or
(ii) a 5- to 6-membered heteroaryl comprising 1-3 nitrogen atoms;
D is selected from $C_6$-$C_{14}$-aryl, $C_3$-$C_{10}$-cycloalkyl, 5-14-membered heteroaryl, and 3- to 14-membered heterocyclyl;
R¹ is selected from halogen, SF₅, sulfamoyl, $C_{1-6}$-alkyl, halo-$C_{1-6}$-alkyl, $C_{1-6}$-alkyl-SO₂—, halo-$C_{1-6}$-alkyl-SO₂—, cyano-$C_{1-6}$-alkyl-SO₂—, $C_3$-$C_{10}$-cycloalkyl-SO₂—, $C_6$-$C_{14}$-aryl-SO₂—, halo-$C_{1-6}$-alkoxy, and a group

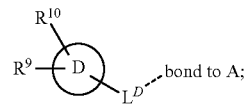

bond to A;

$R^2$ is selected from hydrogen, $C_{1-6}$-alkyl-$SO_2$— and halogen;
$R^3$ and $R^7$ are both hydrogen;
$R^4$ is selected from hydrogen and oxo;
$R^5$ is selected from hydrogen and $C_{1-6}$-alkyl;
$R^6$ is selected from hydrogen, halogen, hydroxy and $C_{1-6}$-alkyl;
$R^8$ is selected from hydrogen and $C_6$-$C_{14}$-aryl;
$R^9$ is selected from hydrogen, hydroxy, oxo, halogen, cyano, carbamoyl, $C_{1-6}$-alkyl, $C_3$-$C_{10}$-cycloalkyl, $C_{1-6}$-alkoxy, halo-$C_{1-6}$-alkyl, hydroxy-$C_{1-6}$-alkyl, halo-$C_{1-6}$-alkoxy, $C_{1-6}$-alkyl-$SO_2$—$C_{1-6}$-alkyl-, $C_{1-6}$-alkyl-$SO_2$—, $C_{1-6}$-alkoxy-carbonyl, wherein said $C_3$-$C_{10}$-cycloalkyl is optionally substituted with one halo-$C_1$-$C_6$-alkyl;
$R^{10}$ is selected from hydrogen, halogen, hydroxy, oxo, $C_{1-6}$-alkyl, and halo-$C_{1-6}$-alkyl; and
$R^{11}$ is selected from hydrogen, $C_{1-6}$-alkyl, $C_{1-6}$-alkoxy-$C_{1-6}$-alkyl, and $C_{3-10}$-cycloalkyl-$C_{1-6}$-alkyl-, $C_6$-$C_{14}$-aryl.

In a preferred embodiment, the present invention provides a compound of formula (I) as defined herein, or a pharmaceutically acceptable salt thereof, wherein:
X is selected from $N(C_{1-6}$-alkyl) and $(CH_2)_m CHR^6$;
Y is $(CH_2)_n CHR^7$;
m is 0;
n is an integer selected from 0 and 1;
L is selected from a covalent bond, —$CHR^8$—, and —$CH_2O$—;
$L^D$ is selected from a covalent bond, —O—, and —$NR^{11}$—;
A is selected from $C_6$-$C_{14}$-aryl and 5- to 14-membered heteroaryl;
B is a 4- to 9-membered heterocycle comprising 1-2 nitrogen atoms;
C is
  (i) a 5-membered heterocyclyle comprising 1-2 heteroatoms independently selected from N and O; or
  (ii) a 5-membered heteroaryl comprising 3 nitrogen atoms;
D is selected from $C_6$-$C_{14}$-aryl, $C_3$-$C_{10}$-cycloalkyl, and 3- to 14-membered heterocyclyl;
$R_L$ is a group

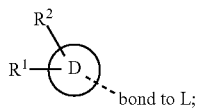

$R^1$ is selected from halo-$C_{1-6}$-alkyl and a group

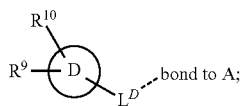

$R^2$ is selected from hydrogen and halogen;
$R^3$, $R^5$, $R^6$, $R^7$ and $R^8$ are all hydrogen;
$R^4$ is selected from hydrogen and oxo;
$R^9$ is selected from hydrogen, halogen, halo-$C_{1-6}$-alkyl, halo-$C_{1-6}$-alkoxy, and $C_{1-6}$-alkyl-$SO_2$—;
$R^{10}$ is selected from hydrogen, halogen, and halo-$C_{1-6}$-alkyl; and $R^{11}$ is selected from $C_{1-6}$-alkyl and $C_{3-10}$-cycloalkyl-$C_{1-6}$-alkyl-.

In one embodiment, the present invention provides a compound of formula (I) as defined herein, or a pharmaceutically acceptable salt thereof, wherein:
X is selected from O, NH, $N(C_{1-6}$-alkyl) and $(CH_2)_m CHR^6$;
Y is $(CH_2)_n CHR^7$;
m and n are each independently an integer selected from 0 and 1;
L is selected from a covalent bond, —$CHR^8$—, —$CH_2O$—, $SO_2$, —$SO_2NH$—, —$SO_2NH$—$C_{1-6}$-alkyl-, —O—, —NH—, —$CH_2NH$—, —$CH_2N(C_{1-6}$-alkyl)-, and —C≡C—;
$L^D$ is selected from a covalent bond, $SO_2$, —O—, —$NR^{11}$—, and —$CH_2NH$—;
A is selected from

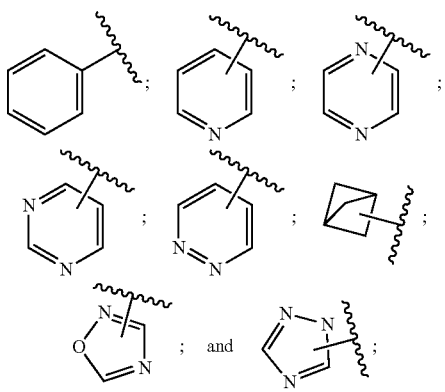

B is selected from

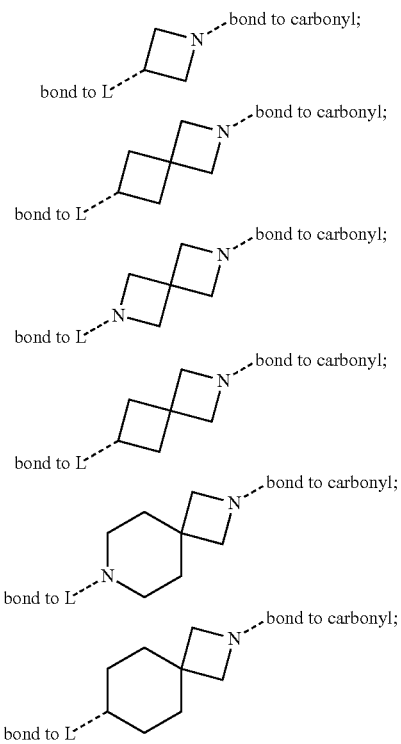

-continued

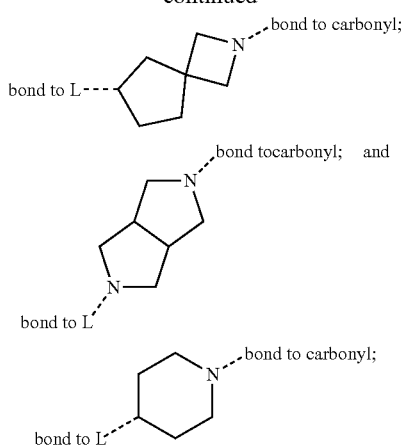

C is selected from

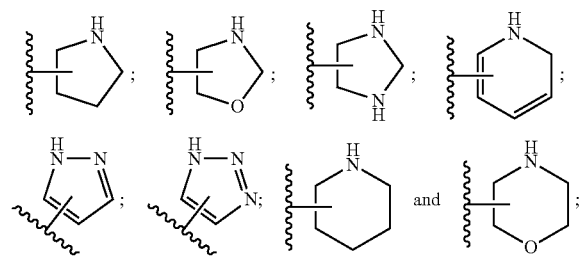

D is selected from:

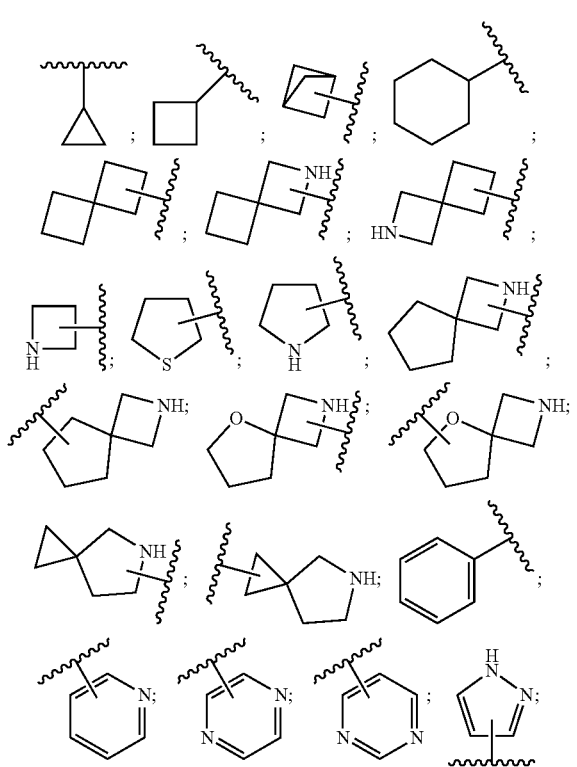

-continued

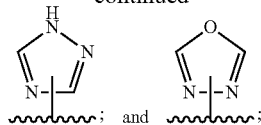

$R^1$ is selected from halogen, $SF_5$, sulfamoyl, $C_{1-6}$-alkyl, halo-$C_{1-6}$-alkyl, $C_{1-6}$-alkyl-$SO_2$—, halo-$C_{1-6}$-alkyl-$SO_2$—, cyano-$C_{1-6}$-alkyl-$SO_2$—, $C_3$-$C_{10}$-cycloalkyl-$SO_2$—, $C_6$-$C_{14}$-aryl-$SO_2$—, halo-$C_{1-6}$-alkoxy, and a group

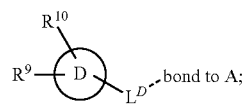

$R^2$ is selected from hydrogen, $C_{1-6}$-alkyl-$SO_2$— and halogen;
$R^3$ and $R^7$ are both hydrogen;
$R^4$ is selected from hydrogen and oxo;
$R^5$ is selected from hydrogen and $C_{1-6}$-alkyl;
$R^6$ is selected from hydrogen, halogen, hydroxy and $C_{1-6}$-alkyl;
$R^8$ is selected from hydrogen and $C_6$-$C_{14}$-aryl;
$R^9$ is selected from hydrogen, hydroxy, oxo, halogen, cyano, carbamoyl, $C_{1-6}$-alkyl, $C_3$-$C_{10}$-cycloalkyl, $C_{1-6}$-alkoxy, halo-$C_{1-6}$-alkyl, hydroxy-$C_{1-6}$-alkyl, halo-$C_{1-6}$-alkoxy, $C_{1-6}$-alkyl-$SO_2$—$C_{1-6}$-alkyl-, $C_{1-6}$-alkyl-$SO_2$—, $C_{1-6}$-alkoxy-carbonyl, wherein said $C_3$-$C_{10}$-cycloalkyl is optionally substituted with one halo-$C_1$-$C_6$-alkyl;
$R^{10}$ is selected from hydrogen, halogen, hydroxy, oxo, $C_{1-6}$-alkyl, and halo-$C_{1-6}$-alkyl; and
$R^{11}$ is selected from hydrogen, $C_{1-6}$-alkyl, $C_{1-6}$-alkoxy-$C_{1-6}$-alkyl, and $C_{3-10}$-cycloalkyl-$C_{1-6}$-alkyl-, $C_6$-$C_{14}$-aryl.

In a preferred embodiment, the present invention provides a compound of formula (I) as defined herein, or a pharmaceutically acceptable salt thereof, wherein:
X is selected from $N(C_{1-6}$-alkyl) and $(CH_2)_mCHR^6$;
Y is $(CH_2)_nCHR^7$;
m is 0;
n is an integer selected from 0 and 1;
L is selected from a covalent bond, —$CHR^8$—, and —$CH_2O$—;
$L^D$ is selected from a covalent bond, —O—, and —$NR^{11}$—;
A is selected from

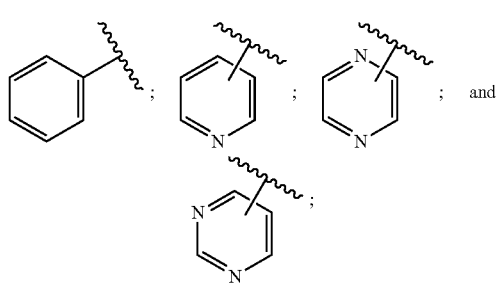

B is selected from

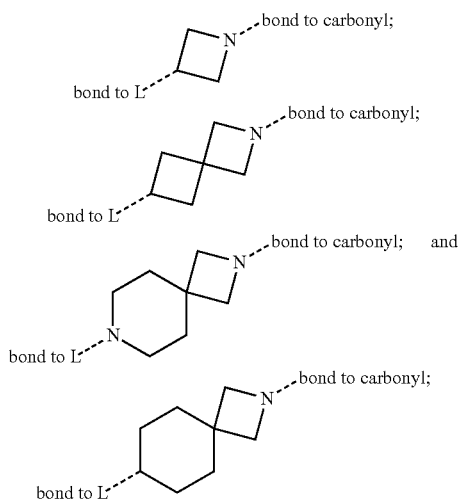

C is selected from

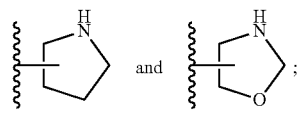

D is selected from:

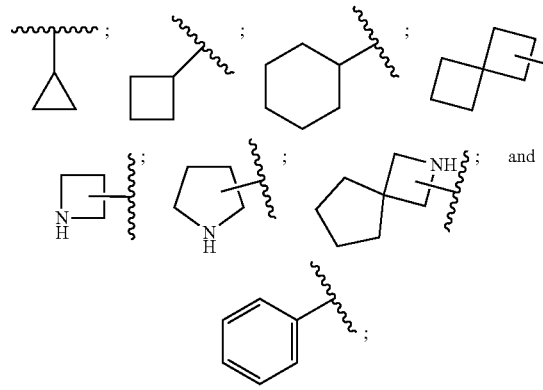

$R_L$ is a group

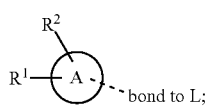

$R^1$ is selected from halo-$C_{1-6}$-alkyl and a group

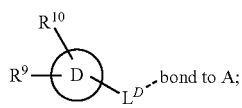

$R^2$ is selected from hydrogen and halogen;
$R^3$, $R^5$, $R^6$, $R^7$ and $R^8$ are all hydrogen;
$R^4$ is selected from hydrogen and oxo;
$R^9$ is selected from hydrogen, halogen, halo-$C_{1-6}$-alkyl, halo-$C_{1-6}$-alkoxy, and $C_{1-6}$-alkyl-$SO_2$—;
$R^{10}$ is selected from hydrogen, halogen, and halo-$C_{1-6}$-alkyl; and
$R^{11}$ is selected from $C_{1-6}$-alkyl and $C_{3-10}$-cycloalkyl-$C_{1-6}$-alkyl-.

In a particularly preferred embodiment, the present invention provides a compound of formula (I) as defined herein, or a pharmaceutically acceptable salt thereof, wherein:
X is selected from N(methyl) and $(CH_2)_m CHR^6$;
Y is $(CH_2)_n CHR^7$;
m is 0;
n is an integer selected from 0 and 1;
L is selected from a covalent bond, —$CHR^8$—, and —$CH_2O$—;
$L^D$ is selected from a covalent bond, —O—, and —$NR^{11}$—;
A is selected from phenyl, pyridyl, pyrazinyl, and pyrimidinyl;
B is selected from

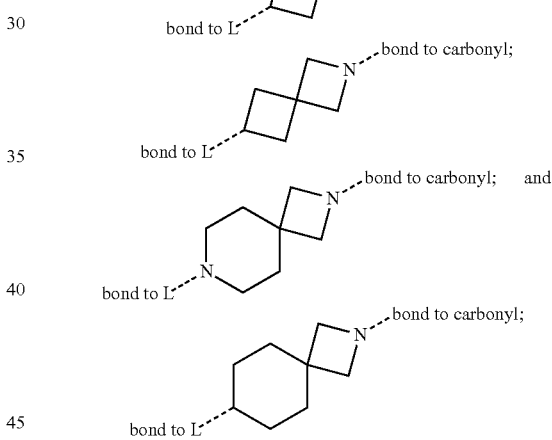

C is selected from

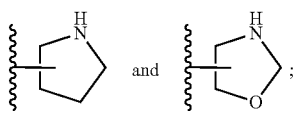

D is selected from phenyl, cyclopropyl, spiro[3.3]heptan-2-yl, cyclobutyl, cyclohexyl, 2-azaspiro[3.4]octan-2-yl, azetidinyl, and pyrrolidinyl;
$R^L$ is a group

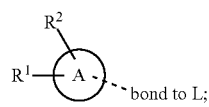

$R^1$ is selected from $CF_3$ and a group

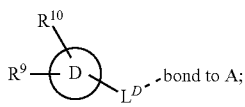

$R^2$ is selected from hydrogen and fluoro;
$R^3$, $R^5$, $R^6$, $R^7$ and $R^8$ are all hydrogen;
$R^4$ is selected from hydrogen and oxo;
$R^9$ is selected from hydrogen, fluoro, chloro, $CF_3$, 2,2,2-trifluoroethoxy, and methylsulfonyl;
$R^{10}$ is selected from hydrogen, chloro, and $CF_3$; and
$R^{11}$ is selected from methyl and cyclopropylmethyl.

In one embodiment, the present invention provides a compound of formula (I) as defined herein, or a pharmaceutically acceptable salt thereof, wherein:
X is selected from O, NH, N($C_{1-6}$-alkyl) and $(CH_2)_m$CHR$^6$;
Y is $(CH_2)_n$CHR$^7$;
m and n are each independently an integer selected from 0 and 1;
L is selected from a covalent bond, —CHR$^8$—, —CH$_2$O—, and —C≡C—;
A is selected from $C_6$-$C_{14}$-aryl and 5- to 14-membered heteroaryl;
B is a 4- to 8-membered heterocycle comprising 1-2 nitrogen atoms;
C is
  (i) a 5- to 6-membered heterocyclyle comprising 1-2 heteroatoms independently selected from N, S and O; or
  (ii) a 5- to 6-membered heteroaryl comprising 1-3 nitrogen atoms;
$R^1$ is selected from halogen, $SF_5$, $C_{1-6}$-alkyl, halo-$C_{1-6}$-alkyl, halo-$C_{1-6}$-alkoxy, $C_6$-$C_{14}$-aryl, $C_3$-$C_{10}$-cycloalkyl, 3- to 14-membered heterocyclyl, $C_6$-$C_{14}$-aryloxy and $C_6$-$C_{14}$-aryl-N($C_{1-6}$-alkyl)-, wherein said $C_6$-$C_{14}$-aryl, $C_3$-$C_{10}$-cycloalkyl, 3- to 14-membered heterocyclyl and $C_6$-$C_{14}$-aryloxy are substituted with 1-2 substituents selected from halogen, halo-$C_{1-6}$-alkyl and halo-$C_{1-6}$-alkoxy;
$R^2$ is selected from hydrogen and halogen;
$R^3$, $R^7$ and $R^8$ are all hydrogen;
$R^4$ is selected from hydrogen and oxo;
$R^5$ is selected from hydrogen and $C_{1-6}$-alkyl; and
$R^6$ is selected from hydrogen, hydroxy and $C_{1-6}$-alkyl.

In a preferred embodiment, the present invention provides a compound of formula (I) as defined herein, or a pharmaceutically acceptable salt thereof, wherein:
X is selected from N($C_{1-6}$-alkyl) and $(CH_2)_m$CHR$^6$;
Y is $(CH_2)_n$CHR$^7$;
m is 0;
n is an integer selected from 0 and 1;
L is selected from a covalent bond and —CH$_2$O—;
A is $C_6$-$C_{14}$-aryl;
B is azetidinyl;
C is
  (i) a 5-membered heterocyclyle comprising 1-2 heteroatoms independently selected from N and O; or
  (ii) a 5-membered heteroaryl comprising 3 nitrogen atoms;
$R^1$ is selected from halo-$C_{1-6}$-alkyl, $C_6$-$C_{14}$-aryl, $C_3$-$C_{10}$-cycloalkyl and $C_6$-$C_{14}$-aryl-N($C_{1-6}$-alkyl)-, wherein said $C_6$-$C_{14}$-aryl and $C_3$-$C_{10}$-cycloalkyl are substituted with 1-2 substituents selected from halogen and halo-$C_{1-6}$-alkyl;

$R^2$ is selected from hydrogen and halogen;
$R^3$, $R^5$, $R^6$, $R^7$ and $R^8$ are all hydrogen; and
$R^4$ is selected from hydrogen and oxo.

In a particularly preferred embodiment, the present invention provides a compound of formula (I) as defined herein, or a pharmaceutically acceptable salt thereof, wherein:
X is selected from N(methyl) and $(CH_2)_m$CHR$^6$;
Y is $(CH_2)_n$CHR$^7$;
m is 0;
n is an integer selected from 0 and 1;
L is selected from a covalent bond and —CH$_2$O—;
A is phenyl;
B is azetidinyl;
C is selected from pyrrolidinyl, oxazolidinyl and triazolyl;
$R^1$ is selected from $CF_3$, phenyl, cyclopropyl and phenyl-N(methyl)-, wherein said phenyl and cyclopropyl are substituted with 1-2 substituents selected from fluoro and $CF_3$;
$R^2$ is selected from hydrogen and fluoro;
$R^3$, $R^5$, $R^6$, $R^7$ and $R^8$ are all hydrogen; and
$R^4$ is selected from hydrogen and oxo.

In one embodiment, the present invention provides a compound of formula (I) as defined herein, or a pharmaceutically acceptable salt thereof, selected from:
(−)-5-[3-[3-[[2-fluoro-4-(trifluoromethyl)phenyl]methoxy]azetidin-1-yl]-3-oxo-propyl]pyrrolidin-2-one;
(+)-5-[3-[3-[[2-fluoro-4-(trifluoromethyl)phenyl]methoxy]azetidin-1-yl]-3-oxo-propyl]pyrrolidin-2-one;
(−)-[3-[3-(4-tert-Butylphenyl)azetidin-1-yl]-3-oxo-propyl]pyrrolidin-2-one;
(+)-5-[3-[3-(4-tert-Butylphenyl)azetidin-1-yl]-3-oxo-propyl]pyrrolidin-2-one;
(−)-5-[3-Oxo-3-[3-[4-[1-(trifluoromethyl)cyclopropyl]phenyl]azetidin-1-yl]propyl]pyrrolidin-2-one;
(+)-5-[3-Oxo-3-[3-[4-[1-(trifluoromethyl)cyclopropyl]phenyl]azetidin-1-yl]propyl]pyrrolidin-2-one;
(−)- or (+)-5-[3-Oxo-3-[3-[4-(2,2,2-trifluoroethyl)phenyl]azetidin-1-yl]propyl]pyrrolidin-2-one;
(+)- or (−)-5-[3-Oxo-3-[3-[4-(2,2,2-trifluoroethyl)phenyl]azetidin-1-yl]propyl]pyrrolidin-2-one;
(−)-5-[3-[3-[4-(2,4-Difluorophenyl)phenyl]azetidin-1-yl]-3-oxo-propyl]pyrrolidin-2-one;
(+)-5-[3-[3-[4-(2,4-Difluorophenyl)phenyl]azetidin-1-yl]-3-oxo-propyl]pyrrolidin-2-one;
(−)-5-[3-Oxo-3-[rac-(3aS,6aS)-2-[[2-fluoro-4-(trifluoromethyl)phenyl]methyl]-1,3,3a,4,6,6a-hexahydropyrrolo[3,4-c]pyrrol-5-yl]propyl]pyrrolidin-2-one;
(+)-5-[3-Oxo-3-[rac-(3aS,6aS)-2-[[2-fluoro-4-(trifluoromethyl)phenyl]methyl]-1,3,3a,4,6,6a-hexahydropyrrolo[3,4-c]pyrrol-5-yl]propyl]pyrrolidin-2-one;
(−)- or (+)-5-[3-[3-[[2-Fluoro-4-(trifluoromethyl)phenyl]methoxy]azetidin-1-yl]-3-oxo-propyl]-5-methyl-pyrrolidin-2-one;
(+)- or (−)-5-[3-[3-[[2-Fluoro-4-(trifluoromethyl)phenyl]methoxy]azetidin-1-yl]-3-oxo-propyl]-5-methyl-pyrrolidin-2-one;
(−)- or (+)-5-Methyl-5-[3-oxo-3-[3-[4-[1-(trifluoromethyl)cyclopropyl]phenyl]azetidin-1-yl]propyl]pyrrolidin-2-one;
(+)- or (−)-5-Methyl-5-[3-oxo-3-[3-[4-[1-(trifluoromethyl)cyclopropyl]phenyl]azetidin-1-yl]propyl]pyrrolidin-2-one;
(−)- or (+)-5-[3-[3-[6-(3-Chlorophenoxy)-3-pyridyl]azetidin-1-yl]-3-oxo-propyl]-5-methyl-pyrrolidin-2-one;
(+)- or (−)-5-[3-[3-[6-(3-Chlorophenoxy)-3-pyridyl]azetidin-1-yl]-3-oxo-propyl]-5-methyl-pyrrolidin-2-one;

(4S)-4-[3-[3-[[2-Fluoro-4-(trifluoromethyl)phenyl]
  methoxy]azetidin-1-yl]-3-oxo-propyl]oxazolidin-2-one;
(4R)-4-[3-[3-[[2-Fluoro-4-(trifluoromethyl)phenyl]
  methoxy]azetidin-1-yl]-3-oxo-propyl]oxazolidin-2-one;
(4S)-4-[3-Oxo-3-[3-[4-[1-(trifluoromethyl)cyclopropyl]
  phenyl]azetidin-1-yl]propyl]oxazolidin-2-one;
(4R)-4-[3-Oxo-3-[3-[4-[1-(trifluoromethyl)cyclopropyl]
  phenyl]azetidin-1-yl]propyl]oxazolidin-2-one;
(4S)-4-[3-[3-[4-(2,4-Difluorophenyl)phenyl]azetidin-1-yl]-
  3-oxo-propyl]oxazolidin-2-one;
(4R)-4-[3-[3-[4-(2,4-Difluorophenyl)phenyl]azetidin-1-yl]-
  3-oxo-propyl]oxazolidin-2-one;
(4R)-4-[3-Oxo-3-[3-[4-(2,2,2-trifluoro-1,1-dimethyl-
  ethoxy)phenyl]azetidin-1-yl]propyl]oxazolidin-2-one;
(4R)-4-[3-[3-[[2-Fluoro-4-(pentafluoro-λ$^6$-sulfanyl)phenyl]
  methoxy]azetidin-1-yl]-3-oxo-propyl]oxazolidin-2-one;
(4R)-4-[3-[6-[(2,4-Difluorophenyl)methyl]-2-azaspiro[3.3]
  heptan-2-yl]-3-oxo-propyl]oxazolidin-2-one;
(4R)-4-[3-[3-[6-(2-Chlorophenoxy)-3-pyridyl]azetidin-1-
  yl]-3-oxo-propyl]oxazolidin-2-one;
(4R)-4-[3-[6-(2-Chloro-4-fluoro-phenoxy)-2-azaspiro[3.3]
  heptan-2-yl]-3-oxo-propyl]oxazolidin-2-one;
(4R)-4-[3-[3-[4-(4-Fluorophenoxy)phenyl]azetidin-1-yl]-3-
  oxo-propyl]oxazolidin-2-one;
(4R)-4-[3-Oxo-3-[3-[6-[4-(trifluoromethoxy)phenoxy]-3-
  pyridyl]azetidin-1-yl]propyl]oxazolidin-2-one;
(4R)-4-[3-Oxo-3-[6-[6-(trifluoromethyl)pyrazin-2-yl]oxy-
  2-azaspiro[3.3]heptan-2-yl]propyl]oxazolidin-2-one;
(4R)-4-[3-[3-[2-(3-Chlorophenyl)ethynyl]azetidin-1-yl]-3-
  oxo-propyl]oxazolidin-2-one;
(4R)-4-[3-Oxo-3-[3-[6-[3-(trifluoromethyl)pyrrolidin-1-yl]-
  3-pyridyl]azetidin-1-yl]propyl]oxazolidin-2-one;
(4R)-4-[3-[3-[[2-Fluoro-4-(trifluoromethyl)phenyl]
  methoxy]azetidin-1-yl]-2-methyl-3-oxo-propyl]oxazoli-
  din-2-one;
1-(3-((2-Fluoro-4-(trifluoromethyl)benzyl)oxy)azetidin-1-
  yl)-3-(1H-1,2,3-triazol-5-yl)propan-1-one;
3-(1H-1,2,3-Triazol-5-yl)-1-(3-(4-(1-(trifluoromethyl)cy-
  clopropyl)phenyl)azetidin-1-yl)propan-1-one;
3-(1H-1,2,3-Triazol-5-yl)-1-(3-(4-((1,1,1-trifluoro-2-meth-
  ylpropan-2-yl)oxy)phenyl)azetidin-1-yl)propan-1-one;
1-[3-[[2-Fluoro-4-(trifluoromethyl)phenyl]methoxy]azeti-
  din-1-yl]-4-(1H-triazol-5-yl)butan-1-one;
4-(1H-Triazol-5-yl)-1-[3-[4-[1-(trifluoromethyl)cyclopro-
  pyl]phenyl]azetidin-1-yl]butan-1-one;
4-(1H-Triazol-5-yl)-1-[3-[4-(2,2,2-trifluoro-1,1-dimethyl-
  ethoxy)phenyl]azetidin-1-yl]butan-1-one;
4-(1H-Triazol-5-yl)-1-[3-[6-[4-(trifluoromethoxy)phe-
  noxy]-3-pyridyl]azetidin-1-yl]butan-1-one;
4-(1H-Triazol-5-yl)-1-[6-[6-(trifluoromethyl)pyrazin-2-yl]
  oxy-2-azaspiro[3.3]heptan-2-yl]butan-1-one;
1-[3-[2-(3-Chlorophenyl)ethynyl]azetidin-1-yl]-4-(1H-tri-
  azol-5-yl)butan-1-one;
rac-4-(1H-Triazol-5-yl)-1-[3-[6-[3-(trifluoromethyl)pyrroli-
  din-1-yl]-3-pyridyl]azetidin-1-yl]butan-1-one;
4-(1H-Triazol-5-yl)-1-[3-[4-[3-(2,2,2-trifluoroethoxy)azeti-
  din-1-yl]phenyl]azetidin-1-yl]butan-1-one;
1-[3-[[2-Fluoro-4-(trifluoromethyl)phenyl]methoxy]azeti-
  din-1-yl]-3-(1H-pyrazol-5-yl)propan-1-one;
6-[3-[3-[[2-Fluoro-4-(trifluoromethyl)phenyl]methoxy]aze-
  tidin-1-yl]-3-oxo-propyl]-1H-pyridin-2-one;
6-[3-[3-[[2-Fluoro-4-(trifluoromethyl)phenyl]methoxy]aze-
  tidin-1-yl]-3-oxo-propyl]piperidin-2-one;
(−)-5-[3-[3-[[2-Fluoro-4-(trifluoromethyl)phenyl]methoxy]
  azetidin-1-yl]-3-oxo-propyl]morpholin-3-one;
(+)-5-[3-[3-[[2-Fluoro-4-(trifluoromethyl)phenyl]methoxy]
  azetidin-1-yl]-3-oxo-propyl]morpholin-3-one;
[(2S)-5-Oxopyrrolidin-2-yl]methyl 3-[[2-fluoro-4-(trifluo-
  romethyl)phenyl]methoxy]azetidine-1-carboxylate;
[(2R)-5-Oxopyrrolidin-2-yl]methyl 3-[[2-fluoro-4-(trifluo-
  romethyl)phenyl]methoxy]azetidine-1-carboxylate;
[(4S)-2-Oxooxazolidin-4-yl]methyl 3-[[2-fluoro-4-(trifluo-
  romethyl)phenyl]methoxy]azetidine-1-carboxylate;
[(4R)-2-Oxooxazolidin-4-yl]methyl 3-[[2-fluoro-4-(trifluo-
  romethyl)phenyl]methoxy]azetidine-1-carboxylate;
[(4S)-2-Oxooxazolidin-4-yl]methyl 3-[4-[1-(trifluorom-
  ethyl)cyclopropyl]phenyl]azetidine-1-carboxylate;
[(4S)-2-Oxooxazolidin-4-yl]methyl 6-[(2,4-difluorophenyl)
  methyl]-2-azaspiro[3.3]heptane-2-carboxylate;
[(4S)-2-Oxooxazolidin-4-yl]methyl 3-[4-(4-fluorophenoxy)
  phenyl]azetidine-1-carboxylate;
[(4R)-2-Oxooxazolidin-4-yl]methyl 6-[(2,4-difluorophenyl)
  methyl]-2-azaspiro[3.3]heptane-2-carboxylate;
[(4S)-2-Oxooxazolidin-4-yl]methyl 3-[6-(2-chlorophe-
  noxy)-3-pyridyl]azetidine-1-carboxylate;
[(4S)-2-Oxooxazolidin-4-yl]methyl 3-[2-[2-(difluorom-
  ethyl)phenyl]ethynyl]azetidine-1-carboxylate;
[(4S)-2-Oxooxazolidin-4-yl]methyl 3-[6-[3-(trifluorom-
  ethyl)pyrrolidin-1-yl]-3-pyridyl]azetidine-1-carboxylate;
2-(1H-Triazol-5-yl)ethyl 3-[[2-fluoro-4-(trifluoromethyl)
  phenyl]methoxy]azetidine-1-carboxylate;
3-[[2-Fluoro-4-(trifluoromethyl)phenyl]methoxy]-N-[2-
  (1H-triazol-5-yl)ethyl]azetidine-1-carboxamide;
N-Methyl-N-[2-(1H-triazol-5-yl)ethyl]-3-[4-[1-(trifluorom-
  ethyl)cyclopropyl]phenyl]azetidine-1-carboxamide;
3-[[2-Fluoro-4-(trifluoromethyl)phenyl]methoxy]-N-
  methyl-N-[2-(1H-triazol-5-yl)ethyl]azetidine-1-carbox-
  amide;
3-[4-(2-Chloro-4-methylsulfonyl-phenyl)phenyl]-N-
  methyl-N-[2-(1H-triazol-5-yl)ethyl]azetidine-1-carbox-
  amide;
2-Methyl-4-(1H-triazol-5-yl)-1-[3-[4-[1-(trifluoromethyl)
  cyclopropyl]phenyl]azetidin-1-yl]butan-1-one;
3-Hydroxy-4-(1H-triazol-5-yl)-1-[3-[4-[1-(trifluoromethyl)
  cyclopropyl]phenyl]azetidin-1-yl]butan-1-one;
2-Fluoro-4-(1H-triazol-5-yl)-1-[3-[4-[1-(trifluoromethyl)
  cyclopropyl]phenyl]azetidin-1-yl]butan-1-one;
(4R)-4-[3-[3-[4-(N-Methylanilino)phenyl]azetidin-1-yl]-3-
  oxo-propyl]oxazolidin-2-one;
(4R)-4-[3-[3-(5-tert-Butyl-2-pyridyl)azetidin-1-yl]-3-oxo-
  propyl]oxazolidin-2-one;
(4R)-4-[3-[3-[4-(2-chloro-4-methylsulfonyl-phenyl)phenyl]
  azetidin-1-yl]-3-oxo-propyl]oxazolidin-2-one;
(4R)-4-[3-[3-[4-(Benzenesulfonyl)phenyl]azetidin-1-yl]-3-
  oxo-propyl]oxazolidin-2-one;
2-[4-[1-[3-[(4R)-2-Oxooxazolidin-4-yl]propanoyl]azetidin-
  3-yl]phenyl]sulfonylacetonitrile;
(4R)-4-[3-Oxo-3-[3-[4-(trifluoromethylsulfonyl)phenyl]
  azetidin-1-yl]propyl]oxazolidin-2-one;
(4R)-4-[3-[3-(4-Cyclohexylsulfonylphenyl)azetidin-1-yl]-
  3-oxo-propyl]oxazolidin-2-one;
1-[5-[1-[3-[(4R)-2-Oxooxazolidin-4-yl]propanoyl]azetidin-
  3-yl]-2-pyridyl]cyclobutanecarbonitrile;
(4R)-4-[3-[3-[4-[(2-Methyl-3-pyridyl)oxy]phenyl]azetidin-
  1-yl]-3-oxo-propyl]oxazolidin-2-one;
(4R)-4-[3-[3-[4-(4-Cyclopropylpyrinidin-2-yl)oxyphenyl]
  azetidin-1-yl]-3-oxo-propyl]oxazolidin-2-one;
(4R)-4-[3-[3-[4-[3-(2,2-Dimethylpropyl)triazol-4-yl]phe-
  nyl]azetidin-1-yl]-3-oxo-propyl]oxazolidin-2-one;
(4R)-4-[3-[3-[4-(4-Chloro-2-methylsulfonyl-phenyl)phe-
  nyl]azetidin-1-yl]-3-oxo-propyl]oxazolidin-2-one;
(+)- or (−)-(4R)-4-[3-[4-[(4-Methylsulfonylphenyl)-phenyl-
  methyl]-1-piperidyl]-3-oxo-propyl]oxazolidin-2-one;

(−)- or (+)-(4R)-4-[3-[4-[(4-Methylsulfonylphenyl)-phenyl-methyl]-1-piperidyl]-3-oxo-propyl]oxazolidin-2-one;
5-Chloro-2-[[5-[1-[3-[(4R)-2-oxooxazolidin-4-yl]propanoyl]azetidin-3-yl]-2-pyridyl]oxy]benzamide;
(−)- or (+)-[(4S)-2-Oxooxazolidin-4-yl]methyl 3-[6-[3-(trifluoromethyl)pyrrolidin-1-yl]-3-pyridyl]azetidine-1-carboxylate;
(+)- or (−)-[(4S)-2-Oxooxazolidin-4-yl]methyl 3-[6-[3-(trifluoromethyl)pyrrolidin-1-yl]-3-pyridyl]azetidine-1-carboxylate;
(5S)-5-[3-[3-[[2-Fluoro-4-(trifluoromethyl)phenyl]methoxy]azetidin-1-yl]-3-oxo-propyl]thiomorpholin-3-one;
(4R)-4-[3-[3-[4-[N-(Cyclopropylmethyl)anilino]phenyl]azetidin-1-yl]-3-oxo-propyl]oxazolidin-2-one;
(4R)-4-[3-Oxo-3-[3-[4-(N-phenylanilino)phenyl]azetidin-1-yl]propyl]oxazolidin-2-one;
(4R)-4-[3-[3-(6-tert-Butyl-3-pyridyl)azetidin-1-yl]-3-oxo-propyl]oxazolidin-2-one;
(4R)-4-[3-[3-[6-[(5-Methoxy-2-pyridyl)-methyl-amino]-3-pyridyl]azetidin-1-yl]-3-oxo-propyl]oxazolidin-2-one;
(4R)-4-[3-[3-[6-(N-Methylanilino)-3-pyridyl]azetidin-1-yl]-3-oxo-propyl]oxazolidin-2-one;
(4R)-4-[3-[3-[6-(4-Isopropyl-N-methyl-anilino)-3-pyridyl]azetidin-1-yl]-3-oxo-propyl]oxazolidin-2-one;
(4R)-4-[3-[3-[6-[N-(Cyclopropylmethyl)anilino]-3-pyridyl]azetidin-1-yl]-3-oxo-propyl]oxazolidin-2-one;
(4R)-4-[3-[3-[4-[2-Methoxyethyl(3-pyridyl)amino]phenyl]azetidin-1-yl]-3-oxo-propyl]oxazolidin-2-one;
(4R)-4-[3-[2-[4-Fluoro-2-(trifluoromethyl)phenyl]sulfonyl-2,6-diazaspiro[3.3]heptan-6-yl]-3-oxo-propyl]oxazolidin-2-one;
(4R)-4-[3-[2-(2,2-Dimethylpropylsulfonyl)-2,6-diazaspiro[3.3]heptan-6-yl]-3-oxo-propyl]oxazolidin-2-one;
(4R)-4-[3-Oxo-3-[3-[4-[3-(2,2,2-trifluoroethoxy)azetidin-1-yl]phenyl]azetidin-1-yl]propyl]oxazolidin-2-one;
(4R)-4-[3-Oxo-3-[3-[4-[3-(trifluoromethyl)azetidin-1-yl]phenyl]azetidin-1-yl]propyl]oxazolidin-2-one;
(4R)-4-[3-Oxo-3-[3-[2-[1-(trifluoromethyl)cyclopropyl]pyrimidin-5-yl]azetidin-1-yl]propyl]oxazolidin-2-one;
(4R)-4-[3-Oxo-3-[3-[6-[1-(trifluoromethyl)cyclopropyl]-3-pyridyl]azetidin-1-yl]propyl]oxazolidin-2-one;
(4R)-4-[3-Oxo-3-[3-[5-[3-(trifluoromethyl)pyrrolidin-1-yl]-2-pyridyl]azetidin-1-yl]propyl]oxazolidin-2-one;
(4R)-4-[3-[3-[4-[3-(Methylsulfonylmethyl)azetidin-1-yl]phenyl]azetidin-1-yl]-3-oxo-propyl]oxazolidin-2-one;
(4R)-4-[3-Oxo-3-[3-[5-[3-(trifluoromethyl)pyrrolidin-1-yl]pyrazin-2-yl]azetidin-1-yl]propyl]oxazolidin-2-one;
(4R)-4-[3-Oxo-3-[3-[5-[3-(trifluoromethyl)pyrrolidin-1-yl]pyrimidin-2-yl]azetidin-1-yl]propyl]oxazolidin-2-one;
(4R)-4-[3-Oxo-3-[3-[2-[3-(trifluoromethyl)pyrrolidin-1-yl]pyrimidin-5-yl]azetidin-1-yl]propyl]oxazolidin-2-one;
(4R)-4-[3-[3-[5-(2-Chloro-4-methylsulfonyl-phenyl)-2-pyridyl]azetidin-1-yl]-3-oxo-propyl]oxazolidin-2-one;
(4R)-4-[3-Oxo-3-[3-[3-[1-(trifluoromethyl)cyclopropyl]phenyl]azetidin-1-yl]propyl]oxazolidin-2-one;
(4R)-4-[3-[3-[5-(2-Chloro-4-methylsulfonyl-phenyl)pyrazin-2-yl]azetidin-1-yl]-3-oxo-propyl]oxazolidin-2-one;
(4R)-4-[3-[3-(6-tert-Butylsulfonyl-3-pyridyl)azetidin-1-yl]-3-oxo-propyl]oxazolidin-2-one;
(4R)-4-[3-[3-[5-(4-Chloro-2-fluoro-phenyl)pyrimidin-2-yl]azetidin-1-yl]-3-oxo-propyl]oxazolidin-2-one;
(4R)-4-[3-[3-[5-(4-Chloro-2-fluoro-phenyl)-2-pyridyl]azetidin-1-yl]-3-oxo-propyl]oxazolidin-2-one;
(4R)-4-[3-[3-[5-(2,4-Dichlorophenyl)-2-pyridyl]azetidin-1-yl]-3-oxo-propyl]oxazolidin-2-one;

(4R)-4-[3-[3-[4-(5-Chloro-3-methylsulfonyl-2-pyridyl)phenyl]azetidin-1-yl]-3-oxo-propyl]oxazolidin-2-one;
(4R)-4-[3-[3-[6-(2-Chloro-4-methylsulfonyl-phenyl)-3-pyridyl]azetidin-1-yl]-3-oxo-propyl]oxazolidin-2-one;
(4R)-4-[3-[3-[6-(4-Chloro-2-methylsulfonyl-phenyl)-3-pyridyl]azetidin-1-yl]-3-oxo-propyl]oxazolidin-2-one;
(4R)-4-[3-[3-[4-(6-Chloro-4-methylsulfonyl-3-pyridyl)phenyl]azetidin-1-yl]-3-oxo-propyl]oxazolidin-2-one;
(4R)-4-[3-Oxo-3-[3-[4-[5-(trifluoromethyl)pyrazin-2-yl]phenyl]azetidin-1-yl]propyl]oxazolidin-2-one;
(4R)-4-[3-[3-[4-(4-Chloro-2-fluoro-phenyl)-3-methylsulfonyl-phenyl]azetidin-1-yl]-3-oxo-propyl]oxazolidin-2-one;
(4R)-4-[3-[3-[5-(4-Chloro-2-methylsulfonyl-phenyl)-2-pyridyl]azetidin-1-yl]-3-oxo-propyl]oxazolidin-2-one;
(4R)-4-[3-[3-[5-(2-Chloro-4-methylsulfonyl-phenyl)pyrimidin-2-yl]azetidin-1-yl]-3-oxo-propyl]oxazolidin-2-one;
(4R)-4-[3-[3-[2-(2-Chloro-4-methylsulfonyl-phenyl)pyrimidin-5-yl]azetidin-1-yl]-3-oxo-propyl]oxazolidin-2-one;
(4R)-4-[3-[3-[4-[2-Methylsulfonyl-5-(trifluoromethyl)-3-pyridyl]phenyl]azetidin-1-yl]-3-oxo-propyl]oxazolidin-2-one;
(4R)-4-[3-Oxo-3-[6-[[6-(trifluoromethyl)-3-pyridyl]methyl]-2-azaspiro[3.3]heptan-2-yl]propyl]oxazolidin-2-one;
(4R)-4-[3-[7-[[2-Fluoro-4-(trifluoromethyl)phenyl]methyl]-2,7-diazaspiro[3.5]nonan-2-yl]-3-oxo-propyl]oxazolidin-2-one;
(4R)-4-[3-Oxo-3-[3-[4-[4-(trifluoromethyl)pyrimidin-2-yl]oxyphenyl]azetidin-1-yl]propyl]oxazolidin-2-one;
(4R)-4-[3-[3-[4-[4-Methylsulfonyl-2-(trifluoromethyl)phenyl]phenyl]azetidin-1-yl]-3-oxo-propyl]oxazolidin-2-one;
(4R)-4-[3-[3-[3-Fluoro-4-[3-(trifluoromethyl)pyrrolidin-1-yl]phenyl]azetidin-1-yl]-3-oxo-propyl]oxazolidin-2-one;
(4R)-4-[3-[3-[4-(1,1-Dioxothiolan-3-yl)phenyl]azetidin-1-yl]-3-oxo-propyl]oxazolidin-2-one;
(4R)-4-[3-[3-[4-(2-Azaspiro[3.4]octan-2-yl)phenyl]azetidin-1-yl]-3-oxo-propyl]oxazolidin-2-one;
(4R)-4-[3-[3-[4-(6,6-Difluoro-2-azaspiro[3.3]heptan-2-yl)phenyl]azetidin-1-yl]-3-oxo-propyl]oxazolidin-2-one;
(4R)-4-[3-Oxo-3-[3-[4-[3-(trifluoromethyl)cyclobutyl]phenyl]azetidin-1-yl]propyl]oxazolidin-2-one;
(4R)-4-[3-[3-[3-Fluoro-4-[3-(trifluoromethyl)azetidin-1-yl]phenyl]azetidin-1-yl]-3-oxo-propyl]oxazolidin-2-one;
(4R)-4-[3-Oxo-3-[3-[4-[3-(trifluoromethyl)pyrrolidin-1-yl]phenyl]azetidin-1-yl]propyl]oxazolidin-2-one;
(4R)-4-[3-Oxo-3-[7-[6-(trifluoromethyl)pyridazin-3-yl]oxy-2-azaspiro[3.5]nonan-2-yl]propyl]oxazolidin-2-one;
(4R)-4-[3-[7-(4-Fluoro-2-methylsulfonyl-phenoxy)-2-azaspiro[3.5]nonan-2-yl]-3-oxo-propyl]oxazolidin-2-one;
N-[2-[3-[(4R)-2-Oxooxazolidin-4-yl]propanoyl]-2-azaspiro[3.5]nonan-7-yl]-3-(trifluoromethoxy)benzenesulfonamide;
(4R)-4-[3-[3-[5-(6,6-Difluoro-2-azaspiro[3.3]heptan-2-yl)pyrazin-2-yl]azetidin-1-yl]-3-oxo-propyl]oxazolidin-2-one;
(4R)-4-[3-[3-[5-(2-Azaspiro[3.4]octan-2-yl)pyrazin-2-yl]azetidin-1-yl]-3-oxo-propyl]oxazolidin-2-one;
(4R)-4-[3-[3-[6-(6,6-Difluoro-2-azaspiro[3.3]heptan-2-yl)-3-pyridyl]azetidin-1-yl]-3-oxo-propyl]oxazolidin-2-one;
(4R)-4-[3-[3-[6-(2-Azaspiro[3.4]octan-2-yl)-3-pyridyl]azetidin-1-yl]-3-oxo-propyl]oxazolidin-2-one;

(4R)-4-[3-[7-[2-Fluoro-4-(trifluoromethyl)phenyl]sulfonyl-2,7-diazaspiro[3.5]nonan-2-yl]-3-oxo-propyl]oxazolidin-2-one;

(4R)-4-[3-[3-[6-[3-Hydroxy-3-(trifluoromethyl)azetidin-1-yl]-3-pyridyl]azetidin-1-yl]-3-oxo-propyl]oxazolidin-2-one;

(4R)-4-[3-[3-[4-(3,5-Dimethylpyrazol-1-yl)phenyl]azetidin-1-yl]-3-oxo-propyl]oxazolidin-2-one;

(4R)-4-[3-[3-[6-[3-Hydroxy-3-(trifluoromethyl)pyrrolidin-1-yl]-3-pyridyl]azetidin-1-yl]-3-oxo-propyl]oxazolidin-2-one;

(4R)-4-[3-Oxo-3-[2-[4-(trifluoromethyl)phenyl]sulfonyl-2,6-diazaspiro[3.3]heptan-6-yl]propyl]oxazolidin-2-one;

(4R)-4-[3-Oxo-3-[2-[2-(trifluoromethoxy)phenyl]sulfonyl-2,6-diazaspiro[3.3]heptan-6-yl]propyl]oxazolidin-2-one;

(4R)-4-[3-Oxo-3-[2-[3-(trifluoromethoxy)phenyl]sulfonyl-2,6-diazaspiro[3.3]heptan-6-yl]propyl]oxazolidin-2-one;

(4R)-4-[3-Oxo-3-[2-[4-(trifluoromethoxy)phenyl]sulfonyl-2,6-diazaspiro[3.3]heptan-6-yl]propyl]oxazolidin-2-one;

2-[[2-[3-[(4R)-2-Oxooxazolidin-4-yl]propanoyl]-2,6-diazaspiro[3.3]heptan-6-yl]methyl]benzenesulfonamide;

N-[2-[3-[(4R)-2-Oxooxazolidin-4-yl]propanoyl]-2-azaspiro[3.3]heptan-6-yl]-3-(trifluoromethyl)benzenesulfonamide;

(4R)-4-[3-Oxo-3-[3-[[4-(trifluoromethyl)phenyl]methylamino]azetidin-1-yl]propyl]oxazolidin-2-one;

(4R)-4-[3-[3-[[2-Fluoro-5-(trifluoromethyl)phenyl]methylamino]azetidin-1-yl]-3-oxo-propyl]oxazolidin-2-one;

(4R)-4-[3-[6-[(4-Fluoro-2-methylsulfonyl-phenyl)methyl]-2-azaspiro[3.3]heptan-2-yl]-3-oxo-propyl]oxazolidin-2-one;

N-[[1-[3-[(4R)-2-Oxooxazolidin-4-yl]propanoyl]-4-piperidyl]methyl]-4-(trifluoromethyl)benzenesulfonamide;

N-[[1-[3-[(4R)-2-Oxooxazolidin-4-yl]propanoyl]-4-piperidyl]methyl]-4-(trifluoromethoxy)benzenesulfonamide;

(4R)-4-[3-[3-[6-(3-Hydroxy-3-methyl-azetidin-1-yl)-3-pyridyl]azetidin-1-yl]-3-oxo-propyl]oxazolidin-2-one;

(4R)-4-[3-Oxo-3-[3-[6-(3-(trifluoromethyl)azetidin-1-yl]-3-pyridyl]azetidin-1-yl]propyl]oxazolidin-2-one;

(4R)-4-[3-[3-[[2-Fluoro-4-(trifluoromethyl)phenyl]methyl-methyl-amino]azetidin-1-yl]-3-oxo-propyl]oxazolidin-2-one;

(4R)-4-[3-Oxo-3-[3-(6-spiro[3.3]heptan-2-yl-3-pyridyl)azetidin-1-yl]propyl]oxazolidin-2-one;

(4R)-4-[3-Oxo-3-[3-(5-spiro[3.3]heptan-2-ylpyrazin-2-yl)azetidin-1-yl]propyl]oxazolidin-2-one;

(4R)-4-[3-[3-[3-[5-(2,2-Dimethylpropyl)-1,3,4-oxadiazol-2-yl]-1-bicyclo[1.1.1]pentanyl]azetidin-1-yl]-3-oxo-propyl]oxazolidin-2-one;

(4R)-4-[3-Oxo-3-[3-[[4-(trifluoromethylsulfonyl)phenyl]methoxy]azetidin-1-yl]propyl]oxazolidin-2-one;

(4R)-4-[3-Oxo-3-[3-[5-[6-(trifluoromethyl)-3-pyridyl]-1,2,4-oxadiazol-3-yl]azetidin-1-yl]propyl]oxazolidin-2-one;

(4R)-4-[3-Oxo-3-[3-[5-[3-(trifluoromethyl)-1-bicyclo[1.1.1]pentanyl]-1,2,4-oxadiazol-3-yl]azetidin-1-yl]propyl]oxazolidin-2-one;

(4R)-4-[3-Oxo-3-[3-[[3-(trifluoromethylsulfonyl)phenyl]methoxy]azetidin-1-yl]propyl]oxazolidin-2-one;

Methyl 5-chloro-2-[[5-[1-[3-[(4R)-2-oxooxazolidin-4-yl]propanoyl]azetidin-3-yl]-2-pyridyl]oxy]benzoate;

(4R)-4-[3-Oxo-3-[3-[[3-(trifluoromethylsulfonyl)phenyl]methoxy]azetidin-1-yl]propyl]oxazolidin-2-one;

(4R)-4-[3-[3-[6-[3-(1-Hydroxy-1-methyl-ethyl)azetidin-1-yl]-3-pyridyl]azetidin-1-yl]-3-oxo-propyl]oxazolidin-2-one;

(4R)-4-[3-[3-[4-[1-(Hydroxymethyl)cyclopropyl]phenyl]azetidin-1-yl]-3-oxo-propyl]oxazolidin-2-one;

(4R)-4-[3-[3-[6-(5-Oxa-2-azaspiro[3.4]octan-2-yl)-3-pyridyl]azetidin-1-yl]-3-oxo-propyl]oxazolidin-2-one;

(4R)-4-[3-[3-[6-(2,2-Difluoro-5-azaspiro[2.4]heptan-5-yl)-3-pyridyl]azetidin-1-yl]-3-oxo-propyl]oxazolidin-2-one;

(4R)-4-[3-Oxo-3-[3-[4-[5-(trifluoromethyl)pyrazin-2-yl]oxyphenyl]azetidin-1-yl]propyl]oxazolidin-2-one;

(4R)-4-[3-Oxo-3-[3-[5-[[1-(trifluoromethyl)cyclopropyl]methylamino]-2-pyridyl]azetidin-1-yl]propyl]oxazolidin-2-one;

(4R)-4-[3-Oxo-3-[3-[5-[[1-(trifluoromethyl)cyclopropyl]methylamino]pyrazin-2-yl]azetidin-1-yl]propyl]oxazolidin-2-one;

(4R)-4-[3-[3-[4-(3-Cyclopropyl-1H-1,2,4-triazol-5-yl)phenyl]azetidin-1-yl]-3-oxo-propyl]oxazolidin-2-one;

(4R)-4-[3-Oxo-3-[3-[4-[3-[1-(trifluoromethyl)cyclopropyl]-1H-1,2,4-triazol-5-yl]phenyl]azetidin-1-yl]propyl]oxazolidin-2-one;

(4R)-4-[3-[6-[(3-Methylsulfonylphenyl)methyl]-2-azaspiro[3.3]heptan-2-yl]-3-oxo-propyl]oxazolidin-2-one;

(4R)-4-[3-[6-[(4-Methylsulfonylphenyl)methyl]-2-azaspiro[3.3]heptan-2-yl]-3-oxo-propyl]oxazolidin-2-one;

(4R)-4-[3-Oxo-3-[6-[[6-(trifluoromethyl)pyridazin-3-yl]methyl]-2-azaspiro[3.3]heptan-2-yl]propyl]oxazolidin-2-one;

(4R)-4-[3-Oxo-3-[6-[[2-(trifluoromethyl)pyrimidin-5-yl]methyl]-2-azaspiro[3.3]heptan-2-yl]propyl]oxazolidin-2-one;

(4R)-4-[3-Oxo-3-[6-[[5-(trifluoromethyl)pyrimidin-2-yl]methyl]-2-azaspiro[3.3]heptan-2-yl]propyl]oxazolidin-2-one;

(4R)-4-[3-[6-[(3-Fluoro-5-methylsulfonyl-phenyl)methyl]-2-azaspiro[3.3]heptan-2-yl]-3-oxo-propyl]oxazolidin-2-one;

(4R)-4-[3-[6-(3-Cyclopropyl-1,2,4-triazol-1-yl)-2-azaspiro[3.3]heptan-2-yl]-3-oxo-propyl]oxazolidin-2-one;

(4R)-4-[3-Oxo-3-[6-[[3-(trifluoromethylsulfonyl)phenyl]methyl]-2-azaspiro[3.3]heptan-2-yl]propyl]oxazolidin-2-one;

(4R)-4-[3-Oxo-3-[6-[[4-(trifluoromethylsulfonyl)phenyl]methyl]-2,6-diazaspiro[3.3]heptan-2-yl]propyl]oxazolidin-2-one;

(4R)-4-[3-Oxo-3-[7-[[6-(trifluoromethyl)-3-pyridyl]methyl]-2-azaspiro[3.5]nonan-2-yl]propyl]oxazolidin-2-one;

(4R)-4-[3-Oxo-3-[7-[[5-(trifluoromethyl)-2-pyridyl]methyl]-2-azaspiro[3.5]nonan-2-yl]propyl]oxazolidin-2-one;

(4R)-4-[3-Oxo-3-[7-[[5-(trifluoromethyl)pyrazin-2-yl]methyl]-2-azaspiro[3.5]nonan-2-yl]propyl]oxazolidin-2-one;

(4R)-4-[3-[7-[[6-(Difluoromethoxy)-3-pyridyl]methyl]-2-azaspiro[3.5]nonan-2-yl]-3-oxo-propyl]oxazolidin-2-one;

(4R)-4-[3-[7-[(4-Methylsulfonylphenyl)methyl]-2,7-diazaspiro[3.5]nonan-2-yl]-3-oxo-propyl]oxazolidin-2-one;

(4R)-4-[3-[7-[(3-Methylsulfonylphenyl)methyl]-2,7-diazaspiro[3.5]nonan-2-yl]-3-oxo-propyl]oxazolidin-2-one;

(4R)-4-[3-Oxo-3-[7-[[4-(trifluoromethylsulfonyl)phenyl]methyl]-2,7-diazaspiro[3.5]nonan-2-yl]propyl]oxazolidin-2-one;

(4R)-4-[3-Oxo-3-[7-[[3-(trifluoromethylsulfonyl)phenyl]methyl]-2,7-diazaspiro[3.5]nonan-2-yl]propyl]oxazolidin-2-one;

(4R)-4-[3-Oxo-3-[7-[[6-(trifluoromethyl)-3-pyridyl]methyl]-2,7-diazaspiro[3.5]nonan-2-yl]propyl]oxazolidin-2-one;

(4R)-4-[3-Oxo-3-[7-[[5-(trifluoromethyl)-2-pyridyl]
methyl]-2,7-diazaspiro[3.5]nonan-2-yl]propyl]oxazolidin-2-one;
(4R)-4-[3-Oxo-3-[6-[[6-(trifluoromethyl)-3-pyridyl]
methyl]-2-azaspiro[3.4]octan-2-yl]propyl]oxazolidin-2-one;
Methyl 5-chloro-2-[[5-[1-[3-[(4R)-2-oxooxazolidin-4-yl]
propanoyl]azetidin-3-yl]-2-pyridyl]oxy]benzoate;
cis-(4R)-4-[3-Oxo-3-[3-[6-[4-(trifluoromethyl)cyclohexyl]-3-pyridyl]azetidin-1-yl]propyl]oxazolidin-2-one;
trans-(4R)-4-[3-Oxo-3-[3-[6-[4-(trifluoromethyl)cyclohexyl]-3-pyridyl]azetidin-1-yl]propyl]oxazolidin-2-one;
cis-(4R)-4-[3-Oxo-3-[3-[6-[3-(trifluoromethyl)cyclobutyl]-3-pyridyl]azetidin-1-yl]propyl]oxazolidin-2-one;
trans-(4R)-4-[3-Oxo-3-[3-[6-[3-(trifluoromethyl)cyclobutyl]-3-pyridyl]azetidin-1-yl]propyl]oxazolidin-2-one;
(−)- or (+)-(4R)-4-[3-[3-[6-[3-Hydroxy-3-(trifluoromethyl)
pyrrolidin-1-yl]-3-pyridyl]azetidin-1-yl]-3-oxo-propyl]
oxazolidin-2-one;
(+)- or (−)-(4R)-4-[3-[3-[6-[3-Hydroxy-3-(trifluoromethyl)
pyrrolidin-1-yl]-3-pyridyl]azetidin-1-yl]-3-oxo-propyl]
oxazolidin-2-one;
(−)- or (+)-(4R)-4-[3-[3-[6-[3-Hydroxy-3-(trifluoromethyl)
pyrrolidin-1-yl]-3-pyridyl]azetidin-1-yl]-3-oxo-propyl]
oxazolidin-2-one;
(+)- or (−)-(4R)-4-[3-[3-[6-[3-Hydroxy-3-(trifluoromethyl)
pyrrolidin-1-yl]-3-pyridyl]azetidin-1-yl]-3-oxo-propyl]
oxazolidin-2-one;
(−)- or (+)-(4R)-4-[3-Oxo-3-[3-[2-[3-(trifluoromethyl)pyrrolidin-1-yl]pyrimidin-5-yl]azetidin-1-yl]propyl]oxazolidin-2-one;
(+)- or (−)-(4R)-4-[3-Oxo-3-[3-[2-[3-(trifluoromethyl)pyrrolidin-1-yl]pyrimidin-5-yl]azetidin-1-yl]propyl]oxazolidin-2-one;
(−)- or (+)-(4R)-4-[3-Oxo-3-[6-[[6-(trifluoromethyl)-3-pyridyl]methyl]-2-azaspiro[3.4]octan-2-yl]propyl]oxazolidin-2-one;
(+)- or (−)-(4R)-4-[3-Oxo-3-[6-[[6-(trifluoromethyl)-3-pyridyl]methyl]-2-azaspiro[3.4]octan-2-yl]propyl]oxazolidin-2-one;
3-[4-(4-Chloro-2-methylsulfonyl-phenyl)phenyl]-N-[(2-oxooxazolidin-4-yl)methyl]azetidine-1-carboxamide;
4-[3-Oxo-3-[6-[[6-(trifluoromethyl)-3-pyridyl]methyl]-2-azaspiro[3.3]heptan-2-yl]propyl]imidazolidin-2-one;
4-[3-Oxo-3-[3-[4-[1-(trifluoromethyl)cyclopropyl]phenyl]
azetidin-1-yl]propyl]imidazolidin-2-one;
4-[3-[3-[[2-Fluoro-4-(trifluoromethyl)phenyl]methoxy]azetidin-1-yl]-3-oxo-propyl]imidazolidin-2-one;
4-[3-[3-[4-(4-Chloro-2-methylsulfonyl-phenyl)phenyl]azetidin-1-yl]-3-oxo-propyl]imidazolidin-2-one;
(−)- or (+)-4-[3-[3-[4-(4-Chloro-2-methylsulfonyl-phenyl)
phenyl]azetidin-1-yl]-3-oxo-propyl]imidazolidin-2-one;
and
(+)- or (−)-4-[3-[3-[4-(4-Chloro-2-methylsulfonyl-phenyl)
phenyl]azetidin-1-yl]-3-oxo-propyl]imidazolidin-2-one.

In one embodiment, the present invention provides a compound of formula (I) as defined herein, or a pharmaceutically acceptable salt thereof, selected from:
(−)-5-[3-[3-[[2-fluoro-4-(trifluoromethyl)phenyl]methoxy]
azetidin-1-yl]-3-oxo-propyl]pyrrolidin-2-one;
(+)-5-[3-[3-[[2-fluoro-4-(trifluoromethyl)phenyl]methoxy]
azetidin-1-yl]-3-oxo-propyl]pyrrolidin-2-one;
(−)-[3-[3-(4-tert-Butylphenyl)azetidin-1-yl]-3-oxo-propyl]
pyrrolidin-2-one;
(+)-5-[3-[3-(4-tert-Butylphenyl)azetidin-1-yl]-3-oxo-propyl]pyrrolidin-2-one;
(−)-5-[3-Oxo-3-[3-[4-[1-(trifluoromethyl)cyclopropyl]phenyl]azetidin-1-yl]propyl]pyrrolidin-2-one;
(+)-5-[3-Oxo-3-[3-[4-[1-(trifluoromethyl)cyclopropyl]phenyl]azetidin-1-yl]propyl]pyrrolidin-2-one;
(−)- or (+)-5-[3-Oxo-3-[3-[4-(2,2,2-trifluoroethyl)phenyl]
azetidin-1-yl]propyl]pyrrolidin-2-one;
(+)- or (−)-5-[3-Oxo-3-[3-[4-(2,2,2-trifluoroethyl)phenyl]
azetidin-1-yl]propyl]pyrrolidin-2-one;
(−)-5-[3-[3-[4-(2,4-Difluorophenyl)phenyl]azetidin-1-yl]-3-oxo-propyl]pyrrolidin-2-one;
(+)-5-[3-[3-[4-(2,4-Difluorophenyl)phenyl]azetidin-1-yl]-3-oxo-propyl]pyrrolidin-2-one;
(−)-5-[3-Oxo-3-[rac-(3aS,6aS)-2-[[2-fluoro-4-(trifluoromethyl)phenyl]methyl]-1,3,3a,4,6,6a-hexahydropyrrolo[3,4-c]pyrrol-5-yl]propyl]pyrrolidin-2-one;
(+)-5-[3-Oxo-3-[rac-(3aS,6aS)-2-[[2-fluoro-4-(trifluoromethyl)phenyl]methyl]-1,3,3a,4,6,6a-hexahydropyrrolo[3,4-c]pyrrol-5-yl]propyl]pyrrolidin-2-one;
(−)- or (+)-5-[3-[3-[[2-Fluoro-4-(trifluoromethyl)phenyl]
methoxy]azetidin-1-yl]-3-oxo-propyl]-5-methyl-pyrrolidin-2-one;
(+)- or (−)-5-[3-[3-[[2-Fluoro-4-(trifluoromethyl)phenyl]
methoxy]azetidin-1-yl]-3-oxo-propyl]-5-methyl-pyrrolidin-2-one;
(−)- or (+)-5-Methyl-5-[3-oxo-3-[3-[4-[1-(trifluoromethyl)
cyclopropyl]phenyl]azetidin-1-yl]propyl]pyrrolidin-2-one;
(+)- or (−)-5-Methyl-5-[3-oxo-3-[3-[4-[1-(trifluoromethyl)
cyclopropyl]phenyl]azetidin-1-yl]propyl]pyrrolidin-2-one;
(R)-5-(3-(3-(6-(3-chlorophenoxy)pyridin-3-yl)azetidin-1-yl)-3-oxopropyl)-5-methylpyrrolidin-2-one;
(S)-5-(3-(3-(6-(3-chlorophenoxy)pyridin-3-yl)azetidin-1-yl)-3-oxopropyl)-5-methylpyrrolidin-2-one compound with methane;
(S)-4-(3-(3-((2-Fluoro-4-(trifluoromethyl)benzyl)oxy)azetidin-1-yl)-3-oxopropyl)oxazolidin-2-one;
(R)-4-(3-(3-((2-Fluoro-4-(trifluoromethyl)benzyl)oxy)azetidin-1-yl)-3-oxopropyl)oxazolidin-2-one;
(S)-4-(3-Oxo-3-(3-(4-(1-(trifluoromethyl)cyclopropyl)phenyl)azetidin-1-yl)propyl)oxazolidin-2-one;
(R)-4-(3-Oxo-3-(3-(4-(1-(trifluoromethyl)cyclopropyl)phenyl)azetidin-1-yl)propyl)oxazolidin-2-one;
(S)-4-(3-(3-(2',4'-Difluoro-[1,1'-biphenyl]-4-yl)azetidin-1-yl)-3-oxopropyl)oxazolidin-2-one;
(R)-4-(3-(3-(2',4'-Difluoro-[1,1'-biphenyl]-4-yl)azetidin-1-yl)-3-oxopropyl)oxazolidin-2-one;
(R)-4-(3-Oxo-3-(3-(4-((1,1,1-trifluoro-2-methylpropan-2-yl)oxy)phenyl)azetidin-1-yl)propyl)oxazolidin-2-one;
(R)-4-(3-(3-((2-Fluoro-4-(pentafluoro-l6-sulfaneyl)benzyl)
oxy)azetidin-1-yl)-3-oxopropyl)oxazolidin-2-one;
(R)-4-(3-(6-(2,4-difluorobenzyl)-2-azaspiro[3.3]heptan-2-yl)-3-oxopropyl)oxazolidin-2-one;
(4R)-4-[3-[3-[6-(2-Chlorophenoxy)-3-pyridyl]azetidin-1-yl]-3-oxo-propyl]oxazolidin-2-one;
(4R)-4-[3-[6-(2-Chloro-4-fluoro-phenoxy)-2-azaspiro[3.3]
heptan-2-yl]-3-oxo-propyl]oxazolidin-2-one;
(4R)-4-[3-[3-[4-(4-Fluorophenoxy)phenyl]azetidin-1-yl]-3-oxo-propyl]oxazolidin-2-one;
(4R)-4-[3-Oxo-3-[3-[6-[4-(trifluoromethoxy)phenoxy]-3-pyridyl]azetidin-1-yl]propyl]oxazolidin-2-one;
(4R)-4-[3-Oxo-3-[6-[6-(trifluoromethyl)pyrazin-2-yl]oxy-2-azaspiro[3.3]heptan-2-yl]propyl]oxazolidin-2-one;
(4R)-4-[3-[3-[2-(3-Chlorophenyl)ethynyl]azetidin-1-yl]-3-oxo-propyl]oxazolidin-2-one;
(4R)-4-[3-Oxo-3-[3-[6-[3-(trifluoromethyl)pyrrolidin-1-yl]-3-pyridyl]azetidin-1-yl]propyl]oxazolidin-2-one;

(4R)-4-[3-[3-[[2-Fluoro-4-(trifluoromethyl)phenyl]
methoxy]azetidin-1-yl]-2-methyl-3-oxo-propyl]oxazoli-
din-2-one;
1-(3-((2-Fluoro-4-(trifluoromethyl)benzyl)oxy)azetidin-1-
yl)-3-(1H-1,2,3-triazol-5-yl)propan-1-one;
3-(1H-1,2,3-Triazol-5-yl)-1-(3-(4-(1-(trifluoromethyl)cy-
clopropyl)phenyl)azetidin-1-yl)propan-1-one;
3-(1H-1,2,3-Triazol-5-yl)-1-(3-(4-((1,1,1-trifluoro-2-meth-
ylpropan-2-yl)oxy)phenyl)azetidin-1-yl)propan-1-one;
1-[3-[[2-Fluoro-4-(trifluoromethyl)phenyl]methoxy]azeti-
din-1-yl]-4-(1H-triazol-5-yl)butan-1-one;
4-(1H-Triazol-5-yl)-1-[3-[4-[1-(trifluoromethyl)cyclopro-
pyl]phenyl]azetidin-1-yl]butan-1-one;
4-(1H-Triazol-5-yl)-1-[3-[4-(2,2,2-trifluoro-1,1-dimethyl-
ethoxy)phenyl]azetidin-1-yl]butan-1-one;
4-(1H-Triazol-5-yl)-1-[3-[6-[4-(trifluoromethoxy)phe-
noxy]-3-pyridyl]azetidin-1-yl]butan-1-one;
4-(1H-Triazol-5-yl)-1-[6-[6-(trifluoromethyl)pyrazin-2-yl]
oxy-2-azaspiro[3.3]heptan-2-yl]butan-1-one;
1-[3-[2-(3-Chlorophenyl)ethynyl]azetidin-1-yl]-4-(1H-tri-
azol-5-yl)butan-1-one;
rac-4-(1H-Triazol-5-yl)-1-[3-[6-[3-(trifluoromethyl)pyrroli-
din-1-yl]-3-pyridyl]azetidin-1-yl]butan-1-one;
4-(1H-Triazol-5-yl)-1-[3-[4-[3-(2,2,2-trifluoroethoxy)azeti-
din-1-yl]phenyl]azetidin-1-yl]butan-1-one;
1-[3-[[2-Fluoro-4-(trifluoromethyl)phenyl]methoxy]azeti-
din-1-yl]-3-(1H-pyrazol-5-yl)propan-1-one;
6-[3-[3-[[2-Fluoro-4-(trifluoromethyl)phenyl]methoxy]aze-
tidin-1-yl]-3-oxo-propyl]-1H-pyridin-2-one;
6-[3-[3-[[2-Fluoro-4-(trifluoromethyl)phenyl]methoxy]aze-
tidin-1-yl]-3-oxo-propyl]piperidin-2-one;
(−)-5-[3-[3-[[2-Fluoro-4-(trifluoromethyl)phenyl]methoxy]
azetidin-1-yl]-3-oxo-propyl]morpholin-3-one;
(+)-5-[3-[3-[[2-Fluoro-4-(trifluoromethyl)phenyl]methoxy]
azetidin-1-yl]-3-oxo-propyl]morpholin-3-one;
(S)-(5-oxopyrrolidin-2-yl)methyl 3-((2-fluoro-4-(trifluo-
romethyl)benzyl)oxy)azetidine-1-carboxylate;
(R)-(5-oxopyrrolidin-2-yl)methyl 3-((2-fluoro-4-(trifluo-
romethyl)benzyl)oxy)azetidine-1-carboxylate;
[(4S)-2-Oxooxazolidin-4-yl]methyl 3-[[2-fluoro-4-(trifluo-
romethyl)phenyl]methoxy]azetidine-1-carboxylate;
[(4R)-2-Oxooxazolidin-4-yl]methyl 3-[[2-fluoro-4-(trifluo-
romethyl)phenyl]methoxy]azetidine-1-carboxylate;
[(4S)-2-Oxooxazolidin-4-yl]methyl 3-[4-[1-(trifluorom-
ethyl)cyclopropyl]phenyl]azetidine-1-carboxylate;
[(4S)-2-Oxooxazolidin-4-yl]methyl 6-[(2,4-difluorophenyl)
methyl]-2-azaspiro[3.3]heptane-2-carboxylate;
[(4S)-2-Oxooxazolidin-4-yl]methyl 3-[4-(4-fluorophenoxy)
phenyl]azetidine-1-carboxylate;
[(4R)-2-Oxooxazolidin-4-yl]methyl 6-[(2,4-difluorophenyl)
methyl]-2-azaspiro[3.3]heptane-2-carboxylate;
[(4S)-2-Oxooxazolidin-4-yl]methyl 3-[6-(2-chlorophe-
noxy)-3-pyridyl]azetidine-1-carboxylate;
[(4S)-2-Oxooxazolidin-4-yl]methyl 3-[2-[2-(difluorom-
ethyl)phenyl]ethynyl]azetidine-1-carboxylate;
[(4S)-2-Oxooxazolidin-4-yl]methyl 3-[6-[3-(trifluorom-
ethyl)pyrrolidin-1-yl]-3-pyridyl]azetidine-1-carboxylate;
2-(1H-Triazol-5-yl)ethyl 3-[[2-fluoro-4-(trifluoromethyl)
phenyl]methoxy]azetidine-1-carboxylate;
3-[[2-fluoro-4-(trifluoromethyl)phenyl]methoxy]-N-[2-
(1H-triazol-5-yl)ethyl]azetidine-1-carboxamide;
N-Methyl-N-[2-(1H-triazol-5-yl)ethyl]-3-[4-[1-(trifluorom-
ethyl)cyclopropyl]phenyl]azetidine-1-carboxamide;
3-[[2-Fluoro-4-(trifluoromethyl)phenyl]methoxy]-N-
methyl-N-[2-(1H-triazol-5-yl)ethyl]azetidine-1-carbox-
amide;
3-[4-(2-Chloro-4-methylsulfonyl-phenyl)phenyl]-N-
methyl-N-[2-(1H-triazol-5-yl)ethyl]azetidine-1-carbox-
amide;
2-Methyl-4-(1H-triazol-5-yl)-1-[3-[4-[1-(trifluoromethyl)
cyclopropyl]phenyl]azetidin-1-yl]butan-1-one;
3-Hydroxy-4-(1H-triazol-5-yl)-1-[3-[4-[1-(trifluoromethyl)
cyclopropyl]phenyl]azetidin-1-yl]butan-1-one;
2-Fluoro-4-(1H-triazol-5-yl)-1-[3-[4-[1-(trifluoromethyl)
cyclopropyl]phenyl]azetidin-1-yl]butan-1-one;
(4R)-4-[3-[3-[4-(N-Methylanilino)phenyl]azetidin-1-yl]-3-
oxo-propyl]oxazolidin-2-one;
(4R)-4-[3-[3-(5-tert-Butyl-2-pyridyl)azetidin-1-yl]-3-oxo-
propyl]oxazolidin-2-one;
(4R)-4-[3-[3-[4-(2-chloro-4-methylsulfonyl-phenyl)phenyl]
azetidin-1-yl]-3-oxo-propyl]oxazolidin-2-one;
(4R)-4-[3-[3-[4-(Benzenesulfonyl)phenyl]azetidin-1-yl]-3-
oxo-propyl]oxazolidin-2-one;
2-[4-[1-[3-[(4R)-2-Oxooxazolidin-4-yl]propanoyl]azetidin-
3-yl]phenyl]sulfonylacetonitrile;
(4R)-4-[3-Oxo-3-[3-[4-(trifluoromethylsulfonyl)phenyl]
azetidin-1-yl]propyl]oxazolidin-2-one;
(4R)-4-[3-[3-(4-Cyclohexylsulfonylphenyl)azetidin-1-yl]-
3-oxo-propyl]oxazolidin-2-one;
1-[5-[1-[3-[(4R)-2-Oxooxazolidin-4-yl]propanoyl]azetidin-
3-yl]-2-pyridyl]cyclobutanecarbonitrile;
(4R)-4-[3-[3-[4-[(2-Methyl-3-pyridyl)oxy]phenyl]azetidin-
1-yl]-3-oxo-propyl]oxazolidin-2-one;
(4R)-4-[3-[3-[4-(4-Cyclopropylpyrimidin-2-yl)oxyphenyl]
azetidin-1-yl]-3-oxo-propyl]oxazolidin-2-one;
(4R)-4-[3-[3-[4-[3-(2,2-Dimethylpropyl)triazol-4-yl]phe-
nyl]azetidin-1-yl]-3-oxo-propyl]oxazolidin-2-one;
(4R)-4-[3-[3-[4-(4-Chloro-2-methylsulfonyl-phenyl)phe-
nyl]azetidin-1-yl]-3-oxo-propyl]oxazolidin-2-one;
(+)- or (−)-(4R)-4-[3-[4-[(4-Methylsulfonylphenyl)-phenyl-
methyl]-1-piperidyl]-3-oxo-propyl]oxazolidin-2-one;
(−)- or (+)-(4R)-4-[3-[4-[(4-Methylsulfonylphenyl)-phenyl-
methyl]-1-piperidyl]-3-oxo-propyl]oxazolidin-2-one;
5-Chloro-2-[[5-[1-[3-[(4R)-2-oxooxazolidin-4-yl]pro-
panoyl]azetidin-3-yl]-2-pyridyl]oxy]benzamide;
(−)- or (+)-[(4S)-2-Oxooxazolidin-4-yl]methyl 3-[6-[3-(tri-
fluoromethyl)pyrrolidin-1-yl]-3-pyridyl]azetidine-1-car-
boxylate;
(+)- or (−)-[(4S)-2-Oxooxazolidin-4-yl]methyl 3-[6-[3-(tri-
fluoromethyl)pyrrolidin-1-yl]-3-pyridyl]azetidine-1-car-
boxylate; and
(5S)-5-[3-[3-[[2-Fluoro-4-(trifluoromethyl)phenyl]
methoxy]azetidin-1-yl]-3-oxo-propyl]thiomorpholin-3-
one.

In a preferred embodiment, the present invention provides
a compound of formula (I) as defined herein, or a pharma-
ceutically acceptable salt thereof, selected from:
(+)-5-[3-[3-[[2-fluoro-4-(trifluoromethyl)phenyl]methoxy]
azetidin-1-yl]-3-oxo-propyl]pyrrolidin-2-one;
(+)-5-[3-Oxo-3-[3-[4-[1-(trifluoromethyl)cyclopropyl]phe-
nyl]azetidin-1-yl]propyl]pyrrolidin-2-one;
(+)-5-[3-[3-[4-(2,4-Difluorophenyl)phenyl]azetidin-1-yl]-3-
oxo-propyl]pyrrolidin-2-one;
(4R)-4-[3-[3-[[2-Fluoro-4-(trifluoromethyl)phenyl]
methoxy]azetidin-1-yl]-3-oxo-propyl]oxazolidin-2-one;
(4R)-4-[3-Oxo-3-[3-[4-[1-(trifluoromethyl)cyclopropyl]
phenyl]azetidin-1-yl]propyl]oxazolidin-2-one;
(4R)-4-[3-[3-[4-(2,4-Difluorophenyl)phenyl]azetidin-1-yl]-
3-oxo-propyl]oxazolidin-2-one;
(4R)-4-[3-[3-[6-(2-Chlorophenoxy)-3-pyridyl]azetidin-1-
yl]-3-oxo-propyl]oxazolidin-2-one;
(4R)-4-[3-[3-[4-(N-Methylanilino)phenyl]azetidin-1-yl]-3-
oxo-propyl]oxazolidin-2-one;

(4R)-4-[3-[3-[4-(4-Chloro-2-methylsulfonyl-phenyl)phenyl]azetidin-1-yl]-3-oxo-propyl]oxazolidin-2-one;
(4R)-4-[3-[3-[4-[N-(Cyclopropylmethyl)anilino]phenyl]azetidin-1-yl]-3-oxo-propyl]oxazolidin-2-one;
(4R)-4-[3-[3-[6-[N-(Cyclopropylmethyl)anilino]-3-pyridyl]azetidin-1-yl]-3-oxo-propyl]oxazolidin-2-one;
(4R)-4-[3-Oxo-3-[3-[4-[3-(2,2,2-trifluoroethoxy)azetidin-1-yl]phenyl]azetidin-1-yl]propyl]oxazolidin-2-one;
(4R)-4-[3-Oxo-3-[3-[4-[3-(trifluoromethyl)azetidin-1-yl]phenyl]azetidin-1-yl]propyl]oxazolidin-2-one;
(4R)-4-[3-[3-[5-(4-Chloro-2-fluoro-phenyl)pyrimidin-2-yl]azetidin-1-yl]-3-oxo-propyl]oxazolidin-2-one;
(4R)-4-[3-[3-[5-(4-Chloro-2-fluoro-phenyl)-2-pyridyl]azetidin-1-yl]-3-oxo-propyl]oxazolidin-2-one;
(4R)-4-[3-[3-[5-(2,4-Dichlorophenyl)-2-pyridyl]azetidin-1-yl]-3-oxo-propyl]oxazolidin-2-one;
(4R)-4-[3-Oxo-3-[6-[[6-(trifluoromethyl)-3-pyridyl]methyl]-2-azaspiro[3.3]heptan-2-yl]propyl]oxazolidin-2-one;
(4R)-4-[3-[7-[[2-Fluoro-4-(trifluoromethyl)phenyl]methyl]-2,7-diazaspiro[3.5]nonan-2-yl]-3-oxo-propyl]oxazolidin-2-one;
(4R)-4-[3-[3-[4-[4-Methylsulfonyl-2-(trifluoromethyl)phenyl]phenyl]azetidin-1-yl]-3-oxo-propyl]oxazolidin-2-one;
(4R)-4-[3-[3-[3-Fluoro-4-[3-(trifluoromethyl)pyrrolidin-1-yl]phenyl]azetidin-1-yl]-3-oxo-propyl]oxazolidin-2-one;
(4R)-4-[3-Oxo-3-[3-[4-[3-(trifluoromethyl)cyclobutyl]phenyl]azetidin-1-yl]propyl]oxazolidin-2-one;
(4R)-4-[3-[3-[6-(2-Azaspiro[3.4]octan-2-yl)-3-pyridyl]azetidin-1-yl]-3-oxo-propyl]oxazolidin-2-one;
(4R)-4-[3-[3-[3-[5-(2,2-Dimethylpropyl)-1,3,4-oxadiazol-2-yl]-1-bicyclo[1.1.1]pentanyl]azetidin-1-yl]-3-oxo-propyl]oxazolidin-2-one;
(4R)-4-[3-Oxo-3-[3-[[4-(trifluoromethylsulfonyl)phenyl]methoxy]azetidin-1-yl]propyl]oxazolidin-2-one;
(4R)-4-[3-Oxo-3-[7-[[6-(trifluoromethyl)-3-pyridyl]methyl]-2-azaspiro[3.5]nonan-2-yl]propyl]oxazolidin-2-one; and
cis-(4R)-4-[3-Oxo-3-[3-[6-[4-(trifluoromethyl)cyclohexyl]-3-pyridyl]azetidin-1-yl]propyl]oxazolidin-2-one.

In a preferred embodiment, the present invention provides a compound of formula (I) as defined herein, or a pharmaceutically acceptable salt thereof, selected from:
(+)-5-[3-[3-[[2-fluoro-4-(trifluoromethyl)phenyl]methoxy]azetidin-1-yl]-3-oxo-propyl]pyrrolidin-2-one;
(+)-5-[3-Oxo-3-[3-[4-[1-(trifluoromethyl)cyclopropyl]phenyl]azetidin-1-yl]propyl]pyrrolidin-2-one;
(+)-5-[3-[3-[4-(2,4-Difluorophenyl)phenyl]azetidin-1-yl]-3-oxo-propyl]pyrrolidin-2-one;
(R)-4-(3-(3-((2-Fluoro-4-(trifluoromethyl)benzyl)oxy)azetidin-1-yl)-3-oxopropyl)oxazolidin-2-one;
(R)-4-(3-Oxo-3-(3-(4-(1-(trifluoromethyl)cyclopropyl)phenyl)azetidin-1-yl)propyl)oxazolidin-2-one;
(R)-4-(3-(3-(2',4'-Difluoro-[1,1'-biphenyl]-4-yl)azetidin-1-yl)-3-oxopropyl)oxazolidin-2-one;
(4R)-4-[3-[3-[4-(N-Methylanilino)phenyl]azetidin-1-yl]-3-oxo-propyl]oxazolidin-2-one; and
(4R)-4-[3-[3-[4-(4-Chloro-2-methylsulfonyl-phenyl)phenyl]azetidin-1-yl]-3-oxo-propyl]oxazolidin-2-one.

In a particular embodiment, the present invention provides pharmaceutically acceptable salts of the compounds according to formula (I) as described herein, especially hydrochloride salts. In a further particular embodiment, the present invention provides compounds according to formula (I) as described herein as free bases.

In some embodiments, the compounds of formula (I) are isotopically-labeled by having one or more atoms therein replaced by an atom having a different atomic mass or mass number. Such isotopically-labeled (i.e., radiolabeled) compounds of formula (I) are considered to be within the scope of this disclosure. Examples of isotopes that can be incorporated into the compounds of formula (I) include isotopes of hydrogen, carbon, nitrogen, oxygen, phosphorous, sulfur, fluorine, chlorine, and iodine, such as, but not limited to, $^{2}$H, $^{3}$H, $^{11}$C, $^{13}$C, $^{14}$C, $^{13}$N, $^{15}$N, $^{15}$O, $^{17}$O, $^{18}$O, $^{31}$P, $^{32}$P, $^{35}$S, $^{18}$F, $^{36}$Cl, $^{123}$I, and $^{125}$I, respectively. Certain isotopically-labeled compounds of formula (I), for example, those incorporating a radioactive isotope, are useful in drug and/or substrate tissue distribution studies. The radioactive isotopes tritium, i.e. $^{3}$H, and carbon-14, i.e., $^{14}$C, are particularly useful for this purpose in view of their ease of incorporation and ready means of detection. For example, a compound of formula (I) can be enriched with 1, 2, 5, 10, 25, 50, 75, 90, 95, or 99 percent of a given isotope.

Substitution with heavier isotopes such as deuterium, i.e. $^{2}$H, may afford certain therapeutic advantages resulting from greater metabolic stability, for example, increased in vivo half-life or reduced dosage requirements.

Substitution with positron emitting isotopes, such as $^{11}$C, $^{18}$F, $^{15}$O and $^{13}$N, can be useful in Positron Emission Topography (PET) studies for examining substrate receptor occupancy. Isotopically-labeled compounds of formula (I) can generally be prepared by conventional techniques known to those skilled in the art or by processes analogous to those described in the Examples as set out below using an appropriate isotopically-labeled reagent in place of the non-labeled reagent previously employed.

Processes of Manufacturing

In one aspect, the present invention provides processes for manufacturing the compounds of formula (I), or pharmaceutically acceptable salts thereof, described herein.

The preparation of compounds of formula (I) of the present invention may be carried out in sequential or convergent synthetic routes. Syntheses of the invention are shown in the following general schemes. The skills required for carrying out the reaction and purification of the resulting products are known to those persons skilled in the art. The substituents and indices used in the following description of the processes have the significance given herein, unless indicated to the contrary.

If one of the starting materials, intermediates or compounds of formula (I) contain one or more functional groups which are not stable or are reactive under the reaction conditions of one or more reaction steps, appropriate protective groups (as described e.g., in "Protective Groups in Organic Chemistry" by T. W. Greene and P. G. M. Wutts, 5th Ed., 2014, John Wiley & Sons, New York) can be introduced before the critical step applying methods well known in the art. Such protective groups can be removed at a later stage of the synthesis using standard methods described in the literature.

If starting materials or intermediates contain stereogenic centers, compounds of formula (I) can be obtained as mixtures of diastereomers or enantiomers, which can be separated by methods well known in the art e.g., chiral HPLC, chiral SFC or chiral crystallization. Racemic compounds can e.g., be separated into their antipodes via diastereomeric salts by crystallization with optically pure acids or by separation of the antipodes by specific chromatographic methods using either a chiral adsorbent or a chiral eluent. It is equally possible to separate starting materials and intermediates containing stereogenic centers to afford diastereomerically/enantiomerically enriched starting materials and intermediates. Using such diastereomerically/enantiomerically enriched starting materials and intermediates in the synthesis of compounds of formula (I) will typically lead to the respective diastereomerically/enantiomerically enriched compounds of formula (I).

A person skilled in the art will acknowledge that in the synthesis of compounds of formula (I)—insofar not desired otherwise—an "orthogonal protection group strategy" will be applied, allowing the cleavage of several protective groups one at a time each without affecting other protective groups in the molecule. The principle of orthogonal protection is well known in the art and has also been described in literature (e.g., Barany, G., Merrifield, R. B., *J. Am. Chem. Soc.* 1977, 99, 7363; Waldmann, H. et al., *Angew. Chem. Int. Ed. Engl.* 1996, 35, 2056).

A person skilled in the art will acknowledge that the sequence of reactions may be varied depending on reactivity and nature of the intermediates.

In more detail, the compounds of formula (I) can be manufactured by the methods given below, by the methods given in the examples or by analogous methods. Appropriate reaction conditions for the individual reaction steps are known to a person skilled in the art. Also, for reaction conditions described in literature affecting the described reactions see for example: "*Comprehensive Organic Transformations: A Guide to Functional Group Preparations*", by Richard C. Larock, 2$^{nd}$ Ed., 1999, John Wiley & Sons, New York. It was found convenient to carry out the reactions in the presence or absence of a solvent. There is no particular restriction on the nature of the solvent to be employed, provided that it has no adverse effect on the reaction or the reagents involved and that it can dissolve the reagents, at least to some extent. The described reactions can take place over a wide range of temperatures, and the precise reaction temperature is not critical to the invention. It is convenient to carry out the described reactions in a temperature range between −78° C. to reflux. The time required for the reaction may also vary widely, depending on many factors, notably the reaction temperature and the nature of the reagents. However, a period of from 0.5 h to several days will usually suffice to yield the described intermediates and compounds. The reaction sequence is not limited to the one displayed in the schemes, however, depending on the starting materials and their respective reactivity, the sequence of reaction steps can be freely altered.

If starting materials or intermediates are not commercially available or their synthesis not described in literature, they can be prepared in analogy to existing procedures for close analogues or as outlined in the experimental section.

The following abbreviations are used in the present text: AcOH=acetic acid, ACN=acetonitrile, BINAP=2,2'-bis(diphenylphosphino)-1,1'-binaphthyl, Bn=benzyl, Boc=tert-butyloxycarbonyl, CAS RN=chemical abstracts registration number, Cbz=benzyloxycarbonyl, CDI=1,1'-carbonyldiimidazole, DAST=(diethylamino)sulfur trifluoride, DBU=1,8-diazabicyclo[5,4,0]undec-7-ene, DCC=N,N'-dicyclohexylcarbodiimide, DEAD=diethyl azodicarboxylate, DIAD=diisopropyl azodicarboxylate, DMAP=4-dimethylaminopyridine, DME=dimethoxyethane, DMF=N,N-dimethylformamide, DMSO=dimethyl sulfoxide, DIPEA=N,N-diisopropylethylamine, EI=electron impact, ESI=electrospray ionization, EtOAc=ethyl acetate, EtOH=ethanol, FG=functional group, h=hour(s), FA=formic acid, HATU=1-[bis(dimethylamino)methylene]-1H-1,2,3-triazolo[4,5-b]pyridinium-3-oxide hexafluorophosphate, HBTU=O-benzotriazole-N,N,N',N'-tetramethyl-uronium hexafluorophosphate, HOBt=1-hydroxy-1H-benzotriazole, HPLC=high performance liquid chromatography, LG=leaving group, LiHMDS=lithium bis(trimethylsilyl)amide, mCPBA=meta-chloroperoxybenzoic acid, Me=methyl, min=minute(s), mL=milliliter, MPLC=medium pressure liquid chromatography, MS=mass spectrum, n-BuLi=n-butyllithium, NEt$_3$=triethylamine (TEA), NMP=N-methyl-2-pyrrolidone, OAc=acetoxy, T$_3$P=propylphosphonic anhydride, PE=petroleum ether, PG=protective group, Pd—C=palladium on activated carbon, R=any group, RT=room temperature, SFC=Supercritical Fluid Chromatography, TBME=tert-butyl methyl ether, TEA=triethylamine, TFA=trifluoroacetic acid, THF=tetrahydrofuran, TLC=thin-layer chromatography, X-PHOS=2-dicyclohexylphosphino-2',4',6'-triisopropylbiphenyl, Xantphos=(9,9-Dimethyl-9H-xanthene-4,5-diyl)bis(diphenylphosphane), Hal=halogen.

Compounds of formula IA wherein A, B, C, L, Y, R$^1$, R$^2$, R$^3$, R$^4$, R$^5$, and R$^6$ are as described herein and X is CHR$^6$, can be synthesized in analogy to literature procedures and/or as depicted for example in Scheme 1A.

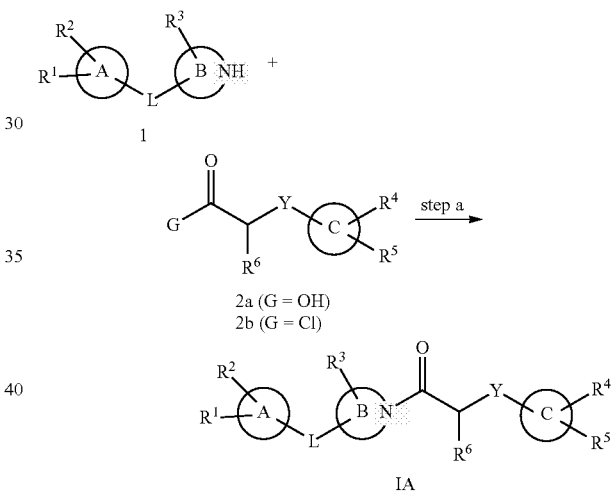

Scheme 1A

Accordingly, intermediates 1 can be coupled with an activated form of a carboxylic acid 2a (G=OH) or alternatively with carboxylic acid chlorides 2b (G=Cl) to provide compounds IA (step a). Amide couplings of this type with carboxylic acids are widely described in the literature and can be accomplished by the usage of coupling reagents such as CDI, DCC, HATU, HBTU, HOBT, TBTU, T$_3$P or Mukaiyama reagent (Mukaiyama T., *Angew. Chem., Int. Ed. Engl.* 1979, 18, 707-808) in a suitable solvent e.g., DMF, DMA, DCM or 1,4-dioxane, optionally in the presence of a base (e.g., TEA, DIPEA (Huenig's base) or DMAP). Carboxylic acids 2 are either commercially available or can be prepared by methods known in the art.

Alternatively, the carboxylic acids 2a can be converted into their acid chlorides 2b by treatment with, e.g., thionyl chloride or oxalyl chloride, neat or optionally in a solvent such as DCM. Subsequent reaction of the acid chloride with intermediates 1 in an appropriate solvent such as DCM or DMF and a base, e.g., TEA, DIPEA (Huenig's base), pyridine, DMAP or lithium bis(trimethylsilyl)amide at temperatures ranging from 0° C. to the reflux temperature of the solvent or solvent mixture yields compounds IA (step a).

Compounds IA with $R^1$ or $R^3$=$CONH_2$ can be prepared from the corresponding carboxylic acid by treatment with, e.g., aqueous ammonium hydroxide in a solvent like ACN at temperatures ranging from RT to the reflux temperature or above the boiling point of the solvent or solvent mixture (Scheme 1B, step a). Appropriate reaction conditions are standard conditions well described in the literature and are known to a person skilled in the art.

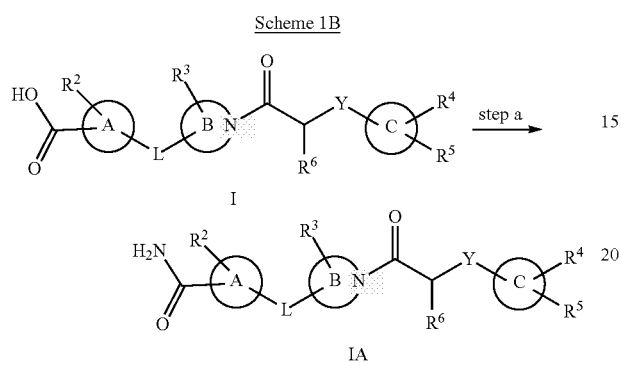

Scheme 1B

Compounds of formula IB wherein A, B, C, L, Y, $R^1$, $R^2$, $R^3$, $R^4$, and $R^5$ are as described herein and X is O, can be synthesized in analogy to literature procedures and/or as depicted for example in Scheme 2.

Scheme 2

Accordingly, compounds 1 are reacted with alcohols 3 in the presence of a carbamate forming reagent such as di(1H-1,2,4-triazol-1-yl)methanone using a suitable base and solvent such as, e.g., sodium hydride or sodium bicarbonate and ACN, THF or DCM (or mixtures thereof), to give compounds of formula IB (step a). Further carbamate forming reagents include but are not limited to phosgene, bis (trichloromethyl) carbonate (BTC, triphosgene), trichloromethyl chloroformate, bis(4-nitrophenyl) carbonate or 1,1'-carbonyldiimidazole. Reactions of this type, the use of these reagents and further carbamate forming strategies are widely described in literature (e.g., G. Sartori et al., *Green Chemistry* 2000, 2, 140-148; A. K. Ghosh et al., *J. Med. Chem.* 2015, 58, 2895-2940). Alcohols 3 are either commercially available or can be prepared by methods known in the art.

Compounds of formula IC wherein A, B, C, L, Y, $R^1$, $R^2$, $R^3$, $R^4$, and $R^5$ are as described herein and X is NH, can be synthesized in analogy to literature procedures and/or as depicted for example in Scheme 3.

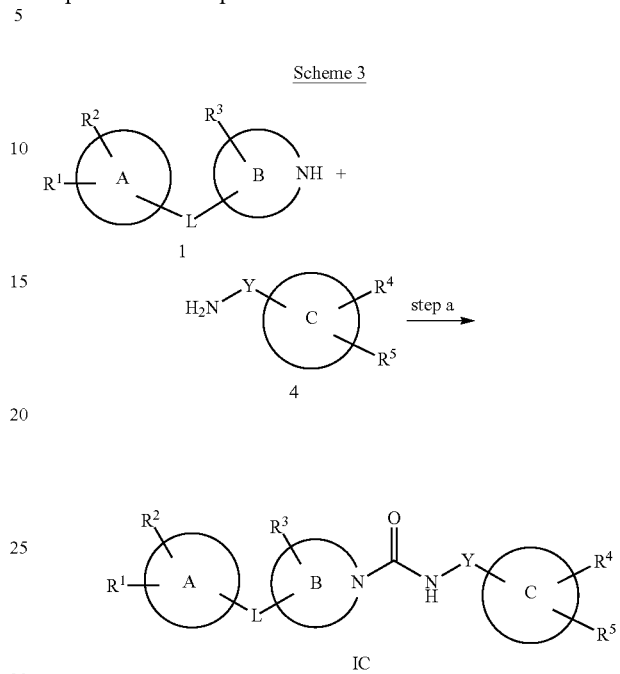

Scheme 3

Accordingly, compounds 1 are reacted with amines 4 in the presence of a urea forming reagent such as 2-(1H-triazol-5-yl)ethanamine using a suitable base and solvent such as, e.g., TEA or DIPEA (Huenig's base) in ACN or sodium bicarbonate in DCM, to give compounds of formula IC (step a). Further urea forming reagents include but are not limited to phosgene, bis(trichloromethyl) carbonate (BTC, triphosgene), trichloromethyl chloroformate, bis(4-nitrophenyl) carbonate or 1,1'-carbonyldiimidazole. Reactions of this type and the use of these reagents are widely described in literature (e.g., G. Sartori et al., *Green Chemistry* 2000, 2, 140). A person skilled in the art will acknowledge that the order of the addition of the reagents can be important in this type of reactions due to the reactivity and stability of the intermediary formed carbamoyl chlorides, as well as for avoiding formation of undesired symmetrical urea by-products. Amines 4 are either commercially available or can be prepared by methods known in the art.

In some embodiments, intermediates 1 are intermediates of type 1a which can be synthesized in analogy to literature procedures and/or as depicted for example in Scheme 4.

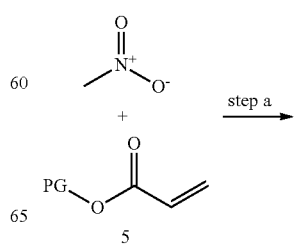

Scheme 4

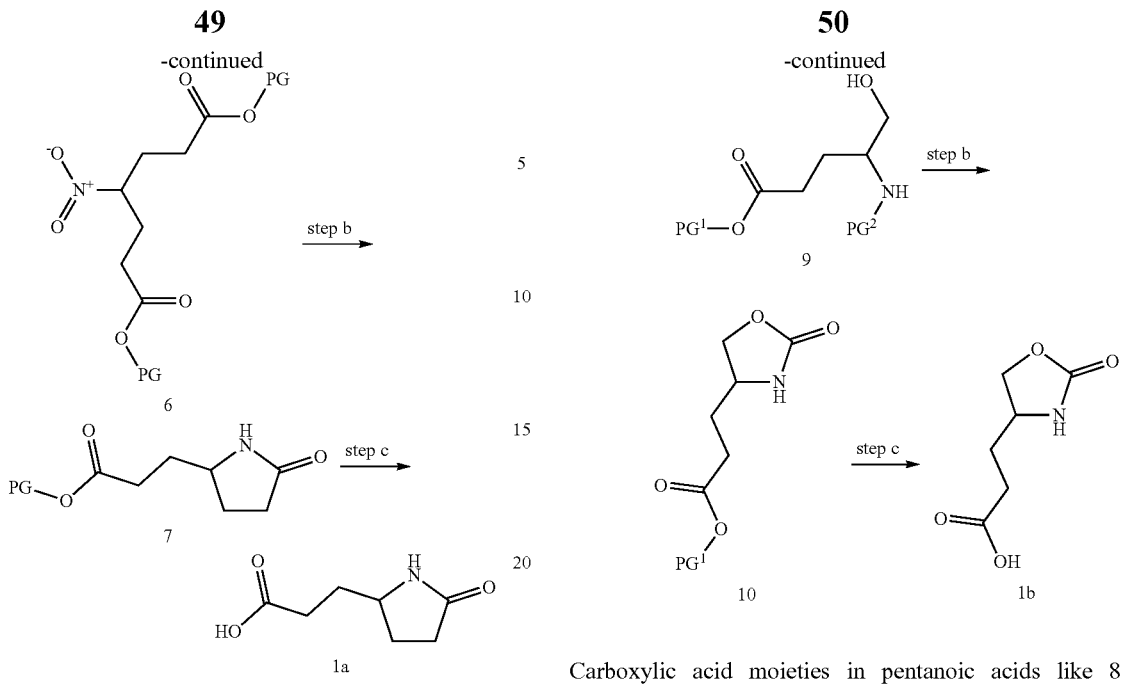

Accordingly, acrylates of type 5, in which PG signifies a suitable protecting group such as methyl, ethyl or tert-butyl are reacted with nitromethane in a solvent like DME and N-benzyl-trimethylammonium hydroxide at elevated temperatures, typically between 50° C. and 100° C. to afford intermediates of type 6. The nitro group can then be reduced to the corresponding amine using standard reaction conditions known to persons skilled in the art, for example hydrogenation conditions (e.g., Pd/C in MeOH under hydrogen atmosphere), giving direct access to pyrrolidons 7. Removal of the PG under classical basic (PG=methyl, ethyl) or acidic (PG=tert-butyl) conditions known to persons skilled in the art affords intermediates of type 1a.

In some embodiments, intermediates 1 are intermediates of type 1b which can be synthesized in analogy to literature procedures and/or as depicted for example in Scheme 5.

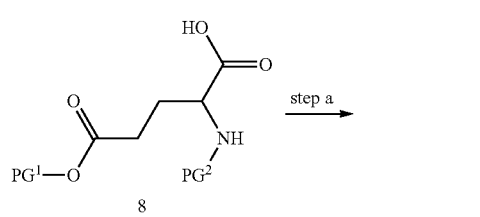

Carboxylic acid moieties in pentanoic acids like 8 (PG$^1$=methyl, ethyl; PG$^2$=tert-butyloxycarbonyl (BOC)) can be reduced to the corresponding hydroxyl compounds 9 upon activation with ethyl chloroformate and subsequent treatment with sodium borohydride in a suitable solvent such as THF or 1,4-dioxane at temperatures between −10° C. and RT, preferentially at temperatures around 0° C. Treatment of intermediate 9 with thionyl chloride in a solvent such as THF or 1,4-dioxane at room temperature affords cyclic carbamates 10. Cleavage under typically basic conditions of alkyl PG$^1$ using e.g., lithium or sodium or potassium hydroxide in a solvent of THF or 1,4-dioxane or mixtures thereof with water, gives then access to intermediates of type 1b. All of these reactions are standard operations and can be carried out under conditions which are usual for such reactions and which are familiar to a person skilled in the art.

In some embodiments, intermediates 1 are intermediates of type 1c and 1d which can be synthesized in analogy to literature procedures and/or as depicted for example in Scheme 6.

Scheme 6

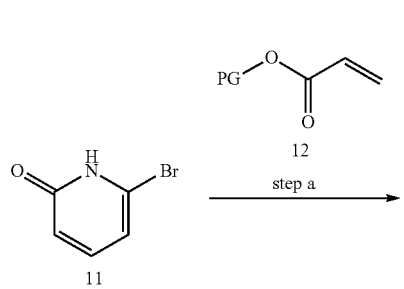

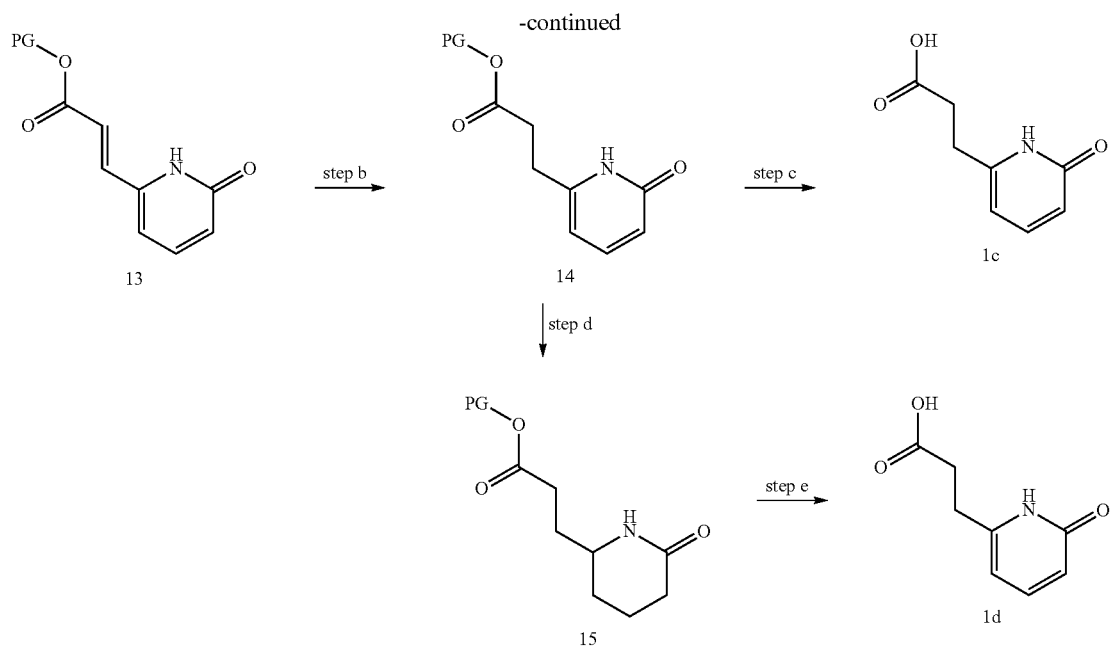

Pyridone intermediates 13 (PG=methyl, ethyl) can be prepared by cross-coupling reactions of pyridone bromide 11 with acrylates such as 12 (PG=methyl, ethyl) using conditions known to persons skilled in the art (step a). Subsequent hydrogenation of the double bond (e.g., $H_2$ over Pd/C) affords intermediates 14 which upon cleavage of the ester provide intermediates of type 1c (step c). Further reduction of the pyridine core in 14 (e.g., $H_2$ over Pd/C) gives access to lactam 15 (step d) and cleavage of the ester moiety provides intermediates of type 1d (step e). All of these reactions are standard operations and can be carried out under conditions which are usual for such reactions and which are familiar to a person skilled in the art.

In some embodiments, intermediates 1 are intermediates of type 1e which can be synthesized in analogy to literature procedures and/or as depicted for example in Scheme 7.

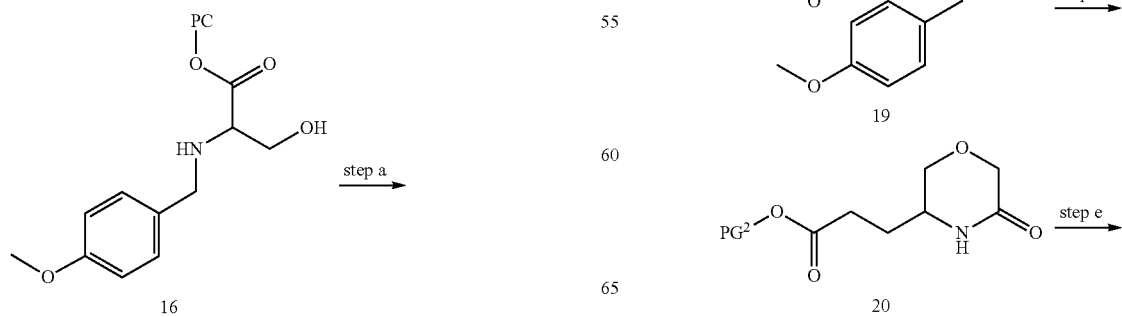

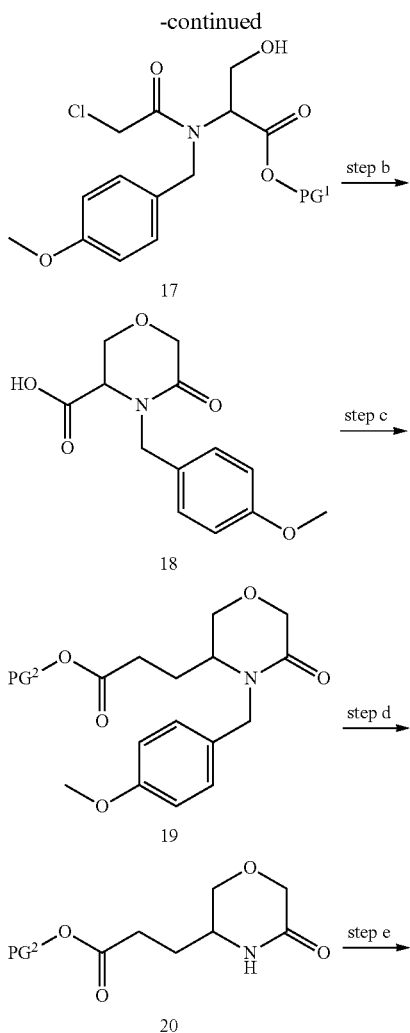

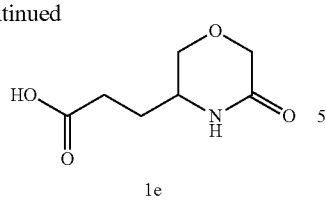

1e

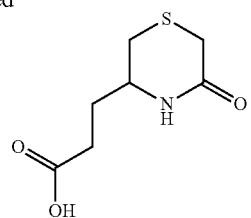

1f

Suitably protected serine methyl esters 16 (PG$^1$=methyl, ethyl) can be treated with chloroacetyl chloride to provide alkyl chloride intermediates 17 (step a), which upon reaction with a base such as potassium tert-butoxide in a suitable solvent like tert-butanol give access to morpholine derivates of type 18 (step b). Decarboxylative carbon-chain homologation using a suitable photoredox catalyst (e.g., Ir[dF(CF$_3$)ppy]$_2$(dtbbpy))PF$_6$) in a suitable solvent such as DMF upon irradiation with blue light (typically between a wavelength of 365 to 450 nm) provide intermediate 19 (step c). Removal of the lactam protection group (e.g., PMB with ammonium cerium(IV) nitrate) affords intermediate 20 (step d), which upon cleavage of the carboxylic acid protection group (PG$^2$=benzyl) by hydrogenation (e.g., H$_2$ over Pd/C) provides intermediates of type 1e (step e). All of these reactions are standard operations and can be carried out under conditions which are usual for such reactions and which are familiar to a person skilled in the art.

In some embodiments, intermediates 1 are intermediates of type 1f which can be synthesized in analogy to literature procedures and/or as depicted for example in Scheme 8.

The alcohol functionality of suitably protected amino alcohols (PG$^1$=tert-butyloxycarbonyl (BOC); PG$^2$=benzyl), either commercially available or prepared by methods known in the art, can be activated with an appropriate leaving group such as mesylate forming intermediates of general structure 21 that can react with thiols of structure 22 (PG$^3$=methyl, ethyl) to form thioethers such as 23 (step a). Removal of the amino protection group in intermediate 23 (step b) typically under acidic conditions, followed by cleavage of the ester functionality under basic reaction conditions results in the formation of intermediates of type 1f (step b).

In some embodiments, intermediates 1 are intermediates of type 1g which can be synthesized in analogy to literature procedures and/or as depicted for example in Scheme 9.

Scheme 9

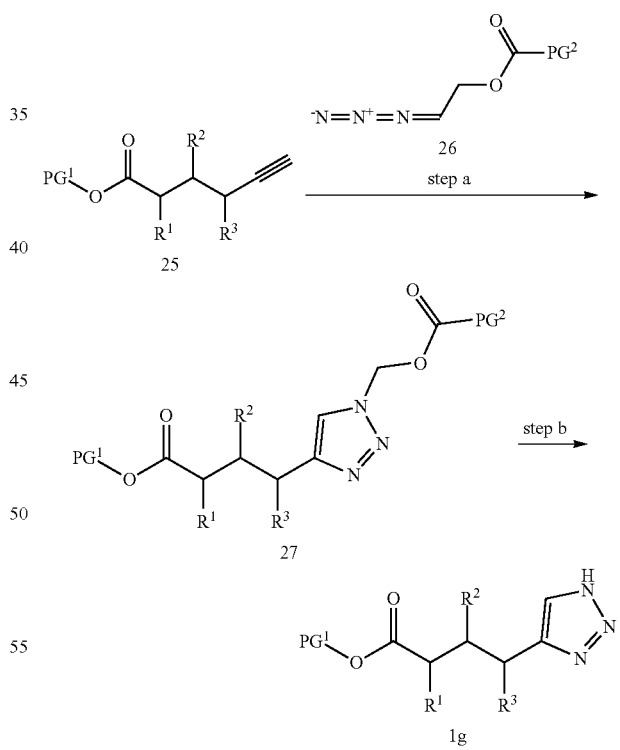

Suitably protected (PG$^1$=methyl, ethyl) acetylenes of general structure 25 can undergo with azides of type 26 (PG$^2$=tert-butyl) an azide-alkyne cycloaddition reaction forming triazoles such as 27 (step a). Removal of the protection groups in intermediate 27 under reaction conditions familiar to a person skilled in the art provides intermediates of type 1g (step b).

Scheme 8

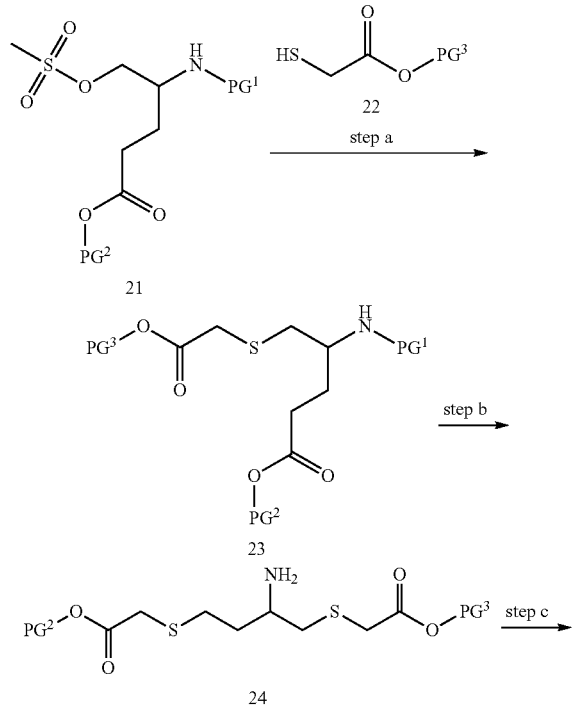

In some embodiments, intermediates 2 are intermediates of type 2a. Intermediates 2a in which $R^1$, $R^2$, $R^3$, A and B are as described herein can be prepared by a methods known in the art and as exemplified by the general synthetic procedure outlined in Scheme 10.

Scheme 10

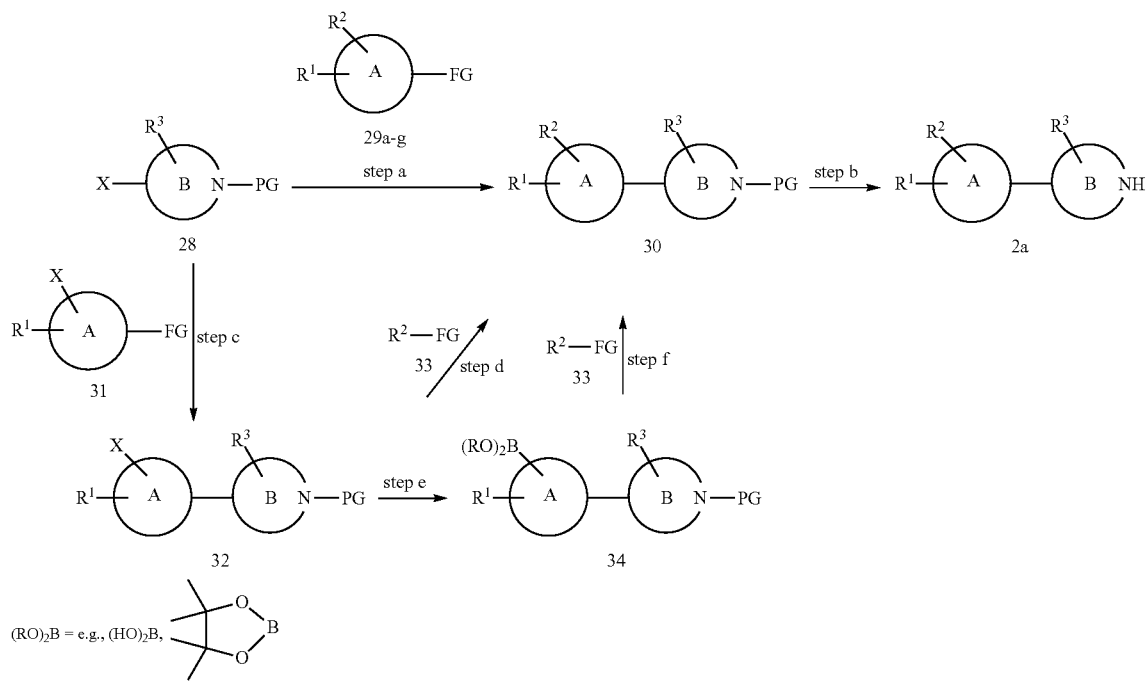

Intermediates 28, either commercially available or prepared by methods known in the art, in which PG signifies a suitable protecting group and X is bromide or iodide can be subjected to cross-coupling reactions such as Negishi, Heck, Stille, Suzuki, Sonogashira or Buchwald-Hartwig coupling reactions with compounds 29, either commercially available or prepared by methods known in the art, in which FG signifies a suitable functional group such as, e.g., chloro, bromo, iodo, —OSO$_2$alkyl (e.g., mesylate (methanesulfonate)), —OSO$_2$fluoroalkyl (e.g., triflate (trifluoromethanesulfonate)) or —OSO$_2$aryl (e.g., tosylate (p-toluenesulfonate)). Reactions of this type are broadly described in literature and well known to persons skilled in the art (step a).

For example, intermediates 28 can be reacted with aryl or heteroaryl boronic acids 29a (FG=B(OH)$_2$) or boronic esters 29b (FG=e.g., 4,4,5,5-tetramethyl-2-phenyl-1,3,2-dioxaborolane (pinacol) ester) either commercially available or prepared using literature procedures as described for example in "Boronic Acids—Preparation and Applications in Organic Synthesis and Medicine" by Dennis G. Hall (ed.) 1$^{st}$ Ed., 2005, John Wiley & Sons, New York, using a suitable catalyst (e.g., 1,1'-bis(diphenylphosphino)ferrocene-palladium(II) dichloride dichloromethane complex, crotyl(amphos)palladium(II) chloride, tetrakis(triphenylphosphine)palladium(0) or palladium(II) acetate with triphenylphosphine) in an appropriate solvent (e.g., 1,4-dioxane, DME, water, toluene, DMF or mixtures thereof) and a suitable base (e.g., Na$_2$CO$_3$, NaHCO$_3$, KF, K$_2$CO$_3$, TEA or DIPEA) at temperatures between room temperature and the boiling point of the solvent or solvent mixture, to yield intermediates 30 (step a). Suzuki reactions of this type are broadly described in literature (e.g., A. Suzuki, *Pure Appl. Chem.* 1991, 63, 419-422; A. Suzuki, N. Miyaura, *Chem. Rev.* 1995, 95, 2457-2483; A. Suzuki, *J. Organomet. Chem.* 1999, 576, 147-168; V. Polshettiwar et al., *ChemSusChem* 2010, 3, 502-522) and are well known to those skilled in the art.

Alternatively, aryl- or heteroaryl-trifluoroborates 29c (FG=BF$_3$) can be used in the cross-coupling reaction applying a palladium catalyst such as, e.g., tetrakis(triphenylphosphine)-palladium(0), palladium(II) acetate with triphenylphosphine or 1,1'-bis(diphenylphosphino)ferrocene-palladium(II) dichloride dichloromethane complex in the presence of a suitable base such as cesium carbonate or potassium phosphate in solvents such as toluene, THF, 1,4-dioxane, water or mixtures thereof, at temperatures between room temperature and the boiling point of the solvent or solvent mixture (step a).

Alternatively, intermediates 28 can be reacted with aryl or heteroaryl stannanes 29d in which FG is Sn(alkyl)$_3$ and alkyl is preferable n-butyl or methyl, using a suitable catalyst and solvent such as, e.g., tetrakis(triphenylphosphine)palladium (0) in DMF at temperatures between room temperature and the boiling point of the solvent or solvent mixture to provide intermediates 30 (step a). Stille reactions of that type are well known in the art and described in literature (e.g., V. Farina et al., *Org. React.* 1997, 50, 1-652; C. Cordovilla et al., *ACS Catal.* 2015, 5, 3040-3053).

Furthermore, intermediates 28 can be reacted with aryl or heteroarylzinc halides 29e in which FG is ZnHal and Hal preferably bromide or iodide, either commercially available or prepared by literature methods, using an appropriate catalyst and solvent system such as, e.g., 1,1'-bis(diphenylphosphino)ferrocene-palladium(II) dichloride dichloromethane complex and copper(I) iodide in DMA, or tetrakis(triphenylphosphine)palladium(0) in THF or DMF at temperatures between room temperature and the boiling point of the solvent to provide intermediates 30 (step a). Negishi reactions of that type are well known in the art and also described in literature, e.g., A. Gavryushin et al., *Org. Lett.* 2005, 7, 4871-4874; D. Haas et al., *ACS Catal.* 2016, 6, 1540-1552; E.-I. Negishi, *Acc. Chem. Res.* 1982, 15, 340-348.

Alternatively, intermediates 30 may be prepared by first converting intermediates 28 in which X is for example iodide into the corresponding zinc species by applying literature methods (e.g., reaction of intermediates 28 with Zn powder in the presence of chlorotrimethylsilane and 1,2-dibromoethane in a suitable solvent such as DMA) and subsequent coupling of the zinc species with aryl- or heteroarylbromides or -iodides under the conditions mentioned before.

Alternatively, intermediates 28 in which X is preferably bromide or iodide can be cross-coupled with aryl- or heteroarylhalides 29f (FG=Br or I) under conditions using an air-stable Ni(II) source such as nickel(II) chloride diglyme in the presence of a diamine ligand such as phenanthroline and a metal reductant like manganese. Reactions of this type are described in literature, e.g., G. A. Molander et al., *J. Org. Chem.* 2014, 79, 5771-5780.

Alternatively, intermediates 28 in which X is preferably bromide can be subjected to a cross-electrophile coupling with aryl- or heteroarylhalides 29f in which FG signifies bromide or iodide under irradiation with blue light (typically between a wavelength of 365 to 450 nm, preferentially at 420 nm) using an appropriate photocatalyst such as bis[3,5-difluoro-2-[5-(trifluoromethyl)-2-pyridyl]phenyl]iridium (1+) 4-tert-butyl-2-(4-tert-butyl-2-pyridyl)pyridine hexafluorophosphate (Ir[dF(CF$_3$)ppy]$_2$(dtbbpy))PF$_6$), a nickel catalyst like nickel(II) chloride ethylene glycol dimethyl ether complex, 4,4'-di-tert-butyl-2,2'-dipyridyl and tris(trimethylsilyl)silane, in the presence of a suitable base such as anhydrous sodium carbonate in a solvent like DME. Reactions of this type are described in literature, e.g., P. Zhang et al., *J. Am. Chem. Soc.* 2016, 138, 8084-8087; C. K. Prier et al., *Chem. Rev.* 2013, 113, 5322-5363 (step a).

Furthermore, intermediates 28 in which X is preferably iodine can be subjected to Suzuki-Miyaura cross coupling reactions with arylboronic acids 31 (FG=B(OH)$_2$) or boronic esters 29b (FG=e.g., 4,4,5,5-tetramethyl-2-phenyl-1,3,2-dioxaborolane (pinacol) ester)) using a suitable nickel catalyst such as nickel(II) iodide in the presence of rac-trans-2-aminocyclohexan-1-ol and a suitable base such as sodium bis(trimethylsilyl)amide in an appropriate solvent like 2-propanol (isopropyl alcohol), 1,4-dioxane, THF or DME, preferably 2-propanol, at temperatures between room temperature and the boiling point of the solvent, optionally applying microwave heating, to yield intermediates 32. Reactions of this type are described in literature, e.g., G. Dequirez et al., *ChemistrySelect* 2017, 2, 8841-8846 (step c).

Intermediates 32 in which X is preferably bromide or iodide can be reacted with primary or secondary amines such as R$^2$—FG 33 applying one of the cross-coupling methods such as Buchwald-Hartwig coupling reactions described before to provide intermediates 30 (step d).

Intermediates 32 in which X is preferably NH can be reacted with alkylhalides such as R$^2$—FG 33 under reaction conditions known to a person skilled in the art to provide intermediates 30 (step d).

Intermediates 32 in which X is preferably NH can be reacted with sulfonyl chlorides such as R$^2$-FG 33 under reaction conditions known to a person skilled in the art to provide intermediates 30 (step d).

The bromo or iodo substituent in intermediates 32 can be converted into a boronic acid or boronic ester (e.g., pinacol ester) according to methods described in literature or as outlined under step a, to yield intermediates 34 (step e).

Intermediates 34 can be converted to intermediates 30 for example using a Suzuki coupling reaction with compounds R$^2$-FG 33 in which FG is for example bromine or iodine applying the conditions described under step a (step f).

Removal of the tert-butyloxycarbonyl (BOC)-protective group from intermediates 30 applying methods well known in the art and as described (see "*Protective Groups in Organic Chemistry*" by T. W. Greene and P. G. M. Wutts, 5$^{th}$ Ed., 2014, John Wiley & Sons, New York), e.g., using TFA or hydrochloric acid in a solvent like DCM, 1,4-dioxane or THF preferable at room temperature or 4-methylbenzenesulfonic acid hydrate in a solvent like ethyl acetate preferably at elevated temperatures, furnishes intermediates 2a (step b).

In some embodiments, intermediates 2 are intermediates of type 2b. Intermediates 2b in which R$^1$, R$^2$, R$^3$, A and B are as described herein can be prepared by a methods well known in the art and as exemplified by the general synthetic procedure outlined in Scheme 11.

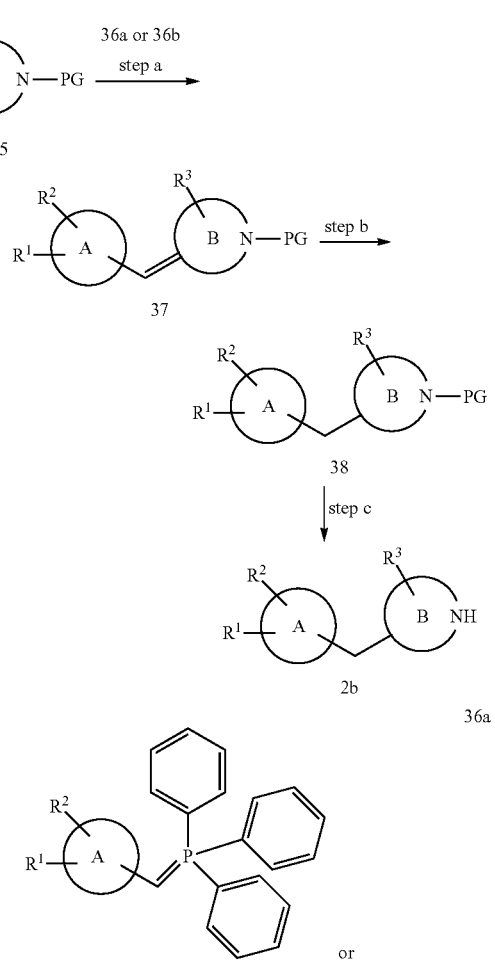

-continued

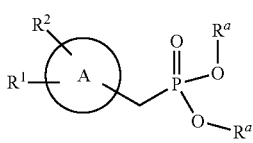
36b

Ketones 35 in which PG is a suitable protective group, either commercially available or prepared by methods known in the art, can be subjected for example to a Wittig reaction with alkylidene triphenylphosphoranes of type 36a in a suitable solvent such as, e.g., THF, Methyl-THF or DMSO to give intermediates 37 (step a). Phosphoranes 36a can be formed by treating the corresponding phosphonium salts with a suitable base such as n-BuLi, NaH, LiHMDS or KOt-Bu in a suitable solvent such as THF, 1,4-dioxane or Methyl-THF and may be isolated or used in situ. Phosphonium salts in turn are readily available from an aryl/heteroaryl/heterocyclic-substituted alkylhalide (with halide being chlorine, bromine and iodide) and triphenylphosphine in a suitable solvent such as toluene. Heating may be applied to accelerate the reaction or drive the reaction to completion (e.g., "Preparation, Properties and Reactions of Phosphonium Salts" by H. J. Cristau, F. Plenat in *The Chemistry of Organophosphorus Compounds: Phosphonium Salts, Ylides And Phosphoranes* (Patai's Chemistry of Functional Groups), Vol. 3, Frank R. Hartley (Ed.), Series Editor: Prof. Saul Patai, John Wiley & Sons, New York).

Alternatively, intermediates 37 can be obtained using a Horner-Wadsworth-Emmons (HWE) reaction using ketones 35 and phosphonates 36b, wherein Ra is alkyl, for example methyl or ethyl. Phosphonates 36b are in situ α-metalated using a suitable base and solvent such as NaH, n-BuLi or KOt-Bu in THF (step a). Phosphonates 36b are readily prepared using for example the Arbuzov reaction by alkylation of an aryl/heteroaryl/heterocyclic halide (with halide being chlorine, bromine and iodide) with commercially available trialkyl phosphites (e.g., Brill, T. B., Landon, S. J., *Chem. Rev.* 1984, 84, 577).

Olefination reactions of both types are broadly described in literature (e.g., Bisceglia, J. A., Orelli, L. R., *Curr. Org. Chem.* 2015, 19, 744; Maryanoff, B. E., Reitz, A. B., *Chem. Rev.* 1989, 89, 863; Wadsworth Jr., W. S., *Org. React.* 1977, 25, 73; Nicolaou, K. C., Härtner, M. W., Gunzner, J. L., Nadin, A., *Liebigs Ann./Recueil* 1997, 1283; Stec, W. J., *Acc. Chem. Res.* 1983, 16, 411).

Reduction of the double bond in intermediates 37 using, e.g., hydrogen in the presence of a suitable catalyst such as palladium on charcoal (Pd/C) in an appropriate solvent or solvent mixture such as EtOAc, MeOH or AcOH yields compounds 38 (step b).

Removal of the protective group from intermediates 38 applying methods known in the art (e.g., a Boc group using TFA in DCM, 4 M HCl in 1,4-dioxane at temperatures between 0° C. and room temperature or 4-methylbenzenesulfonic acid hydrate in a solvent like ethyl acetate preferably at elevated temperatures, a Cbz group using hydrogen in the presence of a suitable catalyst such as Pd or Pd(OH)$_2$ on charcoal in a suitable solvent such as MeOH, EtOH, EtOAc or mixtures thereof and as described for example in *"Protective Groups in Organic Chemistry"* by T. W. Greene and P. G. M. Wutts, 5th Ed., 2014, John Wiley & Sons, New York), furnishes intermediates 2b (sp c).

Alternatively, intermediates 2b in which $R^1$, $R^2$, $R^3$, $R^8$, A and B are as described herein can be prepared by a variety of conditions, which may be exemplified by the general synthetic procedure outlined in Scheme 12.

Scheme 12

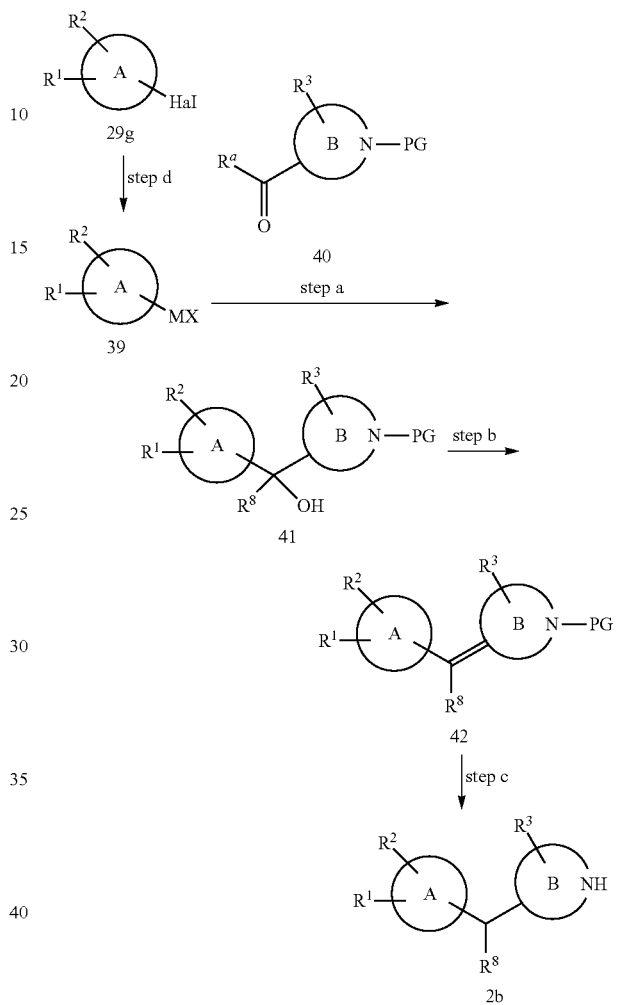

Addition of an organometallic compound of type 39 in which MX is for example Li or MgCl, MgBr or MgI to intermediates 40 in which PG is a suitable protective group, e.g., a Boc group, provides intermediates 41 (step a). Reactions of this type are well known in the art and described in literature (D. A. Walsh et al., *J. Med. Chem.* 1989, 32, 105-118; S. He et al., *J. Med. Chem.* 2014, 57, 1543-1556; T. Senter et al., *Bioorg. Med. Chem. Lett.* 2015, 25, 2720-2725). In case of compounds 13 in which MX=MgHal with Hal being Cl, Br or I (Grignard reagents) that are commercially not available they may be prepared for example by reaction of the corresponding aryl or heteroaryl halides 29g with magnesium in a suitable solvent such as THF, optionally in the presence of catalytic amounts of iodine at temperatures ranging from 0° C. to the boiling point of the solvent (step d). Alternatively, a lithium halogen exchange reaction can be performed with aryl or heteroaryl halides 29g using a solution of LiHMDS or n-BuLi, preferably n-BuLi in a solvent like THF, diethylether, n-pentane, n-hexane or mixtures thereof, preferably THF and in a temperature range between −20° C. and −78° C., preferably at −78° C., to generate the corresponding lithiated aryl or heteroaryl intermediate (M=Li). Nucleophilic addition of the in situ prepared lithiated aryl or heteroaryl intermediate to ketones of type 40 in which PG is a suitable protecting group such as a Boc group in a solvent such as THF and preferably at a temperature of −78° C. gives the corresponding tertiary alcohols 41 (step a).

Subsequent elimination of the secondary ($R^8$=H) or tertiary ($R^8 \neq H$) alcohol in intermediates 41, optionally with concomitant removal of an acid labile protective group (e.g., a Boc protective group) using acidic conditions such as 4 M HCl in 1,4-dioxane in a solvent like MeOH, or preferably TFA in DCM, yields the corresponding olefinic intermediates 42 (step b).

Heterogeneous catalytic hydrogenation of olefins 42 using a catalyst such as Pd(OH)$_2$ or Pd/C in a solvent like THF, MeOH, EtOH, EtOAc or a mixture thereof, preferably Pd/C in THE under e.g., atmospheric pressure of hydrogen, affords intermediates of type 2b (step c).

Intermediates 40 are commercially available and/or can be prepared in analogy to methods described in literature, e.g., K. S. Ashton et al., *Bioorg. Med. Chem. Lett.* 2011, 21, 5191-5196; WO2012/155199; WO2016/180536; K. M. Hutchings et al., *Bioorg. Med. Chem. Lett.* 2008, 18, 5087-5090; WO2007/117557; X. Zhang, D. W. C. MacMillan, *J. Am. Chem. Soc.* 2017, 139, 11353-11356; F. Liu et al., *J. Med. Chem.* 2017, 60, 5507-5520.

In some embodiments, intermediates 2 are intermediates of type 2c. Intermediates 2c in which $R^1$, $R^2$, $R^3$, A and B are as described herein can be prepared by a methods well known in the art and as exemplified by the general synthetic procedure outlined in Scheme 13.

Alcohols of type 43 can be subjected to a Mitsunobu reaction with intermediates 44 in which PG is a suitable protective group such as a Cbz, Boc or Bn, using an appropriate phosphine such as triphenylphosphine and a dialkyl azodicarboxylate such as DEAD or DIAD in a suitable solvent such as THF to give intermediates 45 (step a). Mitsunobu reactions of that type are broadly described in literature (e.g., Fletcher, S., *Org. Chem. Front.* 2015, 2, 739; Kumara Swamy, K. C., et al., *Chem. Rev.* 2009, 109, 2551).

Removal of the protective group from intermediates 45 applying literature methods and as described for example under Scheme 11, step c (e.g., "*Protective Groups in Organic Chemistry*" by T. W. Greene and P. G. M. Wutts, 5$^{th}$ Ed., 2014, John Wiley & Sons, New York), furnishes intermediates 2c (step b).

Alternatively, intermediates 45 may be prepared from alcohols 43 that can be alkylated with compounds 46 in which LG is a suitable leaving group such as chlorine, bromine, iodine, —OSO$_2$alkyl (e.g., mesylate (methanesulfonate)), —OSO$_2$fluoroalkyl (e.g., triflate (trifluoromethanesulfonate)) or —OSO$_2$aryl (e.g., tosylate (p-toluenesulfonate)) using a suitable base in an appropriate solvent (e.g., sodium hydride in DMF) at temperatures between 0° C. and the boiling temperature of the solvent (step c).

Furthermore, intermediates 45 may be synthesized via alkylation of alcohols of type 44 with compounds 47 under the conditions described under step d.

In some embodiments, intermediates 2 are intermediates of type 2d. Intermediates 2d in which $R^1$, $R^2$, $R^3$, A and B are as described herein can be prepared by a methods known in the art and as exemplified by the general synthetic procedure outlined in Scheme 14.

Scheme 13

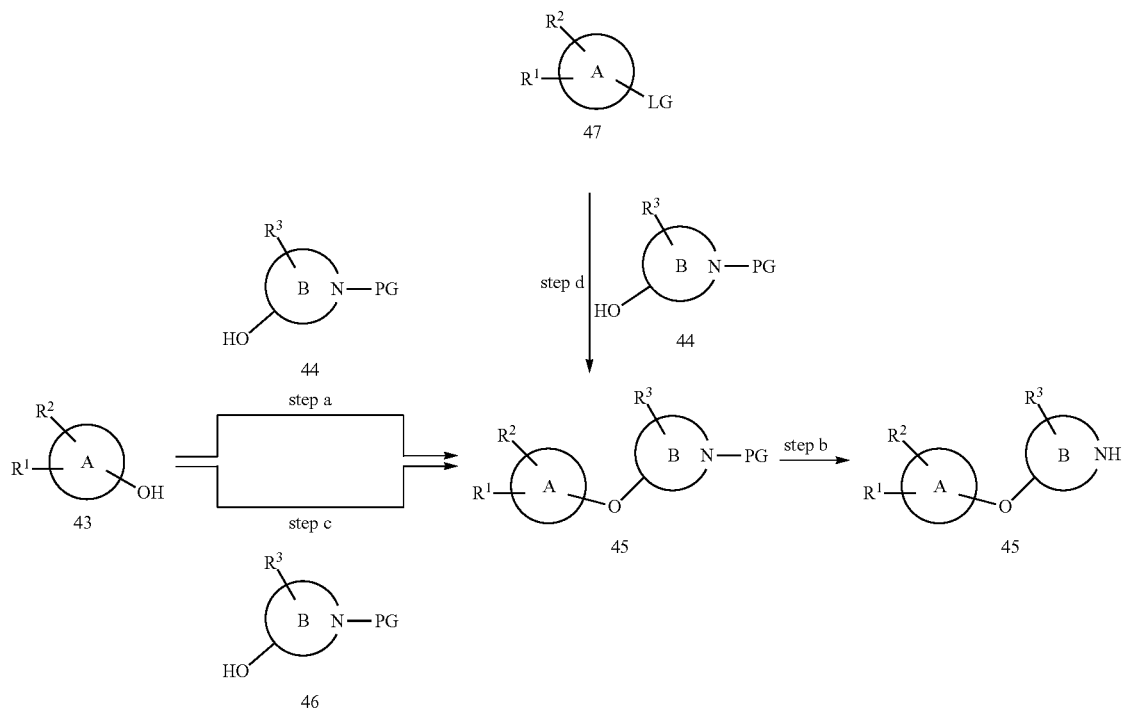

Scheme 14

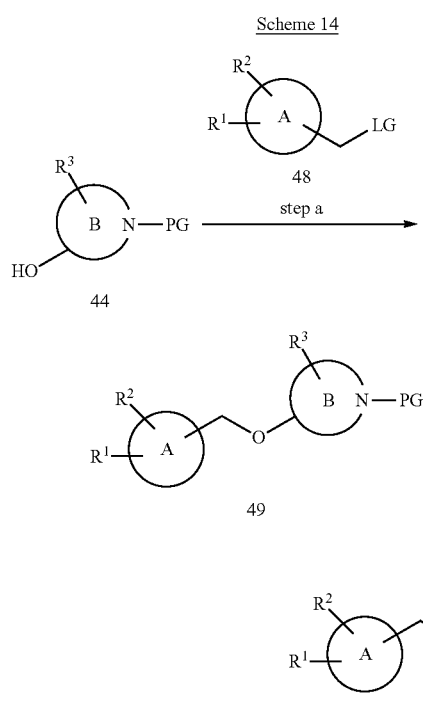

Intermediates 49 may be prepared from alcohols 44, either commercially available or prepared by methods known by a person skilled in the art and in which PG is a suitable protective group such as a Cbz, Boc or Bn, by alkylation with compounds 48 in which LG is a suitable leaving group such as chlorine, bromine, iodine, —OSO$_2$alkyl (e.g., mesylate (methanesulfonate)), —OSO$_2$fluoroalkyl (e.g., triflate (trifluoromethanesulfonate)) or —OSO$_2$aryl (e.g., tosylate (p-toluenesulfonate)) using a suitable base, such as sodium hydride, Huenig's base or KOt-Bu, in an appropriate solvent (e.g., in DMF or THF) at temperatures between 0° C. and the boiling temperature of the solvent (step a).

Removal of the protective group from intermediates 49 applying methods known in the art (e.g., a Boc group using TFA in DCM, 4 M HCl in 1,4-dioxane at temperatures between 0° C. and room temperature or 4-methylbenzenesulfonic acid hydrate in a solvent like ethyl acetate preferably at elevated temperatures, a Cbz group using hydrogen in the presence of a suitable catalyst such as Pd or Pd(OH)$_2$ on charcoal in a suitable solvent such as MeOH, EtOH, EtOAc or mixtures thereof and as described for example in "*Protective Groups in Organic Chemistry*" by T. W. Greene and P. G. M. Wutts, 5$^{th}$ Ed., 2014, John Wiley & Sons, New York), furnishes intermediates 2d (step b).

In some embodiments, intermediates 2 are intermediates of type 2e. Intermediates 2e in which R$^1$, R$^2$, R$^3$, A and B are as described herein can be prepared by a methods known in the art and as exemplified by the general synthetic procedure outlined in Scheme 15.

Scheme 15

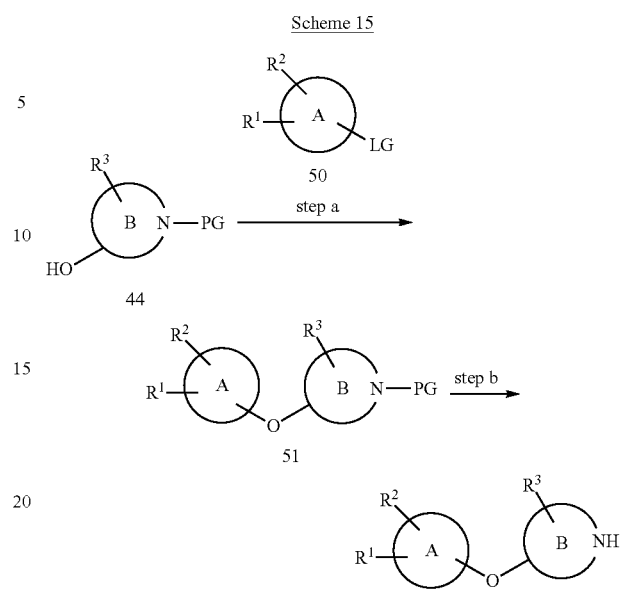

Intermediates 51 may be prepared from alcohols 44 by nucleophilic aromatic substitution with aryls or heteroaryls of general structure 50 in which LG is a suitable leaving group such as fluorine, —OSO$_2$alkyl (e.g., mesylate (methanesulfonate)), —OSO$_2$fluoroalkyl (e.g., triflate (trifluoromethanesulfonate)) or —OSO$_2$aryl (e.g., tosylate (p-toluenesulfonate)) using a suitable base such as Cs$_2$CO$_3$, Huenig's base or NaH, in an appropriate solvent, such as DMF at temperatures between 0° C. and the boiling temperature of the solvent (step a).

Removal of the protective group from intermediates 51 applying methods known in the art (e.g., a Boc group using TFA in DCM, 4 M HCl in 1,4-dioxane at temperatures between 0° C. and room temperature or 4-methylbenzenesulfonic acid hydrate in a solvent like ethyl acetate preferably at elevated temperatures, a Cbz group using hydrogen in the presence of a suitable catalyst such as Pd or Pd(OH)$_2$ on charcoal in a suitable solvent such as MeOH, EtOH, EtOAc or mixtures thereof and as described for example in "*Protective Groups in Organic Chemistry*" by T. W. Greene and P. G. M. Wutts, 5$^{th}$ Ed., 2014, John Wiley & Sons, New York), furnishes intermediates 2e (step b).

In some embodiments, intermediates 2 are intermediates of type 2f. Intermediates 2f in which R$^1$, R$^2$, R$^3$, A and B are as described herein can be prepared by a methods known in the art and as exemplified by the general synthetic procedure outlined in Scheme 16.

Scheme 16

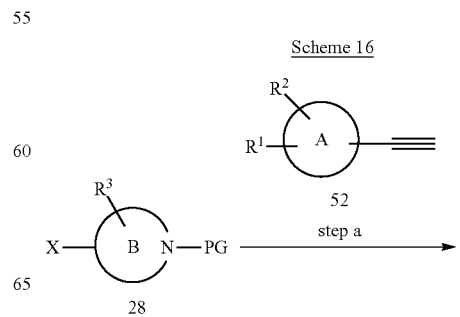

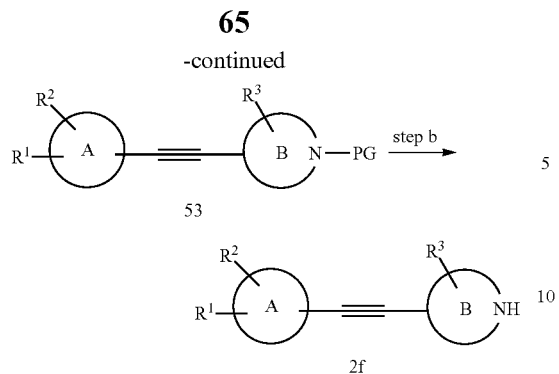

Compounds 28, either commercially available or prepared by methods known in the art, in which PG signifies a suitable protecting group and X is bromide or iodide can be subjected to cross-coupling reactions such as Sonogashira coupling reactions with acetylene compounds 52, either commercially available or prepared by methods known in the art, using a suitable catalyst (e.g., bis(triphenylphosphine)palladium(II) chloride, tetrakis(triphenylphosphine)palladium(0) or palladium(II)acetate with triphenylphosphine) in the presence of a copper(I) source (e.g., copper(I) iodide) in an appropriate solvent (e.g., THF, 1,4-dioxane, DME or mixtures thereof) and a suitable base (e.g., TEA, DIPEA) at temperatures between room temperature and the boiling point of the solvent or solvent mixture to afford intermediates 53 (step a). Reactions of this type are broadly described in literature and well known to persons skilled in the art.

Removal of the protective group from intermediates 53 applying methods known in the art (e.g., "*Protective Groups in Organic Chemistry*" by T. W. Greene and P. G. M. Wutts, 5$^{th}$ Ed., 2014, John Wiley & Sons, New York), furnishes intermediates 2f (step b).

In some embodiments, intermediates 2 are intermediates of type 2g, respectively. Intermediates of type 2g in which $R^1$, $R^2$, $R^3$, $R^4$, $R^5$, A and B are as described herein can be prepared by methods well known by a person skilled in the art and as exemplified by the general synthetic procedures outlined in Scheme 17.

Scheme 17

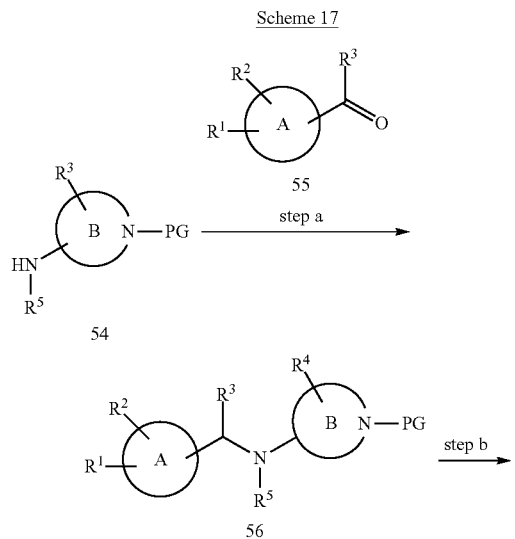

Reductive amination of primary ($R^5$=H) or secondary ($R^5$=alkyl, phenyl) amines like 54 with aldehydes ($R^3$=H) or ketones ($R^3$=alkyl, phenyl) of general structure 55 using a suitable reducing agent (e.g., sodium triacetoxy borohydride, sodium cyano borohydride) in a suitable solvent as MeOH, ethanol, isopropanol or ethylacetate procide intermediates 56 (step a). Removal of the protective group from intermediates 56 applying methods known in the art ("*Protective Groups in Organic Chemistry*" by T. W. Greene and P. G. M. Wutts, 5$^{th}$ Ed., 2014, John Wiley & Sons, New York), furnishes intermediates 2g (step b).

In one aspect, the present invention provides a compound of formula (I) as described herein, or a pharmaceutically acceptable salt thereof, when manufactured according to any one of the processes described herein.

MAGL Inhibitory Activity

Compounds of the present invention are MAGL inhibitors. Thus, in one aspect, the present invention provides the use of compounds of formula (I) as described herein for inhibiting MAGL in a mammal.

In a further aspect, the present invention provides compounds of formula (I) as described herein for use in a method of inhibiting MAGL in a mammal.

In a further aspect, the present invention provides the use of compounds of formula (I) as described herein for the preparation of a medicament for inhibiting MAGL in a mammal.

In a further aspect, the present invention provides a method for inhibiting MAGL in a mammal, which method comprises administering an effective amount of a compound of formula (I) as described herein to the mammal.

Compounds were profiled for MAGL inhibitory activity by determining the enzymatic activity by following the hydrolysis of the natural substrate 2-arachidonoylglycerol resulting in arachidonic acid, which can be followed by mass spectrometry. This assay is hereinafter abbreviated "2-AG assay".

The 2-AG assay was carried out in 384 well assay plates (PP, Greiner Cat #784201) in a total volume of 20 µL. Compound dilutions were made in 100% DMSO (VWR Chemicals 23500.297) in a polypropylene plate in 3-fold dilution steps to give a final concentration range in the assay from 12.5 µM to 0.8 pM. 0.25 µL compound dilutions (100% DMSO) were added to 9 µL MAGL in assay buffer (50 mM TRIS (GIBCO, 15567-027), 1 mM EDTA (Fluka, 03690-100 mL), 0.01% (v/v) Tween. After shaking, the plate was incubated for 15 min at RT. To start the reaction, 10 µL 2-arachidonoylglycerol in assay buffer was added. The final concentrations in the assay was 50 pM MAGL and 8 µM 2-arachidonoylglyerol. After shaking and 30 min incubation at RT, the reaction was quenched by the addition of 40 µL of ACN containing 4 µM of d8-arachidonic acid. The amount of arachidonic acid was traced by an online SPE system (Agilent Rapidfire) coupled to a triple quadrupole mass spectrometer (Agilent 6460). A C18 SPE cartridge (G9205A) was used in an ACN/water liquid setup. The mass spectrometer was operated in negative electrospray mode following the mass transitions 303.1→259.1 for arachidonic acid and 311.1→267.0 for d8-arachidonic acid. The activity of the compounds was calculated based on the ratio of intensities [arachidonic acid/d8-arachidonic acid].

TABLE 1

| Example | IC$_{50}$ MAGL [nM] |
| --- | --- |
| 1 | 3960 |
| 2 | 19 |
| 3 | 273 |
| 4 | 5 |
| 5 | 627 |
| 6 | 3 |
| 7 | 2578 |
| 8 | 26 |
| 9 | 550 |
| 10 | 5 |
| 11 | 12500 |
| 12 | 2313 |
| 13 | 12500 |
| 14 | 2108 |
| 15 | 12500 |
| 16 | 213 |
| 17 | 12500 |
| 18 | 2673 |
| 19 | 1554 |
| 20 | 7 |
| 21 | 254 |
| 22 | 1 |
| 23 | 381 |
| 24 | 2 |
| 25 | 1 |
| 26 | 4 |
| 27 | 0.5 |
| 28 | 10 |
| 29 | 6 |
| 30 | 1 |
| 31 | 83 |
| 32 | 17 |
| 33 | 12 |
| 34 | 14 |
| 35 | 13 |
| 36 | 4032 |
| 37 | 339 |
| 38 | 234 |
| 39 | 58 |
| 40 | 21 |
| 41 | 23 |
| 42 | 218 |
| 43 | 6951 |
| 44 | 61 |
| 45 | 321 |
| 46 | 323 |
| 47 | 430 |
| 48 | 598 |
| 49 | 605 |
| 50 | 12500 |
| 51 | 287 |
| 52 | 167 |
| 53 | 907 |
| 54 | 36 |
| 55 | 33 |
| 56 | 5 |
| 57 | 2 |
| 58 | 4 |
| 59 | 2 |
| 60 | 33 |
| 61 | 13 |
| 62 | 26 |
| 63 | 19 |
| 64 | 93 |
| 65 | 2 |
| 66 | 13 |
| 67 | 27 |
| 68 | 59 |
| 69 | 122 |
| 70 | 62 |
| 71 | 1 |
| 72 | 7 |
| 73 | 1 |
| 74 | 5 |
| 75 | 57 |
| 76 | 81 |
| 77 | 35 |
| 78 | 981 |
| 79 | 33 |
| 80 | 27 |
| 81 | 7 |
| 82 | 0.5 |
| 83 | 44 |
| 84 | 294 |
| 85 | 123 |
| 86 | 54 |
| 87 | 32 |
| 88 | 1298 |
| 89 | 0.02 |
| 90 | 0.02 |
| 91 | 357 |
| 92 | 293 |
| 93 | 173 |
| 94 | 10 |
| 95 | 0.35 |
| 96 | 2 |
| 97 | 350 |
| 98 | 3374 |
| 99 | 5 |
| 100 | 7 |
| 101 | 481 |
| 102 | 420 |
| 103 | 54 |
| 104 | 177 |
| 105 | 43 |
| 106 | 729 |
| 107 | 216 |
| 108 | 7 |
| 109 | 39 |
| 110 | 70 |
| 111 | 1175 |
| 112 | 43 |
| 113 | 3 |
| 114 | 0.18 |
| 115 | 3 |
| 116 | 160 |
| 117 | 10 |
| 118 | 12 |
| 119 | 33 |
| 120 | 19 |
| 121 | 2 |
| 122 | 379 |
| 123 | 982 |
| 124 | 3 |
| 125 | 9 |
| 126 | 25 |
| 127 | 1796 |
| 128 | 0.26 |
| 129 | 3 |
| 130 | 251 |
| 131 | 1 |
| 132 | 9 |
| 133 | 2 |
| 134 | 16 |
| 135 | 5 |
| 136 | 22 |
| 137 | 43 |
| 138 | 62 |
| 139 | 123 |
| 140 | 28 |
| 141 | 78 |
| 142 | 13 |
| 143 | 190 |
| 144 | 172 |
| 145 | 73 |
| 146 | 137 |
| 147 | 2272 |
| 148 | 498 |

TABLE 1-continued

| Example | IC$_{50}$ MAGL [nM] |
|---|---|
| 149 | 976 |
| 150 | 2142 |
| 151 | 1240 |
| 152 | 1411 |
| 153 | 2331 |
| 154 | 95 |
| 155 | 284 |
| 156 | 279 |
| 157 | 25 |
| 158 | 582 |
| 159 | 434 |
| 160 | 1329 |
| 161 | 65 |
| 162 | 108 |
| 163 | 9 |
| 164 | 12 |
| 165 | 24 |
| 166 | 48 |
| 167 | 27 |
| 168 | 2015 |
| 169 | 854 |
| 170 | 329 |
| 171 | 21 |
| 172 | 827 |
| 173 | 45 |
| 174 | 20 |
| 175 | 17 |
| 176 | 12 |
| 177 | 353 |
| 178 | 181 |
| 179 | 46 |
| 180 | 93 |
| 181 | 227 |
| 182 | 246 |
| 183 | 84 |
| 184 | 59 |
| 185 | 464 |
| 186 | 2 |
| 187 | 206 |
| 188 | 25 |
| 189 | 16 |
| 190 | 140 |
| 191 | 37 |
| 192 | 1217 |
| 193 | 794 |
| 194 | 61 |
| 195 | 28 |
| 196 | 507 |
| 197 | 324 |
| 198 | 73 |
| 199 | 14 |
| 200 | 1 |
| 201 | 9 |
| 202 | 37 |
| 203 | 75 |
| 204 | 98 |
| 205 | 170 |
| 206 | 16 |
| 207 | 17 |
| 208 | 138 |
| 209 | 131 |
| 210 | 59 |
| 211 | 84 |
| 212 | 25 |
| 213 | 2250 |
| 214 | 157 |
| 215 | 860 |
| 216 | 68 |
| 217 | 33 |
| 218 | 1215 |

In one aspect, the present invention provides compounds of formula (I) and their pharmaceutically acceptable salts or esters as described herein, wherein said compounds of formula (I) and their pharmaceutically acceptable salts or esters have IC$_{50}$'s for MAGL inhibition below 25 µM, preferably below 10 µM, more preferably below 5 µM as measured in the MAGL assay described herein.

In one embodiment, compounds of formula (I) and their pharmaceutically acceptable salts or esters as described herein have IC$_{50}$ (MAGL inhibition) values between 0.000001 µM and 25 µM, particular compounds have IC$_{50}$ values between 0.000005 µM and 10 µM, further particular compounds have IC$_{50}$ values between 0.00005 µM and 5 µM, as measured in the MAGL assay described herein.

Using the Compounds of the Invention

In one aspect, the present invention provides compounds of formula (I), or pharmaceutically acceptable salts thereof, as described herein for use as therapeutically active substance.

In a further aspect, the present invention provides the use of compounds of formula (I), or pharmaceutically acceptable salts thereof, as described herein for the treatment or prophylaxis of neuroinflammation, neurodegenerative diseases, pain, cancer, mental disorders and/or inflammatory bowel disease in a mammal.

In one embodiment, the present invention provides the use of compounds of formula (I), or pharmaceutically acceptable salts thereof, as described herein for the treatment or prophylaxis of neuroinflammation and/or neurodegenerative diseases in a mammal.

In one embodiment, the present invention provides the use of compounds of formula (I), or pharmaceutically acceptable salts thereof, as described herein for the treatment or prophylaxis of neurodegenerative diseases in a mammal.

In one embodiment, the present invention provides the use of compounds of formula (I), or pharmaceutically acceptable salts thereof, as described herein for the treatment or prophylaxis of cancer in a mammal.

In one embodiment, the present invention provides the use of compounds of formula (I), or pharmaceutically acceptable salts thereof, as described herein for the treatment or prophylaxis of inflammatory bowel disease in a mammal.

In one embodiment, the present invention provides the use of compounds of formula (I), or pharmaceutically acceptable salts thereof, as described herein for the treatment or prophylaxis of pain in a mammal.

In one aspect, the present invention provides the use of compounds of formula (I), or pharmaceutically acceptable salts thereof, as described herein for the treatment or prophylaxis of multiple sclerosis, Alzheimer's disease, Parkinson's disease, amyotrophic lateral sclerosis, traumatic brain injury, neurotoxicity, stroke, epilepsy, anxiety, migraine, depression, hepatocellular carcinoma, colon carcinogenesis, ovarian cancer, neuropathic pain, chemotherapy induced neuropathy, acute pain, chronic pain, spasticity associated with pain, abdominal pain, abdominal pain associated with irritable bowel syndrome and/or visceral pain in a mammal.

In a preferred embodiment, the present invention provides the use of compounds of formula (I), or pharmaceutically acceptable salts thereof, as described herein for the treatment or prophylaxis of multiple sclerosis, Alzheimer's disease and/or Parkinson's disease in a mammal.

In a particularly preferred embodiment, the present invention provides the use of compounds of formula (I), or pharmaceutically acceptable salts thereof, as described herein for the treatment or prophylaxis of multiple sclerosis in a mammal.

In one aspect, the present invention provides compounds of formula (I), or pharmaceutically acceptable salts thereof, as described herein for use in the treatment or prophylaxis of neuroinflammation, neurodegenerative diseases, pain, cancer, mental disorders and/or inflammatory bowel disease in a mammal.

In one embodiment, the present invention provides compounds of formula (I), or pharmaceutically acceptable salts thereof, as described herein for use in the treatment or prophylaxis of neuroinflammation and/or neurodegenerative diseases in a mammal.

In one embodiment, the present invention provides compounds of formula (I), or pharmaceutically acceptable salts thereof, as described herein for use in the treatment or prophylaxis of cancer in a mammal.

In one embodiment, the present invention provides compounds of formula (I), or pharmaceutically acceptable salts thereof, as described herein for use in the treatment or prophylaxis of neurodegenerative diseases in a mammal.

In one embodiment, the present invention provides compounds of formula (I), or pharmaceutically acceptable salts thereof, as described herein for use in the treatment or prophylaxis of inflammatory bowel disease in a mammal.

In one embodiment, the present invention provides compounds of formula (I), or pharmaceutically acceptable salts thereof, as described herein for use in the treatment or prophylaxis of pain in a mammal.

In one aspect, the present invention provides compounds of formula (I), or pharmaceutically acceptable salts thereof, as described herein for use in the treatment or prophylaxis of multiple sclerosis, Alzheimer's disease, Parkinson's disease, amyotrophic lateral sclerosis, traumatic brain injury, neurotoxicity, stroke, epilepsy, anxiety, migraine, depression, hepatocellular carcinoma, colon carcinogenesis, ovarian cancer, neuropathic pain, chemotherapy induced neuropathy, acute pain, chronic pain, spasticity associated with pain, abdominal pain, abdominal pain associated with irritable bowel syndrome and/or visceral pain in a mammal.

In a preferred embodiment, the present invention provides compounds of formula (I), or pharmaceutically acceptable salts thereof, as described herein for use in the treatment or prophylaxis of multiple sclerosis, Alzheimer's disease and/or Parkinson's disease in a mammal.

In a particularly preferred embodiment, the present invention provides compounds of formula (I), or pharmaceutically acceptable salts thereof, as described herein for use in the treatment or prophylaxis of multiple sclerosis in a mammal.

In one aspect, the present invention provides the use of compounds of formula (I), or pharmaceutically acceptable salts thereof, as described herein for the preparation of a medicament for the treatment or prophylaxis of neuroinflammation, neurodegenerative diseases, pain, cancer, mental disorders and/or inflammatory bowel disease in a mammal.

In one embodiment, the present invention provides the use of compounds of formula (I), or pharmaceutically acceptable salts thereof, as described herein for the preparation of a medicament for the treatment or prophylaxis of neuroinflammation and/or neurodegenerative diseases in a mammal.

In one embodiment, the present invention provides the use of compounds of formula (I), or pharmaceutically acceptable salts thereof, as described herein for the preparation of a medicament for the treatment or prophylaxis of neurodegenerative diseases in a mammal.

In one embodiment, the present invention provides the use of compounds of formula (I), or pharmaceutically acceptable salts thereof, as described herein for the preparation of a medicament for the treatment or prophylaxis of cancer in a mammal.

In one embodiment, the present invention provides the use of compounds of formula (I), or pharmaceutically acceptable salts thereof, as described herein for the preparation of a medicament for the treatment or prophylaxis of inflammatory bowel disease in a mammal.

In one embodiment, the present invention provides the use of compounds of formula (I), or pharmaceutically acceptable salts thereof, as described herein for the preparation of a medicament for the treatment or prophylaxis of pain in a mammal.

In a further aspect, the present invention provides the use of compounds of formula (I), or pharmaceutically acceptable salts thereof, as described herein for the preparation of a medicament for the treatment or prophylaxis of multiple sclerosis, Alzheimer's disease, Parkinson's disease, amyotrophic lateral sclerosis, traumatic brain injury, neurotoxicity, stroke, epilepsy, anxiety, migraine, depression, hepatocellular carcinoma, colon carcinogenesis, ovarian cancer, neuropathic pain, chemotherapy induced neuropathy, acute pain, chronic pain, spasticity associated with pain, abdominal pain, abdominal pain associated with irritable bowel syndrome and/or visceral pain in a mammal.

In a preferred embodiment, the present invention provides the use of compounds of formula (I), or pharmaceutically acceptable salts thereof, as described herein for the preparation of a medicament for the treatment or prophylaxis of multiple sclerosis, Alzheimer's disease and/or Parkinson's disease in a mammal.

In a particularly preferred embodiment, the present invention provides the use of compounds of formula (I), or pharmaceutically acceptable salts thereof, as described herein for the preparation of a medicament for the treatment or prophylaxis of multiple sclerosis in a mammal.

In one aspect, the present invention provides a method for the treatment or prophylaxis of neuroinflammation, neurodegenerative diseases, pain, cancer, mental disorders and/or inflammatory bowel disease in a mammal, which method comprises administering an effective amount of a compound of formula (I), or a pharmaceutically acceptable salt thereof, as described herein to the mammal.

In one embodiment, the present invention provides a method for the treatment or prophylaxis of neuroinflammation and/or neurodegenerative diseases in a mammal, which method comprises administering an effective amount of a compound of formula (I), or a pharmaceutically acceptable salt thereof, as described herein to the mammal.

In one embodiment, the present invention provides a method for the treatment or prophylaxis of neurodegenerative diseases in a mammal, which method comprises administering an effective amount of a compound of formula (I), or a pharmaceutically acceptable salt thereof, as described herein to the mammal.

In one embodiment, the present invention provides a method for the treatment or prophylaxis of cancer in a mammal, which method comprises administering an effective amount of a compound of formula (I), or a pharmaceutically acceptable salt thereof, as described herein to the mammal.

In one embodiment, the present invention provides a method for the treatment or prophylaxis of inflammatory bowel disease in a mammal, which method comprises administering an effective amount of a compound of formula (I), or a pharmaceutically acceptable salt thereof, as described herein to the mammal.

In one embodiment, the present invention provides a method for the treatment or prophylaxis of pain in a mammal, which method comprises administering an effective amount of a compound of formula (I), or a pharmaceutically acceptable salt thereof, as described herein to the mammal.

In a further aspect, the present invention provides a method for the treatment or prophylaxis of multiple sclerosis, Alzheimer's disease, Parkinson's disease, amyotrophic lateral sclerosis, traumatic brain injury, neurotoxicity, stroke, epilepsy, anxiety, migraine, depression, hepatocellular carcinoma, colon carcinogenesis, ovarian cancer, neuropathic pain, chemotherapy induced neuropathy, acute pain, chronic pain, spasticity associated with pain, abdominal pain, abdominal pain associated with irritable bowel syndrome and/or visceral pain in a mammal, which method comprises administering an effective amount of a compound of formula (I), or a pharmaceutically acceptable salt thereof, as described herein to the mammal.

In a preferred embodiment, the present invention provides a method for the treatment or prophylaxis of multiple sclerosis, Alzheimer's disease and/or Parkinson's disease in a mammal, which method comprises administering an effective amount of a compound of formula (I), or a pharmaceutically acceptable salt thereof, as described herein to the mammal.

In a particularly preferred embodiment, the present invention provides a method for the treatment or prophylaxis of multiple sclerosis in a mammal, which method comprises administering an effective amount of a compound of formula (I), or a pharmaceutically acceptable salt thereof, as described herein to the mammal.

Pharmaceutical Compositions and Administration

In one aspect, the present invention provides a pharmaceutical composition comprising a compound of formula (I), or a pharmaceutically acceptable salt thereof, as described herein and a therapeutically inert carrier.

In one embodiment, the present invention provides the pharmaceutical compositions disclosed in Examples 219 and 220.

The compounds of formula (I) and their pharmaceutically acceptable salts and esters can be used as medicaments (e.g., in the form of pharmaceutical preparations). The pharmaceutical preparations can be administered internally, such as orally (e.g., in the form of tablets, coated tablets, dragées, hard and soft gelatin capsules, solutions, emulsions or suspensions), nasally (e.g., in the form of nasal sprays) or rectally (e.g., in the form of suppositories). However, the administration can also be effected parentally, such as intramuscularly or intravenously (e.g., in the form of injection solutions).

The compounds of formula (I) and their pharmaceutically acceptable salts and esters can be processed with pharmaceutically inert, inorganic or organic adjuvants for the production of tablets, coated tablets, dragées and hard gelatin capsules. Lactose, corn starch or derivatives thereof, talc, stearic acid or its salts etc. can be used, for example, as such adjuvants for tablets, dragées and hard gelatin capsules.

Suitable adjuvants for soft gelatin capsules are, for example, vegetable oils, waxes, fats, semi-solid substances and liquid polyols, etc.

Suitable adjuvants for the production of solutions and syrups are, for example, water, polyols, saccharose, invert sugar, glucose, etc.

Suitable adjuvants for injection solutions are, for example, water, alcohols, polyols, glycerol, vegetable oils, etc.

Suitable adjuvants for suppositories are, for example, natural or hardened oils, waxes, fats, semi-solid or liquid polyols, etc.

Moreover, the pharmaceutical preparations can contain preservatives, solubilizers, viscosity-increasing substances, stabilizers, wetting agents, emulsifiers, sweeteners, colorants, flavorants, salts for varying the osmotic pressure, buffers, masking agents or antioxidants. They can also contain still other therapeutically valuable substances.

The dosage can vary in wide limits and will, of course, be fitted to the individual requirements in each particular case. In general, in the case of oral administration a daily dosage of about 0.1 mg to 20 mg per kg body weight, preferably about 0.5 mg to 4 mg per kg body weight (e.g., about 300 mg per person), divided into preferably 1-3 individual doses, which can consist, for example, of the same amounts, should be appropriate. It will, however, be clear that the upper limit given herein can be exceeded when this is shown to be indicated.

EXAMPLES

The invention will be more fully understood by reference to the following examples. The claims should not, however, be construed as limited to the scope of the examples.

In case the preparative examples are obtained as a mixture of enantiomers, the pure enantiomers can be separated by methods described herein or by methods known to the man skilled in the art, such as e.g., chiral chromatography (e.g., chiral SFC) or crystallization.

All reaction examples and intermediates were prepared under an argon atmosphere if not specified otherwise.

The number of counterions present in a final salt depends on the number of basic atoms within a structure. For the sake of simplicity, the generation of salt names always assumes the formation of compounds with a single anion.

Example 1 and Example 2

(−)-5-[3-[3-[[2-Fluoro-4-(trifluoromethyl)phenyl]methoxy]azetidin-1-yl]-3-oxo-propyl]pyrrolidin-2-one and (+)-5-[3-[3-[[2-Fluoro-4-(trifluoromethyl)phenyl]methoxy]azetidin-1-yl]-3-oxo-propyl]pyrrolidin-2-one

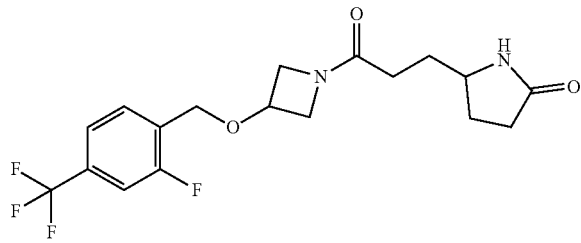 [SMILES: O=C1CCC(CCC(=O)N2CC(OCc3ccc(C(F)(F)F)cc3F)C2)N1]

The enantiomers of 5-[3-[3-[[2-fluoro-4-(trifluoromethyl)phenyl]methoxy]azetidin-1-yl]-3-oxo-propyl]pyrrolidin-2-one (78.0 mg, 0.20 mmol) were separated by chiral SFC (Chiralpak AD-H column (250 mm×20 mm, 5 μm), eluent: 35% MeOH (0.1% $NH_4OH$) in supercritical $CO_2$) to give (−)-5-[3-[3-[[2-fluoro-4-(trifluoromethyl)phenyl]methoxy]azetidin-1-yl]-3-oxo-propyl]pyrrolidin-2-one (23.4 mg, 29%) and (+)-5-[3-[3-[[2-fluoro-4-(trifluoromethyl)phenyl]methoxy]azetidin-1-yl]-3-oxo-propyl]pyrrolidin-2-one (29.4 mg, 36%) as light brown oil.

(−)-Enantiomer: MS (ESI): m/z=389.0 $[M+H]^+$. Specific Rotation: −8.49°

(+)-Enantiomer: MS (ESI): m/z=389.1 $[M+H]^+$. Specific Rotation: +8.25°

5-[3-[3-[[2-Fluoro-4-(trifluoromethyl phenyl]methoxy]azetidin-1-yl]-3-oxo-propyl]pyrrolidin-2-one A solution of 3-(5-oxopyrrolidin-2-yl)propanoic acid (250.0 mg, 1.59 mmol, 1.0 equiv; BB 1), 3-[[2-fluoro-4-(trifluoromethyl)phenyl]methoxy]azetidine; 4-methylbenzenesulfonic acid (670.0 mg, 1.59 mmol, 1.0 equiv; BB 2), $T_3P$/ethyl acetate (732.1 mg, 3.18 mmol, 2.0 equiv, wt. 50%) and DIPEA (1.23 g, 9.54 mmol, 6.0 equiv) in DMF (6 mL) was stirred at 25° C. for 12 h. The reaction mixture was diluted with water (20 mL) and extracted with ethyl acetate (3×10 mL). The combined organic layers were dried over $MgSO_4$, concentrated and the residue purified by preparative HPLC (Shim-pack C18 column (150 mm×25 mm, 10 μm); 0.225% v/v FA in water and MeCN) to give the desired product as colorless oil (78 mg, 13%). MS (ESI): m/z=389.2 $[M+H]^+$.

Example 3 and Example 4

(−)-5-[3-[3-(4-tert-Butylphenyl)azetidin-1-yl]-3-oxo-propyl]pyrrolidin-2-one and (+)-5-[3-[3-(4-tert-Butylphenyl)azetidin-1-yl]-3-oxo-propyl]pyrrolidin-2-one

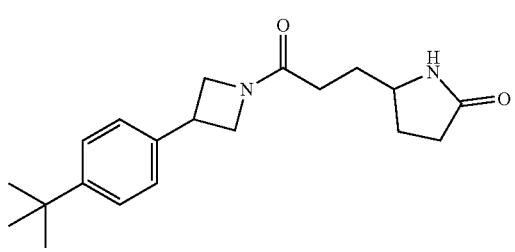 [SMILES: CC(C)(C)c1ccc(C2CN(C(=O)CCC3CCC(=O)N3)C2)cc1]

The enantiomers of 5-[3-[3-(4-tert-butylphenyl)azetidin-1-yl]-3-oxo-propyl]pyrrolidin-2-one (41 mg, 0.13 mmol) were separated by chiral HPLC (Chiralcel OD column (500 mm×50 mm, 20 μm), eluent: 60% MeOH/40% EtOH ($NH_4OH$)) to give (−)-5-[3-[3-(4-tert-butylphenyl)azetidin-1-yl]-3-oxo-propyl]pyrrolidin-2-one (4.7 mg, 9%; first eluting isomer) as brown solid and (+)-5-[3-[3-(4-tert-butylphenyl)azetidin-1-yl]-3-oxo-propyl]pyrrolidin-2-one (8.5 mg, 14%; second eluting isomer) as brown solid. MS (ESI): m/z=329.3 $[M+H]^+$ for both examples.

5-[3-[3-(4-tert-Butylphenyl)azetidin-1-yl]-3-oxo-propyl]pyrrolidin-2-one

A solution of 3-(5-oxopyrrolidin-2-yl)propanoic acid (50 mg, 0.32 mmol, 1.0 equiv; BB 1), 3-(4-(tert-butyl)phenyl)azetidine; 4-methylbenzenesulfonic acid (119.3 mg, 0.33 mmol, 1.05 equiv; BB 3), $T_3P$/ethyl acetate (304 mg, 0.48 mmol, 1.5 equiv; wt. 50%) and TEA (247 mg, 0.34 mL, 2.44 mmol, 7.7 equiv) in ethyl acetate (4 mL) was stirred at RT for 12 h. The solvent was removed under vacuo, FA (100 μL) was added and the residue purified by preparative HPLC (Phenomenex Gemini 5 μm C18 110 A Axia column (75 mm×30 mm, 5 μm); 0.1% v/v FA in water and MeCN) to give the title compound as colorless oil (41 mg, 39%). MS (ESI): m/z=329.3 $[M+H]^+$.

If not indicated otherwise the following examples were synthesized in analogy to the synthesis described for Example 3 and Example 4 using suitable building blocks, respectively.

| Ex. | Systematic Name | Structure | Building blocks | Comment | MS m/z |
|---|---|---|---|---|---|
| 5 | (−)-5-[3-Oxo-3-[3-[4-[1-(trifluoromethyl)cyclopropyl]phenyl]azetidin-1-yl]propyl]pyrrolidin-2-one | 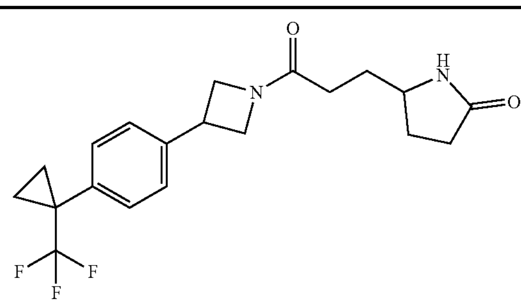 | 3-(5-Oxopyrrolidin-2-yl)propanoic acid (BB 1) and 3-[4-[1-(Trifluoromethyl)cyclopropyl]phenyl]azetidine; 4-methylbenzenesulfonic acid (BB 4) | Chiralcel OD; first eluting enantiomer | 381.3 $[M + H]^+$ |

-continued

| Ex. | Systematic Name | Structure | Building blocks | Comment | MS m/z |
|---|---|---|---|---|---|
| 6 | (+)-5-[3-Oxo-3-[3-[4-[1-(trifluoromethyl)cyclopropyl]phenyl]azetidin-1-yl]propyl]pyrrolidin-2-one | 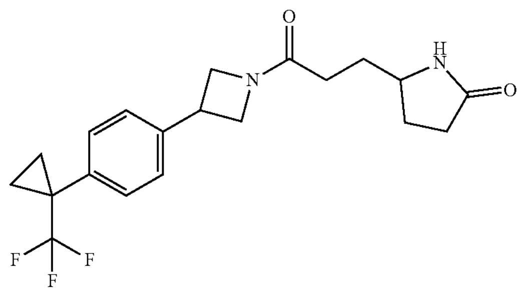 [SMILES: O=C1CCC(CCC(=O)N2CC(c3ccc(C4(C(F)(F)F)CC4)cc3)C2)N1] | 3-(5-Oxopyrrolidin-2-yl)propanoic acid (BB 1) and 3-[4-[1-(Trifluoromethyl)cyclopropyl]phenyl]azetidine; 4-methyl-benzenesulfonic acid (BB 4) | Chiralcel OD; second eluting enantiomer | 381.3 [M + H]⁺ |
| 7 | (−)- or (+)-5-[3-Oxo-3-[3-[4-(2,2,2-trifluoroethyl)phenyl]azetidin-1-yl]propyl]pyrrolidin-2-one | 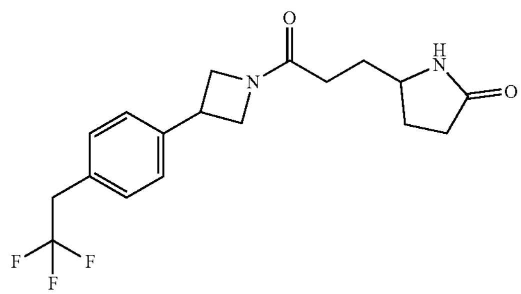 [SMILES: O=C1CCC(CCC(=O)N2CC(c3ccc(CC(F)(F)F)cc3)C2)N1] | 3-(5-Oxopyrrolidin-2-yl)propanoic acid (BB 1) and 3-[4-(2,2,2-Trifluoroethyl)phenyl]azetidine; 4-methylbenzene-sulfonic acid (BB 5) | Chiralpak AD; first eluting enantiomer | 355.1 [M + H]⁺ |
| 8 | (+)- or (−)-5-[3-Oxo-3-[3-[4-(2,2,2-trifluoroethyl)phenyl]azetidin-1-yl]propyl]pyrrolidin-2-one | 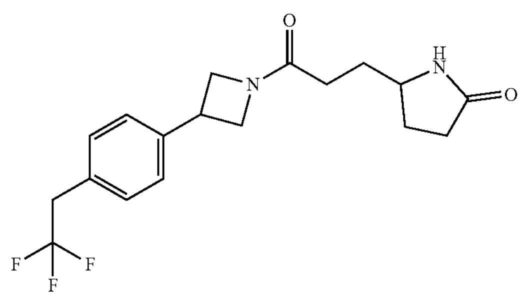 [SMILES: O=C1CCC(CCC(=O)N2CC(c3ccc(CC(F)(F)F)cc3)C2)N1] | 3-(5-Oxopyrrolidin-2-yl)propanoic acid (BB 1) and 3-[4-(2,2,2-Trifluoroethyl)phenyl]azetidine; 4-methylbenzene-sulfonic acid (BB 5) | Chiralpak AD; second eluting enantiomer | 355.3 [M + H]⁺ |
| 9 | (−)-5-[3-[3-[4-(2,4-Difluorophenyl)phenyl]azetidin-1-yl]-3-oxo-propyl]pyrrolidin-2-one | 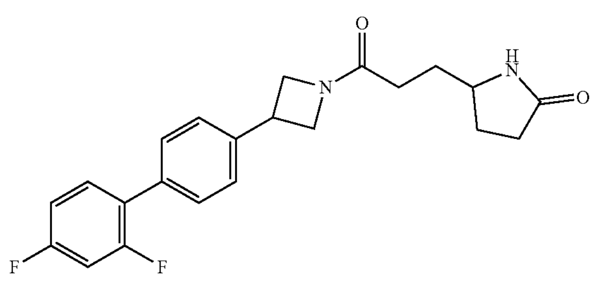 [SMILES: O=C1CCC(CCC(=O)N2CC(c3ccc(-c4ccc(F)cc4F)cc3)C2)N1] | 3-(5-Oxopyrrolidin-2-yl)propanoic acid (BB 1) and 3-[4-(2,4-Difluoro-phenyl)phenyl]azetidine; 4-methylbenzene-sulfonic acid (BB 6) | Chiralcel OD; first eluting enantiomer | 385.2 [M + H]⁺ |
| 10 | (+)-5-[3-[3-[4-(2,4-Difluorophenyl)phenyl]azetidin-1-yl]-3-oxo-propyl]pyrrolidin-2-one | 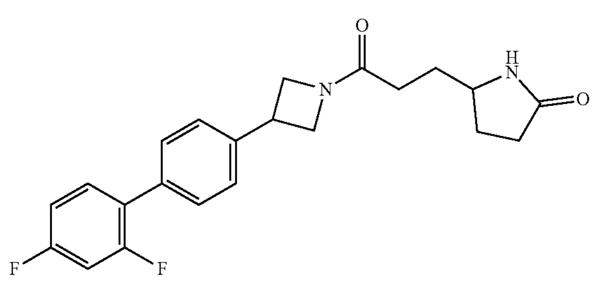 [SMILES: O=C1CCC(CCC(=O)N2CC(c3ccc(-c4ccc(F)cc4F)cc3)C2)N1] | 3-(5-Oxopyrrolidin-2-yl)propanoic acid (BB 1) and 3-[4-(2,4-Difluoro-phenyl)phenyl]azetidine; 4-methylbenzene-sulfonic acid (BB 6) | Chiralcel OD; second eluting enantiomer | 385.3 [M + H]⁺ |

Example 11 and Example 12

(−)-5-[3-Oxo-3-[rac-(3aS,6aS)-2-[[2-fluoro-4-(trifluoromethyl)phenyl]methyl]-1,3,3a,4,6,6a-hexahydropyrrolo[3,4-c]pyrrol-5-yl]propyl]pyrrolidin-2-one and (+)-5-[3-Oxo-3-[rac-(3aS,6aS)-2-[[2-fluoro-4-(trifluoromethyl)phenyl]methyl]-1,3,3a,4,6,6a-hexahydropyrrolo[3,4-c]pyrrol-5-yl]propyl]pyrrolidin-2-one

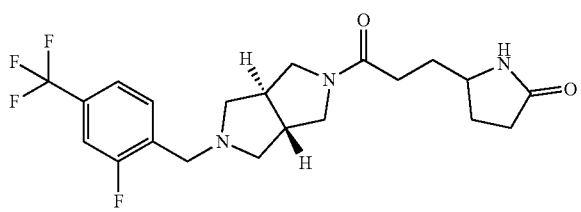 [SMILES: O=C1CCC(CCC(=O)N2C[C@@H]3CN(Cc4ccc(C(F)(F)F)cc4F)C[C@H]3C2)N1]

The enantiomers of 5-[3-oxo-3-[rac-(3aS,6aS)-2-[[2-fluoro-4-(trifluoromethyl)phenyl]methyl]-1,3,3a,4,6,6a-hexahydropyrrolo[3,4-c]pyrrol-5-yl]propyl]pyrrolidin-2-one (28 mg, 0.066 mmol) were separated by chiral HPLC (Chiralcel OD column (500 mm×50 mm, 20 μm), eluent: 60% MeOH/40% EtOH (0.1% NH$_4$OH)) to give (−)-5-[3-oxo-3-[rac-(3aS,6aS)-2-[[2-fluoro-4-(trifluoromethyl)phenyl]methyl]-1,3,3a,4,6,6a-hexahydropyrrolo[3,4-c]pyrrol-5-yl]propyl]pyrrolidin-2-one (4.9 mg, 5%; first eluting compound) as brown viscous oil and (+)-5-[3-oxo-3-[rac-(3aS,6aS)-2-[[2-fluoro-4-(trifluoromethyl)phenyl]methyl]-1,3,3a,4,6,6a-hexahydropyrrolo[3,4-c]pyrrol-5-yl]propyl]pyrrolidin-2-one (3.7 mg, 4%; second eluting compound) as brown viscous oil. MS (ESI): m/z=428.3 [M+H]$^+$ for both examples.

Step 1: Tert-Butyl Rac-(3aR,6aR)-2-[3-(5-oxopyrrolidin-2-yl)propanoyl]-1,3,3a,4,6,6a-hexahydropyrrolo[3,4-c]pyrrole-5-carboxylate To a solution of 3-(5-oxopyrrolidin-2-yl)propanoic acid (150 mg, 0.95 mmol, 1.0 equiv; BB 1), TBTU (322 mg, 1.0 mmol, 1.05 equiv) and DIPEA (370 mg, 500 μL, 2.86 mmol, 3.0 equiv) in DMF (3.4 mL) was added tert-butyl rac-(3aR,6aR)-2,3,3a,4,6,6a-hexahydro-1H-pyrrolo[3,4-c]pyrrole-5-carboxylate hydrochloride (249 mg, 1.0 mmol, 1.05 equiv; CAS RN 1812198-23-4) at RT. The reaction mixture was stirred for 5 h and allowed to stand overnight at 0° C. The solid was filtered off to provide the title compound as an off-white solid (181 mg, 54%). MS (ESI): m/z=296.1 [M+H]$^+$.

Step 2: 5-[3-Oxo-3-[rac-(3aS,6aS)-2,3,3a,4,6,6a-hexahydro-1H-pyrrolo[3,4-c]pyrrol-5-yl]propyl]pyrrolidin-2-one Hydrochloride To a solution of tert-butyl rac-(3aR,6aR)-2-[3-(5-oxopyrrolidin-2-yl)propanoyl]-1,3,3a,4,6,6a-hexahydropyrrolo[3,4-c]pyrrole-5-carboxylate (180 mg, 0.51 mmol, 1.0 equiv) in DCM (20 mL) was added HCl (1.28 mL, 5.12 mmol, 10 equiv; 4 M sol. in dioxan) and the reaction mixture was stirred at RT. After 2 h, the solvent was evaporated, the white precipitate filtered, washed with diethylether and dried under vacuum. The title compound was obtained as a brown solid (101 mg, 69%). MS (ESI): m/z=252.2 [M+H]$^+$.

Step 3: 5-[3-Oxo-3-[rac-(3aS,6aS)-2-[[2-fluoro-4-(trifluoromethyl)phenyl]methyl]-1,3,3a,4,6,6a-hexahydropyrrolo[3,4-c]pyrrol-5-yl]propyl]pyrrolidin-2-one To a suspension of 5-[3-oxo-3-[rac-(3aS,6aS)-2,3,3a,4,6,6a-hexahydro-1H-pyrrolo[3,4-c]pyrrol-5-yl]propyl]pyrrolidin-2-one hydrochloride (60 mg, 0.21 mmol, 1.0 equiv) in DMF (0.75 mL) was added potassium carbonate (115 mg, 0.83 mmol, 4.0 equiv) and the reaction mixture was stirred at RT. After 10 min, 1-(bromomethyl)-2-fluoro-4-(trifluoromethyl)benzene (59 mg, 0.036 mL, 0.23 mmol, 1.1 equiv) in DMF (1.5 mL) was added and stirring continued at RT for 2 h. The reaction mixture was filtered and the crude reaction product purified by preparative HPLC (Phenomenex Gemini 5 μm C18 110 A Axia column (75 mm×30 mm, 5 μm); 0.1% v/v FA in water and MeCN) to give the title compound as a brown viscous oil (28 mg, 32%). MS (ESI): m/z=428.3 [M+H]$^+$.

Example 13 and Example 14

(−)- or (+)-5-[3-[3-[[2-Fluoro-4-(trifluoromethyl)phenyl]methoxy]azetidin-1-yl]-3-oxo-propyl]-5-methyl-pyrrolidin-2-one and (+)- or (−)-5-[3-[3-[[2-Fluoro-4-(trifluoromethyl)phenyl]methoxy]azetidin-1-yl]-3-oxo-propyl]-5-methyl-pyrrolidin-2-one

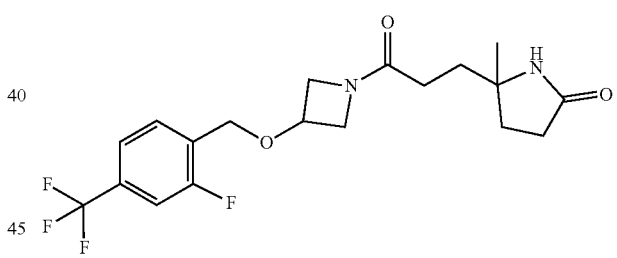

The enantiomers of 5-[3-[3-[[2-fluoro-4-(trifluoromethyl)phenyl]methoxy]azetidin-1-yl]-3-oxo-propyl]-5-methyl-pyrrolidin-2-one (96 mg, 0.23 mmol) were separated by chiral SFC (Chiralpak AD-H column (250 mm×20 mm, 5 μm), eluent: 35% MeOH (0.1% NH$_4$OH) in supercritical CO$_2$) to give (−)- or (+)-5-[3-[3-[[2-fluoro-4-(trifluoromethyl)phenyl]methoxy]azetidin-1-yl]-3-oxo-propyl]-5-methyl-pyrrolidin-2-one (38.3 mg, 41%; first eluting enantiomer) as colorless waxy solid and (+)- or (−)-5-[3-[3-[[2-fluoro-4-(trifluoromethyl)phenyl]methoxy]azetidin-1-yl]-3-oxo-propyl]-5-methyl-pyrrolidin-2-one (41.2 mg, 45%; second eluting enantiomer) as colorless waxy solid. MS (ESI): m/z=403.2 [M+H]$^+$ for both examples.

[3-[3-[[2-Fluoro-4-(trifluoromethyl)phenyl]methoxy]azetidin-1-yl]-3-oxo-propyl]-5-methyl-pyrrolidin-2-one A solution of 3-(2-methyl-5-oxo-pyrrolidin-2-yl)propanoic acid (60.0 mg, 0.35 mmol, 1.0 equiv; CAS RN 60769-61-1), 3-[[2-fluoro-4-(trifluoromethyl)phenyl]methoxy]azetidine; 4-methylbenzenesulfonic acid (147.5 mg, 0.35 mmol, 1.0 equiv; BB 2), TBTU (113 mg, 0.35 mmol, 1.0 equiv) and TEA (254 mg, 0.35 µL, 2.51 mmol, 7.2 equiv) in DMF (2 mL) was stirred at RT for 12 h. To the crude reaction product was added FA (150 µL) and the residue purified by preparative HPLC (Phenomenex Gemini 5 µm C18 110 A Axia column (75 mm×30 mm, 5 µm); 0.1% v/v FA in water and MeCN) to give the desired product as colorless oil (96 mg, 66%). MS (ESI): m/z=403.3 [M+H]⁺.

Example 15 and Example 16

(−)- or (+)-5-Methyl-5-[3-oxo-3-[3-[4-[1-(trifluoromethyl)cyclopropyl]phenyl]azetidin-1-yl]propyl]pyrrolidin-2-one and (+)- or (−)-5-Methyl-5-[3-oxo-3-[3-[4-[1-(trifluoromethyl)cyclopropyl]phenyl]azetidin-1-yl]propyl]pyrrolidin-2-one

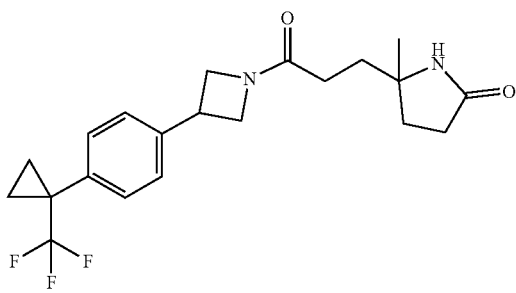 [SMILES: CC1(CCC(=O)N2CC(c3ccc(C4(C(F)(F)F)CC4)cc3)C2)CCC(=O)N1]

The enantiomers of 5-methyl-5-[3-oxo-3-[3-[4-[1-(trifluoromethyl)cyclopropyl]phenyl]azetidin-1-yl]propyl]pyrrolidin-2-one (80 mg, 0.19 mmol) were separated by chiral SFC (Chiralpak AD-H column (250 mm×20 mm, 5 µm), eluent: 35% MeOH (0.1% NH₄OH) in supercritical CO₂) to give (−)- or (+)-5-methyl-5-[3-oxo-3-[3-[4-[1-(trifluoromethyl)cyclopropyl]phenyl]azetidin-1-yl]propyl]pyrrolidin-2-one (34.5 mg, 47%; first eluting enantiomer) as colorless waxy solid and (+)- or (−)-5-methyl-5-[3-oxo-3-[3-[4-[1-(trifluoromethyl)cyclopropyl]phenyl]azetidin-1-yl]propyl]pyrrolidin-2-one (34.3 mg, 47%; second eluting enantiomer) as colorless waxy solid. MS (ESI): m/z=395.2 [M+H]⁺ for both examples.

5-Methyl-5-[3-oxo-3-[3-[4-[1-(trifluoromethyl)cyclopropyl]phenyl]azetidin-1-yl]propyl]pyrrolidin-2-one A solution of 3-(2-methyl-5-oxo-pyrrolidin-2-yl)propanoic acid (60.0 mg, 0.35 mmol, 1.0 equiv; CAS RN 60769-61-1), 3-[4-[1-(trifluoromethyl)cyclopropyl]phenyl]azetidine; 4-methylbenzenesulfonic acid (144.7 mg, 0.35 mmol, 1.0 equiv; BB 4), TBTU (113 mg, 0.35 mmol, 1.0 equiv) and TEA (254 mg, 0.35 µL, 2.51 mmol, 7.2 equiv) in DMF (2 mL) was stirred at RT for 12 h. To the crude reaction product was added FA (150 µL) and the residue purified by preparative HPLC (Phenomenex Gemini 5 µm C18 110 A Axia column (75 mm×30 mm, 5 µm); 0.1% v/v FA in water and MeCN) to give the desired product as colorless oil (80 mg, 53%). MS (ESI): m/z=395.3 [M+H]⁺.

Example 17 and Example 18

(−)- or (+)-5-[3-[3-[6-(3-Chlorophenoxy)-3-pyridyl]azetidin-1-yl]-3-oxo-propyl]-5-methyl-pyrrolidin-2-one and (+)- or (−)-5-[3-[3-[6-(3-Chlorophenoxy)-3-pyridyl]azetidin-1-yl]-3-oxo-propyl]-5-methyl-pyrrolidin-2-one

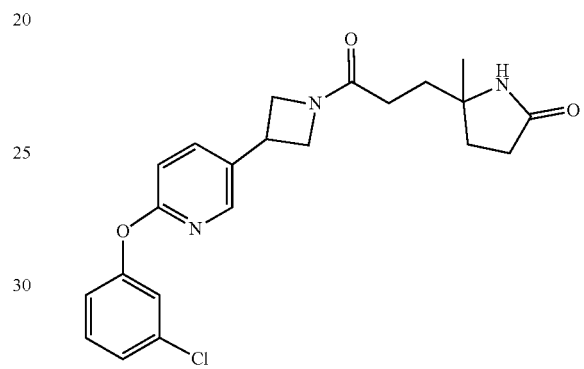

The enantiomers of 5-[3-[3-[6-(3-chlorophenoxy)-3-pyridyl]azetidin-1-yl]-3-oxo-propyl]-5-methyl-pyrrolidin-2-one (79 mg, 0.18 mmol) were separated by chiral SFC (Chiralpak AD-H column (250 mm×20 mm, 5 µm), eluent: 35% MeOH (0.1% NH₄OH) in supercritical CO₂) to give (−)- or (+)-5-[3-[3-[6-(3-chlorophenoxy)-3-pyridyl]azetidin-1-yl]-3-oxo-propyl]-5-methyl-pyrrolidin-2-one (34.8 mg, 46%; first eluting enantiomer) as an off-white waxy solid and (+)- or (−)-5-[3-[3-[6-(3-chlorophenoxy)-3-pyridyl]azetidin-1-yl]-3-oxo-propyl]-5-methyl-pyrrolidin-2-one (37.6 mg, 50%; second eluting enantiomer) as an off-white waxy solid. MS (ESI): m/z=414.2 [M+H]⁺ for both examples.

5-[3-[3-[6-(3-Chlorophenoxy)-3-pyridyl]azetidin-1-yl]-3-oxo-propyl]-5-methyl-pyrrolidin-2-one A solution of 3-(2-methyl-5-oxo-pyrrolidin-2-yl)propanoic acid (60.0 mg, 0.35 mmol, 1.0 equiv; CAS RN 60769-61-1), 5-(azetidin-3-yl)-2-(3-chlorophenoxy)pyridine; 4-methylbenzenesulfonic acid (151.5 mg, 0.35 mmol, 1.0 equiv; BB 7), TBTU (113 mg, 0.35 mmol, 1.0 equiv) and TEA (254 mg, 0.35 µL, 2.51 mmol, 7.2 equiv) in DMF (2 mL) was stirred at RT for 12 h. To the crude reaction product was added FA (150 µL) and the residue purified by preparative HPLC (Phenomenex Gemini 5 µm C18 110 A Axia column (75 mm×30 mm, 5 µm); 0.1% v/v FA in water and MeCN) to give the desired product as colorless oil (79 mg, 52%). MS (ESI): m/z=414.3 [M+H]⁺.

Example 19

(4S)-4-[3-[3-[[2-Fluoro-4-(trifluoromethyl)phenyl]methoxy]azetidin-1-yl]-3-oxo-propyl]oxazolidin-2-one

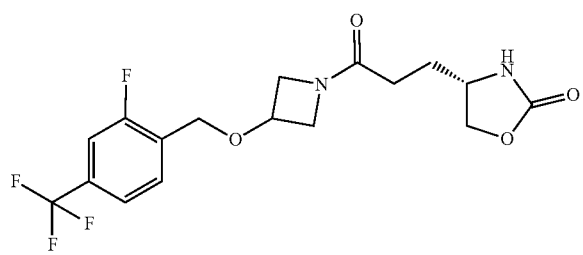 [SMILES: O=C1N[C@@H](CCC(=O)N2CC(OCc3ccc(C(F)(F)F)cc3F)C2)CO1]

To a mixture of 3-[(4S)-2-oxooxazolidin-4-yl]propanoic acid (30 mg, 0.19 mmol, 1.0 equiv; BB 8) and HATU (71.7 mg, 0.19 mmol, 1.0 equiv) in DMF (0.5 mL) was added DIPEA (122 mg, 165 µL, 0.94 mmol, 5.0 equiv) and the suspension was stirred at RT for 20 min before 3-[[2-fluoro-4-(trifluoromethyl)phenyl]methoxy]azetidine; 4-methylbenzenesulfonic acid (79.4 mg, 0.19 mmol, 1.0 equiv; BB 2) was added in one portion. Stirring was continued at RT overnight. The title compound was purified by silica gel chromatography using a MPLC system eluting with a gradient of n-heptane:ethyl acetate/EtOH (3:1) (80:10 to 0:100) to provide the title compound as colorless oil (17 mg, 23%). MS (ESI): m/z=391.2 [M+H]$^+$.

If not indicated otherwise the following examples were synthesized in analogy to the synthesis described for Example 19 using suitable building blocks, respectively.

| Ex. | Systematic Name | Structure | Building blocks | MS m/z |
|---|---|---|---|---|
| 20 | (4R)-4-[3-[3-[[2-Fluoro-4-(trifluoromethyl)phenyl]methoxy]azetidin-1-yl]-3-oxo-propyl]oxazolidin-2-one | 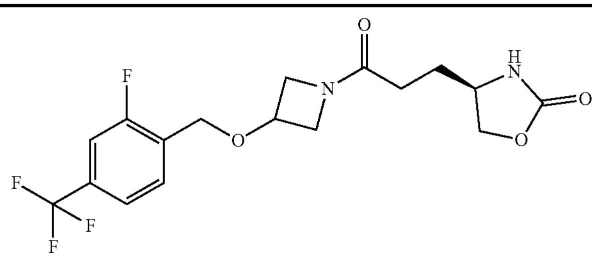 | 3-[(4R)-2-Oxooxazolidin-4-yl]propanoic acid (BB 9) and 3-[[2-Fluoro-4-(trifluoromethyl)phenyl]methoxy]azetidine; 4-methylbenzenesulfonic acid (BB 2) | 391.2 [M + H]$^+$ |
| 21 | (4S)-4-[3-Oxo-3-[3-[4-[1-(trifluoromethyl)cyclopropyl]phenyl]azetidin-1-yl]propyl]oxazolidin-2-one | 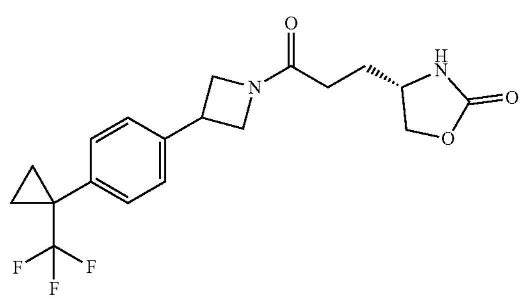 [SMILES: O=C1N[C@@H](CCC(=O)N2CC(c3ccc(C4(C(F)(F)F)CC4)cc3)C2)CO1] | 3-[(4S)-2-Oxooxazolidin-4-yl]propanoic acid (BB 8) and 3-[4-[1-(Trifluoromethyl)cyclopropyl]phenyl]azetidine; 4-methylbenzenesulfonic acid (BB 4) | 383.2 [M + H]$^+$ |
| 22 | (4R)-4-[3-Oxo-3-[3-[4-[1-(trifluoromethyl)cyclopropyl]phenyl]azetidin-1-yl]propyl]oxazolidin-2-one | 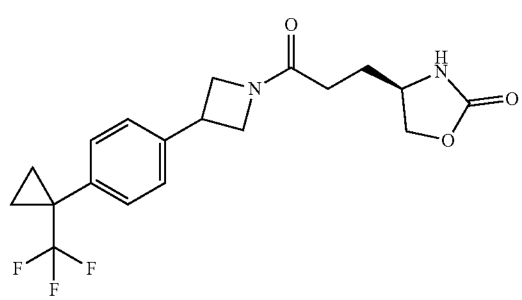 [SMILES: O=C1N[C@H](CCC(=O)N2CC(c3ccc(C4(C(F)(F)F)CC4)cc3)C2)CO1] | 3-[(4R)-2-Oxooxazolidin-4-yl]propanoic acid (BB 9) and 3-[4-[1-(Trifluoromethyl)cyclopropyl]phenyl]azetidine; 4-methylbenzenesulfonic acid (BB 4) | 383.2 [M + H]$^+$ |
| 23 | (4S)-4-[3-[3-[4-(2,4-Difluorophenyl)phenyl]azetidin-1-yl]-3-oxo-propyl]oxazolidin-2-one | 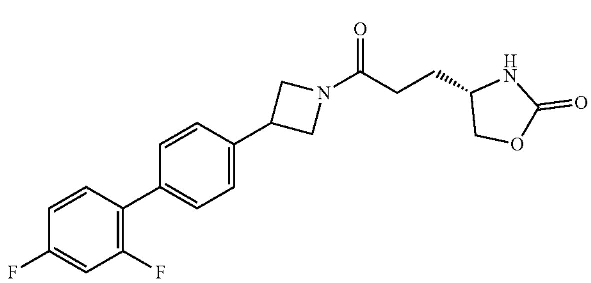 [SMILES: O=C1N[C@@H](CCC(=O)N2CC(c3ccc(-c4ccc(F)cc4F)cc3)C2)CO1] | 3-[(4S)-2-Oxooxazolidin-4-yl]propanoic acid (BB 8) and 3-[4-(2,4-Difluorophenyl)phenyl]azetidine; 4-methylbenzenesulfonic acid (BB 6) | 387.2 [M + H]$^+$ |

-continued

| Ex. | Systematic Name | Structure | Building blocks | MS m/z |
|---|---|---|---|---|
| 24 | (4R)-4-[3-[3-[4-(2,4-Difluorophenyl)phenyl]azetidin-1-yl]-3-oxo-propyl]oxazolidin-2-one | 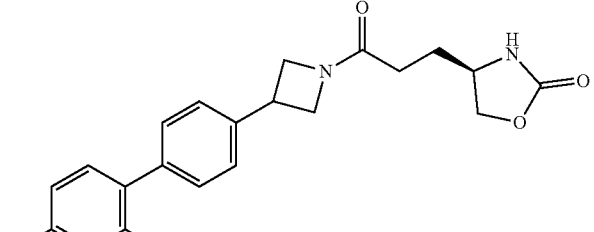 | 3-[(4R)-2-Oxooxazolidin-4-yl]propanoic acid (BB 9) and 3-[4-(2,4-Difluorophenyl)phenyl]azetidine; 4-methylbenzenesulfonic acid (BB 6) | 387.2 [M + H]$^+$ |
| 25 | (4R)-4-[3-Oxo-3-[3-[4-(2,2,2-trifluoro-1,1-dimethyl-ethoxy)phenyl]azetidin-1-yl]propyl]oxazolidin-2-one | 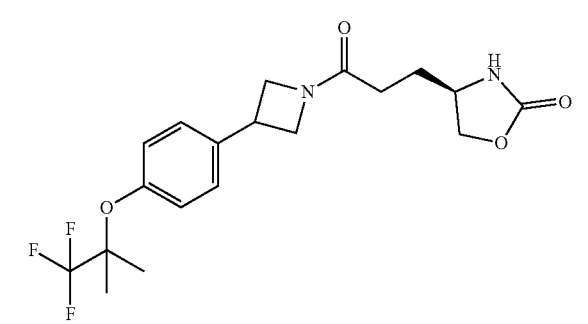 [SMILES: CC(C)(Oc1ccc(C2CN(C(=O)CC[C@@H]3COC(=O)N3)C2)cc1)C(F)(F)F] | 3-[(4R)-2-Oxooxazolidin-4-yl]propanoic acid (BB 9) and 3-(4-((1,1,1-Trifluoro-2-methylpropan-2-yl)oxy)phenyl)azetidine; 4-methylbenzenesulfonic acid (BB 10) | 401.3 [M + H]$^+$ |
| 26 | (4R)-4-[3-[3-[[2-Fluoro-4-(pentafluoro-$\lambda^6$-sulfanyl)phenyl]methoxy]azetidin-1-yl]-3-oxo-propyl]oxazolidin-2-one | 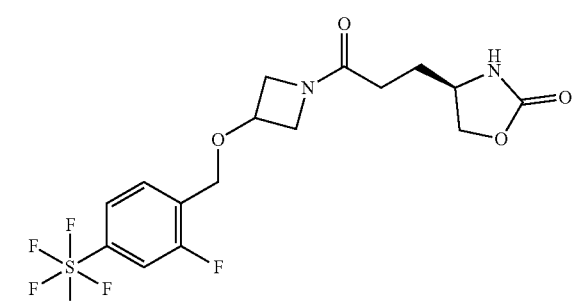 | 3-[(4R)-2-Oxooxazolidin-4-yl]propanoic acid (BB 9) and [4-(Azetidin-3-yloxy-methyl)-3-fluoro-phenyl]-pentafluoro-$\lambda^6$-sulfane; 2,2,2-trifluoroacetic acid (BB 11) | 449.3 [M + H]$^+$ |
| 27 | (4R)-4-[3-[6-[(2,4-Difluorophenyl)methyl]-2-azaspiro[3.3]heptan-2-yl]-3-oxo-propyl]oxazolidin-2-one | 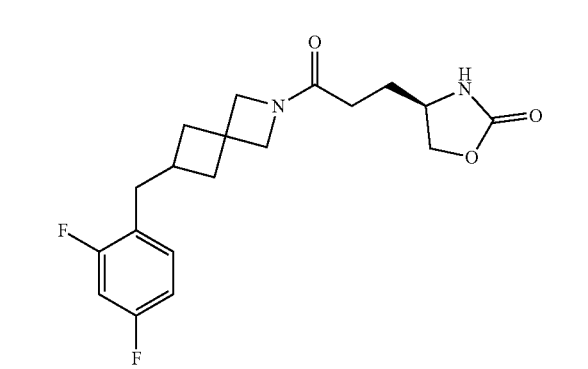 [SMILES: O=C1N[C@H](CCC(=O)N2CC3(CC(Cc4ccc(F)cc4F)C3)C2)CO1] | 3-[(4R)-2-Oxooxazolidin-4-yl]propanoic acid (BB 9) and 6-[(2,4-Difluorophenyl)methyl]-2-azaspiro[3.3]heptane; 2,2,2-trifluoroacetic acid (BB 12) | 365.2 [M + H]$^+$ |
| 28 | (4R)-4-[3-[3-[6-(2-Chlorophenoxy)-3-pyridyl]azetidin-1-yl]-3-oxo-propyl]oxazolidin-2-one | 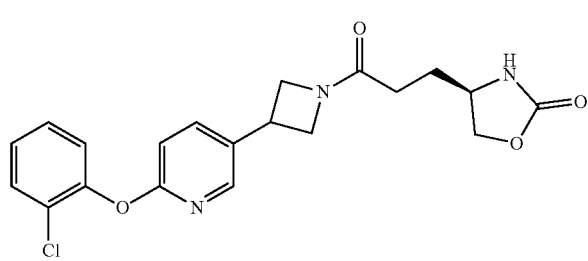 [SMILES: O=C1N[C@H](CCC(=O)N2CC(c3ccc(Oc4ccccc4Cl)nc3)C2)CO1] | 3-[(4R)-2-Oxooxazolidin-4-yl]propanoic acid (BB 9) and 5-(Azetidin-3-yl)-2-(2-chlorophenoxy)pyridine; 4-methylbenzenesulfonic acid (BB 13) | 402.1 [M + H]$^+$ |

-continued

| Ex. | Systematic Name | Structure | Building blocks | MS m/z |
|---|---|---|---|---|
| 29 | (4R)-4-[3-[6-(2-Chloro-4-fluoro-phenoxy)-2-azaspiro[3.3]heptan-2-yl]-3-oxo-propyl]oxazolidin-2-one | 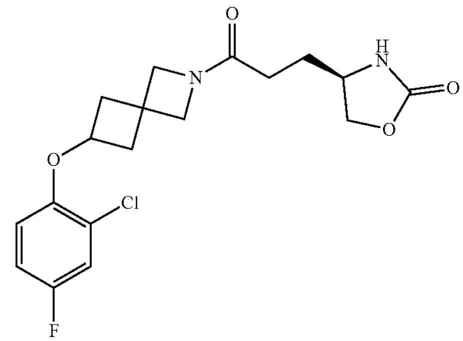 [SMILES: O=C1N[C@H](CCC(=O)N2CC3(CC(Oc4ccc(F)cc4Cl)C3)C2)CO1] | 3-[(4R)-2-Oxooxazolidin-4-yl]propanoic acid (BB 9) and 6-(2-Chloro-4-fluoro-phenoxy)-2-azaspiro[3.3]heptane (BB 14) | 383.1 [M + H]⁺ |
| 30 | (4R)-4-[3-[3-[4-(4-Fluorophenoxy)phenyl]azetidin-1-yl]-3-oxo-propyl]oxazolidin-2-one | 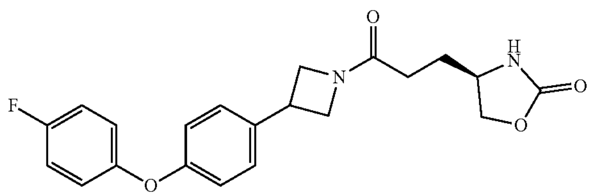 [SMILES: O=C1N[C@H](CCC(=O)N2CC(c3ccc(Oc4ccc(F)cc4)cc3)C2)CO1] | 3-[(4R)-2-Oxooxazolidin-4-yl]propanoic acid (BB 9) and 3-[4-(4-Fluoro-phenoxy)phenyl]azetidine; 4-methylbenzenesulfonic acid (BB 15) | 385.1 [M + H]⁺ |
| 31 | (4R)-4-[3-Oxo-3-[3-[6-[4-(trifluoromethoxy)phenoxy]-3-pyridyl]azetidin-1-yl]propyl]oxazolidin-2-one | 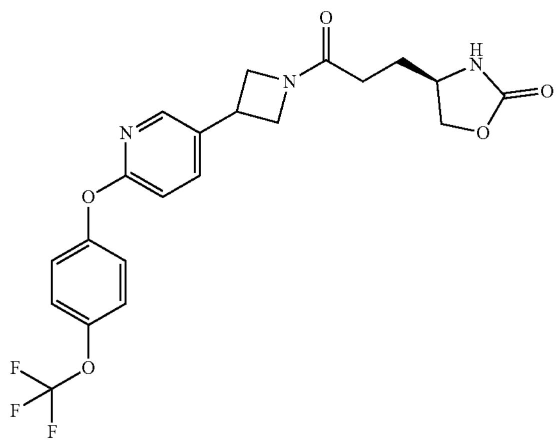 [SMILES: O=C1N[C@H](CCC(=O)N2CC(c3ccc(Oc4ccc(OC(F)(F)F)cc4)nc3)C2)CO1] | 3-[(4R)-2-Oxooxazolidin-4-yl]propanoic acid (BB 9) and 5-(Azetidin-3-yl)-2-[4-(trifluoromethoxy)phenoxy]pyridine; 4-methylbenzenesulfonic acid (BB 16) | 452.2 [M + H]⁺ |
| 32 | (4R)-4-[3-Oxo-3-[6-[6-(trifluoromethyl)pyrazin-2-yl]oxy-2-azaspiro[3.3]heptan-2-yl]propyl]oxazolidin-2-one | 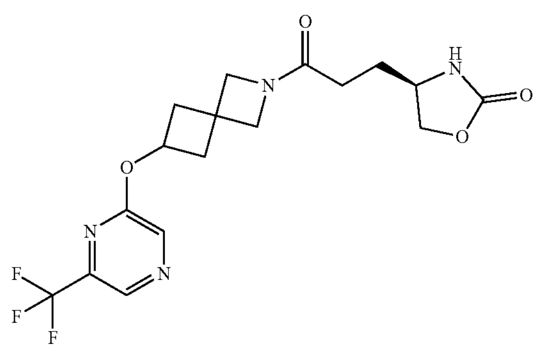 [SMILES: O=C1N[C@H](CCC(=O)N2CC3(CC(Oc4cncc(C(F)(F)F)n4)C3)C2)CO1] | 3-[(4R)-2-Oxooxazolidin-4-yl]propanoic acid (BB 9) and 6-[6-(Trifluoromethyl)pyrazin-2-yl]oxy-2-azaspiro[3.3]heptane (BB 17) | 401.1 [M + H]⁺ |
| 33 | (4R)-4-[3-[3-[2-(3-Chlorophenyl)ethynyl]azetidin-1-yl]-3-oxo-propyl]oxazolidin-2-one | 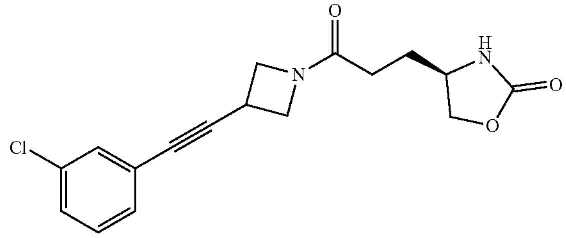 [SMILES: O=C1N[C@H](CCC(=O)N2CC(C#Cc3cccc(Cl)c3)C2)CO1] | 3-[(4R)-2-Oxooxazolidin-4-yl]propanoic acid (BB9) and 3-[2-(3-Chloro-phenyl)ethynyl]azetidine; hydrochloride (BB 18) | 333.1 [M + H]⁺ |

| Ex. | Systematic Name | Structure | Building blocks | MS m/z |
|---|---|---|---|---|
| 34 | (4R)-4-[3-Oxo-3-[3-[6-[3-(trifluoromethyl)pyrrolidin-1-yl]-3-pyridyl]azetidin-1-yl]propyl]oxazolidin-2-one | 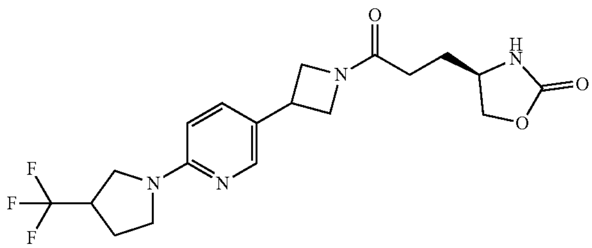 [SMILES: O=C1N[C@H](CCC(=O)N2CC(c3ccc(N4CCC(C(F)(F)F)C4)nc3)C2)CO1] | 3-[(4R)-2-Oxooxazolidin-4-yl]propanoic acid (BB 9) and 5-(Azetidin-3-yl)-2-[3-(trifluoromethyl)pyrrolidin-1-yl]pyridine (BB 19) | 413.2 [M + H]+ |
| 35 | (4R)-4-[3-[3-[[2-Fluoro-4-(trifluoromethyl)phenyl]methoxy]azetidin-1-yl]-2-methyl-3-oxo-propyl]oxazolidin-2-one | 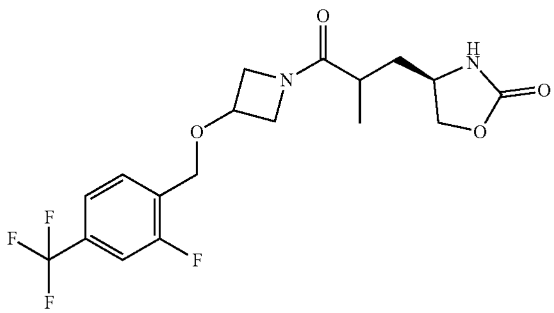 [SMILES: CC(C[C@@H]1COC(=O)N1)C(=O)N1CC(OCc2ccc(C(F)(F)F)cc2F)C1] | 2-Methyl-3-[(4R)-2-oxooxazolidin-4-yl]propanoic acid (BB 20) and 3-[[2-Fluoro-4-(trifluoromethyl)phenyl]methoxy]azetidine; 4-methylbenzenesulfonic acid (BB 2) | 405.1 [M + H]+ |
| 36 | 1-(3-((2-Fluoro-4-(trifluoromethyl)benzyl)oxy)azetidin-1-yl)-3-(1H-1,2,3-triazol-5-yl)propan-1-one | 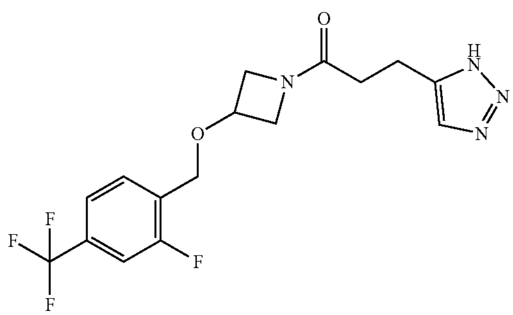 [SMILES: O=C(CCc1cnn[nH]1)N1CC(OCc2ccc(C(F)(F)F)cc2F)C1] | 3-(1H-1,2,3-Triazol-5-yl)propanoic acid (CAS RN 1225439-19-9) and 3-[[2-Fluoro-4-(trifluoromethyl)phenyl]methoxy]azetidine; 4-methylbenzenesulfonic acid (BB 2) | 373.3 [M + H]+ |
| 37 | 3-(1H-1,2,3-Triazol-5-yl)-1-(3-(4-(1-(trifluoromethyl)cyclopropyl)phenyl)azetidin-1-yl)propan-1-one | 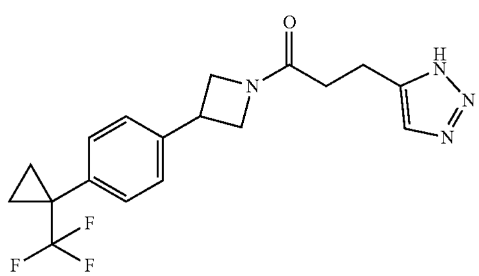 [SMILES: O=C(CCc1cnn[nH]1)N1CC(c2ccc(C3(C(F)(F)F)CC3)cc2)C1] | 3-(1H-1,2,3-Triazol-5-yl)propanoic acid (CAS RN 1225439-19-9) and 3-[4-[1-(Trifluoromethyl)cyclopropyl]phenyl]azetidine; 4-methylbenzenesulfonic acid (BB 4) | 365.3 [M + H]+ |
| 38 | 3-(1H-1,2,3-Triazol-5-yl)-1-(3-(4-((1,1,1-trifluoro-2-methylpropan-2-yl)oxy)phenyl)azetidin-1-yl)propan-1-one | 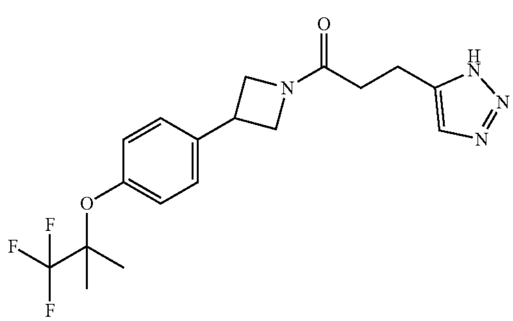 [SMILES: CC(C)(Oc1ccc(C2CN(C(=O)CCc3cnn[nH]3)C2)cc1)C(F)(F)F] | 3-(1H-1,2,3-Triazol-5-yl)propanoic acid (CAS RN 1225439-19-9) and 3-(4-((1,1,1-Trifluoro-2-methylpropan-2-yl)oxy)phenyl)azetidine; 4-methylbenzenesulfonic acid (BB 10) | 383.2 [M + H]+ |

-continued

| Ex. | Systematic Name | Structure | Building blocks | MS m/z |
|---|---|---|---|---|
| 39 | 1-[3-[[2-Fluoro-4-(trifluoromethyl)phenyl]methoxy]azetidin-1-yl]-4-(1H-triazol-5-yl)butan-1-one | 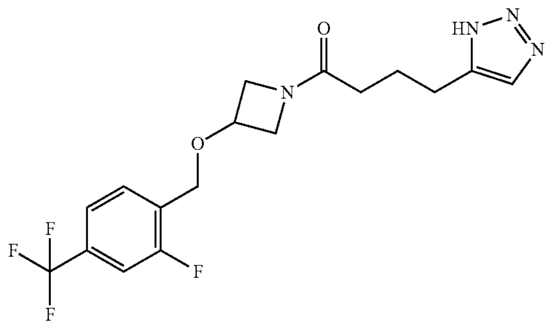 [SMILES: O=C(CCCc1cnn[nH]1)N1CC(OCc2ccc(C(F)(F)F)cc2F)C1] | 4-(1H-1,2,3-Triazol-5-yl)butanoic acid (CAS RN 872701-04-7) and 3-[[2-Fluoro-4-(trifluoromethyl)phenyl]methoxy]azetidine; 4-methylbenzenesulfonic acid (BB 2) | 387.2 [M + H]+ |
| 40 | 4-(1H-Triazol-5-yl)-1-[3-[4-[1-(trifluoromethyl)cyclopropyl]phenyl]azetidin-1-yl]butan-1-one | 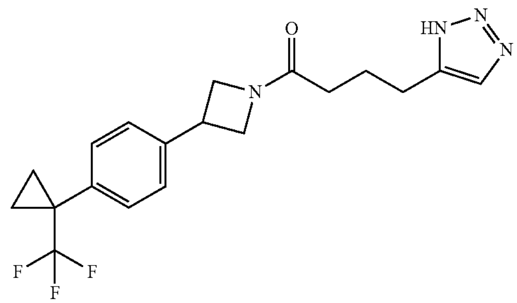 [SMILES: O=C(CCCc1cnn[nH]1)N1CC(c2ccc(C3(C(F)(F)F)CC3)cc2)C1] | 4-(1H-1,2,3-Triazol-5-yl)butanoic acid (CAS RN 872701-04-7) and 3-[4-[1-(Trifluoromethyl)cyclopropyl]phenyl]azetidine; 4-methylbenzenesulfonic acid (BB 4) | 379.2 [M + H]+ |
| 41 | 4-(1H-Triazol-5-yl)-1-[3-[4-(2,2,2-trifluoro-1,1-dimethyl-ethoxy)phenyl]azetidin-1-yl]butan-1-one | 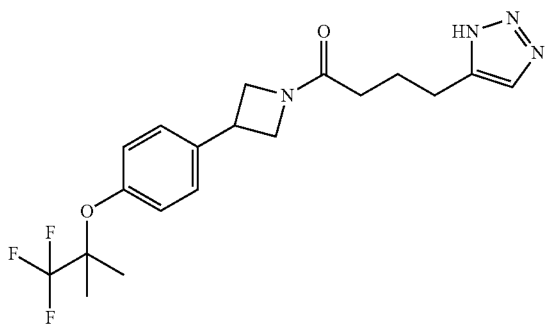 [SMILES: CC(C)(Oc1ccc(C2CN(C(=O)CCCc3cnn[nH]3)C2)cc1)C(F)(F)F] | 4-(1H-1,2,3-Triazol-5-yl)butanoic acid (CAS RN 872701-04-7) and 3-(4-((1,1,1-Trifluoro-2-methylpropan-2-yl)oxy)phenyl)azetidine; 4-methylbenzenesulfonic acid (BB 10) | 397.2 [M + H]+ |
| 42 | 4-(1H-Triazol-5-yl)-1-[3-[6-[4-(trifluoromethoxy)phenoxy]-3-pyridyl]azetidin-1-yl]butan-1-one | 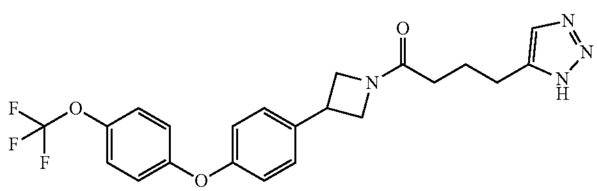 [SMILES: O=C(CCCc1cnn[nH]1)N1CC(c2ccc(Oc3ccc(OC(F)(F)F)cc3)cc2)C1] | 4-(1H-1,2,3-Triazol-5-yl)butanoic acid (CAS RN 872701-04-7) and 5-(Azetidin-3-yl)-2-[4-(trifluoromethoxy)phenoxy]pyridine; 4-methylbenzenesulfonic acid (BB 16) | 448.2 [M + H]+ |
| 43 | 4-(1H-Triazol-5-yl)-1-[6-[6-(trifluoromethyl)pyrazin-2-yl]oxy-2-azaspiro[3.3]heptan-2-yl]butan-1-one | 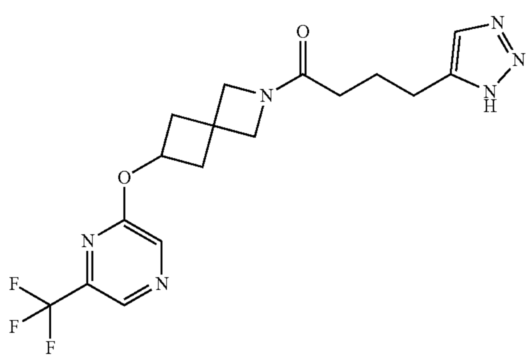 [SMILES: O=C(CCCc1cnn[nH]1)N1CC2(CC(Oc3cncc(C(F)(F)F)n3)C2)C1] | 4-(1H-1,2,3-Triazol-5-yl)butanoic acid (CAS RN 872701-04-7) and 6-[6-(Trifluoromethyl)pyrazin-2-yl]oxy-2-azaspiro[3.3]heptane (BB 17) | 397.1 [M + H]+ |

| Ex. | Systematic Name | Structure | Building blocks | MS m/z |
|---|---|---|---|---|
| 44 | 1-[3-[2-(3-Chlorophenyl)ethynyl]azetidin-1-yl]-4-(1H-triazol-5-yl)butan-1-one | 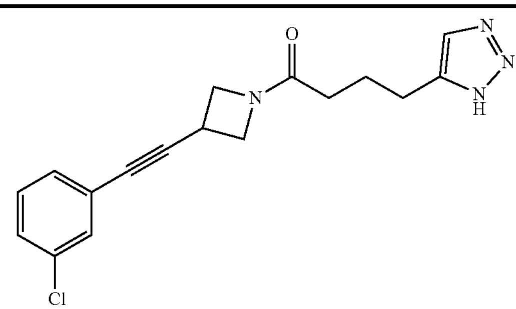 | 4-(1H-1,2,3-Triazol-5-yl)butanoic acid (CAS RN 872701-04-7) and 3-[2-(3-Chlorophenyl)ethynyl]azetidine; hydrochloride (BB 18) | 329.1 [M + H]+ |
| 45 | rac-4-(1H-Triazol-5-yl)-1-[3-[6-[3-(trifluoromethyl)pyrrolidin-1-yl]-3-pyridyl]azetidin-1-yl]butan-1-one | 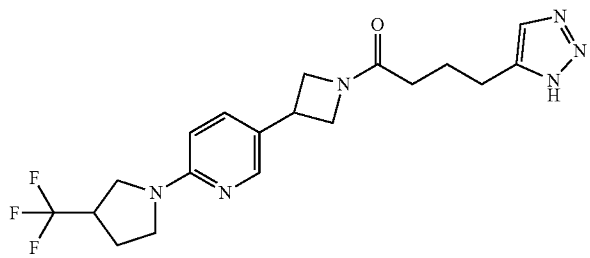 [SMILES: O=C(CCCc1cnn[nH]1)N1CC(c2ccc(N3CCC(C(F)(F)F)C3)nc2)C1] | 4-(1H-1,2,3-Triazol-5-yl)butanoic acid (CAS RN 872701-04-7) and 5-(Azetidin-3-yl)-2-[3-(trifluoromethyl)pyrrolidin-1-yl]pyridine (BB 19) | 409.2 [M + H]+ |
| 46 | 4-(1H-Triazol-5-yl)-1-[3-[4-[3-(2,2,2-trifluoroethoxy)azetidin-1-yl]phenyl]azetidin-1-yl]butan-1-one | 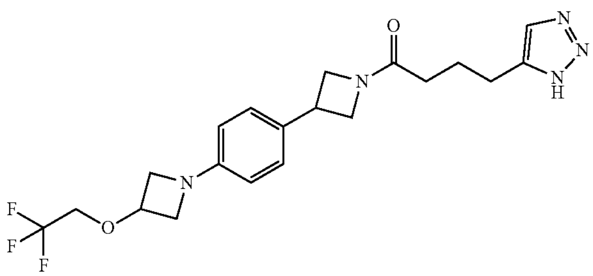 [SMILES: O=C(CCCc1cnn[nH]1)N1CC(c2ccc(N3CC(OCC(F)(F)F)C3)cc2)C1] | 4-(1H-1,2,3-Triazol-5-yl)butanoic acid (CAS RN 872701-04-7) and 1-[4-(Azetidin-3-yl)phenyl]-3-(2,2,2-trifluoroethoxy)azetidine; 4-methylbenzenesulfonic acid (BB 21) | 424.2 [M + H]+ |

Example 47

1-[3-[[2-Fluoro-4-(trifluoromethyl)phenyl]methoxy]azetidin-1-yl]-3-(1H-pyrazol-5-yl)propan-1-one

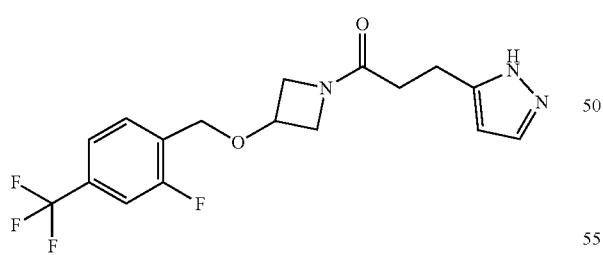

A solution of 3-[[2-fluoro-4-(trifluoromethyl)phenyl]methoxy]azetidine trifluoroacetic acid (155.5 mg, 0.43 mmol, 1.0 equiv; BB 22), 3-(1H-pyrazol-5-yl)propanoic acid (60.0 mg, 0.43 mmol, 1.0 equiv; CAS RN 1368382-98-2), T$_3$P/ethyl acetate (197.1 mg, 0.86 mmol, 2.0 equiv; wt. 50%) and DIPEA (0.33 g, 0.45 mL, 2.57 mmol, 6.0 equiv) in DMF (1.6 mL) was stirred at RT for 12 h. The reaction mixture was diluted with water (10 mL) and extracted with ethyl acetate (3×20 mL). The organic phase was dried over MgSO$_4$, evaporated and the residue purified by preparative HPLC (Shim-pack C18 column (150 mm×25 mm, 10 μm); 0.225% v/v FA in water and MeCN) to give the title compound as a light yellow oil (49.7 mg, 31%). MS (ESI): m/z=372.4 [M+H]+.

Example 48

6-[3-[3-[[2-Fluoro-4-(trifluoromethyl)phenyl]methoxy]azetidin-1-yl]-3-oxo-propyl]-1H-pyridin-2-one A solution of 3-[[2-fluoro-4-(trifluoromethyl)phenyl]methoxy]azetidine trifluoroacetic acid (195.57 mg, 0.54 mmol, 1.0 equiv; BB 22), 3-(6-oxo-1H-pyridin-2-yl)propanoic acid (90.0 mg, 0.54 mmol, 1.0 equiv; BB 23), T₃P/ethyl acetate (247.8 mg, 1.08 mmol, 2.0 equiv; wt. 50%) and DIPEA (0.44 g, 0.60 mL, 3.24 mmol, 6.0 equiv) in DMF (2 mL) was stirred at RT for 12 h. The reaction mixture was diluted with water (10 mL) and extracted with ethyl acetate (3×20 mL). The organic phase was dried over MgSO₄, evaporated and the residue purified by preparative HPLC (Shim-pack C18 column (150 mm×25 mm, 10 μm); 0.225% v/v FA in water and MeCN) and preparative TLC (DCM:MeOH=10:1) to give the title compound as a light yellow oil (8.6 mg, 4%). MS (ESI): m/z=399.4 [M+H]⁺.

Example 49

6-[3-[3-[[2-Fluoro-4-(trifluoromethyl)phenyl]methoxy]azetidin-1-yl]-3-oxo-propyl]piperidin-2-one

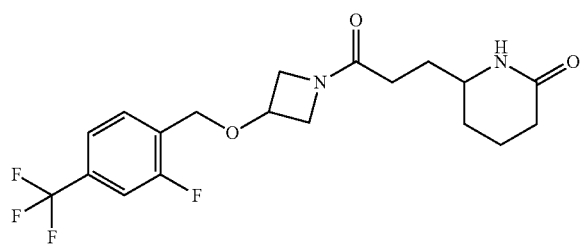 [SMILES: O=C1CCCC(CCC(=O)N2CC(OCc3ccc(C(F)(F)F)cc3F)C2)N1]

A solution of 3-[[2-fluoro-4-(trifluoromethyl)phenyl]methoxy]azetidine trifluoroacetic acid (275.83 mg, 0.76 mmol, 1.0 equiv; BB 22), 3-(6-oxo-2-piperidyl)propanoic acid (130.0 mg, 0.43 mmol, 1.8 equiv; BB 24), T₃P/ethyl acetate (349.5 mg, 1.52 mmol, 2.0 equiv; wt. 50%) and DIPEA (0.59 g, 0.80 mL, 4.56 mmol, 6.0 equiv) in DMF (2 mL) was stirred at RT for 12 h. The reaction mixture was diluted with water (10 mL) and extracted with ethyl acetate (3×20 mL). The organic phase was dried over MgSO₄, evaporated and the residue purified by preparative HPLC (Shim-pack C18 column (150 mm×25 mm, 10 μm); 0.225% v/v FA in water and MeCN) and preparative TLC (DCM:MeOH=10:1) to give the title compound as a light brown oil (6.8 mg, 2%). MS (ESI): m/z=403.5 [M+H]⁺.

Example 50 and Example 51

(−)-5-[3-[3-[[2-Fluoro-4-(trifluoromethyl)phenyl]methoxy]azetidin-1-yl]-3-oxo-propyl]morpholin-3-one and (+)-5-[3-[3-[[2-Fluoro-4-(trifluoromethyl)phenyl]methoxy]azetidin-1-yl]-3-oxo-propyl]morpholin-3-one The enantiomers of 5-[3-[3-[[2-fluoro-4-(trifluoromethyl)phenyl]methoxy]azetidin-1-yl]-3-oxo-propyl]morpholin-3-one (24 mg, 0.059 mmol) were separated by preparative chiral SFC (Chiralpak AD-H column (250 mm×20 mm, 10 μm), eluent: 50% MeOH (0.1% NH₄OH) in supercritical CO₂) to give (−)-5-[3-[3-[[2-fluoro-4-(trifluoromethyl)phenyl]methoxy]azetidin-1-yl]-3-oxo-propyl]morpholin-3-one (8 mg, 33%) as light yellow gum and (+)-5-[3-[3-[[2-fluoro-4-(trifluoromethyl)phenyl]methoxy]azetidin-1-yl]-3-oxo-propyl]morpholin-3-one (8 mg, 32%) as light brown gum.

(−)-Enantiomer: MS (ESI): m/z=405.2 [M+H]⁺. Specific Rotation: −8.54°
(+)-Enantiomer: MS (ESI): m/z=405.3 [M+H]⁺. Specific Rotation: +8.58°

5-[3-[3-[[2-Fluoro-4-(trifluoromethyl)phenyl]methoxy]azetidin-1-yl]-3-oxo-propyl]morpholin-3-one

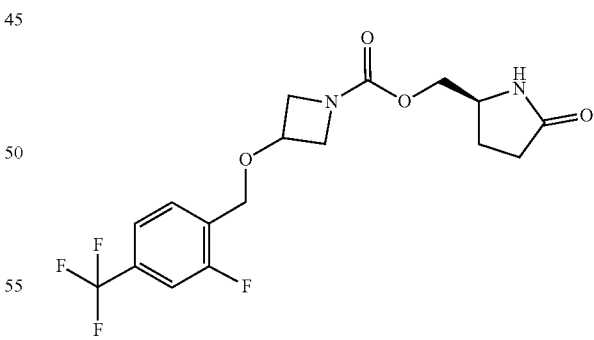

A solution of 3-[[2-fluoro-4-(trifluoromethyl)phenyl]methoxy]azetidine trifluoroacetic acid (104.9 mg, 0.29 mmol, 1.0 equiv; BB 22), 3-(5-oxomorpholin-3-yl)propanoic acid (50.0 mg, 0.29 mmol, 1.0 equiv; BB 25), T₃P/ethyl acetate (199.4 mg, 0.43 mmol, 1.5 equiv; wt. 50%) and NEt₃ (0.24 mL, 1.73 mmol, 6.0 equiv) in DMF (1.7 mL) was stirred at RT for 16 h. The reaction mixture was diluted with water (10 mL) and extracted with ethyl acetate (3×5 mL). The organic phase was dried over MgSO₄, evaporated and the residue purified by preparative HPLC (Shim-pack C18 column (150 mm×25 mm, 10 μm); 0.225% v/v FA in water and MeCN) to give the title compound as a light yellow oil (24 mg, 21%). MS (ESI): m/z=405.2 [M+H]⁺.

Example 52

[(2S)-5-Oxopyrrolidin-2-yl]methyl 3-[[2-fluoro-4-(trifluoromethyl)phenyl]methoxy]azetidine-1-carboxylate To a suspension of 3-[[2-fluoro-4-(trifluoromethyl)phenyl]methoxy]azetidine; 4-methylbenzenesulfonic acid (109.3 mg, 0.26 mmol, 1.0 equiv; BB 2) in ACN (0.43 mL) were added NEt₃ (0.15 mL, 1.82 mmol, 7.0 equiv) and di(1H-1,2,4-triazol-1-yl)methanone (42.6 mg, 0.26 mmol, 1.0 equiv; CAS RN 41864-22-6). The reaction mixture was stirred at RT for 1.5 h. In a second reaction flask, (5S)-5-(hydroxymethyl)pyrrolidin-2-one (31.4 mg, 0.27 mmol, 1.05 equiv; CAS RN 17342-08-4) was dissolved in THF (0.43 mL) and sodium hydride (22.3 mg, 0.56 mmol, 2.15 equiv; 55% in mineral oil) was added. The first prepared mixture was added to the sodium alkoxide mixture, then stirred overnight at 50° C. The reaction was quenched with sat. aqueous NH₄Cl solution (0.5 mL), extracted with water/ethyl acetate (3×30 mL) and the combined organic phase dried over MgSO₄. The crude product was purified by silica gel chromatography using a MPLC system eluting with a gradient of n-heptane:ethyl acetate/EtOH (3:1) (100:0 to 0:100) to get the title compound as a white solid (23 mg, 95%). MS (ESI): m/z=391.2 [M+H]⁺.

If not indicated otherwise the following examples were synthesized in analogy to the synthesis described for Example 52 using suitable building blocks, respectively.

| Ex. | Systematic Name | Structure | Building blocks | MS m/z |
|---|---|---|---|---|
| 53 | [(2R)-5-Oxopyrrolidin-2-yl]methyl 3-[[2-fluoro-4-(trifluoromethyl)phenyl]methoxy]azetidine-1-carboxylate | 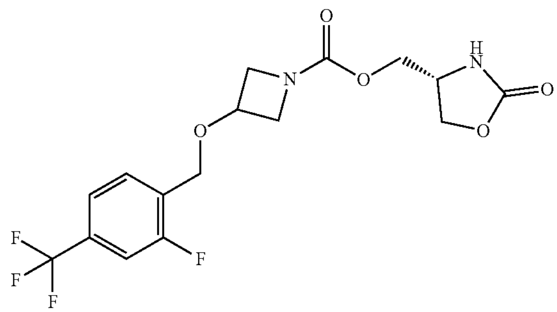 [SMILES: O=C1N[C@@H](COC(=O)N2CC(OCc3ccc(C(F)(F)F)cc3F)C2)CO1] | (5R)-5-(Hydroxymethyl)pyrrolidin-2-one (CAS RN 66673-40-3) and 3-[[2-Fluoro-4-(trifluoromethyl)phenyl]methoxy]azetidine; 4-methylbenzenesulfonic acid (BB 2) | 391.2 [M + H]⁺ |
| 54 | [(4S)-2-Oxooxazolidin-4-yl]methyl 3-[[2-fluoro-4-(trifluoromethyl)phenyl]methoxy]azetidine-1-carboxylate | 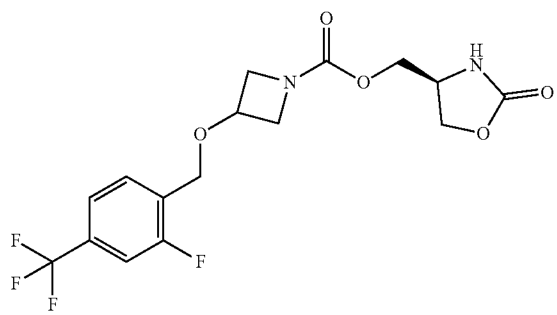 [SMILES: O=C1N[C@H](COC(=O)N2CC(OCc3ccc(C(F)(F)F)cc3F)C2)CO1] | (4R)-4-(Hydroxymethyl)oxazolidin-2-one (CAS RN 132682-23-6) and 3-[[2-Fluoro-4-(trifluoromethyl)phenyl]methoxy]azetidine; 4-methylbenzenesulfonic acid (BB 2) | 393.2 [M + H]⁺ |
| 55 | [(4R)-2-Oxooxazolidin-4-yl]methyl 3-[[2-fluoro-4-(trifluoromethyl)phenyl]methoxy]azetidine-1-carboxylate | 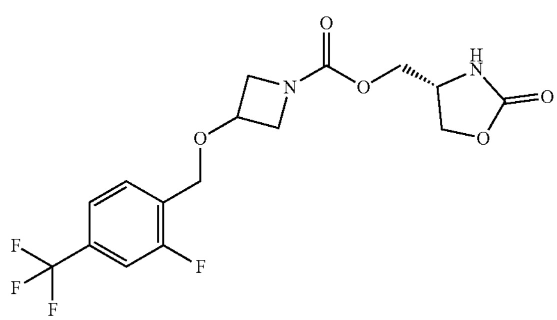 [SMILES: O=C1N[C@@H](COC(=O)N2CC(OCc3ccc(C(F)(F)F)cc3F)C2)CO1] | (4S)-4-(Hydroxymethyl)oxazolidin-2-one (CAS RN 144542-44-9) and 3-[[2-Fluoro-4-(trifluoromethyl)phenyl]methoxy]azetidine; 4-methylbenzenesulfonic acid (BB 2) | 393.2 [M + H]⁺ |
| 56 | [(4S)-2-Oxooxazolidin-4-yl]methyl 3-[4-[1-(trifluoromethyl)cyclopropyl]phenyl]azetidine-1-carboxylate | 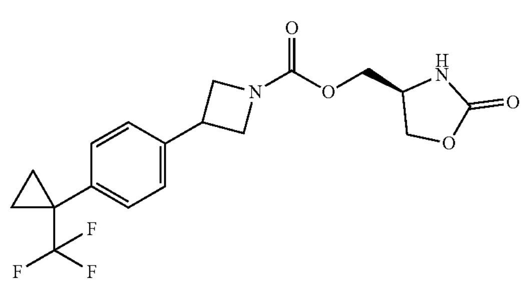 [SMILES: O=C1N[C@H](COC(=O)N2CC(c3ccc(C4(C(F)(F)F)CC4)cc3)C2)CO1] | (4R)-4-(Hydroxymethyl)oxazolidin-2-one (CAS RN 132682-23-6) and 3-[4-[1-(Trifluoromethyl)cyclopropyl]phenyl]azetidine; 4-methylbenzenesulfonic acid (BB 4) | 385.2 [M + H]⁺ |
| 57 | [(4S)-2-Oxooxazolidin-4-yl]methyl 6-[(2,4-difluorophenyl)methyl]-2-azaspiro[3.3]heptane-2-carboxylate | 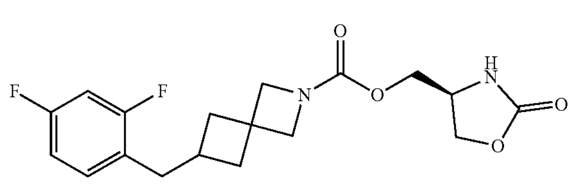 [SMILES: O=C1N[C@H](COC(=O)N2CC3(CC(Cc4ccc(F)cc4F)C3)C2)CO1] | (4R)-4-(Hydroxymethyl)oxazolidin-2-one (CAS RN 132682-23-6) and 6-[(2,4-Difluorophenyl)methyl]-2-azaspiro[3.3]heptane; 2,2,2-trifluoroacetic acid (BB 12) | 367.1 [M + H]⁺ |

| Ex. | Systematic Name | Structure | Building blocks | MS m/z |
|---|---|---|---|---|
| 58 | [(4S)-2-Oxooxazolidin-4-yl]methyl 3-[4-(4-fluorophenoxy)phenyl]azetidine-1-carboxylate | 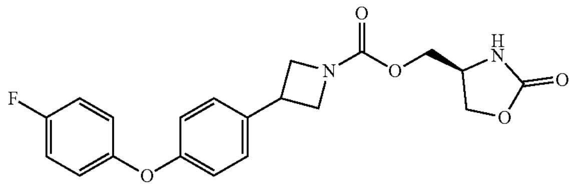 [SMILES: O=C1N[C@H](COC(=O)N2CC(c3ccc(Oc4ccc(F)cc4)cc3)C2)CO1] | (4R)-4-(Hydroxymethyl)oxazolidin-2-one (CAS RN 132682-23-6) and 3-[4-(4-Fluorophenoxy)phenyl]azetidine; 4-methylbenzenesulfonic acid (BB 15) | 387.1 [M + H]$^+$ |
| 59 | [(4R)-2-Oxooxazolidin-4-yl]methyl 6-[(2,4-difluorophenyl)methyl]-2-azaspiro[3.3]heptane-2-carboxylate | 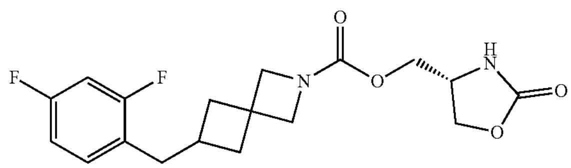 [SMILES: O=C1N[C@@H](COC(=O)N2CC3(CC(Cc4ccc(F)cc4F)C3)C2)CO1] | (4S)-4-(Hydroxymethyl)oxazolidin-2-one (CAS RN 144542-44-9) and 6-[(2,4-Difluorophenyl)methyl]-2-azaspiro[3.3]heptane; 2,2,2-trifluoroacetic acid (BB 12) | 367.2 [M + H]$^+$ |
| 60 | [(4S)-2-Oxooxazolidin-4-yl]methyl 3-[6-(2-chlorophenoxy)-3-pyridyl]azetidine-1-carboxylate | 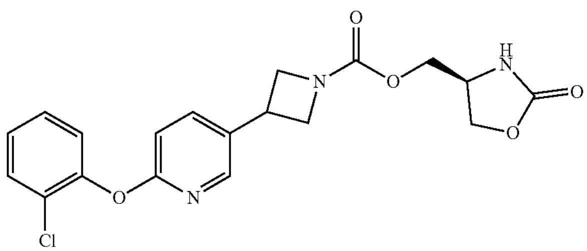 [SMILES: O=C1N[C@H](COC(=O)N2CC(c3ccc(Oc4ccccc4Cl)nc3)C2)CO1] | (4R)-4-(Hydroxymethyl)oxazolidin-2-one (CAS RN 132682-23-6) and 5-(Azetidin-3-yl)-2-(2-chlorophenoxy)pyridine; 4-methylbenzenesulfonic acid (BB 13) | 404.1 [M + H]$^+$ |
| 61 | [(4S)-2-Oxooxazolidin-4-yl]methyl 3-[2-[2-(difluoromethyl)phenyl]ethynyl]azetidine-1-carboxylate | 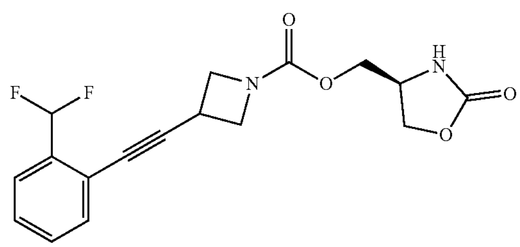 [SMILES: O=C1N[C@H](COC(=O)N2CC(C#Cc3ccccc3C(F)F)C2)CO1] | (4R)-4-(Hydroxymethyl)oxazolidin-2-one (CAS RN 132682-23-6) and 3-[2-[2-(Difluoromethyl)phenyl]ethynyl]azetidine; hydrochloride (BB 26) | 395.1 [M + MECN]$^+$ |
| 62 | [(4S)-2-Oxooxazolidin-4-yl]methyl 3-[6-[3-(trifluoromethyl)pyrrolidin-1-yl]-3-pyridyl]azetidine-1-carboxylate | 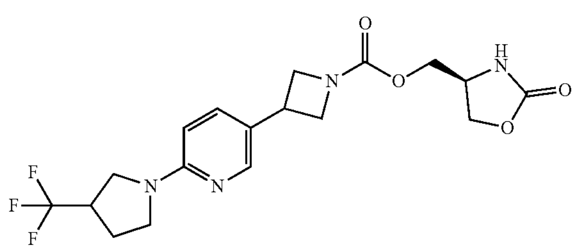 [SMILES: O=C1N[C@H](COC(=O)N2CC(c3ccc(N4CCC(C(F)(F)F)C4)nc3)C2)CO1] | (4R)-4-(Hydroxymethyl)oxazolidin-2-one (CAS RN 132682-23-6) and 5-(Azetidin-3-yl)-2-[3-(trifluoromethyl)pyrrolidin-1-yl]pyridine (BB 19) | 415.1 [M + H]$^+$ |
| 63 | 2-(1H-Triazol-5-yl)ethyl 3-[[2-fluoro-4-(trifluoromethyl)phenyl]methoxy]azetidine-1-carboxylate | 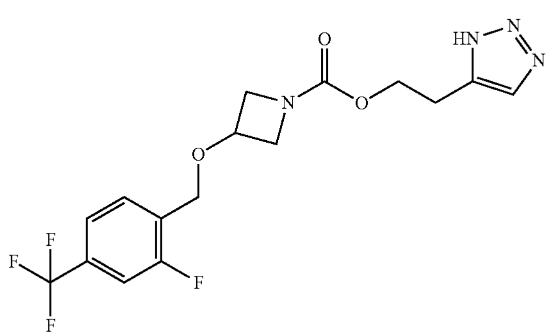 [SMILES: O=C(OCCc1cnn[nH]1)N1CC(OCc2ccc(C(F)(F)F)cc2F)C1] | 2-(1H-1,2,3-Triazol-4-yl)ethan-1-ol (CAS RN 1012040-40-2) and 3-[[2-Fluoro-4-(trifluoromethyl)phenyl]methoxy]azetidine; 4-methylbenzenesulfonic acid (BB 2) | 389.1 [M + H]$^+$ |

Example 64

3-[[2-Fluoro-4-(trifluoromethyl)phenyl]methoxy]-N-[2-(1H-triazol-5-yl)ethyl]azetidine-1-carboxamide

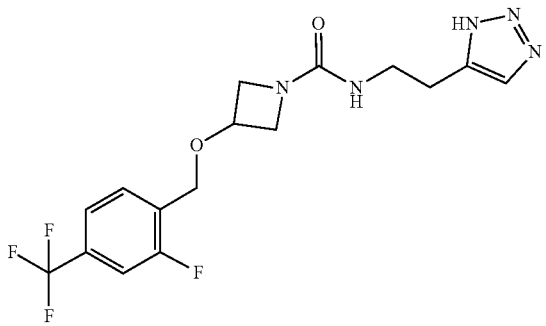 [SMILES: O=C(NCCc1cnn[nH]1)N1CC(OCc2ccc(C(F)(F)F)cc2F)C1]

To a suspension of 3-[[2-fluoro-4-(trifluoromethyl)phenyl]methoxy]azetidine; 4-methylbenzenesulfonic acid (84.3 mg, 0.20 mmol, 1.0 equiv; BB 2) in ACN (0.67 mL) were added DIPEA (52 mg, 70 µL, 0.40 mmol, 2.0 equiv) and di(1H-1,2,4-triazol-1-yl)methanone (36.2 mg, 0.22 mmol, 1.1 equiv; CAS RN 41864-22-6). After stirring of the reaction mixture at RT for 1.5 h, 2-(1H-triazol-5-yl)ethanamine (22.5 mg, 0.20 mmol, 1.0 equiv; CAS RN 52845-67-7) and additional DIPEA (52 mg, 70 µL, 0.40 mmol, 2.0 equiv) and di(1H-1,2,4-triazol-1-yl)methanone (22.5 mg, 0.20 mmol, 1.0 equiv) were added and the reaction mixture was heated to 80° C. overnight. The crude product was concentrated under reduced pressure and the residue purified by preparative HPLC (Phenomenex Gemini 5 µm C18 110 A Axia column (75 mm×30 mm, 5 µm); 0.1% v/v FA in water and MeCN) to give the title compound as a colourless solid (15.7 mg, 19%). MS (ESI): m/z=388.1 [M+H]$^+$.

If not indicated otherwise the following examples were synthesized in analogy to the synthesis described for Example 64 using suitable building blocks, respectively.

| Ex. | Systematic Name | Structure | Building blocks | MS m/z |
|---|---|---|---|---|
| 65 | N-Methyl-N-[2-(1H-triazol-5-yl)ethyl]-3-[4-[1-(trifluoromethyl)cyclopropyl]phenyl]azetidine-1-carboxamide | 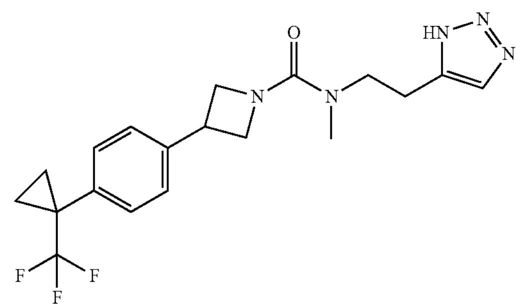 [SMILES: CN(CCc1cnn[nH]1)C(=O)N1CC(c2ccc(C3(C(F)(F)F)CC3)cc2)C1] | N-Methyl-2-(1H-triazol-5-yl)ethanamine (CAS RN 1501093-75-9) and 3-[4-[1-(Trifluoromethyl)cyclopropyl]phenyl]azetidine; 4-methylbenzenesulfonic acid (BB 4) | 394.3 [M + H]$^+$ |
| 66 | 3-[[2-Fluoro-4-(trifluoromethyl)phenyl]methoxy]-N-methyl-N-[2-(1H-triazol-5-yl)ethyl]azetidine-1-carboxamide | 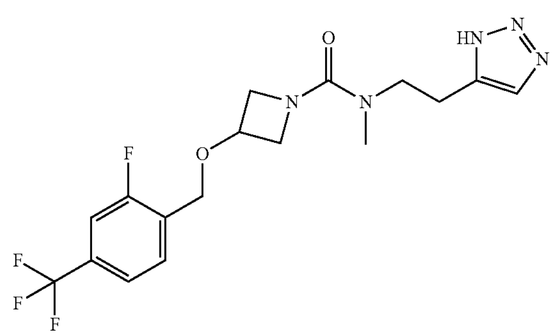 [SMILES: CN(CCc1cnn[nH]1)C(=O)N1CC(OCc2ccc(C(F)(F)F)cc2F)C1] | N-Methyl-2-(1H-triazol-5-yl)ethanamine (CAS RN 1501093-75-9) and 3-[[2-Fluoro-4-(trifluoromethyl)phenyl]methoxy]azetidine; 2,2,2-trifluoroacetic acid (BB 22) | 402.2 [M + H]$^+$ |
| 67 | 3-[4-(2-Chloro-4-methylsulfonyl-phenyl)phenyl]-N-methyl-N-[2-(1H-triazol-5-yl)ethyl]azetidine-1-carboxamide | 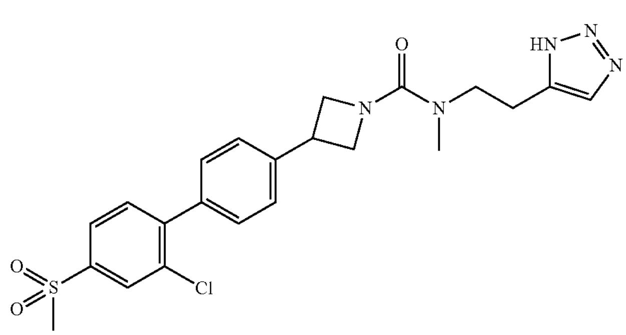 [SMILES: CN(CCc1cnn[nH]1)C(=O)N1CC(c2ccc(-c3ccc(S(C)(=O)=O)cc3Cl)cc2)C1] | N-Methyl-2-(1H-triazol-5-yl)ethanamine (CAS RN 1501093-75-9) and 3-[4-(2-Chloro-4-methylsulfonyl-phenyl)phenyl]azetidine; 4-methylbenzenesulfonic acid (BB 27) | 474.3 [M + H]$^+$ |

Example 68

2-Methyl-4-(1H-triazol-5-yl)-1-[3-[4-[1-(trifluoromethyl)cyclopropyl]phenyl]azetidin-1-yl]butan-1-one

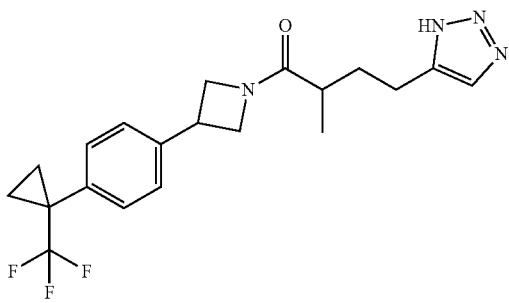 [SMILES: CC(CCc1cnn[nH]1)C(=O)N1CC(c2ccc(C3(C(F)(F)F)CC3)cc2)C1]

To a stirred solution of 2-methyl-4-(1H-triazol-5-yl)butanoic acid hydrochloride (56.7 mg, 0.28 mmol, 1.0 equiv; BB 28), 3-[4-[1-(trifluoromethyl)cyclopropyl]phenyl]azetidine; 4-methylbenzenesulfonic acid (115.8 mg, 0.28 mmol, 1.0 equiv; BB 4) and HATU (136.2 mg, 0.36 mmol, 1.3 equiv) in DMF (2 mL) was added triethylamine (0.19 mL, 1.38 mmol, 5.0 equiv) in one portion. The resulting mixture was stirred for 18 h at rt. The reaction mixture was poured into water (70 mL), extracted with ethyl acetate (3×50 mL) and the combined organic layers were successively washed with water (30 mL) and a sat. aqueous NaCl solution (30 mL). The combined organic phase was dried over $Na_2SO_4$ and the solvent was removed in vacuo. The crude product was purified by preparative HPLC (SunFire column (100 mm×19 mm, 5 μm); water and MeCN) to give the title compound as a light yellow viscous oil (27.9 mg, 25%). MS (ESI): m/z=393.2 [M+H]$^+$.

Example 69

3-Hydroxy-4-(1H-triazol-5-yl)-1-[3-[4-[1-(trifluoromethyl)cyclopropyl]phenyl]azetidin-1-yl]butan-1-one

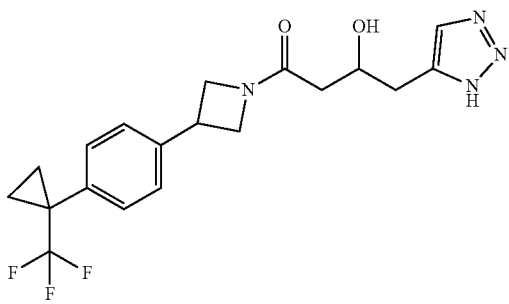 [SMILES: O=C(CC(O)Cc1cnn[nH]1)N1CC(c2ccc(C3(C(F)(F)F)CC3)cc2)C1]

The title compound was obtained in analogy to Example 68 starting from 3-hydroxy-4-(1H-triazol-5-yl)butanoic acid hydrochloride (90 mg, 0.43 mmol, 1.0 equiv; BB 29) and 3-[4-[1-(trifluoromethyl)cyclopropyl]phenyl]azetidine; 4-methylbenzenesulfonic acid (177.8 mg, 0.43 mmol, 1.0 equiv; BB 4) as a colorless oil (8.8 mg, 5%). MS (ESI): m/z=395.4 [M+H]$^+$.

Example 70

2-Fluoro-4-(1H-triazol-5-yl)-1-[3-[4-[1-(trifluoromethyl)cyclopropyl]phenyl]azetidin-1-yl]butan-1-one

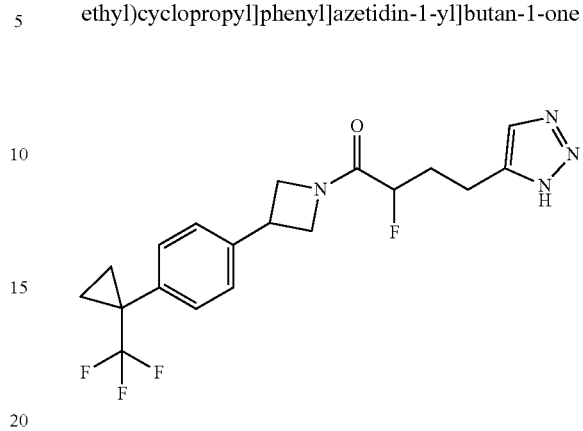

The title compound was obtained in analogy to Example 68 starting from 2-fluoro-4-(1H-triazol-5-yl)butanoic acid hydrochloride (90 mg, 0.43 mmol, 1.0 equiv; BB 30) and 3-[4-[1-(trifluoromethyl)cyclopropyl]phenyl]azetidine; 4-methylbenzenesulfonic acid (177.8 mg, 0.43 mmol, 1.0 equiv; BB 4) as a colorless oil (19.7 mg, 12%). MS (ESI): m/z=397.2 [M+H]$^+$.

Example 71

(4R)-4-[3-[3-[4-(N-Methylanilino)phenyl]azetidin-1-yl]-3-oxo-propyl]oxazolidin-2-one

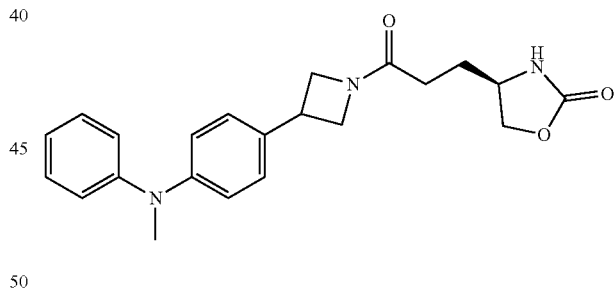

To a solution of 3-[(4R)-2-oxooxazolidin-4-yl]propanoic acid (23.4 mg, 0.15 mmol, 1.0 equiv; BB 9) and 4-(azetidin-3-yl)-N-methyl-N-phenyl-aniline (35 mg, 0.15 mmol, 1.0 equiv; BB 31) in N,N-dimethylacetamide (0.93 mL) was added HATU (61.4 mg, 0.16 mmol, 1.1 equiv) and DIPEA (48 mg, 64 μL, 0.37 mmol, 2.5 equiv). The reaction mixture was stirred at RT overnight. The reaction was quenched with water (5 mL), extracted with ethyl acetate (3×20 mL) and the combined organic phase dried over $Na_2SO_4$. The crude product was purified by silica gel chromatography using a MPLC system eluting with a gradient of DCM:MeOH (100:0 to 90:10) to get the title compound as a light brown oil (21 mg, 35%). MS (ESI): m/z=380.2 [M+H]$^+$.

Example 72

(4R)-4-[3-[3-(5-tert-Butyl-2-pyridyl)azetidin-1-yl]-3-oxo-propyl]oxazolidin-2-one

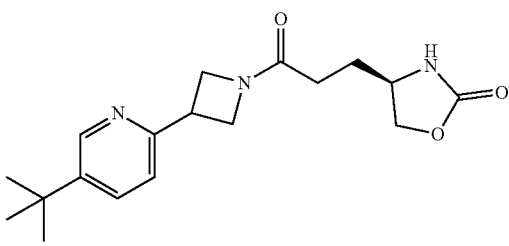 [SMILES: CC(C)(C)c1ccc(C2CN(C(=O)CC[C@@H]3COC(=O)N3)C2)nc1]

To a mixture of 3-[(4R)-2-oxooxazolidin-4-yl]propanoic acid (12.4 mg, 0.078 mmol, 1.0 equiv; BB 9) and HATU (29.7 mg, 0.078 mmol, 1.0 equiv) in DMF (0.3 mL) was added DIPEA (40 mg, 55 μL, 0.31 mmol, 4.0 equiv) and the suspension was stirred at RT for 15 min before 2-(azetidin-3-yl)-5-tert-butyl-pyridine; 4-methylbenzenesulfonic acid (44 mg, 0.078 mmol, 1.0 equiv; BB 32) was added in one portion. Stirring was continued at RT overnight. The crude reaction product was purified by preparative HPLC (YMC-Triart C18 column; 0.1% v/v TEA in water and MeCN) to give the desired product as a colorless gum (16 mg, 62%). MS (ESI): m/z=332.3 [M+H]$^+$.

If not indicated otherwise the following examples were synthesized in analogy to the synthesis described for Example 72 using suitable building blocks, respectively.

| Ex. | Systematic Name | Structure | Building blocks | MS m/z |
|---|---|---|---|---|
| 73 | (4R)-4-[3-[3-[4-(2-Chloro-4-methyl-sulfonyl-phenyl)phenyl]azetidin-1-yl]-3-oxo-propyl]oxazolidin-2-one | 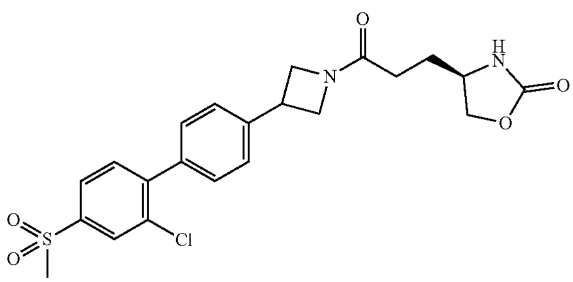 [SMILES: CS(=O)(=O)c1ccc(-c2ccc(C3CN(C(=O)CC[C@@H]4COC(=O)N4)C3)cc2)c(Cl)c1] | 3-[(4R)-2-Oxooxazolidin-4-yl]propanoic acid (BB 9) and 3-[4-(2-Chloro-4-methylsulfonyl-phenyl)phenyl]azetidine; 4-methylbenzenesulfonic acid (BB 27) | 463.2 [M + H]$^+$ |
| 74 | (4R)-4-[3-[3-[4-(Benzenesulfonyl)phenyl]azetidin-1-yl]-3-oxo-propyl]oxazolidin-2-one | 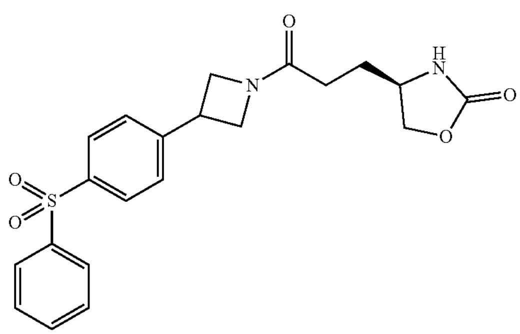 [SMILES: O=C1N[C@H](CCC(=O)N2CC(c3ccc(S(=O)(=O)c4ccccc4)cc3)C2)CO1] | 3-[(4R)-2-Oxooxazolidin-4-yl]propanoic acid (BB 9) and 3-[4-(Benzene-sulfonyl)phenyl]azetidine; 4-methylbenzenesulfonic acid (BB 33) | 415.2 [M + H]$^+$ |
| 75 | 2-[4-[1-[3-[(4R)-2-Oxooxazolidin-4-yl]propanoyl]azetidin-3-yl]phenyl]sulfonyl-acetonitrile | 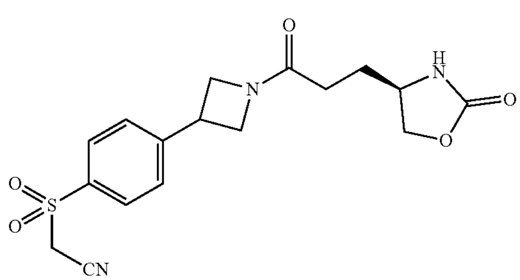 [SMILES: N#CCS(=O)(=O)c1ccc(C2CN(C(=O)CC[C@@H]3COC(=O)N3)C2)cc1] | 3-[(4R)-2-Oxooxazolidin-4-yl]propanoic acid (BB 9) and 2-[4-(Azetidin-3-yl)phenyl]sulfonylacetonitrile; 4-methylbenzenesulfonic acid (BB 34) | 378.2 [M + H]$^+$ |

-continued

| Ex. | Systematic Name | Structure | Building blocks | MS m/z |
|---|---|---|---|---|
| 76 | (4R)-4-[3-Oxo-3-[3-[4-(trifluoro-methylsulfonyl)phenyl]azetidin-1-yl]propyl]oxazolidin-2-one | 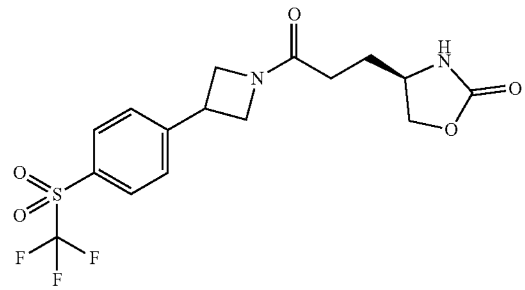 [SMILES: O=C1N[C@H](CCC(=O)N2CC(c3ccc(S(=O)(=O)C(F)(F)F)cc3)C2)CO1] | 3-[(4R)-2-Oxooxazolidin-4-yl]propanoic acid (BB 9) and 3-[4-(Trifluoromethylsulfonyl)phenyl]azetidine; 4-methylbenzenesulfonic acid (BB 35) | 407.2 [M + H]$^+$ |
| 77 | (4R)-4-[3-[3-(4-Cyclohexylsulfonyl-phenyl)azetidin-1-yl]-3-oxo-propyl]oxazolidin-2-one | 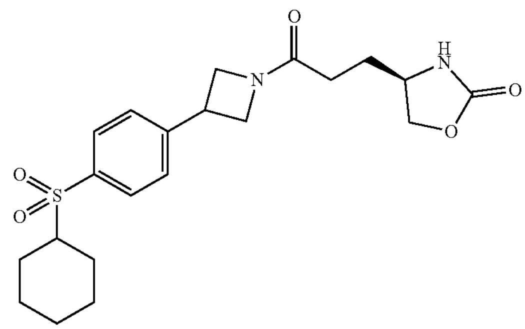 [SMILES: O=C1N[C@H](CCC(=O)N2CC(c3ccc(S(=O)(=O)C4CCCCC4)cc3)C2)CO1] | 3-[(4R)-2-Oxooxazolidin-4-yl]propanoic acid (BB 9) and 3-(4-Cyclohexylsulfonylphenyl)azetidine; 4-methylbenzenesulfonic acid (BB 36) | 421.2 [M + H]$^+$ |
| 78 | 1-[5-[1-[3-[(4R)-2-Oxooxazolidin-4-yl]propanoyl]azetidin-3-yl]-2-pyridyl]cyclobutane-carbonitrile | 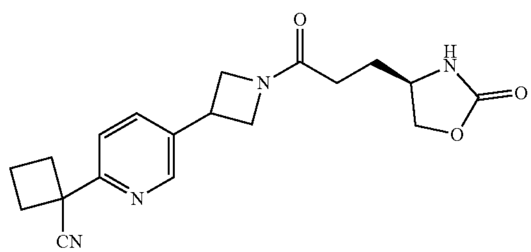 [SMILES: N#CC1(c2ccc(C3CN(C(=O)CC[C@@H]4COC(=O)N4)C3)cn2)CCC1] | 3-[(4R)-2-Oxooxazolidin-4-yl]propanoic acid (BB 9) and 1-[5-(Azetidin-3-yl)-2-pyridyl]cyclobutane-carbonitrile; 4-methylbenzenesulfonic acid (BB 37) | 355.2 [M + H]$^+$ |
| 79 | (4R)-4-[3-[3-[4-[(2-Methyl-3-pyridyl)oxy]phenyl]azetidin-1-yl]-3-oxo-propyl]oxazolidin-2-one | 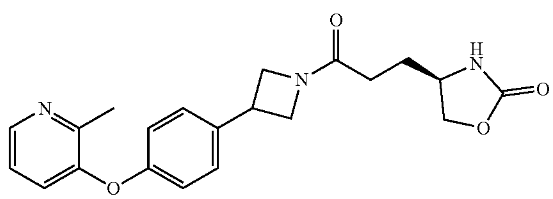 [SMILES: Cc1ncccc1Oc1ccc(C2CN(C(=O)CC[C@@H]3COC(=O)N3)C2)cc1] | 3-[(4R)-2-Oxooxazolidin-4-yl]propanoic acid (BB 9) and 3-[4-(Azetidin-3-yl)phenoxy]-2-methyl-pyridine; 4-methyl-benzenesulfonic acid (BB 38) | 382.2 [M + H]$^+$ |
| 80 | (4R)-4-[3-[3-[4-(4-Cyclopropyl-pyrimidin-2-yl)oxyphenyl]azetidin-1-yl]-3-oxo-propyl]oxazolidin-2-one | 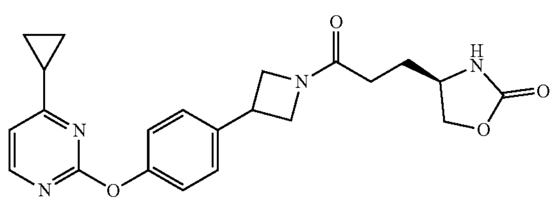 [SMILES: O=C1N[C@H](CCC(=O)N2CC(c3ccc(Oc4nccc(C5CC5)n4)cc3)C2)CO1] | 3-[(4R)-2-Oxooxazolidin-4-yl]propanoic acid (BB 9) and 2-[4-(Azetidin-3-yl)phenoxy]-4-cyclopropyl-pyrimidine; 4-methylbenzenesulfonic acid (BB 39) | 409.3 [M + H]$^+$ |
| 81 | (4R)-4-[3-[3-[4-[3-(2,2-Dimethyl-propyl)triazol-4-yl]phenyl]azetidin-1-yl]-3-oxo-propyl]oxazolidin-2-one | 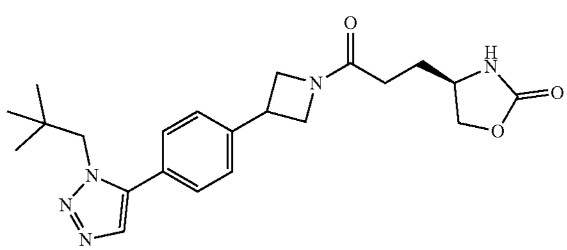 [SMILES: CC(C)(C)Cn1nncc1-c1ccc(C2CN(C(=O)CC[C@@H]3COC(=O)N3)C2)cc1] | 3-[(4R)-2-Oxooxazolidin-4-yl]propanoic acid (BB 9) and 5-[4-(Azetidin-3-yl)phenyl]-1-(2,2-dimethyl-propyl)triazole; 4-methylbenzenesulfonic acid (BB 40) | 412.3 [M + H]$^+$ |

-continued

| Ex. | Systematic Name | Structure | Building blocks | MS m/z |
|---|---|---|---|---|
| 82 | (4R)-4-[3-[3-[4-(4-Chloro-2-methyl-sulfonyl-phenyl)phenyl]azetidin-1-yl]-3-oxo-propyl]oxazolidin-2-one | 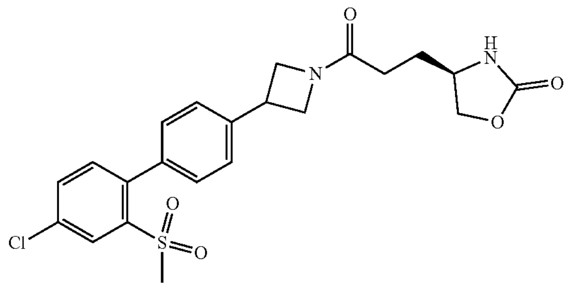 [SMILES: CS(=O)(=O)c1cc(Cl)ccc1-c1ccc(C2CN(C(=O)CC[C@@H]3COC(=O)N3)C2)cc1] | 3-[(4R)-2-Oxooxazolidin-4-yl]propanoic acid (BB 9) and 3-[4-(4-Chloro-2-methylsulfonyl-phenyl)phenyl]azetidine; 4-methylbenzene-sulfonic acid (BB 41) | 463.2 [M + H]⁺ |
| 83 | (+)- or (−)-(4R)-4-[3-[4-[(4-Methyl-sulfonylphenyl)-phenyl-methyl]-1-piperidyl]-3-oxo-propyl]oxazolidin-2-one | 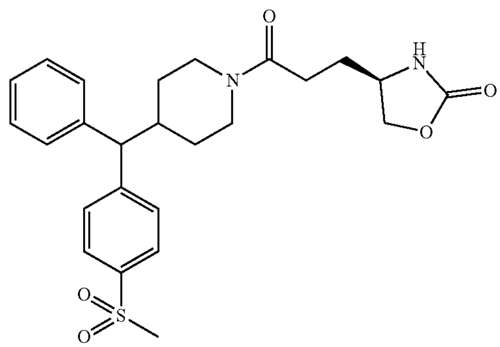 [SMILES: CS(=O)(=O)c1ccc(C(c2ccccc2)C2CCN(C(=O)CC[C@@H]3COC(=O)N3)CC2)cc1] | 3-[(4R)-2-Oxooxazolidin-4-yl]propanoic acid (BB 9) and (+)- or (−)-4-[(4-Methylsulfonylphenyl)-phenyl-methyl]piperidine; 4-methylbenzene-sulfonic acid (BB 42A) | 471.3 [M + H]⁺ |
| 84 | (−)- or (+)-(−)-(4R)-4-[3-[4-[(4-Methyl-sulfonylphenyl)-phenyl-methyl]-1-piperidyl]-3-oxo-propyl]oxazolidin-2-one | 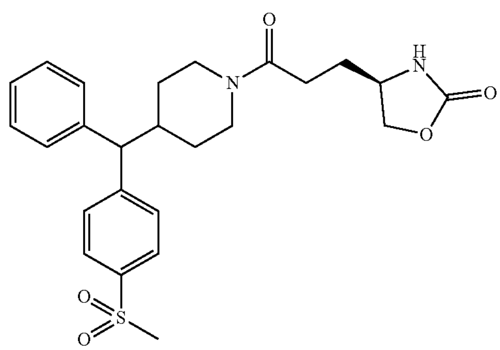 [SMILES: CS(=O)(=O)c1ccc(C(c2ccccc2)C2CCN(C(=O)CC[C@@H]3COC(=O)N3)CC2)cc1] | 3-[(4R)-2-Oxooxazolidin-4-yl]propanoic acid (BB 9) and (−)- or (+)-4-[(4-Methylsulfonylphenyl)-phenyl-methyl]piperidine; 4-methylbenzene-sulfonic acid (BB 42B) | 471.3 [M + H]⁺ |

Example 85

5-Chloro-2-[[5-[1-[3-[(4R)-2-oxooxazolidin-4-yl]propanoyl]azetidin-3-yl]-2-pyridyl]oxy]benzamide

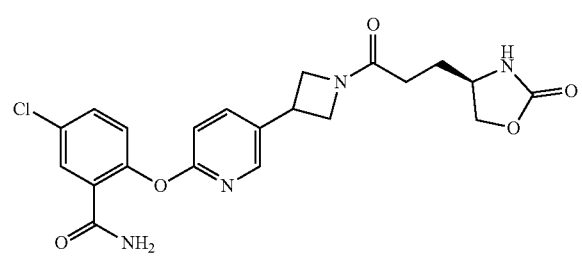 [SMILES: NC(=O)c1cc(Cl)ccc1Oc1ccc(C2CN(C(=O)CC[C@@H]3COC(=O)N3)C2)cn1]

Step 1: Methyl 5-chloro-2-[[5-[1-[3-[(4R)-2-oxooxazolidin-4-yl]propanoyl]azetidin-3-yl]-2-pyridyl]oxy]benzoate To a mixture of 3-[(4R)-2-oxooxazolidin-4-yl]propanoic acid (42.3 mg, 0.27 mmol, 1.0 equiv; BB 9) and HATU (101.0 mg, 0.27 mmol, 1.0 equiv) in DMF (7.3 mL) was added DIPEA (172 mg, 230 µL, 1.33 mmol, 5.0 equiv) and the suspension was stirred at RT for 15 min before methyl 2-[[5-(azetidin-3-yl)-2-pyridyl]oxy]-5-chloro-benzoate; 4-methylbenzenesulfonic acid (44 mg, 0.078 mmol, 1.0 equiv; BB 43) was added in one portion. Stirring was continued at RT overnight. The crude reaction product was purified by preparative HPLC (Gemini NX column (100 mm×30 mm, 5 µm); 0.1% v/v FA in water and MeCN) to give the desired product as a colorless oil (40 mg, 31%). MS (ESI): m/z=460.1 [M+H]⁺.

Step 2: 5-Chloro-2-[[5-[1-[3-[(4R)-2-oxooxazolidin-4-yl]propanoyl]azetidin-3-yl]-2-pyridyl]oxy]benzamide To a solution of methyl 5-chloro-2-[[5-[I-[3-[(4R)-2-oxooxazolidin-4-yl]propanoyl]azetidin-3-yl]-2-pyridyl]

oxy]benzoate (27.4 mg, 0.06 mmol, 1.0 equiv) in ACN (0.5 mL) was added a solution of aqueous ammonium hydroxide (2 mL, 50 mmol, 835 equiv; 25 M) and the reaction mixture was stirred at RT for 18 h. Concentration in vacuo provided the desired product as a colorless oil (14 mg, 47%). MS (ESI): m/z=443.4 [M+H]+.

Example 86 and Example 87

(−)- or (+)-[(4S)-2-Oxooxazolidin-4-yl]methyl 3-[6-[3-(trifluoromethyl)pyrrolidin-1-yl]-3-pyridyl]azetidine-1-carboxylate and (+)- or (−)-[(4S)-2-Oxooxazolidin-4-yl]methyl 3-[6-[3-(trifluoromethyl)pyrrolidin-1-yl]-3-pyridyl]azetidine-1-carboxylate

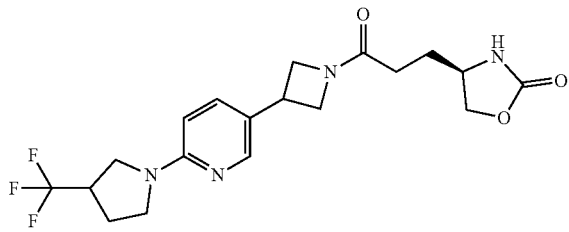 [SMILES: O=C1N[C@H](CCC(=O)N2CC(c3ccc(N4CCC(C(F)(F)F)C4)nc3)C2)CO1]

The enantiomers of [(4S)-2-oxooxazolidin-4-yl]methyl 3-[6-[3-(trifluoromethyl)pyrrolidin-1-yl]-3-pyridyl]azetidine-1-carboxylate (50 mg, 0.12 mmol; Example 62) were separated by chiral SFC (Chiralpak IC column (250 mm×20 mm, 5 μm), eluent: 35% MeOH in supercritical $CO_2$) to give (−)- or (+)-[(4S)-2-oxooxazolidin-4-yl]methyl 3-[6-[3-(trifluoromethyl)pyrrolidin-1-yl]-3-pyridyl]azetidine-1-carboxylate (20 mg, 40%; first eluting compound) as an off-white solid and (+)- or (−)-[(4S)-2-oxooxazolidin-4-yl] methyl 3-[6-[3-(trifluoromethyl)pyrrolidin-1-yl]-3-pyridyl] azetidine-1-carboxylate (20 mg, 40%; second eluting compound) as an off-white solid. MS (ESI): m/z=415.2 [M+H]+ for both examples.

Example 88

(5S)-5-[3-[3-[[2-Fluoro-4-(trifluoromethyl)phenyl] methoxy]azetidin-1-yl]-3-oxo-propyl]thiomorpholin-3-one

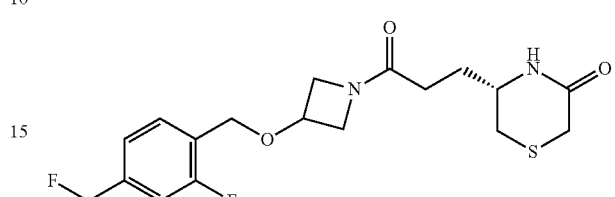

A solution of 3-[(3S)-5-oxothiomorpholin-3-yl]propanoic acid (30 mg, 0.16 mmol, 1.0 equiv; BB 44), 3-[[2-fluoro-4-(trifluoromethyl)phenyl]methoxy]azetidine; 2,2,2-trifluoroacetic acid (57.6 mg, 0.16 mmol, 1.0 equiv; BB 22), $T_3P$/ethyl acetate (54.7 mg, 0.24 mmol, 1.5 equiv, wt. 50%) and TEA (48.1 mg, 7 μL, 0.48 mmol, 3.0 equiv) in DMF (1 mL) was stirred at RT for 16 h. The reaction mixture was diluted with water (10 mL) and extracted with ethyl acetate (3×10 mL). The combined organic layers were dried over $MgSO_4$, concentrated and the residue purified by preparative SFC (Chiralpak AS-3 column (50 mm×4.6 mm, 3 m); eluent: 40% MeOH (0.05% diethylamine) in supercritical $CO_2$) to give the desired product as a light yellow oil (6.4 mg, 10%). MS (ESI): m/z=421.2 [M+H]+.

If not indicated otherwise the following examples were synthesized in analogy to the synthesis described for Example 72 using suitable building blocks, respectively.

| Ex. | Systematic Name | Structure | Building blocks | MS m/z |
|---|---|---|---|---|
| 89 | (4R)-4-[3-[3-[4-[N-(Cyclopropylmethyl) anilino]phenyl] azetidin-1-yl]-3-oxo-propyl] oxazolidin-2-one | 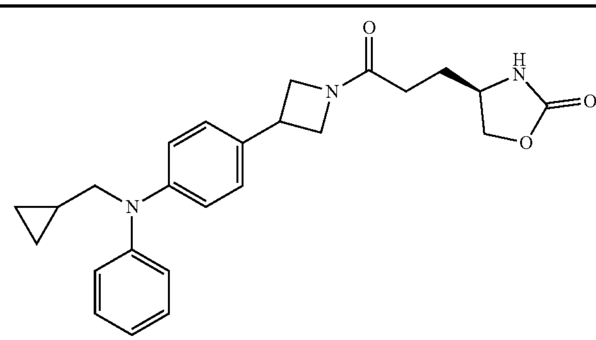 | 3-[(4R)-2-Oxooxazolidin-4-yl]propanoic acid (BB 9) and 4-(Azetidin-3-yl)-N-(cyclopropylmethyl)-N-phenyl-aniline (BB 45) | 420.4 [M + H]+ |
| 90 | (4R)-4-[3-Oxo-3-[3-[4-(N-phenylanilino) phenyl]azetidin-1-yl]propyl] oxazolidin-2-one | 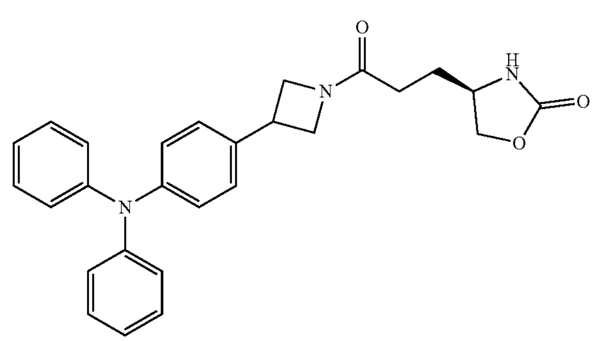 [SMILES: O=C1N[C@H](CCC(=O)N2CC(c3ccc(N(c4ccccc4)c4ccccc4)cc3)C2)CO1] | 3-[(4R)-2-Oxooxazolidin-4-yl]propanoic acid (BB 9) and 4-(Azetidin-3-yl)-N,N-diphenyl-aniline; 4-methyl-benzenesulfonic acid (BB 46) | 442.3 [M + H]+ |

-continued

| Ex. | Systematic Name | Structure | Building blocks | MS m/z |
|---|---|---|---|---|
| 91 | (4R)-4-[3-[3-(6-tert-Butyl-3-pyridyl)azetidin-1-yl]-3-oxo-propyl]oxazolidin-2-one | 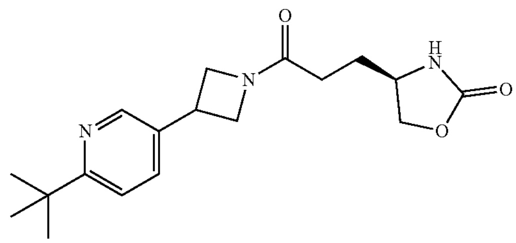 [SMILES: CC(C)(C)c1ccc(C2CN(C(=O)CC[C@@H]3COC(=O)N3)C2)cn1] | 3-[(4R)-2-Oxooxazolidin-4-yl]propanoic acid (BB 9) and 5-(Azetidin-3-yl)-2-tert-butyl-pyridine (BB 47) | 332.2 [M + H]⁺ |
| 92 | (4R)-4-[3-[3-[6-[(5-Methoxy-2-pyridyl)-methyl-amino]-3-pyridyl]azetidin-1-yl]-3-oxo-propyl]oxazolidin-2-one | 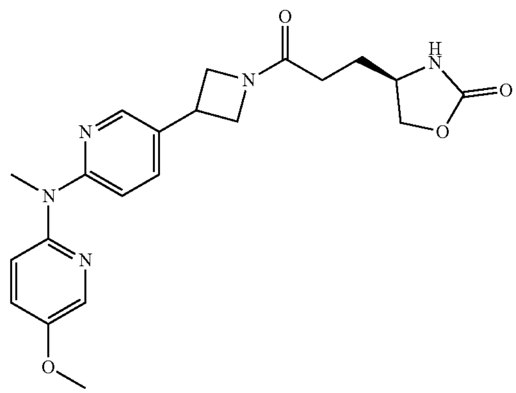 [SMILES: COc1ccc(N(C)c2ccc(C3CN(C(=O)CC[C@@H]4COC(=O)N4)C3)cn2)nc1] | 3-[(4R)-2-Oxooxazolidin-4-yl]propanoic acid (BB 9) and 5-(Azetidin-3-yl)-N-(5-methoxy-2-pyridyl)-N-methyl-pyridin-2-amine (BB 48) | 412.3 [M + H]⁺ |
| 93 | (4R)-4-[3-[3-[6-(N-Methyl-anilino)-3-pyridyl]azetidin-1-yl]-3-oxo-propyl]oxazolidin-2-one | 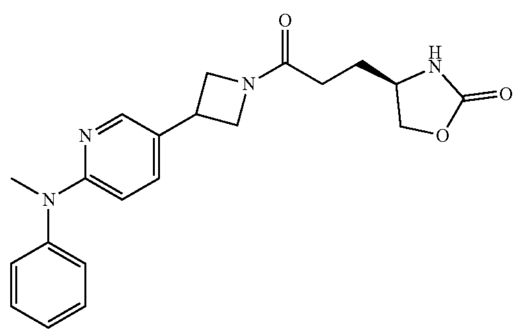 [SMILES: CN(c1ccccc1)c1ccc(C2CN(C(=O)CC[C@@H]3COC(=O)N3)C2)cn1] | 3-[(4R)-2-Oxooxazolidin-4-yl]propanoic acid (BB 9) and 5-(Azetidin-3-yl)-N-methyl-N-phenyl-pyridin-2-amine (BB 49) | 381.3 [M + H]⁺ |
| 94 | (4R)-4-[3-[3-[6-(4-Isopropyl-N-methyl-anilino)-3-pyridyl]azetidin-1-yl]-3-oxo-propyl]oxazolidin-2-one | 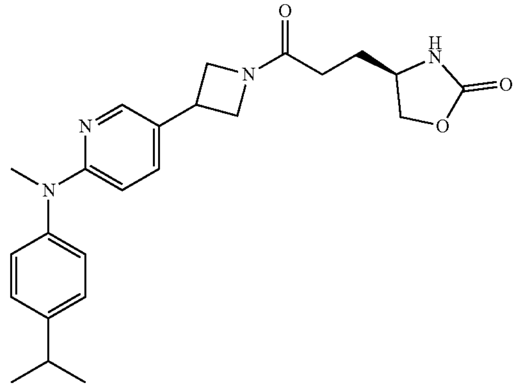 [SMILES: CC(C)c1ccc(N(C)c2ccc(C3CN(C(=O)CC[C@@H]4COC(=O)N4)C3)cn2)cc1] | 3-[(4R)-2-Oxooxazolidin-4-yl]propanoic acid (BB 9) and 5-(Azetidin-3-yl)-N-(4-isopropylphenyl)-N-methyl-pyridin-2-amine (BB 50) | 423.3 [M + H]⁺ |

-continued

| Ex. | Systematic Name | Building blocks | MS m/z |
|---|---|---|---|
| 95 | (4R)-4-[3-[3-[6-[N-(Cyclopropyl-methyl)anilino]-3-pyridyl]azetidin-1-yl]-3-oxo-propyl]oxazolidin-2-one | 3-[(4R)-2-Oxooxazolidin-4-yl]propanoic acid (BB 9) and 5-(Azetidin-3-yl)-N-(cyclopropylmethyl)-N-phenyl-pyridin-2-amine (BB 51) | 421.3 [M + H]+ |
| 96 | (4R)-4-[3-[3-[4-[2-Methoxyethyl(3-pyridyl)amino]phenyl]azetidin-1-yl]-3-oxo-propyl]oxazolidin-2-one | 3-[(4R)-2-Oxooxazolidin-4-yl]propanoic acid (BB 9) and N-[4-(Azetidin-3-yl)phenyl]-N-(2-methoxyethyl)pyridin-3-amine (BB 52) | 425.3 [M + H]+ |
| 97 | (4R)-4-[3-[2-[4-Fluoro-2-(trifluoromethyl)phenyl]sulfonyl-2,6-diazaspiro[3.3]heptan-6-yl]-3-oxo-propyl]oxazolidin-2-one | 3-[(4R)-2-Oxooxazolidin-4-yl]propanoic acid (BB 9) and Trifluoromethyl 2-[4-fluoro-2-(trifluoromethyl)phenyl]sulfonyl-2,6-diazaspiro[3.3]heptane; 2,2,2-trifluoroacetic acid (BB 53) | 466.3 [M + H]+ |
| 98 | (4R)-4-[3-[2-(2,2-Dimethylpropyl-sulfonyl)-2,6-diazaspiro[3.3]heptan-6-yl]-3-oxo-propyl]oxazolidin-2-one | 3-[(4R)-2-Oxooxazolidin-4-yl]propanoic acid (BB 9) and 2-(2,2-Dimethyl-propylsulfonyl)-2,6-diazaspiro[3.3]heptane; 2,2,2-trifluoroacetic acid (BB 54) | 374.3 [M + H]+ |
| 99 | (4R)-4-[3-Oxo-3-[3-[4-[3-(2,2,2-trifluoro-ethoxy)azetidin-1-yl]phenyl]azetidin-1-yl]propyl]oxazolidin-2-one | 3-[(4R)-2-Oxooxazolidin-4-yl]propanoic acid (BB 9) and 1-[4-(Azetidin-3-yl)phenyl]-3-(2,2,2-trifluoroethoxy)azetidine; 4-methyl-benzenesulfonic acid (BB 21) | 428.3 [M + H]+ |

| Ex. | Systematic Name | Structure | Building blocks | MS m/z |
|---|---|---|---|---|
| 100 | (4R)-4-[3-Oxo-3-[3-[4-[3-(trifluoromethyl)azetidin-1-yl]phenyl]azetidin-1-yl]propyl]oxazolidin-2-one | 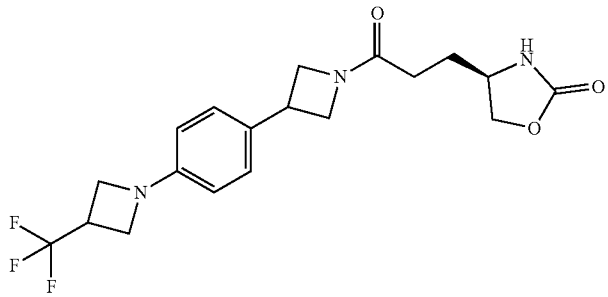 [SMILES: O=C1N[C@H](CCC(=O)N2CC(c3ccc(N4CC(C(F)(F)F)C4)cc3)C2)CO1] | 3-[(4R)-2-Oxooxazolidin-4-yl]propanoic acid (BB 9) and 1-[4-(Azetidin-3-yl)phenyl]-3-(trifluoromethyl)azetidine; 2,2,2-trifluoroacetic acid (BB 55) | 398.2 [M + H]⁺ |
| 101 | (4R)-4-[3-Oxo-3-(3-[2-[1-(trifluoromethyl)cyclopropyl]pyrimidin-5-yl]azetidin-1-yl]propyl]oxazolidin-2-one | 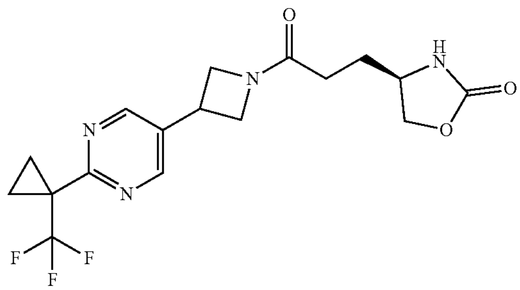 [SMILES: O=C1N[C@H](CCC(=O)N2CC(c3cnc(C4(C(F)(F)F)CC4)nc3)C2)CO1] | 3-[(4R)-2-Oxooxazolidin-4-yl]propanoic acid (BB 9) and 5-(Azetidin-3-yl)-2-[1-(trifluoromethyl)cyclopropyl]pyrimidine; 4-methylbenzenesulfonic acid (BB 56) | 385.2 [M + H]⁺ |
| 102 | (4R)-4-[3-Oxo-3-[3-[6-[1-(trifluoromethyl)cyclopropyl]-3-pyridyl]azetidin-1-yl]propyl]oxazolidin-2-one | 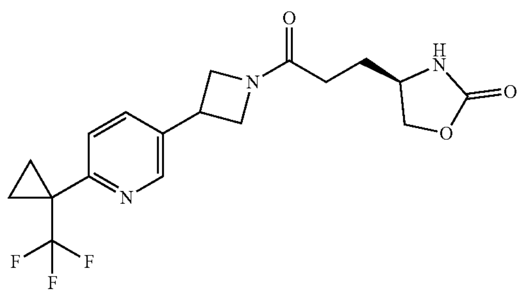 [SMILES: O=C1N[C@H](CCC(=O)N2CC(c3ccc(C4(C(F)(F)F)CC4)nc3)C2)CO1] | 3-[(4R)-2-Oxooxazolidin-4-yl]propanoic acid (BB 9) and 5-(Azetidin-3-yl)-2-[1-(trifluoromethyl)cyclopropyl]pyridine; 4-methylbenzenesulfonic acid (BB 57) | 384.2 [M + H]⁺ |
| 103 | (4R)-4-[3-Oxo-3-[3-[5-[3-(trifluoromethyl)pyrrolidin-1-yl]-2-pyridyl]azetidin-1-yl]propyl]oxazolidin-2-one | 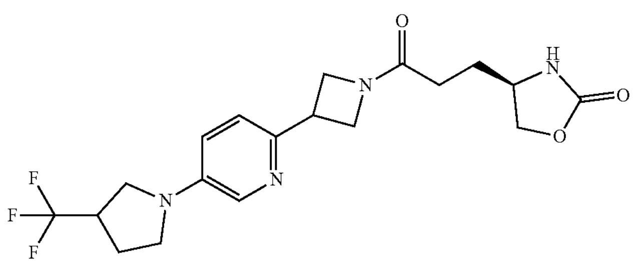 [SMILES: O=C1N[C@H](CCC(=O)N2CC(c3ccc(N4CCC(C(F)(F)F)C4)cn3)C2)CO1] | 3-[(4R)-2-Oxooxazolidin-4-yl]propanoic acid (BB 9) and 2-(Azetidin-3-yl)-5-[3-(trifluoromethyl)pyrrolidin-1-yl]pyridine; 4-methylbenzenesulfonic acid (BB 58) | 413.2 [M + H]⁺ |
| 104 | (4R)-4-[3-[3-[4-[3-(Methylsulfonylmethyl)azetidin-1-yl]phenyl]azetidin-1-yl]-3-oxopropyl]oxazolidin-2-one | 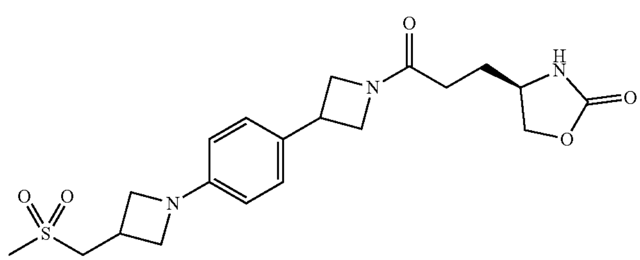 [SMILES: CS(=O)(=O)CC1CN(c2ccc(C3CN(C(=O)CC[C@@H]4COC(=O)N4)C3)cc2)C1] | 3-[(4R)-2-Oxooxazolidin-4-yl]propanoic acid (BB 9) and 1-[4-(Azetidin-3-yl)phenyl]-3-(methylsulfonylmethyl)azetidine; 4-methylbenzenesulfonic acid (BB 59) | 422.2 [M + H]⁺ |

-continued

| Ex. | Systematic Name | Building blocks | MS m/z |
|---|---|---|---|
| 105 | (4R)-4-[3-Oxo-3-[3-[5-[3-(trifluoro-methyl)pyrrolidin-1-yl]pyrazin-2-yl]azetidin-1-yl]propyl]oxazolidin-2-one | 3-[(4R)-2-Oxooxazolidin-4-yl]propanoic acid (BB 9) and 2-(Azetidin-3-yl)-5-[3-(trifluoro-methyl)pyrrolidin-1-yl]pyrazine; 4-methylbenzene-sulfonic acid (BB 60) | 414.2 [M + H]⁺ |
| 106 | (4R)-4-[3-Oxo-3-[3-[5-[3-(trifluoro-methyl)pyrrolidin-1-yl]pyrimidin-2-yl]azetidin-1-yl]propyl]oxazolidin-2-one | 3-[(4R)-2-Oxooxazolidin-4-yl]propanoic acid (BB 9) and 2-(Azetidin-3-yl)-5-[3-(trifluoro-methyl)pyrrolidin-1-yl]pyrimidine; 4-methylbenzene-sulfonic acid (BB 61) | 414.2 [M + H]⁺ |
| 107 | (4R)-[3-Oxo-3-[3-[2-[3-(trifluoro-methyl)pyrrolidin-1-yl]pyrimidin-5-yl]azetidin-1-yl]propyl]oxazolidin-2-one | 3-[(4R)-2-Oxooxazolidin-4-yl]propanoic acid (BB 9) and 5-(Azetidin-3-yl)-2-[3-(trifluoro-methyl)pyrrolidin-1-yl]pyrimidine; 4-methylbenzene-sulfonic acid (BB 62) | 414.2 [M + H]⁺ |
| 108 | (4R)-4-[3-[3-[5-(2-Chloro-4-methylsulfonyl-phenyl)-2-pyridyl]azetidin-1-yl]-3-oxo-propyl]oxazolidin-2-one | 3-[(4R)-2-Oxooxazolidin-4-yl]propanoic acid (BB 9) and 2-(Azetidin-3-yl)-5-(2-chloro-4-methylsulfonyl-phenyl)pyridine; 4-methylbenzene-sulfonic acid (BB 63) | 464.2 [M + H]⁺ |
| 109 | (4R)-4-[3-Oxo-3-[3-[3-[1-(trifluoromethyl)cyclopropyl]phenyl]azetidin-1-yl]propyl]oxazolidin-2-one | 3-[(4R)-2-Oxooxazolidin-4-yl]propanoic acid (BB 9) and 4-Methylbenzene-sulfonic acid; 3-[3-[1-(trifluoromethyl)cyclopropyl]phenyl]azetidine (BB 64) | 383.2 [M + H]⁺ |

| Ex. | Systematic Name | Structure | Building blocks | MS m/z |
|---|---|---|---|---|
| 110 | (4R)-4-[3-[3-[5-(2-Chloro-4-methylsulfonyl-phenyl)pyrazin-2-yl]azetidin-1-yl]-3-oxo-propyl]oxazolidin-2-one | 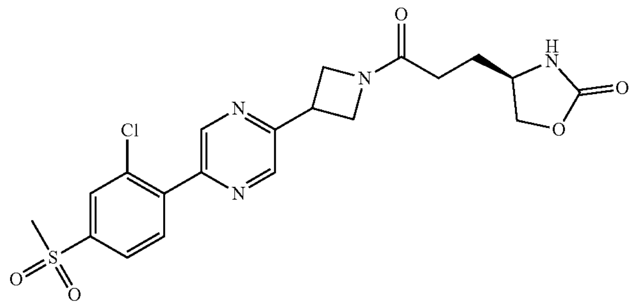 [SMILES: CS(=O)(=O)c1ccc(-c2cnc(C3CN(C(=O)CC[C@@H]4COC(=O)N4)C3)cn2)c(Cl)c1] | 3-[(4R)-2-Oxooxazolidin-4-yl]propanoic acid (BB 9) and 2-(Azetidin-3-yl)-5-(2-chloro-4-methylsulfonyl-phenyl)pyrazine; 4-methylbenzene-sulfonic acid (BB 65) | 465.1 [M + H]$^+$ |
| 111 | (4R)-4-[3-[3-(6-tert-Butylsulfonyl-3-pyridyl)azetidin-1-yl]-3-oxo-propyl]oxazolidin-2-one | 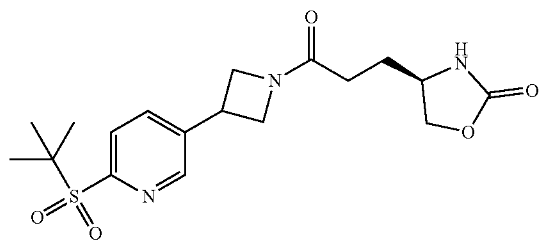 [SMILES: CC(C)(C)S(=O)(=O)c1ccc(C2CN(C(=O)CC[C@@H]3COC(=O)N3)C2)cn1] | 3-[(4R)-2-Oxooxazolidin-4-yl]propanoic acid (BB 9) and 5-(Azetidin-3-yl)-2-tert-butyl-sulfonyl-pyridine; 4-methylbenzene-sulfonic acid (BB 66) | 396.2 [M + H]$^+$ |
| 112 | (4R)-4-[3-[3-[5-(4-Chloro-2-fluoro-phenyl)pyrimidin-2-yl]azetidin-1-yl]-3-oxo-propyl]oxazolidin-2-one | 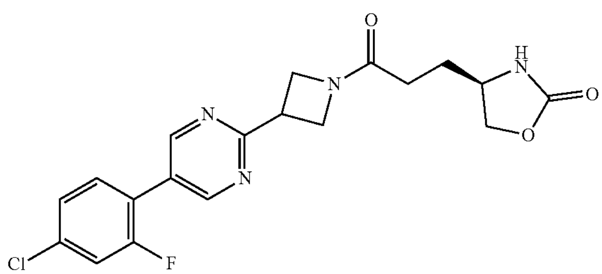 [SMILES: O=C1N[C@H](CCC(=O)N2CC(c3ncc(-c4ccc(Cl)cc4F)cn3)C2)CO1] | 3-[(4R)-2-Oxooxazolidin-4-yl]propanoic acid (BB 9) and 2-(Azetidin-3-yl)-5-(4-chloro-2-fluoro-phenyl)pyrimidine; 4-methylbenzene-sulfonic acid (BB 67) | 405.1 [M + H]$^+$ |
| 113 | (4R)-4-[3-[3-[5-(4-Chloro-2-fluoro-phenyl)-2-pyridyl]azetidin-1-yl]-3-oxo-propyl]oxazolidin-2-one | 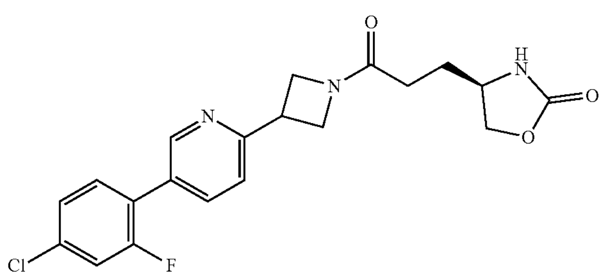 [SMILES: O=C1N[C@H](CCC(=O)N2CC(c3ccc(-c4ccc(Cl)cc4F)cn3)C2)CO1] | 3-[(4R)-2-Oxooxazolidin-4-yl]propanoic acid (BB 9) and 2-(Azetidin-3-yl)-5-(4-chloro-2-fluoro-phenyl)pyridine; 4-methylbenzene-sulfonic acid (BB 68) | 404.1 [M + H]$^+$ |
| 114 | (4R)-4-[3-[3-[5-(2,4-Dichloro-phenyl)-2-pyridyl]azetidin-1-yl]-3-oxo-propyl]oxazolidin-2-one | 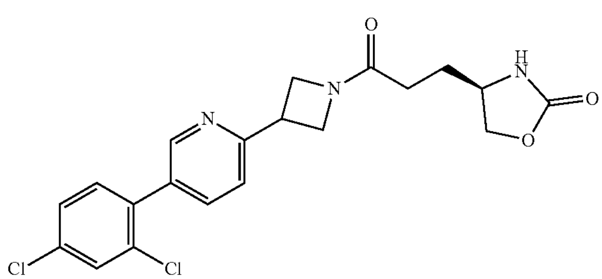 [SMILES: O=C1N[C@H](CCC(=O)N2CC(c3ccc(-c4ccc(Cl)cc4Cl)cn3)C2)CO1] | 3-[(4R)-2-Oxooxazolidin-4-yl]propanoic acid (BB 9) and 2-(Azetidin-3-yl)-5-(2,4-dichloro-phenyl)pyridine; 4-methylbenzene-sulfonic acid (BB 69) | 420.1 [M + H]$^+$ |

-continued

| Ex. | Systematic Name | Structure | Building blocks | MS m/z |
|---|---|---|---|---|
| 115 | (4R)-4-[3-[3-[4-(5-Chloro-3-methylsulfonyl-2-pyridyl)phenyl]azetidin-1-yl]-3-oxo-propyl]oxazolidin-2-one | 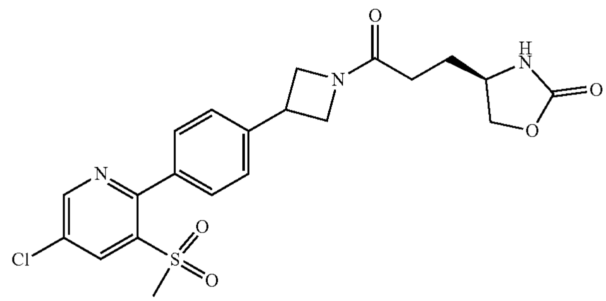 [SMILES: CS(=O)(=O)c1cc(Cl)cnc1-c1ccc(C2CN(C(=O)CC[C@@H]3COC(=O)N3)C2)cc1] | 3-[(4R)-2-Oxooxazolidin-4-yl]propanoic acid (BB 9) and 2-[4-(Azetidin-3-yl)phenyl]-5-chloro-3-methylsulfonyl-pyridine; 4-methylbenzene-sulfonic acid (BB 70) | 464.1 [M + H]⁺ |
| 116 | (4R)-4-[3-[3-[6-(2-Chloro-4-methylsulfonyl-phenyl)-3-pyridyl]azetidin-1-yl]-3-oxo-propyl]oxazolidin-2-one | 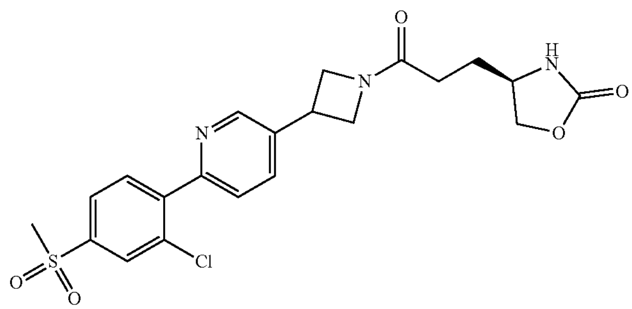 [SMILES: CS(=O)(=O)c1ccc(-c2ccc(C3CN(C(=O)CC[C@@H]4COC(=O)N4)C3)cn2)c(Cl)c1] | 3-[(4R)-2-Oxooxazolidin-4-yl]propanoic acid (BB 9) and 5-(Azetidin-3-yl)-2-(2-chloro-4-methylsulfonyl-phenyl)pyridine; 4-methylbenzene-sulfonic acid (BB 71) | 464.1 [M + H]⁺ |
| 117 | (4R)-4-[3-[3-[6-(4-Chloro-2-methylsulfonyl-phenyl)-3-pyridyl]azetidin-1-yl]-3-oxo-propyl]oxazolidin-2-one | 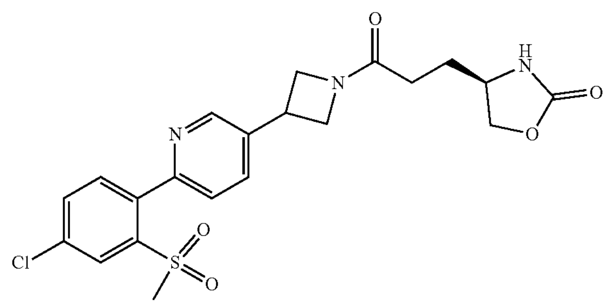 [SMILES: CS(=O)(=O)c1cc(Cl)ccc1-c1ccc(C2CN(C(=O)CC[C@@H]3COC(=O)N3)C2)cn1] | 3-[(4R)-2-Oxooxazolidin-4-yl]propanoic acid (BB 9) and 5-(Azetidin-3-yl)-2-(4-chloro-2-methylsulfonyl-phenyl)pyridine; 4-methylbenzene-sulfonic acid (BB 72) | 464.1 [M + H]⁺ |
| 118 | (4R)-4-[3-[3-[4-(6-Chloro-4-methylsulfonyl-3-pyridyl)phenyl]azetidin-1-yl]-3-oxo-propyl]oxazolidin-2-one | 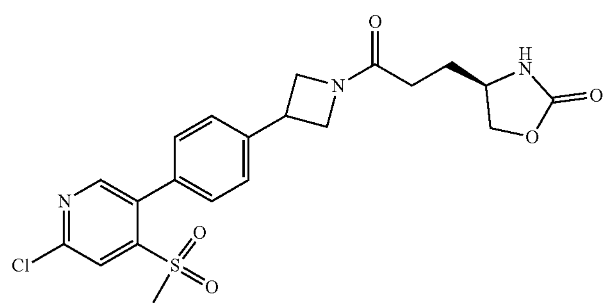 [SMILES: CS(=O)(=O)c1cc(Cl)ncc1-c1ccc(C2CN(C(=O)CC[C@@H]3COC(=O)N3)C2)cc1] | 3-[(4R)-2-Oxooxazolidin-4-yl]propanoic acid (BB 9) and 5-[4-(Azetidin-3-yl)phenyl]-2-chloro-4-methylsulfonyl-pyridine; 4-methylbenzene-sulfonic acid (BB 73) | 464.1 [M + H]⁺ |
| 119 | (4R)-4-[3-Oxo-3-[3-[4-[5-(trifluoromethyl)pyrazin-2-yl]phenyl]azetidin-1-yl]propyl]oxazolidin-2-one | 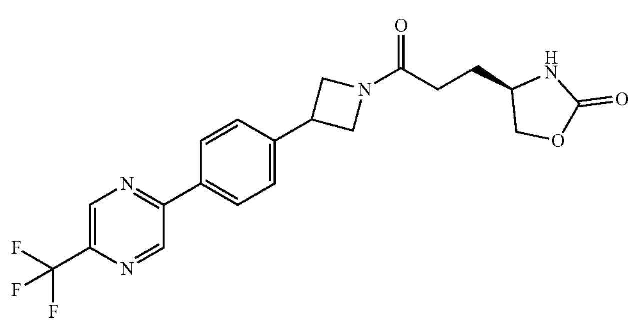 [SMILES: O=C1N[C@H](CCC(=O)N2CC(c3ccc(-c4cnc(C(F)(F)F)cn4)cc3)C2)CO1] | 3-[(4R)-2-Oxooxazolidin-4-yl]propanoic acid (BB 9) and 2-[4-(Azetidin-3-yl)phenyl]-5-(trifluoromethyl)pyrazine; 4-methylbenzene-sulfonic acid (BB 74) | 421.1 [M + H]⁺ |

-continued

| Ex. | Systematic Name | Structure | Building blocks | MS m/z |
|---|---|---|---|---|
| 120 | (4R)-4-[3-[3-[4-(4-Chloro-2-fluoro-phenyl)-3-methylsulfonyl-phenyl]azetidin-1-yl]-3-oxo-propyl]oxazolidin-2-one | 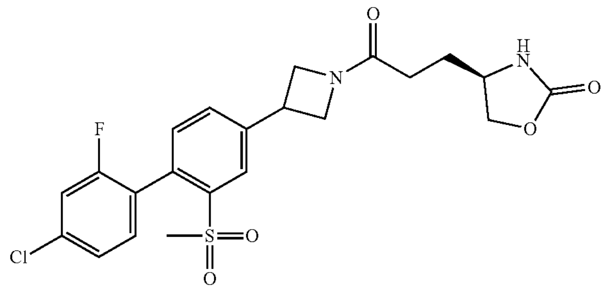 [SMILES: CS(=O)(=O)c1cc(C2CN(C(=O)CC[C@@H]3COC(=O)N3)C2)ccc1-c1ccc(Cl)cc1F] | 3-[(4R)-2-Oxooxazolidin-4-yl]propanoic acid (BB 9) and 3-[4-(4-Chloro-2-fluoro-phenyl)-3-methylsulfonyl-phenyl]azetidine; 4-methylbenzene-sulfonic acid (BB 75) | 481.1 [M + H]+ |
| 121 | (4R)-4-[3-[3-[5-(4-Chloro-2-methylsulfonyl-phenyl)-2-pyridyl]azetidin-1-yl]-3-oxo-propyl]oxazolidin-2-one | 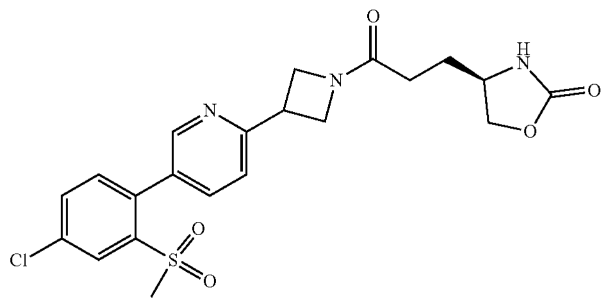 [SMILES: CS(=O)(=O)c1cc(Cl)ccc1-c1ccc(C2CN(C(=O)CC[C@@H]3COC(=O)N3)C2)nc1] | 3-[(4R)-2-Oxooxazolidin-4-yl]propanoic acid (BB 9) and 2-(Azetidin-3-yl)-5-(4-chloro-2-methylsulfonyl-phenyl)pyridine; 4-methylbenzene-sulfonic acid (BB 76) | 464.1 [M + H]+ |
| 122 | (4R)-4-[3-[3-[5-(2-Chloro-4-methylsulfonyl-phenyl)pyrimidin-2-yl]azetidin-1-yl]-3-oxo-propyl]oxazolidin-2-one | 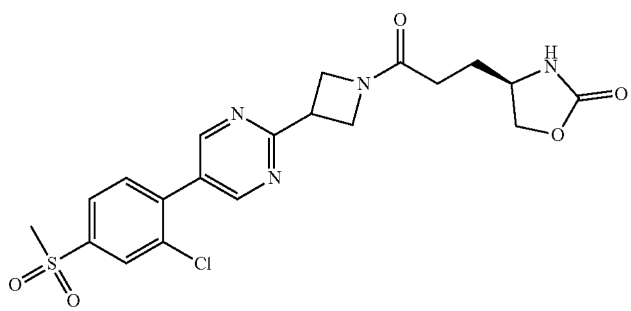 [SMILES: CS(=O)(=O)c1ccc(-c2cnc(C3CN(C(=O)CC[C@@H]4COC(=O)N4)C3)nc2)c(Cl)c1] | 3-[(4R)-2-Oxooxazolidin-4-yl]propanoic acid (BB 9) and 2-(Azetidin-3-yl)-5-(2-chloro-4-methylsulfonyl-phenyl)pyrimidine; 4-methylbenzene-sulfonic acid (BB 77) | 465.1 [M + H]+ |
| 123 | (4R)-4-[3-[3-[2-(2-Chloro-4-methylsulfonyl-phenyl)pyrimidin-5-yl]azetidin-1-yl]-3-oxo-propyl]oxazolidin-2-one | 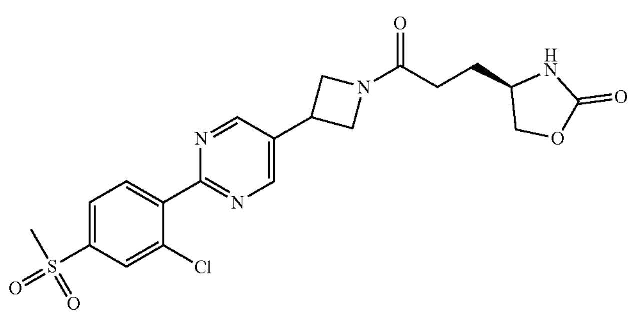 [SMILES: CS(=O)(=O)c1ccc(-c2ncc(C3CN(C(=O)CC[C@@H]4COC(=O)N4)C3)cn2)c(Cl)c1] | 3-[(4R)-2-Oxooxazolidin-4-yl]propanoic acid (BB 9) and 5-(Azetidin-3-yl)-2-(2-chloro-4-methylsulfonyl-phenyl)pyrimidine; 4-methylbenzene-sulfonic acid (BB 78) | 465.1 [M + H]+ |
| 124 | (4R)-4-[3-[3-[4-[2-Methyl-sulfonyl-5-(trifluoromethyl)-3-pyridyl]phenyl]azetidin-1-yl]-3-oxo-propyl]oxazolidin-2-one | 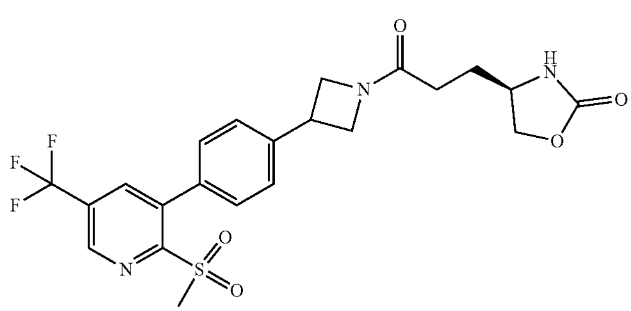 [SMILES: CS(=O)(=O)c1ncc(C(F)(F)F)cc1-c1ccc(C2CN(C(=O)CC[C@@H]3COC(=O)N3)C2)cc1] | 3-[(4R)-2-Oxooxazolidin-4-yl]propanoic acid (BB 9) and 3-[4-(Azetidin-3-yl)phenyl]-2-methylsulfonyl-5-(trifluoromethyl)pyridine; 4-methyl-benzenesulfonic acid (BB 79) | 498.1 [M + H]+ |

-continued

| Ex. | Systematic Name | Structure | Building blocks | MS m/z |
|---|---|---|---|---|
| 125 | (4R)-4-[3-Oxo-3-[6-[[6-(trifluoromethyl)-3-pyridyl]methyl]-2-azaspiro[3.3]heptan-2-yl]propyl]oxazolidin-2-one | 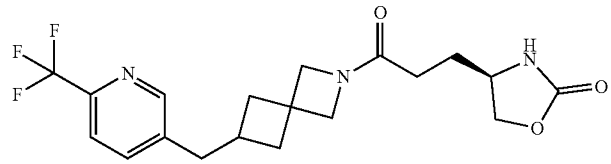 [SMILES: O=C1N[C@H](CCC(=O)N2CC3(CC(Cc4ccc(C(F)(F)F)nc4)C3)C2)CO1] | 3-[(4R)-2-Oxooxazolidin-4-yl]propanoic acid (BB 9) and 4-Methylbenzenesulfonic acid; 6-[[6-(trifluoromethyl)-3-pyridyl]methyl]-2-azaspiro[3.3]heptane (BB 80) | 442.3 [M + H]+ |
| 126 | (4R)-4-[3-[7-[[2-Fluoro-4-(trifluoromethyl)phenyl]methyl]-2,7-diazaspiro[3.5]nonan-2-yl]-3-oxo-propyl]oxazolidin-2-one | 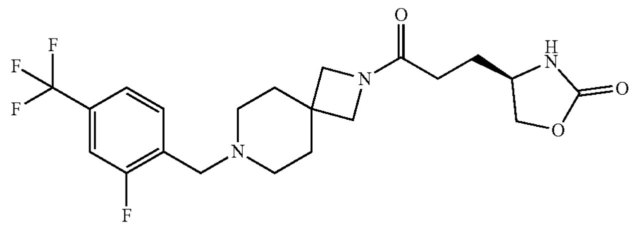 [SMILES: O=C1N[C@H](CCC(=O)N2CC3(CCN(Cc4ccc(C(F)(F)F)cc4F)CC3)C2)CO1] | 3-[(4R)-2-Oxooxazolidin-4-yl]propanoic acid (BB 9) and 7-[[2-Fluoro-4-(trifluoromethyl)phenyl]methyl]-2,7-diazaspiro[3.5]nonane; 4-methylbenzenesulfonic acid (BB 81) | 444.2 [M + H]+ |
| 127 | (4R)-4-[3-Oxo-3-[3-[4-[4-(trifluoromethyl)pyrimidin-2-yl]oxyphenyl]azetidin-1-yl]propyl]oxazolidin-2-one | 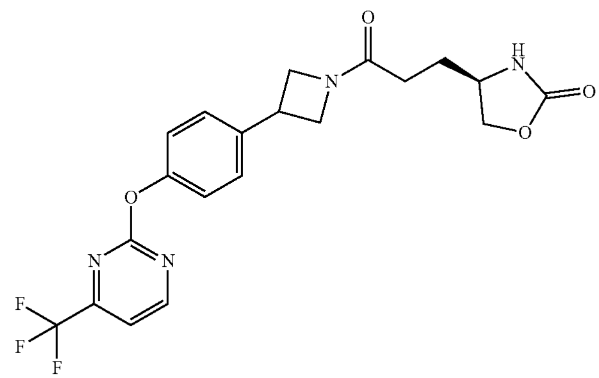 [SMILES: O=C1N[C@H](CCC(=O)N2CC(c3ccc(Oc4nccc(C(F)(F)F)n4)cc3)C2)CO1] | 3-[(4R)-2-Oxooxazolidin-4-yl]propanoic acid (BB 9) and 2-[4-(Azetidin-3-yl)phenoxy]-4-(trifluoromethyl)pyrimidine; 4-methylbenzenesulfonic acid (BB 82) | 437.1 [M + H]+ |
| 128 | (4R)-4-[3-[3-[4-[4-Methylsulfonyl-2-(trifluoromethyl)phenyl]phenyl]azetidin-1-yl]-3-oxo-propyl]oxazolidin-2-one | 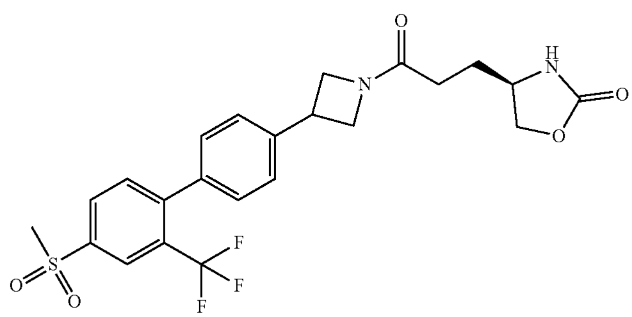 [SMILES: CS(=O)(=O)c1ccc(-c2ccc(C3CN(C(=O)CC[C@@H]4COC(=O)N4)C3)cc2)c(C(F)(F)F)c1] | 3-[(4R)-2-Oxooxazolidin-4-yl]propanoic acid (BB 9) and 4-Methylbenzenesulfonic acid; 3-[4-[4-methylsulfonyl-2-(trifluoromethyl)phenyl]phenyl]azetidine (BB 83) | 497.1 [M + H]+ |
| 129 | (4R)-4-[3-[3-[3-Fluoro-4-[3-(trifluoromethyl)pyrrolidin-1-yl]phenyl]azetidin-1-yl]-3-oxo-propyl]oxazolidin-2-one | 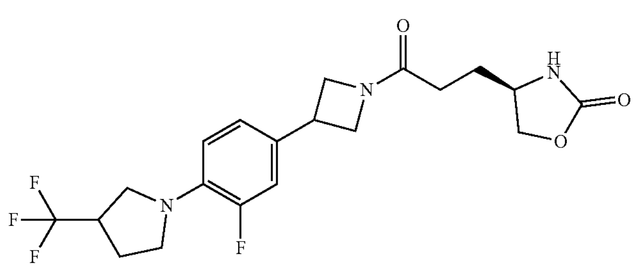 [SMILES: O=C1N[C@H](CCC(=O)N2CC(c3ccc(N4CCC(C(F)(F)F)C4)c(F)c3)C2)CO1] | 3-[(4R)-2-Oxooxazolidin-4-yl]propanoic acid (BB 9) and 1-[4-(Azetidin-3-yl)-2-fluoro-phenyl]-3-(trifluoromethyl)pyrrolidine; 4-methylbenzenesulfonic acid (BB 84) | 430.2 [M + H]+ |

| Ex. | Systematic Name | Structure | Building blocks | MS m/z |
|---|---|---|---|---|
| 130 | (4R)-4-[3-[3-[4-(1,1-Dioxothiolan-3-yl)phenyl]azetidin-1-yl]-3-oxo-propyl]oxazolidin-2-one | 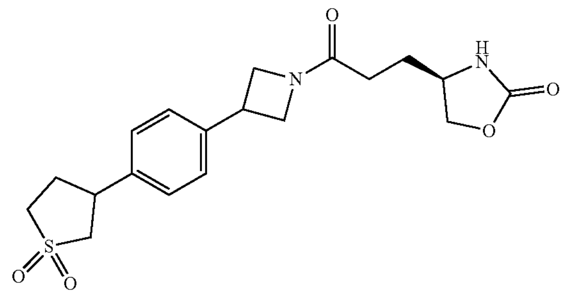 [SMILES: O=C1N[C@H](CCC(=O)N2CC(c3ccc(C4CCS(=O)(=O)C4)cc3)C2)CO1] | 3-[(4R)-2-Oxooxazolidin-4-yl]propanoic acid (BB 9) and 3-[4-(Azetidin-3-yl)phenyl]thiolane 1,1-dioxide; 4-methylbenzene-sulfonic acid (BB 85) | 393.2 [M + H]⁺ |
| 131 | (4R)-4-[3-[3-[4-(2-Azaspiro[3.4]octan-2-yl])phenyl]azetidin-1-yl]-3-oxo-propyl]oxazolidin-2-one | 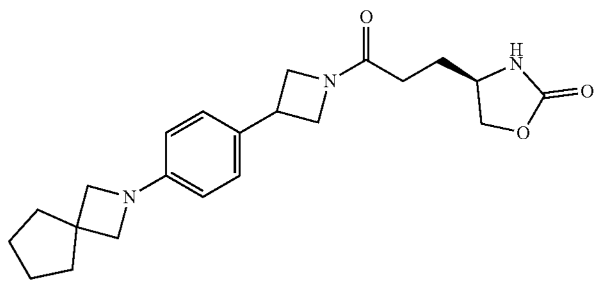 [SMILES: O=C1N[C@H](CCC(=O)N2CC(c3ccc(N4CC5(CCCC5)C4)cc3)C2)CO1] | 3-[(4R)-2-Oxooxazolidin-4-yl]propanoic acid (BB 9) and 2-[4-(Azetidin-3-yl)phenyl]-2-azaspiro[3.4]octane; 4-methylbenzene-sulfonic acid (BB 86) | 384.2 [M + H]⁺ |
| 132 | (4R)-4-[3-[3-[4-(6,6-Difluoro-2-azaspiro[3.3]heptan-2-yl)phenyl]azetidin-1-yl]-3-oxo-propyl]oxazolidin-2-one | 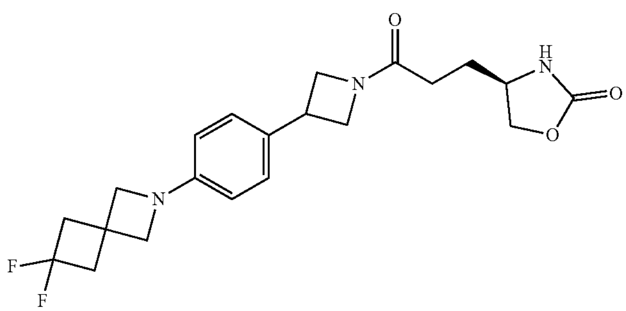 [SMILES: O=C1N[C@H](CCC(=O)N2CC(c3ccc(N4CC5(C4)CC(F)(F)C5)cc3)C2)CO1] | 3-[(4R)-2-Oxooxazolidin-4-yl]propanoic acid (BB 9) and 2-[4-(Azetidin-3-yl)phenyl]-6,6-difluoro-2-azaspiro[3.3]heptane; 4-methylbenzene-sulfonic acid (BB 87) | 406.2 [M + H]⁺ |
| 133 | (4R)-4-[3-Oxo-3-[3-[4-[3-(trifluoromethyl)cyclobutyl]phenyl]azetidin-1-yl]propyl]oxazolidin-2-one | 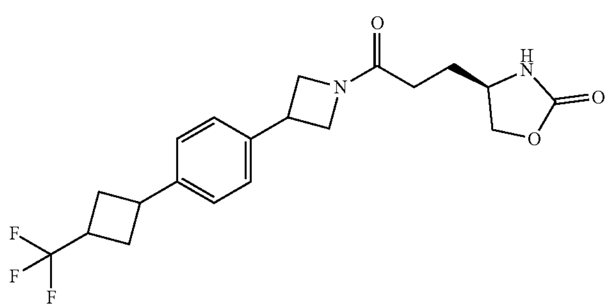 [SMILES: O=C1N[C@H](CCC(=O)N2CC(c3ccc(C4CC(C(F)(F)F)C4)cc3)C2)CO1] | 3-[(4R)-2-Oxooxazolidin-4-yl]propanoic acid (BB 9) and 4-Methylbenzene-sulfonic acid; 3-[4-[3-(trifluoromethyl)cyclobutyl]phenyl]azetidine (BB 88) | 397.2 [M + H]⁺ |
| 134 | (4R)-4-[3-[3-[3-Fluoro-4-[3-(trifluoromethyl)azetidin-1-yl]phenyl]azetidin-1-yl]-3-oxo-propyl]oxazolidin-2-one | 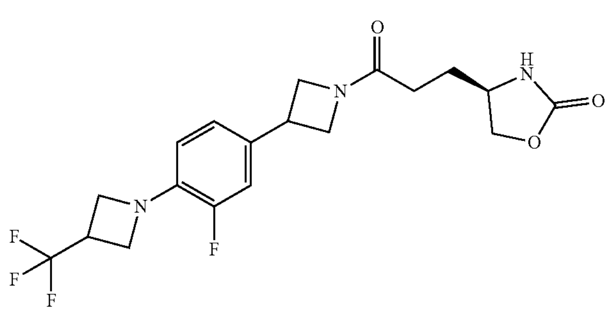 [SMILES: O=C1N[C@H](CCC(=O)N2CC(c3ccc(N4CC(C(F)(F)F)C4)c(F)c3)C2)CO1] | 3-[(4R)-2-Oxooxazolidin-4-yl]propanoic acid (BB 9) and 1-[4-(Azetidin-3-yl)-2-fluoro-phenyl]-3-(trifluoromethyl)azetidine; 4-methyl-benzenesulfonic acid (BB 89) | 416.2 [M + H]⁺ |

| Ex. | Systematic Name | Structure | Building blocks | MS m/z |
|---|---|---|---|---|
| 135 | (4R)-4-[3-Oxo-3-[3-[4-[3-(trifluoromethyl)pyrrolidin-1-yl]phenyl]azetidin-1-yl]propyl]oxazolidin-2-one | 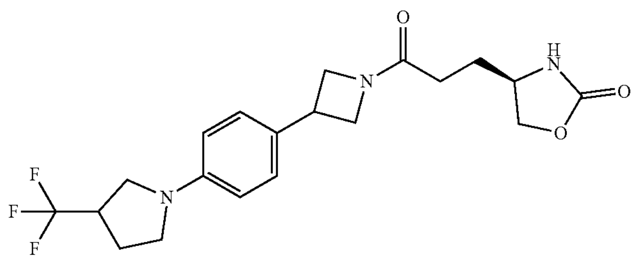 | 3-[(4R)-2-Oxooxazolidin-4-yl]propanoic acid (BB 9) and 1-[4-(Azetidin-3-yl)phenyl]-3-(trifluoromethyl)pyrrolidine; 4-methylbenzenesulfonic acid (BB 90) | 412.2 [M + H]+ |
| 136 | (4R)-4-[3-Oxo-3-[7-[6-(trifluoromethyl)pyridazin-3-yl]oxy-2-azaspiro[3.5]nonan-2-yl]propyl]oxazolidin-2-one | 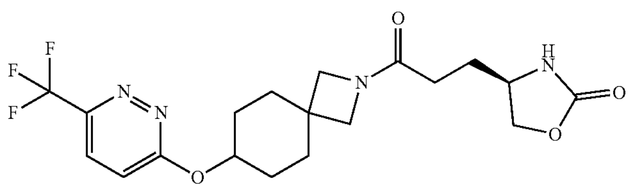 [SMILES: O=C1N[C@H](CCC(=O)N2CC3(CCC(Oc4ccc(C(F)(F)F)nn4)CC3)C2)CO1] | 3-[(4R)-2-Oxooxazolidin-4-yl]propanoic acid (BB 9) and 4-Methylbenzenesulfonic acid; 7-[6-(trifluoromethyl)pyridazin-3-yl]oxy-2-azaspiro[3.5]nonane (BB 91) | 429.2 [M + H]+ |
| 137 | (4R)-4-[3-[7-(4-Fluoro-2-methylsulfonyl-phenoxy)-2-azaspiro[3.5]nonan-2-yl]-3-oxo-propyl]oxazolidin-2-one | 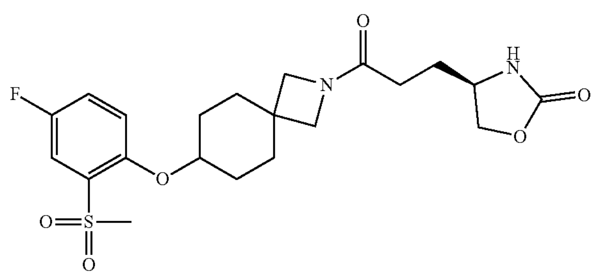 [SMILES: CS(=O)(=O)c1cc(F)ccc1OC1CCC2(CC1)CN(C(=O)CC[C@@H]1COC(=O)N1)C2] | 3-[(4R)-2-Oxooxazolidin-4-yl]propanoic acid (BB 9) and 7-(4-Fluoro-2-methylsulfonyl-phenoxy)-2-azaspiro[3.5]nonane; 4-methylbenzenesulfonic acid (BB 92) | 455.2 [M + H]+ |
| 138 | N-[2-[3-[(4R)-2-Oxooxazolidin-4-yl]propanoyl]-2-azaspiro[3.5]nonan-7-yl]-3-(trifluoromethoxy)benzenesulfonamide | 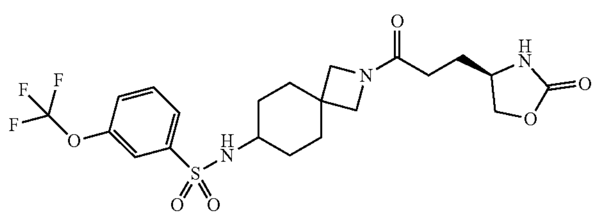 [SMILES: O=C1N[C@H](CCC(=O)N2CC3(CCC(NS(=O)(=O)c4cccc(OC(F)(F)F)c4)CC3)C2)CO1] | 3-[(4R)-2-Oxooxazolidin-4-yl]propanoic acid (BB 9) and N-(2-Azaspiro[3.5]nonan-7-yl)-3-(trifluoromethoxy)benzenesulfonamide; 4-methylbenzenesulfonic acid (BB 93) | 506.2 [M + H]+ |
| 139 | (4R)-4-[3-[3-[5-(6,6-Difluoro-2-azaspiro[3.3]heptan-2-yl)pyrazin-2-yl]azetidin-1-yl]-3-oxo-propyl]oxazolidin-2-one | 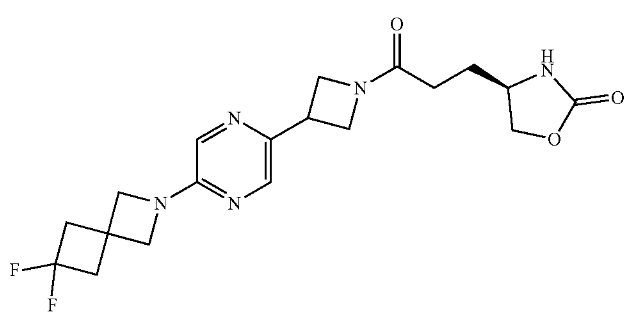 [SMILES: O=C1N[C@H](CCC(=O)N2CC(c3cnc(N4CC5(C4)CC(F)(F)C5)cn3)C2)CO1] | 3-[(4R)-2-Oxooxazolidin-4-yl]propanoic acid (BB 9) and 2-[5-(Azetidin-3-yl)pyrazin-2-yl]-6,6-difluoro-2-azaspiro[3.3]heptane; 4-methylbenzenesulfonic acid (BB 94) | 408.2 [M + H]+ |

| Ex. | Systematic Name | Structure | Building blocks | MS m/z |
|---|---|---|---|---|
| 140 | (4R)-4-[3-[3-[5-(2-Azaspiro[3.4]octan-2-yl)pyrazin-2-yl]azetidin-1-yl]-3-oxo-propyl]oxazolidin-2-one | 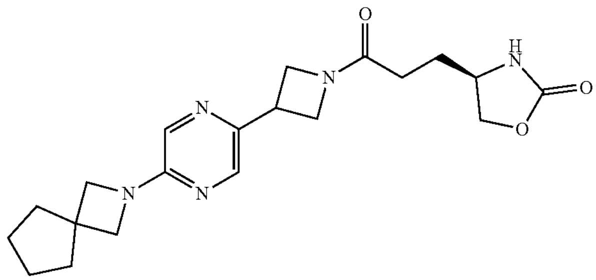 [SMILES: O=C1N[C@H](CCC(=O)N2CC(c3cnc(N4CC5(CCCC5)C4)cn3)C2)CO1] | 3-[(4R)-2-Oxooxazolidin-4-yl]propanoic acid (BB 9) and 2-[5-(Azetidin-3-yl)pyrazin-2-yl]-2-azaspiro[3.4]octane; 4-methylbenzene-sulfonic acid (BB 95) | 386.2 [M + H]+ |
| 141 | (4R)-4-[3-[3-[6-(6,6-Difluoro-2-azaspiro[3.3]heptan-2-yl)-3-pyridyl]azetidin-1-yl]-3-oxo-propyl]oxazolidin-2-one | 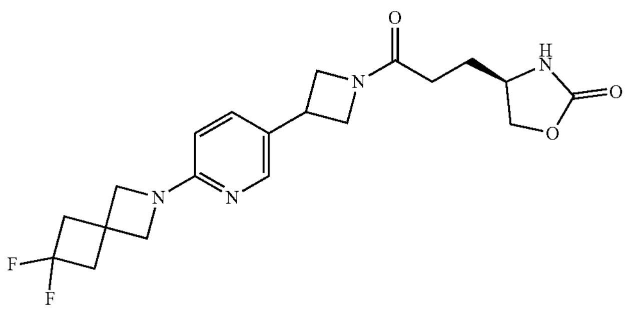 [SMILES: O=C1N[C@H](CCC(=O)N2CC(c3ccc(N4CC5(C4)CC(F)(F)C5)nc3)C2)CO1] | 3-[(4R)-2-Oxooxazolidin-4-yl]propanoic acid (BB 9) and 2-[5-(Azetidin-3-yl)-2-pyridyl]-6,6-difluoro-2-azaspiro[3.3]heptane; 4-methylbenzene-sulfonic acid (BB 96) | 407.2 [M + H]+ |
| 142 | (4R)-4-[3-[3-[6-(2-Azaspiro[3.4]octan-2-yl)-3-pyridyl]azetidin-1-yl]-3-oxo-propyl]oxazolidin-2-one | 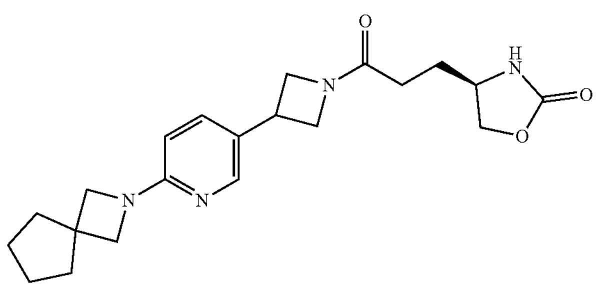 [SMILES: O=C1N[C@H](CCC(=O)N2CC(c3ccc(N4CC5(CCCC5)C4)nc3)C2)CO1] | 3-[(4R)-2-Oxooxazolidin-4-yl]propanoic acid (BB 9) and 2-[5-(Azetidin-3-yl)-2-pyridyl]-2-azaspiro[3.4]octane; 4-methylbenzene-sulfonic acid (BB 97) | 385.2 [M + H]+ |
| 143 | (4R)-4-[3-[7-[2-Fluoro-4-(trifluoromethyl)phenyl]sulfonyl-2,7-diazaspiro[3.5]nonan-2-yl]-3-oxo-propyl]oxazolidin-2-one | 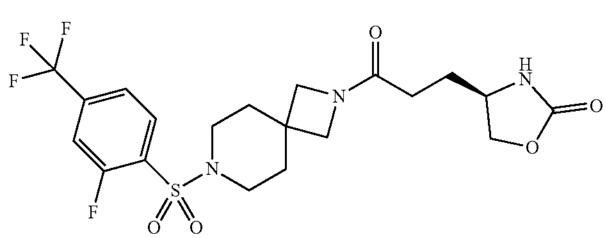 [SMILES: O=C1N[C@H](CCC(=O)N2CC3(CCN(S(=O)(=O)c4ccc(C(F)(F)F)cc4F)CC3)C2)CO1] | 3-[(4R)-2-Oxooxazolidin-4-yl]propanoic acid (BB 9) and 7-[2-Fluoro-4-(trifluoromethyl)phenyl]sulfonyl-2,7-diazaspiro[3.5]nonane; 2,2,2-trifluoroacetic acid (BB 98) | 494.3 [M + H]+ |

-continued

| Ex. | Systematic Name | Structure | Building blocks | MS m/z |
|---|---|---|---|---|
| 144 | (4R)-4-[3-[3-[6-[3-Hydroxy-3-(trifluoromethyl)azetidin-1-yl]-3-pyridyl]azetidin-1-yl]-3-oxo-propyl]oxazolidin-2-one | 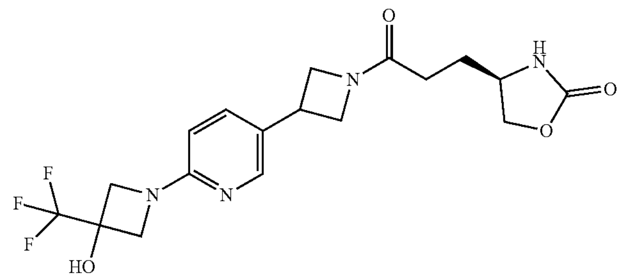 [SMILES: O=C1N[C@H](CCC(=O)N2CC(c3ccc(N4CC(O)(C(F)(F)F)C4)nc3)C2)CO1] | 3-[(4R)-2-Oxooxazolidin-4-yl]propanoic acid (BB 9) and 1-[5-(Azetidin-3-yl)-2-pyridyl]-3-(trifluoromethyl)azetidin-3-ol; 4-methylbenzene-sulfonic acid (BB 99) | 415.2 [M + H]+ |
| 145 | (4R)-4-[3-[3-[4-(3,5-Dimethyl-pyrazol-1-yl]phenyl]azetidin-1-yl]-3-oxo-propyl]oxazolidin-2-one | 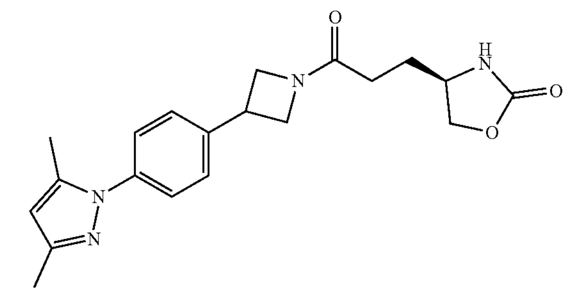 [SMILES: Cc1cc(C)n(-c2ccc(C3CN(C(=O)CC[C@@H]4COC(=O)N4)C3)cc2)n1] | 3-[(4R)-2-Oxooxazolidin-4-yl]propanoic acid (BB 9) and 1-[4-(Azetidin-3-yl)phenyl]-3,5-dimethyl-pyrazole; 4-methylbenzene-sulfonic acid (BB 100) | 369.2 [M + H]+ |
| 146 | (4R)-4-[3-[3-[6-[3-Hydroxy-3-(trifluoromethyl)pyrrolidin-1-yl]-3-pyridyl]azetidin-1-yl]-3-oxo-propyl]oxazolidin-2-one | 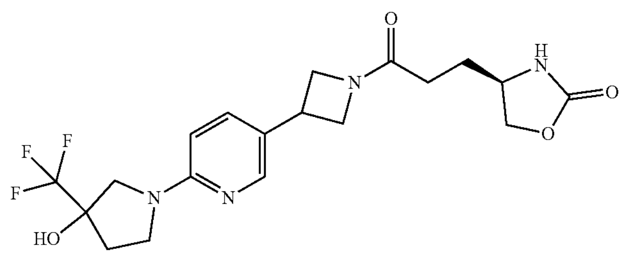 [SMILES: O=C1N[C@H](CCC(=O)N2CC(c3ccc(N4CCC(O)(C(F)(F)F)C4)nc3)C2)CO1] | 3-[(4R)-2-Oxooxazolidin-4-yl]propanoic acid (BB 9) and 1-[5-(Azetidin-3-yl)-2-pyridyl]-3-(trifluoromethyl)pyrrolidin-3-ol; 4-methylbenzene-sulfonic acid (BB 101) | 429.2 [M + H]+ |
| 147 | (4R)-4-[3-Oxo-3-[2-[4-(trifluoromethyl)phenyl]sulfonyl-2,6-diazaspiro[3.3]heptan-6-yl]propyl]oxazolidin-2-one | 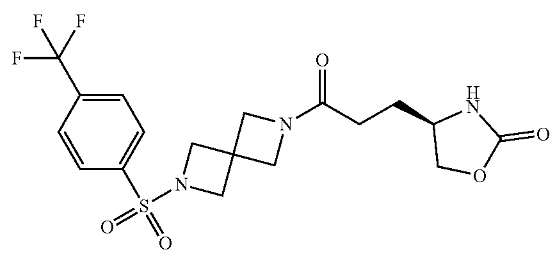 [SMILES: O=C1N[C@H](CCC(=O)N2CC3(C2)CN(S(=O)(=O)c2ccc(C(F)(F)F)cc2)C3)CO1] | 3-[(4R)-2-Oxooxazolidin-4-yl]propanoic acid (BB 9) and 4-Methylbenzene-sulfonic acid; 2-[4-(trifluoromethyl)phenyl]sulfonyl-2,6-diazaspiro[3.3]heptane (BB 102) | 448.2 [M + H]+ |
| 148 | (4R)-4-[3-Oxo-3-[2-[2-(trifluoromethoxy)phenyl]sulfonyl-2,6-diazaspiro[3.3]heptan-6-yl]propyl]oxazolidin-2-one | 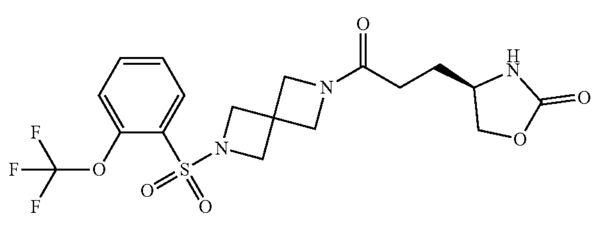 [SMILES: O=C1N[C@H](CCC(=O)N2CC3(C2)CN(S(=O)(=O)c2ccccc2OC(F)(F)F)C3)CO1] | 3-[(4R)-2-Oxooxazolidin-4-yl]propanoic acid (BB 9) and 2,2,2-Trifluoro-acetic acid; 2-[2-(trifluoromethoxy)phenyl]sulfonyl-2,6-diazaspiro[3.3]heptane (BB 103) | 464.2 [M + H]+ |
| 149 | (4R)-4-[3-Oxo-3-[2-[3-(trifluoromethoxy)phenyl]sulfonyl-2,6-diazaspiro[3.3]heptan-6-yl]propyl]oxazolidin-2-one | 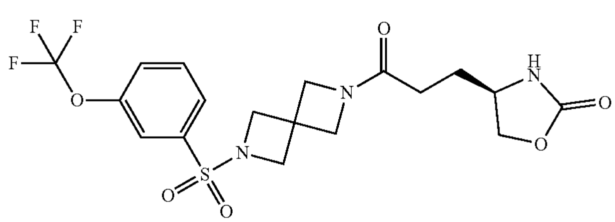 [SMILES: O=C1N[C@H](CCC(=O)N2CC3(C2)CN(S(=O)(=O)c2cccc(OC(F)(F)F)c2)C3)CO1] | 3-[(4R)-2-Oxooxazolidin-4-yl]propanoic acid (BB 9) and 2,2,2-Trifluoro-acetic acid; 2-[3-(trifluoromethoxy)phenyl]sulfonyl-2,6-diazaspiro[3.3]heptane (BB 105) | 464.2 [M + H]+ |

| Ex. | Systematic Name | Structure | Building blocks | MS m/z |
|---|---|---|---|---|
| 150 | (4R)-4-[3-Oxo-3-[2-[4-(trifluoromethoxy)phenyl]sulfonyl-2,6-diazaspiro[3.3]heptan-6-yl]propyl]oxazolidin-2-one | 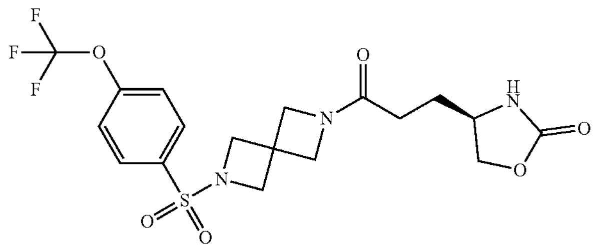 [SMILES: O=C1N[C@H](CCC(=O)N2CC3(C2)CN(S(=O)(=O)c2ccc(OC(F)(F)F)cc2)C3)CO1] | 3-[(4R)-2-Oxooxazolidin-4-yl]propanoic acid (BB 9) and 2,2,2-Trifluoroacetic acid; 2-[4-(trifluoromethoxy)phenyl]sulfonyl-2,6-diazaspiro[3.3]heptane (BB 105) | 464.2 [M + H]⁺ |
| 151 | (4R)-4-[3-Oxo-3-[6-[[6-(trifluoromethyl)pyridazin-3-yl]amino]-2-azaspiro[3.3]heptan-2-yl]propyl]oxazolidin-2-one | 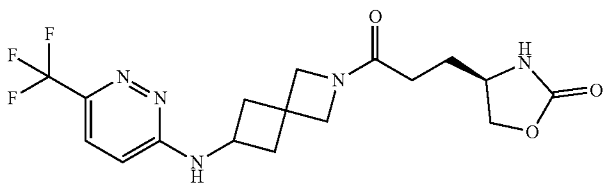 [SMILES: O=C1N[C@H](CCC(=O)N2CC3(CC(Nc4ccc(C(F)(F)F)nn4)C3)C2)CO1] | 3-[(4R)-2-Oxooxazolidin-4-yl]propanoic acid (BB 9) and 2,2,2-Trifluoroacetic acid; N-[6-(trifluoromethyl)pyridazin-3-yl]-2-azaspiro[3.3]heptan-6-amine (BB 106) | 400.2 [M + H]⁺ |
| 152 | (4R)-4-[3-Oxo-3-[6-[6-(trifluoromethyl)pyridazin-3-yl]oxy-2-azaspiro[3.3]heptan-2-yl]propyl]oxazolidin-2-one | 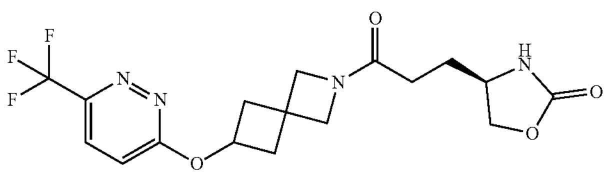 [SMILES: O=C1N[C@H](CCC(=O)N2CC3(CC(Oc4ccc(C(F)(F)F)nn4)C3)C2)CO1] | 3-[(4R)-2-Oxooxazolidin-4-yl]propanoic acid (BB 9) and 2,2,2-Trifluoroacetic acid; 6-[6-(trifluoromethyl)pyridazin-3-yl]oxy-2-azaspiro[3.3]heptane (BB 107) | 401.2 [M + H]⁺ |
| 153 | 2-[[2-[3-[(4R)-2-Oxooxazolidin-4-yl]propanoyl]-2,6-diazaspiro[3.3]heptan-6-yl]methyl]benzenesulfonamide | 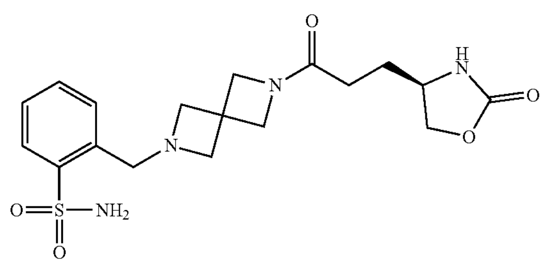 [SMILES: NS(=O)(=O)c1ccccc1CN1CC2(C1)CN(C(=O)CC[C@@H]1COC(=O)N1)C2] | 3-[(4R)-2-Oxooxazolidin-4-yl]propanoic acid (BB 9) and 2-(2,6-Diazaspiro[3.3]heptan-2-ylmethyl)benzenesulfonamide; 4-methylbenzenesulfonic acid (BB 108) | 409.2 [M + H]⁺ |
| 154 | N-[2-[3-[(4R)-2-Oxooxazolidin-4-yl]propanoyl]-2-azaspiro[3.3]heptan-6-yl]-3-(trifluoromethyl)benzenesulfonamide | 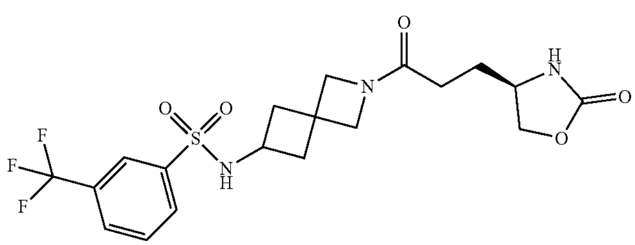 [SMILES: O=C1N[C@H](CCC(=O)N2CC3(CC(NS(=O)(=O)c4cccc(C(F)(F)F)c4)C3)C2)CO1] | 3-[(4R)-2-Oxooxazolidin-4-yl]propanoic acid (BB 9) and N-(2-Azaspiro[3.3]heptan-6-yl)-3-(trifluoromethyl)benzenesulfonamide; 2,2,2-trifluoroacetic acid (BB 109) | 462.1 [M + H]⁺ |
| 155 | (4R)-4-[3-Oxo-3-[3-[[4-(trifluoromethyl)phenyl]methylamino]azetidin-1-yl]propyl]oxazolidin-2-one | 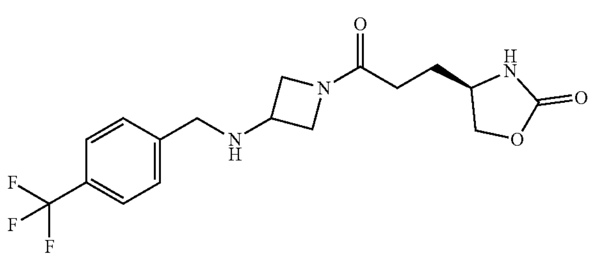 [SMILES: O=C1N[C@H](CCC(=O)N2CC(NCc3ccc(C(F)(F)F)cc3)C2)CO1] | 3-[(4R)-2-Oxooxazolidin-4-yl]propanoic acid (BB 9) and 4-Methylbenzenesulfonic acid; N-[[4-(trifluoromethyl)phenyl]methyl]azetidin-3-amine (BB 110) | 372.2 [M + H]⁺ |

| Ex. | Systematic Name | Building blocks | MS m/z |
|---|---|---|---|
| 156 | (4R)-4-[3-[3-[[2-Fluoro-5-(trifluoromethyl)phenyl]methylamino]azetidin-1-yl]-3-oxo-propyl]oxazolidin-2-one | 3-[(4R)-2-Oxooxazolidin-4-yl]propanoic acid (BB 9) and N-[[2-Fluoro-5-(trifluoromethyl)phenyl]methyl]azetidin-3-amine; 4-methylbenzenesulfonic acid (BB 111) | 390.2 [M + H]+ |
| 157 | (4R)-4-[3-[6-[(4-Fluoro-2-methylsulfonylphenyl)methyl]-2-azaspiro[3.3]heptan-2-yl]-3-oxo-propyl]oxazolidin-2-one | 3-[(4R)-2-Oxooxazolidin-4-yl]propanoic acid (BB 9) and 6-[(4-Fluoro-2-methylsulfonyl-phenyl)methyl]-2-azaspiro[3.3]heptane; 4-methylbenzenesulfonic acid (BB 112) | 425.2 [M + H]+ |
| 158 | N-[[1-[3-[(4R)-2-Oxooxazolidin-4-yl]propanoyl]-4-piperidyl]methyl]-4-(trifluoromethyl)benzenesulfonamide | 3-[(4R)-2-Oxooxazolidin-4-yl]propanoic acid (BB 9) and N-(4-Piperidylmethyl)-4-(trifluoromethyl)benzenesulfonamide; hydrochloride (BB 113) | 464.2 [M + H]+ |
| 159 | N-[[1-[3-[(4R)-2-Oxooxazolidin-4-yl]propanoyl]-4-piperidyl]methyl]-4-(trifluoromethoxy)benzenesulfonamide | 3-[(4R)-2-Oxooxazolidin-4-yl]propanoic acid (BB 9) and N-(4-Piperidylmethyl)-4-(trifluoromethoxy)benzenesulfonamide; hydrochloride (BB 114) | 480.2 [M + H]+ |
| 160 | (4R)-4-[3-[3-[6-(3-Hydroxy-3-methyl-azetidin-1-yl)-3-pyridyl]azetidin-1-yl]-3-oxo-propyl]oxazolidin-2-one | 3-[(4R)-2-Oxooxazolidin-4-yl]propanoic acid (BB 9) and 1-[5-(Azetidin-3-yl)-2-pyridyl]-3-methyl-azetidin-3-ol; 4-methylbenzenesulfonic acid (BB 115) | 361.2 [M + H]+ |
| 161 | (4R)-4-[3-Oxo-3-[3-[6-[3-(trifluoromethyl)azetidin-1-yl]-3-pyridyl]azetidin-1-yl]propyl]oxazolidin-2-one | 3-[(4R)-2-Oxooxazolidin-4-yl]propanoic acid (BB 9) and 5-(Azetidin-3-yl)-2-[3-(trifluoromethyl)azetidin-1-yl]pyridine; 4-methylbenzenesulfonic acid (BB 116) | 399.2 [M + H]+ |

-continued

| Ex. | Systematic Name | Structure | Building blocks | MS m/z |
|---|---|---|---|---|
| 162 | (4R)-4-[3-[3-[[2-Fluoro-4-(trifluoromethyl)phenyl]methyl-methyl-amino]azetidin-1-yl]-3-oxo-propyl]oxazolidin-2-one | 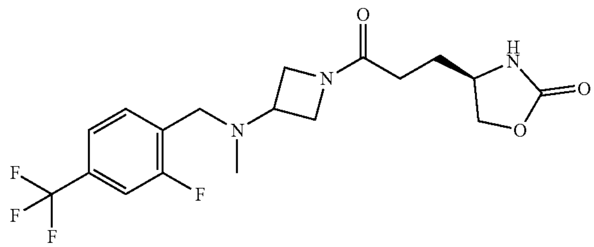 [SMILES: CN(Cc1ccc(C(F)(F)F)cc1F)C1CN(C(=O)CC[C@@H]2COC(=O)N2)C1] | 3-[(4R)-2-Oxooxazolidin-4-yl]propanoic acid (BB 9) and N-[[2-Fluoro-4-(trifluoromethyl)phenyl]methyl]-N-methyl-azetidin-3-amine; 4-methyl-benzenesulfonic acid (BB 117) | 404.2 [M + H]+ |
| 163 | (4R)-4-[3-Oxo-3-[3-(6-spiro[3.3]heptan-2-yl-3-pyridyl)azetidin-1-yl]propyl]oxazolidin-2-one | 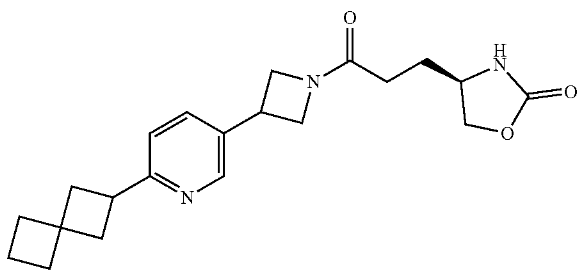 [SMILES: O=C1N[C@H](CCC(=O)N2CC(c3ccc(C4CC5(CCC5)C4)nc3)C2)CO1] | 3-[(4R)-2-Oxooxazolidin-4-yl]propanoic acid (BB 9) and 5-(Azetidin-3-yl)-2-spiro[3.3]heptan-2-yl-pyridine; 4-methylbenzene-sulfonic acid (BB 118) | 370.2 [M + H]+ |
| 164 | (4R)-4-[3-Oxo-3-[3-(5-spiro[3.3]heptan-2-ylpyrazin-2-yl)azetidin-1-yl]propyl]oxazolidin-2-one | 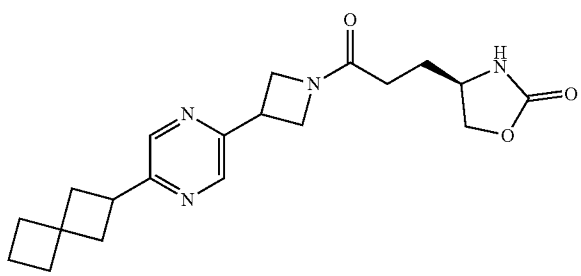 [SMILES: O=C1N[C@H](CCC(=O)N2CC(c3cnc(C4CC5(CCC5)C4)cn3)C2)CO1] | 3-[(4R)-2-Oxooxazolidin-4-yl]propanoic acid (BB 9) and 2-(Azetidin-3-yl)-5-spiro[3.3]heptan-2-yl-pyrazine; 4-methylbenzene-sulfonic acid (BB 119) | 371.2 [M + H]+ |
| 165 | (4R)-4-[3-[3-[3-[5-(2,2-Dimethyl-propyl)-1,3,4-oxadiazol-2-yl]-1-bicyclo[1.1.1]pentanyl]azetidin-1-yl]-3-oxo-propyl]oxazolidin-2-one | 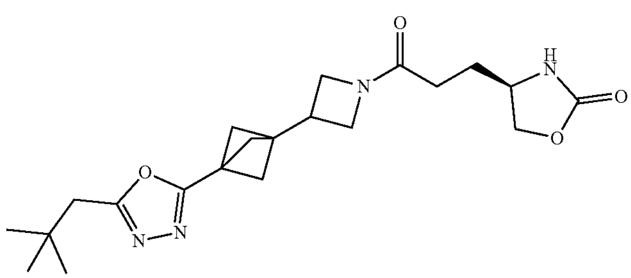 [SMILES: CC(C)(C)Cc1nnc(C23CC(C4CN(C(=O)CC[C@@H]5COC(=O)N5)C4)(C2)C3)o1] | 3-[(4R)-2-Oxooxazolidin-4-yl]propanoic acid (BB 9) and 2-[3-(Azetidin-3-yl)-1-bicyclo[1.1.1]pentanyl]-5-(2,2-dimethylpropyl)-1,3,4-oxadiazole; 2,2,2-trifluoroacetic acid (BB 120) | 403.3 [M + H]+ |
| 166 | (4R)-4-[3-Oxo-3-[3-[[4-(trifluoro-methylsulfonyl)phenyl]methoxy]azetidin-1-yl]propyl]oxazolidin-2-one | 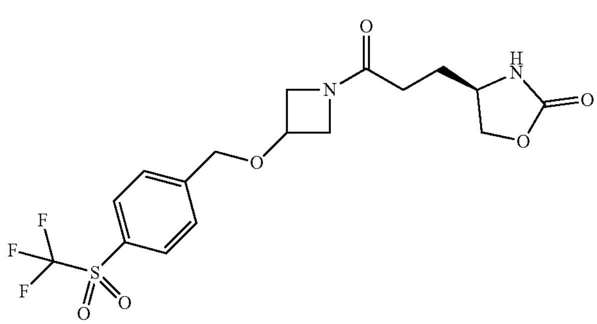 [SMILES: O=C1N[C@H](CCC(=O)N2CC(OCc3ccc(S(=O)(=O)C(F)(F)F)cc3)C2)CO1] | 3-[(4R)-2-Oxooxazolidin-4-yl]propanoic acid (BB 9) and 4-Methylbenzene-sulfonic acid; 3-[[4-(trifluoromethyl-sulfonyl)phenyl]methoxy]azetidine (BB 121) | 437.2 [M + H]+ |

-continued

| Ex. | Systematic Name | Structure | Building blocks | MS m/z |
|---|---|---|---|---|
| 167 | (4R)-4-[3-Oxo-3-[3-[[3-(trifluoromethylsulfonyl)phenyl]methoxy]azetidin-1-yl]propyl]oxazolidin-2-one | 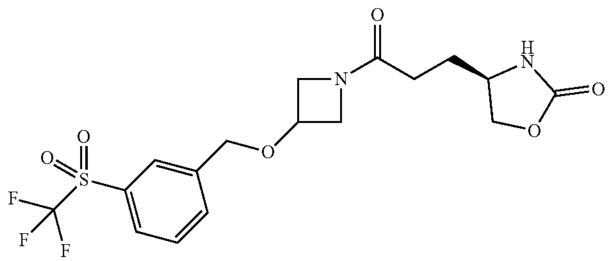 [SMILES: O=C1N[C@H](CCC(=O)N2CC(OCc3cccc(S(=O)(=O)C(F)(F)F)c3)C2)CO1] | 3-[(4R)-2-Oxooxazolidin-4-yl]propanoic acid (BB 9) and 4-Methylbenzenesulfonic acid; 3-[[3-(trifluoromethylsulfonyl)phenyl]methoxy]azetidine (BB 122) | 437.2 [M + H]⁺ |
| 168 | (4R)-4-[3-Oxo-3-[3-[5-[6-(trifluoromethyl)-3-pyridyl]-1,2,4-oxadiazol-3-yl]azetidin-1-yl]propyl]oxazolidin-2-one | 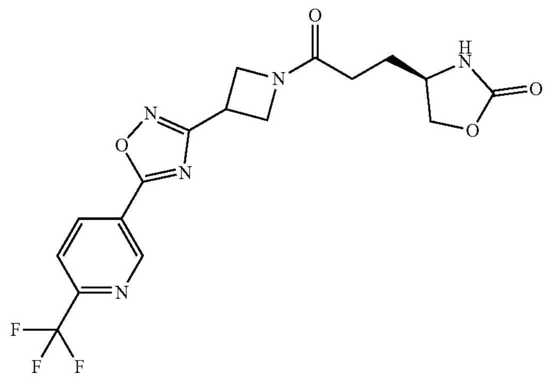 [SMILES: O=C1N[C@H](CCC(=O)N2CC(c3noc(-c4ccc(C(F)(F)F)nc4)n3)C2)CO1] | 3-[(4R)-2-Oxooxazolidin-4-yl]propanoic acid (BB 9) and 3-(Azetidin-3-yl)-5-[6-(trifluoromethyl)-3-pyridyl]-1,2,4-oxadiazole; hydrochloride (BB 123) | 412.2 [M + H]⁺ |
| 169 | (4R)-4-[3-Oxo-3-[3-[5-[3-(trifluoromethyl)-1-bicyclo[1.1.1]pentanyl]-1,2,4-oxadiazol-3-yl]azetidin-1-yl]propyl]oxazolidin-2-one | 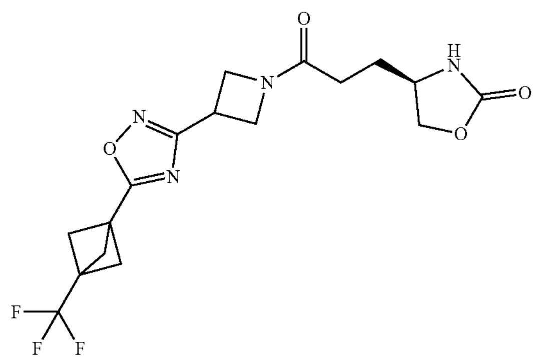 [SMILES: O=C1N[C@H](CCC(=O)N2CC(c3noc(C45CC(C(F)(F)F)(C4)C5)n3)C2)CO1] | 3-[(4R)-2-Oxooxazolidin-4-yl]propanoic acid (BB 9) and 3-(Azetidin-3-yl)-5-[3-(trifluoromethyl)-1-bicyclo[1.1.1]pentanyl]-1,2,4-oxadiazole; hydrochloride (BB 124) | 401.2 [M + H]⁺ |
| 170 | (4R)-4-[3-[3-[6-[3-(1-Hydroxy-1-methyl-ethyl)azetidin-1-yl]-3-pyridyl]azetidin-1-yl]-3-oxo-propyl]oxazolidin-2-one | 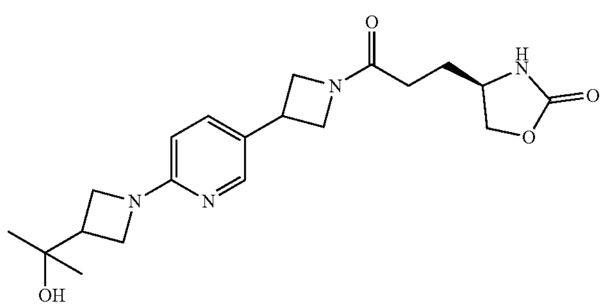 [SMILES: CC(C)(O)C1CN(c2ccc(C3CN(C(=O)CC[C@@H]4COC(=O)N4)C3)cn2)C1] | 3-[(4R)-2-Oxooxazolidin-4-yl]propanoic acid (BB 9) and 2-[1-[5-(Azetidin-3-yl)-2-pyridyl]azetidin-3-yl]propan-2-ol; 4-methylbenzenesulfonic acid (BB 125) | 389.3 [M + H]⁺ |
| 171 | (4R)-4-[3-[3-[4-[1-(Hydroxymethyl)cyclopropyl]phenyl]azetidin-1-yl]-3-oxo-propyl]oxazolidin-2-one | 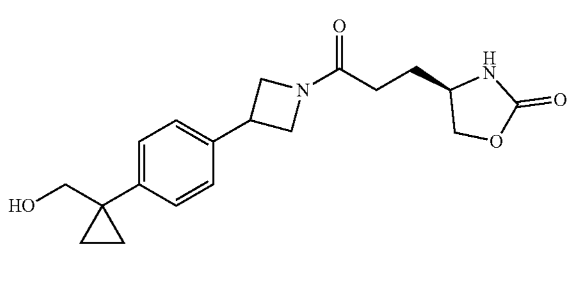 [SMILES: O=C1N[C@H](CCC(=O)N2CC(c3ccc(C4(CO)CC4)cc3)C2)CO1] | 3-[(4R)-2-Oxooxazolidin-4-yl]propanoic acid (BB 9) and [1-[4-(Azetidin-3-yl)phenyl]cyclopropyl]methanol; hydrochloride (BB 126) | 345.1 [M + H]⁺ |

-continued

| Ex. | Systematic Name | Structure | Building blocks | MS m/z |
|---|---|---|---|---|
| 172 | (4R)-4-[3-[3-[6-(5-Oxa-2-azaspiro[3.4]octan-2-yl)-3-pyridyl]azetidin-1-yl]-3-oxo-propyl]oxazolidin-2-one | 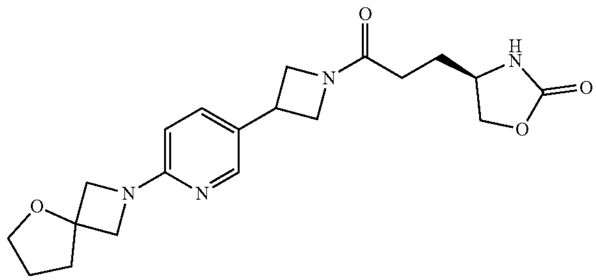 [SMILES: O=C1N[C@H](CCC(=O)N2CC(c3ccc(N4CC5(CCCO5)C4)nc3)C2)CO1] | 3-[(4R)-2-Oxooxazolidin-4-yl]propanoic acid (BB 9) and 2-[5-(Azetidin-3-yl)-2-pyridyl]-5-oxa-2-azaspiro[3.4]octane; 4-methylbenzenesulfonic acid (BB 127) | 387.2 [M + H]⁺ |
| 173 | (4R)-4-[3-[3-[6-(2,2-Difluoro-5-azaspiro[2.4]heptan-5-yl)-3-pyridyl]azetidin-1-yl]-3-oxo-propyl]oxazolidin-2-one | 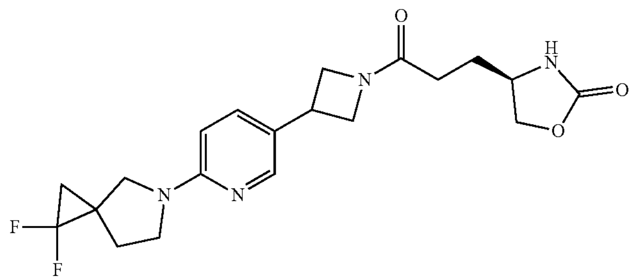 [SMILES: O=C1N[C@H](CCC(=O)N2CC(c3ccc(N4CCC5(C4)CC5(F)F)nc3)C2)CO1] | 3-[(4R)-2-Oxooxazolidin-4-yl]propanoic acid (BB 9) and 5-[5-(Azetidin-3-yl)-2-pyridyl]-2,2-difluoro-5-azaspiro[2.4]heptane; 4-methyl-benzenesulfonic acid (BB 128) | 407.2 [M + H]⁺ |
| 174 | (4R)-4-[3-Oxo-3-[3-[4-[5-(trifluoromethyl)pyrazin-2-yl]oxyphenyl]azetidin-1-yl]propyl]oxazolidin-2-one | 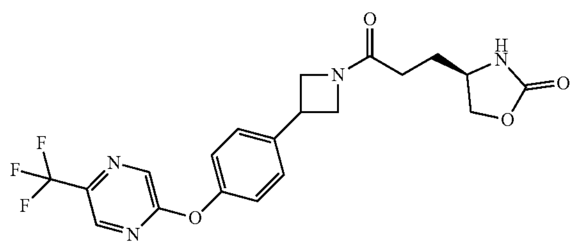 [SMILES: O=C1N[C@H](CCC(=O)N2CC(c3ccc(Oc4cnc(C(F)(F)F)cn4)cc3)C2)CO1] | 3-[(4R)-2-Oxooxazolidin-4-yl]propanoic acid (BB 9) and 2-[4-(Azetidin-3-yl)phenoxy]-5-(trifluoromethyl)pyrazine; 4-methylbenzenesulfonic acid (BB 129) | 437.2 [M + H]⁺ |
| 175 | (4R)-4-[3-Oxo-3-[3-[5-[[1-(trifluoromethyl)cyclopropyl]methylamino]-2-pyridyl]azetidin-1-yl]propyl]oxazolidin-2-one | 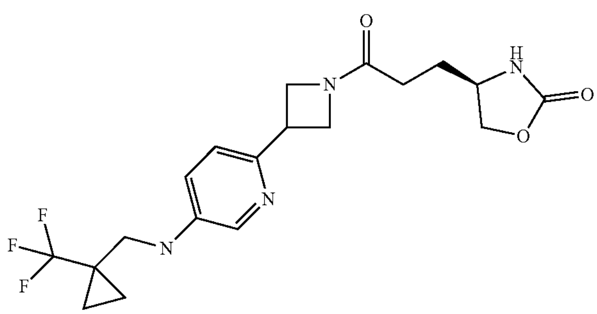 [SMILES: O=C1N[C@H](CCC(=O)N2CC(c3ccc(NCC4(C(F)(F)F)CC4)cn3)C2)CO1] | 3-[(4R)-2-Oxooxazolidin-4-yl]propanoic acid (BB 9) and 6-(Azetidin-3-yl)-N-[[1-(trifluoromethyl)cyclopropyl]methyl]pyridin-3-amine; 4-methyl-benzenesulfonic acid (BB 130) | 413.2 [M + H]⁺ |
| 176 | (4R)-4-[3-Oxo-3-[3-[5-[[1-(trifluoromethyl)cyclopropyl]methylamino]pyrazin-2-yl]azetidin-1-yl]propyl]oxazolidin-2-one | 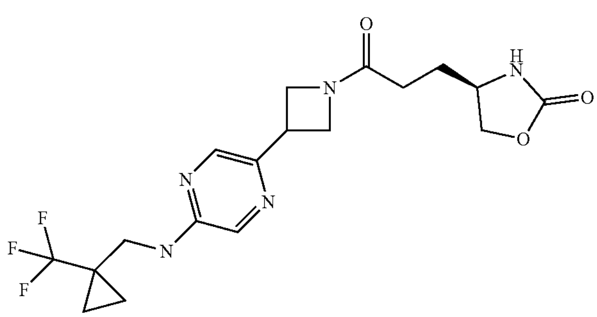 [SMILES: O=C1N[C@H](CCC(=O)N2CC(c3cnc(NCC4(C(F)(F)F)CC4)cn3)C2)CO1] | 3-[(4R)-2-Oxooxazolidin-4-yl]propanoic acid (BB 9) and 5-(Azetidin-3-yl)-N-[[1-(trifluoromethyl)cyclopropyl]methyl]pyrazin-2-amine; 4-methyl-benzenesulfonic acid (BB 131) | 414.2 [M + H]⁺ |

-continued

| Ex. | Systematic Name | Structure | Building blocks | MS m/z |
|---|---|---|---|---|
| 177 | (4R)-4-[3-[3-[4-(3-Cyclopropyl-1H-1,2,4-triazol-5-yl)phenyl]azetidin-1-yl]-3-oxo-propyl]oxazolidin-2-one | 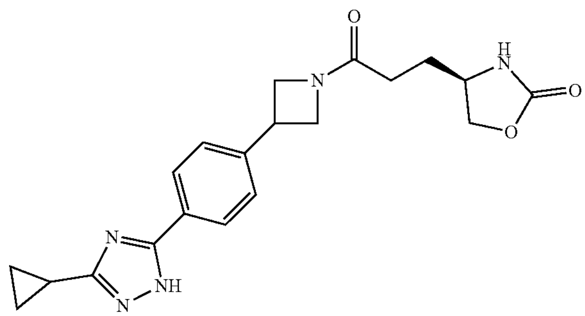 [SMILES: O=C1N[C@H](CCC(=O)N2CC(c3ccc(-c4nc(C5CC5)n[nH]4)cc3)C2)CO1] | 3-[(4R)-2-Oxooxazolidin-4-yl]propanoic acid (BB 9) and 5-[4-(Azetidin-3-yl)phenyl]-3-cyclopropyl-1H-1,2,4-triazole; 4-methyl-benzenesulfonic acid (BB 132) | 382.2 [M + H]⁺ |
| 178 | (4R)-4-[3-Oxo-3-[3-[4-[3-[1-(trifluoro-methyl)cyclo-propyl]-1H-1,2,4-triazol-5-yl]phenyl]azetidin-1-yl]propyl]oxazolidin-2-one | 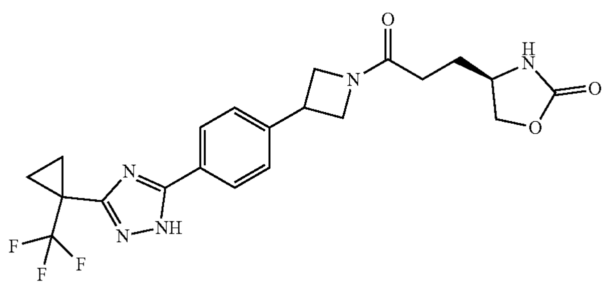 [SMILES: O=C1N[C@H](CCC(=O)N2CC(c3ccc(-c4nc(C5(C(F)(F)F)CC5)n[nH]4)cc3)C2)CO1] | 3-[(4R)-2-Oxooxazolidin-4-yl]propanoic acid (BB 9) and 5-[4-(Azetidin-3-yl)phenyl]-3-[1-(trifluoromethyl)cyclopropyl]-1H-1,2,4-triazole; 4-methylbenzene-sulfonic acid (BB 133) | 450.2 [M + H]⁺ |
| 179 | (4R)-4-[3-[6-[(3-Methyl-sulfonylphenyl)methyl]-2-azaspiro[3.3]heptan-2-yl]-3-oxo-propyl]oxazolidin-2-one | 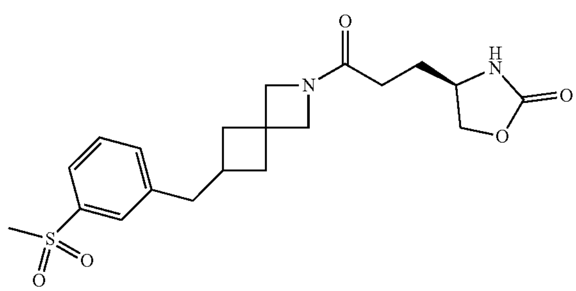 [SMILES: CS(=O)(=O)c1cccc(CC2CC3(C2)CN(C(=O)CC[C@@H]2COC(=O)N2)C3)c1] | 3-[(4R)-2-Oxooxazolidin-4-yl]propanoic acid (BB 9) and 4-Methylbenzene-sulfonic acid; 6-[(3-methylsulfonyl-phenyl)methyl]-2-azaspiro[3.3]heptane (BB 134) | 407.2 [M + H]⁺ |
| 180 | (4R)-4-[3-[6-[(4-Methyl-sulfonylphenyl)methyl]-2-azaspiro[3.3]heptan-2-yl]-3-oxo-propyl]oxazolidin-2-one | 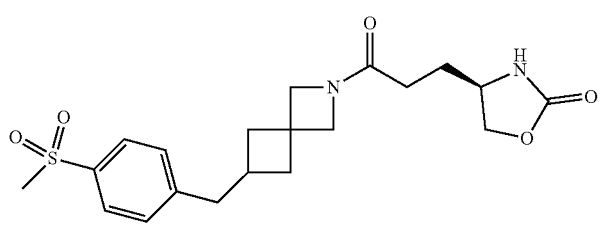 [SMILES: CS(=O)(=O)c1ccc(CC2CC3(C2)CN(C(=O)CC[C@@H]2COC(=O)N2)C3)cc1] | 3-[(4R)-2-Oxooxazolidin-4-yl]propanoic acid (BB 9) and 4-Methylbenzene-sulfonic acid; 6-[(4-methyl-sulfonylphenyl)methyl]-2-azaspiro[3.3]heptane (BB 135) | 407.2 [M + H]⁺ |
| 181 | (4R)-4-[3-Oxo-3-[6-[[6-(trifluoro-methyl)pyridazin-3-yl]methyl]-2-azaspiro[3.3]heptan-2-yl]propyl]oxazolidin-2-one | 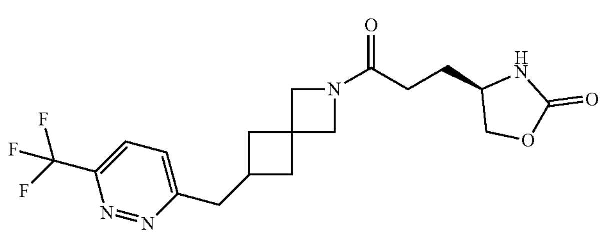 [SMILES: O=C1N[C@H](CCC(=O)N2CC3(CC(Cc4ccc(C(F)(F)F)nn4)C3)C2)CO1] | 3-[(4R)-2-Oxooxazolidin-4-yl]propanoic acid (BB 9) and 4-Methylbenzene-sulfonic acid; 6-[[6-(trifluoro-methyl)pyridazin-3-yl]methyl]-2-azaspiro[3.3]heptane (BB 136) | 399.2 [M + H]⁺ |

| Ex. | Systematic Name | Structure | Building blocks | MS m/z |
|---|---|---|---|---|
| 182 | (4R)-4-[3-Oxo-3-[6-[[2-(trifluoro-methyl)pyrimidin-5-yl]methyl]-2-azaspiro[3.3]heptan-2-yl]propyl]oxazolidin-2-one | 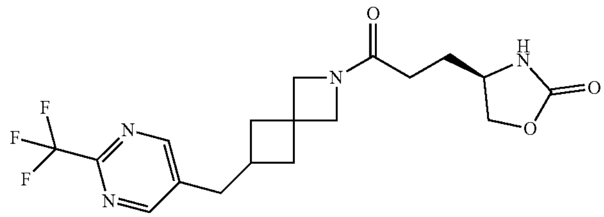 [SMILES: O=C1N[C@H](CCC(=O)N2CC3(CC(Cc4cnc(C(F)(F)F)nc4)C3)C2)CO1] | 3-[(4R)-2-Oxooxazolidin-4-yl]propanoic acid (BB 9) and 4-Methylbenzene-sulfonic acid; 6-[[2-(trifluoro-methyl)pyrimidin-5-yl]methyl]-2-azaspiro[3.3]heptane (BB 137) | 399.2 [M + H]⁺ |
| 183 | (4R)-4-[3-Oxo-3-[6-[[5-(trifluoro-methyl)pyrimidin-2-yl]methyl]-2-azaspiro[3.3]heptan-2-yl]propyl]oxazolidin-2-one | 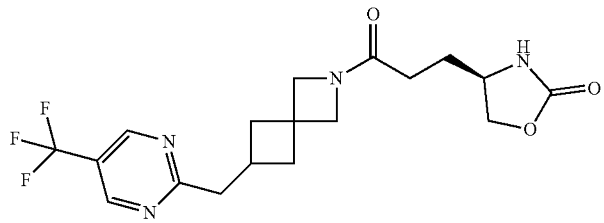 [SMILES: O=C1N[C@H](CCC(=O)N2CC3(CC(Cc4ncc(C(F)(F)F)cn4)C3)C2)CO1] | 3-[(4R)-2-Oxooxazolidin-4-yl]propanoic acid (BB 9) and 4-Methylbenzene-sulfonic acid; 6-[[5-(trifluoro-methyl)pyrimidin-2-yl]methyl]-2-azaspiro[3.3]heptane (BB 138) | 399.2 [M + H]⁺ |
| 184 | (4R)-4-[3-[6-[(3-Fluoro-5-methylsulfonyl-phenyl)methyl]-2-azaspiro[3.3]heptan-2-yl]-3-oxo-propyl]oxazolidin-2-one | 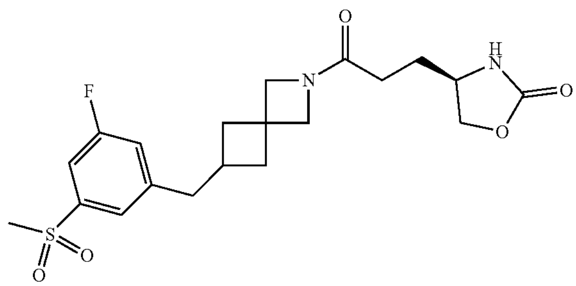 [SMILES: CS(=O)(=O)c1cc(F)cc(CC2CC3(C2)CN(C(=O)CC[C@@H]2COC(=O)N2)C3)c1] | 3-[(4R)-2-Oxooxazolidin-4-yl]propanoic acid (BB 9) and 6-[(3-Fluoro-5-methylsulfonyl-phenyl)methyl]-2-azaspiro[3.3]heptane; 4-methylbenzene-sulfonic acid (BB 139) | 425.2 [M + H]⁺ |
| 185 | (4R)-4-[3-[6-(3-Cyclopropyl-1,2,4-triazol-1-yl)-2-azaspiro[3.3]heptan-2-yl]-3-oxo-propyl]oxazolidin-2-one | 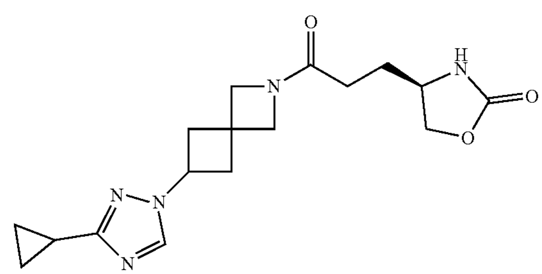 [SMILES: O=C1N[C@H](CCC(=O)N2CC3(CC(n4cnc(C5CC5)n4)C3)C2)CO1] | 3-[(4R)-2-Oxooxazolidin-4-yl]propanoic acid (BB 9) and 6-(3-Cyclopropyl-1,2,4-triazol-1-yl)-2-azaspiro[3.3]heptane; 4-methylbenzene-sulfonic acid (BB 140) | 346.2 [M + H]⁺ |
| 186 | (4R)-4-[3-Oxo-3-[6-[[3-(trifluoro-methylsulfonyl)phenyl]methyl]-2-azaspiro[3.3]heptan-2-yl]propyl]oxazolidin-2-one | 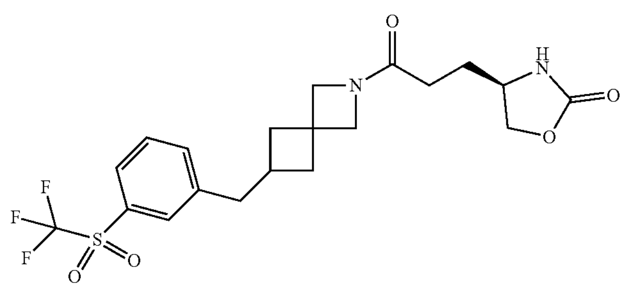 [SMILES: O=C1N[C@H](CCC(=O)N2CC3(CC(Cc4cccc(S(=O)(=O)C(F)(F)F)c4)C3)C2)CO1] | 3-[(4R)-2-Oxooxazolidin-4-yl]propanoic acid (BB 9) and 4-Methylbenzene-sulfonic acid; 6-[[3-(trifluoro-methylsulfonyl)phenyl]methyl]-2-azaspiro[3.3]heptane (BB 141) | 461.2 [M + H]⁺ |
| 187 | (4R)-4-[3-Oxo-3-[6-[[4-(trifluoro-methylsulfonyl)phenyl]methyl]-2,6-diazaspiro[3.3]heptan-2-yl]propyl]oxazolidin-2-one | 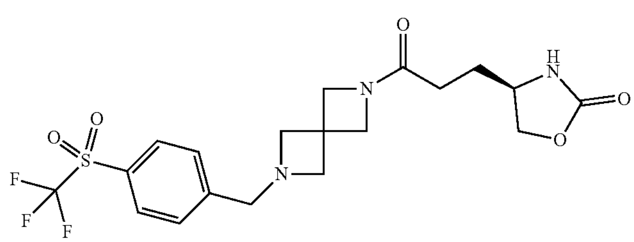 [SMILES: O=C1N[C@H](CCC(=O)N2CC3(CN(Cc4ccc(S(=O)(=O)C(F)(F)F)cc4)C3)C2)CO1] | 3-[(4R)-2-Oxooxazolidin-4-yl]propanoic acid (BB 9) and 4-Methylbenzene-sulfonic acid; 2-[[4-(trifluoro-methylsulfonyl)phenyl]methyl]-2,6-diazaspiro[3.3]heptane (BB 142) | 462.2 [M + H]⁺ |

-continued

| Ex. | Systematic Name | Structure | Building blocks | MS m/z |
|---|---|---|---|---|
| 188 | (4R)-4-[3-Oxo-3-[7-[[6-(trifluoromethyl)-3-pyridyl]methyl]-2-azaspiro[3.5]nonan-2-yl]propyl]oxazolidin-2-one | 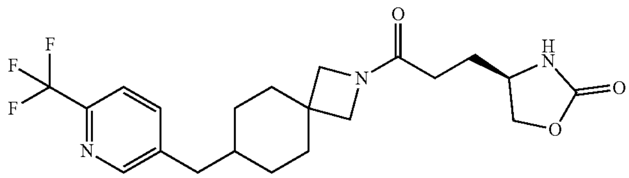 [SMILES: O=C1N[C@H](CCC(=O)N2CC3(CCC(Cc4ccc(C(F)(F)F)nc4)CC3)C2)CO1] | 3-[(4R)-2-Oxooxazolidin-4-yl]propanoic acid (BB 9) and 4-Methylbenzenesulfonic acid; 7-[[6-(trifluoromethyl)-3-pyridyl]methyl]-2-azaspiro[3.5]nonane (BB 143) | 426.3 [M + H]$^+$ |
| 189 | (4R)-4-[3-Oxo-3-[7-[[5-(trifluoromethyl)-2-pyridyl]methyl]-2-azaspiro[3.5]nonan-2-yl]propyl]oxazolidin-2-one | 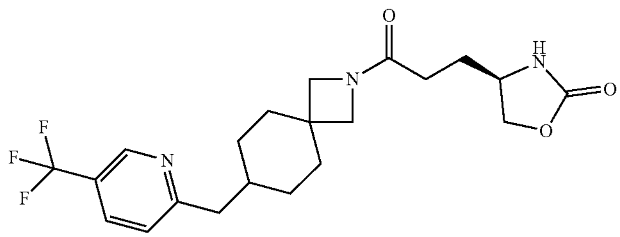 [SMILES: O=C1N[C@H](CCC(=O)N2CC3(CCC(Cc4ccc(C(F)(F)F)cn4)CC3)C2)CO1] | 3-[(4R)-2-Oxooxazolidin-4-yl]propanoic acid (BB 9) and 4-Methylbenzenesulfonic acid; 7-[[5-(trifluoromethyl)-2-pyridyl]methyl]-2-azaspiro[3.5]nonane (BB 144) | 426.3 [M + H]$^+$ |
| 190 | (4R)-4-[3-Oxo-3-[7-[[5-(trifluoromethyl)pyrazin-2-yl]methyl]-2-azaspiro[3.5]nonan-2-yl]propyl]oxazolidin-2-one | 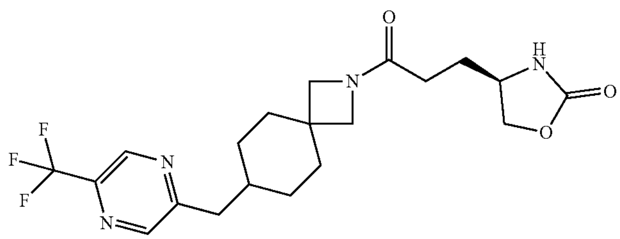 [SMILES: O=C1N[C@H](CCC(=O)N2CC3(CCC(Cc4cnc(C(F)(F)F)cn4)CC3)C2)CO1] | 3-[(4R)-2-Oxooxazolidin-4-yl]propanoic acid (BB 9) and 4-Methylbenzenesulfonic acid; 7-[[5-(trifluoromethyl)pyrazin-2-yl]methyl]-2-azaspiro[3.5]nonane (BB 145) | 427.3 [M + H]$^+$ |
| 191 | (4R)-4-[3-[7-[[6-(Difluoromethoxy)-3-pyridyl]methyl]-2-azaspiro[3.5]nonan-2-yl]-3-oxo-propyl]oxazolidin-2-one | 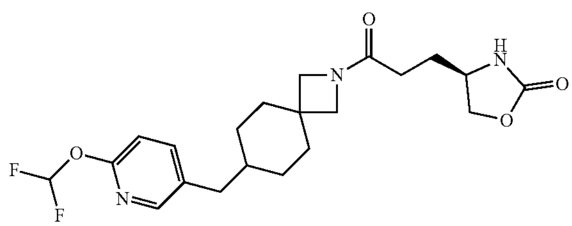 [SMILES: O=C1N[C@H](CCC(=O)N2CC3(CCC(Cc4ccc(OC(F)F)nc4)CC3)C2)CO1] | 3-[(4R)-2-Oxooxazolidin-4-yl]propanoic acid (BB 9) and 7-[[6-(Difluoromethoxy)-3-pyridyl]methyl]-2-azaspiro[3.5]nonane; 4-methylbenzenesulfonic acid (BB 146) | 424.3 [M + H]$^+$ |
| 192 | (4R)-4-[3-[7-[(4-Methylsulfonylphenyl)methyl]-2,7-diazaspiro[3.5]nonan-2-yl]-3-oxo-propyl]oxazolidin-2-one | 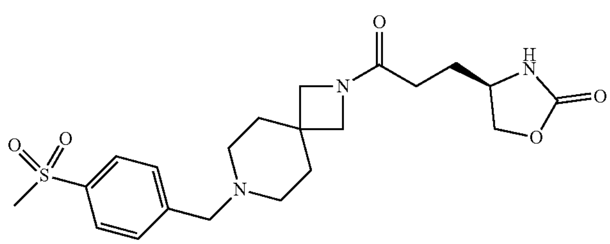 [SMILES: CS(=O)(=O)c1ccc(CN2CCC3(CC2)CN(C(=O)CC[C@@H]2COC(=O)N2)C3)cc1] | 3-[(4R)-2-Oxooxazolidin-4-yl]propanoic acid (BB 9) and 4-Methylbenzenesulfonic acid; 7-[(4-methylsulfonylphenyl)methyl]-2,7-diazaspiro[3.5]nonane (BB 147) | 436.3 [M + H]$^+$ |
| 193 | (4R)-4-[3-[7-[(3-Methylsulfonylphenyl)methyl]-2,7-diazaspiro[3.5]nonan-2-yl]-3-oxo-propyl]oxazolidin-2-one | 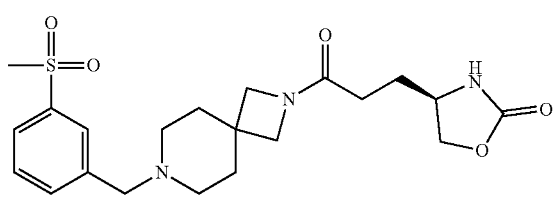 [SMILES: CS(=O)(=O)c1cccc(CN2CCC3(CC2)CN(C(=O)CC[C@@H]2COC(=O)N2)C3)c1] | 3-[(4R)-2-Oxooxazolidin-4-yl]propanoic acid (BB 9) and 4-Methylbenzenesulfonic acid; 7-[(3-methylsulfonylphenyl)methyl]-2,7-diazaspiro[3.5]nonane (BB 148) | 436.3 [M + H]$^+$ |

-continued

| Ex. | Systematic Name | Structure | Building blocks | MS m/z |
|---|---|---|---|---|
| 194 | (4R)-4-[3-Oxo-3-[7-[[4-(trifluoro-methylsulfonyl)phenyl]methyl]-2,7-diazaspiro[3.5]nonan-2-yl]propyl]oxazolidin-2-one | 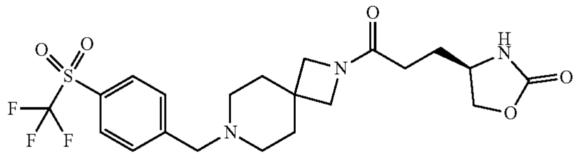 [SMILES: O=C1N[C@H](CCC(=O)N2CC3(CCN(Cc4ccc(S(=O)(=O)C(F)(F)F)cc4)CC3)C2)CO1] | 3-[(4R)-2-Oxooxazolidin-4-yl]propanoic acid (BB 9) and 4-Methylbenzene-sulfonic acid; 7-[[4-(trifluoro-methylsulfonyl)phenyl]methyl]-2,7-diazaspiro[3.5]nonane (BB 149) | 490.2 [M + H]⁺ |
| 195 | (4R)-4-[3-Oxo-3-[7-[[3-(trifluoro-methylsulfonyl)phenyl]methyl]-2,7-diazaspiro[3.5]nonan-2-yl]propyl]oxazolidin-2-one | 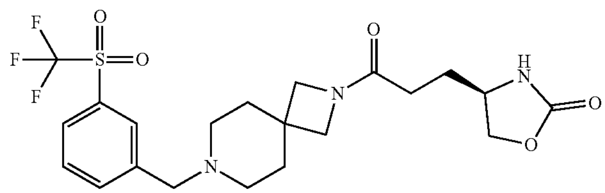 [SMILES: O=C1N[C@H](CCC(=O)N2CC3(CCN(Cc4cccc(S(=O)(=O)C(F)(F)F)c4)CC3)C2)CO1] | 3-[(4R)-2-Oxooxazolidin-4-yl]propanoic acid (BB 9) and 4-Methylbenzene-sulfonic acid; 7-[[3-(trifluoro-methylsulfonyl)phenyl]methyl]-2,7-diazaspiro[3.5]nonane (BB 150) | 490.2 [M + H]⁺ |
| 196 | (4R)-4-[3-Oxo-3-[7-[[6-(trifluoro-methyl)-3-pyridyl]methyl]-2,7-diazaspiro[3.5]nonan-2-yl]propyl]oxazolidin-2-one | 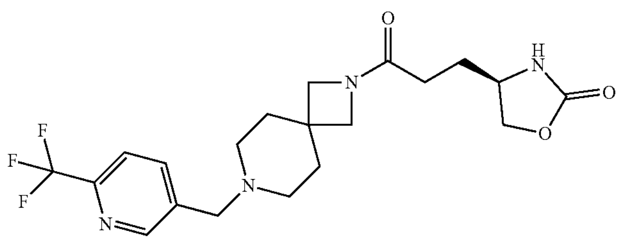 [SMILES: O=C1N[C@H](CCC(=O)N2CC3(CCN(Cc4ccc(C(F)(F)F)nc4)CC3)C2)CO1] | 3-[(4R)-2-Oxooxazolidin-4-yl]propanoic acid (BB 9) and 4-Methylbenzene-sulfonic acid; 7-[[6-(trifluoro-methyl)-3-pyridyl]methyl]-2,7-diazaspiro[3.5]nonane (BB 151) | 427.3 [M + H]⁺ |
| 197 | (4R)-4-[3-Oxo-3-[7-[[5-(trifluoro-methyl)-2-pyridyl]methyl]-2,7-diazaspiro[3.5]nonan-2-yl]propyl]oxazolidin-2-one | 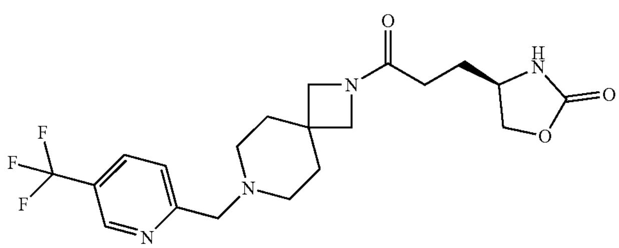 [SMILES: O=C1N[C@H](CCC(=O)N2CC3(CCN(Cc4ccc(C(F)(F)F)cn4)CC3)C2)CO1] | 3-[(4R)-2-Oxooxazolidin-4-yl]propanoic acid (BB 9) and 4-Methylbenzene-sulfonic acid; 7-[[5-(trifluoromethyl)-2-pyridyl]methyl]-2,7-diazaspiro[3.5]nonane (BB 152) | 427.3 [M + H]⁺ |
| 198 | (4R)-4-[3-Oxo-3-[6-[[6-(trifluoro-methyl)-3-pyridyl]methyl]-2-azaspiro[3.4]octan-2-yl]propyl]oxazolidin-2-one | 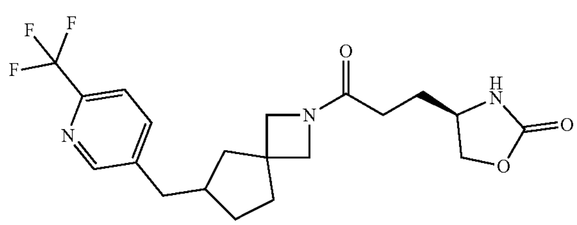 [SMILES: O=C1N[C@H](CCC(=O)N2CC3(CCC(Cc4ccc(C(F)(F)F)nc4)C3)C2)CO1] | 3-[(4R)-2-Oxooxazolidin-4-yl]propanoic acid (BB 9) and 4-Methylbenzene-sulfonic acid; 6-[[6-(trifluoromethyl)-3-pyridyl]methyl]-2-azaspiro[3.4]octane (BB 153) | 412.2 [M + H]⁺ |
| 199 | Methyl 5-chloro-2-[[5-[1-[3-[(4R)-2-oxooxazolidin-4-yl]propanoyl]azetidin-3-yl]-2-pyridyl]oxy]benzoate | 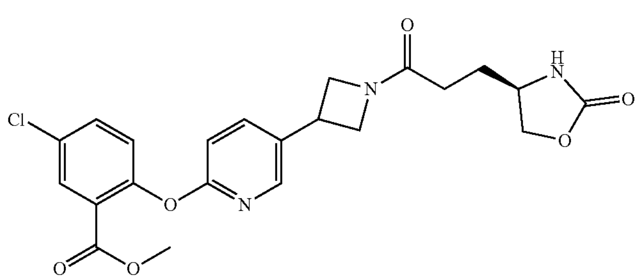 [SMILES: COC(=O)c1cc(Cl)ccc1Oc1ccc(C2CN(C(=O)CC[C@@H]3COC(=O)N3)C2)cn1] | Example 85 / Step 1 | 460.1 [M + H]⁺ |

Example 200 and Example 201

Cis-(4R)-4-[3-Oxo-3-[3-[6-[4-(trifluoromethyl)cyclohexyl]-3-pyridyl]azetidin-1-yl]propyl]oxazolidin-2-one and Trans-(4R)-4-[3-Oxo-3-[3-[6-[4-(trifluoromethyl)cyclohexyl]-3-pyridyl]azetidin-1-yl]propyl]oxazolidin-2-one

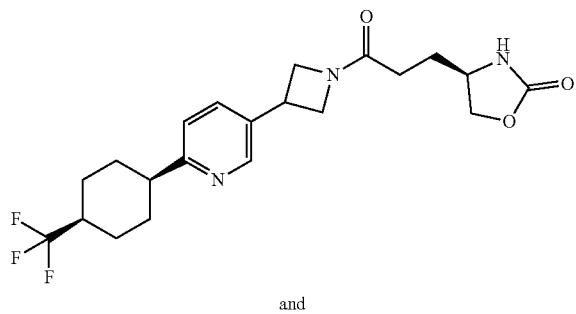

and

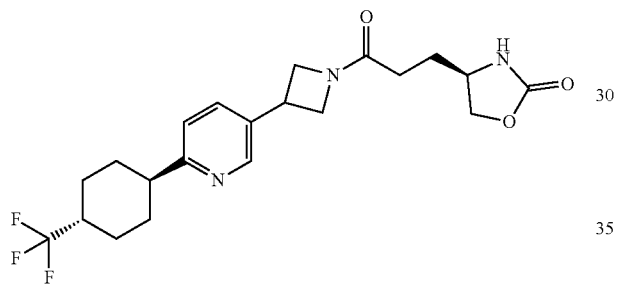

Step 1: Tert-Butyl 3-[6-[4-(trifluoromethyl)cyclohexyl]-3-pyridyl]azetidine-1-carboxylate The title compound was obtained in analogy to BB 4/Step 1 starting from tert-butyl 3-(6-bromo-3-pyridyl)azetidine-1-carboxylate (180 mg, 0.58 mmol, 1.0 equiv; BB 71/Step 1) and 1-bromo-4-(trifluoromethyl)cyclohexane (265.6 mg, 1.15 mmol, 2.0 equiv; CAS RN 30129-20-5) by irradiating (420 nm) for 16 h as a colorless solid (63 mg, 25%). MS (ESI): m/z=385.2 [M+H]$^+$.

Step 2: 5-(Azetidin-3-yl)-2-[4-(trifluoromethyl)cyclohexyl]pyridine: 4-methylbenzenesulfonic Acid The title compound was obtained in analogy to BB 4/Step 2 starting from tert-butyl 3-[6-[4-(trifluoromethyl)cyclohexyl]-3-pyridyl]azetidine-1-carboxylate (63 mg, 0.15 mmol, 1.0 equiv) as a colorless solid (70 mg, 69%). MS (ESI): m/z=285.2 [M+H]$^+$.

Step 3: cis-(4R)-4-[3-Oxo-3-[3-[6-[4-(trifluoromethyl)cyclohexyl]-3-pyridyl]azetidin-1-yl]propyl]oxazolidin-2-one and trans-(4R)-4-[3-Oxo-3-[3-[6-[4-(trifluoromethyl)cyclohexyl]-3-pyridyl]azetidin-1-yl]propyl]oxazolidin-2-one The title compounds were prepared in analogy to Example 19 starting from 5-(azetidin-3-yl)-2-[4-(trifluoromethyl)cyclohexyl]pyridine; 4-methylbenzenesulfonic acid (70 mg, 0.10 mmol, 1.0 equiv) and 3-[(4R)-2-oxooxazolidin-4-yl]propanoic acid (16.0 mg, 0.10 mmol, 1.0 equiv; BB 9). The two diastereomers were purified by preparative HPLC (Gemini NX column (100 mm×30 mm, 5 μm); 0.1% v/v TEA in water and MeCN) to give cis-(4R)-4-[3-oxo-3-[3-[6-[4-(trifluoromethyl)cyclohexyl]-3-pyridyl]azetidin-1-yl]propyl]oxazolidin-2-one (4 mg, 9%; first eluting compound) and trans-(4R)-4-[3-oxo-3-[3-[6-[4-(trifluoromethyl)cyclohexyl]-3-pyridyl]azetidin-1-yl]propyl]oxazolidin-2-one (21 mg, 49%; second eluting compound) as colorless gums. MS (ESI): m/z=426.3 [M+H]$^+$ for both examples.

Example 202 and Example 203

Cis-(4R)-4-[3-Oxo-3-[3-[6-[3-(trifluoromethyl)cyclobutyl]-3-pyridyl]azetidin-1-yl]propyl]oxazolidin-2-one and Trans-(4R)-4-[3-Oxo-3-[3-[6-[3-(trifluoromethyl)cyclobutyl]-3-pyridyl]azetidin-1-yl]propyl]oxazolidin-2-one

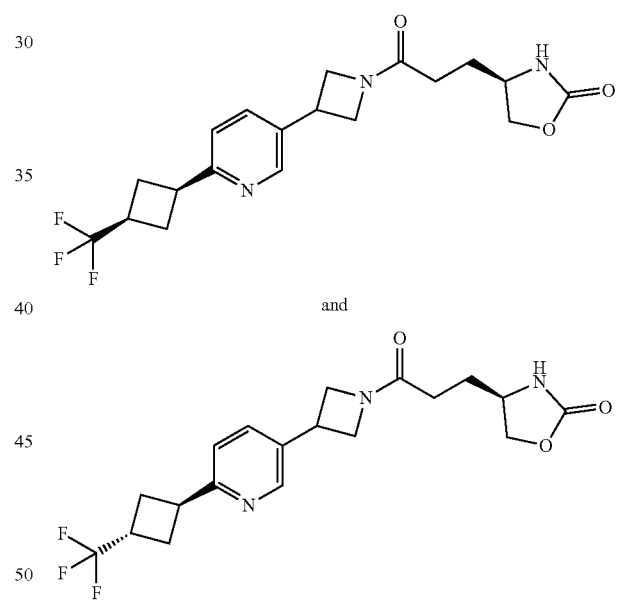

Step 1: Cis-[tert-Butyl 3-[6-[3-(trifluoromethyl)cyclobutyl]-3-pyridyl]azetidine-1-carboxylate] and Trans-[tert-Butyl 3-[6-[3-(trifluoromethyl)cyclobutyl]-3-pyridyl]azetidine-1-carboxylate]

The title compounds were prepared in analogy to BB 4/Step 1 starting from tert-butyl 3-(6-bromo-3-pyridyl)azetidine-1-carboxylate (150 mg, 0.48 mmol, 1.0 equiv; BB 71/Step 1) and 1-bromo-3-(trifluoromethyl)cyclobutane (194.5 mg, 0.96 mmol, 2.0 equiv; CAS RN 2247103-30-4) by irradiating (420 nm) for 16 h. The two geometric isomers were separated by silica gel chromatography using a MPLC system eluting with a gradient of n-heptane:ethyl acetate (100:0 to 0:100) to give trans-[tert-butyl 3-[6-[3-(trifluoromethyl)cyclobutyl]-3-pyridyl]azetidine-1-carboxylate] (32 mg, 16%; first eluting compound) and cis-[tert-butyl 3-[6-[3-(trifluoromethyl)cyclobutyl]-3-pyridyl]azetidine-1-carboxylate] (24 mg, 14%; second eluting compound) as light brown oils. MS (ESI): m/z=357.2 [M+H]$^+$) for both isomers.

Step 2A: Cis-5-(Azetidin-3-yl)-2-[3-(trifluoromethyl)cyclobutyl]pyridine; 4-methylbenzenesulfonic Acid The title compound was obtained in analogy to BB 4/Step 2 starting from cis-[tert-butyl 3-[6-[3-(trifluoromethyl)cyclobutyl]-3-pyridyl]azetidine-1-carboxylate] (38 mg, 0.11 mmol, 1.0 equiv) as a light yellow gum (73 mg, 91%). MS (ESI): m/z=257.2 [M+H]$^+$.

Step 2B: Trans-5-(Azetidin-3-yl)-2-[3-(trifluoromethyl)cyclobutyl]pyridine: 4-methylbenzenesulfonic Acid The title compound was obtained in analogy to BB 4/Step 2 starting from trans-[tert-butyl 3-[6-[3-(trifluoromethyl)cyclobutyl]-3-pyridyl]azetidine-1-carboxylate] (52 mg, 0.12 mmol, 1.0 equiv) as a colorless solid (51 mg, 68%). MS (ESI): m/z=257.2 [M+H]$^+$.

Step 3A: Cis-[tert-Butyl 3-[6-[3-(trifluoromethyl)cyclobutyl]-3-pyridyl]azetidine-1-carboxylate]

The title compound was obtained in analogy to Example 19 starting from cis-5-(azetidin-3-yl)-2-[3-(trifluoromethyl)cyclobutyl]pyridine; 4-methylbenzenesulfonic acid (73 mg, 0.10 mmol, 1.0 equiv) and 3-[(4R)-2-oxooxazolidin-4-yl]propanoic acid (16.0 mg, 0.10 mmol, 1.0 equiv; BB 9) as a colorless gum (19 mg, 49%). MS (ESI): m/z=398.2 [M+H]$^+$.

Step 3B: Trans-[tert-Butyl 3-[6-[3-(trifluoromethyl)cyclobutyl]-3-pyridyl]azetidine-1-carboxylate]

The title compound was obtained in analogy to Example 19 starting from trans-5-(azetidin-3-yl)-2-[3-(trifluoromethyl)cyclobutyl]pyridine; 4-methylbenzenesulfonic acid (51 mg, 0.085 mmol, 1.0 equiv) and 3-[(4R)-2-oxooxazolidin-4-yl]propanoic acid (13.5 mg, 0.085 mmol, 1.0 equiv; BB 9) as a colorless gum (16 mg, 47%). MS (ESI): m/z=398.2 [M+H]$^+$.

Example 204 and Example 205

(−)- or (+)-(4R)-4-[3-[3-[6-[3-Hydroxy-3-(trifluoromethyl)pyrrolidin-1-yl]-3-pyridyl]azetidin-1-yl]-3-oxo-propyl]oxazolidin-2-one and (+)- or (−)-(4R)-4-[3-[3-[6-[3-Hydroxy-3-(trifluoromethyl)pyrrolidin-1-yl]-3-pyridyl]azetidin-1-yl]-3-oxo-propyl]oxazolidin-2-one

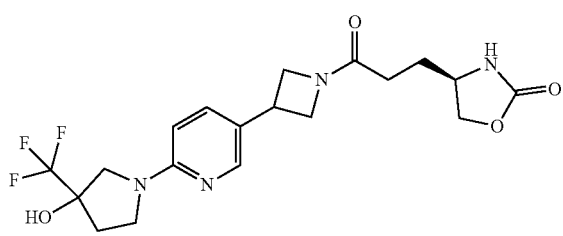 [SMILES: O=C1N[C@H](CCC(=O)N2CC(c3ccc(N4CCC(O)(C(F)(F)F)C4)nc3)C2)CO1]

The two diastereomers of (4R)-4-[3-[3-[6-[3-hydroxy-3-(trifluoromethyl)pyrrolidin-1-yl]-3-pyridyl]azetidin-1-yl]-3-oxo-propyl]oxazolidin-2-one (60 mg, 0.13 mmol; Example 146) were separated by chiral SFC (Chiralpak IB column (250 mm×20 mm, 5 µm), eluent: 20% MeOH (0.2% diethylamine) in supercritical CO$_2$) to give (−)- or (+)-(4R)-4-[3-[3-[6-[3-Hydroxy-3-(trifluoromethyl)pyrrolidin-1-yl]-3-pyridyl]azetidin-1-yl]-3-oxo-propyl]oxazolidin-2-one (18.1 mg, 32%; first eluting enantiomer) as a colorless waxy solid and (+)- or (−)-(4R)-4-[3-[3-[6-[3-hydroxy-3-(trifluoromethyl)pyrrolidin-1-yl]-3-pyridyl]azetidin-1-yl]-3-oxo-propyl]oxazolidin-2-one (22.0 mg, 39%; second eluting enantiomer) as a colorless waxy solid. MS (ESI): m/z=429.2 [M+H]$^+$ for both examples.

Example 206 and Example 207

(−)- or (+)-(4R)-4-[3-[3-[6-[3-Hydroxy-3-(trifluoromethyl)pyrrolidin-1-yl]-3-pyridyl]azetidin-1-yl]-3-oxo-propyl]oxazolidin-2-one and (+)- or (−)-(4R)-4-[3-[3-[6-[3-Hydroxy-3-(trifluoromethyl)pyrrolidin-1-yl]-3-pyridyl]azetidin-1-yl]-3-oxo-propyl]oxazolidin-2-one

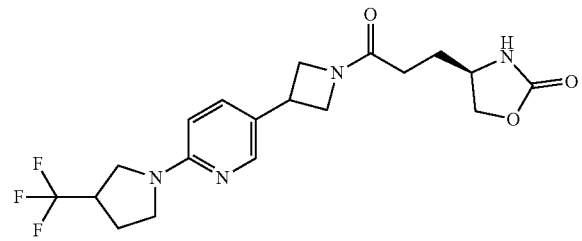

Step 1: (−)- or (+)-tert-Butyl 3-[6-[3-(trifluoromethyl)pyrrolidin-1-yl]-3-pyridyl]azetidine-1-carboxylate and (+)- or (−)-tert-Butyl 3-[6-[3-(trifluoromethyl)pyrrolidin-1-yl]-3-pyridyl]azetidine-1-carboxylate The two enantiomers of tert-butyl 3-[6-[3-(trifluoromethyl)pyrrolidin-1-yl]-3-pyridyl]azetidine-1-carboxylate (5.80 g, 15.62 mmol; BB 19/Step 2) were separated by chiral SFC (Chiralpak IG-3 column (50 mm×4.6 mm, 3 µm), eluent: 5 to 40% MeOH (0.05% diethylamine) in supercritical CO$_2$) to give (−)- or (+)-tert-butyl 3-[6-[3-(trifluoromethyl)pyrrolidin-1-yl]-3-pyridyl]azetidine-1-carboxylate (1.05 g, 36%; first eluting enantiomer) as a white solid and (+)- or (−)-tert-butyl 3-[6-[3-(trifluoromethyl)pyrrolidin-1-yl]-3-pyridyl]azetidine-1-carboxylate (1.05 g, 36%; second eluting enantiomer) as a white solid. MS (ESI): m/z=372.3 [M+H]$^+$ for both isomers.

Step 2A: (−)- or (+)-5-(Azetidin-3-yl)-2-[3-(trifluoromethyl)pyrrolidin-1-yl]pyridine; 4-methylbenzenesulfonic Acid The title compound was obtained in analogy to BB 4/Step 2 starting from (−)- or (+)-tert-butyl 3-[6-[3-(trifluoromethyl)pyrrolidin-1-yl]-3-pyridyl]azetidine-1-carboxylate (1.00 g, 2.69 mmol, 1.0 equiv) as a light yellow solid (1.41 g, 83%). MS (ESI): m/z=272.1 [M+H]⁺.

Step 2B: (+)- or (-)-5-(Azetidin-3-yl)-2-[3-(trifluoromethyl)pyrrolidin-1-yl]pyridine; 4-methylbenzenesulfonic Acid The title compound was obtained in analogy to BB 4/Step 2 starting from (+)- or (-)-tert-butyl 3-[6-[3-(trifluoromethyl)pyrrolidin-1-yl]-3-pyridyl]azetidine-1-carboxylate (1.00 g, 2.69 mmol, 1.0 equiv) as a light yellow solid (1.45 g, 87%). MS (ESI): m/z=272.2 [M+H]⁺.

Step 3A: (-)- or (+)-(4R)-4-[3-[3-[6-[3-Hydroxy-3-(trifluoromethyl)pyrrolidin-1-yl]-3-pyridyl]azetidin-1-yl]-3-oxo-propyl]oxazolidin-2-one The title compound was obtained in analogy to Example 19 starting from (-)- or (+)-5-(azetidin-3-yl)-2-[3-(trifluoromethyl)pyrrolidin-1-yl]pyridine; 4-methylbenzenesulfonic acid (81.2 mg, 0.13 mmol, 1.05 equiv) and 3-[(4R)-2-oxooxazolidin-4-yl]propanoic acid (20.0 mg, 0.13 mmol, 1.0 equiv; BB 9) as a colorless solid (35 mg, 68%). MS (ESI): m/z=413.2 [M+H]⁺.

Step 3B: (+)- or (-)-(4R)-4-[3-[3-[6-[3-Hydroxy-3-(trifluoromethyl)pyrrolidin-1-yl]-3-pyridyl]azetidin-1-yl]-3-oxo-propyl]oxazolidin-2-one The title compound was obtained in analogy to Example 19 starting from (+)- or (-)-5-(azetidin-3-yl)-2-[3-(trifluoromethyl)pyrrolidin-1-yl]pyridine; 4-methylbenzenesulfonic acid (81.2 mg, 0.13 mmol, 1.05 equiv) and 3-[(4R)-2-oxooxazolidin-4-yl]propanoic acid (20.0 mg, 0.13 mmol, 1.0 equiv; BB 9) as a colorless solid (34 mg, 65%). MS (ESI): m/z=413.2 [M+H]⁺.

Example 208 and Example 209

(-)- or (+)-(4R)-4-[3-Oxo-3-[3-[2-[3-(trifluoromethyl)pyrrolidin-1-yl]pyrimidin-5-yl]azetidin-1-yl]propyl]oxazolidin-2-one and (+)- or (-)-(4R)-4-[3-Oxo-3-[3-[2-[3-(trifluoromethyl)pyrrolidin-1-yl]pyrimidin-5-yl]azetidin-1-yl]propyl]oxazolidin-2-one

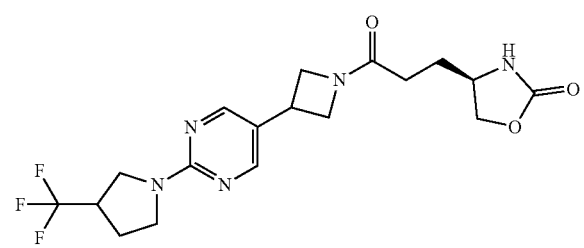 [SMILES: O=C1N[C@H](CCC(=O)N2CC(c3cnc(N4CCC(C(F)(F)F)C4)nc3)C2)CO1]

Step 1: (-)- or (+)-tert-Butyl 3-[2-[3-(trifluoromethyl)pyrrolidin-1-yl]pyrimidin-5-yl]azetidine-1-carboxylate and (+)- or (-)-tert-Butyl 3-[2-[3-(trifluoromethyl)pyrrolidin-1-yl]pyrimidin-5-yl]azetidine-1-carboxylate The two enantiomers of tert-butyl 3-[2-[3-(trifluoromethyl)pyrrolidin-1-yl]pyrimidin-5-yl]azetidine-1-carboxylate (7.04 g, 18.91 mmol; BB 62/Step 2) were separated by chiral SFC (Chiralpak AD-3 column (50 mm×4.6 mm, 3 μm), eluent: 5 to 40% MeOH (0.05% diethylamine) in supercritical CO₂) to give (-)- or (+)-tert-butyl 3-[2-[3-(trifluoromethyl)pyrrolidin-1-yl]pyrimidin-5-yl]azetidine-1-carboxylate (0.87 g, 25%; first eluting enantiomer) as a yellow solid and (+)- or (-)-tert-butyl 3-[2-[3-(trifluoromethyl)pyrrolidin-1-yl]pyrimidin-5-yl]azetidine-1-carboxylate (0.86 g, 25%; second eluting enantiomer) as a yellow solid. MS (ESI): m/z=373.1 [M+H]⁺ for both isomers.

Step 2A: (-)- or (+)-5-(Azetidin-3-yl)-2-[3-(trifluoromethyl)pyrrolidin-1-yl]pyrimidine 4-methylbenzenesulfonic Acid The title compound was obtained in analogy to BB 4/Step 2 starting from (-)- or (+)-tert-butyl 3-[2-[3-(trifluoromethyl)pyrrolidin-1-yl]pyrimidin-5-yl]azetidine-1-carboxylate (0.82 g, 2.20 mmol, 1.0 equiv) as a white solid (0.96 g, 96%). MS (ESI): m/z=273.2 [M+H]⁺.

Step 2B: (+)- or (-)-5-(Azetidin-3-yl)-2-[3-(trifluoromethyl)pyrrolidin-1-yl]pyrimidine; 4-methylbenzenesulfonic Acid The title compound was obtained in analogy to BB 4/Step 2 starting from (+)- or (-)-tert-butyl 3-[2-[3-(trifluoromethyl)pyrrolidin-1-yl]pyrimidin-5-yl]azetidine-1-carboxylate (0.83 g, 2.23 mmol, 1.0 equiv) as a yellow solid (0.99 g, 99%). MS (ESI): m/z=273.2 [M+H]⁺.

Step 3A: (-)- or (+)-(4R)-4-[3-Oxo-3-[3-[2-[3-(trifluoromethyl)pyrrolidin-1-yl]pyrimidin-5-yl]azetidin-1-yl]propyl]oxazolidin-2-one The title compound was obtained in analogy to Example 19 starting from (-)- or (+)-5-(azetidin-3-yl)-2-[3-(trifluoromethyl)pyrrolidin-1-yl]pyrimidine; 4-methylbenzenesulfonic acid (81.4 mg, 0.13 mmol, 1.05 equiv) and 3-[(4R)-2-oxooxazolidin-4-yl]propanoic acid (20.0 mg, 0.13 mmol, 1.0 equiv; BB 9) as a colorless solid (43 mg, 82%). MS (ESI): m/z=414.2 [M+H]⁺.

Step 3B: (+)- or (-)-(4R)-4-[3-Oxo-3-[3-[2-[3-(trifluoromethyl)pyrrolidin-1-yl]pyrimidin-5-yl]azetidin-1-yl]propyl]oxazolidin-2-one The title compound was obtained in analogy to Example 19 starting from (+)- or (-)-5-(azetidin-3-yl)-2-[3-(trifluoromethyl)pyrrolidin-1-yl]pyrimidine; 4-methylbenzenesulfonic acid (81.4 mg, 0.13 mmol, 1.05 equiv) and 3-[(4R)-2-oxooxazolidin-4-yl]propanoic acid (20.0 mg, 0.13 mmol, 1.0 equiv; BB 9) as a colorless solid (42 mg, 81%). MS (ESI): m/z=414.2 [M+H]⁺.

Example 210 and Example 211

(−)- or (+)-(4R)-4-[3-Oxo-3-[6-[[6-(trifluoromethyl)-3-pyridyl]methyl]-2-azaspiro[3.4]octan-2-yl]propyl]oxazolidin-2-one and (+)- or (−)-(4R)-4-[3-Oxo-3-[6-[[6-(trifluoromethyl)-3-pyridyl]methyl]-2-azaspiro[3.4]octan-2-yl]propyl]oxazolidin-2-one

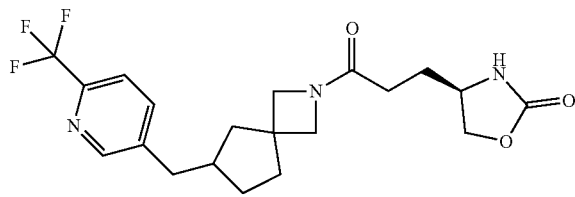 [SMILES: O=C1N[C@H](CCC(=O)N2CC3(CCC(Cc4ccc(C(F)(F)F)nc4)C3)C2)CO1]

The two diastereomers of (4R)-4-[3-oxo-3-[6-[[6-(trifluoromethyl)-3-pyridyl]methyl]-2-azaspiro[3.4]octan-2-yl]propyl]oxazolidin-2-one (45 mg, 0.10 mmol; Example 198) were separated by chiral SFC (Chiralpak IH column (250 mm×20 mm, 5 μm), eluent: 25% MeOH in supercritical CO$_2$) to give (−)- or (+)-(4R)-4-[3-oxo-3-[6-[[6-(trifluoromethyl)-3-pyridyl]methyl]-2-azaspiro[3.4]octan-2-yl]propyl]oxazolidin-2-one (14.3 mg, 17%; first eluting enantiomer) as a colorless waxy solid and (+)- or (−)-(4R)-4-[3-oxo-3-[6-[[6-(trifluoromethyl)-3-pyridyl]methyl]-2-azaspiro[3.4]octan-2-yl]propyl]oxazolidin-2-one (15.2 mg, 18%; second eluting enantiomer) as a colorless waxy solid. MS (ESI): m/z=412.3 [M+H]$^+$ for both examples.

Example 212

3-[4-(4-Chloro-2-methylsulfonyl-phenyl)phenyl]-N-[(2-oxooxazolidin-4-yl)methyl]azetidine-1-carboxamide

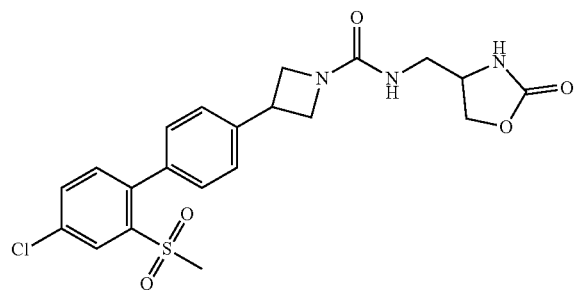 [SMILES: CS(=O)(=O)c1cc(Cl)ccc1-c1ccc(C2CN(C(=O)NCC3COC(=O)N3)C2)cc1]

To an ice-cold suspension of bis(trichloromethyl) carbonate (126.1 mg, 0.43 mmol, 2.1 equiv) and sodium bicarbonate (204.1 mg, 2.43 mmol, 12.0 equiv) in DCM (0.5 mL) was added 4-(aminomethyl)oxazolidin-2-one; hydrochloride (92.7 mg, 0.61 mmol, 3.0 equiv; CAS RN 1803589-70-9) and the reaction mixture was stirred at RT overnight. To the suspension was added 3-[4-(4-chloro-2-methylsulfonyl-phenyl)phenyl]azetidine; 4-methylbenzenesulfonic acid (100 mg, 0.20 mmol, 1.0 equiv; BB 41) and DIPEA (104.6 mg, 141 μL, 0.81 mmol, 4.0 equiv) and stirring was continued at RT for 6 h. The reaction suspension was diluted with MeOH (0.5 mL) and stirred for 15 min before being filtered. The filtrate was evaporated under reduced pressure and the crude product purified by preparative HPLC (YMC Triart C18 column (150 mm×4.6 mm, 5 μm); 0.1% v/v FA in water and MeCN) to give the title compound as a colorless gum (48 mg, 51%). MS (ESI): m/z=464.2 [M+H]$^+$.

Example 213

4-[3-Oxo-3-[6-[[6-(trifluoromethyl)-3-pyridyl]methyl]-2-azaspiro[3.3]heptan-2-yl]propyl]imidazolidin-2-one

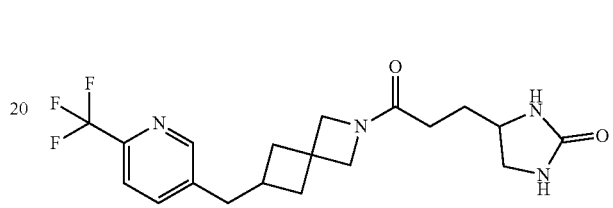

To a solution of 3-(2-oxoimidazolidin-4-yl)propanoic acid (25.8 mg, 0.16 mmol, 1.0 equiv; CAS RN 45967-46-2) in DMF (0.500 mL) were added HATU (68.3 mg, 0.18 mmol, 1.1 equiv) and DIPEA (105.6 mg, 143 μL, 0.82 mmol, 5.0 equiv) and the reaction mixture was stirred at RT for 15 min. To the solution was added to 4-methylbenzenesulfonic acid; 6-[[6-(trifluoromethyl)-3-pyridyl]methyl]-2-azaspiro[3.3]heptane (70 mg, 0.16 mmol, 1.0 equiv; BB 80) and the reaction mixture was stirred at RT for 64 h. The crude product was purified by preparative HPLC (YMC Triart C18 column (150 mm×4.6 mm, 5 μm); 0.1% v/v FA in water and MeCN) to give the title compound as a light brown gum (28 mg, 43%). MS (ESI): m/z=397.2 [M+H]$^+$.

Example 214

4-[3-Oxo-3-[3-[4-[1-(trifluoromethyl)cyclopropyl]phenyl]azetidin-1-yl]propyl]imidazolidin-2-one

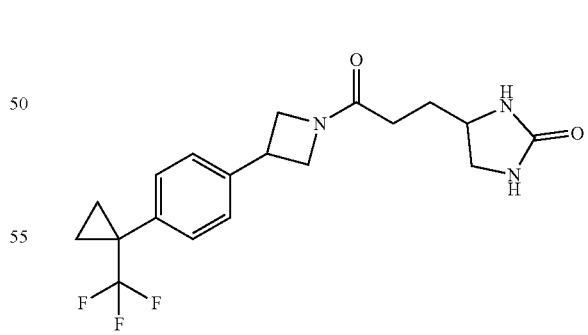

The title compound was obtained in analogy to Example 213 starting from 3-(2-oxoimidazolidin-4-yl)propanoic acid (30.6 mg, 0.19 mmol, 1.0 equiv; CAS RN 45967-46-2) and 3-[4-[1-(trifluoromethyl)cyclopropyl]phenyl]azetidine; 4-methylbenzenesulfonic acid (80 mg, 0.19 mmol, 1.0 equiv; BB 4) as a colorless solid (34 mg, 46%). MS (ESI): m/z=382.2 [M+H]$^+$.

Example 215

4-[3-[3-[[2-Fluoro-4-(trifluoromethyl)phenyl]methoxy]azetidin-1-yl]-3-oxo-propyl]imidazolidin-2-one

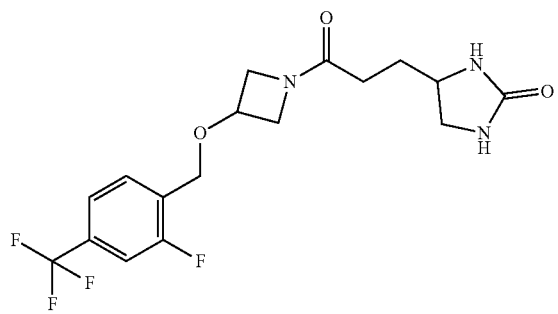 [SMILES: O=C1NCC(CCC(=O)N2CC(OCc3ccc(C(F)(F)F)cc3F)C2)N1]

The title compound was obtained in analogy to Example 213 starting from 3-(2-oxoimidazolidin-4-yl)propanoic acid (38.1 mg, 0.24 mmol, 1.0 equiv; CAS RN 45967-46-2) and 3-[[2-fluoro-4-(trifluoromethyl)phenyl]methoxy]azetidine; 4-methylbenzenesulfonic acid (101.6 mg, 0.24 mmol, 1.0 equiv; BB 2) as a colorless gum (8 mg, 9%). MS (ESI): m/z=390.1 [M+H]$^+$.

Example 216

4-[3-[3-[4-(4-Chloro-2-methylsulfonyl-phenyl)phenyl]azetidin-1-yl]-3-oxo-propyl]imidazolidin-2-one

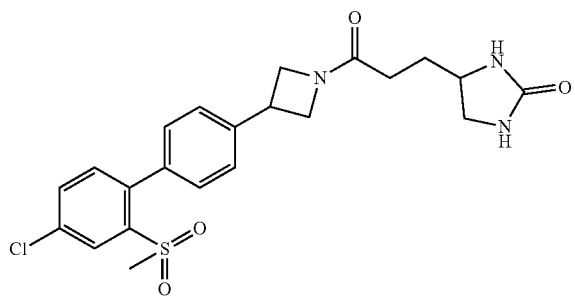 [SMILES: CS(=O)(=O)c1cc(Cl)ccc1-c1ccc(C2CN(C(=O)CCC3CNC(=O)N3)C2)cc1]

The title compound was obtained in analogy to Example 213 starting from 3-(2-oxoimidazolidin-4-yl)propanoic acid (25.6 mg, 0.16 mmol, 1.0 equiv; CAS RN 45967-46-2) and 3-[4-(4-chloro-2-methylsulfonyl-phenyl)phenyl]azetidine; 4-methylbenzenesulfonic acid (80.0 mg, 0.16 mmol, 1.0 equiv; BB 41) as a colorless solid (39 mg, 52%). MS (ESI): m/z=462.1 [M+H]$^+$.

Example 217 and Example 218

(−)- or (+)-4-[3-[3-[4-(4-Chloro-2-methylsulfonyl-phenyl)phenyl]azetidin-1-yl]-3-oxo-propyl]imidazolidin-2-one and (+)- or (−)-4-[3-[3-[4-(4-Chloro-2-methylsulfonyl-phenyl)phenyl]azetidin-1-yl]-3-oxo-propyl]imidazolidin-2-one

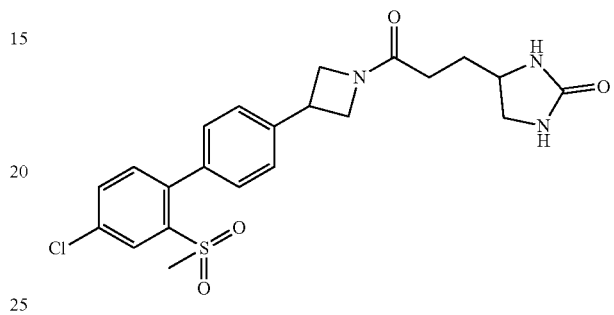

The two enantiomers of 4-[3-[3-[4-(4-chloro-2-methylsulfonyl-phenyl)phenyl]azetidin-1-yl]-3-oxo-propyl]imidazolidin-2-one (16 mg, 0.035 mmol; Example 216) were separated by chiral SFC (Chiralpak IA column (250 mm×20 mm, 5 µm), eluent: 45% MeOH in supercritical CO$_2$) to give (−)- or (+)-4-[3-[3-[4-(4-chloro-2-methylsulfonyl-phenyl)phenyl]azetidin-1-yl]-3-oxo-propyl]imidazolidin-2-one (7 mg, 88%; first eluting enantiomer) as a light brown solid and (+)- or (−)-4-[3-[3-[4-(4-chloro-2-methylsulfonyl-phenyl)phenyl]azetidin-1-yl]-3-oxo-propyl]imidazolidin-2-one (7 mg, 88%; second eluting enantiomer) as a light brown solid. MS (ESI): m/z=462.2 [M+H]$^+$ for both isomers.

Synthesis of Building Blocks

BB 1

3-(5-Oxopyrrolidin-2-yl)propanoic Acid

Step 1: Diethyl 4-nitroheptanedioate

To a solution of nitromethane (0.89 mL, 16.38 mmol, 1.0 equiv; CAS RN 75-52-5) in DME (20 mL) was added N-benzyl-trimethylammonium hydroxide (1.0 mL; CAS RN 100-85-6). The solution was warmed to 70° C., ethyl acrylate (4.92 g, 49.15 mmol, 3.0 equiv; CAS RN 140-88-5) was added in portions followed by N-benzyl-trimethylammonium hydroxide (1.0 mL). The reaction mixture was stirred at 70° C. for 1 h, then another batch of N-benzyl-trimethylammonium hydroxide (1.0 mL) was added. After stirring for another hour at 70° C., the reaction mixture was concentrated, and the residue was purified by silica gel column chromatography (petroleum ether:ethyl acetate=20:1) to give the desired product as light yellow oil (1.1 g, 26%). $^1$H NMR (400 MHz, CDCl$_3$): δ=4.73-4.47 (m, 1H), 4.22-4.12 (m, 4H), 2.51-2.37 (m, 3H), 2.36-2.09 (m, 5H), 1.28 (t, J=7.2 Hz, 6H).

Step 2: Ethyl 3-(5-oxopyrrolidin-2-yl)propanoate

To a solution of diethyl 4-nitroheptanedioate (900.0 mg, 3.44 mmol, 1.0 equiv) in MeOH (30 mL) was added wet Pd/C (200 mg, 3.44 mmol, 1.0 equiv; wt. 10%) and the reaction mixture was stirred at RT for 48 h under an atmosphere of $H_2$ (balloon). The reaction mixture was filtered and the filtrate was concentrated to give the crude product as light yellow oil (640 mg, quant.), which was used in the next step without further purification.

Step 3: 3-(5-Oxopyrrolidin-2-yl)propanoic Acid

To a solution of ethyl 3-(5-oxopyrrolidin-2-yl)propanoate (640.0 mg, 3.46 mmol, 1.0 equiv) in THF (12 mL), water (12 mL) and MeOH (12 mL) was added NaOH (414.6 mg, 10.4 mmol, 3.0 equiv) and the reaction mixture was stirred at 20° C. for 2 h. THF was removed under reduced pressure and the residue was acidified to pH=4~5 with aqueous HCl (3 M). The solution was concentrated, the residue was redissolved in a mixture of DCM:MeOH (10:1, 30 mL), filtered and the filtrate was concentrated to give the crude product as light yellow oil (500 mg, 92%) which was used in the next step without further purification.

BB 2

3-[[2-Fluoro-4-(trifluoromethyl)phenyl]methoxy]azetidine; 4-methylbenzenesulfonic Acid Step 1: Tert-Butyl 3-[[2-fluoro-4-(trifluoromethyl)phenyl]methoxy]azetidine-1-carboxylate To an ice-cold solution of tert-butyl 3-hydroxyazetidine-1-carboxylate (2.02 g, 11.7 mmol, 1.0 equiv; CAS RN 141699-55-0) in DMF (25 mL) was added sodium hydride (0.56 g, 12.8 mmol, 1.1 equiv; 55% in mineral oil) in portions and the reaction mixture was stirred for 30 min. A solution of 1-(bromomethyl)-2-fluoro-4-(trifluoromethyl)benzene (3.0 g, 11.7 mmol, 1.0 equiv) in DMF (5 mL) was added dropwise to the reaction mixture and stirring continued at RT for 3 h. The reaction mixture was poured on a mixture of a sat. aqueous $NH_4Cl$ solution:ethyl acetate (1:1, 140 mL) and the aqueous layer was extracted twice with ethyl acetate. The combined organic layers were dried over $MgSO_4$, filtered and evaporated. The crude product was purified by silica gel chromatography using a MPLC system eluting with a gradient of n-heptane:ethyl acetate (100:0 to 60:40) to yield the title compound as light yellow oil (3.66 g, 90%). MS (ESI): m/z=294.1 $[M+2H-tBu]^+$.

Step 2: 3-[[2-Fluoro-4-(trifluoromethyl)phenyl]methoxy]azetidine: 4-methylbenzenesulfonic Acid To a solution of tert-butyl 3-[[2-fluoro-4-(trifluoromethyl)phenyl]methoxy]azetidine-1-carboxylate (7.8 g, 22.3 mmol, 1.0 equiv) in ethyl acetate (130 mL) was added 4-methylbenzenesulfonic acid hydrate (4.61 g, 26.8 mmol, 1.2 equiv) and the reaction mixture was heated at reflux for 2 h. The suspension was cooled in the fridge at 0° C. for 1 h and filtered. The precipitate was washed with ethyl acetate and dried to yield the title compound as colorless solid (7.3 g, 81%). MS (ESI): m/z=250.2 $[M+H]^+$.

BB 3

3-(4-(tert-Butyl)phenyl)azetidine; 4-methylbenzenesulfonic Acid

To a solution of tert-butyl 3-(4-tert-butylphenyl)azetidine-1-carboxylate (1.8 g, 6.22 mmol, 1.0 equiv; CAS RN 1629889-13-9) in ethyl acetate (15 mL) was added 4-methylbenzenesulfonic acid hydrate (1.66 g, 8.70 mmol, 1.4 equiv) and the reaction mixture was heated at reflux for 12 h. The solution was evaporated to get the title compound as a brown oil (1.69 g, 66%). MS (ESI): m/z=190.2 $[M+H-Ts]^+$.

BB 4

3-[4-[1-(Trifluoromethyl)cyclopropyl]phenyl]azetidine; 4-methylbenzenesulfonic Acid Step 1: Tert-Butyl 3-[4-[1-(trifluoromethyl)cyclopropyl]phenyl]azetidine-1-carboxylate To a 20 mL vial, equipped with a stir bar, was added 1-bromo-4-(1-(trifluoromethyl)cyclopropyl)benzene (561 mg, 2.12 mmol, 1.0 equiv; CAS RN 1227160-18-0), tert-butyl 3-iodoazetidine-1-carboxylate (600 mg, 2.12 mmol, 1.0 equiv; CAS RN 254454-54-1), tris(trimethylsilyl)silane (527 mg, 653 µL, 2.12 mmol, 1.0 equiv), photocatalyst bis[3,5-difluoro-2-[5-(trifluoromethyl)-2-pyridyl]phenyl]iridium(1+) 4-tert-butyl-2-(4-tert-butyl-2-pyridyl)pyridine hexafluorophosphate (23.8 mg, 21.2 µmol, 0.01 equiv; Ir[dF(CF$_3$)ppy]$_2$(dtbbpy))PF$_6$; CAS RN 870987-63-6) and anhydrous sodium carbonate (449 mg, 4.24 mmol, 2.0 equiv). The vial was sealed and placed under Ar before DME (9 mL) was added. To a separate vial was added nickel(II) chloride ethylene glycol dimethyl ether complex (4.65 mg, 21.2 µmol, 0.01 equiv; CAS RN 29046-78-4) and 4,4'-di-tert-butyl-2,2'-bipyridine (5.68 mg, 21.2 µmol, 0.01 equiv). The vial was sealed, purged with Ar, and DME (4 mL) was added. The precatalyst solution was sonicated for 5 min, after which 2 mL were syringed into the reaction vessel. The reaction mixture was degassed with Ar and irradiated with a blue LED lamp (420 nm) for 1 h. The reaction was quenched by exposure to air, filtered and the solvent evaporated. The crude reaction mixture was purified by silica gel chromatography using a MPLC system eluting with a gradient of n-heptane:ethyl acetate (100:0 to 70:30) to furnish the title compound as a colorless solid (0.51 g, 66%). MS (ESI): m/z=286.1 $[M+2H-tBu]^+$.

Step 2: 3-[4-[1-(Trifluoromethyl)cyclopropyl]phenyl]azetidine; 4-methylbenzenesulfonic Acid To a solution of tert-butyl 3-[4-[1-(trifluoromethyl)cyclopropyl]phenyl]azetidine-1-carboxylate (0.5 g, 1.46 mmol, 1.0 equiv) in ethyl acetate (5 mL) was added 4-methylbenzenesulfonic acid hydrate (0.29 g, 1.54 mmol, 1.1 equiv) and the reaction mixture was heated at reflux for 2 h. The suspension was cooled in the fridge at 0° C. for 1 h and the filtered. The precipitate was washed with ethyl acetate and dried to yield the title compound as a colorless solid (0.52 g, 82%). MS (ESI): m/z=242.2 $[M+H]^+$.

BB 5

3-[4-(2,2,2-Trifluoroethyl)phenyl]azetidine; 4-methylbenzenesulfonic Acid

Step 1: Tert-Butyl 3-[4-(2,2,2-trifluoroethyl)phenyl]azetidine-1-carboxylate

The product was obtained in analogy to BB 4/Step 1 starting from 1-bromo-4-(2,2,2-trifluoroethyl)benzene (1.0 g, 4.18 mmol, 1.0 equiv; CAS RN 155820-88-5) and tert-butyl 3-bromoazetidine-1-carboxylate (0.99 g, 4.18 mmol, 1.0 equiv; CAS RN 1064194-10-0) by irradiating (420 nm) for 24 h as a colorless oil (0.98 g, 74%). MS (ESI): m/z=260.1 [M+2H-tBu]$^+$.

Step 2: 3-[4-(2,2,2-Trifluoroethyl)phenyl]azetidine; 4-methylbenzenesulfonic Acid To a solution of tert-butyl 3-[4-(2,2,2-trifluoroethyl)phenyl]azetidine-1-carboxylate (0.98 g, 3.09 mmol, 1.0 equiv) in ethyl acetate (12 mL) was added 4-methylbenzenesulfonic acid hydrate (0.64 g, 3.71 mmol, 1.2 equiv) and the reaction mixture was heated at reflux for 2 h. The suspension was cooled in the fridge at 0° C. for 1 h and filtered. The precipitate was washed with ethyl acetate and dried to yield the title compound as a colorless solid (0.54 g, 45%). MS (ESI): m/z=216.1 [M+H]$^+$.

BB 6

3-[4-(2,4-Difluorophenyl)phenyl]azetidine; 4-methylbenzenesulfonic Acid

Step 1: Tert-Butyl 3-(4-bromophenyl)azetidine-1-carboxylate

To a suspension of tert-butyl 3-iodoazetidine-1-carboxylate (2.0 g, 7.06 mmol, 1.0 equiv; CAS RN 254454-54-1) and (4-bromophenyl)boronic acid (2.84 g, 14.1 mmol, 2.0 equiv; CAS RN 5467-74-3) in 2-propanol (25 mL) was added rac-trans-2-aminocyclohexan-1-ol (48.8 mg, 424 µmol, 0.06 equiv), nickel(II) iodide (132 mg, 424 µmol, 0.06 equiv) and sodium bis(trimethylsilyl)amide (6.48 g, 14.1 mmol, 2.0 equiv; 40% in THF) at RT under Ar. The reaction mixture was heated by microwave irradiation to 80° C. for 30 min. The reaction mixture was then poured on water and ethyl acetate (contains an insoluble solid) and the aqueous layer extracted twice with ethyl acetate. The organic layers were dried over MgSO$_4$, filtered, treated with silica gel and evaporated. The compound was purified by silica gel chromatography using a MPLC system eluting with a gradient of n-heptane:ethyl acetate (100:0 to 50:50) to provide the title compound as a colorless oil (1.33 g, 60%). MS (ESI): m/z=256.0 [M+2H-tBu]$^+$.

Step 2: Tert-Butyl 3-[4-(2,4-difluorophenyl)phenyl]azetidine-1-carboxylate

A suspension of tert-butyl 3-(4-bromophenyl)azetidine-1-carboxylate (1.3 g, 4.16 mmol, 1.0 equiv; BB 6/Step 1; CAS RN 1203681-52-0), (2,4-difluorophenyl)boronic acid (658 mg, 4.16 mmol, 1.0 equiv; CAS RN 144025-03-6), potassium carbonate (2.88 g, 20.8 mmol, 5.0 equiv), tetrakis(triphenylphosphine)palladium(0) (241 mg, 208 µmol, 0.05 equiv) in a mixture of THF:water (10:1, 11 mL) was heated by microwave irradiation to 110° C. for 15 min. The reaction mixture was then poured on water and ethyl acetate and the aqueous layer extracted with ethyl acetate. The organic layers were dried over MgSO$_4$, filtered, treated with silica gel and evaporated. The compound was purified by silica gel chromatography using a MPLC system eluting with a gradient of n-heptane:ethyl acetate (100:0 to 50:50) to yield the title compound as a yellow oil (1.20 g, 79%). MS (ESI): m/z=290.2 [M+2H-tBu]$^+$.

Step 3: 3-[2-[2-Fluoro-4-(trifluoromethyl)phenyl]ethyl]azetidine; 4-methylbenzenesulfonic Acid To a solution of tert-butyl 3-[4-(2,4-difluorophenyl)phenyl]azetidine-1-carboxylate (1.20 g, 3.47 mmol, 1.0 equiv) in ethyl acetate (5 mL) was added 4-methylbenzenesulfonic acid hydrate (0.72 g, 4.17 mmol, 1.2 equiv) and the reaction mixture was heated at reflux for 2 h. The suspension was cooled in the fridge at 0° C. for 1 h and filtered. The precipitate was washed with ethyl acetate and dried to yield the title compound as a colorless solid (0.92 g, 63%). MS (ESI): m/z=246.2 [M+H]$^+$.

BB 7

5-(Azetidin-3-yl)-2-(3-chlorophenoxy)pyridine; 4-methylbenzenesulfonic Acid

Step 1: Tert-Butyl 3-[6-(3-chlorophenoxy)-3-pyridyl]azetidine-1-carboxylate

The title compound was obtained in analogy to BB 4/Step 1 starting from 5-bromo-2-(3-chlorophenoxy)pyridine (0.80 g, 2.81 mmol, 1.0 equiv; CAS RN 28373-85-5) and tert-butyl 3-bromoazetidine-1-carboxylate (0.66 g, 2.81 mmol, 1.0 equiv; CAS RN 1064194-10-0) by irradiating (420 nm) for 2 h as an off-white solid (0.28 g, 44%). MS (ESI): m/z=361.2 [M+H]$^+$.

Step 2: 5-(Azetidin-3-yl)-2-(3-chlorophenoxy)pyridine; 4-methylbenzenesulfonic Acid To a solution of tert-butyl 3-[6-(3-chlorophenoxy)-3-pyridyl]azetidine-1-carboxylate (0.49 g, 1.36 mmol, 1.0 equiv) in ethyl acetate (5 mL) was added 4-methylbenzenesulfonic acid hydrate (0.27 g, 1.43 mmol, 1.1 equiv) and the reaction mixture was heated at 80° C. for 22 h. The suspension was cooled in the fridge at 0° C. for 2 h and then filtered. The precipitate was washed with ethyl acetate and dried to yield the title compound as an off-white solid (0.54 g, 92%). MS (ESI): m/z=261.2 [M+H]$^+$.

BB 8

3-[(4S)-2-Oxooxazolidin-4-yl]propanoic Acid

Step 1: Methyl (S)-4-((tert-butoxycarbonyl)amino)-5-hydroxypentanoate

To a solution of (S)-2-((tert-butoxycarbonyl)amino)-5-methoxy-5-oxopentanoic acid (1 g, 3.83 mmol, 1.0 equiv; CAS RN 45214-91-3) in THF (15 mL) at −10° C. was added N-methylmorpholine (421 µL, 3.83 mmol, 1.0 equiv), followed by ethyl chloroformate (368 µL, 3.83 mmol, 1.0 equiv) and the reaction mixture was stirred at this temperature for 10 min. Addition of NaBH$_4$ (434 mg, 11.5 mmol, 3.0 equiv) in one portion did not cause a temperature increase. MeOH (35 mL) was added dropwise between −1° C. and 17° C. over 30 min. Stirring was continued in an ice bath for 1 h. A 1 M aqueous KHSO$_4$ sol. (40 mL) was added dropwise to the reaction mixture and then the organic solvents were evaporated. The aqueous layer was extracted twice with ethyl acetate. The combined organic layers were washed with aqueous 1 M KHSO$_4$ solution and sat. aqueous NaHCO$_3$ solution, dried over MgSO$_4$, filtered, treated with silica gel and evaporated. The crude compound was purified by silica gel chromatography using a MPLC system eluting with a gradient of n-heptane:ethyl acetate (100:0 to 30:70) to get the title compound as a colorless oil (0.70 g, 66%). MS (ESI): m/z=192.1 [M+H]$^+$.

Step 2: Methyl (S)-3-(2-oxooxazolidin-4-yl)propanoate

To a solution of methyl (S)-4-((tert-butoxycarbonyl)amino)-5-hydroxypentanoate (690 mg, 2.79 mmol, 1.0 equiv) in THF (8.8 mL) was added dropwise thionyl chloride (611 µL, 8.37 mmol, 3.0 equiv) and the solution was stirred at RT for 3 h. Silica gel was added and the reaction mixture was evaporated. The compound was purified by silica gel chromatography using a MPLC system eluting with a gradient of n-heptane:ethyl acetate (100:0 to 0:100) to afford the title compound as a colorless oil (404 mg, 79%). MS (ESI): m/z=174.1 [M+H]$^+$.

Step 3: (S)-3-(2-Oxooxazolidin-4-yl)propanoic Acid

To a solution of methyl (S)-3-(2-oxooxazolidin-4-yl)propanoate (400 mg, 2.31 mmol, 1.0 equiv) in 1,4-dioxane (2 mL) and water (2 mL) was added lithium hydroxide monohydrate (107 mg, 2.54 mmol, 1.1 equiv) and the reaction mixture was stirred at RT for 2 h. 1,4-Dioxane was evaporated and aqueous HCl (2.54 mL, 2.54 mmol, 1.1 equiv) was added dropwise to the solution. The aqueous layer was extracted five times with ethyl acetate. The combined organic layers were dried over MgSO$_4$, filtered and evaporated to get the title compound as a colorless solid (330 mg, 86%). MS (ESI): m/z=160.1 [M+H]$^+$.

BB 9

3-[(4R)-2-Oxooxazolidin-4-yl]propanoic Acid

Step 1: Methyl (4R)-4-(tert-butoxycarbonylamino)-5-hydroxy-pentanoate

The title compound was obtained in analogy to BB 8/Step 1 starting from (R)-2-((tert-butoxycarbonyl)amino)-5-methoxy-5-oxopentanoic acid (1 g, 3.83 mmol, 1.0 equiv; CAS RN 76379-01-6) as a colorless oil (0.70 g, 66%). MS (ESI): m/z=192.1 [M+H]$^+$.

Step 2: Methyl 3-[(4R)-2-oxooxazolidin-4-yl]propanoate

The title compound was obtained in analogy to BB 8/Step 2 starting from methyl (4R)-4-(tert-butoxycarbonylamino)-5-hydroxy-pentanoate (0.69 g, 2.79 mmol, 1.0 equiv) as a colorless oil (0.40 g, 79%). MS (ESI): m/z=174.1 [M+H]$^+$.

Step 2: 3-[(4R)-2-Oxooxazolidin-4-yl]propanoic Acid

The title compound was obtained in analogy to BB 8/Step 3 starting from methyl 3-[(4R)-2-oxooxazolidin-4-yl]propanoate (395 mg, 2.28 mmol, 1.0 equiv) as a colorless solid (331 mg, 87%). MS (ESI): m/z=160.1 [M+H]$^+$.

BB 10

3-(4-((1,1,1-Trifluoro-2-methylpropan-2-yl)oxy)phenyl)azetidine; 4-methylbenzenesulfonic Acid

Step 1: 1-Nitro-4-((1,1,1-trifluoro-2-methylpropan-2-yl)oxy)benzene

To an ice-cold solution of 1,1,1-trifluoro-2-methylpropan-2-ol (327 mg, 2.55 mmol, 1.2 equiv; CAS RN507-52-8) in DMF (4 mL) was added sodium hydride (102 mg, 2.55 mmol, 1.2 equiv; 55% in mineral oil) and the reaction mixture was stirred at RT. After 1 h, 1-fluoro-4-nitrobenzene (300 mg, 2.13 mmol, 1.0 equiv; CAS RN350-46-9) was added portionwise and stirring was continued overnight at RT. The reaction mixture was poured on a sat. aqueous NH$_4$Cl solution and ethyl acetate and the layers were separated. The aqueous layer was extracted twice with ethyl acetate. The combined organic layers were washed three times with water, dried over MgSO$_4$, filtered, treated with silica gel and evaporated. The crude compound was purified by silica gel chromatography using a MPLC system eluting with a gradient of n-heptane:ethyl acetate (100:0 to 50:50) to get the title compound as a colorless oil (0.42 g, 75%), which was used without further purification in the consecutive step.

Step 2: 4-((1,1,1-Trifluoro-2-methylpropan-2-yl)oxy)aniline

To a solution of 1-nitro-4-((1,1,1-trifluoro-2-methylpropan-2-yl)oxy)benzene (420 mg, 1.69 mmol, 1.0 equiv) in ethyl acetate (2 mL) and MeOH (2 mL) was added Pd/C (39.5 mg, 37.1 µmol, 0.022 equiv; wt. 10%) and the suspension was stirred at RT for 5 h under an atmosphere of H$_2$ (balloon). The suspension was filtered and the filtrate evaporated to get the title compound as a colorless solid (0.36 g, 92%). MS (ESI): m/z=220.2 [M+H]$^+$.

Step 3: 1-Bromo-4-((1,1,1-trifluoro-2-methylpropan-2-yl)oxy)benzene

To a solution of 4-((1,1,1-trifluoro-2-methylpropan-2-yl)oxy)aniline (360 mg, 1.64 mmol, 1.0 equiv) in ACN (8 mL) was added copper(II) bromide (477 mg, 2.13 mmol, 1.3 equiv). The dark suspension was heated to 60° C. At this temperature tert-butyl nitrite (220 mg, 2.13 mmol, 1.3 equiv) was added dropwise and the reaction mixture was stirred at 70° C. overnight. After cooling down, the dark reaction mixture was poured on a sat. aqueous NaHCO$_3$ solution. The aqueous layer was extracted twice with ethyl acetate. The combined organic layers were dried over MgSO$_4$, filtered, treated with silica gel and evaporated. The crude compound was purified by silica gel chromatography using a MPLC system eluting with a gradient of n-heptane:ethyl acetate (100:0 to 50:50) to get the title compound as a colorless oil (0.38 g, 40%).

Step 4: Tert-Butyl 3-(4-((1,1,1-trifluoro-2-methylpropan-2-yl)oxy)phenyl)azetidine-1-carboxylate The title compound was obtained in analogy to BB 4/Step 1 starting from 1-bromo-4-((1,1,1-trifluoro-2-methylpropan-2-yl)oxy)benzene (375 mg, 1.32 mmol, 1.0 equiv) and tert-butyl 3-bromoazetidine-1-carboxylate (313 mg, 1.32 mmol, 1.0 equiv; CAS RN 1064194-10-0) by irradiating (420 nm) for 16 h as a light brown solid (99 mg, 20%). MS (ESI): m/z=304.2 [M+2H-tBu]$^+$.

Step 5: 3-(4-((1,1,1-Trifluoro-2-methylpropan-2-yl)oxy)phenyl)azetidine; 4-methylbenzenesulfonic Acid To a solution of tert-butyl 3-(4-((1,1,1-trifluoro-2-methylpropan-2-yl)oxy)phenyl)azetidine-1-carboxylate (98 mg, 0.273 mmol, 1.0 equiv) in ethyl acetate (1 mL) was added 4-methylbenzenesulfonic acid hydrate (55 mg, 0.286 mmol, 1.1 equiv) and the reaction mixture was heated at reflux for 1.5 h. The suspension was cooled in the fridge at 0° C. for 30 min and filtered. The precipitate was washed with ethyl acetate and dried to yield the title compound as a colorless solid (81 mg, 65%). MS (ESI): m/z=260.2 [M+H]$^+$.

BB 11

[4-(Azetidin-3-yloxymethyl)-3-fluoro-phenyl]-pentafluoro-6-sulfane; 2,2,2-trifluoroacetic Acid Step 1: Tert-Butyl 3-[[2-fluoro-4-(pentafluoro-$\lambda^6$-sulfanyl)phenyl]methoxy]azetidine-1-carboxylate To a solution of tert-butyl 3-hydroxyazetidine-1-carboxylate (5.5 g, 31.8 mmol, 1.0 equiv; CAS RN 141699-55-0) in dry THF (4 mL) was added KOt-Bu (33.3 mL, 33.3 mmol, 1.05 equiv; 1 M in THF) and the turbid reaction mixture was stirred at RT for 15 min followed by addition of [4-(bromomethyl)-3-fluoro-phenyl]-pentafluoro-$\lambda^6$-sulfane (10 g, 31.8 mmol, 1.0 equiv; CAS RN 1240257-17-3). The reaction mixture was then stirred at RT overnight. The crude reaction was diluted with ethyl acetate and extracted with water, the organic phase collected and the aqueous phase back-extracted with ethyl acetate. The combined organic phases were dried over Na$_2$SO$_4$ and evaporated down to dryness. The crude material was purified by silica gel chromatography using a MPLC system eluting with a gradient of n-heptane:ethyl acetate (100:0 to 20:80) to get the title compound as a yellow oil (9.72 g, 71%). MS (ESI): m/z=352.1 [M+2H-tBu]$^+$.

Step 2: [4-(Azetidin-3-yloxymethyl)-3-fluoro-phenyl]-pentafluoro-$\lambda^6$-sulfane; 2,2,2-trifluoroacetic Acid To a solution of tert-butyl 3-((2-fluoro-4-(pentafluoro-$\lambda^6$-sulfaneyl)benzyl)oxy)azetidine-1-carboxylate (9.72 g, 23.9 mmol, 1.0 equiv) in DCM (100 mL) was added TFA (27.2 g, 18.4 mL, 239 mmol, 10.0 equiv). The reaction mixture was stirred at RT for 1 h and then evaporated. The residue was treated with toluene and evaporated to get the desired product as yellow oil (10.1 g, quant.). MS (ESI): m/z=308.1 [M+H]$^+$.

BB 12

6-[(2,4-Difluorophenyl)methyl]-2-azaspiro[3.3]heptane; 2,2,2-trifluoroacetic Acid Step 1: (2,4-Difluorobenzyl)triphenylphosphonium Bromide To a solution of triphenylphosphine (1.27 g, 4.83 mmol, 1.0 equiv) in ACN (10 mL) was added 1-(bromomethyl)-2,4-difluorobenzene (1.0 g, 4.83 mmol, 1.0 equiv; CAS RN 23915-07-3) under Ar. The reaction mixture was stirred at 80° C. for 3 h and then allowed to cool to RT. TBME (100 mL) was added and the suspension stirred at RT for 30 min. The solid was filtered off, washed with TBME and the solid dried. The title compound was obtained as a white solid (2.02 g, 98%). MS (ESI): m/z=439.2 [M+H]$^+$.

Step 2: Tert-Butyl 6-[(2,4-difluorophenyl)methylene]-2-azaspiro[3.3]heptane-2-carboxylate To a solution of (2,4-difluorobenzyl)triphenylphosphonium bromide (1.7 g, 3.62 mmol, 1.0 equiv) in dry THF (10 mL) was added LiH-MDS (7.24 mL, 7.24 mmol, 2.0 equiv; 1 M in THF) at −78° C. under Ar and the reaction mixture was stirred for 2 h. Then at rt, tert-butyl 6-oxo-2-azaspiro[3.3]heptane-2-carboxylate (1.53 g, 7.24 mmol, 2.0 equiv; CAS RN 1181816-12-5) was added and the reaction mixture stirred at 85° C. overnight. TBME was added and the precipitate (triphenylphosphine oxide) filtered off. The filtrate was concentrated and purified by silica gel chromatography using a MPLC system eluting with a gradient of n-heptane:ethyl acetate (100:0 to 70:30) to yield the title compound as a white solid (0.35 g, 30%). MS (ESI): m/z=266.2 [M+2H-tBu]$^+$.

Step 3: Tert-Butyl 6-[(2,4-difluorophenyl)methyl]-2-azaspiro[3.3]heptane-2-carboxylate To a solution of tert-butyl 6-[(2,4-difluorophenyl)methylene]-2-azaspiro[3.3]heptane-2-carboxylate (0.35 g, 1.09 mmol, 1.0 equiv) in ethyl acetate (10 mL) was added Pd/C (116 mg, 0.11 mmol, 0.1 equiv; wt. 10%) and the reaction mixture was stirred under an atmosphere of H$_2$ (1 bar) at RT for 2 h. The suspension was filtered through a Celite pad, washed with ethyl acetate and dried under vacuum. The title compound was obtained as a white solid (0.35 g, 98%). MS (ESI): m/z=268.2 [M+2H-tBu]$^+$.

Step 4: 6-[(2,4-Difluorophenyl)methyl]-2-azaspiro [3.3]heptane: 2,2,2-trifluoroacetic Acid To a solution of tert-butyl 6-[(2,4-difluorophenyl)methyl]-2-azaspiro[3.3]heptane-2-carboxylate (55 mg, 170 μmol, 1.0 equiv) in DCM (3 mL) was added TFA (78 mg, 52 μl, 680 μmol, 4.0 equiv). The resultant reaction mixture was stirred at RT for 2 h and was then concentrated in vacuo (azeotrop with toluene). The title compound was obtained as a colorless oil and used in the next step without further purification (58 mg, quant). MS (ESI): m/z=224.2 [M+H]$^+$.

BB 13

5-(Azetidin-3-yl)-2-(2-chlorophenoxy)pyridine; 4-methylbenzenesulfonic Acid

Step 1: Tert-Butyl 3-(6-(2-chlorophenoxy)pyridin-3-yl)azetidine-1-carboxylate

The title compound was obtained in analogy to BB 4/Step 1 starting from 5-bromo-2-(2-chlorophenoxy)pyridine (722 mg, 2.54 mmol, 1.0 equiv; CAS RN 1240670-82-9) and tert-butyl 3-bromoazetidine-1-carboxylate (599 mg, 2.54 mmol, 1.0 equiv; CAS RN 1064194-10-0) by irradiating (420 nm) for 2 h as a yellow oil (0.44 g, 48%). MS (ESI): m/z=361.2 [M+H]$^+$.

Step 2: 5-(Azetidin-3-yl)-2-(2-chlorophenoxy)pyridine; 4-methylbenzenesulfonic Acid To a solution of tert-butyl 3-(6-(2-chlorophenoxy)pyridin-3-yl)azetidine-1-carboxylate (436 mg, 1.21 mmol, 1.0 equiv) in ethyl acetate (6 mL) was added 4-methylbenzenesulfonic acid hydrate (237 mg, 1.24 mmol, 1.03 equiv) and the reaction mixture was heated at reflux for 18 h. The suspension was cooled in the fridge at 0° C. for 1 h and filtered. The precipitate was washed with diethylether and dried to yield the title compound as a white solid (470 mg, 89%). MS (ESI): m/z=261.1 [M+H]$^+$.

BB 14

6-(2-Chloro-4-fluoro-phenoxy)-2-azaspiro[3.3]heptane

Step 1: Tert-Butyl 6-(2-chloro-4-fluoro-phenoxy)-2-azaspiro[3.3]heptane-2-carboxylate To a solution of 2-chloro-4-fluorophenol (756 mg, 0.56 mL, 5.16 mmol, 1.1 equiv; CAS RN 1996-41-4), tert-butyl 6-hydroxy-2-azaspiro[3.3]heptane-2-carboxylate (1.0 g, 4.69 mmol, 1.0 equiv; CAS RN 1147557-97-8) and triphenylphosphine (1.48 g, 5.63 mmol, 1.2 equiv) in THF (23.4 mL) was added DIAD (1.09 mL, 5.63 mmol, 1.2 equiv; CAS N 2446-83-5) dropwise at 0° C. and the reaction was stirred at RT for 18 h. Another batch of triphenylphosphine (738 mg, 2.81 mmol, 0.6 equiv), followed by DIAD (0.55 mL, 2.81 mmol, 0.6 equiv) were added and the reaction was stirred at RT for 6 h. The reaction mixture was poured into sat. aqueous NaHCO$_3$ solution (50 mL) and ethyl acetate (30 mL) was added. The phases were separated and the aqueous phase was extracted with ethyl acetate (3×50 mL). The combined organic layers were washed with a sat. aqueous NaCl solution, dried over Na$_2$SO$_4$, filtered and concentrated. The crude orange oil was immobilized on Isolute and purified by silica gel chromatography using a MPLC system eluting with a gradient of n-heptane:ethyl acetate (100:0 to 70:30) to yield the title compound as a yellow solid (1.50 g, 89%). MS (ESI): m/z=286.2 [M+2H-tBu]$^+$.

Step 2: 6-(2-Chloro-4-fluoro-phenoxy)-2-azaspiro[3.3]heptane

To a solution of tert-butyl 6-(2-chloro-4-fluoro-phenoxy)-2-azaspiro[3.3]heptane-2-carboxylate (605 mg, 1.77 mmol, 1.0 equiv) in DCM (7 mL) was added TFA (1.36 mL, 17.7 mmol, 10.0 equiv) and the reaction mixture was stirred at RT for 1 h. Volatiles were removed in vacuo, the crude material dissolved in sat. aqueous Na$_2$CO$_3$ solution (50 mL) and extracted with ethyl acetate (3×50 mL). The combined organic phases were dried over Na$_2$SO$_4$ and evaporated to yield the title compound as a light brown oil (352 mg, 66%). MS (ESI): m/z=242.2 [M+H]$^+$.

BB 15

3-[4-(4-Fluorophenoxy)phenyl]azetidine; 4-methylbenzenesulfonic Acid

Step 1: Tert-Butyl 3-(4-hydroxyphenyl)azetidine-1-carboxylate

The title compound was obtained in analogy to BB 4/Step 1 starting from 4-bromophenol (3.66 g, 21.18 mmol, 1.0 equiv; CAS RN 106-41-2) and tert-butyl 3-bromoazetidine-1-carboxylate (5.0 g, 21.18 mmol, 1.0 equiv; CAS RN 1064194-10-0) by irradiating (420 nm) for 14 h as an off-white solid (3.20 g, 61%). MS (ESI): m/z=194.0 [M+2H-tBu]$^+$.

Step 2: Tert-Butyl 3-[4-(4-fluorophenoxy)phenyl]azetidine-1-carboxylate

To a dry tube was added tert-butyl 3-(4-hydroxyphenyl)azetidine-1-carboxylate (1.50 g, 6.02 mmol, 1.0 equiv), 4-fluoroiodobenzene (1.74 g, 7.82 mmol, 1.3 equiv; CAS RN 352-34-1), copper(I) iodide (229 mg, 1.2 mmol, 0.2 equiv), cesium carbonate (3.92 g, 12.03 mmol, 2.0 equiv) and dimethylaminoacetic acid (124 mg, 1.2 mmol, 0.2 equiv). Under an atmosphere of Ar, 1,4-dioxane (30 mL) was added and the reaction mixture was stirred at 90° C. for 48 h. The reaction mixture was filtered, the filtrate diluted with ethyl acetate (100 mL) and then washed with water and a sat. aqueous NaCl solution. The combined organic phases were dried over Na$_2$SO$_4$, filtered and concentrated. The crude reaction product was purified by reversed-phase flash column chromatography (0.05% v/v FA in water and MeCN) to give the title compound (1.44 g, 70%) as a colorless oil. MS (ESI): m/z=288.4 [M+2H-tBu]$^+$.

Step 3: 3-[4-(4-Fluorophenoxy)phenyl]azetidine; 4-methylbenzenesulfonic Acid To a solution of tert-butyl 3-(6-(2-chlorophenoxy)pyridin-3-yl)azetidine-1-carboxylate (1.60 g, 4.66 mmol, 1.0 equiv) in ethyl acetate (32 mL) was added 4-methylbenzenesulfonic acid hydrate (963 mg, 5.59 mmol, 1.2 equiv) and the reaction mixture was heated at reflux for 12 h. The suspension was cooled in the fridge at 0° C. for 1 h and filtered. The precipitate was washed with ethyl acetate and dried to yield the title compound as an off-white solid (1.74 g, 89%). MS (ESI): m/z=244.5 [M+H]$^+$.

BB 16

5-(Azetidin-3-yl)-2-[4-(trifluoromethoxy)phenoxy]pyridine; 4-methylbenzenesulfonic Acid

Step 1: Tert-Butyl 3-[4-[3-(2,2,2-trifluoroethoxy)azetidin-1-yl]phenyl]azetidine-1-carboxylate The title compound was obtained in analogy to BB 4/Step 1 starting from 5-bromo-2-(4-(trifluoromethoxy)phenoxy)pyridine (1.28 g, 3.83 mmol, 1.0 equiv; CAS RN 909849-01-0) and tert-butyl 3-bromoazetidine-1-carboxylate (0.91 g, 3.83 mmol, 1.0 equiv; CAS RN 1064194-10-0) by irradiating (420 nm) for 2 h as a light yellow waxy solid (0.64 g, 35%). MS (ESI): m/z=411.2 [M+H]$^+$.

Step 2: 5-(Azetidin-3-yl)-2-[4-(trifluoromethoxy)phenoxy]pyridine; 4-methylbenzenesulfonic Acid To a solution of tert-butyl 3-[4-[3-(2,2,2-trifluoroethoxy)azetidin-1-yl]phenyl]azetidine-1-carboxylate (638 mg, 1.55 mmol, 1.0 equiv) in ethyl acetate (7 mL) was added 4-methylbenzenesulfonic acid hydrate (296 mg, 1.55 mmol, 1.0 equiv) and the reaction mixture was heated at reflux overnight. The reaction mixture was cooled to RT, diluted with diethylether (3 mL), stirred for 1 h and filtered to get the title compound as an off-white solid (0.12 g, 72%). MS (ESI): m/z=311.1 [M+H]$^+$.

BB 17

6-[6-(Trifluoromethyl)pyrazin-2-yl]oxy-2-azaspiro[3.3]heptane

Step 1: Tert-Butyl 6-[6-(trifluoromethyl)pyrazin-2-yl]oxy-2-azaspiro[3.3]heptane-2-carboxylate To a solution of tert-butyl 6-hydroxy-2-azaspiro[3.3]heptane-2-carboxylate (350 mg, 1.64 mmol, 1.0 equiv; CAS RN 1147557-97-8) in dry DMF (5 mL) under Ar was added sodium hydride (43.3 mg, 1.81 mmol, 1.1 equiv; 55% in mineral oil) and the reaction mixture was stirred at RT for 30 min, followed by addition of 2-chloro-6-(trifluoromethyl) pyrazine (38.3 mg, 0.210 mmol, 1.1 equiv; CAS RN 61655-69-4). The reaction mixture was then stirred at 90° C. for 18 h. The reaction mixture was cooled to RT, quenched by addition of water (0.2 mL), diluted with ethyl acetate (100 mL) and then washed with water and a sat. aqueous NaCl solution. The combined organic phases were dried over $Na_2SO_4$, filtered and concentrated. The crude reaction product was immobilized on Isolute and purified by silica gel chromatography using a MPLC system eluting with a gradient of n-heptane:ethyl acetate (100:0 to 40:60) to yield the title compound as a colorless oil (304 mg, 52%). MS (ESI): m/z=304.1 $[M+H]^+$.

Step 2: 6-[6-(Trifluoromethyl)pyrazin-2-yl]oxy-2-azaspiro[3.3]heptane

To a solution of tert-butyl 6-[6-(trifluoromethyl)pyrazin-2-yl]oxy-2-azaspiro[3.3]heptane-2-carboxylate (0.54 g, 1.6 mmol, 1.0 equiv) in ethyl acetate (7 mL) was added 4-methylbenzenesulfonic acid monohydrate (77.4 mg, 0.41 mmol, 0.3 equiv) and the reaction mixture was stirred at reflux for 18 h. After cooling down, the reaction mixture was passed through an aminophase column (Si—$NH_2$) washing with $CH_3CN$:MeOH (1:1) as long as the filtrate is basic (20 mL). The crude reaction product was immobilized on Isolute and purified by silica gel chromatography using a MPLC system eluting with a gradient of n-heptane:TBME/MeOH (4:1) (80:20 to 0:100) to yield the title compound as a colorless oil (127 mg, 54%). MS (ESI): m/z=260.1 $[M+H]^+$.

BB 18

3-[2-(3-Chlorophenyl)ethynyl]azetidine; Hydrochloride

Step 1: Tert-Butyl 3-[2-(3-chlorophenyl)ethynyl] azetidine-1-carboxylate

A solution of tert-butyl 3-ethynylazetidine-1-carboxylate (1.0 g, 5.52 mmol, 1.0 equiv; CAS RN 287193-01-5), 1-bromo-3-chlorobenzene (1.58 g, 8.28 mmol, 1.5 equiv; CAS RN 108-37-2), bis(triphenylphosphine)palladium(II) chloride (310 mg, 0.44 mmol, 0.08 equiv), copper(I) iodide (21 mg, 0.11 mmol, 0.02 equiv) and TEA (5.59 g, 7.69 mL, 55.2 mmol, 10.0 equiv) in THF (15 mL) was placed in a sealed tube under Ar and heated to 70° C. overnight. The reaction mixture mixture was diluted with ethyl acetate, filtered through Dicalite and evaporated. The crude reaction product was purified by silica gel chromatography using a MPLC system eluting with a gradient of n-heptane:ethyl acetate (100:0 to 40:60) to yield the title compound as an orange oil (1.08 g, 67%). MS (ESI): m/z=236.0 $[M+2H-tBu]^+$.

Step 2: 3-[2-(3-Chlorophenyl)ethynyl]azetidine; Hydrochloride

To a solution of tert-butyl 3-[2-(3-chlorophenyl)ethynyl] azetidine-1-carboxylate (52.7 mg, 0.18 mmol, 1.0 equiv) in 1,4-dioxane (0.5 mL) at 0° C. was added HCl (0.45 mL, 1.81 mmol, 10.0 equiv; 4 M sol. in 1,4-dioxane). The reaction was stirred at RT for 8 h. The crude reaction mixture was evaporated to dryness yielding the title compound as an off-white solid (34 mg, quant.). MS (ESI): m/z=192.1 $[M+H]^+$.

BB 19

5-(Azetidin-3-yl)-2-[3-(trifluoromethyl)pyrrolidin-1-yl]pyridine

Step 1: 5-Bromo-2-(3-(trifluoromethyl)pyrrolidin-1-yl)pyridine

To a solution of 5-bromo-2-fluoropyridine (1.06 g, 0.62 mL, 6.0 mmol, 1.0 equiv; CAS RN 766-11-0) and 3-(trifluoromethyl)pyrrolidine; hydrochloride (1.11 g, 6.3 mmol, 1.05 equiv; CAS RN 1189485-03-7) in DMF (12 mL) was added potassium carbonate (1.66 g, 12.0 mmol, 2.0 equiv) and the reaction mixture was stirred at 110° C. for 3 h. The reaction mixture was filtered, the filter cake washed with diethyl acetate and the filtrate evaporated. The crude reaction product was purified by silica gel chromatography using a MPLC system eluting with a gradient of n-heptane:ethyl acetate (100:0 to 50:50) to yield the title compound as a colorless oil (1.77 g, 25%). MS (ESI): m/z=295.0 $[M+H]^+$.

Step 2: Tert-Butyl 3-[6-[3-(trifluoromethyl)pyrrolidin-1-yl]-3-pyridyl]azetidine-1-carboxylate The title compound was obtained in analogy to BB 4/Step 1 starting from 5-bromo-2-(3-(trifluoromethyl)pyrrolidin-1-yl)pyridine (0.72 g, 2.44 mmol, 1.0 equiv) and tert-butyl 3-bromoazetidine-1-carboxylate (0.58 g, 2.44 mmol, 1.0 equiv; CAS RN 1064194-10-0) by irradiating (465 nm) for 20 h as a light yellow waxy solid (0.41 g, 45%). MS (ESI): m/z=372.2 $[M+H]^+$.

Step 3: 5-(Azetidin-3-yl)-2-[3-(trifluoromethyl)pyrrolidin-1-yl]pyridine

To a solution of tert-butyl 3-[6-[3-(trifluoromethyl)pyrrolidin-1-yl]-3-pyridyl]azetidine-1-carboxylate (408 mg, 1.11 mmol, 1.0 equiv) in ethyl acetate (7 mL) was added 4-methylbenzenesulfonic acid hydrate (422 mg, 2.22 mmol, 2.0 equiv) and the reaction mixture was stirred at reflux overnight. After cooling down, the reaction mixture was passed through an aminophase column (Si—$NH_2$) washing with $CH_3CN$:MeOH (1:1) as long as the filtrate is basic (50 mL). The solvent mixture was evaporated to get the desired product as a yellow waxy solid (318 mg, 94%). MS (ESI): m/z=272.1 $[M+H]^+$.

BB 20

2-Methyl-3-[(4R)-2-oxooxazolidin-4-yl]propanoic Acid

Step 1: Methyl 2-methyl-3-[(4R)-2-oxooxazolidin-4-yl]propanoate

A solution of methyl 3-[(4R)-2-oxooxazolidin-4-yl]propanoate (147 mg, 0.85 mmol, 1.0 equiv; BB 9/Step 2) in dry THF (1.5 mL) was cooled to −78° C. and LiHMDS (1.7 mL, 1.7 mmol, 2.0 equiv) was added dropwise. After stirring for 1 h at −78° C., MeI (181 mg, 80 μL, 1.27 mmol, 1.5 equiv) was added and stirring continued for an additional 2.5 h. The crude reaction mixture was quenched with sat. aqueous $NH_4Cl$ solution and extracted with ethyl acetate. The combined organic phases were dried over $Na_2SO_4$, filtered and concentrated. The crude reaction product was immobilized on Isolute and purified by silica gel chromatography using a MPLC system eluting with a gradient of n-heptane:ethyl acetate (100:0 to 0:100) to yield the title compound as a light brown oil (110 mg, 66%). MS (ESI): m/z=188.1 [M+H]+.

Step 2: 2-Methyl-3-[(4R)-2-oxooxazolidin-4-yl]propanoic Acid

The title compound was obtained in analogy to BB 8/Step 3 starting from methyl 2-methyl-3-[(4R)-2-oxooxazolidin-4-yl]propanoate (110 mg, 0.59 mmol, 1.0 equiv) as a white solid (67 mg, 66%). MS (ESI): m/z=174.0 [M+H]+.

BB 21

1-[4-(Azetidin-3-yl)phenyl]-3-(2,2,2-trifluoroethoxy)azetidine; 4-methylbenzenesulfonic Acid Step 1: Tert-Butyl 3-[4-[3-(2,2,2-trifluoroethoxy)azetidin-1-yl]phenyl]azetidine-1-carboxylate To a suspension of tert-butyl 3-(4-bromophenyl)azetidine-1-carboxylate (115 mg, 0.37 mmol, 1.0 equiv; BB 6/Step 1; CAS RN 1203681-52-0) and 3-(2,2,2-trifluoroethoxy)azetidine (57.1 mg, 0.37 mmol, 1.0 equiv; CAS RN 1333106-09-4) in tert-butanol (2.2 mL) under Ar were added X-PHOS (15.8 mg, 33.2 µmol, 0.09 equiv; CAS RN 564483-18-7), tris(dibenzylideneacetone)dipalladium (0) chloroform adduct (11.4 mg, 11.1 µmol, 0.03 equiv; CAS RN 52522-40-4) and cesium carbonate (480 mg, 1.47 mmol, 4.0 equiv) and the reaction mixture was heated by microwave irradiation to 90° C. for 30 min. The reaction mixture was filtered, the filtrate treated with silica gel and concentrated. The compound was purified by silica gel chromatography using a MPLC system eluting with a gradient of n-heptane:ethyl acetate (100:0 to 50:50) to get the title compound as a light yellow oil (74 mg, 48%). MS (ESI): m/z=387.2 [M+H]+.

Step 2: 1-[4-(Azetidin-3-yl)phenyl]-3-(2,2,2-trifluoroethoxy)azetidine 4-methylbenzenesulfonic Acid To a solution of tert-butyl 3-[4-[3-(2,2,2-trifluoroethoxy)azetidin-1-yl]phenyl]azetidine-1-carboxylate (0.67 g, 1.73 mmol, 1.0 equiv) in ethyl acetate (5 mL) was added 4-methylbenzenesulfonic acid hydrate (0.47 g, 2.48 mmol, 1.4 equiv) and the reaction mixture was heated at reflux overnight. The reaction mixture was cooled to RT, filtered and the precipitate washed with ethyl acetate to afford the title compound as a grey solid (0.28 g, 25%). MS (ESI): m/z=287.2 [M+H]+.

BB 22

3-[[2-Fluoro-4-(trifluoromethyl)phenyl]methoxy]azetidine; 2,2,2-trifluoroacetic Acid To a solution of tert-butyl 3-[[2-fluoro-4-(trifluoromethyl)phenyl]methoxy]azetidine-1-carboxylate (80.0 mg, 0.23 mmol, 1.0 equiv; BB 2/Step 1) in DCM (1 mL) was added TFA (0.2 mL, 0.23 mmol, 1.0 equiv) and the reaction mixture was stirred at RT for 12 h. The reaction mixture was concentrated to provide the title compound as a light yellow oil (80 mg, 96%). MS (ESI): m/z=250.4 [M+H]+.

BB 23

3-(6-Oxo-1H-pyridin-2-yl)propanoic Acid

Step 1: Ethyl (E)-3-(6-oxo-1H-pyridin-2-yl)prop-2-enoate

To a solution of 6-bromo-1H-pyridin-2-one (0.50 g, 2.87 mmol, 1.0 equiv; CAS RN 27992-32-1) in DMF (16 mL), BINAP (0.537 g, 0.860 mmol, 0.3 equiv), ethyl acrylate (1.15 g, 11.49 mmol, 4.0 equiv; CAS RN 140-88-5), DIPEA (1.49 g, 2.0 mL, 11.49 mmol, 4.0 equiv) and Pd(OAc)$_2$ (96.8 mg, 0.43 mmol, 0.15 equiv) were added. The reaction mixture was heated under an atmosphere of N$_2$ at 100° C. for 12 h. The reaction mixture was diluted with water (50 mL) and extracted with ethyl acetate (3×30 mL). The combined organic layers were dried over Na$_2$SO$_4$, filtered and concentrated. The crude compound was purified by reversed-phase flash column chromatography (0.05% v/v FA in water and MeCN) to give the desired product (containing a regio-isomer) as a dark green oil (300 mg, 54%). MS (ESI): m/z=194.1 [M+H]+.

Step 2: Ethyl 3-(6-oxo-1H-pyridin-2-yl)propanoate

To a solution of ethyl (E)-3-(6-oxo-1H-pyridin-2-yl)prop-2-enoate (250 mg, 1.29 mmol, 1.0 equiv) in ethyl acetate (7.5 mL) was added wet Pd/C (100 mg, 1.72 mmol, 1.33 equiv; wt. 10%) and the suspension was stirred at RT for 12 h under an atmosphere of H$_2$ (balloon). The reaction mixture was filtered, the filtrate evaporated and the residue was purified by reversed-phase flash column chromatography (0.05% v/v FA in water and MeCN) to give the desired product (containing a regio-isomer) as a light brown oil (100 mg, 40%). MS (ESI): m/z=196.7 [M+H]+.

Step 3: 3-(6-Oxo-1H-Pyridin-2-yl)propanoic Acid

To a solution of ethyl 3-(6-oxo-1H-pyridin-2-yl)propanoate (100 mg, 0.51 mmol, 1.0 equiv) in THF (2 mL) was added a solution of sodium hydroxide (41 mg, 1.02 mmol, 2.0 equiv) in water (2 mL) and the reaction mixture was stirred at RT for 12 h. The reaction mixture was concentrated and the pH was adjusted to pH=3~4 with aqueous HCl (1 M). The reaction mixture was concentrated to give the crude product (containing a regio-isomer) as a light brown oil (85 mg, quant.) which was used in the next step without further purification. MS (ESI): m/z=168.7 [M+H]+.

BB 24

3-(6-Oxo-2-piperidyl)propanoic Acid

Step 1: Ethyl 3-(6-oxo-2-piperidyl)propanoate

To a solution of ethyl (E)-3-(6-oxo-1H-pyridin-2-yl)prop-2-enoate (200 mg, 1.04 mmol, 1.0 equiv; BB 23/Step 1) in ethyl acetate (10 mL) was added wet Pd/C (100 mg, 1.38 mmol, 1.33 equiv; wt. 10%) and the suspension was stirred at RT for 12 h under an atmosphere of H$_2$ (balloon). The reaction mixture was filtered, the filtrate evaporated and the residue was purified by reversed-phase flash column chromatography (0.05% v/v FA in water and MeCN) to give the desired product as a dark brown oil (150 mg, 73%). MS (ESI): m/z=200.5 [M+H]+.

Step 2: 3-(6-Oxo-2-piperidyl)propanoic Acid

To a solution of ethyl 3-(6-oxo-2-piperidyl)propanoate (130 mg, 0.65 mmol, 1.0 equiv) in THF (2.6 mL) was added a solution of sodium hydroxide (52.2 mg, 1.3 mmol, 2.0 equiv) in water (2.6 mL) and the reaction mixture was stirred at RT for 12 h. The reaction mixture was concentrated and the pH was adjusted to pH=3~4 with aqueous HCl (3 M). The reaction mixture was concentrated to give the crude product as a light brown oil (110 mg, quant.) which was used in the next step without further purification.

BB 25

3-(5-Oxomorpholin-3-yl)propanoic Acid

Step 1: Methyl 3-hydroxy-2-[(4-methoxyphenyl)methylamino]propanoate

D-serine methyl ester hydrochloride (5.0 g, 32.1 mmol, 1.0 equiv; CAS RN 2788-84-3) was suspended in DCM (50 mL) and cooled to 0° C. TEA (4.7 mL, 33.7 mmol, 1.05 equiv) was added dropwise, followed by p-anisaldehyde (3.41 g, 3.9 mL, 32.1 mmol, 1.0 equiv; CAS RN 123-11-5). The reaction mixture was then warmed up and stirred at RT for 12 h. The reaction mixture was concentrated and the residue dissolved in MeOH (80 mL). NaBH$_4$ (1.82 g, 48.2 mmol, 1.5 equiv) was added in small portions over 30 min at 0° C. and the resulting mixture stirred at RT for 4 h. The reaction was quenched with sat. aqueous NH$_4$Cl solution (10 mL), diluted with water (200 mL) and extracted with ethyl acetate (3×80 mL). The combined organic layers were washed with a sat. aqueous NaCl solution, dried over Na$_2$SO$_4$, filtered and the filtrate was concentrated to furnish the desired product as a colorless oil (7.6 g, 99%). MS (ESI): m/z=262.4 [M+Na]$^+$.

Step 2: Methyl 2-[(2-chloroacetyl-[(4-methoxyphenyl)methyl]amino]-3-hydroxy-propanoate To a solution of methyl 3-hydroxy-2-[(4-methoxyphenyl)methylamino]propanoate (5.6 g, 23.4 mmol, 1.0 equiv) and TEA (4.74 g, 6.52 mL, 46.8 mmol, 2.0 equiv) in DCM (100 mL) was added chloroacetyl chloride (3172 mg, 28.1 mmol, 1.2 equiv) at 0° C. and the reaction mixture was stirred at RT for 12 h. The reaction mixture was washed with sat. aqueous Na$_2$CO$_3$ solution followed by a sat. aqueous NaCl solution and the organic phase was dried over Na$_2$SO$_4$ and concentrated. The residue was purified by silica gel column chromatography (petroleum ether:ethyl acetate=3:1) to give the desired product as a light brown oil (3.70 g, 50%). MS (ESI): m/z=338.3 [M+Na]$^+$.

Step 3: 4-[(4-Methoxyphenyl)methyl]-5-oxo-morpholine-3-carboxylic Acid

To a solution of methyl 2-[(2-chloroacetyl)-[(4-methoxyphenyl)methyl]amino]-3-hydroxy-propanoate (3.0 g, 9.5 mmol, 1.0 equiv) in tert-butanol (120 mL) was added potassium tert-butoxide (2.67 g, 14.25 mmol, 1.5 equiv) and the reaction mixture was heated at 90° C. for 3 h. The reaction mixture was filtered and the precipitate purified by reversed-phase flash column chromatography (0.1% v/v FA in water and MeCN) to yield the desired product as a light yellow oil (1.10 g, 44%). MS (ESI): m/z=288.3 [M+Na]$^+$.

Step 4: Benzyl 3-[4-[(4-methoxyphenyl)methyl]-5-oxo-morpholin-3-yl]propanoate

An oven-dried vial equipped with magnetic stirring bar was charged with 4-[(4-methoxyphenyl)methyl]-5-oxo-morpholine-3-carboxylic acid (1.10 g, 4.15 mmol, 1.0 equiv), benzyl acrylate (672.6 mg, 4.15 mmol, 1.0 equiv), bis[3,5-difluoro-2-[5-(trifluoromethyl)-2-pyridyl]phenyl]iridium (1+) 4-tert-butyl-2-(4-tert-butyl-2-pyridyl)pyridine hexafluorophosphate (46.5 mg, 40 µmol, 0.01 equiv; Ir[dF(CF$_3$)ppy]$_2$(dtbbpy))PF$_6$; CAS RN 870987-63-6) and K$_2$HPO$_4$ (866.8 mg, 4.98 mmol, 1.2 equiv) in DMF (25 mL). The reaction mixture was degassed with Ar and then irradiated with two 34 W blue LED lamps (at a distance of approximately 7 cm from the light source to avoid warming of the reaction mixture). The reaction mixture was filtered, the filtrate diluted with ethyl acetate (50 mL), washed with water and a sat. aqueous NaCl solution, the combined organic phases dried over Na$_2$SO$_4$ and then concentrated. The residue was purified by silica gel column chromatography (petroleum ether:ethyl acetate=5:1) to give the desired product as a light yellow oil (430 mg, 27%). MS (ESI): m/z=384.1 [M+H]$^+$.

Step 5: Benzyl 3-(5-oxomorpholin-3-yl)propanoate

To a solution of benzyl 3-[4-[(4-methoxyphenyl)methyl]-5-oxo-morpholin-3-yl]propanoate (400 mg, 1.04 mmol, 1.0 equiv) in a mixture of ACN:water (1:1, 26 mL) was added ammonium cerium(IV) nitrate (2.86 g, 5.22 mmol, 5.0 equiv) at 0° C. and the reaction mixture stirred at 0° C. for 2 h. DIPEA was added at 0° C. to adjust the pH to 6~7, the suspension filtered, the filtrate diluted with water (50 mL) and extracted with ethyl acetate (3×50 mL). The combined organic layers were washed with a sat. aqueous NaCl solution, dried over Na$_2$SO$_4$ and concentrated. The residue was purified by reversed-phase flash column chromatography (0.1% v/v FA in water and MeCN) to yield the desired product as an off-white solid (83 mg, 30%). MS (ESI): m/z=264.4 [M+H]$^+$.

Step 6: 3-(5-Oxomorpholin-3-yl)propanoic Acid

To a solution of benzyl 3-(5-oxomorpholin-3-yl)propanoate (80 mg, 0.30 mmol, 1.0 equiv) in ethyl acetate (4 mL) was added wet Pd/C (20 mg, 0.34 mmol, 1.15 equiv; wt. 10%) and the suspension was stirred at RT for 3 h under an atmosphere of H$_2$ (balloon). The reaction mixture was filtered and the filtrate concentrated to give the crude product as a light yellow oil which was used in the subsequent step without further purification (50 mg, 95%). MS (ESI): m/z=174.1 [M+H]$^+$.

BB 26

3-[2-[2-(Difluoromethyl)phenyl]ethynyl]azetidine; Hydrochloride

Step 1: Tert-Butyl 3-((2-(difluoromethyl)phenyl)ethynyl)azetidine-1-carboxylate

To a solution of tert-butyl 3-ethynylazetidine-1-carboxylate (100 mg, 0.55 mmol, 1.0 equiv; CAS RN 287193-01-5) in THF (1.8 ml) were added 1-bromo-2-(difluoromethyl)benzene (114 mg, 0.55 mmol, 1.0 equiv; CAS RN 845866-82-2) and TEA (558 mg, 0.77 mL, 5.52 mmol, 10.0 equiv) and the reaction mixture was degassed with Ar. Then, bis(triphenylphosphine)palladium(II) chloride (31 mg, 0.044 mmol, 0.08 equiv) was added followed by copper(I) iodide (2.1 mg, 11 µmol, 0.02 equiv) and the reaction mixture was heated under Ar to 70° C. overnight. The crude reaction product was purified by silica gel chromatography using a MPLC system eluting with a gradient of n-heptane:ethyl acetate (100:0 to 40:60) to yield the title compound as a yellow oil (45 mg, 27%). MS (ESI): m/z=252.2 [M+2H-tBu]$^+$.

Step 2: 3-[2-[2-(Difluoromethyl)phenyl]ethynyl]azetidine; Hydrochloride

To a solution of tert-butyl 3-((2-(difluoromethyl)phenyl)ethynyl)azetidine-1-carboxylate (45 mg, 0.15 mmol, 1.0 equiv) in 1,4-dioxane (0.5 mL) at 0° C. was added HCl (0.37 mL, 1.46 mmol, 10.0 equiv; 4 M sol. in 1,4-dioxane). The reaction was stirred at RT for 8 h. The crude reaction mixture was evaporated to dryness, the precipitate triturated in diisopropylether and the solid material further dried in vacuo to yield the title compound as an off-white solid (20 mg, 56%). MS (ESI): m/z=208.2 [M+H]$^+$.

BB 27

3-[4-(2-Chloro-4-methylsulfonyl-phenyl)phenyl]azetidine; 4-methylbenzenesulfonic Acid

Step 1: Tert-Butyl 3-[4-(2-chloro-4-methylsulfonyl-phenyl)phenyl]azetidine-1-carboxylate To a suspension of 2-(2-chloro-4-methylsulfonyl-phenyl)-4,4,5,5-tetramethyl-1,3,2-dioxaborolane (304 mg, 0.96 mmol, 1.0 equiv; CAS RN 2377012-74-1) and tert-butyl 3-(4-bromophenyl)azetidine-1-carboxylate (300 mg, 0.96 mmol, 1.0 equiv; BB 6/Step 1; CAS RN 1203681-52-0) in a mixture of THF (3.75 mL) and water (0.38 mL) under Ar were added tetrakis(triphenylphosphine)palladium(0) (5.6 mg, 5 µmol, 0.005 equiv; CAS RN 14221-01-3) and potassium carbonate (664 mg, 4.8 mmol, 5.0 equiv) and the reaction mixture was heated by microwave irradiation to 110° C. for 30 min. The reaction mixture was filtered, the filtrate diluted with ethyl acetate (50 mL), washed with water and a sat. aqueous NaCl solution, the combined organic phases dried over MgSO$_4$ and then concentrated. The crude compound was purified by silica gel chromatography using a MPLC system eluting with a gradient of n-heptane:ethyl acetate (100:0 to 50:50) to get the title compound as a light brown oil (346 mg, 77%). MS (ESI): m/z=366.1 [M+2H-tBu]$^+$.

Step 2: 3-[4-(2-Chloro-4-methylsulfonyl-phenyl)phenyl]azetidine: 4-methylbenzenesulfonic Acid To a solution of tert-butyl 3-[4-(2-chloro-4-methylsulfonyl-phenyl)phenyl]azetidine-1-carboxylate (384 mg, 0.82 mmol, 1.0 equiv) in ethyl acetate (2.5 mL) was added 4-methylbenzenesulfonic acid hydrate (195 mg, 1.0 mmol, 1.25 equiv) and the reaction mixture was heated at reflux for 30 min. The reaction mixture was cooled to RT, filtered and the precipitate washed with ethyl acetate to afford the title compound as a colorless solid (300 mg, 70%). MS (ESI): m/z=322.1 [M+H]$^+$.

BB 28

2-Methyl-4-(1H-triazol-5-yl)butanoic Acid Hydrochloride

Step 1: Methyl 4-[1-(2,2-dimethylpropanoyloxymethyl)triazol-4-yl]-2-methyl-butanoate To a solution of copper(II) sulfate pentahydrate (50 mg, 0.20 mmol, 0.1 equiv) in a mixture of tert-butanol (5 mL) and water (5 mL) was added methyl 2-methylhex-5-ynoate (350 mg, 2.0 mmol, 1.0 equiv; CAS RN 1622092-88-9) and azidomethyl 2,2-dimethylpropanoate (314 mg, 2.0 mmol, 1.0 equiv; CAS RN 872700-68-0). The solution was degassed (Ar) and sodium ascorbate (237 mg, 1.2 mmol, 0.6 equiv) was added. The obtained solution was stirred at RT under an atmosphere of Ar for 18 h. The reaction mixture was concentrated, poured into water (20 mL) and extracted with ethyl acetate (3×50 mL). The organic layers were combined, washed with a sat. aqueous NaCl solution (20 mL), dried over Na$_2$SO$_4$ and concentrated in vacuo to obtain the title compound (550 mg, 79%) as a yellow oil. The crude product was used to the next step without further purification. MS (ESI): m/z=298.0 [M+H]$^+$.

Step 2: 2-Methyl-4-(1H-triazol-5-yl)butanoic Acid Hydrochloride

To a solution of methyl 4-[1-(2,2-dimethylpropanoyloxymethyl)triazol-4-yl]-2-methyl-butanoate (500 mg, 1.43 mmol, 1.0 equiv) in MeOH (10 mL) was added a a solution of sodium hydroxide (5 mL, 5.0 mmol, 3.5 equiv; 1 M) and the reaction mixture was stirred at RT overnight. The crude reaction mixture was evaporated to dryness, water was added (5 mL) and the solution acidified to pH 2 by addition of an aqueous solution of HCl (2 M). The resulting solution was evaporated in vacuo and the residue was stirred with THF (30 mL) for 10 min. The obtained precipitate (NaCl) was filtered off and the filtrate concentrated to obtain the title compound as a light yellow viscous oil (230 mg, 67%). MS (ESI): m/z=170.2 [M+H]$^+$.

BB 29

3-Hydroxy-4-(1H-triazol-5-yl)butanoic Acid Hydrochloride

Step 1: [4-(4-Ethoxy-2-hydroxy-4-oxo-butyl)triazol-1-yl]methyl 2,2-dimethylpropanoate The title compound was obtained in analogy to BB 28/Step 1 starting from ethyl 3-hydroxyhex-5-ynoate (300 mg, 1.92 mmol, 1.0 equiv; CAS RN 1807969-29-4) and azidomethyl 2,2-dimethylpropanoate (301.9 mg, 1.92 mmol, 1.0 equiv; CAS RN 872700-68-0) as a light brown oil (420 mg, 70%). MS (ESI): m/z=314.2 [M+H]$^+$.

Step 2: 3-Hydroxy-4-(1H-triazol-5-yl)butanoic Acid Hydrochloride

The title compound was obtained in analogy to BB 28/Step 2 starting from [4-(4-ethoxy-2-hydroxy-4-oxo-butyl)triazol-1-yl]methyl 2,2-dimethylpropanoate (420 mg, 1.34 mmol, 1.0 equiv) as a light brown oil (200 mg, 74%). MS (ESI): m/z=172.0 [M+H]$^+$.

BB 30

2-Fluoro-4-(1H-triazol-5-yl)butanoic Acid Hydrochloride

Step 1: Diethyl 2-but-3-ynyl-2-fluoro-propanedioate

To a solution of diethyl 2-fluoropropanedioate (2.0 g, 11.23 mmol, 1.0 equiv; CAS RN 685-88-1) in acetone (60 mL) were added 4-bromo-1-butyne (5.97 g, 44.9 mmol, 4.0 equiv; CAS RN 38771-21-0) and cesium carbonate (7.32 g, 22.5 mmol, 2.0 equiv) and the reaction mixture was heated to reflux for 72 h. The reaction mixture was quenched by addition of sat. aqueous NH$_4$Cl (50 mL) and extracted with methyl tert-butyl ether (3×100 mL). The combined organic phases were dried over Na$_2$SO$_4$ and the solvent was removed under reduced pressure to obtain the title compound as light brown liquid (1.9 g, 65%).

Step 2: Diethyl 2-[2-[1-(2,2-dimethylpropanoyloxymethyl)triazol-4-yl]ethyl]-2-fluoro-propanedioate The title compounds was obtained in analogy to BB 28/Step 1 starting from diethyl 2-but-3-ynyl-2-fluoro-propanedioate (1.0 g, 4.34 mmol, 1.0 equiv) and azidomethyl 2,2-dimethylpropanoate (0.68 g, 4.34 mmol, 1.0 equiv; CAS RN 872700-68-0) as a light brown oil (1.1 g, 65%). MS (ESI): m/z=388.2 [M+H]$^+$.

Step 3: [4-(4-Ethoxy-3-fluoro-4-oxo-butyl)triazol-1-yl]methyl 2,2-dimethylpropanoate A solution of diethyl 2-[2-[1-(2,2-dimethylpropanoyloxymethyl)triazol-4-yl]ethyl]-2-fluoro-propanedioate (600 mg, 1.55 mmol, 1.0 equiv) in DMSO (6 mL) was added to a solution of lithium chloride (131.3 mg, 3.1 mmol, 2.0 equiv) in water (0.11 mL) and the reaction mixture was stirred at 170° C. for 148 h. The reaction was cooled to rt, water (50 mL) was added and the reaction mixture extracted with ethyl acetate (3×30 mL). The combined organic phase was dried over Na$_2$SO$_4$ and the solvent was removed in vacuo. The crude product was purified by preparative HPLC (SunFire (100 mm×19 mm, 5 μm); water and MeCN) to give the title compound as a light brown oil (180 mg, 37%). MS (ESI): m/z=316.0 [M+H]$^+$.

Step 4: 2-Fluoro-4-(1H-triazol-5-yl)butanoic Acid Hydrochloride

The title compound was obtained in analogy to BB 28/Step 2 starting from [4-(4-ethoxy-3-fluoro-4-oxo-butyl)triazol-1-yl]methyl 2,2-dimethylpropanoate (180 mg, 0.57 mmol, 1.0 equiv) and replacing solvent MeOH by EtOH as a white solid (90 mg, 74%). MS (ESI): m/z=174.2 [M+H]$^+$.

BB 31

4-(Azetidin-3-yl)-N-methyl-N-phenyl-aniline

Step 1: Tert-Butyl 3-[4-(N-methylanilino)phenyl]azetidine-1-carboxylate

The title compound was obtained in analogy to BB 4/Step 1 starting from 4-bromo-N-methyl-N-phenyl-aniline (250 mg, 0.95 mmol, 1.0 equiv; CAS RN 336190-16-0) and tert-butyl 3-bromoazetidine-1-carboxylate (225 mg, 0.95 mmol, 1.0 equiv; CAS RN 1064194-10-0) by irradiating (420 nm) for 16 h as a yellow oil (118 mg, 35%). MS (ESI): m/z=339.2 [M+H)].

Step 2: 4-(Azetidin-3-yl)-N-methyl-N-phenyl-aniline

To a solution of tert-butyl 3-[4-(N-methylanilino)phenyl]azetidine-1-carboxylate (118 mg, 0.35 mmol, 1.0 equiv) in 1,4-dioxane (1.3 mL) was added 4-methylbenzenesulfonic acid hydrate (200 mg, 1.1 mmol, 3.0 equiv) and the reaction mixture was heated to 80° C. for 4 h. The reaction mixture was concentrated in vacuo and the crude material purified by flash chromatography using an amine phase eluting with a gradient of ACN:MeOH (100:0 to 80:20) to give the title compound as a light yellow oil (80 mg, 87%). MS (ESI): m/z=239.1 [M+H]$^+$.

BB 32

2-(Azetidin-3-yl)-5-tert-butyl-pyridine; 4-methylbenzenesulfonic Acid

Step 1: Tert-Butyl 3-(5-tert-butyl-2-pyridyl)azetidine-1-carboxylate

The title compound was obtained in analogy to BB 4/Step 1 starting from 2-bromo-5-tert-butyl-pyridine (535 mg, 2.5 mmol, 1.0 equiv; CAS RN 1142197-19-0) and tert-butyl 3-bromoazetidine-1-carboxylate (590 mg, 2.5 mmol, 1.0 equiv; CAS RN 1064194-10-0) by irradiating (420 nm) for 16 h as a yellow oil (88 mg, 11%). MS (ESI): m/z=235.2 [M+2H-tBu]$^+$.

Step 2: 2-(Azetidin-3-yl)-5-tert-butyl-pyridine; 4-methylbenzenesulfonic Acid

The title compound was obtained in analogy to BB 4/Step 2 starting from tert-butyl 3-(5-tert-butyl-2-pyridyl)azetidine-1-carboxylate (88 mg, 0.28 mmol, 1.0 equiv) as a colorless solid (136 mg, 87%). MS (ESI): m/z=191.2 [M+H]$^+$.

BB 33

3-[4-(Benzenesulfonyl)phenyl]azetidine; 4-methylbenzenesulfonic Acid

Step 1: Tert-Butyl 3-[4-(benzenesulfonyl)phenyl]azetidine-1-carboxylate

The title compound was obtained in analogy to BB 4/Step 1 starting from 1-(benzenesulfonyl)-4-bromo-benzene (500 mg, 1.68 mmol, 1.0 equiv; CAS RN 23038-36-0) and tert-butyl 3-bromoazetidine-1-carboxylate (397 mg, 1.68 mmol, 1.0 equiv; CAS RN 1064194-10-0) by irradiating (420 nm) for 16 h as a colorless solid (292 mg, 42%). MS (ESI): m/z=318.1 [M+2H-tBu]$^+$.

Step 2: 3-[4-(Benzenesulfonyl)phenyl]azetidine; 4-methylbenzenesulfonic Acid

The title compound was obtained in analogy to BB 4/Step 2 starting from tert-butyl 3-[4-(benzenesulfonyl)phenyl]azetidine-1-carboxylate (110 mg, 0.27 mmol, 1.0 equiv) as a colorless solid (110 mg, 86%). MS (ESI): m/z=274.1 [M+H]$^+$.

BB 34

2-[4-(Azetidin-3-yl)phenyl]sulfonylacetonitrile; 4-methylbenzenesulfonic Acid

Step 1: Tert-Butyl 3-[4-(cyanomethylsulfonyl)phenyl]azetidine-1-carboxylate

The title compound was obtained in analogy to BB 4/Step 1 starting from 2-(4-bromophenyl)sulfonylacetonitrile (650 mg, 2.5 mmol, 1.0 equiv; CAS RN 126891-45-0) and tert-butyl 3-bromoazetidine-1-carboxylate (590 mg, 2.5 mmol, 1.0 equiv; CAS RN 1064194-10-0) by irradiating (420 nm) for 16 h as a light yellow oil (220 mg, 25%). MS (ESI): m/z=281.1 [M+2H-tBu]$^+$.

Step 2: 2-[4-(Azetidin-3-yl)phenyl]sulfonylacetonitrile; 4-methylbenzenesulfonic Acid The title compound was obtained in analogy to BB 4/Step 2 starting from tert-butyl 3-[4-(cyanomethylsulfonyl)phenyl]azetidine-1-carboxylate (220 mg, 0.63 mmol, 1.0 equiv) as a colorless solid (210 mg, 81%). MS (ESI): m/z=237.1 [M+H]$^+$.

BB 35

3-[4-(Trifluoromethylsulfonyl)phenyl]azetidine; 4-methylbenzenesulfonic Acid

Step 1: Tert-Butyl 3-[4-(trifluoromethylsulfonyl) phenyl]azetidine-1-carboxylate The title compound was obtained in analogy to BB 4/Step 1 starting from 1-bromo-4-(trifluoromethylsulfonyl)benzene (250 mg, 0.87 mmol, 1.0 equiv; CAS RN 312-20-9) and tert-butyl 3-bromoazetidine-1-carboxylate (204 mg, 0.87 mmol, 1.0 equiv; CAS RN 1064194-10-0) by irradiating (420 nm) for 16 h as a light brown oil (104 mg, 31%). MS (ESI): m/z=310.1 [M+2H-tBu]$^+$.

Step 2: 3-[4-(Trifluoromethylsulfonyl)phenyl]azetidine; 4-methylbenzenesulfonic Acid The title compound was obtained in analogy to BB 4/Step 2 starting from tert-butyl 3-[4-(trifluoromethylsulfonyl)phenyl]azetidine-1-carboxylate (104 mg, 0.27 mmol, 1.0 equiv) as a light brown solid (101 mg, 85%). MS (ESI): m/z=266.1 [M+H]$^+$.

BB 36

3-(4-Cyclohexylsulfonylphenyl)azetidine; 4-methylbenzenesulfonic Acid

Step 1: Tert-Butyl 3-(4-cyclohexylsulfonylphenyl) azetidine-1-carboxylate

The title compound was obtained in analogy to BB 4/Step 1 starting from 1-bromo-4-cyclohexylsulfonyl-benzene (250 mg, 0.82 mmol, 1.0 equiv; CAS RN 861113-45-3) and tert-butyl 3-bromoazetidine-1-carboxylate (195 mg, 0.82 mmol, 1.0 equiv; CAS RN 1064194-10-0) by irradiating (420 nm) for 16 h as a light yellow oil (172 mg, 52%). MS (ESI): m/z=324.2 [M+2H-tBu]$^+$.

Step 2: 3-(4-Cyclohexylsulfonylphenyl)azetidine; 4-methylbenzenesulfonic Acid

The title compound was obtained in analogy to BB 4/Step 2 starting from tert-butyl 3-(4-cyclohexylsulfonylphenyl) azetidine-1-carboxylate (172 mg, 0.43 mmol, 1.0 equiv) as a colorless solid (167 mg, 86%). MS (ESI): m/z=280.2 [M+H]$^+$.

BB 37

1-[5-(Azetidin-3-yl)-2-pyridyl]cyclobutanecarbonitrile; 4-methylbenzenesulfonic Acid Step 1: Tert-Butyl 3-[6-(1-cyanocyclobutyl)-3-pyridyl]azetidine-1-carboxylate The title compound was obtained in analogy to BB 4/Step 1 starting from 1-(5-bromo-2-pyridyl)cyclobutanecarbonitrile (251 mg, 1.06 mmol, 1.0 equiv; CAS RN 485828-81-7) and tert-butyl 3-bromoazetidine-1-carboxylate (250 mg, 1.06 mmol, 1.0 equiv; CAS RN 1064194-10-0) by irradiating (420 nm) for 16 h as a light yellow oil (120 mg, 36%). MS (ESI): m/z=314.2 [M+H]$^+$.

Step 2: 1-[5-(Azetidin-3-yl)-2-pyridyl]cyclobutanecarbonitrile; 4-methylbenzenesulfonic Acid The title compound was obtained in analogy to BB 4/Step 2 starting from tert-butyl 3-[6-(1-cyanocyclobutyl)-3-pyridyl]azetidine-1-carboxylate (120 mg, 0.38 mmol, 1.0 equiv) as a colorless solid (123 mg, 75%). MS (ESI): m/z=214.1 [M+H]$^+$.

BB 38

3-[4-(Azetidin-3-yl)phenoxy]-2-methyl-pyridine; 4-methylbenzenesulfonic Acid

Step 1: Tert-Butyl 3-[4-[(2-methyl-3-pyridyl)oxy] phenyl]azetidine-1-carboxylate To a solution of tert-butyl 3-(4-hydroxyphenyl)azetidine-1-carboxylate (1.0 g, 4.01 mmol, 1.0 equiv; BB 15/Step 1; CAS RN 1782327-13-2) and 3-bromo-2-methyl-pyridine (1.04 g, 6.02 mmol, 1.5 equiv; CAS RN 38749-79-0) in 1,4-dioxane (10 mL) were added copper(I) acetylacetonate (105 mg, 0.40 mmol, 0.1 equiv; CAS RN 14220-26-9) and cesium carbonate (2.61 g, 8.02 mmol, 2.0 equiv). The reaction mixture was heated under an atmosphere of $N_2$ to 100° C. After 12 h, the reaction mixture was filtered, the filtrate concentrated and the residue purified by silica gel column chromatography (petroleum ether:ethyl acetate=20:1 to 5:1) to give the desired product as light yellow oil (0.61 g, 45%). MS (ESI): m/z=341.3 [M+H]$^+$.

Step 2: 3-[4-(Azetidin-3-yl)phenoxy]-2-methyl-pyridine: 4-methylbenzenesulfonic Acid The title compound was obtained in analogy to BB 4/Step 2 starting from tert-butyl 3-[4-[(2-methyl-3-pyridyl)oxy] phenyl]azetidine-1-carboxylate (600 mg, 1.76 mmol, 1.0 equiv) as a light yellow solid (654 mg, 63%). MS (ESI): m/z=241.4 [M+H]$^+$.

BB 39

2-[4-(Azetidin-3-yl)phenoxy]-4-cyclopropyl-pyrimidine; 4-methylbenzenesulfonic Acid Step 1: Tert-Butyl 3-[4-(4-cyclopropylpyrimidin-2-yl)oxyphenyl]azetidine-1-carboxylate The title compound was obtained in analogy to BB 38/Step 1 starting from tert-butyl 3-(4-hydroxyphenyl)azetidine-1-carboxylate (700 mg, 2.81 mmol, 1.0 equiv; BB 15/Step 1; CAS RN 1782327-13-2) and 2-chloro-4-cyclopropyl-pyrimidine (521 mg, 3.37 mmol, 1.2 equiv; CAS RN 954237-31-1) by heating at 50° C. for 16 h as an off-white solid (840 mg, 81%). MS (ESI): m/z=312.4 [M+2H-tBu]$^+$.

Step 2: 2-[4-(Azetidin-3-yl)phenoxy]-4-cyclopropyl-pyrimidine; 4-methylbenzenesulfonic Acid The title compound was obtained in analogy to BB 4/Step 2 starting from tert-butyl 3-[4-(4-cyclopropylpyrimidin-2-yl)oxyphenyl]azetidine-1-carboxylate (740 mg, 2.01 mmol, 1.0 equiv) as an off-white solid (326 mg, 36%). MS (ESI): m/z=268.4 [M+H]$^+$.

BB 40

5-[4-(Azetidin-3-yl)phenyl]-1-(2,2-dimethylpropyl)triazole; 4-methylbenzenesulfonic Acid Step 1: 1-Azido-4-nitro-benzene A solution of 4-nitroaniline (2.0 g, 14.48 mmol, 1.0 equiv) in ACN (20 mL) was cooled to 0° C. in an ice-salt bath. To the stirred solution was added tert-butyl nitrite (1.79 g, 17.38 mmol, 1.2 equiv) and the reaction mixture was stirred for 10 min. Then, azidotrimethylsilane (2.88 mL, 2.50 g, 21.72 mmol, 1.5 equiv) was added dropwise and the resulting brown solution was stirred at RT for 2 h. The reaction mixture was poured into water (100 mL), extracted with EtOAc (3×100 mL), the organic layers combined, dried over Na$_2$SO$_4$ and concentrated in vacuo. The residue was purified by silica gel column chromatography (petroleum ether) to give the desired product as a yellow solid (2.1 g, 87%).

Step 2: 5-(4-Bromophenyl)-1-(2,2-dimethylpropyl)triazole

To the solution of 4'-bromoacetophenone (1.94 g, 9.75 mmol, 1.0 equiv), neopentylamine (1.10 g, 12.67 mmol, 1.3 equiv), 1-azido-4-nitro-benzene (1.60 g, 9.75 mmol, 1.0 equiv) and AcOH (175.6 mg, 2.92 mmol, 0.3 equiv) in toluene (64 mL) were added molecular sieves (4 A, 500 mg) and the reaction mixture was stirred at 100° C. for 16 h. The reaction mixture was filtered and the filtrate evaporated under reduced pressure. The residue was purified by silica gel column chromatography (petroleum ether:ethyl acetate=3:1) to give the desired product as a yellow gum (1.0 g, 35%). $^1$H NMR (400 MHz, CDCl$_3$): δ=7.59 (s, 1H), 7.56 (d, J=8.3 Hz, 2H), 7.16 (d, J=8.3 Hz, 2H), 4.12 (s, 2H), 0.75 (s, 9H).

Step 3: Tert-Butyl 3-[4-[3-(2,2-dimethylpropyl)triazol-4-yl]phenyl]azetidine-1-carboxylate The title compound was obtained in analogy to BB 4/Step 1 starting from 5-(4-bromophenyl)-1-(2,2-dimethylpropyl)triazole (420 mg, 1.43 mmol, 1.0 equiv) and tert-butyl 3-bromoazetidine-1-carboxylate (337 mg, 1.43 mmol, 1.0 equiv; CAS RN 1064194-10-0) by irradiating (420 nm) for 14 h as a yellow gum (500 mg, 76%). MS (ESI): m/z=371.0 [M+H]$^+$.

Step 4: 5-[4-(Azetidin-3-yl)phenyl]-1-(2,2-dimethylpropyl)triazole; 4-methylbenzenesulfonic Acid The title compound was obtained in analogy to BB 4/Step 2 starting from tert-butyl 3-[4-[3-(2,2-dimethylpropyl)triazol-4-yl]phenyl]azetidine-1-carboxylate (100 mg, 0.27 mmol, 1.0 equiv) as a colorless oil (73 mg, 90%). MS (ESI): m/z=271.4 [M+H]$^+$.

BB 41

3-[4-(4-Chloro-2-methylsulfonyl-phenyl)phenyl]azetidine; 4-methylbenzenesulfonic Acid Step 1: Tert-Butyl 3-[4-(4-chloro-2-fluoro-phenyl)phenyl]azetidine-1-carboxylate A suspension of tert-butyl 3-(4-bromophenyl)azetidine-1-carboxylate (250 mg, 0.80 mmol, 1.0 equiv; BB 6/Step 1; CAS RN 1203681-52-0), (4-chloro-2-fluoro-phenyl)boronic acid (140 mg, 0.80 mmol, 1.0 equiv; CAS RN 160591-91-3), potassium carbonate (553 mg, 4.0 mmol, 5.0 equiv), tetrakis (triphenylphosphine)palladium(0) (46.3 mg, 40 µmol, 0.05 equiv) in a mixture of THF:water (10:1, 4.4 mL) was heated to 80° C. for 3 h. The reaction mixture was then poured on water and ethyl acetate and the aqueous layer extracted three times with ethyl acetate. The combined organic layers were dried over MgSO$_4$, filtered, treated with silica gel and evaporated. The crude compound was purified by silica gel chromatography using a MPLC system eluting with a gradient of n-heptane:TBME/MeOH (9:1) (100:0 to 50:50) to yield the title compound as a colorless solid (318 mg, 98%). MS (ESI): m/z=306.0 [M−2H-tBu]$^+$.

Step 2: Tert-Butyl 3-[4-(4-chloro-2-methylsulfanyl-phenyl)phenyl]azetidine-1-carboxylate To a solution of tert-butyl 3-[4-(4-chloro-2-fluoro-phenyl)phenyl]azetidine-1-carboxylate (310 mg, 0.86 mmol, 1.0 equiv) in a mixture of DMSO (1 mL) and DMF (2.5 mL) was added sodium methanethiolate (63.1 mg, 0.9 mmol, 1.1 equiv; CAS RN 5188-07-8) and the reaction mixture was heated to 100° C. for 2 h. The reaction mixture was then poured on water and extracted with TBME (2×25 mL). The combined organic layers were dried over MgSO$_4$, filtered, treated with silica gel and evaporated. The crude compound was purified by silica gel chromatography using a MPLC system eluting with a gradient of n-heptane:ethyl acetate (100:0 to 50:50) to give the title compound as a light yellow oil (251 mg, 75%). MS (ESI): m/z=334.0 [M+2H-tBu]$^+$.

Step 3: Tert-Butyl 3-[4-(4-chloro-2-methylsulfonyl-phenyl)phenyl]azetidine-1-carboxylate To a solution of tert-butyl 3-[4-(4-chloro-2-methylsulfanyl-phenyl)phenyl]azetidine-1-carboxylate (251 mg, 0.65 mmol, 1.0 equiv) in DCM (15 mL) was added m-chlorperbenzoic acid (465 mg, 1.88 mmol, 2.2 equiv; 70% in water) and the reaction mixture was stirred at RT overnight. The reaction mixture was concentrated and the crude material purified by silica gel chromatography using a MPLC system eluting with a gradient of n-heptane:ethyl acetate (100:0 to 50:50) to give the title compound as a white waxy solid (142 mg, 37%). MS (ESI): m/z=366.0 [M+2H-tBu]$^+$. $^1$H NMR (300 MHz, CDCl$_3$): δ=8.23 (d, J=2.2 Hz, 1H), 7.62 (dd, J=8.2 Hz, J=2.3 Hz, 1H), 7.5-7.4 (m, 4H), 7.31 (d, J=8.1 Hz, 11H), 4.4-4.3 (m, 2H), 4.02 (dd, J=8.7 Hz, J=6.0 Hz, 2H), 3.9-3.7 (m, 1H), 2.64 (s, 3H), 1.48 (s, 9H).

Step 4: 3-[4-(4-Chloro-2-methylsulfonyl-phenyl)phenyl]azetidine; 4-methylbenzenesulfonic Acid The title compound was obtained in analogy to BB 4/Step 2 starting from tert-butyl 3-[4-(4-chloro-2-methylsulfonylphenyl)phenyl]azetidine-1-carboxylate (140 mg, 0.33 mmol, 1.0 equiv) as a white solid (125 mg, 76%). MS (ESI): m/z=139.0 [M+H]⁺.

BB 42A and BB 42B (+)- or (−)-4-[(4-Methylsulfonylphenyl)-phenyl-methyl]piperidine; 4-methylbenzenesulfonic Acid and (−)- or (+)-4-[(4-Methylsulfonylphenyl)-phenyl-methyl]piperidine; 4-methylbenzenesulfonic Acid Step 1: Tert-Butyl 4-[(Z)—C-phenyl-N-(p-tolylsulfonylamino)carbonimidoyl]piperidine-1-carboxylate To a solution of tert-butyl 4-benzoylpiperidine-1-carboxylate (5.75 g, 19.87 mmol, 1.0 equiv; CAS RN 193217-39-9) and 4-methylbenzenesulfonohydrazide (3.70 g, 19.87 mmol, 1.0 equiv; CAS RN 1576-35-8) in MeOH (60 mL) was stirred at RT for 12 h and at 60° C. for an additional time period of 12 h. The reaction mixture was concentrated under reduced pressure to provide the title compound as yellow oil (9.1 g, quant.). MS (ESI): m/z=458.2 [M+H]⁺.

Step 2: Tert-Butyl 4-[(4-methylsulfonylphenyl)-phenyl-methylene]piperidine-1-carboxylate A solution of tert-butyl 4-[(Z)—C-phenyl-N-(p-tolylsulfonylamino)carbonimidoyl]piperidine-1-carboxylate (2.0 g, 4.37 mmol, 1.0 equiv), 1-bromo-4-methylsulfonyl-benzene (1.23 g, 5.24 mmol, 1.2 equiv; CAS RN 3466-32-8), lithium tert-butoxide (0.70 g, 8.74 mmol, 2.0 equiv) and bis(triphenylphosphine)palladium(II) chloride (0.92 g, 1.31 mmol, 0.3 equiv) in DMF (30 mL) was stirred under an atmosphere of N₂ at 100° C. for 16 h. The reaction mixture was filtered through a Celite pad, the filtrate concentrated and the residue purified by silica gel column chromatography (petroleum ether:ethyl acetate=10:1 to 5:1) to give the desired product as light yellow oil (1.2 g, 64%). MS (ESI): m/z=372.3 [M+2H-tBu]⁺.

Step 3: tert-Butyl 4-[(4-methylsulfonylphenyl)-phenyl-methyl]piperidine-1-carboxylate To a solution of tert-butyl 4-[(4-methylsulfonylphenyl)-phenyl-methylene]piperidine-1-carboxylate (600 mg, 1.40 mmol, 1.0 equiv) in DMF (30 mL) was added Pd/C (300 mg, 1.40 mmol, 1.0 equiv; wt. 10%) and the suspension was stirred at RT for 16 h under an atmosphere of H₂ (balloon). The reaction mixture was filtered, the filtrate concentrated and the crude material redissolved in DMF (30 mL). Again, Pd/C (300 mg, 1.40 mmol, 1.0 equiv; wt. 10%) was added and the suspension stirred at RT for 16 h under an atmosphere of H₂ (balloon). The suspension was filtered and the filtrate evaporated to get the title compound as a light yellow oil (510 mg, 85%). MS (ESI): m/z=330.0 [M+H-Boc]⁺.

Step 4: (+)- or (−)-tert-Butyl 4-[(4-methylsulfonylphenyl)-phenyl-methyl]piperidine-1-carboxylate and (−)- or (+)-tert-Butyl 4-[(4-methylsulfonylphenyl)-phenyl-methyl]piperidine-1-carboxylate The enantiomers of tert-butyl 4-[(4-methylsulfonylphenyl)-phenyl-methyl]piperidine-1-carboxylate (760 mg, 1.77 mmol) were separated by chiral SFC (Chiralpak IC column (250 mm×30 mm, 10 μm), eluent: 40% EtOH (0.1% NH₄OH) in supercritical CO₂) to give (+)- or (−)-tert-butyl 4-[(4-methylsulfonylphenyl)-phenyl-methyl]piperidine-1-carboxylate (304 mg, 40%; first eluting compound) as an off-white solid and (−)- or (+)-tert-butyl 4-[(4-methylsulfonylphenyl)-phenyl-methyl]piperidine-1-carboxylate (273 mg, 36%; second eluting compound) as an off-white solid. MS (ESI): m/z=374.1 [M+2H-tBu]⁺) for both examples.

Step 5A: (+)- or (−)-4-[(4-Methylsulfonylphenyl)-phenyl-methyl]piperidine: 4-methylbenzenesulfonic Acid (BB 42A)

The product (+)- or (−)-4-[(4-methylsulfonylphenyl)-phenyl-methyl]piperidine; 4-methylbenzenesulfonic acid (BB 42A) was obtained in analogy to BB 4/Step 2 starting from (+)- or (−)-tert-butyl 4-[(4-methylsulfonylphenyl)-phenyl-methyl]piperidine-1-carboxylate (294 mg, 0.68 mmol, 1.0 equiv) as a light yellow solid (323 mg, 94%). MS (ESI): m/z=330.4 [M+H]⁺.

Step 5B: (−)- or (+)-4-[(4-Methylsulfonylphenyl)-phenyl-methyl]piperidine; 4-methylbenzenesulfonic Acid (BB 42B)

The product (−)- or (+)-4-[(4-methylsulfonylphenyl)-phenyl-methyl]piperidine; 4-methylbenzenesulfonic acid (BB 42B) was obtained in analogy to BB 4/Step 2 starting from (−)- or (+)-tert-butyl 4-[(4-methylsulfonylphenyl)-phenyl-methyl]piperidine-1-carboxylate (263 mg, 0.61 mmol, 1.0 equiv) as a white solid (282 mg, 91%). MS (ESI): m/z=330.3 [M+H]⁺.

BB 43

Methyl 2-[[5-(azetidin-3-yl)-2-pyridyl]oxy]-5-chloro-benzoate; 4-methylbenzenesulfonic Acid Step 1: Methyl 2-[(5-bromo-2-pyridyl)oxy]-5-chloro-benzoate To a solution of methyl 5-chloro-2-hydroxy-benzoate (2.0 g, 10.72 mmol, 1.0 equiv; CAS RN 4068-78-4) and 5-bromo-2-fluoro-pyridine (1.92 g, 10.93 mmol, 1.02 equiv; CAS RN 766-11-0) in DMF (20 mL) was added cesium carbonate (5.24 g, 16.08 mmol, 1.5 equiv) and the reaction mixture was stirred at RT overnight. The reaction mixture was diluted with a sat. solution of KHCO₃ (100 mL) and extracted with ethyl acetate (3×50 mL). The combined organic layers were dried over Na₂SO₄, filtered and concentrated. The combined organic layers were dried over MgSO₄, filtered and evaporated. The crude product was purified by silica gel chromatography using a MPLC system eluting with a gradient of n-heptane:ethyl acetate (100:0 to 50:50) to yield the title compound as light yellow oil (1.1 g, 27%). MS (ESI): m/z=343.9 [M+H]⁺.

Step 2: Tert-Butyl 3-[6-(4-chloro-2-methoxycarbonyl-phenoxy)-3-pyridyl]azetidine-1-carboxylate The title compound was obtained in analogy to BB 4/Step 1 starting from methyl 2-[(5-bromo-2-pyridyl)oxy]-5-chloro-benzoate (1.0 g, 2.92 mmol, 1.0 equiv) and tert-butyl 3-bromoazetidine-1-carboxylate (0.69 g, 2.92 mmol, 1.0 equiv; CAS RN 1064194-10-0) by irradiating (420 nm) for 16 h as a light yellow oil (1.11 g, 86%). MS (ESI): m/z=419.2 [M+H]$^+$.

Step 3: Methyl 2-[[5-(azetidin-3-yl)-2-pyridyl]oxy]-5-chloro-benzoate: 4-methylbenzenesulfonic Acid The title compound was obtained in analogy to BB 4/Step 2 starting from tert-butyl 3-[6-(4-chloro-2-methoxycarbonyl-phenoxy)-3-pyridyl]azetidine-1-carboxylate (380 mg, 0.91 mmol, 1.0 equiv) as a light yellow foam (246 mg, 55%). MS (ESI): m/z=319.1 [M+H]$^+$.

BB 44

3-[(3S)-5-Oxothiomorpholin-3-yl]propanoic Acid

Step 1: Benzyl (4S)-4-(tert-butoxycarbonylamino)-5-methylsulfonyloxy-pentanoate

To a solution of benzyl (4S)-4-(tert-butoxycarbonylamino)-5-hydroxy-pentanoate (2.0 g, 6.18 mmol, 1.0 equiv; CAS RN 79069-62-8) and TEA (1.88 g, 2.59 mL, 18.55 mmol, 3.0 equiv) in DCM (60 mL) was added methanesulfonyl chloride (1.06 g, 0.72 mL, 9.28 mmol, 1.5 equiv) and the reaction mixture was stirred at 0° C. After 2 h, the reaction mixture was poured into a sat. aqueous Na$_2$CO$_3$ solution (20 mL) and ethyl acetate (30 mL) was added. The phases were separated and the aqueous phase was extracted with ethyl acetate (3×50 mL). The combined organic layers were washed with a sat. aqueous NaCl solution, dried over Na$_2$SO$_4$, filtered and concentrated to give the desired product as a light brown solid (2.3 g, 93%). MS (ESI): m/z=302.3 [M+2H-tBu]$^+$.

Step 2: Benzyl (4S)-4-(tert-butoxycarbonylamino)-5-(2-ethoxy-2-oxo-ethyl)sulfanyl-pentanoate To a solution of benzyl (4S)-4-(tert-butoxycarbonylamino)-5-methylsulfonyloxy-pentanoate (2.0 g, 4.98 mmol, 1.0 equiv) and ethyl thioglycolate (1.80 g, 14.95 mmol, 3.0 equiv) in DMF (40 mL) was added cesium carbonate (6.49 g, 19.93 mmol, 4.0 equiv) and the reaction mixture was stirred at RT. After 3 h, the reaction mixture was diluted with water (150 mL) and extracted with ethyl acetate (3×50 mL). The combined organic layers were washed with a sat. aqueous NaCl solution, dried over Na$_2$SO$_4$, filtered and concentrated. The crude material was purified by reversed-phase flash chromatography (0.1% v/v FA in water and MeCN) to give the title compound as an off-white solid (1.41 g, 67%). MS (ESI): m/z=370.2 [M+2H-tBu]$^+$.

Step 3: Benzyl (4S)-4-amino-5-(2-ethoxy-2-oxo-ethyl)sulfanyl-pentanoate; 2,2,2-trifluoroacetic Acid To a solution of benzyl (4S)-4-(tert-butoxycarbonylamino)-5-(2-ethoxy-2-oxo-ethyl)sulfanyl-pentanoate (500 mg, 1.17 mmol, 1.0 equiv) in DCM (5 mL) was added TFA (1.48 g, 1.0 mL, 13.0 mmol, 11.0 equiv). The reaction mixture was stirred at RT for 12 h and then evaporated. The residue was treated with toluene and evaporated to get the desired product as yellow oil (500 mg, 97%). MS (ESI): m/z=326.4 [M+H]$^+$.

Step 4: 3-[(3S)-5-Oxothiomorpholin-3-yl]propanoic Acid

To a solution of benzyl (4S)-4-amino-5-(2-ethoxy-2-oxo-ethyl)sulfanyl-pentanoate; 2,2,2-trifluoroacetic acid (200 mg, 0.46 mmol, 1.0 equiv) in a mixture of MeOH (1.5 mL) and water (0.5 mL) was added lithium hydroxide monohydrate (76.4 mg, 1.82 mmol, 4.0 equiv) and the reaction mixture was stirred at RT for 12 h. The reaction mixture was diluted with water (5 mL) and acidified to pH=4~5 with aqueous HCl (4 M). The aqueous layer was washed with ethyl acetate (3×5 mL) and concentrated. The residue was treated with THF (10 mL), the suspension filtered and the filtrate evaporated to get the title compound as a light yellow oil (40 mg, 47%). MS (ESI): m/z=190.5 [M+H]$^+$.

BB 45

4-(Azetidin-3-yl)-N-(cyclopropylmethyl)-N-phenyl-aniline

Step 1: 4-Bromo-N-(cyclopropylmethyl)-N-phenyl-aniline

To a solution of (4-bromophenyl)-phenyl-amine (200 mg, 0.81 mmol, 1.0 equiv; CAS RN 54446-36-5) in THF (2.5 mL) were added dibutyltin dichloride (49.0 mg, 0.16 mmol, 0.2 equiv) and cyclopropanecarboxaldehyde (303.8 µL, 4.0 mmol, 5.0 equiv) and the reaction mixture was stirred at RT for 20 min. Phenylsilane (119.2 µL, 0.97 mmol, 1.2 equiv) was added to the reaction mixture and stirring at RT continued overnight. The reaction mixture was heated to 50° C. and stirring continued overnight. The crude product was purified by silica gel chromatography using a MPLC system eluting with a gradient of n-heptane:ethyl acetate (100:0 to 65:35). After evaporation of the solvent, the title compound was obtained as a colorless liquid (170 mg, 68%). MS (ESI): m/z=304.1 [M+H]$^+$.

Step 2: Tert-Butyl 3-[4-[N-(cyclopropylmethyl)anilino]phenyl]azetidine-1-carboxylate The title compound was obtained in analogy to BB 4/Step 1 starting from 4-bromo-N-(cyclopropylmethyl)-N-phenyl-aniline (165 mg, 0.55 mmol, 1.0 equiv) and tert-butyl 3-bromoazetidine-1-carboxylate (193.4 mg, 0.82 mmol, 1.5 equiv; CAS RN 1064194-10-0) by irradiating (420 nm) for 16 h as a colorless oil (0.12 g, 56%). MS (ESI): m/z=379.3 [M+H]$^+$.

Step 3: 4-(Azetidin-3-yl)-N-(cyclopropylmethyl)-N-phenyl-aniline

A mixture of tert-butyl 3-[4-[N-(cyclopropylmethyl)anilino]phenyl]azetidine-1-carboxylate (116 mg, 0.31 mmol, 1.0 equiv) and p-toluenesulfonic acid monohydrate (128.3 mg, 0.67 mmol, 2.2 equiv) in ethyl acetate (1.2 mL) was heated at reflux for 1 h and stirring continued at RT for 6 h. The solvent was removed by evaporation and the crude product purified by silica gel chromatography (aminophase Si—NH$_2$) using a MPLC system eluting with an isocratic mixture of MeOH:ACN (1:4). After evaporation of the solvent, the title compound was obtained as a light yellow oil (44 mg, 51%). MS (ESI): m/z=279.3 [M+H]$^+$.

BB 46

4-(Azetidin-3-yl)-N,N-diphenyl-aniline; 4-methylbenzenesulfonic Acid

Step 1: Tert-Butyl 3-[4-(N-phenylanilino)phenyl]azetidine-1-carboxylate

The title compound was obtained in analogy to BB 4/Step 1 starting from (4-bromophenyl)-diphenyl-amine (1.0 g, 3.08 mmol, 1.0 equiv; CAS RN 36809-26-4) and tert-butyl 3-bromoazetidine-1-carboxylate (1.09 g, 4.63 mmol, 1.5 equiv; CAS RN 1064194-10-0) by irradiating (420 nm) for 16 h as a colorless oil (0.63 g, 47%). MS (ESI): m/z=345.3 [M+2H-tBu]$^+$.

Step 2: 4-(Azetidin-3-yl)-N,N-diphenyl-aniline; 4-methylbenzenesulfonic Acid

The title compound was obtained in analogy to BB 4/Step 2 starting from tert-butyl 3-[4-(N-phenylanilino)phenyl]azetidine-1-carboxylate (518 mg, 0.996 mmol, 1.0 equiv) as a colorless solid (0.40 g, 82%). MS (ESI): m/z=301.2 [M+H]$^+$.

BB 47

5-(Azetidin-3-yl)-2-tert-butyl-pyridine

Step 1: Tert-Butyl 3-(6-tert-butyl-3-pyridyl)azetidine-1-carboxylate

The title compound was obtained in analogy to BB 4/Step 1 starting from 5-bromo-2-tert-butyl-pyridine (500 mg, 2.34 mmol, 1.0 equiv; CAS RN 39919-58-9) and tert-butyl 3-bromoazetidine-1-carboxylate (827.1 mg, 3.5 mmol, 1.5 equiv; CAS RN 1064194-10-0) by irradiating (420 nm) for 16 h as a light brown oil (0.40 g, 59%). MS (ESI): m/z=291.3 [M+H]$^+$.

Step 2: 5-(Azetidin-3-yl)-2-tert-butyl-pyridine

The title compound was obtained in analogy to BB 45/Step 3 starting from tert-butyl 3-(6-tert-butyl-3-pyridyl)azetidine-1-carboxylate (395 mg, 1.36 mmol, 1.0 equiv) as a light yellow oil (0.26 g, 97%). MS (ESI): m/z=191.2 [M+H]$^+$.

BB 48

5-(Azetidin-3-yl)-N-(5-methoxy-2-pyridyl)-N-methyl-pyridin-2-amine

Step 1: N-(5-Bromo-2-pyridyl)-5-methoxy-pyridin-2-amine

To a solution of 2,5-dibromopyridine (500 mg, 2.11 mmol, 1.0 equiv; CAS RN 624-28-2) and 5-methoxypyridin-2-amine (262 mg, 2.11 mmol, 1.0 equiv, CAS RN 10167-97-2) in toluene (15 mL) were added tris(dibenzylideneacetone)dipalladium(0) (38.7 mg, 42.2 µmol, 0.02 equiv), 1,3-bis(diphenylphosphino)propane (34.8 mg, 84.4 µmol, 0.04 equiv) and sodium tert-butoxide (284 mg, 2.95 mmol, 1.4 equiv) and the reaction mixture was heated to 70° C. for 15 h. The reaction mixture was poured into a sat. aqueous NaCl solution (100 mL) and extracted with ethyl acetate (3×100 mL). The combined organic layers were dried over MgSO$_4$ and then concentrated in vacuo. The crude product was purified by silica gel chromatography eluting with a gradient of n-heptane:ethyl acetate (70:30 to 0:100). The combined fractions were concentrated in vacuo and the material triturated with diethyl ether (5 mL). The suspension was filtered and the title compound obtained as a light brown solid (0.48 g, 80%). MS (ESI): m/z=280.1 [M+H]$^+$.

Step 2: N-(5-Bromo-2-pyridyl)-5-methoxy-N-methyl-pyridin-2-amine

To an ice-cold solution of N-(5-bromo-2-pyridyl)-5-methoxy-pyridin-2-amine (0.28 g, 1.00 mmol, 1.0 equiv) in THF (2.5 mL) was added NaH (52.2 mg, 1.20 mmol, 1.2 equiv; 55% in mineral oil) and the reaction mixture was stirred at ice-bath temperature for 45 min. After adding iodomethane (198 mg, 87 µL, 1.39 mmol, 1.4 equiv), the reaction mixture was stirred at RT for 5 h. The crude reaction mixture was poured on water and ethyl acetate and the water phase extracted twice with ethyl acetate. The combined organic layers were washed with water, dried over MgSO$_4$, filtered and evaporated. The crude product was purified by silica gel chromatography using a MPLC system eluting with a gradient of n-heptane:ethyl acetate (100:0 to 50:50) to get the desired product as a colorless solid (0.20 g, 70%). MS (ESI): m/z=294.1 [M+H]$^+$.

Step 3: tert-Butyl 3-[6-[(5-methoxy-2-pyridyl)-methyl-amino]-3-pyridyl]azetidine-1-carboxylate The title compound was obtained in analogy to BB 4/Step 1 starting from N-(5-bromo-2-pyridyl)-5-methoxy-N-methyl-pyridin-2-amine (200 mg, 0.68 mmol, 1.0 equiv) and tert-butyl 3-bromoazetidine-1-carboxylate (240.8 mg, 1.02 mmol, 1.5 equiv; CAS RN 1064194-10-0) by irradiating (420 nm) for 16 h as a light yellow oil (0.15 g, 56%). MS (ESI): m/z=371.3 [M+H]$^+$.

Step 4: 5-(Azetidin-3-yl)-N-(5-methoxy-2-pyridyl)-N-methyl-pyridin-2-amine

The title compound was obtained in analogy to BB 45/Step 3 starting from tert-butyl 3-[6-[(5-methoxy-2-pyridyl)-methyl-amino]-3-pyridyl]azetidine-1-carboxylate (148 mg, 0.38 mmol, 1.0 equiv) as a light yellow oil (0.10 g, 92%). MS (ESI): m/z=271.3 [M+H]$^+$.

BB 49

5-(Azetidin-3-yl)-N-methyl-N-phenyl-pyridin-2-amine

Step 1: Tert-Butyl 3-[6-(N-methylanilino)-3-pyridyl]azetidine-1-carboxylate

The title compound was obtained in analogy to BB 4/Step 1 starting from 5-bromo-N-methyl-N-phenyl-pyridin-2-amine (410 mg, 1.56 mmol, 1.0 equiv; CAS RN 1125410-02-7) and tert-butyl 3-bromoazetidine-1-carboxylate (551.9 mg, 2.34 mmol, 1.5 eq; CAS RN 1064194-10-0) by irradiating (420 nm) for 16 h as a light brown oil (0.42 g, 80%). MS (ESI): m/z=340.3 [M+H]$^+$.

Step 2: 5-(Azetidin-3-yl)-N-methyl-N-phenyl-pyridin-2-amine

The title compound was obtained in analogy to BB 45/Step 3 starting from tert-butyl 3-[6-(N-methylanilino)-3-pyridyl]azetidine-1-carboxylate (423 mg, 1.25 mmol, 1.0 equiv) to get the title compound as a light yellow oil (0.25 g, 81%). MS (ESI): m/z=240.2 [M+H]$^+$.

BB 50

5-(Azetidin-3-yl)-N-(4-isopropylphenyl)-N-methyl-pyridin-2-amine

Step 1: Tert-Butyl 3-[6-(4-isopropyl-N-methyl-anilino)-3-pyridyl]azetidine-1-carboxylate The title compound was obtained in analogy to BB 4/Step 1 starting from 5-bromo-N-(4-isopropylphenyl)-N-methyl-pyridin-2-amine (360 mg, 1.18 mmol, 1.0 equiv; CAS RN 1895155-65-3) and tert-butyl 3-bromoazetidine-1-carboxylate (417.7 mg, 1.77 mmol, 1.5 equiv; CAS RN 1064194-10-0) by irradiating (420 nm) for 16 h as a light yellow oil (0.33 g, 74%). MS (ESI): m/z=382.3 $[M+H]^+$.

Step 2: 5-(Azetidin-3-yl)-N-(4-isopropylphenyl)-N-methyl-pyridin-2-amine

A solution of tert-butyl 3-[6-(4-isopropyl-N-methyl-anilino)-3-pyridyl]azetidine-1-carboxylate (334 mg, 0.88 mmol, 1.0 equiv) and p-toluenesulfonic acid monohydrate (499.6 mg, 2.63 mmol, 3.0 equiv) in ethyl acetate (3 mL) was heated at reflux for 1 h. The solvent was removed by evaporation and the crude product purified by silica gel chromatography (aminophase Si—$NH_2$) using a MPLC system eluting with an isocratic mixture of MeOH:ACN (1:9). After evaporation of the solvent, the title compound was obtained as a light yellow oil (211 mg, 86%). MS (ESI): m/z=282.3 $[M+H]^+$.

BB 51

5-(Azetidin-3-yl)-N-(cyclopropylmethyl)-N-phenyl-pyridin-2-amine

Step 1: (5-Bromo-2-pyridyl)-(cyclopropylmethyl)-phenyl-amine

To a solution of 5-bromo-N-phenyl-pyridin-2-amine (500 mg, 2.01 mmol, 1.0 equiv; CAS RN 54904-03-9) in DMF (2.4 mL) was added cesium carbonate (1.63 g, 5.02 mmol, 2.5 equiv) and the reaction mixture was stirred at RT for 20 min. After that, bromomethylcyclopropane (406.5 mg, 292 μL, 3.01 mmol, 1.5 equiv) was added slowly and stirring of the brown reaction mixture continued at rt overnight. The reaction mixture was heated to 50° C. to an additional 2 d. The crude reaction mixture was poured on water and ethyl acetate and the water phase extracted twice with ethyl acetate. The combined organic layers were washed with water, dried over $MgSO_4$, filtered and evaporated. The crude product was purified by silica gel chromatography using a MPLC system eluting with a gradient of n-heptane:ethyl acetate (100:0 to 80:20) to get the desired product as a colorless oil (0.40 g, 66%). MS (ESI): m/z=305.2 $[M+H]^+$.

Step 2: 3-[6-[N-(Cyclopropylmethyl)anilino]-3-pyridyl]azetidine-1-carboxylic Acid Tert-butyl Ester The title compound was obtained in analogy to BB 4/Step 1 starting from (5-bromo-2-pyridyl)-(cyclopropylmethyl)-phenyl-amine (440 mg, 1.45 mmol, 1.0 equiv) and tert-butyl 3-bromoazetidine-1-carboxylate (514 mg, 2.18 mmol, 1.5 equiv; CAS RN 1064194-10-0) by irradiating (420 nm) for 16 h as a light yellow oil (0.47 g, 83%). MS (ESI): m/z=380.3 $[M+H]^+$.

Step 3: 5-(Azetidin-3-yl)-N-(cyclopropylmethyl)-N-phenyl-pyridin-2-amine

The title compound was obtained in analogy to BB 45/Step 3 starting from 3-[6-[N-(cyclopropylmethyl)anilino]-3-pyridyl]azetidine-1-carboxylic acid tert-butyl ester (474 mg, 1.2 mmol, 1.0 equiv) as a light yellow oil (0.27 g, 73%). MS (ESI): m/z=280.3 $[M+H]^+$.

BB 52

N-[4-(Azetidin-3-yl)phenyl]-N-(2-methoxyethyl)pyridin-3-amine

Step 1: N-(4-Bromophenyl)-N-(2-methoxyethyl)pyridin-3-amine

To a solution of N-(4-bromophenyl)pyridin-3-amine (500 mg, 2.01 mmol, 1.0 equiv; CAS RN 941585-04-2) in DMF (4 mL) at RT was added NaH (96.3 mg, 2.41 mmol, 1.2 equiv; 55% in mineral oil) and the reaction mixture was stirred at RT for 15 min. After adding 1-bromo-2-methoxyethane (283 μL, 3.01 mmol, 1.5 equiv), the reaction mixture was stirred at RT overnight. The crude reaction mixture was poured on water and ethyl acetate and the water phase extracted twice with ethyl acetate. The combined organic layers were washed with water, dried over $MgSO_4$, filtered and evaporated. The crude product was purified by silica gel chromatography using a MPLC system eluting with a gradient of n-heptane:ethyl acetate (100:0 to 0:100) to get the desired product as a colorless oil (0.51 g, 68%). MS (ESI): m/z=307.1 $[M+H]^+$.

Step 2: 3-[4-[2-Methoxyethyl(3-pyridyl)amino]phenyl]azetidine-1-carboxylic Acid Tert-butyl Ester The title compound was obtained in analogy to BB 4/Step 1 starting from N-(4-bromophenyl)-N-(2-methoxyethyl)pyridin-3-amine (155.8 mg, 0.51 mmol, 1.0 equiv) and tert-butyl 3-bromoazetidine-1-carboxylate (179.6 mg, 0.76 mmol, 1.5 equiv; CAS RN 1064194-10-0) by irradiating (420 nm) for 16 h as a light yellow gum (75 mg, 39%). MS (ESI): m/z=384.3 $[M+H]^+$.

Step 3: N-[4-(Azetidin-3-yl)phenyl]-N-(2-methoxyethyl)pyridin-3-amine

The title compound was obtained in analogy to BB 45/Step 3 starting from 3-[4-[2-methoxyethyl(3-pyridyl)amino]phenyl]azetidine-1-carboxylic acid tert-butyl ester (75 mg, 0.20 mmol, 1.0 equiv) as a light yellow gum (50 mg, 83%). MS (ESI): m/z=284.2 $[M+H]^+$.

BB 53

Trifluoromethyl 2-[4-fluoro-2-(trifluoromethyl)phenyl]sulfonyl-2,6-diazaspiro[3.3]heptane; 2,2,2-trifluoroacetic Acid

Step 1: Tert-Butyl 6-((4-fluoro-2-(trifluoromethyl)phenyl)sulfonyl)-2,6-diazaspiro[3.3]heptane-2-carboxylate To a solution of tert-butyl 2,6-diazaspiro[3.3]heptane-2-carboxylate (350 mg, 1.77 mmol, 1.0 equiv) in DCM (10 mL) cooled down to 0° C. was added DIPEA (615 μL, 3.53 mmol, 3.0 equiv) and 4-fluoro-2-(trifluoromethyl)benzenesulfonyl chloride (486.8 mg, 1.85 mmol, 1.05 equiv) after which the reaction mixture was stirred at 0° C. for 10 min and at RT for 1 h. The reaction mixture was diluted with DCM and extracted with sat. aqueous $Na_2CO_3$ solution (50 mL), the organic phase was collected and the aqueous phase was back-extracted with DCM. The combined organic phases were dried over $Na_2SO_4$ and evaporated down to dryness to yield the crude desired product, which was used without further purification (0.75 g, ca. 85%). MS (ESI): m/z=369.1 $[M+2H-tBu]^+$.

Step 2: Trifluoromethyl 2-[4-fluoro-2-(trifluoromethyl)phenyl]sulfonyl-2,6-diazaspiro[3.3]heptane; 2,2,2-trifluoroacetic Acid To a solution of tert-butyl 6-((4-fluoro-2-(trifluoromethyl)phenyl)sulfonyl)-2,6-diazaspiro[3.3]heptane-2-carboxylate (269 mg, 0.63 mmol, 1.0 equiv) in DCM (2 mL) was added TFA (434 mg, 293 μL, 3.80 mmol, 6.0 equiv). The reaction mixture was stirred at RT for 4 h and then evaporated. The residue was treated with a mixture of n-heptane:ethyl acetate (1:1) and the solvent evaporated. The solid material was taken up in diethyl ether and sonicated for 3 min. The suspension was filtered to give the desired product as a white solid (264 mg, 95%). MS (ESI): m/z=325.1 $[M+H]^+$.

BB 54

2-(2,2-Dimethylpropylsulfonyl)-2,6-diazaspiro[3.3]heptane; 2,2,2-trifluoroacetic Acid Step 1: Tert-Butyl 2-(2,2-dimethylpropylsulfonyl)-2,6-diazaspiro[3.3]heptane-6-carboxylate The title compound was obtained in analogy to BB 53/Step 1 starting from tert-butyl 2,6-diazaspiro[3.3]heptane-2-carboxylate (1.16 g, 5.86 mmol, 1.0 equiv) and 2,2-dimethylpropane-1-sulfonyl chloride (1.0 g, 5.86 mmol, 1.0 equiv) as a light yellow gum (1.59 g, 80%). MS (ESI): m/z=277.2 $[M+2H-tBu]^+$.

Step 2: 2-(2,2-Dimethylpropylsulfonyl)-2,6-diazaspiro[3.3]heptane; 2,2,2-trifluoroacetic Acid The title compound was obtained in analogy to BB 53/Step 2 starting from tert-butyl 2-(2,2-dimethylpropylsulfonyl)-2,6-diazaspiro[3.3]heptane-6-carboxylate (1.59 g, 4.78 mmol, 1.0 equiv) as a light yellow solid (2.71 g, 98%; ca. 60% purity). MS (ESI): m/z=233.2 $[M+H]^+$.

BB 55

1-[4-(Azetidin-3-yl)phenyl]-3-(trifluoromethyl)azetidine; 2,2,2-trifluoroacetic Acid Step 1: Tert-Butyl 3-[4-[3-(trifluoromethyl)azetidin-1-yl]phenyl]azetidine-1-carboxylate To a solution of tert-butyl 3-(4-bromophenyl)azetidine-1-carboxylate (500 mg, 1.60 mmol, 1.0 equiv; BB 6/Step 1; CAS RN 1203681-52-0), 3-(trifluoromethyl)azetidine; hydrochloride (388.1 mg, 2.40 mmol, 1.5 eq; CAS RN 1221272-90-7) and sodium tert-butoxide (615.7 mg, 6.41 mmol, 4.0 equiv) in 1,4-dioxane (10 mL) was added (R)-(+)-2,2'-bis(diphenylphosphino))-1,1'-binaphthalene (100 mg, 0.16 mmol, 0.10 equiv) and palladium(II) acetate (36.0 mg, 0.16 mmol, 0.10 equiv), and the reaction mixture was stirred under an atmosphere of $N_2$ at 110° C. for 12 h. The reaction mixture was filtered and the filtrate concentrated by evaporation under reduced pressure. The crude product was purified by silica gel chromatography eluting with a gradient of petroleum ether:ethyl acetate (95:5 to 80:20) to give the title compound as light yellow solid (450 mg, 79%). MS (ESI): m/z=357.3 $[M+H]^+$.

Step 2: 1-[4-(Azetidin-3-yl)phenyl]-3-(trifluoromethyl)azetidine; 2,2,2-trifluoroacetic Acid To a solution of tert-butyl 3-[4-[3-(trifluoromethyl)azetidin-1-yl]phenyl]azetidine-1-carboxylate (831 mg, 2.30 mmol, 1.0 equiv) in DCM (8 mL) was added TFA (0.89 g, 0.60 mL, 7.82 mmol, 3.4 equiv) and the reaction mixture was stirred at RT for 16 h. The crude reaction mixture was concentrated and lyophilized to give the title compound as a brown oil (1.02 g, 84%). MS (ESI): m/z=257.4 $[M+H]^+$.

BB 56

5-(Azetidin-3-yl)-2-[1-(trifluoromethyl)cyclopropyl]pyrimidine; 4-methylbenzenesulfonic Acid Step 1: 5-Bromo-2-[1-(trifluoromethyl)vinyl]pyrimidine To a solution of 1-(trifluoromethyl)vinylboronic acid hexylene glycol ester (4.7 g, 21.19 mmol, 1.2 equiv; CAS RN 1011460-68-6) and 2,5-dibromopyrimidine (4.2 g, 17.66 mmol, 1.0 equiv), potassium carbonate (4.88 g, 35.31 mmol, 2.0 equiv) in 1,4-dioxane (50 mL) and water (10 mL) was added 1,1'-bis(diphenylphosphino)ferrocene-palladium(II) dichloride dichloromethane complex (1.44 g, 1.77 mmol, 0.1 equiv), and the reaction mixture was stirred under an atmosphere of $N_2$ at 80° C. for 12 h. The reaction mixture was diluted with water (100 mL) and extracted with ethyl acetate (3×100 mL), the combined organic phase was then washed with a sat. aqueous NaCl solution, dried over $Na_2SO_4$ and concentrated. The crude product was purified by silica gel chromatography eluting with a gradient of petroleum ether:ethyl acetate (100:0 to 90:10) to give the title compound as a colorless solid (2.4 g, 54%). $^1$H NMR (400 MHz, $CDCl_3$): δ=8.83 (s, 2H), 7.01 (d, J=1.8 Hz, 1H), 6.41 (s, 1H).

Step 2: 5-Bromo-2-[1-(trifluoromethyl)cyclopropyl]pyrimidine

To a solution of 5-bromo-2-[1-(trifluoromethyl)vinyl]pyrimidine (1.9 g, 7.51 mmol, 1.0 equiv) in THF (60 mL) was added diphenyl(methyl)sulfonium tetrafluoroborate (2.81 g, 9.76 mmol, 1.3 equiv). After the suspension was stirred at RT for 0.5 h, a solution of NaHMDS (12.01 mL, 12.01 mmol, 1.6 equiv) was added dropwise and stirring was continued at RT for 1 h. The reaction mixture was quenched by addition of MeOH (10 mL) and the solvent removed by evaporation. The crude product was purified by silica gel chromatography eluting with a gradient of petroleum ether:ethyl acetate (100:0 to 90:10) to give the title compound as a colorless solid (1.4 g, 70%). MS (ESI): m/z=269.0 $[M+H]^+$.

Step 3: Tert-Butyl 3-[2-[1-(trifluoromethyl)cyclopropyl]pyrimidin-5-yl]azetidine-1-carboxylate The title compound was obtained in analogy to BB 4/Step 1 starting from 5-bromo-2-[1-(trifluoromethyl)cyclopropyl]

pyrimidine (1.20 g, 4.49 mmol, 1.0 equiv) and tert-butyl 3-bromoazetidine-1-carboxylate (1.38 g, 5.84 mmol, 1.3 equiv; CAS RN 1064194-10-0) by irradiating (420 nm) for 24 h as a yellow solid (0.90 g, 58%). MS (ESI): m/z=344.4 $[M+H]^+$.

Step 4: 5-(Azetidin-3-yl)-2-[1-(trifluoromethyl)cyclopropyl]pyrimidine; 4-methylbenzenesulfonic Acid The title compound was obtained in analogy to BB 4/Step 2 starting from tert-butyl 3-[2-[1-(trifluoromethyl)cyclopropyl]pyrimidin-5-yl]azetidine-1-carboxylate (100 mg, 0.29 mmol, 1.0 equiv) as a grey solid (121 mg, quant.). MS (ESI): m/z=244.5 $[M+H]^+$.

BB 57

5-(Azetidin-3-yl)-2-[1-(trifluoromethyl)cyclopropyl]pyridine; 4-methylbenzenesulfonic Acid Step 1: 5-Bromo-2-[1-(trifluoromethyl)vinyl]pyridine The title compound was obtained in analogy to BB 56/Step 1 starting from 2,5-dibromopyridine (3.0 g, 12.66 mmol, 1.0 equiv) and tetrakis(triphenylphosphine)palladium (0) (1.46 g, 1.27 mmol, 0.10 equiv) as a light yellow oil (0.60 g, 19%). MS (ESI): m/z=252.2 $[M+H]^+$.

Step 2: 5-Bromo-2-[1-(trifluoromethyl)cyclopropyl]pyridine

The title compound was obtained in analogy to BB 56/Step 2 starting from 5-bromo-2-[1-(trifluoromethyl)vinyl]pyridine (1.10 g, 4.36 mmol, 1.0 equiv) as a yellow oil (0.90 g, 78%). MS (ESI): m/z=266.3 $[M+H]^+$.

Step 3: Tert-Butyl 3-[6-[1-(trifluoromethyl)cyclopropyl]-3-pyridyl]azetidine-1-carboxylate The title compound was obtained in analogy to BB 4/Step 1 starting from 5-bromo-2-[1-(trifluoromethyl)cyclopropyl]pyridine (0.80 g, 3.01 mmol, 1.0 equiv) and tert-butyl 3-bromoazetidine-1-carboxylate (0.92 g, 3.91 mmol, 1.3 equiv; CAS RN 1064194-10-0) by irradiating (420 nm) for 24 h as a yellow solid (0.60 g, 58%). MS (ESI): m/z=343.2 $[M+H]^+$.

Step 4: 5-(Azetidin-3-yl)-2-[1-(trifluoromethyl)cyclopropyl]pyridine; 4-methylbenzenesulfonic Acid The title compound was obtained in analogy to BB 4/Step 2 starting from tert-butyl 3-[6-[1-(trifluoromethyl)cyclopropyl]-3-pyridyl]azetidine-1-carboxylate (0.80 g, 2.34 mmol, 1.0 equiv) as a white solid (1.13 g, 82%). MS (ESI): m/z=243.1 $[M+H]^+$.

BB 58

2-(Azetidin-3-yl)-5-[3-(trifluoromethyl)pyrrolidin-1-yl]pyridine; 4-methylbenzenesulfonic Acid Step 1: 3-[5-[3-(Trifluoromethyl)pyrrolidino]-2-pyridyl]azetidine-1-carboxylic Acid Tert-butyl Ester To a suspension of tert-butyl 3-(5-bromo-2-pyridyl)azetidine-1-carboxylate (100 mg, 0.30 mmol, 1.0 equiv; CAS RN 1922143-52-9) and 3-(trifluoromethyl)pyrrolidine; hydrochloride (52.1 mg, 44.2 µL, 0.30 mmol, 1.0 equiv; CAS RN 1189485-03-7) in tert-butanol (1.77 mL) under Ar were added X-PHOS (12.7 mg, 0.027 mmol, 0.09 equiv; CAS RN 564483-18-7), tris(dibenzylideneacetone)dipalladium (0) chloroform adduct (9.22 mg, 0.009 mmol, 0.03 equiv; CAS RN 52522-40-4) and cesium carbonate (387.7 mg, 1.19 mmol, 4.0 equiv) and the reaction mixture was heated by microwave irradiation at 90° C. for 1 h followed by 100° C. for 30 min. The reaction mixture was filtered, and the crude material purified by silica gel chromatography using a MPLC system eluting with a gradient of n-heptane: ethyl acetate (100:0 to 50:50) to get the title compound as a yellow waxy solid (106 mg, 87%). MS (ESI): m/z=372.3 $[M+H]^+$.

Step 2: 2-(Azetidin-3-yl)-5-[3-(trifluoromethyl)pyrrolidin-1-yl]pyridine; 4-methylbenzenesulfonic Acid The title compound was obtained in analogy to BB 4/Step 2 starting from 3-[5-[3-(trifluoromethyl)pyrrolidino]-2-pyridyl]azetidine-1-carboxylic acid tert-butyl ester (104 mg, 0.25 mmol, 1.0 equiv) as an off-white solid (120 mg, 69%). MS (ESI): m/z=272.2 $[M+H]^+$.

BB 59

1-[4-(Azetidin-3-yl)phenyl]-3-(methylsulfonylmethyl)azetidine; 4-methylbenzenesulfonic Acid Step 1: 1-(4-Bromophenyl)-3-(methylsulfonylmethyl)azetidine To a suspension of 1-bromo-4-iodobenzene (500 mg, 1.77 mmol, 1.0 equiv; CAS RN 589-87-7), 3-(methylsulfonylmethyl)azetidine (342.8 mg, 2.30 mmol, 1.3 equiv; CAS RN 1359656-22-6) and cesium carbonate (2.31 g, 7.07 mmol, 4.0 equiv) in toluene (5 mL) under an atmosphere of $N_2$ were added Xantphos (61.4 mg, 0.11 mmol, 0.06 equiv) and tris(dibenzylideneacetone)dipalladium (0) chloroform adduct (32.4 mg, 0.035 mmol, 0.02 equiv) and the reaction mixture was stirred at 100° C. for 3.5 h. The reaction mixture was diluted with water (100 mL) and extracted with ethyl acetate (3×100 mL), the combined organic phase was then washed with a sat. aqueous NaCl solution, dried over $Na_2SO_4$ and concentrated. The crude product was purified by silica gel chromatography eluting with a gradient of n-heptane:ethyl acetate (100:0 to 50:50) to give the title compound as an off-white solid (276 mg, 45%). MS (ESI): m/z=304.4 $[M+H]^+$.

Step 2: Tert-Butyl 3-[4-[3-(methylsulfonylmethyl)azetidin-1-yl]phenyl]azetidine-1-carboxylate The title compound was obtained in analogy to BB 4/Step 1 starting from 1-(4-bromophenyl)-3-(methylsulfonylmethyl)azetidine (211 mg, 0.69 mmol, 1.0 equiv) and and tert-butyl 3-bromoazetidine-1-carboxylate (245.7 mg, 1.04 mmol, 1.5 equiv; CAS RN 1064194-10-0) by irradiating (420 nm) for 16 h as a light brown oil (75 mg, 26%). MS (ESI): m/z=381.2 $[M+H]^+$.

Step 3: 1-[4-(Azetidin-3-yl)phenyl]-3-(methylsulfonylmethyl)azetidine; 4-methylbenzenesulfonic Acid The title compound was obtained in analogy to BB 4/Step 2 starting from tert-butyl 3-[4-[3-(methylsulfonylmethyl)

azetidin-1-yl]phenyl]azetidine-1-carboxylate (75 mg, 0.18 mmol, 1.0 equiv) as a light brown oil (144 mg, 89%). MS (ESI): m/z=281.1 [M+H]⁺.

BB 60

2-(Azetidin-3-yl)-5-[3-(trifluoromethyl)pyrrolidin-1-yl]pyrazine; 4-methylbenzenesulfonic Acid Step 1: Tert-Butyl 3-(5-bromopyrazin-2-yl)azetidine-1-carboxylate To a suspension of zinc dust (346.4 mg, 5.30 mmol, 1.5 equiv) in THF (8 mL) were added 1,2-dibromoethane (66.4 mg, 30.4 µL, 0.35 mmol, 0.10 equiv) and chlorotrimethylsilane (44.9 µL, 0.35 mmol, 0.10 equiv) and the suspension was stirred at 60° C. for 15 min. A solution of tert-butyl 3-iodoazetidine-1-carboxylate (1.0 g, 613.5 µL, 3.53 mmol, 1.0 equiv, CAS RN 254454-54-1) in DMA (8 mL) was added and the reaction mixture was stirred at 60° C. for 15 min. The reaction mixture was cooled down to RT and 2-bromo-5-iodo-pyrazine (1.06 g, 3.71 mmol, 1.05 equiv; CAS RN 622392-04-5), 1,1'-bis(diphenylphosphino)ferrocene-palladium(II) dichloride dichloromethane complex (144.2 mg, 0.18 mmol, 0.05 equiv) and copper(I) iodide (34.3 mg, 0.18 mmol, 0.05 equiv) were added and stirring continued at 80° C. for 2 h. The reaction mixture was diluted with ethyl acetate and water and then filtered over Dicalite. The filtrate was extracted with ethyl acetate (3×100 mL), the combined organic phase was then washed with a sat. aqueous NaCl solution, dried over MgSO₄ and concentrated. The crude product was purified by silica gel chromatography eluting with a gradient of n-heptane:ethyl acetate (100:0 to 70:30) to give the title compound as a colorless solid (212 mg, 18%). MS (ESI): m/z=260.0 [M+2H-tBu]⁺.

Step 2: Tert-Butyl 3-[5-[3-(trifluoromethyl)pyrrolidin-1-yl]pyrazin-2-yl]azetidine-1-carboxylate The title compound was obtained in analogy to BB 58/Step 1 starting from tert-butyl 3-(5-bromopyrazin-2-yl)azetidine-1-carboxylate (150 mg, 0.48 mmol, 1.0 equiv) and 3-(trifluoromethyl)pyrrolidine; hydrochloride (83.8 mg, 71.0 µL, 0.48 mmol, 1.0 equiv; CAS RN 1189485-03-7) as a light brown solid (58 mg, 31%). MS (ESI): m/z=317.1 [M+2H-tBu]⁺.

Step 3: 2-(Azetidin-3-yl)-5-[3-(trifluoromethyl)pyrrolidin-1-yl]pyrazine; 4-methylbenzenesulfonic Acid The title compound was obtained in analogy to BB 4/Step 2 starting from tert-butyl 3-[5-[3-(trifluoromethyl)pyrrolidin-1-yl]pyrazin-2-yl]azetidine-1-carboxylate (56 mg, 0.14 mmol, 1.0 equiv) as a light brown solid (81 mg, 91%). MS (ESI): m/z=273.1 [M+H]⁺.

BB 61

2-(Azetidin-3-yl)-5-[3-(trifluoromethyl)pyrrolidin-1-yl]pyrimidine; 4-methylbenzenesulfonic Acid Step 1: Tert-Butyl 3-(5-bromopyrimidin-2-yl)azetidine-1-carboxylate The title compound was obtained in analogy to BB 60/Step 1 starting from tert-butyl 3-iodoazetidine-1-carboxylate (0.50 g, 306.8 µL, 1.77 mmol, 1.0 equiv, CAS RN 254454-54-1) and 5-bromo-2-iodo-pyrimidine (0.53 g, 1.85 mmol, 1.05 equiv; CAS RN 223463-13-6) as a light yellow oil (140 mg, 22%). MS (ESI): m/z=258.0 [M+2H-tBu]⁺.

Step 2: Tert-Butyl 3-[5-[3-(trifluoromethyl)pyrrolidin-1-yl]pyrimidin-2-yl]azetidine-1-carboxylate The title compound was obtained in analogy to BB 58/Step 1 starting from tert-butyl 3-(5-bromopyrimidin-2-yl)azetidine-1-carboxylate (140 mg, 0.45 mmol, 1.0 equiv) and 3-(trifluoromethyl)pyrrolidine; hydrochloride (78.2 mg, 66.3 µL, 0.45 mmol, 1.0 equiv; CAS RN 1189485-03-7) as a light brown solid (81 mg, 44%). MS (ESI): m/z=317.1 [M+2H-tBu]⁺.

Step 3: 2-(Azetidin-3-yl)-5-[3-(trifluoromethyl)pyrrolidin-1-yl]pyrimidine; 4-methylbenzenesulfonic Acid The title compound was obtained in analogy to BB 4/Step 2 starting from tert-butyl 3-[5-[3-(trifluoromethyl)pyrrolidin-1-yl]pyrimidin-2-yl]azetidine-1-carboxylate (81 mg, 0.18 mmol, 1.0 equiv) as a light brown solid (96 mg, 87%). MS (ESI): m/z=273.1 [M+H]⁺.

BB 62

5-(Azetidin-3-yl)-2-[3-(trifluoromethyl)pyrrolidin-1-yl]pyrimidine; 4-methylbenzenesulfonic Acid Step 1: Tert-Butyl 3-(2-chloropyrimidin-5-yl)azetidine-1-carboxylate The title compound was obtained in analogy to BB 60/Step 1 starting from tert-butyl 3-iodoazetidine-1-carboxylate (1.0 g, 613.5 µL, 3.53 mmol, 1.0 equiv, CAS RN 254454-54-1) and 5-bromo-2-chloro-pyrimidine (0.89 g, 3.71 mmol, 1.05 equiv; CAS RN 32779-36-5) as a light brown oil (310 mg, 26%). MS (ESI): m/z=214. [M+2H-tBu]⁺.

Step 2: Tert-Butyl 3-[2-[3-(trifluoromethyl)pyrrolidin-1-yl]pyrimidin-5-yl]azetidine-1-carboxylate The title compound was obtained in analogy to BB 58/Step 1 starting from tert-butyl 3-(2-chloropyrimidin-5-yl)azetidine-1-carboxylate (308 mg, 1.14 mmol, 1.0 equiv) and 3-(trifluoromethyl)pyrrolidine; hydrochloride (200.5 mg, 169.9 µL, 1.14 mmol, 1.0 equiv; CAS RN 1189485-03-7) as a light brown solid (120 mg, 23%). MS (ESI): m/z=373.2 [M+H]⁺.

Step 3: 5-(Azetidin-3-yl)-2-[3-(trifluoromethyl)pyrrolidin-1-yl]pyrimidine; 4-methylbenzenesulfonic Acid The title compound was obtained in analogy to BB 4/Step 2 starting from tert-butyl 3-[2-[3-(trifluoromethyl)pyrrolidin-1-yl]pyrimidin-5-yl]azetidine-1-carboxylate (120 mg, 0.32 mmol, 1.0 equiv) as a light yellow oil (230 mg, 87%). MS (ESI): m/z=273.1 [M+H]⁺.

BB 63

2-(Azetidin-3-yl)-5-(2-chloro-4-methylsulfonyl-phenyl)pyridine; 4-methylbenzenesulfonic Acid Step 1: Tert-Butyl 3-[5-(2-chloro-4-methylsulfonyl-phenyl)-2-pyridyl]azetidine-1-carboxylate To a solution of tert-butyl 3-(5-bromo-2-pyridyl)azetidine-1-carboxylate (100 mg, 0.30 mmol, 1.0 equiv; CAS RN 1922143-52-9) in a mixture of THF (1.5 mL) and water (0.15 mL) under Ar were added 2-(2-chloro-4-methylsulfonyl-phenyl)-4,4,5,5-tetramethyl-1,3,2-dioxaborolane (115.2 mg, 0.36 mmol, 1.2 equiv; CAS RN 2377012-74-1), tetrakis (triphenylphosphine)palladium(0) (17.5 mg, 0.015 mmol, 0.05 equiv; CAS RN 14221-01-3) and potassium carbonate (209.6 mg, 1.52 mmol, 5.0 equiv) and the reaction mixture was heated in a sealed tube at 80° C. for 2.5 h. The reaction mixture was filtered, the filtrate diluted with ethyl acetate (50 mL), washed with water and a sat. aqueous NaCl solution, the combined organic phases dried over MgSO$_4$ and then concentrated. The crude compound was purified by silica gel chromatography using a MPLC system eluting with a gradient of n-heptane:ethyl acetate (100:0 to 0:100) to get the title compound as a light brown gum (127 mg, 94%). MS (ESI): m/z=367.0 [M+2H-tBu]$^+$.

Step 2: 2-(Azetidin-3-yl)-5-(2-chloro-4-methylsulfonyl-phenyl)pyridine; 4-methylbenzenesulfonic Acid The title compound was obtained in analogy to BB 4/Step 2 starting from tert-butyl 3-[5-(2-chloro-4-methylsulfonyl-phenyl)-2-pyridyl]azetidine-1-carboxylate (127 mg, 0.29 mmol, 1.0 equiv) as an off-white solid (160 mg, 84%). MS (ESI): m/z=323.0 [M+H]$^+$.

BB 64

4-Methylbenzenesulfonic Acid; 3-[3-[1-(trifluoromethyl)cyclopropyl]phenyl]azetidine Step 1: Tert-Butyl 3-[3-[1-(trifluoromethyl)cyclopropyl]phenyl]azetidine-1-carboxylate The title compound was obtained in analogy to BB 4/Step 1 starting from 1-bromo-3-[1-(trifluoromethyl)cyclopropyl] benzene (1.0 g, 3.77 mmol, 1.0 equiv; CAS RN 1707572-80-2) and and tert-butyl 3-bromoazetidine-1-carboxylate (891 mg, 3.77 mmol, 1.5 equiv; CAS RN 1064194-10-0) by irradiating (420 nm) for 16 h as a light brown oil (616 mg, 43%). MS (ESI): m/z=286.1 [M+2H-tBu]$^+$.

Step 2: 4-Methylbenzenesulfonic Acid: 3-[3-[1-(trifluoromethyl)cyclopropyl]phenyl]azetidine The title compound was obtained in analogy to BB 4/Step 2 starting from tert-butyl 3-[3-[1-(trifluoromethyl)cyclopropyl]phenyl]azetidine-1-carboxylate (615 mg, 1.80 mmol, 1.0 equiv) as a light yellow gum (725 mg, 93%). MS (ESI): m/z=242.1 [M+H]$^+$.

BB 65

2-(Azetidin-3-yl)-5-(2-chloro-4-methylsulfonyl-phenyl)pyrazine; 4-methylbenzenesulfonic Acid Step 1: Tert-Butyl 3-[5-(2-chloro-4-methylsulfonyl-phenyl)pyrazin-2-yl]azetidine-1-carboxylate The title compound was obtained in analogy to BB 63/Step 1 starting from tert-butyl 3-(5-bromopyrazin-2-yl) azetidine-1-carboxylate (84 mg, 0.27 mmol, 1.0 equiv; BB 60/Step 1) and 2-(2-chloro-4-methylsulfonyl-phenyl)-4,4,5,5-tetramethyl-1,3,2-dioxaborolane (101.6 mg, 0.32 mmol, 1.2 equiv; CAS RN 2377012-74-1) as a light brown foam (98 mg, 83%). MS (ESI): m/z=368.1 [M+2H-tBu]$^+$.

Step 2: 2-(Azetidin-3-yl)-5-(2-chloro-4-methylsulfonyl-phenyl)pyrazine; 4-methylbenzenesulfonic Acid The title compound was obtained in analogy to BB 4/Step 2 starting from tert-butyl 3-[5-(2-chloro-4-methylsulfonyl-phenyl)pyrazin-2-yl]azetidine-1-carboxylate (98 mg, 0.22 mmol, 1.0 equiv) as a colorless solid (81 mg, 74%). MS (ESI): m/z=324.0 [M+H]$^+$.

BB 66

5-(Azetidin-3-yl)-2-tert-butylsulfonyl-pyridine; 4-methylbenzenesulfonic Acid

Step 1: Tert-Butyl 3-(6-fluoro-3-pyridyl)azetidine-1-carboxylate

The title compound was obtained in analogy to BB 4/Step 1 starting from 5-bromo-2-fluoro-pyridine (6.0 g, 34.1 mmol, 1.0 equiv) and tert-butyl 3-bromoazetidine-1-carboxylate (8.85 g, 37.5 mmol, 1.1 equiv; CAS RN 1064194-10-0) by irradiating (420 nm) for 20 h as a light orange oil (5.69 g, 60%). MS (ESI): m/z=253.1 [M+H]$^+$.

Step 2: Tert-Butyl 3-(6-tert-butylsulfanyl-3-pyridyl) azetidine-1-carboxylate

To a solution of tert-butyl 3-(6-fluoro-3-pyridyl)azetidine-1-carboxylate (555.6 mg, 1.98 mmol, 1.0 equiv) in DMSO (8.9 mL) was added sodium 2-methyl-2-propanethiolate (222.3 mg, 1.98 mmol, 1.0 equiv; CAS RN 29364-29-2) and the reaction mixture was heated at 100° C. for 2 d. Again, sodium 2-methyl-2-propanethiolate (333.5 mg, 2.97 mmol, 1.5 equiv; CAS RN 29364-29-2) was added and heating at 100° C. continued for 1 d. The reaction mixture was poured on water and extracted with ethyl acetate, the organic phase washed with water and dried over MgSO$_4$ and then concentrated. The crude compound was purified by silica gel chromatography using a MPLC system eluting with a gradient of n-heptane:ethyl acetate (100:0 to 70:30) to give the title compound as an orange oil (121 mg, 19%). MS (ESI): m/z=323.2 [M+H]$^+$.

Step 3: Tert-Butyl 3-(6-tert-butylsulfonyl-3-pyridyl) azetidine-1-carboxylate

To a solution of tert-butyl 3-(6-tert-butylsulfanyl-3-pyridyl)azetidine-1-carboxylate (121 mg, 0.38 mmol, 1.0 equiv) in DCM (3 mL) was added at 0° C. 3-chloroperoxybenzoic acid (161.9 mg, 0.94 mmol, 2.5 equiv; CAS RN 937-14-4) and the reaction mixture was stirred at RT for 3 h. The reaction mixture was filtered and the filtrate washed with DCM and a sat. aqueous NaHCO$_3$ solution. The aqueous layer was extracted with DCM, the combined organic phase dried over MgSO$_4$ and concentrated to yield the title compound as a light yellow solid (150 mg, quant.). MS (ESI): m/z=355.2 [M+H]$^+$.

Step 4: 5-(Azetidin-3-yl)-2-tert-butylsulfonyl-pyridine; 4-methylbenzenesulfonic Acid The title compound was obtained in analogy to BB 4/Step 2 starting from tert-butyl 3-(6-tert-butylsulfonyl-3-pyridyl) azetidine-1-carboxylate (151 mg, 0.43 mmol, 1.0 equiv) as a white solid (139 mg, 50%). MS (ESI): m/z=255.1 [M+H]$^+$.

BB 67

2-(Azetidin-3-yl)-5-(4-chloro-2-fluoro-phenyl)pyrimidine; 4-methylbenzenesulfonic Acid

Step 1: Tert-Butyl 3-[5-(4-chloro-2-fluoro-phenyl)pyrimidin-2-yl]azetidine-1-carboxylate The title compound was obtained in analogy to BB 63/Step 1 starting from tert-butyl 3-(5-bromopyrimidin-2-yl)azetidine-1-carboxylate (140.7 mg, 0.39 mmol, 1.0 equiv; BB 61/Step 1) and (4-chloro-2-fluoro-phenyl)boronic acid (120.8 mg, 0.69 mmol, 1.8 equiv; CAS RN 160591-91-3) as a yellow gum (104 mg, 71%). MS (ESI): m/z=308.1 [M+2H-tBu]$^+$.

Step 2: 2-(Azetidin-3-yl)-5-(4-chloro-2-fluoro-phenyl)pyrimidine; 4-methylbenzenesulfonic Acid The title compound was obtained in analogy to BB 4/Step 2 starting from tert-butyl 3-[5-(4-chloro-2-fluoro-phenyl)pyrimidin-2-yl]azetidine-1-carboxylate (97.8 mg, 0.27 mmol, 1.0 equiv) as a white solid (125 mg, 89%). MS (ESI): m/z=264.1 [M+H]$^+$.

BB 68

2-(Azetidin-3-yl)-5-(4-chloro-2-fluoro-phenyl)pyridine; 4-methylbenzenesulfonic acid

Step 1: Tert-Butyl 3-[5-(4-chloro-2-fluoro-phenyl)-2-pyridyl]azetidine-1-carboxylate The title compound was obtained in analogy to BB 63/Step 1 starting from tert-butyl 3-(5-bromo-2-pyridyl)azetidine-1-carboxylate (300 mg, 0.96 mmol, 1.0 equiv; CAS RN 1922143-52-9) and (4-chloro-2-fluoro-phenyl)boronic acid (167 mg, 0.96 mmol, 1.0 equiv; CAS RN 160591-91-3) as an off-white solid (263 mg, 70%). MS (ESI): m/z=307.1 [M+2H-tBu]$^+$.

Step 2: 2-(Azetidin-3-yl)-5-(4-chloro-2-fluoro-phenyl)pyridine; 4-methylbenzenesulfonic Acid The title compound was obtained in analogy to BB 4/Step 2 starting from tert-butyl 3-[5-(4-chloro-2-fluoro-phenyl)-2-pyridyl]azetidine-1-carboxylate (140 mg, 0.36 mmol, 1.0 equiv) as a colorless solid (216 mg, 99%). MS (ESI): m/z=263.1 [M+H]$^+$.

BB 69

2-(Azetidin-3-yl)-5-(2,4-dichlorophenyl)pyridine; 4-methylbenzenesulfonic Acid

Step 1: Tert-Butyl 3-[5-(2,4-dichlorophenyl)-2-pyridyl]azetidine-1-carboxylate The title compound was obtained in analogy to BB 63/Step 1 starting from tert-butyl 3-(5-bromo-2-pyridyl)azetidine-1-carboxylate (800 mg, 2.55 mmol, 1.0 equiv; CAS RN 1922143-52-9) and (2,4-dichlorophenyl)boronic acid (633.7 mg, 3.32 mmol, 1.3 equiv; CAS RN 68716-47-2) as a light grey solid (700 mg, 69%). MS (ESI): m/z=379.0 [M+H]$^+$.

Step 2: 2-(Azetidin-3-yl)-5-(2,4-dichlorophenyl)pyridine; 4-methylbenzenesulfonic Acid The title compound was obtained in analogy to BB 4/Step 2 starting tert-butyl 3-[5-(2,4-dichlorophenyl)-2-pyridyl]azetidine-1-carboxylate (550 mg, 1.45 mmol, 1.0 equiv) as a white solid (870 mg, 93%). MS (ESI): m/z=279.4 [M+H]$^+$.

BB 70

2-[4-(Azetidin-3-yl)phenyl]-5-chloro-3-methylsulfonyl-pyridine; 4-methylbenzenesulfonic Acid

Step 1: 2-Bromo-5-chloro-3-methylsulfonyl-pyridine

Mixture A: To ice-cold water (2.61 g, 2.61 mL, 144.61 mmol, 60.0 equiv) in a three neck flask was added dropwise below −5° C. thionyl chloride (716.8 mg, 439.8 µL, 6.03 mmol, 2.5 equiv) and the solution was allowed to warm up overnight before adding copper(I) chloride (4.8 mg, 0.048 mmol, 0.02 equiv). Mixture B: To ice cold 2-bromo-5-chloro-pyridin-3-amine (500 mg, 2.41 mmol, 1.0 equiv) was added portionwise 12 M HCl (2.84 g, 2.41 mL, 28.92 mmol, 12.0 equiv) and the suspension was allowed to stir at RT for 15 min before again cooling down to −8° C. A solution of sodium nitrite (199.6 mg, 2.89 mmol, 1.2 equiv) in water (0.8 mL) was added dropwise over 20 min between −8° C. and −10° C. The reaction mixture was stirred at approx. −10° C. for another 30 min. Mixture B was portionwise transferred to Mixture A between −8° C. and −10° C. over 10 min. The reaction mixture was allowed to stir at 0° C. for 1.5 h. TBME was added to the suspension and the layers were separated. The aqueous layer was washed twice with TBME. The organic layers were washed with a sat. aqueous NaCl solution, dried over MgSO$_4$, filtered and evaporated. The crude product was dissolved in THF (2.5 mL) and added to a stirred solution of sodium bicarbonate (136.7 mg, 1.63 mmol, 0.68 equiv) and sodium sulfite (188.3 mg, 1.49 mmol, 0.62 equiv) in water (4 mL) and the reaction mixture was vigorously stirred at 75° C. for 2 h. After cooling down to RT, iodomethane (752.6 mg, 331.5 µL, 5.3 mmol, 2.2 equiv) was added and stirring was continued overnight at 50° C. After cooling down the reaction mixture was diluted with ethyl acetate and water and the layers were separated. The aqueous layer was extracted twice with ethyl acetate. The organic layers were washed once with water, dried over MgSO$_4$, filtered, treated with silica gel and evaporated. The crude product was purified by silica gel chromatography using a MPLC system eluting with a gradient of n-heptane:ethyl acetate (100:0 to 50:50) to get the title compound as a light yellow solid (105 mg, 13%). MS (ESI): m/z=271.9 [M+H]$^+$.

Step 2: Tert-Butyl 3-[4-(5-chloro-3-methylsulfonyl-2-pyridyl)phenyl]azetidine-1-carboxylate A mixture of 2-bromo-5-chloro-3-methylsulfonyl-pyridine (105 mg, 0.31 mmol, 1.0 equiv), tert-butyl 3-[4-(4,4,5,5-tetramethyl-1,3,2-dioxaborolan-2-yl)phenyl]azetidine-1-carboxylate (116.2 mg, 0.31 mmol, 1.0 eq; CAS RN 1613259-77-0), potassium carbonate (214.6 mg, 1.55 mmol, 5.0 equiv) and tetrakis(triphenylphosphine)palladium(0) (17.9 mg, 0.016 mmol, 0.05 equiv) in THF (1.5 mL) and water (0.15 mL) was vigorously stirred under Ar at 80° C. for 6 h. The reaction mixture was poured on water and ethyl acetate and the layers were separated. The aqueous layer was extracted twice with ethyl acetate. The organic layers were washed with water, combined and dried over MgSO$_4$, filtered, treated with silica gel and evaporated. The crude compound was purified by silica gel chromatography using a MPLC system eluting with a gradient of n-heptane:ethyl acetate (100:0 to 50:50) to give the desired product as a light brown gum (109 mg, 83%). MS (ESI): m/z=367.1 [M+2H-tBu]$^+$.

Step 3: 2-[4-(Azetidin-3-yl)phenyl]-5-chloro-3-methylsulfonyl-pyridine: 4-methylbenzenesulfonic Acid The title compound was obtained in analogy to BB 4/Step 2 starting from tert-butyl 3-[4-(5-chloro-3-methylsulfonyl-2-pyridyl)phenyl]azetidine-1-carboxylate (109 mg, 0.26 mmol, 1.0 equiv) as a colorless solid (94 mg, 74%). MS (ESI): m/z=323.0 [M+H]$^+$.

BB 71

5-(Azetidin-3-yl)-2-(2-chloro-4-methylsulfonyl-phenyl)pyridine; 4-methylbenzenesulfonic Acid Step 1: Tert-Butyl 3-(6-bromo-3-pyridyl)azetidine-1-carboxylate To a solution of tert-butyl 3-iodoazetidine-1-carboxylate (1.0 g, 3.53 mmol, 1.0 equiv; CAS RN 254454-54-1) in isopropanol (10 mL) were added (6-bromo-3-pyridyl)boronic acid (1.43 g, 7.06 mmol, 2.0 equiv; CAS RN 223463-14-7), rac-(1S,2S)-2-aminocyclohexanol (24.4 mg, 0.21 mmol, 0.06 equiv), nickel(II) iodide (66.2 mg, 0.21 mmol, 0.06 equiv) and sodium bis(trimethylsilyl)amide (3.53 mL, 7.06 mmol, 2.0 equiv; 2 M in THF) and the reaction mixture was stirred under Ar at RT for 10 min before it was heated to 80° C. for 30 min by microwave irradiation. The reaction mixture was poured on water and ethyl acetate and the layers were filtered. The aqueous layer was extracted twice with ethyl acetate. The combined organic layers were washed with water, dried over MgSO$_4$, filtered, treated with silica gel and evaporated. The crude compound was purified by silica gel chromatography using a MPLC system eluting with a gradient of n-heptane:ethyl acetate (100:0 to 50:50) to get the title compound as a colorless semi-solid (0.44 g, 38%). MS (ESI): m/z=315.1 [M+H]$^+$.

Step 2: Tert-Butyl 3-[6-(2-chloro-4-methylsulfonyl-phenyl)-3-pyridyl]azetidine-1-carboxylate The title compound was obtained in analogy to BB 63/Step 1 starting from tert-butyl 3-(6-bromo-3-pyridyl)azetidine-1-carboxylate (109 mg, 0.26 mmol, 1.0 equiv) and 2-(2-chloro-4-methylsulfonyl-phenyl)-4,4,5,5-tetramethyl-1,3,2-dioxaborolane (279 mg, 0.88 mmol, 1.2 equiv; CAS RN 2377012-74-1) as a light brown oil (0.31 g, 92%). MS (ESI): m/z=423.1 [M+H]$^+$.

Step 3: 5-(Azetidin-3-yl)-2-(2-chloro-4-methylsulfonyl-phenyl)pyridine; 4-methylbenzenesulfonic Acid The title compound was obtained in analogy to BB 4/Step 2 starting from tert-butyl 3-[6-(2-chloro-4-methylsulfonyl-phenyl)-3-pyridyl]azetidine-1-carboxylate (306 mg, 0.67 mmol, 1.0 equiv) as a colorless solid (0.36 g, 80%). MS (ESI): m/z=323.0 [M+H]$^+$.

BB 72

5-(Azetidin-3-yl)-2-(4-chloro-2-methylsulfonyl-phenyl)pyridine; 4-methylbenzenesulfonic Acid Step 1: Tert-Butyl 3-[6-(4-chloro-2-methylsulfonyl-phenyl)-3-pyridyl]azetidine-1-carboxylate The title compound was obtained in analogy to BB 63/Step 1 starting from tert-butyl 3-(6-chloro-3-pyridyl)azetidine-1-carboxylate (170 mg, 0.63 mmol, 1.0 equiv; CAS RN 87069-19-3) and 2-(4-chloro-2-methylsulfonyl-phenyl)-4,4,5,5-tetramethyl-1,3,2-dioxaborolane (210.3 mg, 0.66 mmol, 1.1 equiv; CAS RN 13136117-75-2) as a light yellow gum (114 mg, 41%). MS (ESI): m/z=423.1 [M+H]$^+$.

Step 2: 5-(Azetidin-3-yl)-2-(4-chloro-2-methylsulfonyl-phenyl)pyridine; 4-methylbenzenesulfonic Acid The title compound was obtained in analogy to BB 4/Step 2 starting from tert-butyl 3-[6-(4-chloro-2-methylsulfonyl-phenyl)-3-pyridyl]azetidine-1-carboxylate (114 mg, 0.26 mmol, 1.0 equiv) as a light yellow foam (184 mg, 96%). MS (ESI): m/z=323.0 [M+H]$^+$.

BB 73

5-[4-(Azetidin-3-yl)phenyl]-2-chloro-4-methylsulfonyl-pyridine; 4-methylbenzenesulfonic Acid Step 1: 2-Chloro-5-iodo-4-methylsulfonyl-pyridine To a suspension of 2-chloro-4-fluoro-5-iodo-pyridine (100 mg, 0.39 mmol, 1.0 equiv; CAS RN 1370534-60-3) in DMSO (0.5 mL) under Ar was added sodium methanesulfinate (39.7 mg, 0.39 mmol, 1.0 equiv) and the suspension was stirred at 75° C. overnight. Another batch of sodium methanesulfinate (19.8 mg, 0.19 mmol, 0.5 equiv) was added and the reaction left to stir for 1 h. The reaction was poured on water (10 mL) and the aqueous phase extracted with ethyl acetate (3×10 mL). The combined organic layers were dried over Na$_2$SO$_4$, filtered and evaporated to give the desired product as a waxy orange solid (109 mg, 84%). MS (ESI): m/z=317.9 [M+H]$^+$.

Step 2: Tert-butyl 3-[4-(6-Chloro-4-methylsulfonyl-3-pyridyl)phenyl]azetidine-1-carboxylate The title compound was obtained in analogy to BB 63/Step 1 starting from 2-chloro-5-iodo-4-methylsulfonyl-pyridine (200.1 mg, 0.60 mmol, 1.0 equiv) and tert-butyl 3-[4-(4,4,5,5-tetramethyl-1,3,2-dioxaborolan-2-yl)phenyl]azetidine-1-carboxylate (224 mg, 0.60 mmol, 1.0 equiv; CAS RN 1613259-77-0) as a yellow gum (109 mg, 41%). MS (ESI): m/z=367.0 [M+2H-tBu]$^+$.

Step 3: 5-[4-(Azetidin-3-yl)phenyl]-2-chloro-4-methylsulfonyl-pyridine; 4-methylbenzenesulfonic Acid The title compound was obtained in analogy to BB 4/Step 2 starting from tert-butyl 3-[4-(6-chloro-4-methylsulfonyl-3-pyridyl)phenyl]azetidine-1-carboxylate (110 mg, 0.26 mmol, 1.0 equiv) as a yellow foam (129 mg, 96%). MS (ESI): m/z=323.0 [M+H]$^+$.

BB 74

2-[4-(Azetidin-3-yl)phenyl]-5-(trifluoromethyl)pyrazine; 4-methylbenzenesulfonic Acid

Step 1: Tert-Butyl 3-[4-[5-(trifluoromethyl)pyrazin-2-yl]phenyl]azetidine-1-carboxylate The title compound was obtained in analogy to BB 63/Step 1 starting from 2-chloro-5-(trifluoromethyl)pyrazine (60 mg, 0.33 mmol, 1.0 equiv; CAS RN 799557-87-2) and tert-butyl 3-[4-(4,4,5,5-tetramethyl-1,3,2-dioxaborolan-2-yl)phenyl]azetidine-1-carboxylate (124 mg, 0.35 mmol, 1.0 equiv; CAS RN 1613259-77-0) as a colorless solid (101 mg, 78%). MS (ESI): m/z=324.1 [M+2H-tBu]$^+$.

Step 2: 2-[4-(Azetidin-3-yl)phenyl]-5-(trifluoromethyl)pyrazine; 4-methylbenzenesulfonic Acid The title compound was obtained in analogy to BB 4/Step 2 starting from tert-butyl 3-[4-[5-(trifluoromethyl)pyrazin-2-yl]phenyl]azetidine-1-carboxylate (101 mg, 0.27 mmol, 1.0 equiv) as a colorless solid (107 mg, 86%). MS (ESI): m/z=280.1 [M+H]$^+$.

BB 75

3-[4-(4-Chloro-2-fluoro-phenyl)-3-methylsulfonyl-phenyl]azetidine; 4-methylbenzenesulfonic Acid

Step 1: Tert-Butyl 3-(4-bromo-3-methylsulfonyl-phenyl)azetidine-1-carboxylate To a solution of tert-butyl 3-(4-bromo-3-fluoro-phenyl)azetidine-1-carboxylate (448 mg, 1.11 mmol, 1.0 equiv; CAS RN 2222938-11-4) in DMSO (2.8 mL) under Ar was added sodium methanethiolate (117 mg, 1.67 mmol, 1.5 equiv; CAS RN 5188-07-8) and the reaction mixture was stirred at 100° C. for 5 h. The reaction mixture was poured on water (15 mL) and ethyl acetate (15 mL) and the layers were separated. The aqueous layer was extracted twice with ethyl acetate (2×15 mL). The organic layers were washed with water, dried over MgSO$_4$, filtered and evaporated to get the desired intermediate crude product as a light yellow oil. It was dissolved in DCM (3.5 mL), cooled down in an ice-bath and under stirring 3-chloroperoxybenzoic acid (562.3 mg, 2.28 mmol, 2.1 equiv) was added. The reaction mixture was stirred at RT overnight. A suspension formed which was diluted with MeOH. Isolute was added and the reaction mixture evaporated. The crude compound was purified by silica gel chromatography using a MPLC system eluting with a gradient of n-heptane:ethyl acetate (100:0 to 0:100) to afford the desired product as a colourless gum (0.28 g, 63%). MS (ESI): m/z=335.9 [M+2H-tBu]$^+$.

Step 2: Tert-Butyl 3-[4-(4-chloro-2-fluoro-phenyl)-3-methylsulfonyl-phenyl]azetidine-1-carboxylate The title compound was obtained in analogy to BB 63/Step 1 starting from tert-butyl 3-(4-bromo-3-methylsulfonyl-phenyl)azetidine-1-carboxylate (139 mg, 0.32 mmol, 1.0 equiv) and (4-chloro-2-fluoro-phenyl)boronic acid (83.8 mg, 0.48 mmol, 1.5 equiv; CAS RN 160591-91-3) as a white foam (86 mg, 58%). MS (ESI): m/z=384.0 [M+2H-tBu]$^+$.

Step 3: 3-[4-(4-Chloro-2-fluoro-phenyl)-3-methylsulfonyl-phenyl]azetidine; 4-methylbenzenesulfonic Acid The title compound was obtained in analogy to BB 4/Step 2 starting from tert-butyl 3-[4-(4-chloro-2-fluoro-phenyl)-3-methylsulfonyl-phenyl]azetidine-1-carboxylate (85 mg, 0.19 mmol, 1.0 equiv) as a yellow foam (93 mg, 90%). MS (ESI): m/z=340.0 [M+H]$^+$.

BB 76

2-(Azetidin-3-yl)-5-(4-chloro-2-methylsulfonyl-phenyl)pyridine; 4-methylbenzenesulfonic Acid

Step 1: Tert-Butyl 3-[5-(4-chloro-2-methylsulfonyl-phenyl)-2-pyridyl]azetidine-1-carboxylate The title compound was obtained in analogy to BB 63/Step 1 starting from tert-butyl 3-(5-bromo-2-pyridyl)azetidine-1-carboxylate (227.5 mg, 0.69 mmol, 1.0 equiv; CAS RN 1922143-52-9) and 2-(4-chloro-2-methylsulfonyl-phenyl)-4,4,5,5-tetramethyl-1,3,2-dioxaborolane (230 mg, 0.69 mmol, 1.0 equiv; CAS RN 13136117-75-2) as a colorless foam (221 mg, 76%). MS (ESI): m/z=367.0 [M+2H-tBu]$^+$.

Step 2: 2-(Azetidin-3-yl)-5-(4-chloro-2-methylsulfonyl-phenyl)pyridine; 4-methylbenzenesulfonic Acid The title compound was obtained in analogy to BB 4/Step 2 starting from tert-butyl 3-[5-(4-chloro-2-methylsulfonyl-phenyl)-2-pyridyl]azetidine-1-carboxylate (221 mg, 0.52 mmol, 1.0 equiv) as a light yellow foam (342 mg, 88%). MS (ESI): m/z=323.0 [M+H]$^+$.

BB 77

2-(Azetidin-3-yl)-5-(2-chloro-4-methylsulfonyl-phenyl)pyrimidine; 4-methylbenzenesulfonic Acid

Step 1: Tert-Butyl 3-[5-(2-chloro-4-methylsulfonyl-phenyl)pyrimidin-2-yl]azetidine-1-carboxylate The title compound was obtained in analogy to BB 63/Step 1 starting tert-butyl 3-(5-bromopyrimidin-2-yl)azetidine-1-carboxylate (100 mg, 0.19 mmol, 1.0 equiv; CAS RN 2224427-47-6) and 2-(2-chloro-4-methylsulfonyl-phenyl)-4,4,5,5-tetramethyl-1,3,2-dioxaborolane (90.7 mg, 0.29 mmol, 1.5 equiv; CAS RN 2377012-74-1) as a colorless foam (100 mg, 99%). MS (ESI): m/z=368.0 [M+2H-tBu]$^+$.

Step 2: 2-(Azetidin-3-yl)-5-(2-chloro-4-methylsulfonyl-phenyl)pyrimidine: 4-methylbenzenesulfonic Acid The title compound was obtained in analogy to BB 4/Step 2 starting from tert-butyl 3-[5-(2-chloro-4-methylsulfonyl-phenyl)pyrimidin-2-yl]azetidine-1-carboxylate (100 mg, 0.19 mmol, 1.0 equiv) as a colorless solid (107 mg, 85%). MS (ESI): m/z=324.0 [M+H]$^+$.

BB 78

5-(Azetidin-3-yl)-2-(2-chloro-4-methylsulfonyl-phenyl)pyrimidine; 4-methylbenzenesulfonic Acid

Step 1: Tert-Butyl 3-(2-chloropyrimidin-5-yl)azetidine-1-carboxylate

The title compound was obtained in analogy to BB 60/Step 1 starting from tert-butyl 3-iodoazetidine-1-carboxylate (0.61 mL, 3.53 mmol, 1.0 equiv; CAS RN 254454-54-1) and 5-bromo-2-chloro-pyrimidine (0.72 g, 3.71 mmol, 1.1 equiv; CAS RN 32779-36-5) as a brown oil (0.46 g, 44%). MS (ESI): m/z=214.0 [M+2H-tBu]$^+$.

Step 2: Tert-Butyl 3-[2-(2-chloro-4-methylsulfonyl-phenyl)pyrimidin-5-yl]azetidine-1-carboxylate The title compound was obtained in analogy to BB 63/Step 1 starting from tert-butyl 3-(2-chloropyrimidin-5-yl)azetidine-1-carboxylate (100 mg, 0.19 mmol, 1 equiv) and 2-(2-chloro-4-methylsulfonyl-phenyl)-4,4,5,5-tetramethyl-1,3,2-dioxaborolane (91 mg, 0.29 mmol, 1.0 equiv; CAS RN 2377012-74-1) as a colorless foam (100 mg, 99%). MS (ESI): m/z=368.0 [M+2H-tBu]$^+$.

Step 3: 5-(Azetidin-3-yl)-2-(2-chloro-4-methylsulfonyl-phenyl)pyrimidine; 4-methylbenzenesulfonic Acid The title compound was obtained in analogy to BB 4/Step 2 starting from tert-butyl 3-[2-(2-chloro-4-methylsulfonyl-phenyl)pyrimidin-5-yl]azetidine-1-carboxylate (305 mg, 0.604 mmol, 1 equiv) as a light yellow foam (107 mg, 85%). MS (ESI): m/z=324.0 [M+H]$^+$.

BB 79

3-[4-(Azetidin-3-yl)phenyl]-2-methylsulfonyl-5-(trifluoromethyl)pyridine; 4-methylbenzenesulfonic Acid

Step 1: 3-Bromo-2-methylsulfonyl-5-(trifluoromethyl)pyridine

To a solution of 3-bromo-2-fluoro-5-(trifluoromethyl)pyridine (0.34 mL, 2.05 mmol, 1.0 equiv; CAS RN 1031929-01-7) in DMSO (2.6 mL) under Ar was added sodium methanethiolate (259 mg, 2.46 mmol, 1.2 equiv; CAS RN 5188-07-8) and the suspension was stirred at 80° C. for 72 h. The reaction mixture was poured on water (15 mL) and ethyl acetate (15 mL) and the layers were separated. The aqueous layer was extracted twice with ethyl acetate (2×15 mL). The organic layers were washed with water, dried over MgSO$_4$, filtered, treated with silica gel and evaporated. The crude compound was purified by silica gel chromatography using a MPLC system eluting with a gradient of n-heptane:ethyl acetate (100:0 to 0:100) to yield the title compound as a colorless solid (260 mg, 38%). MS (ESI): m/z=305.9 [M+H]$^+$.

Step 2: Tert-Butyl 3-[4-[2-methylsulfonyl-5-(trifluoromethyl)-3-pyridyl]phenyl]azetidine-1-carboxylate The title compound was obtained in analogy to BB 63/Step 1 starting from tert-butyl 3-[4-(4,4,5,5-tetramethyl-1,3,2-dioxaborolan-2-yl)phenyl]azetidine-1-carboxylate (94.5 mg, 0.26 mmol, 1.0 equiv; CAS RN 1613259-77-0) and 3-bromo-2-methylsulfonyl-5-(trifluoromethyl)pyridine (80 mg, 0.263 mmol, 1.0 equiv) as a colorless gum (65 mg, 48%). MS (ESI): m/z=401.0 [M+2H-tBu]$^+$.

Step 3: 3-[4-(Azetidin-3-yl)phenyl]-2-methylsulfonyl-5-(trifluoromethyl)pyridine; 4-methylbenzenesulfonic Acid The title compound was obtained in analogy to BB 4/Step 2 starting from tert-butyl 3-[4-[2-methylsulfonyl-5-(trifluoromethyl)-3-pyridyl]phenyl]azetidine-1-carboxylate (65 mg, 0.13 mmol, 1.0 equiv) as a yellow gum (84 mg, 71%). MS (ESI): m/z=357.0 [M+H]$^+$.

BB 80

4-Methylbenzenesulfonic Acid; 6-[[6-(trifluoromethyl)-3-pyridyl]methyl]-2-azaspiro[3.3]heptane

Step 1: Tert-Butyl 6-[(4,4,5,5-tetramethyl-1,3,2-dioxaborolan-2-yl)methylene]-2-azaspiro[3.3]heptane-2-carboxylate To a solution of 2,2,6,6-tetramethylpiperidine (9.59 mL, 56.8 mmol, 1.2 equiv; CAS RN 768-66-1) in THF (120 mL) at −30° C. under an atmosphere of N$_2$ was added dropwise n-BuLi (22.7 mL, 56.8 mmol, 1.2 equiv) and the reaction mixture was stirred at the same temperature for 30 min. Next, the reaction was cooled to −78° C., and a solution of tert-butyl 6-oxo-2-azaspiro[3.3]heptane-2-carboxylate (10 g, 47.3 mmol, 1.0 eq; CAS RN 1181816-12-5) in THF (120 mL) was added dropwise. After stirring for 30 min, a solution of 4,4,5,5-tetramethyl-2-[(4,4,5,5-tetramethyl-1,3,2-dioxaborolan-2-yl)methyl]-1,3,2-dioxaborolane (14.0 g, 52.1 mmol, 1.1 equiv; CAS RN 78782-17-9) in THF (48 mL) was added dropwise at −78° C. The reaction mixture was allowed to slowly warm up to RT, and stirred for 12 h. The reaction mixture was quenched with a sat. aqueous NH$_4$Cl solution (500 mL) and extracted with ethyl acetate (3×300 mL). The combined organic phases were dried over MgSO$_4$ and concentrated under vacuum. The crude product was purified by silica gel chromatography eluting with petroleum ether:ethyl acetate (90:10) to give the title compound as a white solid (14 g, 88%). $^1$H NMR (400 MHz, CDCl$_3$): δ=5.12 (quin, J=2.3 Hz, 1H), 3.94-3.79 (m, 4H), 3.01 (d, J=2.4 Hz, 2H), 2.86 (d, J=1.4 Hz, 2H), 1.36 (s, 9H), 1.17 (s, 12H).

Step 2: Tert-Butyl 6-[[6-(trifluoromethyl)-3-pyridyl]methylene]-2-azaspiro[3.3]heptane-2-carboxylate To a solution of 5-bromo-2-(trifluoromethyl)pyridine (67.4 mg, 0.30 mmol, 1.0 equiv; CAS RN 436799-32-5) and tert-butyl 6-[(4,4,5,5-tetramethyl-1,3,2-dioxaborolan-2-yl)methylene]-2-azaspiro[3.3]heptane-2-carboxylate (100 mg, 0.30 mmol, 1.0 equiv), potassium carbonate (82.5 mg, 0.60 mmol, 2.0 equiv) in 1,4-dioxane (2 mL) and water (0.4 mL) was added 1,1'-bis(diphenylphosphino)ferrocene-palladium (II) dichloride dichloromethane complex (24.3 mg, 0.03 mmol, 0.1 equiv), and the reaction mixture was stirred under an atmosphere of N$_2$ at 80° C. for 12 h. The crude product was purified by silica gel chromatography eluting with a gradient of petroleum ether:ethyl acetate (100:0 to 90:10) to give the title compound as a colorless solid (43 mg, 41%). MS (ESI): m/z=355.1 [M+H]+.

Step 3: Tert-Butyl 6-[[6-(trifluoromethyl)-3-pyridyl]methyl]-2-azaspiro[3.3]heptane-2-carboxylate To a solution of tert-butyl 6-[[6-(trifluoromethyl)-3-pyridyl]methylene]-2-azaspiro[3.3]heptane-2-carboxylate (1.2 g, 3.37 mmol, 1.0 equiv) in ethyl acetate (50 mL) was added wet Pd/C (300 mg, 3.37 mmol, 1.0 equiv; wt. 10%) and the reaction mixture was stirred at RT for 12 h under an atmosphere of $H_2$ (balloon). The suspension was filtered over Dicalite and the filtrate evaporated to get the title compound as light yellow oil (1.0 g, 83%). MS (ESI): m/z=301.2 [M+2H-tBu]+.

Step 4: 4-Methylbenzenesulfonic acid; 6-[[6-(trifluoromethyl)-3-pyridyl]methyl]-2-azaspiro[3.3]heptane The title compound was obtained in analogy to BB 4/Step 2 starting from tert-butyl 6-[[6-(trifluoromethyl)-3-pyridyl]methyl]-2-azaspiro[3.3]heptane-2-carboxylate (1.3 g, 3.65 mmol, 1.0 equiv) as a white solid (2.0 g, 90%). MS (ESI): m/z=257.1 [M+H]+.

BB 81

7-[[2-Fluoro-4-(trifluoromethyl)phenyl]methyl]-2,7-diazaspiro[3.5]nonane; 4-methylbenzenesulfonic Acid Step 1: Tert-Butyl 7-[[2-fluoro-4-(trifluoromethyl)phenyl]methyl]-2,7-diazaspiro[3.5]nonane-2-carboxylate To a solution of 2-fluoro-4-(trifluoromethyl)benzaldehyde (1.0 g, 5.21 mmol, 1.0 equiv; CAS RN 89763-93-9) and tert-butyl 2,7-diazaspiro[3.5]nonane-2-carboxylate (1.18 g, 5.21 mmol, 1.0 equiv; CAS RN 236406-55-6) in DCM (10 mL) was added sodium triacetoxy borohydride (1.21 g, 5.73 mmol, 1.1 equiv) and acetic acid (0.63 g, 0.60 mL, 10.4 mmol, 2.0 equiv) and the reaction mixture was stirred at RT. After 4 h, the reaction mixture was poured into a mixture of ethyl acetate:THF (2:1), washed with a sat. aqueous $NaHCO_3$ solution and water and extracted with ethyl acetate. The combined organic phases were dried over $Na_2SO_4$ and concentrated under vacuum. The crude compound was purified by silica gel chromatography using a MPLC system eluting with a gradient of n-heptane:ethyl acetate (100:0 to 70:30) to yield the title compound as a white solid (1.23 g, 56%). MS (ESI): m/z=403.4 [M+H]+.

Step 2: 7-[[2-Fluoro-4-(trifluoromethyl)phenyl]methyl]-2,7-diazaspiro[3.5]nonane: 4-methylbenzenesulfonic Acid The title compound was obtained in analogy to BB 4/Step 2 starting from tert-butyl 7-[[2-fluoro-4-(trifluoromethyl)phenyl]methyl]-2,7-diazaspiro[3.5]nonane-2-carboxylate (1.23 g, 2.9 mmol, 1.0 equiv) as a white solid (1.75 g, 89%). MS (ESI): m/z=303.1 [M+H]+.

BB 82

2-[4-(Azetidin-3-yl)phenoxy]-4-(trifluoromethyl)pyrimidine; 4-methylbenzenesulfonic Acid Step 1: Tert-Butyl 3-[4-[4-(trifluoromethyl)pyrimidin-2-yl]oxyphenyl]azetidine-1-carboxylate To a solution of tert-butyl 3-(4-hydroxyphenyl)azetidine-1-carboxylate (500 mg, 2.01 mmol, 1.0 equiv; BB 15/Step 1; CAS RN 1782327-13-2) and 2-chloro-4-(trifluoromethyl)pyrimidine (0.55 g, 0.36 mL, 3.01 mmol, 1.5 equiv; CAS RN 33034-67-2) in dry DMF (15 mL) were added cesium carbonate (1.31 g, 4.03 mmol, 2.01 equiv) and Cu (12.8 mg, 0.20 mmol, 0.10 equiv) powder and the reaction mixture was stirred under an atmosphere of $N_2$ at 100° C. for 2.5 h. The suspension was filtered over Dicalite and the filtrate evaporated. The crude compound was purified by silica gel chromatography using a MPLC system eluting with a gradient of n-heptane:TBME (95:5 to 60:40) to yield the title compound as a light yellow solid (0.74 g, 93%). MS (ESI): m/z=340.2 [M+2H-tBu]+.

Step 2: 2-[4-(Azetidin-3-yl)phenoxy]-4-(trifluoromethyl)pyrimidine; 4-methylbenzenesulfonic Acid The title compound was obtained in analogy to BB 4/Step 2 starting from tert-butyl 3-[4-[4-(trifluoromethyl)pyrimidin-2-yl]oxyphenyl]azetidine-1-carboxylate (0.73 g, 1.85 mmol, 1.0 equiv) as a white solid (0.73 g, 84%). MS (ESI): m/z=296.1 [M+H]+.

BB 83

4-Methylbenzenesulfonic Acid; 3-[4-[4-methylsulfonyl-2-(trifluoromethyl)phenyl]phenyl]azetidine Step 1: Tert-Butyl 3-[4-[4-methylsulfonyl-2-(trifluoromethyl)phenyl]phenyl]azetidine-1-carboxylate The title compound was obtained in analogy to BB 63/Step 1 starting from tert-butyl 3-(4-bromophenyl)azetidine-1-carboxylate (112 mg, 0.36 mmol, 1.0 equiv; BB 6/Step 1; CAS RN 1203681-52-0) and 4,4,5,5-tetramethyl-2-[4-methylsulfonyl-2-(trifluoromethyl)phenyl]-1,3,2-dioxaborolane (132 mg, 0.36 mmol, 1.0 equiv; CAS RN 1628013-46-6) as a light yellow solid (96 mg, 59%). MS (ESI): m/z=400.01 [M+H]+.

Step 2: 4-Methylbenzenesulfonic Acid; 3-[4-[4-methylsulfonyl-2-(trifluoromethyl)phenyl]phenyl]azetidine The title compound was obtained in analogy to BB 4/Step 2 starting from tert-butyl 3-[4-[4-methylsulfonyl-2-(trifluoromethyl)phenyl]phenyl]azetidine-1-carboxylate (0.73 g, 1.85 mmol, 1.0 equiv) as a yellow gum (61 mg, 55%). MS (ESI): m/z=356.1 [M+H]+.

BB 84

1-[4-(Azetidin-3-yl)-2-fluoro-phenyl]-3-(trifluoromethyl)pyrrolidine; 4-methylbenzenesulfonic Acid Step 1: Tert-Butyl 3-(4-bromo-3-fluoro-phenyl)azetidine-1-carboxylate The title compound was obtained in analogy to BB 71/Step 1 starting from tert-butyl 3-iodoazetidine-1-car boxylate (0.80 g, 2.83 mmol, 1.0 equiv; CAS RN 254454-54-1) and (4-bromo-3-fluoro-phenyl)boronic acid (1.24 g, 5.65 mmol, 2.0 equiv; CAS RN 374790-97-3) as a colorless oil (469 mg, 42%). MS (ESI): m/z=274.0 [M+2H-tBu]$^+$.

Step 2: Tert-Butyl 3-[3-fluoro-4-[3-(trifluoromethyl)pyrrolidin-1-yl]phenyl]azetidine-1-carboxylate The title compound was obtained in analogy to BB 58/Step 1 starting from tert-butyl 3-(4-bromo-3-fluoro-phenyl)azetidine-1-carboxylate (100 mg, 0.25 mmol, 1.0 equiv) and 3-(trifluoromethyl)pyrrolidine; hydrochloride (44.1 mg, 37.4 µL, 0.25 mmol, 1.0 equiv; CAS RN 1189485-03-7) as a colorless oil (21 mg, 17%). MS (ESI): m/z=389.2 [M+H]$^+$.

Step 3: 1-[4-(Azetidin-3-yl)-2-fluoro-phenyl]-3-(trifluoromethyl)pyrrolidine; 4-methylbenzenesulfonic Acid The title compound was obtained in analogy to BB 4/Step 2 starting from tert-butyl 3-[3-fluoro-4-[3-(trifluoromethyl)pyrrolidin-1-yl]phenyl]azetidine-1-carboxylate (21 mg, 0.042 mmol, 1.0 equiv) as an orange gum (26 mg, 89%). MS (ESI): m/z=289.1 [M+H]$^+$.

BB 85

3-[4-(Azetidin-3-yl)phenyl]thiolane 1,1-dioxide; 4-methylbenzenesulfonic Acid

Step 1: Tert-Butyl 3-[4-(1,1-dioxothiolan-3-yl)phenyl]azetidine-1-carboxylate

The title compound was obtained in analogy to BB 4/Step 1 starting from tert-butyl 3-(4-bromophenyl)azetidine-1-carboxylate (0.50 g, 1.6 mmol, 1.0 equiv; BB 6/Step 1; CAS RN 1203681-52-0) and 3-bromosulfolane (0.48 g, 2.4 mmol, 1.5 equiv; CAS RN 14008-53-8) by irradiating (420 nm) for 16 h as a colorless oil (102 mg, 5%). MS (ESI): m/z=296.1 [M+2H-tBu]$^+$.

Step 2: 3-[4-(Azetidin-3-yl)phenyl]thiolane 1,1-dioxide; 4-methylbenzenesulfonic Acid The title compound was obtained in analogy to BB 4/Step 2 starting from tert-butyl 3-[4-(1,1-dioxothiolan-3-yl)phenyl]azetidine-1-carboxylate (102 mg, 0.073 mmol, 1.0 equiv) as an off-white solid (122 mg, 99%). MS (ESI): m/z=252.1 [M+H]$^+$.

BB 86

2-[4-(Azetidin-3-yl)phenyl]-2-azaspiro[3.4]octane; 4-methylbenzenesulfonic Acid

Step 1: Tert-Butyl 3-[4-(2-azaspiro[3.4]octan-2-yl)phenyl]azetidine-1-carboxylate The title compound was obtained in analogy to BB 58/Step 1 starting from tert-butyl 3-(4-bromophenyl)azetidine-1-carboxylate (140 mg, 0.45 mmol, 1.0 equiv; BB 6/Step 1; CAS RN 1203681-52-0) and 2-azaspiro[3.4]octane (49.9 mg, 0.45 mmol, 1.0 equiv; CAS RN 665-41-8) as an orange gum (118 mg, 69%). MS (ESI): m/z=343.2 [M+H]$^+$.

Step 2: 2-[4-(Azetidin-3-yl)phenyl]-2-azaspiro[3.4]octane; 4-methylbenzenesulfonic Acid The title compound was obtained in analogy to BB 4/Step 2 starting from tert-butyl 3-[4-(2-azaspiro[3.4]octan-2-yl)phenyl]azetidine-1-carboxylate (110 mg, 0.29 mmol, 1.0 equiv) as a light yellow solid (165 mg, 88%). MS (ESI): m/z=243.2 [M+H]$^+$.

BB 87

2-[4-(Azetidin-3-yl)phenyl]-6,6-difluoro-2-azaspiro[3.3]heptane; 4-methylbenzenesulfonic Acid Step 1: Tert-Butyl 3-[4-(6,6-difluoro-2-azaspiro[3.3]heptan-2-yl)phenyl]azetidine-1-carboxylate The title compound was obtained in analogy to BB 58/Step 1 starting from tert-butyl 3-(4-bromophenyl)azetidine-1-carboxylate (130 mg, 0.42 mmol, 1.0 equiv; BB 6/Step 1; CAS RN 1203681-52-0) and 6,6-difluoro-2-azaspiro[3.3]heptane; hydrochloride (70.6 mg, 0.42 mmol, 1.0 equiv; CAS RN 1420294-83-2) as an off-white solid (98 mg, 64%). MS (ESI): m/z=365.2 [M+H]$^+$.

Step 2: 2-[4-(Azetidin-3-yl)phenyl]-6,6-difluoro-2-azaspiro[3.3]heptane; 4-methylbenzenesulfonic Acid The title compound was obtained in analogy to BB 4/Step 2 starting from tert-butyl 3-[4-(6,6-difluoro-2-azaspiro[3.3]heptan-2-yl)phenyl]azetidine-1-carboxylate (102 mg, 0.28 mmol, 1.0 equiv) as an orange gum (173 mg, 97%). MS (ESI): m/z=265.2 [M+H]$^+$.

BB 88

4-Methylbenzenesulfonic acid; 3-[4-[3-(trifluoromethyl)cyclobutyl]phenyl]azetidine Step 1: Tert-Butyl 3-[4-[3-(trifluoromethyl)cyclobutyl]phenyl]azetidine-1-carboxylate The title compound was obtained in analogy to BB 4/Step 1 starting from tert-butyl 3-(4-bromophenyl)azetidine-1-carboxylate (250 mg, 0.80 mmol, 1.0 equiv; BB 6/Step 1; CAS RN 1203681-52-0) and 1-bromo-3-(trifluoromethyl)cyclobutane (178.8 mg, 0.88 mmol, 1.1 equiv; CAS RN 2247103-30-4) by irradiating (420 nm) for 16 h as a colorless oil (100 mg, 26%). MS (ESI): m/z=300.1 [M+2H-tBu]$^+$.

Step 2: 4-Methylbenzenesulfonic Acid; 3-[4-[3-(trifluoromethyl)cyclobutyl]phenyl]azetidine The title compound was obtained in analogy to BB 4/Step 2 starting from tert-butyl 3-[4-[3-(trifluoromethyl)cyclobutyl]phenyl]azetidine-1-carboxylate (100 mg, 0.21 mmol, 1.0 equiv) as an off-white solid (116 mg, 97%). MS (ESI): m/z=256.1 [M+H]$^+$.

BB 89

1-[4-(Azetidin-3-yl)-2-fluoro-phenyl]-3-(trifluoromethyl)azetidine; 4-methylbenzenesulfonic Acid Step 1: tert-Butyl 3-[3-fluoro-4-[3-(trifluoromethyl)azetidin-1-yl]phenyl]azetidine-1-carboxylate The title compound was obtained in analogy to BB 58/Step 1 starting from tert-butyl 3-(4-bromo-3-fluoro-phenyl)azetidine-1-carboxylate (167.8 mg, 0.42 mmol, 1.0 equiv; BB 84/Step 1; CAS RN 2222938-11-4) and 3-(trifluoromethyl)azetidine (45.1 µL, 0.42 mmol, 1.0 equiv; CAS RN 1221349-18-3) as an off-white solid (94 mg, 57%). MS (ESI): m/z=319.1 [M+2H-tBu]$^+$.

Step 2: 2-[4-(Azetidin-3-yl)phenyl]-6,6-difluoro-2-azaspiro[3.3]heptane; 4-methylbenzenesulfonic Acid The title compound was obtained in analogy to BB 4/Step 2 starting from tert-butyl 3-[3-fluoro-4-[3-(trifluoromethyl) azetidin-1-yl]phenyl]azetidine-1-carboxylate (94 mg, 0.25 mmol, 1.0 equiv) as an off-white solid (151 mg, 57%). MS (ESI): m/z=275.1 [M+H]$^+$.

BB 90

1-[4-(Azetidin-3-yl)phenyl]-3-(trifluoromethyl)pyrrolidine; 4-methylbenzenesulfonic Acid Step 1: Tert-Butyl 3-[4-[3-(trifluoromethyl)pyrrolidin-1-yl]phenyl]azetidine-1-carboxylate The title compound was obtained in analogy to BB 58/Step 1 starting from tert-butyl 3-(4-bromophenyl)azetidine-1-carboxylate (130 mg, 0.42 mmol, 1.0 equiv; BB 6/Step 1; CAS RN 1203681-52-0) and 3-(trifluoromethyl)pyrrolidine; hydrochloride (73.1 mg, 0.42 mmol, 1.0 equiv; CAS RN 1189485-03-7) as a waxy orange solid (99 mg, 61%). MS (ESI): m/z=371.2 [M+2H-tBu]$^+$.

Step 2: 1-[4-(Azetidin-3-yl)phenyl]-3-(trifluoromethyl)pyrrolidine; 4-methylbenzenesulfonic Acid The title compound was obtained in analogy to BB 4/Step 2 starting from tert-butyl 3-[4-[3-(trifluoromethyl)pyrrolidin-1-yl]phenyl]azetidine-1-carboxylate (99 mg, 0.27 mmol, 1.0 equiv) as an off-white solid (139 mg, 60%). MS (ESI): m/z=271.1 [M+H]$^+$.

BB 91

4-Methylbenzenesulfonic Acid; 7-[6-(trifluoromethyl)pyridazin-3-yl]oxy-2-azaspiro[3.5]nonane Step 1: Tert-Butyl 7-[6-(trifluoromethyl)pyridazin-3-yl]oxy-2-azaspiro[3.5]nonane-2-carboxylate To a solution of tert-butyl 7-hydroxy-2-azaspiro[3.5] nonane-2-carboxylate (350 mg, 1.45 mmol, 1.0 equiv; CAS RN 1363383-18-9) and potassium tert-butoxide (195.3 mg, 1.74 mmol, 1.2 equiv) in DMF (3.5 mL) was added 3-fluoro-6-(trifluoromethyl)pyridazine (248.1 mg, 1.49 mmol, 1.03 eq; CAS RN 1206524-32-4) and the reaction mixture was stirred at 80° C. After 15 h, the reaction mixture was poured into ethyl acetate, washed with a sat. aqueous NaCl solution and water and extracted with ethyl acetate. The combined organic phases were dried over Na$_2$SO$_4$ and concentrated under vacuum. The crude compound was purified by silica gel chromatography using a MPLC system eluting with a gradient of n-heptane:ethyl acetate (100:0 to 60:40) to yield the title compound as a white solid (353 mg, 60%). MS (ESI): m/z=332.1 [M+2H-tBu]$^+$.

Step 2: 4-Methylbenzenesulfonic Acid; 7-[6-(trifluoromethyl)pyridazin-3-yl]oxy-2-azaspiro[3.5]nonane The title compound was obtained in analogy to BB 4/Step 2 starting from tert-butyl 7-[6-(trifluoromethyl)pyridazin-3-yl]oxy-2-azaspiro[3.5]nonane-2-carboxylate (350 mg, 0.90 mmol, 1.0 equiv) as a colorless solid (420 mg, 88%). MS (ESI): m/z=288.0 [M+H]$^+$.

BB 92

7-(4-Fluoro-2-methylsulfonyl-phenoxy)-2-azaspiro [3.5]nonane; 4-methylbenzenesulfonic Acid Step 1: Tert-Butyl 7-(4-fluoro-2-methylsulfonyl-phenoxy)-2-azaspiro[3.5]nonane-2-carboxylate The title compound was obtained in analogy to BB 91/Step 1 starting from tert-butyl 7-hydroxy-2-azaspiro[3.5] nonane-2-carboxylate (300 mg, 1.24 mmol, 1.0 equiv; CAS RN 1363383-18-9) and 1,4-difluoro-2-methylsulfonyl-benzene (250.9 mg, 1.31 mmol, 1.05 equiv; CAS RN 61655-69-4) to get the title compound as a white solid (449 mg, 83%). MS (ESI): m/z=358.1 [M+2H-tBu]$^+$.

Step 2: 7-(4-Fluoro-2-methylsulfonyl-phenoxy)-2-azaspiro[3.5]nonane: 4-methylbenzenesulfonic Acid The title compound was obtained in analogy to BB 4/Step 2 starting from tert-butyl 7-(4-fluoro-2-methylsulfonyl-phenoxy)-2-azaspiro[3.5]nonane-2-carboxylate (445 mg, 1.08 mmol, 1.0 equiv) as a white solid (445 mg, 77%). MS (ESI): m/z=314.1 [M+H]$^-$.

BB 93

N-(2-Azaspiro[3.5]nonan-7-yl)-3-(trifluoromethoxy) benzenesulfonamide; 4-methylbenzenesulfonic Acid Step 1: Tert-Butyl 7-[[3-(trifluoromethoxy)phenyl] sulfonylamino]-2-azaspiro[3.5]nonane-2-carboxylate To a solution of tert-butyl 7-amino-2-azaspiro[3.5] nonane-2-carboxylate (700 mg, 2.91 mmol, 1.0 equiv; CAS RN 1408075-19-3) and DIPEA (0.76 mL, 4.37 mmol, 1.5 equiv) in DCM (12 mL) was added 3-(trifluoromethoxy) benzenesulfonyl chloride (759.1 mg, 2.91 mmol, 1.0 equiv; CAS 220227-84-9) at 0° C. The reaction mixture was allowed to warm up to RT and stirred for 2 h. The reaction mixture was poured into ethyl acetate, washed with a sat. aqueous NaCl solution and water and extracted with ethyl acetate. The combined organic phases were dried over Na$_2$SO$_4$ and concentrated under vacuum. The crude compound was purified by silica gel chromatography using a MPLC system eluting with a gradient of n-heptane:ethyl acetate (100:0 to 60:40) to yield the title compound as a white solid (1.01 g, 71%). MS (ESI): m/z=409.1 [M+2H-tBu]$^+$.

Step 2: N-(2-Azaspiro[3.5]nonan-7-yl)-3-(trifluoromethoxy)benzenesulfonamide: 4-methylbenzenesulfonic Acid The title compound was obtained in analogy to BB 4/Step 2 starting from tert-butyl 7-[[3-(trifluoromethoxy)phenyl] sulfonylamino]-2-azaspiro[3.5]nonane-2-carboxylate (1.05 g, 2.26 mmol, 1.0 equiv) as a colorless solid (1.09 g, 85%). MS (ESI): m/z=365.1 [M+H]$^+$.

BB 94

2-[5-(Azetidin-3-yl)pyrazin-2-yl]-6,6-difluoro-2-azaspiro[3.3]heptane; 4-methylbenzenesulfonic Acid

Step 1: Tert-Butyl 3-[5-(6,6-difluoro-2-azaspiro[3.3]heptan-2-yl)pyrazin-2-yl]azetidine-1-carboxylate The title compound was obtained in analogy to BB 58/Step 1 starting from tert-butyl 3-(5-bromopyrazin-2-yl)azetidine-1-carboxylate (47 mg, 0.15 mmol, 1.0 equiv; BB 60/Step 1) and 6,6-difluoro-2-azaspiro[3.3]heptane; hydrochloride (25.4 mg, 0.42 mmol, 1.0 equiv; CAS RN 1420294-83-2) as an off-white solid (18 mg, 33%). MS (ESI): m/z=367.2 $[M+H]^+$.

Step 2: 2-[5-(Azetidin-3-yl)pyrazin-2-yl]-6,6-difluoro-2-azaspiro[3.3]heptane: 4-methylbenzenesulfonic Acid The title compound was obtained in analogy to BB 4/Step 2 starting from tert-butyl 3-[5-(6,6-difluoro-2-azaspiro[3.3]heptan-2-yl)pyrazin-2-yl]azetidine-1-carboxylate (15 mg, 0.041 mmol, 1.0 equiv) as a yellow gum (23 mg, 83%). MS (ESI): m/z=267.2 $[M+H]^+$.

BB 95

2-[5-(Azetidin-3-yl)pyrazin-2-yl]-2-azaspiro[3.4]octane; 4-methylbenzenesulfonic Acid

Step 1: Tert-Butyl 3-[5-(2-azaspiro[3.4]octan-2-yl)pyrazin-2-yl]azetidine-1-carboxylate The title compound was obtained in analogy to BB 58/Step 1 starting from tert-butyl 3-(5-bromopyrazin-2-yl)azetidine-1-carboxylate (47 mg, 0.15 mmol, 1.0 equiv; BB 60/Step 1) and 2-azaspiro[3.4]octane (16.6 mg, 0.15 mmol, 1.0 equiv; CAS RN 665-41-8) as waxy light yellow solid (16 mg, 29%). MS (ESI): m/z=345.2 $[M+H]^+$.

Step 2: 2-[5-(Azetidin-3-yl)pyrazin-2-yl]-2-azaspiro[3.4]octane; 4-methylbenzenesulfonic Acid The title compound was obtained in analogy to BB 4/Step 2 starting from tert-butyl 3-[5-(2-azaspiro[3.4]octan-2-yl)pyrazin-2-yl]azetidine-1-carboxylate (12 mg, 0.035 mmol, 1.0 equiv) as a light yellow solid (20 mg, 88%). MS (ESI): m/z=245.2 $[M+H]^+$.

BB 96

2-[5-(Azetidin-3-yl)-2-pyridyl]-6,6-difluoro-2-azaspiro[3.3]heptane; 4-methylbenzenesulfonic Acid

Step 1: Tert-Butyl 3-[6-(6,6-difluoro-2-azaspiro[3.3]heptan-2-yl)-3-pyridyl]azetidine-1-carboxylate The title compound was obtained in analogy to BB 58/Step 1 starting from tert-butyl 3-(6-chloro-3-pyridyl)azetidine-1-carboxylate (100 mg, 0.37 mmol, 1.0 equiv; CAS RN 870689-19-3) and 6,6-difluoro-2-azaspiro[3.3]heptane; hydrochloride (63.1 mg, 0.37 mmol, 1.0 equiv; CAS RN 1420294-83-2) as an off-white solid (79 mg, 55%). MS (ESI): m/z=366.2 $[M+H]^+$.

Step 2: 2-[5-(Azetidin-3-yl)-2-pyridyl]-6,6-difluoro-2-azaspiro[3.3]heptane: 4-methylbenzenesulfonic Acid The title compound was obtained in analogy to BB 4/Step 2 starting from tert-butyl 3-[6-(6,6-difluoro-2-azaspiro[3.3]heptan-2-yl)-3-pyridyl]azetidine-1-carboxylate (40 mg, 0.11 mmol, 1.0 equiv) as an orange gum (73 mg, 99%). MS (ESI): m/z=266.2 $[M+H]^+$.

BB 97

2-[5-(Azetidin-3-yl)-2-pyridyl]-2-azaspiro[3.4]octane; 4-methylbenzenesulfonic Acid

Step 1: Tert-Butyl 3-[6-(2-azaspiro[3.4]octan-2-yl)-3-pyridyl]azetidine-1-carboxylate The title compound was obtained in analogy to BB 58/Step 1 starting from tert-butyl 3-(6-chloro-3-pyridyl)azetidine-1-carboxylate (78 mg, 0.29 mmol, 1.0 equiv; CAS RN 870689-19-3) and 2-azaspiro[3.4]octane (32.3 mg, 0.29 mmol, 1.0 equiv; CAS RN 665-41-8) as a yellow solid (36 mg, 35%). MS (ESI): m/z=344.2 $[M+H]^+$.

Step 2: 2-[5-(Azetidin-3-yl)-2-pyridyl]-2-azaspiro[3.4]octane; 4-methylbenzenesulfonic Acid The title compound was obtained in analogy to BB 4/Step 2 starting from tert-butyl 3-[6-(2-azaspiro[3.4]octan-2-yl)-3-pyridyl]azetidine-1-carboxylate (31 mg, 0.09 mmol, 1.0 equiv) as a light yellow solid (57 mg, 97%). MS (ESI): m/z=244.2 $[M+H]^+$.

BB 98

7-[2-Fluoro-4-(trifluoromethyl)phenyl]sulfonyl-2,7-diazaspiro[3.5]nonane; 2,2,2-trifluoroacetic Acid

Step 1: Tert-Butyl 7-[2-fluoro-4-(trifluoromethyl)phenyl]sulfonyl-2,7-diazaspiro[3.5]nonane-2-carboxylate To a solution of tert-butyl 2,7-diazaspiro[3.5]nonane-2-carboxylate (700 mg, 3.09 mmol, 1.0 equiv; CAS RN 236406-55-6) in DCM (15 mL) at 0° C. was added DIPEA (0.81 mL, 4.64 mmol, 1.5 equiv) and 2-fluoro-4-(trifluoromethyl)benzenesulfonyl chloride (852.9 mg, 3.25 mmol, 1.05 equiv; CAS RN 1177009-38-9) and the reaction mixture was stirred at 0° C. for 15 min and at RT for 1 h. The reaction mixture was diluted with DCM, washed with an aqueous $Na_2CO_3$ solution (1 M) and water and extracted with DCM. The combined organic phases were dried over $Na_2SO_4$ and concentrated under vacuum. The title compound was obtained as a brown oil and used in the consecutive reaction step without further purification (1.38 g, 94%). MS (ESI): m/z=397.1 $[M+2H-tBu]^+$.

Step 2: 7-[2-Fluoro-4-(trifluoromethyl)phenyl]sulfonyl-2,7-diazaspiro[3.5]nonane; 2,2,2-trifluoroacetic Acid To a solution of tert-butyl 7-[2-fluoro-4-(trifluoromethyl)phenyl]sulfonyl-2,7-diazaspiro[3.5]nonane-2-carboxylate (1.38 g, 3.05 mmol, 1.0 equiv) in DCM (6 mL) was added TFA (2.35 mL, 30.5 mmol, 10.0 equiv) and the reaction mixture was stirred at RT for 18 h. The reaction mixture was concentrated to provide the title compound as a brown oil (2.15 g, 91%; ca. 60% purity). MS (ESI): m/z=353.1 [M+H]$^+$.

BB 99

1-[5-(Azetidin-3-yl)-2-pyridyl]-3-(trifluoromethyl) azetidin-3-ol; 4-methylbenzenesulfonic Acid Step 1: 1-(5-Bromo-2-pyridyl)-3-(trifluoromethyl) azetidin-3-ol A solution of 3-(trifluoromethyl)azetidin-3-ol; hydrochloride (2.0 g, 11.26 mmol, 1.0 equiv; CAS RN 848192-96-1), 5-bromo-2-fluoro-pyridine (3.96 g, 22.53 mmol, 2.0 equiv; CAS RN 766-11-0) and DIPEA (4.37 g, 33.79 mmol, 3.0 equiv) in DMSO (40 mL) was stirred at 100° C. for 16 h. The reaction mixture was diluted with water and extracted with ethyl acetate, the combined organic phase was then washed with a sat. aqueous NaCl solution, dried over Na$_2$SO$_4$ and concentrated. The crude product was purified by silica gel chromatography eluting with a gradient of petroleum ether: ethyl acetate (100:0 to 70:30 to afford the title compound as a colorless solid (2.84 g, 85%). MS (ESI): m/z=297.1 [M+H]$^+$.

Step 2: Tert-Butyl 3-[6-[3-hydroxy-3-(trifluoromethyl)azetidin-1-yl]-3-pyridyl]azetidine-1-carboxylate The title compound was obtained in analogy to BB 4/Step 1 starting from 1-(5-bromo-2-pyridyl)-3-(trifluoromethyl) azetidin-3-ol (2.7 g, 9.09 mmol, 1.0 equiv) and tert-butyl 3-bromoazetidine-1-carboxylate (2.79 g, 11.82 mmol, 1.3 equiv; CAS RN 1064194-10-0) by irradiating (420 nm) for 14 h as a yellow oil (2.99 g, 88%). $^1$H NMR (400 MHz, CDCl$_3$): δ=7.99 (d, J=1.7 Hz, 1H), 7.66 (br d, J=8.7 Hz, 1H), 6.49-6.40 (m, 1H), 4.43-4.35 (m, 2H), 4.31 (t, J=8.7 Hz, 2H), 4.20 (br d, J=7.1 Hz, 2H), 3.85 (dd, J=5.9, 8.6 Hz, 2H), 3.70-3.56 (m, 1H), 1.47 (s, 9H).

Step 3: 1-[5-(Azetidin-3-yl)-2-pyridyl]-3-(trifluoromethyl)azetidin-3-ol; 4-methylbenzenesulfonic Acid The title compound was obtained in analogy to BB 4/Step 2 starting from tert-butyl 3-[6-[3-hydroxy-3-(trifluoromethyl)azetidin-1-yl]-3-pyridyl]azetidine-1-carboxylate (2.95 g, 7.9 mmol, 1.0 equiv) as a light yellow solid (3.61 g, 74%). MS (ESI): m/z=274.2 [M+H]$^+$.

BB 100

1-[4-(Azetidin-3-yl)phenyl]-3,5-dimethyl-pyrazole; 4-methylbenzenesulfonic Acid

Step 1: Tert-Butyl 3-[4-(3,5-dimethylpyrazol-1-yl) phenyl]azetidine-1-carboxylate The title compound was obtained in analogy to BB 4/Step 1 starting from tert-butyl 3-bromoazetidine-1-carboxylate (564.1 mg, 2.39 mmol, 1.2 equiv; CAS RN 1064194-10-0) and 1-(4-bromophenyl)-3,5-dimethyl-pyrazole (500 mg, 1.99 mmol, 1.0 equiv; CAS RN 62546-27-4) by irradiating (420 nm) for 16 h as a colorless oil (512 mg, 73%). MS (ESI): m/z=328.4 [M+H]$^+$.

Step 2: 1-[4-(Azetidin-3-yl)phenyl]-3,5-dimethyl-pyrazole 4-methylbenzenesulfonic Acid The title compound was obtained in analogy to BB 4/Step 2 starting from tert-butyl 3-[4-(3,5-dimethylpyrazol-1-yl) phenyl]azetidine-1-carboxylate (512 mg, 1.45 mmol, 1.0 equiv) as a light yellow solid (509 mg, 83%). MS (ESI): m/z=228.1 [M+H]$^+$.

BB 101

1-[5-(Azetidin-3-yl)-2-pyridyl]-3-(trifluoromethyl) pyrrolidin-3-ol; 4-methylbenzenesulfonic Acid Step 1: 1-(5-Bromo-2-pyridyl)-3-(trifluoromethyl) pyrrolidin-3-ol The title compound was obtained in analogy to BB 99/Step 1 starting from 5-bromo-2-fluoro-pyridine (3.67 g, 20.88 mmol, 2.0 equiv; CAS RN 766-11-0) and 3-(trifluoromethyl)pyrrolidin-3-ol; hydrochloride (2.00 g, 10.44 mmol, 1.0 equiv; CAS RN 1334147-81-7) as light yellow oil (2.50 g, 75%). MS (ESI): m/z=311.0 [M+H]$^+$.

Step 2: Tert-Butyl 3-[6-[3-hydroxy-3-(trifluoromethyl)pyrrolidin-1-yl]-3-pyridyl]azetidine-1-carboxylate The title compound was obtained in analogy to BB 4/Step 1 starting from tert-butyl 3-bromoazetidine-1-carboxylate (2.47 in, 10.45 mmol, 1.3 equiv; CAS RN 1064194-10-0) and 1-(5-bromo-2-pyridyl)-3-(trifluoromethyl)pyrrolidin-3-ol (2.50 g, 8.04 mmol, 1.0 equiv) by irradiating (420 nm) for 14 h as a yellow oil (2.00 g, 64%). MS (ESI): m/z=388.3 [M+H]$^+$.

Step 3: 1-[5-(Azetidin-3-yl)-2-pyridyl]-3-(trifluoromethyl)pyrrolidin-3-ol: 4-methylbenzenesulfonic Acid The title compound was obtained in analogy to BB 4/Step 2 starting from tert-butyl 3-[6-[3-hydroxy-3-(trifluoromethyl)pyrrolidin-1-yl]-3-pyridyl]azetidine-1-carboxylate (1.00 g, 2.58 mmol, 1.0 equiv) as an off-white solid (1.23 mg, 74%). MS (ESI): m/z=288.1 [M+H]$^+$.

BB 102

4-Methylbenzenesulfonic acid; 2-[4-(trifluoromethyl)phenyl]sulfonyl-2,6-diazaspiro[3.3]heptane Step 1: Tert-Butyl 2-[4-(trifluoromethyl)phenyl] sulfonyl-2,6-diazaspiro[3.3]heptane-6-carboxylate The title compound was obtained in analogy to BB 98/Step 1 starting from tert-butyl 2,6-diazaspiro[3.3]heptane-2-carboxylate; hydrochloride (875 mg, 3.73 mmol, 1.0 equiv; CAS RN 1207840-19-4) and 4-(trifluoromethyl)benzenesulfonyl chloride (912 mg, 3.73 mmol, 1.0 equiv; CAS RN 2991-42-6) as light yellow solid (1.15 g, 69%). MS (ESI): m/z=307.0 [M+2H-tBu]$^+$.

Step 2: 4-Methylbenzenesulfonic acid; 2-[4-(trifluoromethyl)phenyl]sulfonyl-2,6-diazaspiro[3.3]heptane The title compound was obtained in analogy to BB 4/Step 2 starting from tert-butyl 2-[4-(trifluoromethyl)phenyl]

sulfonyl-2,6-diazaspiro[3.3]heptane-6-carboxylate (1.15 g, 2.83 mmol, 1.0 equiv) as a white solid (585 mg, 42%). MS (ESI): m/z=307.0 [M+H]$^+$.

BB 103

2,2,2-Trifluoroacetic Acid; 2-[2-(trifluoromethoxy)phenyl]sulfonyl-2,6-diazaspiro[3.3]heptane Step 1: Tert-Butyl 2-[2-(trifluoromethoxy)phenyl]sulfonyl-2,6-diazaspiro[3.3]heptane-6-carboxylate The title compound was obtained in analogy to BB 98/Step 1 starting from tert-butyl 2,6-diazaspiro[3.3]heptane-2-carboxylate; oxalic acid (700 mg, 1.44 mmol, 0.5 equiv; CAS RN 1041026-71-4) and 2-(trifluoromethoxy)benzenesulfonyl chloride (750 mg, 2.88 mmol, 1.0 equiv; CAS RN 103008-51-1) as light brown oil (1.17 g, 87%; ca. 90% purity). MS (ESI): m/z=367.1 [M+2H-tBu]$^+$.

Step 2: 2,2,2-Trifluoroacetic Acid; 2-[2-(trifluoromethoxy)phenyl]sulfonyl-2,6-diazaspiro[3.3]heptane The title compound was obtained in analogy to BB 98/Step 2 starting from tert-butyl 2-[2-(trifluoromethoxy)phenyl]sulfonyl-2,6-diazaspiro[3.3]heptane-6-carboxylate (1.05 g, 2.49 mmol, 1.0 equiv) as a brown oil (1.90 g, 96%; ca. 55% purity). MS (ESI): m/z=323.2 [M+H]$^+$.

BB 104

2,2,2-Trifluoroacetic Acid; 2-[3-(trifluoromethoxy)phenyl]sulfonyl-2,6-diazaspiro[3.3]heptane Step 1: Tert-Butyl 2-[3-trifluoromethoxy)phenyl]sulfonyl-2,6-diazaspiro[3.3]heptane-6-carboxylate The title compound was obtained in analogy to BB 98/Step 1 starting from tert-butyl 2,6-diazaspiro[3.3]heptane-2-carboxylate; oxalic acid (700 mg, 1.44 mmol, 0.5 equiv; CAS RN 1041026-71-4) and 3-(trifluoromethoxy)benzenesulfonyl chloride (750 mg, 2.88 mmol, 1.0 equiv; CAS RN 220227-84-9) as light brown oil (1.28 g, 84%; ca. 80% purity). MS (ESI): m/z=367.1 [M+2H-tBu]$^+$.

Step 2: 2,2,2-Trifluoroacetic Acid; 2-[3-(trifluoromethoxy)phenyl]sulfonyl-2,6-diazaspiro[3.3]heptane The title compound was obtained in analogy to BB 98/Step 2 starting from tert-butyl 2-[3-(trifluoromethoxy)phenyl]sulfonyl-2,6-diazaspiro[3.3]heptane-6-carboxylate (1.02 g, 2.42 mmol, 1.0 equiv) as a brown oil (1.89 g, 98%; ca. 55% purity). MS (ESI): m/z=323.1 [M+H]$^+$.

BB 105

2,2,2-Trifluoroacetic Acid; 2-[4-(trifluoromethoxy)phenyl]sulfonyl-2,6-diazaspiro[3.3]heptane Step 1: Tert-Butyl 2-[4-(trifluoromethoxy)phenyl]sulfonyl-2,6-diazaspiro[3.3]heptane-6-carboxylate The title compound was obtained in analogy to BB 98/Step 1 starting from tert-butyl 2,6-diazaspiro[3.3]heptane-2-carboxylate; oxalic acid (700 mg, 1.44 mmol, 0.5 equiv; CAS RN 1041026-71-4) and 4-(trifluoromethoxy)benzenesulfonyl chloride (750 mg, 2.88 mmol, 1.0 equiv; CAS RN 94108-56-2) as light brown oil (1.02 g, 76%; ca. 90% purity). MS (ESI): m/z=367.1 [M+2H-tBu]$^+$.

Step 2: 2,2,2-Trifluoroacetic Acid; 2-[4-(trifluoromethoxy)phenyl]sulfonyl-2,6-diazaspiro[3.3]heptane The title compound was obtained in analogy to BB 98/Step 2 starting from tert-butyl 2-[4-(trifluoromethoxy)phenyl]sulfonyl-2,6-diazaspiro[3.3]heptane-6-carboxylate (0.92 g, 2.17 mmol, 1.0 equiv) as a brown oil (1.52 g, 96%; ca. 60% purity). MS (ESI): m/z=323.2 [M+H]$^+$.

BB 106

2,2,2-Trifluoroacetic Acid; N-[6-(trifluoromethyl)pyridazin-3-yl]-2-azaspiro[3.3]heptan-6-amine Step 1: Tert-Butyl 6-[[6-(trifluoromethyl)pyridazin-3-yl]amino]-2-azaspiro[3.3]heptane-2-carboxylate A solution of tert-butyl 6-amino-2-azaspiro[3.3]heptane-2-carboxylate (0.83 g, 3.92 mmol, 1.1 equiv; CAS RN 1211586-09-2), 3-chloro-6-(trifluoromethyl)pyridazine (0.65 g, 3.56 mmol, 1.0 equiv; CAS RN 258506-68-2) and DIPEA (0.69 g, 5.34 mmol, 1.5 equiv) in DMF (12 mL) was stirred at 80° C. for 18 h. The reaction mixture was concentrated by evaporation, the crude material diluted with a sat. aqueous NH$_4$Cl solution and extracted with ethyl acetate. The combined organic phase was then washed with a sat. aqueous NaCl solution, dried over Na$_2$SO$_4$ and concentrated. The crude product was purified by silica gel chromatography eluting with a gradient of DCM:MeOH (100:0 to 90:10) to afford the title compound as a colorless solid (0.71 g, 54%). MS (ESI): m/z=359.2 [M+H]$^+$.

Step 2: 2,2,2-Trifluoroacetic Acid: N-[6-(trifluoromethyl)pyridazin-3-yl]-2-azaspiro[3.3]heptan-6-amine The title compound was obtained in analogy to BB 98/Step 2 starting from tert-butyl 6-[[6-(trifluoromethyl)pyridazin-3-yl]amino]-2-azaspiro[3.3]heptane-2-carboxylate (0.71 g, 1.94 mmol, 1.0 equiv) as a brown oil (1.31 g, 99%; ca. 55% purity). MS (ESI): m/z=259.1 [M+H]$^+$.

BB 107

2,2,2-Trifluoroacetic Acid; 6-[6-(trifluoromethyl)pyridazin-3-yl]oxy-2-azaspiro[3.3]heptane Step 1: Tert-Butyl 6-[6-(trifluoromethyl)pyridazin-3-yl]oxy-2-azaspiro[3.3]heptane-2-carboxylate A solution of tert-butyl 6-hydroxy-2-azaspiro[3.3]heptane-2-carboxylate (0.75 g, 3.52 mmol, 1.0 equiv; CAS RN 1147557-97-8) and potassium tert-butoxide (3.69 mL, 3.69 mmol, 1.05 equiv; 1 M in THF) in THF (12 mL) was stirred at RT for 30 min. To the solution was added 3-chloro-6-(trifluoromethyl)pyridazine (0.71 g, 3.87 mmol, 1.1 equiv; CAS RN 258506-68-2) and the reaction mixture was stirred at RT. After 18 h, the reaction mixture was quenched by addition of a few drops of water, the crude material diluted with an aqueous NaHCO$_3$ solution (1 M) and extracted with ethyl acetate. The combined organic phase was then washed with a sat. aqueous NaCl solution, dried over Na$_2$SO$_4$ and concentrated. The title compound was obtained as a brown oil and used in the consecutive reaction step without further purification (1.26 g, 98%). MS (ESI): m/z=360.2 [M+H]$^+$.

Step 2: 2,2,2-Trifluoroacetic Acid: 6-[6-(trifluoromethyl)pyridazin-3-yl]oxy-2-azaspiro[3.3]heptane The title compound was obtained in analogy to BB 98/Step 2 starting from tert-butyl 6-[6-(trifluoromethyl)pyridazin-3-yl]oxy-2-azaspiro[3.3]heptane-2-carboxylate (1.26 g, 3.44 mmol, 1.0 equiv) as a brown oil (2.29 g, 98%; ca. 55% purity). MS (ESI): m/z=260.1 [M+H]$^+$.

BB 108

2-(2,6-Diazaspiro[3.3]heptan-2-ylmethyl)benzenesulfonamide; 4-methylbenzenesulfonic Acid Step 1: Tert-Butyl 6-[(2-sulfamoylphenyl)methyl]-2,6-diazaspiro[3.3]heptane-2-carboxylate To a stirred solution of tert-butyl 2,6-diazaspiro[3.3]heptane-2-carboxylate; hydrochloride (651 mg, 2.77 mmol, 1.0 equiv; CAS RN 1207840-19-4) and DIPEA (1.08 g, 1.45 mL, 8.31 mmol, 3.0 equiv) in ACN (80 mL) was added 2-(chloromethyl)benzenesulfonamide (570 mg, 2.77 mmol, 1.0 equiv; CAS RN 81629-77-8) at 0° C. and the reaction mixture was allowed to warm up to RT. After stirring for 18 h, the reaction mixture was diluted with water and extracted with ethyl acetate. The combined organic phase was then washed with a sat. aqueous NaCl solution, dried over Na$_2$SO$_4$ and concentrated. The title compound was obtained as a yellow solid and used in the consecutive reaction step without further purification (0.95 g, 91%). MS (ESI): m/z=368.1 [M+H]$^+$.

Step 2: 2-(2,6-Diazaspiro[3.3]heptan-2-ylmethyl)benzenesulfonamide; 4-methylbenzenesulfonic Acid The title compound was obtained in analogy to BB 4/Step 2 starting from tert-butyl 6-[(2-sulfamoylphenyl)methyl]-2,6-diazaspiro[3.3]heptane-2-carboxylate (1.10 g, 2.99 mmol, 1.0 equiv) as a white solid (1.36 g, 71%). MS (ESI): m/z=266.2 [M–H]$^-$.

BB 109

N-(2-Azaspiro[3.3]heptan-6-yl)-3-(trifluoromethyl)benzenesulfonamide; 2,2,2-trifluoroacetic Acid Step 1: Tert-Butyl 6-[[3-(trifluoromethyl)phenyl]sulfonylamino]-2-azaspiro[3.3]heptane-2-carboxylate To a solution of tert-butyl 6-amino-2-azaspiro[3.3]heptane-2-carboxylate (750 mg, 3.53 mmol, 1.0 equiv; CAS RN 1211586-09-2) in DCM (15 mL) at 0° C. was added DIPEA (0.93 mL, 5.30 mmol, 1.5 equiv) and 3-(trifluoromethyl)benzenesulfonyl chloride (907 mg, 3.71 mmol, 1.05 equiv; CAS RN 777-44-6) and the reaction mixture was stirred at 0° C. for 15 min and at RT for 18 h. The reaction mixture was diluted with DCM, washed with an aqueous Na$_2$CO$_3$ solution (1 M) and water and extracted with DCM. The combined organic phases were dried over Na$_2$SO$_4$ and concentrated under vacuum. The crude product was purified by silica gel chromatography using a MPLC system eluting with a gradient of n-heptane:ethyl acetate (95:5 to 40:60) to yield the title compound as light yellow solid (479 mg, 32%). MS (ESI): m/z=365.1 [M+2H-tBu]$^+$.

Step 2: N-(2-Azaspiro[3.3]heptan-6-yl)-3-(trifluoromethyl)benzenesulfonamide; 2,2,2-trifluoroacetic Acid The title compound was obtained in analogy to BB 98/Step 2 starting from tert-butyl 6-[[3-(trifluoromethyl)phenyl]sulfonylamino]-2-azaspiro[3.3]heptane-2-carboxylate (1.25 g, 2.96 mmol, 1.0 equiv) as a brown oil (1.91 g, 97%; ca. 65% purity). MS (ESI): m/z=321.1 [M+H]$^+$.

BB 110

4-Methylbenzenesulfonic Acid; N-[[4-(trifluoromethyl)phenyl]methyl]azetidin-3-amine Step 1: Tert-Butyl 3-[[4-(trifluoromethyl)phenyl]methylamino]azetidine-1-carboxylate To a solution of 4-(trifluoromethyl)benzaldehyde (2.00 g, 11.49 mmol, 1.0 equiv; CAS RN 455-19-6) and tert-butyl 3-aminoazetidine-1-carboxylate (2.08 g, 12.06 mmol, 1.05 equiv; CAS RN 193269-78-2) in MeOH (50 mL) was added acetic acid (0.69 g, 0.66 mL, 11.49 mmol, 1.0 equiv) and the reaction mixture was stirred at RT. After 2 h, sodium cyanoborohydride (3.61 g, 57.43 mmol, 5.0 equiv) was added to the reaction mixture and stirring at RT was continued for 12 h. The crude reaction mixture was concentrated under vacuum and purified by silica gel chromatography eluting with a gradient of petroleum ether:ethyl acetate (100:0 to 70:30) to give the title compound as a colorless oil (900 mg, 24%). MS (ESI): m/z=275.0 [M+2H-tBu]$^+$.

Step 2: 4-Methylbenzenesulfonic Acid; N-[[4-(trifluoromethyl)phenyl]methyl]azetidin-3-amine The title compound was obtained in analogy to BB 4/Step 2 starting from tert-butyl 3-[[4-(trifluoromethyl)phenyl]methylamino]azetidine-1-carboxylate (0.90 g, 2.72 mmol, 1.0 equiv) as a white solid (1.24 g, 83%). MS (ESI): m/z=231.0 [M+H]$^+$.

BB 111

N-[[2-Fluoro-5-(trifluoromethyl)phenyl]methyl]azetidin-3-amine; 4-methylbenzenesulfonic acid Step 1: Tert-Butyl 3-[[2-fluoro-5-(trifluoromethyl)phenyl]methylamino]azetidine-1-carboxylate The title compound was obtained in analogy to BB 110/Step 1 starting from 2-fluoro-5-(trifluoromethyl)benzaldehyde (2.00 g, 10.41 mmol, 1.0 equiv; CAS RN 146137-78-2) and tert-butyl 3-aminoazetidine-1-carboxylate (1.88 g, 10.93 mmol, 1.05 equiv; CAS RN 193269-78-2) as a colorless oil (2.80 g, 76%). MS (ESI): m/z=293.1 [M+2H-tBu]$^+$.

Step 2: N-[[2-Fluoro-5-(trifluoromethyl)phenyl]methyl]azetidin-3-amine; 4-methylbenzenesulfonic Acid The title compound was obtained in analogy to BB 4/Step 2 starting from tert-butyl 3-[[2-fluoro-5-(trifluoromethyl)

phenyl]methylamino]azetidine-1-carboxylate (1.40 g, 4.02 mmol, 1.0 equiv) as a white solid (1.84 g, 81%). MS (ESI): m/z=249.0 [M+H]$^+$.

BB 112

6-[(4-Fluoro-2-methylsulfonyl-phenyl)methyl]-2-azaspiro[3.3]heptane; 4-methylbenzenesulfonic Acid Step 1: Tert-Butyl 6-[(4-fluoro-2-methylsulfonyl-phenyl)methylene]-2-azaspiro[3.3]heptane-2-carboxylate The title compound was obtained in analogy to BB 80/Step 2 starting from 1-bromo-4-fluoro-2-methylsulfonyl-benzene (1.50 g, 5.93 mmol, 1.0 equiv; CAS RN 628692-10-4) and tert-butyl 6-[(4,4,5,5-tetramethyl-1,3,2-dioxaborolan-2-yl)methylene]-2-azaspiro[3.3]heptane-2-carboxylate (1.99 g, 5.93 mmol, 1.0 equiv; BB 80/Step 1) as a light yellow solid (0.89 g, 39%). MS (ESI): m/z=326.3 [M+2H-tBu]$^+$.

Step 2: Tert-Butyl 6-[(4-fluoro-2-methylsulfonyl-phenyl)methyl]-2-azaspiro[3.3]heptane-2-carboxylate The title compound was obtained in analogy to BB 80/Step 3 starting from tert-butyl 6-[(4-fluoro-2-methylsulfonyl-phenyl)methylene]-2-azaspiro[3.3]heptane-2-carboxylate (0.89 g, 2.33 mmol, 1.0 equiv) as a yellow oil (0.80 g, 89%). MS (ESI): m/z=330.3 [M+2H-tBu]$^+$.

Step 3: 6-[(4-Fluoro-2-methylsulfonyl-phenyl)methyl]-2-azaspiro[3.3]heptane; 4-methylbenzenesulfonic Acid The title compound was obtained in analogy to BB 4/Step 2 starting from tert-butyl 6-[(4-fluoro-2-methylsulfonyl-phenyl)methyl]-2-azaspiro[3.3]heptane-2-carboxylate (0.80 g, 2.08 mmol, 1.0 equiv) as an off-white solid (0.79 g, 83%). MS (ESI): m/z=284.4 [M+H]$^+$.

BB 113

N-(4-Piperidylmethyl)-4-(trifluoromethyl)benzenesulfonamide; Hydrochloride

Step 1: Tert-Butyl 4-[[[4-(trifluoromethyl)phenyl]sulfonylamino]methyl]piperidine-1-carboxylate To a solution of tert-butyl 4-(aminomethyl)piperidine-1-carboxylate (500 mg, 2.33 mmol, 1.0 equiv; CAS RN 144222-22-0) in DCM (10 mL) at 0° C. was added DIPEA (0.61 mL, 3.50 mmol, 1.5 equiv) and 4-(trifluoromethyl)benzenesulfonyl chloride (628 mg, 2.57 mmol, 1.1 equiv; CAS RN 2991-42-6) and the reaction mixture was stirred at 0° C. for 15 min and at RT for 5 h. The reaction mixture was diluted with DCM, washed with an aqueous Na$_2$CO$_3$ solution (1 M) and water and extracted with DCM. The combined organic phases were dried over Na$_2$SO$_4$ and concentrated under vacuum. The title compound was obtained as a light brown oil and used in the consecutive reaction step without further purification (925 mg, 99%). MS (ESI): m/z=367.1 [M+2H-tBu]$^+$.

Step 2: N-(4-Piperidylmethyl)-4-(trifluoromethyl)benzenesulfonamide; Hydrochloride The title compound was obtained in analogy to BB 18/Step 2 starting from tert-butyl 4-[[[4-(trifluoromethyl)phenyl]sulfonylamino]methyl]piperidine-1-carboxylate (925 mg, 2.19 mmol, 1.0 equiv) as a light brown solid (786 mg, quant.). MS (ESI): m/z=323.1 [M+H]$^+$.

BB 114

N-(4-Piperidylmethyl)-4-(trifluoromethoxy)benzenesulfonamide; Hydrochloride Step 1: Tert-Butyl 4-[[[4-(trifluoromethoxy)phenyl]sulfonylamino]methyl]piperidine-1-carboxylate The title compound was obtained in analogy to BB 113/Step 1 starting from tert-butyl 4-(aminomethyl)piperidine-1-carboxylate (500 mg, 2.33 mmol, 1.0 equiv; CAS RN 144222-22-0) and 4-(trifluoromethoxy)benzenesulfonyl chloride (669 mg, 2.57 mmol, 1.1 equiv; CAS RN 94108-56-2) as a light brown oil (971 mg, 99%). MS (ESI): m/z=383.1 [M+2H-tBu]$^+$.

Step 2: N-(4-Piperidylmethyl)-4-(trifluoromethoxy)benzenesulfonamide; Hydrochloride The title compound was obtained in analogy to BB 18/Step 2 starting from tert-butyl 4-[[[4-(trifluoromethoxy)phenyl]sulfonylamino]methyl]piperidine-1-carboxylate (971 mg, 2.21 mmol, 1.0 equiv) as a light brown solid (830 mg, quant.). MS (ESI): m/z=339.1 [M+H]$^+$.

BB 115

1-[5-(Azetidin-3-yl)-2-pyridyl]-3-methyl-azetidin-3-ol; 4-methylbenzenesulfonic Acid Step 1: 1-(5-Bromo-2-pyridyl)-3-methyl-azetidin-3-ol The title compound was obtained in analogy to BB 99/Step 1 starting from 3-methylazetidin-3-ol; hydrochloride (1.0 g, 8.09 mmol, 1.0 equiv) and 5-bromo-2-fluoropyridine (2.85 g, 16.18 mmol, 2.0 equiv; CAS RN 124668-46-8) as an off-white solid (1.66 g, 84%). MS (ESI): m/z=245.3 [M+H]$^+$.

Step 2: Tert-Butyl 3-[6-(3-hydroxy-3-methyl-azetidin-1-yl)-3-pyridyl]azetidine-1-carboxylate The title compound was obtained in analogy to BB 4/Step 1 starting from 1-(5-bromo-2-pyridyl)-3-methyl-azetidin-3-ol (1.5 g, 6.17 mmol, 1.0 equiv) and tert-butyl 3-bromoazetidine-1-carboxylate (1.89 g, 8.02 mmol, 1.3 equiv; CAS RN 1064194-10-0) by irradiating (420 nm) for 20 h as a light yellow solid (1.20 g, 61%). MS (ESI): m/z=320.4 [M+H]$^+$.

Step 3: 1-[5-(Azetidin-3-yl)-2-pyridyl]-3-methyl-azetidin-3-ol; 4-methylbenzenesulfonic Acid The title compound was obtained in analogy to BB 4/Step 2 starting from tert-butyl 3-[6-(3-hydroxy-3-methyl-azetidin-1-yl)-3-pyridyl]azetidine-1-carboxylate (1.15 g, 3.60 mmol, 1.0 equiv) as a light yellow solid (1.42 g, 69%). MS (ESI): m/z=220.6 [M+H]$^+$.

BB 116

5-(Azetidin-3-yl)-2-[3-(trifluoromethyl)azetidin-1-yl]pyridine; 4-methylbenzenesulfonic Acid

Step 1: Tert-Butyl 3-[6-[3-(trifluoromethyl)azetidin-1-yl]-3-pyridyl]azetidine-1-carboxylate The title compound was obtained in analogy to BB 58/Step 1 starting from tert-butyl 3-(6-bromo-3-pyridyl)azetidine-1-carboxylate (500 mg, 1.60 mmol, 1.0 equiv; BB 71/Step 1) and 3-(trifluoromethyl)azetidine; hydrochloride (309.5 mg, 1.92 mmol, 1.2 equiv; CAS RN 1221272-90-7) as an orange gum (212 mg, 35%). MS (ESI): m/z=358.2 [M+H]$^+$.

Step 3: 5-(Azetidin-3-yl)-2-[3-(trifluoromethyl)azetidin-1-yl]pyridine; 4-methylbenzenesulfonic Acid The title compound was obtained in analogy to BB 4/Step 2 starting from tert-butyl 3-[6-[3-(trifluoromethyl)azetidin-1-yl]-3-pyridyl]azetidine-1-carboxylate (212 mg, 0.56 mmol, 1.0 equiv) as a light brown solid (272 mg, 80%). MS (ESI): m/z=258.2 [M+H]$^+$.

BB 117

N-[[2-Fluoro-4-(trifluoromethyl)phenyl]methyl]-N-methyl-azetidin-3-amine; 4-methylbenzenesulfonic Acid

Step 1: Tert-Butyl 3-[[2-fluoro-4-(trifluoromethyl)phenyl]methyl-methyl-amino]azetidine-1-carboxylate A solution of 2-fluoro-4-(trifluoromethyl)benzaldehyde (0.90 g, 4.69 mmol, 0.97 equiv; CAS RN 89763-93-9) and tert-butyl 3-(methylamino)azetidine-1-carboxylate (900 mg, 4.83 mmol, 1.0 equiv; CAS RN 454703-20-9) in DCM (10 mL) and acetic acid (0.58 mL, 10.14 mmol, 2.1 equiv) was stirred at RT for 10 min, then sodium triacetoxy borohydride (1.21 g, 5.73 mmol, 1.15 equiv) was added. After 4 h, another batch of sodium triacetoxy borohydride (0.60 g, 2.84 mmol, 0.57 equiv) was added and the reaction mixture was stirred at RT overnight. The reaction mixture was poured into a sat. aqueous NaHCO$_3$ solution (30 mL) and stirred for 1.5 h. The layers were separated and the aqueous phase extracted with DCM (2×30 mL). The combined organic phase was washed with water (30 mL) and a sat. aqueous NaCl solution (30 mL), dried over Na$_2$SO$_4$ and concentrated in vacuo. The compound was purified by silica gel chromatography using a MPLC system eluting with a gradient of n-heptane:TBME (100:0 to 0:100) to yield the title compound as a colorless oil (1.07 g, 58%). MS (ESI): m/z=363.2 [M+H]$^+$.

Step 2: N-[[2-Fluoro-4-(trifluoromethyl)phenyl]methyl]-N-methyl-azetidin-3-amine; 4-methylbenzenesulfonic Acid The title compound was obtained in analogy to BB 4/Step 2 starting from tert-butyl 3-[[2-fluoro-4-(trifluoromethyl)phenyl]methyl-methyl-amino]azetidine-1-carboxylate (1.0 g, 2.7 mmol, 1.0 equiv) as a white solid (1.64 g, quant.). MS (ESI): m/z=263.1 [M+H]$^+$.

BB 118

5-(Azetidin-3-yl)-2-spiro[3.3]heptan-2-yl-pyridine; 4-methylbenzenesulfonic Acid

Step 1: Tert-Butyl 3-(6-spiro[3.3]heptan-2-yl-3-pyridyl)azetidine-1-carboxylate The title compound was obtained in analogy to BB 4/Step 1 starting from 2-bromospiro[3.3]heptane (223.6 mg, 1.28 mmol, 2.0 equiv; CAS RN 102115-82-2) and tert-butyl 3-(6-bromo-3-pyridyl)azetidine-1-carboxylate (200 mg, 0.64 mmol, 1.0 equiv; BB 71/Step 1) by irradiating (420 nm) for 16 h as a colorless solid (55 mg, 24%). MS (ESI): m/z=329.3 [M+H]$^+$.

Step 2: 5-(Azetidin-3-yl)-2-spiro[3.3]heptan-2-yl-pyridine: 4-methylbenzenesulfonic Acid The title compound was obtained in analogy to BB 4/Step 2 starting from tert-butyl 3-(6-spiro[3.3]heptan-2-yl-3-pyridyl)azetidine-1-carboxylate (55 mg, 0.16 mmol, 1.0 equiv) as a light yellow oil (95 mg, 91%). MS (ESI): m/z=229.2 [M+H]$^+$.

BB 119

2-(Azetidin-3-yl)-5-spiro[3.3]heptan-2-yl-pyrazine; 4-methylbenzenesulfonic Acid

Step 1: Tert-Butyl 3-(5-spiro[3.3]heptan-2-ylpyrazin-2-yl)azetidine-1-carboxylate The title compound was obtained in analogy to BB 4/Step 1 starting from 2-bromospiro[3.3]heptane (100.3 mg, 0.57 mmol, 1.2 equiv; CAS RN 102115-82-2) and tert-butyl 3-(5-bromopyrazin-2-yl)azetidine-1-carboxylate (150 mg, 0.48 mmol, 1.0 equiv; BB 60/Step 1) by irradiating (420 nm) for 16 h as a light brown solid (27 mg, 11%). MS (ESI): m/z=330.2 [M+H]$^+$.

Step 2: 2-(Azetidin-3-yl)-5-spiro[3.3]heptan-2-yl-pyrazine; 4-methylbenzenesulfonic Acid The title compound was obtained in analogy to BB 4/Step 2 starting from tert-butyl 3-(5-spiro[3.3]heptan-2-ylpyrazin-2-yl)azetidine-1-carboxylate (27 mg, 0.077 mmol, 1.0 equiv) as a light yellow oil (62 mg, 98%). MS (ESI): m/z=230.2 [M+H]$^+$.

BB 120

2-[3-(Azetidin-3-yl)-1-bicyclo[1.1.1]pentanyl]-5-(2,2-dimethylpropyl)-1,3,4-oxadiazole; 2,2,2-trifluoroacetic Acid

Step 1: Tert-Butyl 3-[3-[(3,3-dimethylbutanoylamino)carbamoyl]-1-bicyclo[1.1.1]pentanyl]azetidine-1-carboxylate To a solution of 3-(1-tert-butoxycarbonylazetidin-3-yl)bicyclo[1.1.1]pentane-1-carboxylic acid (250 mg, 0.94 mmol, 1.0 equiv; CAS RN 2227205-20-9) in DCM (5 mL) at 0° C. was added CDI (159.2 mg, 0.98 mmol, 1.05 equiv) and the reaction mixture was stirred at 0° C. for 15 min and at RT for 45 min. 3,3-Dimethylbutanehydrazide (133.9 mg, 1.03 mmol, 1.1 equiv; CAS RN 712303-26-9) was added to the reaction mixture and stirring continued at RT for 18 h. The reaction mixture was diluted with DCM, washed with an aqueous Na$_2$CO$_3$ solution (1 M) and water and extracted with DCM. The combined organic phases were dried over Na$_2$SO$_4$ and concentrated under vacuum. The title compound was obtained as a light brown oil and used in the consecutive reaction step without further purification (375 mg, 99%; ca. 94% purity). MS (ESI): m/z=324.2 [M+2H-tBu]$^+$.

Step 2: Tert-Butyl 3-[3-[5-(2,2-dimethylpropyl)-1,3, 4-oxadiazol-2-yl]-1-bicyclo[1.1.1]pentanyl]azetidine-1-carboxylate To a solution of tert-butyl 3-[3-[(3,3-dimethylbutanoylamino)carbamoyl]-1-bicyclo[1.1.1]pentanyl]azetidine-1-carboxylate (375 mg, 0.93 mmol, 1.0 equiv) in THF (8 mL) under an atmosphere of N$_2$ was added (methoxycarbonylsulfamoyl)triethylammonium hydroxide, inner salt (553.4 mg, 2.32 mmol, 2.5 equiv; Burgess' reagent; CAS RN 29684-56-8) and the reaction mixture was stirred at 70° C. for 18 h. The reaction mixture was diluted with DCM, washed with an aqueous Na$_2$CO$_3$ solution (1 M) and water and extracted with DCM. The combined organic phases were dried over Na$_2$SO$_4$ and concentrated under vacuum. The crude reaction product was purified by silica gel chromatography using a MPLC system eluting with a gradient of n-heptane:ethyl acetate (95:5 to 20:80) to yield the title compound as a light yellow oil (264 mg, 75%). MS (ESI): m/z=362.3 [M+H]$^+$.

Step 3: 2-[3-(Azetidin-3-yl)-1-bicyclo[1.1.1]pentanyl]-5-(2,2-dimethylpropyl)-1,3,4-oxadiazole; 2,2,2-trifluoroacetic Acid The title compound was obtained in analogy to BB 98/Step 2 starting from tert-butyl 3-[3-[5-(2,2-dimethylpropyl)-1,3,4-oxadiazol-2-yl]-1-bicyclo[1.1.1]pentanyl]azetidine-1-carboxylate (260 mg, 0.68 mmol, 1.0 equiv) as a brown oil (425 mg, 99%; ca. 60% purity). MS (ESI): m/z=262.2 [M+H]$^+$.

BB 121

4-Methylbenzenesulfonic Acid; 3-[[4-(trifluoromethylsulfonyl)phenyl]methoxy]azetidine Step 1: Tert-Butyl 3-[(4-iodophenyl)methoxy]azetidine-1-carboxylate To a solution of tert-butyl 3-hydroxyazetidine-1-carboxylate (2.92 g, 16.84 mmol, 1.0 equiv; CAS RN 141699-55-0) and potassium tert-butoxide (3.78 g, 33.68 mmol, 2.0 equiv) in THF (60 mL) was added 1-(bromomethyl)-4-iodo-benzene (5.00 g, 16.84 mmol, 1.0 equiv; CAS RN 16004-15-2) and the reaction mixture was stirred at 30° C. for 12 h. The reaction mixture was concentrated by evaporation under reduced pressure and the crude product purified by silica gel chromatography eluting with a gradient of petroleum ether: ethyl acetate (100:0 to 70:30) to give the title compound as a colorless oil (4.10 g, 63%). MS (ESI): m/z=290.1 [M+2H-tBu]$^+$. $^1$H NMR (400 MHz, CDCl$_3$): δ=7.69 (d, J=8.3 Hz, 2H), 7.08 (d, J=8.2 Hz, 2H), 4.39 (s, 2H), 4.30 (s, 1H), 4.06 (dd, J=6.6, 9.4 Hz, 2H), 3.86 (dd, J=4.2, 9.6 Hz, 2H), 1.44 (s, 9H).

Step 2: Tert-Butyl 3-[[4-(trifluoromethylsulfanyl)phenyl]methoxy]azetidine-1-carboxylate To a solution of tert-butyl 3-[(4-iodophenyl)methoxy]azetidine-1-carboxylate (1000 mg, 2.57 mmol, 1.0 equiv) in ACN (20 mL) was added silver trifluoromethanethiolate (805.2 mg, 3.85 mmol, 1.5 equiv; CAS RN 811-68-7), copper(I) iodide (489.3 mg, 2.57 mmol, 1.0 equiv) and 2,2'-bipyridine (401.3 mg, 2.57 mmol, 1.0 equiv; CAS RN 366-18-7) and the reaction mixture was stirred at 100° C. for 17 h. The reaction mixture was filtered and the filtrate evaporated under reduced pressure. The residue was purified by silica gel chromatography eluting with a gradient of petroleum ether:ethyl acetate (100:0 to 70:30) to give the title compound as a light yellow oil (825 mg, 88%). MS (ESI): m/z=308.2 [M+2H-tBu]$^+$. $^1$H NMR (400 MHz, CDCl$_3$): δ=7.65 (d, J=7.9 Hz, 2H), 7.40 (d, J=8.1 Hz, 2H), 4.49 (s, 2H), 4.37-4.30 (m, 1H), 4.09 (dd, J=6.5, 9.4 Hz, 2H), 3.89 (dd, J=4.2, 9.6 Hz, 2H), 1.44 (s, 9H).

Step 3: tert-Butyl 3-[[4-(trifluoromethylsulfonyl)phenyl]methoxy]azetidine-1-carboxylate To a solution of tert-butyl 3-[[4-(trifluoromethylsulfanyl)phenyl]methoxy]azetidine-1-carboxylate (1080 mg, 2.97 mmol, 1.0 equiv) in a mixture of 1,2-dichloroethane (25 mL), ACN (25 mL) and water (50 mL) at 0° C. was added sodium periodate (1907 mg, 8.92 mmol, 3.0 equiv) and ruthenium(III) chloride hydrate (6.7 mg, 0.030 mmol, 0.010 equiv) and the reaction mixture was stirred at 30° C. for 12 h. The reaction mixture was diluted with water (10 mL) and extracted with ethyl acetate (3×200 mL). The organic phase was dried over Na$_2$SO$_4$, evaporated and the residue purified by silica gel chromatography eluting with a gradient of petroleum ether:ethyl acetate (100:0 to 70:30) to give the title compound as a yellow oil (755 mg, 64%). MS (ESI): m/z=340.1 [M+2H-tBu]$^+$. $^1$H NMR (400 MHz, CDCl$_3$): δ=8.03 (d, J=8.2 Hz, 2H), 7.65 (d, J=8.3 Hz, 2H), 4.59 (s, 2H), 4.41-4.34 (m, 1H), 4.16-4.12 (m, 2H), 3.92 (dd, J=4.2, 9.5 Hz, 2H), 1.45 (s, 9H).

Step 4: 4-Methylbenzenesulfonic Acid; 3-[[4-(trifluoromethylsulfonyl)phenyl]methoxy]azetidine The title compound was obtained in analogy to BB 4/Step 2 starting from tert-butyl 3-[[4-(trifluoromethylsulfonyl)phenyl]methoxy]azetidine-1-carboxylate (736 mg, 1.86 mmol, 1.0 equiv) as a white solid (564 mg, 65%). MS (ESI): m/z=296.1 [M+H]$^+$.

BB 122

4-Methylbenzenesulfonic acid; 3-[[3-(trifluoromethylsulfonyl)phenyl]methoxy]azetidine Step 1: Tert-Butyl 3-[(3-iodophenyl)methoxy]azetidine-1-carboxylate The title compound was obtained in analogy to BB 121/Step 1 starting from tert-butyl 3-hydroxyazetidine-1-carboxylate (2.54 g, 14.64 mmol, 1.0 equiv; CAS RN 141699-55-0) and 1-(bromomethyl)-3-iodo-benzene (4.35 g, 14.64 mmol, 1.0 equiv; CAS RN 49617-83-6) as a colorless oil (2.00 g, 35%). MS (ESI): m/z=290.2 [M+2H-tBu]$^+$.

Step 2: Tert-Butyl 3-[[3-(trifluoromethylsulfanyl)phenyl]methoxy]azetidine-1-carboxylate The title compound was obtained in analogy to BB 121/Step 2 starting from tert-butyl 3-[(3-iodophenyl)methoxy]azetidine-1-carboxylate (1.00 g, 2.57 mmol, 1.0 equiv) and silver trifluoromethanethiolate (805.2 mg, 3.85 mmol, 1.5 equiv; CAS RN 811-68-7) as a light yellow oil (800 mg, 86%). MS (ESI): m/z=308.2 [M+2H-tBu]$^+$.

Step 3: tert-Butyl 3-[[3-(trifluoromethylsulfonyl)phenyl]]azetidine-1-carboxylate The title compound was obtained in analogy to BB 121/Step 3 starting from tert-butyl 3-[[3-(trifluoromethylsulfanyl)phenyl]methoxy]azetidine-1-carboxylate (1.08 g, 2.97 mmol, 1.0 equiv) as a light yellow oil (644 mg, 55%). MS (ESI): m/z=340.3 [M+2H-tBu]$^+$.

Step 4: 4-Methylbenzenesulfonic Acid; 3-[[3-(trifluoromethylsulfonyl)phenyl]methoxy]azetidine The title compound was obtained in analogy to BB 4/Step 2 starting from tert-butyl 3-[[3-(trifluoromethylsulfonyl)phenyl]methoxy]azetidine-1-carboxylate (614 mg, 1.55 mmol, 1.0 equiv) as an off-white gum (538 mg, 74%). MS (ESI): m/z=296.3 [M+H]$^+$.

BB 123

3-(Azetidin-3-yl)-5-[6-(trifluoromethyl)-3-pyridyl]-1,2,4-oxadiazole; Hydrochloride Step 1: 3-(1-Benzhydrylazetidin-3-yl)-5-[6-(trifluoromethyl)-3-pyridyl]-1,2,4-oxadiazole To a solution of 1-benzhydryl-N'-hydroxy-azetidine-3-carboxamidine (200 mg, 0.63 mmol, 1.0 equiv; CAS RN 2634758-73-7) and DIPEA (0.33 mL, 1.88 mmol, 3.0 equiv) in DMF (1.5 mL) was added dropwise a solution of 6-(trifluoromethyl)pyridine-3-carbonyl chloride (131.1 mg, 0.63 mmol, 1.0 equiv; CAS RN 358780-13-9) in DMF (0.5 mL) and the reaction mixture was stirred at RT for 2 h. Then, the reaction mixture was heated at 100° C. for 4 h, allowed to cool down and stirred at RT overnight. The reaction mixture was diluted with water and extracted with ethyl acetate. The organic phase was dried over MgSO$_4$, evaporated and the residue purified by silica gel chromatography using a MPLC system eluting with a gradient of n-heptane ethyl acetate (100:0 to 50:50) to yield the title compound as a colorless solid (129 mg, 47%). MS (ESI): m/z=437.2 [M+H]$^+$.

Step 2: 3-(Azetidin-3-yl)-5-[6-(trifluoromethyl)-3-pyridyl]-1,2,4-oxadiazole; Hydrochloride To a suspension of 3-(1-benzhydrylazetidin-3-yl)-5-[6-(trifluoromethyl)-3-pyridyl]-1,2,4-oxadiazole (129 mg, 0.30 mmol, 1.0 equiv) in DCM (0.75 mL) was added 1-chloroethyl chloroformate (41.9 µL, 0.38 mmol, 1.3 equiv) and the suspension was stirred at 50° C. for 1 h. After cooling down, MeOH (0.75 mL) was added and the solution was stirred at 50° C. for 15 min. The reaction mixture was concentrated by evaporation under reduced pressure, to the colorless oil was added TBME (2 mL) and the suspension filtered. The filter cake was washed with a small volume of TBME to get the title product as a colorless solid (46 mg, 50%). MS (ESI): m/z=271.1 [M+H]$^+$.

BB 124

3-(Azetidin-3-yl)-5-[3-(trifluoromethyl)-1-bicyclo[1.1.1]pentanyl]-1,2,4-oxadiazole; Hydrochloride Step 1: 3-(1-Benzhydrylazetidin-3-yl)-5-[3-(trifluoromethyl)-1-bicyclo[1.1.1]pentanyl]-1,2,4-oxadiazole To a solution of 3-(trifluoromethyl)bicyclo[1.1.1]pentane-1-carboxylic acid (101.4 mg, 0.56 mmol, 1.0 equiv; CAS RN 224584-18-3) and DIPEA (218.3 mg, 295.0 µL, 1.69 mmol, 3.0 equiv) in DMF (1.5 mL) was added HATU (214.1 mg, 0.56 mmol, 1.0 equiv) and the reaction mixture was stirred at RT for 30 min. To the solution was added 1-benzhydryl-N'-hydroxy-azetidine-3-carboxamidine (180 mg, 0.56 mmol, 1.0 equiv; CAS RN 2634758-73-7) in one portion and the reaction mixture was stirred at 100° C. for 2 h and at RT overnight. The reaction mixture was diluted with water and extracted with ethyl acetate. The organic phase was dried over MgSO$_4$, evaporated and the residue purified by silica gel chromatography using a MPLC system eluting with a gradient of n-heptane:ethyl acetate (100:0 to 50:50) to yield the title compound as a colorless oil (188 mg, 68%). MS (ESI): m/z=426.2 [M+H]$^+$.

Step 2: 3-(Azetidin-3-yl)-5-[3-(trifluoromethyl)-1-bicyclo[1.1.1]pentanyl]-1,2,4-oxadiazole; Hydrochloride The title compound was obtained in analogy to BB 124/Step 2 starting from 3-(1-benzhydrylazetidin-3-yl)-5-[3-(trifluoromethyl)-1-bicyclo[1.1.1]pentanyl]-1,2,4-oxadiazole (188 mg, 0.384 mmol, 1 equiv) as a colorless solid (81 mg, 60%). MS (ESI): m/z=260.1 [M+H]$^+$.

BB 125

2-[1-[5-(Azetidin-3-yl)-2-pyridyl]azetidin-3-yl]propan-2-ol; 4-methylbenzenesulfonic Acid Step 1: Tert-Butyl 3-[6-[3-(1-hydroxy-1-methylethyl)azetidin-1-yl]-3-pyridyl]azetidine-1-carboxylate The title compound was obtained in analogy to BB 58/Step 1 starting from tert-butyl 3-(6-chloro-3-pyridyl)azetidine-1-carboxylate (205 mg, 0.76 mmol, 1.0 equiv; CAS RN 870689-19-3) and 2-(azetidin-3-yl)propan-2-ol; hydrochloride (115.7 mg, 0.76 mmol, 1.0 equiv; CAS RN 1357923-33-1) as an off-white gum (538 mg, 74%). MS (ESI): m/z=296.3 [M+H]$^+$.

Step 2: 2-[1-[5-(Azetidin-3-yl)-2-pyridyl]azetidin-3-yl]propan-2-ol; 4-methylbenzenesulfonic Acid The title compound was obtained in analogy to BB 4/Step 2 starting from tert-butyl 3-[6-[3-(1-hydroxy-1-methylethyl)azetidin-1-yl]-3-pyridyl]azetidine-1-carboxylate (50 mg, 0.13 mmol, 1.0 equiv) as a light brown gum (91 mg, 94%). MS (ESI): m/z=248.1 [M+H]$^+$.

BB 126

[1-[4-(Azetidin-3-yl)phenyl]cyclopropyl]methanol; Hydrochloride

Step 1: Tert-Butyl 3-[4-(1-methoxycarbonylcyclopropyl)phenyl]azetidine-1-carboxylate The title compound was obtained in analogy to BB 4/Step 1 starting from methyl 1-(4-bromophenyl)cyclopropanecarboxylate (300 mg, 1.18 mmol, 1.0 equiv; CAS RN 638220-35-6) and tert-butyl 3-bromoazetidine-1-carboxylate (416.5 mg, 1.76 mmol, 1.5 equiv; CAS RN 1064194-10-0) by irradiating (420 nm) for 16 h as a light yellow oil (270 mg, 66%). MS (ESI): m/z=276.1 [M+2H-tBu]$^+$.

Step 2: Tert-Butyl 3-[4-[1-(hydroxymethyl)cyclopropyl]phenyl]azetidine-1-carboxylate To an ice-cold solution of tert-butyl 3-[4-(1-methoxycarbonylcyclopropyl)phenyl]azetidine-1-carboxylate (250 mg, 0.75 mmol, 1.0 equiv) in THF (2.1 mL) under an atmosphere of Ar was added dropwise LiAlH$_4$ (754.2 µL, 0.75 mmol, 1.0 equiv; 1 M in THF) and stirred at 0° C. for 1.25 h. The reaction was quenched with sat. aqueous NH$_4$Cl solution, extracted with water/ethyl acetate (3×30 mL) and the combined organic phase dried over MgSO$_4$. The title compound was obtained as a colorless oil and used in the consecutive reaction step without further purification (154 mg, 61%). MS (ESI): m/z=248.1 [M+2H-tBu]$^+$.

Step 3: [1-[4-(Azetidin-3-yl)phenyl]cyclopropyl]methanol; Hydrochloride

The title compound was obtained in analogy to BB 18/Step 2 starting tert-butyl 3-[4-[1-(hydroxymethyl)cyclopropyl]phenyl]azetidine-1-carboxylate (154 mg, 0.46 mmol, 1.0 equiv) as a light yellow gum (115 mg, 84%; ca. 80% purity). MS (ESI): m/z=204.1 [M+H]$^+$.

BB 127

2-[5-(Azetidin-3-yl)-2-pyridyl]-5-oxa-2-azaspiro[3.4]octane; 4-methylbenzenesulfonic Acid

Step 1: Tert-Butyl 3-[6-(5-oxa-2-azaspiro[3.4]octan-2-yl)-3-pyridyl]azetidine-1-carboxylate To a suspension of tert-butyl 3-(6-bromo-3-pyridyl)azetidine-1-carboxylate (150 mg, 0.48 mmol, 1.0 equiv; BB 71/Step 1) and 5-oxa-2-azaspiro[3.4]octane; oxalic acid (151.5 mg, 0.48 mmol, 1.0 equiv; CAS RN 145309-24-6) in 1,4-dioxane (3 mL) under Ar was added Crotyl(Amphos)palladium(II) chloride (11.8 mg, 0.024 mmol, 0.05 equiv; CAS RN 1334497-06-1) and sodium tert-butoxide (0.72 mL, 1.44 mmol, 3.0 equiv; 2 M in THF) and the reaction mixture was heated by microwave irradiation at 80° C. for 3 h. The reaction mixture was filtered, and the crude material purified by silica gel chromatography using a MPLC system eluting with a gradient of DCM:MeOH (100:0 to 90:10) to get the title compound as a yellow solid (130 mg, 75%). MS (ESI): m/z=346.2 [M+H]$^+$.

Step 2: 2-[5-(Azetidin-3-yl)-2-pyridyl]-5-oxa-2-azaspiro[3.4]octane: 4-methylbenzenesulfonic Acid The title compound was obtained in analogy to BB 4/Step 2 starting from tert-butyl 3-[6-(5-oxa-2-azaspiro[3.4]octan-2-yl)-3-pyridyl]azetidine-1-carboxylate (125 mg, 0.36 mmol, 1.0 equiv) as a light yellow foam (221 mg, 86%). MS (ESI): m/z=246.2 [M+H]$^+$.

BB 128

5-[5-(Azetidin-3-yl)-2-pyridyl]-2,2-difluoro-5-azaspiro[2.4]heptane; 4-methylbenzenesulfonic Acid

Step 1: Tert-Butyl 3-[6-(2,2-difluoro-5-azaspiro[2.4]heptan-5-yl)-3-pyridyl]azetidine-1-carboxylate The title compound was obtained in analogy to BB 127/Step 1 starting from tert-butyl 3-(6-bromo-3-pyridyl)azetidine-1-carboxylate (175 mg, 0.56 mmol, 1.0 equiv; BB 71/Step 1) and 2,2-difluoro-5-azaspiro[2.4]heptane; hydrochloride (94.8 mg, 0.56 mmol, 1.0 equiv; CAS RN 1215071-12-7) as a yellow solid (107 mg, 50%). MS (ESI): m/z=366.2 [M+H]$^+$.

Step 2: 5-[5-(Azetidin-3-yl)-2-pyridyl]-2,2-difluoro-5-azaspiro[2.4]heptane: 4-methylbenzenesulfonic Acid The title compound was obtained in analogy to BB 4/Step 2 starting from tert-butyl 3-[6-(2,2-difluoro-5-azaspiro[2.4]heptan-5-yl)-3-pyridyl]azetidine-1-carboxylate (91 mg, 0.25 mmol, 1.0 equiv) as a light yellow foam (160 mg, 83%). MS (ESI): m/z=266.2 [M+H]$^+$.

BB 129

2-[4-(Azetidin-3-yl)phenoxy]-5-(trifluoromethyl)pyrazine; 4-methylbenzenesulfonic acid

Step 1: Tert-Butyl 3-[4-[5-(trifluoromethyl)pyrazin-2-yl]oxyphenyl]azetidine-1-carboxylate To a solution of tert-butyl 3-(4-hydroxyphenyl)azetidine-1-carboxylate (50 mg, 0.20 mmol, 1.0 equiv; BB 15/Step 1; CAS RN 1782327-13-2) and potassium carbonate (83.2 mg, 0.60 mmol, 3.0 equiv) in DMSO (2 mL) was added 2-bromo-5-(trifluoromethyl)pyrazine (68.3 mg, 0.30 mmol, 1.5 equiv; CAS RN 1196152-38-1) and the reaction mixture was stirred at 100° C. for 2 h. The reaction mixture was then poured on water and ethyl acetate and the aqueous layer extracted three times with ethyl acetate. The combined organic layers were dried over MgSO$_4$, filtered and evaporated. The crude compound was purified by silica gel chromatography using a MPLC system eluting with a gradient of n-heptane:TBME (95:5 to 30:70) to yield the title compound as a light yellow solid (76 mg, 92%). MS (ESI): m/z=340.1 [M+2H-tBu]$^+$.

Step 2: 2-[4-(Azetidin-3-yl)phenoxy]-5-(trifluoromethyl)pyrazine; 4-methylbenzenesulfonic Acid The title compound was obtained in analogy to BB 4/Step 2 starting from tert-butyl 3-[4-[5-(trifluoromethyl)pyrazin-2-yl]oxyphenyl]azetidine-1-carboxylate (71 mg, 0.17 mmol, 1.0 equiv) as a white solid (71 mg, 78%). MS (ESI): m/z=296.1 [M+H]$^+$.

BB 130

6-(Azetidin-3-yl)-N-[[1-(trifluoromethyl)cyclopropyl]methyl]pyridin-3-amine; 4-methylbenzenesulfonic Acid

Step 1: Tert-Butyl 3-[5-[[1-(trifluoromethyl)cyclopropyl]methylamino]-2-pyridyl]azetidine-1-carboxylate To a solution of tert-butyl 3-(5-bromo-2-pyridyl)azetidine-1-carboxylate (1.0 g, 3.19 mmol, 1.0 equiv; CAS RN 1922143-52-9) and [1-(trifluoromethyl)cyclopropyl]methanamine; hydrochloride (0.56 g, 3.19 mmol, 1.0 equiv; CAS RN 1783418-59-6) in tert-amyl alcohol (10 mL) under Ar was added tBuXPhos Pd G3 (0.25 g, 0.32 mmol, 0.10 equiv; CAS RN 1447963-75-8) and sodium tert-butoxide (1.23 g, 12.77 mmol, 4.0 equiv) and the reaction mixture was heated at 110° C. for 12 h. The reaction mixture was filtered, and the crude material purified by preparative HPLC (Phenomenex Gemini 5 µm C18 110 A Axia column (75 mm×30 mm, 5 µm); 0.1% v/v FA in water and MeCN) to give the title compound as a yellow solid (380 mg, 32%). MS (ESI): m/z=316.2 [M+2H-tBu]$^+$.

Step 2: 6-(Azetidin-3-yl)-N-[[1-(trifluoromethyl) cyclopropyl]methyl]pyridin-3-amine; 4-methylbenzenesulfonic Acid The title compound was obtained in analogy to BB 4/Step 2 starting from tert-butyl 3-[5-[[1-(trifluoromethyl)cyclopropyl]methylamino]-2-pyridyl]azetidine-1-carboxylate (380 mg, 1.02 mmol, 1.0 equiv) as a brown solid (385 mg, 59%). MS (ESI): m/z=272.2 [M+H]$^+$.

BB 131

5-(Azetidin-3-yl)-N-[[1-(trifluoromethyl)cyclopropyl]methyl]pyrazin-2-amine; 4-methylbenzenesulfonic Acid Step 1: Tert-Butyl 3-[5-[[1-(trifluoromethyl)cyclopropyl]methylamino]pyrazin-2-yl]azetidine-1-carboxylate The title compound was obtained in analogy to BB 130/Step 1 starting from tert-butyl 3-(5-bromopyrazin-2-yl) azetidine-1-carboxylate (1.62 g, 5.16 mmol, 1.0 equiv; BB 60/Step 1) and [1-(trifluoromethyl)cyclopropyl]methanamine; hydrochloride (0.90 g, 5.13 mmol, 1.0 equiv; CAS RN 1783418-59-6) as a light yellow oil (0.55 g, 28%). MS (ESI): m/z=373.1 [M+H]$^+$.

Step 2: 5-(Azetidin-3-yl)-N-[[1-(trifluoromethyl) cyclopropyl]methyl]pyrazin-2-amine; 4-methylbenzenesulfonic Acid The title compound was obtained in analogy to BB 4/Step 2 starting from tert-butyl 3-[5-[[1-(trifluoromethyl)cyclopropyl]methylamino]pyrazin-2-yl]azetidine-1-carboxylate (620 mg, 1.66 mmol, 1.0 equiv) as a yellow solid (708 mg, 67%). MS (ESI): m/z=273.1 [M+H]$^+$.

BB 132

5-[4-(Azetidin-3-yl)phenyl]-3-cyclopropyl-1H-1,2,4-triazole; 4-methylbenzenesulfonic Acid Step 1: Tert-Butyl 3-(p-tolylsulfonylhydrazono) azetidine-1-carboxylate A solution of tert-butyl 3-oxoazetidine-1-carboxylate (70.0 g, 408.9 mmol, 1.0 equiv; CAS RN 398489-26-4) and 4-methylbenzenesulfonohydrazide (76.2 g, 408.9 mmol, 1.0 equiv; CAS RN 1576-35-8) in toluene (1300 mL) was heated to reflux for 3 h. The reaction mixture was cooled to RT, the formed precipitate filtered and dried under vacuum. The title compound was obtained as a white solid (109 g, 75%). MS (ESI): m/z=338.0 [M−H]$^-$.

Step 2: Tert-Butyl 3-(4-cyanophenyl)azetidine-1-carboxylate

To a solution of tert-butyl 3-(p-tolylsulfonylhydrazono) azetidine-1-carboxylate (23.0 g, 67.8 mmol, 1.0 equiv; CAS RN 1510865-66-3) and (4-cyanophenyl)boronic acid (13.24 g, 90.1 mmol, 1.3 equiv; CAS RN 126747-14-6) in 1,4-dioxane (800 mL) was added potassium carbonate (14.05 g, 101.65 mmol, 1.5 equiv) and the reaction mixture was heated to reflux overnight. The formed precipitate was filtered off and dried under vacuum. The precipate was taken up in TBME (500 mL), washed with water (100 mL) and a sat. aqueous NaCl solution (100 mL). The combined organic phases were dried over Na$_2$SO$_4$ and then concentrated. The crude compound was purified by silica gel chromatography eluting with a gradient of ACN:chloroform (100:0 to 100:0) to get the title compound as a light yellow oil (8.0 g, 43%). MS (ESI): m/z=259.0 [M+H]$^+$.

Step 3: Tert-Butyl 3-[4-(3-cyclopropyl-1H-1,2,4-triazol-5-yl)phenyl]azetidine-1-carboxylate To a solution of tert-butyl 3-(4-cyanophenyl)azetidine-1-carboxylate (2.0 g, 7.74 mmol, 1.0 equiv) and cyclopropanecarbohydrazide (7.75 g, 77.42 mmol, 10.0 equiv; CAS RN 6952-93-8) in 1-butanol (150 mL) was added potassium carbonate (10.70 g, 77.42 mmol, 10.0 equiv) and the reaction mixture was heated to reflux overnight. The formed precipitate was filtered off and dried under reduced pressure. The precipate was purified by silica gel chromatography eluting with a gradient of ACN:chloroform (100:0 to 70:30) to get the title compound as a white solid (0.86 g, 31%). MS (ESI): m/z=341.0 [M+H]$^+$.

Step 4: 5-[4-(Azetidin-3-yl)phenyl]-3-cyclopropyl-1H-1,2,4-triazole; 4-methylbenzenesulfonic Acid The title compound was obtained in analogy to BB 4/Step 2 starting from tert-butyl 3-[4-(3-cyclopropyl-1H-1,2,4-triazol-5-yl)phenyl]azetidine-1-carboxylate (700 mg, 2.06 mmol, 1.0 equiv) as a white solid (859 mg, 68%). MS (ESI): m/z=241.2 [M+H]$^+$.

BB 133

5-[4-(Azetidin-3-yl)phenyl]-3-[1-(trifluoromethyl) cyclopropyl]-1H-1,2,4-triazole; 4-methylbenzenesulfonic Acid Step 1: Tert-Butyl 3-[4-[3-[1-(trifluoromethyl)cyclopropyl]-1H-1,2,4-triazol-5-yl]phenyl]azetidine-1-carboxylate The title compound was obtained in analogy to BB 132/Step 3 starting from tert-butyl 3-(4-cyanophenyl)azetidine-1-carboxylate (0.20 g, 0.77 mmol, 1.0 equiv; BB 132/Step 2) and 1-(trifluoromethyl)cyclopropanecarbohydrazide (0.65 g, 3.87 mmol, 5.0 equiv; CAS RN 1016557-86-0) as a white solid (0.16 g, 41%). MS (ESI): m/z=409.2 [M+H]$^+$.

Step 2: 5-[4-(Azetidin-3-yl)phenyl]-3-[1-(trifluoromethyl)cyclopropyl]-1H-1,2,4-triazole: 4-methylbenzenesulfonic Acid The title compound was obtained in analogy to BB 4/Step 2 starting from tert-butyl 3-[4-[3-[1-(trifluoromethyl)cyclopropyl]-1H-1,2,4-triazol-5-yl]phenyl]azetidine-1-carboxylate (700 mg, 1.71 mmol, 1.0 equiv) as a white solid (604 mg, 54%). MS (ESI): m/z=309.4 [M+H]$^+$.

BB 134

4-Methylbenzenesulfonic Acid; 6-[(3-methylsulfonylphenyl)methyl]-2-azaspiro[3.3]heptane

Step 1: Tert-Butyl 6-[(3-methylsulfonylphenyl)methylene]-2-azaspiro[3.3]heptane-2-carboxylate The title compound was obtained in analogy to BB 80/Step 2 starting from 1-bromo-3-methylsulfonyl-benzene (1.05 g, 4.47 mmol, 1.0 equiv; CAS RN 34896-80-5) and tert-butyl 6-[(4,4,5,5-tetramethyl-1,3,2-dioxaborolan-2-yl)methylene]-2-azaspiro[3.3]heptane-2-carboxylate (1.50 g, 4.47 mmol, 1.0 equiv; BB 80/Step 1) as a light yellow solid (0.90 g, 55%). MS (ESI): m/z=308.3 [M+2H-tBu]$^+$.

Step 2: Tert-Butyl 6-[(3-methylsulfonylphenyl)methyl]-2-azaspiro[3.3]heptane-2-carboxylate The title compound was obtained in analogy to BB 80/Step 3 starting from tert-butyl 6-[(3-methylsulfonylphenyl)methylene]-2-azaspiro[3.3]heptane-2-carboxylate (0.75 g, 2.06 mmol, 1.0 equiv) as a white solid (0.75 g, 99%). MS (ESI): m/z=310.3 [M+2H-tBu]$^+$.

Step 3: 4-Methylbenzenesulfonic Acid; 6-[(3-methylsulfonylphenyl)methyl]-2-azaspiro[3.3]heptane The title compound was obtained in analogy to BB 4/Step 2 starting from tert-butyl 6-[(3-methylsulfonylphenyl)methyl]-2-azaspiro[3.3]heptane-2-carboxylate (0.60 g, 1.64 mmol, 1.0 equiv) as a white solid (0.67 g, 80%). MS (ESI): m/z=266.4 [M+H]$^+$.

BB 135

4-Methylbenzenesulfonic acid; 6-[(4-methylsulfonylphenyl)methyl]-2-azaspiro[3.3]heptane

Step 1: Tert-Butyl 6-[(4-methylsulfonylphenyl)methylene]-2-azaspiro[3.3]heptane-2-carboxylate The title compound was obtained in analogy to BB 80/Step 2 starting from 1-bromo-4-methylsulfonyl-benzene (1.75 g, 7.46 mmol, 1.0 equiv; CAS RN 3466-32-8) and tert-butyl 6-[(4,4,5,5-tetramethyl-1,3,2-dioxaborolan-2-yl)methylene]-2-azaspiro[3.3]heptane-2-carboxylate (2.50 g, 7.46 mmol, 1.0 equiv; BB 80/Step 1) as a yellow solid (1.90 g, 70%). MS (ESI): m/z=308.1 [M+2H-tBu]$^+$.

Step 2: Tert-Butyl 6-[(4-methylsulfonylphenyl)methyl]-2-azaspiro[3.3]heptane-2-carboxylate The title compound was obtained in analogy to BB 80/Step 3 starting from tert-butyl 6-[(4-methylsulfonylphenyl)methylene]-2-azaspiro[3.3]heptane-2-carboxylate (1.70 g, 4.68 mmol, 1.0 equiv) as a colorless oil (1.68 g, 98%). MS (ESI): m/z=310.0 [M+2H-tBu]$^+$.

Step 3: 4-Methylbenzenesulfonic Acid: 6-[(4-methylsulfonylphenyl)methyl]-2-azaspiro[3.3]heptane The title compound was obtained in analogy to BB 4/Step 2 starting from tert-butyl 6-[(4-methylsulfonylphenyl)methyl]-2-azaspiro[3.3]heptane-2-carboxylate (1.58 g, 4.32 mmol, 1.0 equiv) as a white solid (1.23 g, 64%). MS (ESI): m/z=266.2 [M+H]$^+$.

BB 136

4-Methylbenzenesulfonic Acid; 6-[[6-(trifluoromethyl)pyridazin-3-yl]methyl]-2-azaspiro[3.3]heptane

Step 1: Tert-Butyl 6-[[6-(trifluoromethyl)pyridazin-3-yl]methylene]-2-azaspiro[3.3]heptane-2-carboxylate The title compound was obtained in analogy to BB 80/Step 2 starting from 3-bromo-6-(trifluoromethyl)pyridazine (1.35 g, 5.97 mmol, 1.0 equiv; CAS RN 174607-37-5) and tert-butyl 6-[(4,4,5,5-tetramethyl-1,3,2-dioxaborolan-2-yl)methylene]-2-azaspiro[3.3]heptane-2-carboxylate (2.00 g, 5.97 mmol, 1.0 equiv; BB 80/Step 1) as a yellow solid (1.90 g, 70%). MS (ESI): m/z=308.1 [M+2H-tBu]$^+$.

Step 2: Tert-Butyl 6-[[6-(trifluoromethyl)pyridazin-3-yl]methyl]-2-azaspiro[3.3]heptane-2-carboxylate The title compound was obtained in analogy to BB 80/Step 3 starting from tert-butyl 6-[[6-(trifluoromethyl)pyridazin-3-yl]methylene]-2-azaspiro[3.3]heptane-2-carboxylate (1.05 g, 2.95 mmol, 1.0 equiv) as a yellow solid (0.95 g, 81%). $^1$H NMR (400 MHz, CDCl$_3$): δ=7.73 (d, J=8.68 Hz, 1H), 7.44 (d, J=8.68 Hz, 1H), 3.93 (s, 2H), 3.85 (s, 2H), 3.15 (d, J=7.70 Hz, 2H), 2.60-2.74 (m, 1H), 2.25-2.41 (m, 2H), 1.93-2.08 (m, 2H), 1.43 (s, 9H).

Step 3: 4-Methylbenzenesulfonic Acid; 6-[[6-(trifluoromethyl)pyridazin-3-yl]methyl]-2-azaspiro[3.3]heptane The title compound was obtained in analogy to BB 4/Step 2 starting from tert-butyl 6-[[6-(trifluoromethyl)pyridazin-3-yl]methyl]-2-azaspiro[3.3]heptane-2-carboxylate (0.84 g, 2.35 mmol, 1.0 equiv) as a dark brown solid (0.66 g, 63%). MS (ESI): m/z=258.4 [M+H]$^+$.

BB 137

4-Methylbenzenesulfonic Acid; 6-[[2-(trifluoromethyl)pyrimidin-5-yl]methyl]-2-azaspiro[3.3]heptane

Step 1: Tert-Butyl 6-[[2-(trifluoromethyl)pyrimidin-5-yl]methylene]-2-azaspiro[3.3]heptane-2-carboxylate The title compound was obtained in analogy to BB 80/Step 2 starting from 5-bromo-2-(trifluoromethyl)pyrimidine (0.96 g, 4.23 mmol, 1.0 equiv; CAS RN 799557-86-1) and tert-butyl 6-[(4,4,5,5-tetramethyl-1,3,2-dioxaborolan-2-yl)methylene]-2-azaspiro[3.3]heptane-2-carboxylate (1.42 g, 4.23 mmol, 1.0 equiv; BB 80/Step 1) as a yellow solid (1.27 g, 85%). $^1$H NMR (400 MHz, CDCl$_3$): δ=8.68 (s, 2H), 6.18 (br s, 1H), 4.01 (s, 4H), 3.24 (br s, 2H), 3.13 (br s, 2H), 1.44 (s, 9H).

Step 2: Tert-Butyl 6-[[2-(trifluoromethyl)pyrimidin-5-yl]methyl]-2-azaspiro[3.3]heptane-2-carboxylate The title compound was obtained in analogy to BB 80/Step 3 starting from tert-butyl 6-[[2-(trifluoromethyl)pyrimidin-5-yl]methylene]-2-azaspiro[3.3]heptane-2-carboxylate (1.34 g, 3.77 mmol, 1.0 equiv) as a white solid (1.00 g, 67%). MS (ESI): m/z=302.3 [M+2H-tBu]$^+$. $^1$H NMR (400 MHz, CDCl$_3$): δ=8.67 (s, 2H), 3.93 (s, 2H), 3.84 (s, 2H), 2.77 (d, J=7.46 Hz, 2H), 2.39-2.52 (m, 1H), 2.28-2.38 (m, 2H), 1.86-1.98 (m, 2H), 1.43 (s, 9H).

Step 3: 4-Methylbenzenesulfonic Acid; 6-[[2-(trifluoromethyl)pyrimidin-5-yl]methyl]-2-azaspiro[3.3]heptane The title compound was obtained in analogy to BB 4/Step 2 starting from tert-butyl 6-[[2-(trifluoromethyl)pyrimidin-5-yl]methyl]-2-azaspiro[3.3]heptane-2-carboxylate (0.90 g, 2.52 mmol, 1.0 equiv) as a light yellow gum (0.87 g, 79%). MS (ESI): m/z=258.1 [M+H]$^+$.

BB 138

4-Methylbenzenesulfonic acid; 6-[[5-(trifluoromethyl)pyrimidin-2-yl]methyl]-2-azaspiro[3.3]heptane Step 1: Tert-Butyl 6-[[5-(trifluoromethyl)pyrimidin-2-yl]methylene]-2-azaspiro[3.3]heptane-2-carboxylate The title compound was obtained in analogy to BB 80/Step 2 starting from 2-bromo-5-(trifluoromethyl)pyrimidine (1.35 g, 5.97 mmol, 1.0 equiv; CAS RN 69034-09-9) and tert-butyl 6-[(4,4,5,5-tetramethyl-1,3,2-dioxaborolan-2-yl)methylene]-2-azaspiro[3.3]heptane-2-carboxylate (2.00 g, 5.97 mmol, 1.0 equiv; BB 80/Step 1) as a yellow solid (1.60 g, 76%). MS (ESI): m/z=299.9 [M+2H-tBu]$^+$. $^1$H NMR (400 MHz, CDCl$_3$): δ=8.84-8.90 (m, 2H), 6.43-6.48 (m, 1H), 4.01-4.04 (m, 4H), 3.43-3.48 (m, 2H), 3.13-3.19 (m, 2H), 2.81-2.87 (m, 1H), 1.44-1.46 (m, 10H).

Step 2: Tert-Butyl 6-[[5-(trifluoromethyl)pyrimidin-2-yl]methyl]-2-azaspiro[3.3]heptane-2-carboxylate The title compound was obtained in analogy to BB 80/Step 3 starting from tert-butyl 6-[[5-(trifluoromethyl)pyrimidin-2-yl]methylene]-2-azaspiro[3.3]heptane-2-carboxylate (1.50 g, 4.22 mmol, 1.0 equiv) as a white solid (1.30 g, 86%). $^1$H NMR (400 MHz, CDCl$_3$): δ=8.89 (s, 2H), 3.91-3.98 (m, 2H), 3.82-3.88 (m, 2H), 3.08-3.15 (m, 2H), 2.66-2.78 (m, 1H), 2.28-2.36 (m, 2H), 1.94-2.03 (m, 2H), 1.60-1.66 (m, 2H), 1.40-1.45 (m, 10H).

Step 3: 4-Methylbenzenesulfonic Acid; 6-[[5-(trifluoromethyl)pyrimidin-2-yl]methyl]-2-azaspiro[3.3]heptane The title compound was obtained in analogy to BB 4/Step 2 starting from tert-butyl 6-[[5-(trifluoromethyl)pyrimidin-2-yl]methyl]-2-azaspiro[3.3]heptane-2-carboxylate (1.25 g, 3.50 mmol, 1.0 equiv) as a white solid (0.39 g, 18%). MS (ESI): m/z=258.0 [M+H]$^+$.

BB 139

6-[(3-Fluoro-5-methylsulfonyl-phenyl)methyl]-2-azaspiro[3.3]heptane; 4-methylbenzenesulfonic Acid Step 1: Tert-Butyl 6-[(3-fluoro-5-methylsulfonyl-phenyl)methylene]-2-azaspiro[3.3]heptane-2-carboxylate The title compound was obtained in analogy to BB 80/Step 2 starting from 1-bromo-3-fluoro-5-methylsulfonyl-benzene (1.51 g, 5.97 mmol, 1.0 equiv; CAS RN 1207970-78-2) and tert-butyl 6-[(4,4,5,5-tetramethyl-1,3,2-dioxaborolan-2-yl)methylene]-2-azaspiro[3.3]heptane-2-carboxylate (2.00 g, 5.97 mmol, 1.0 equiv; BB 80/Step 1) as a yellow solid (1.20 g, 48%). MS (ESI): m/z=326.2 [M+2H-tBu]$^+$.

Step 2: Tert-Butyl 6-[(3-fluoro-5-methylsulfonyl-phenyl)methyl]-2-azaspiro[3.3]heptane-2-carboxylate The title compound was obtained in analogy to BB 80/Step 3 starting from tert-butyl 6-[(3-fluoro-5-methylsulfonyl-phenyl)methylene]-2-azaspiro[3.3]heptane-2-carboxylate (1.15 g, 3.01 mmol, 1.0 equiv) as a yellow solid (0.90 g, 70%). $^1$H NMR (400 MHz, CDCl$_3$): δ=7.43-7.53 (m, 2H), 7.11 (br d, J=8.93 Hz, 1H), 3.93 (s, 2H), 3.83 (s, 2H), 3.06 (s, 3H), 2.77 (d, J=7.46 Hz, 2H) 2.38-2.49 (m, 1H) 2.24-2.34 (m, 2H) 1.84-1.95 (m, 2H) 1.43 (s, 9H).

Step 3: 6-[(3-Fluoro-5-methylsulfonyl-phenyl)methyl]-2-azaspiro[3.3]heptane; 4-methylbenzenesulfonic Acid The title compound was obtained in analogy to BB 4/Step 2 starting from tert-butyl 6-[(3-fluoro-5-methylsulfonyl-phenyl)methyl]-2-azaspiro[3.3]heptane-2-carboxylate (0.85 g, 2.22 mmol, 1.0 equiv) as a light yellow gum (0.89 g, 84%). MS (ESI): m/z=284.0 [M+H]$^+$.

BB 140

6-(3-Cyclopropyl-1,2,4-triazol-1-yl)-2-azaspiro[3.3]heptane; 4-methylbenzenesulfonic Acid Step 1: Tert-Butyl 6-methylsulfonyloxy-2-azaspiro[3.3]heptane-2-carboxylate To a solution of tert-butyl 6-hydroxy-2-azaspiro[3.3]heptane-2-carboxylate (14.5 g, 67.99 mmol, 1.0 equiv; CAS RN 1147557-97-8) in DCM (270 mL) was added at 0° C. triethylamine (18.95 mL, 13.76 g, 135.97 mmol, 2.0 equiv) followed by methanesulfonyl chloride (5.79 mL, 8.57 g, 74.79 mmol, 1.1 equiv). The reaction mixture was stirred at 0° C. for 20 min and at RT overnight. The reaction mixture was diluted with DCM (200 mL) and washed with water (300 mL). The organic layer was washed with a sat. aqueous NaCl solution, dried over Na$_2$SO$_4$, filtered and concentrated. The title compound was obtained as a yellow solid and used in the consecutive reaction step without further purification (19.2 g, 97%). MS (ESI): m/z=236.1 [M+2H-tBu]$^+$.

Step 2: Tert-Butyl 6-(3-cyclopropyl-1,2,4-triazol-1-yl)-2-azaspiro[3.3]heptane-2-carboxylate To a solution of 3-cyclopropyl-1H-1,2,4-triazole (0.95 g, 8.68 mmol, 1.1 equiv; CAS RN 1211390-33-8) in DMF (36.7 mL) at 0° C. under an atmosphere of N$_2$ was added sodium hydride (0.38 g, 8.68 mmol, 1.1 equiv; 55% in mineral oil) and the reaction mixture was stirred at RT for 20 min. Then, tert-butyl 6-methylsulfonyloxy-2-azaspiro[3.3]heptane-2-carboxylate (2.30 g, 7.89 mmol, 1.0 equiv) was added and the reaction mixture was stirred at 90° C. overnight. The reaction mixture was quenched with sat. aqueous NH$_4$Cl solution (0.5 mL), diluted with aqueous NaHCO$_3$ solution (1 M) and extracted with ethyl acetate. The combined organic phase was dried over MgSO$_4$ and concentrated under reduced pressure. The two regioisomers were purified by preparative SFC (Chiralpak IC column (250 mm×20 mm, 5 μm), eluent: 20% MeOH in supercritical $CO_2$) to give the title compound as a yellow viscous oil (1.46 g, 58%) and tert-butyl 6-(5-cyclopropyl-1,2,4-triazol-1-yl)-2-azaspiro[3.3]heptane-2-carboxylate as a white solid (0.79 g, 31%). MS (ESI): m/z=305.3 $[M+2H-tBu]^+$ for both compounds.

Step 3: 6-(3-Cyclopropyl-1,2,4-triazol-1-yl)-2-azaspiro[3.3]heptane; 4-methylbenzenesulfonic Acid The title compound was obtained in analogy to BB 4/Step 2 starting from tert-butyl 6-(3-cyclopropyl-1,2,4-triazol-1-yl)-2-azaspiro[3.3]heptane-2-carboxylate (0.99 g, 3.26 mmol, 1.0 equiv) as a white solid (1.20 g, 78%). MS (ESI): m/z=205.2 $[M+H]^+$.

BB 141

4-Methylbenzenesulfonic Acid; 6-[[3-(trifluoromethylsulfonyl)phenyl]methyl]-2-azaspiro[3.3]heptane Step 1: Tert-Butyl 6-[[3-(trifluoromethylsulfonyl)phenyl]methylene]-2-azaspiro[3.3]heptane-2-carboxylate The title compound was obtained in analogy to BB 80/Step 2 starting from 1-bromo-3-(trifluoromethylsulfonyl)benzene (0.45 g, 1.57 mmol, 1.05 equiv; CAS RN 2728-70-3) and tert-butyl 6-[(4,4,5,5-tetramethyl-1,3,2-dioxaborolan-2-yl)methylene]-2-azaspiro[3.3]heptane-2-carboxylate (0.50 g, 1.49 mmol, 1.0 equiv; BB 80/Step 1) as a light yellow oil (0.49 g, 75%). MS (ESI): m/z=362.1 $[M+2H-tBu]^+$.

Step 2: Tert-Butyl 6-[[3-(trifluoromethylsulfonyl)phenyl]methyl]-2-azaspiro[3.3]heptane-2-carboxylate The title compound was obtained in analogy to BB 80/Step 3 starting from tert-butyl 6-[[3-(trifluoromethylsulfonyl)phenyl]methylene]-2-azaspiro[3.3]heptane-2-carboxylate (0.49 g, 1.12 mmol, 1.0 equiv) as a colorless oil (0.17 g, 37%). MS (ESI): m/z=364.1 $[M+2H-tBu]^+$.

Step 3: 4-Methylbenzenesulfonic Acid; 6-[[3-(trifluoromethylsulfonyl)phenyl]methyl]-2-azaspiro[3.3]heptane The title compound was obtained in analogy to BB 4/Step 2 starting from tert-butyl 6-[[3-(trifluoromethylsulfonyl)phenyl]methyl]-2-azaspiro[3.3]heptane-2-carboxylate (0.17 g, 0.42 mmol, 1.0 equiv) as a colorless oil (0.28 g, 80%). MS (ESI): m/z=320.1 $[M+H]^+$.

BB 142

4-Methylbenzenesulfonic Acid; 2-[[4-(trifluoromethylsulfonyl)phenyl]methyl]-2,6-diazaspiro[3.3]heptane Step 1: Tert-Butyl 6-[[4-(trifluoromethylsulfonyl)phenyl]methyl]-2,6-diazaspiro[3.3]heptane-2-carboxylate The title compound was obtained in analogy to BB 81/Step 1 starting from 4-(trifluoromethylsulfonyl)benzaldehyde (0.25 g, 1.05 mmol, 1.0 equiv; CAS RN 650-89-5) and tert-butyl 2,6-diazaspiro[3.3]heptane-2-carboxylate; oxalic acid (0.22 g, 1.10 mmol, 1.05 equiv; CAS RN 1041026-71-4) as a colorless oil (0.42 g, 85%). MS (ESI): m/z=421.1 $[M+H]^+$.

Step 2: 4-Methylbenzenesulfonic Acid; 2-[[4-(trifluoromethylsulfonyl)phenyl]methyl]-2,6-diazaspiro[3.3]heptane The title compound was obtained in analogy to BB 4/Step 2 starting from tert-butyl 6-[[4-(trifluoromethylsulfonyl)phenyl]methyl]-2,6-diazaspiro[3.3]heptane-2-carboxylate (0.41 g, 0.98 mmol, 1.0 equiv) as a white solid (0.54 g, 84%). MS (ESI): m/z=321.1 $[M+H]^+$.

BB 143

4-Methylbenzenesulfonic acid; 7-[[6-(trifluoromethyl)-3-pyridyl]methyl]-2-azaspiro[3.5]nonane Step 1: Tert-Butyl 7-[(4,4,5,5-tetramethyl-1,3,2-dioxaborolan-2-yl)methylene]-2-azaspiro[3.5]nonane-2-carboxylate To a solution of 4,4,5,5-tetramethyl-2-[(4,4,5,5-tetramethyl-1,3,2-dioxaborolan-2-yl)methyl]-1,3,2-dioxaborolane (2.50 g, 9.33 mmol, 1.1 equiv; CAS RN 78782-17-9) in THF (30 mL) at −75° C. under an atmosphere of $N_2$ was added dropwise LDA (4.88 mL, 9.76 mmol, 1.15 equiv; 2 M solution in THF/heptane/ethylbenzene) and the reaction mixture was stirred for 15 min. A solution of tert-butyl 7-oxo-2-azaspiro[3.5]nonane-2-carboxylate (2.03 g, 8.48 mmol, 1.0 equiv; CAS RN 1363381-22-9) in THF (12 mL) was added below −70° C. After 30 min, the reaction mixture was allowed to warm up to RT and stirred overnight. The reaction mixture was quenched with a sat. aqueous $NH_4Cl$ solution and extracted with ethyl acetate. The combined organic phases were dried over $MgSO_4$ and concentrated under vacuum. The crude product was purified by silica gel chromatography using a MPLC system eluting with a gradient of n-heptane:ethyl acetate (100:0 to 85:15) to yield the title compound as a white solid (0.78 g, 24%). MS (ESI): m/z=308.2 $[M+2H-tBu]^+$.

Step 2: Tert-Butyl 7-[[6-(trifluoromethyl)-3-pyridyl]methylene]-2-azaspiro[3.5]nonane-2-carboxylate The title compound was obtained in analogy to BB 80/Step 2 starting from 5-bromo-2-(trifluoromethyl)pyridine (0.48 g, 2.11 mmol, 1.05 equiv; CAS RN 436799-32-5) and tert-butyl 7-[(4,4,5,5-tetramethyl-1,3,2-dioxaborolan-2-yl)methylene]-2-azaspiro[3.5]nonane-2-carboxylate (0.77 g, 2.01 mmol, 1.0 equiv) as a light yellow oil (0.61 g, 75%). MS (ESI): m/z=327.1 $[M+2H-tBu]^+$.

Step 3: Tert-Butyl 7-[[6-(trifluoromethyl)-3-pyridyl]methyl]-2-azaspiro[3.5]nonane-2-carboxylate The title compound was obtained in analogy to BB 80/Step 3 starting from tert-butyl 7-[[6-(trifluoromethyl)-3-pyridyl]methylene]-2-azaspiro[3.5]nonane-2-carboxylate (0.60 g, 1.58 mmol, 1.0 equiv) as a brown solid (0.62 g, 97%). MS (ESI): m/z=329.1 $[M+2H-tBu]^+$.

Step 4: 4-Methylbenzenesulfonic Acid; 7-[[6-(trifluoromethyl)-3-pyridyl]methyl]-2-azaspiro[3.5]nonane The title compound was obtained in analogy to BB 4/Step 2 starting from tert-butyl 7-[[6-(trifluoromethyl)-3-pyridyl]methyl]-2-azaspiro[3.5]nonane-2-carboxylate (0.61 g, 1.59 mmol, 1.0 equiv) as a white solid (0.65 g, 76%). MS (ESI): m/z=285.2 [M+H]$^+$.

BB 144

4-Methylbenzenesulfonic Acid; 7-[[5-(trifluoromethyl)-2-pyridyl]methyl]-2-azaspiro[3.5]nonane Step 1: Tert-Butyl 7-[[5-(trifluoromethyl)-2-pyridyl]methylene]-2-azaspiro[3.5]nonane-2-carboxylate The title compound was obtained in analogy to BB 80/Step 2 starting from 2-bromo-5-(trifluoromethyl)pyridine (2.09 g, 9.25 mmol, 1.2 equiv; CAS RN 50488-42-1) and tert-butyl 7-[(4,4,5,5-tetramethyl-1,3,2-dioxaborolan-2-yl)methylene]-2-azaspiro[3.5]nonane-2-carboxylate (2.80 g, 7.71 mmol, 1.0 equiv; BB 143/Step 1) as a white solid (1.30 g, 44%). MS (ESI): m/z=327.0 [M+2H-tBu]$^+$.

Step 2: Tert-Butyl 7-[[5-(trifluoromethyl)-2-pyridyl]methyl]-2-azaspiro[3.5]nonane-2-carboxylate The title compound was obtained in analogy to BB 80/Step 3 starting from tert-butyl 7-[[5-(trifluoromethyl)-2-pyridyl]methylene]-2-azaspiro[3.5]nonane-2-carboxylate (1.30 g, 3.40 mmol, 1.0 equiv) as a white solid (1.00 g, 77%). MS (ESI): m/z=329.2 [M+2H-tBu]$^+$.

Step 3: 4-Methylbenzenesulfonic Acid; 7-[[5-(trifluoromethyl)-2-pyridyl]methyl]-2-azaspiro[3.5]nonane The title compound was obtained in analogy to BB 4/Step 2 starting from tert-butyl 7-[[5-(trifluoromethyl)-2-pyridyl]methyl]-2-azaspiro[3.5]nonane-2-carboxylate (1.00 g, 2.60 mmol, 1.0 equiv) as a white solid (0.81 g, 47%). MS (ESI): m/z=285.2 [M+H]$^+$.

BB 145

4-Methylbenzenesulfonic Acid; 7-[[5-(trifluoromethyl)pyrazin-2-yl]methyl]-2-azaspiro[3.5]nonane Step 1: Tert-Butyl 7-[[5-(trifluoromethyl)pyrazin-2-yl]methylene]-2-azaspiro[3.5]nonane-2-carboxylate The title compound was obtained in analogy to BB 80/Step 2 starting from 2-bromo-5-(trifluoromethyl)pyrazine (2.10 g, 9.25 mmol, 1.2 equiv; CAS RN 1196152-38-1) and tert-butyl 7-[(4,4,5,5-tetramethyl-1,3,2-dioxaborolan-2-yl)methylene]-2-azaspiro[3.5]nonane-2-carboxylate (2.80 g, 7.71 mmol, 1.0 equiv; BB 143/Step 1) as a white solid (1.40 g, 43%). MS (ESI): m/z=328.2 [M+2H-tBu]$^+$.

Step 2: Tert-Butyl 7-[[5-(trifluoromethyl)pyrazin-2-yl]methyl]-2-azaspiro[3.5]nonane-2-carboxylate The title compound was obtained in analogy to BB 80/Step 3 starting from tert-butyl 7-[[5-(trifluoromethyl)pyrazin-2-yl]methylene]-2-azaspiro[3.5]nonane-2-carboxylate (1.30 g, 3.39 mmol, 1.0 equiv) as a light brown solid (1.20 g, 89%). MS (ESI): m/z=330.0 [M+2H-tBu]$^+$.

Step 3: 4-Methylbenzenesulfonic Acid; 7-[[5-(trifluoromethyl)pyrazin-2-yl]methyl]-2-azaspiro[3.5]nonane The title compound was obtained in analogy to BB 4/Step 2 starting from tert-butyl 7-[[5-(trifluoromethyl)pyrazin-2-yl]methyl]-2-azaspiro[3.5]nonane-2-carboxylate (1.20 g, 3.11 mmol, 1.0 equiv) as a grey solid (0.91 g, 61%). MS (ESI): m/z=285.0 [M+H]$^+$.

BB 146

7-[[6-(Difluoromethoxy)-3-pyridyl]methyl]-2-azaspiro[3.5]nonane; 4-methylbenzenesulfonic acid Step 1: Tert-Butyl 7-[[6-(difluoromethoxy)-3-pyridyl]methylene]-2-azaspiro[3.5]nonane-2-carboxylate The title compound was obtained in analogy to BB 80/Step 2 starting from 5-bromo-2-(difluoromethoxy)pyridine (2.07 g, 9.25 mmol, 1.2 equiv; CAS RN 899452-26-7) and tert-butyl 7-[(4,4,5,5-tetramethyl-1,3,2-dioxaborolan-2-yl)methylene]-2-azaspiro[3.5]nonane-2-carboxylate (2.80 g, 7.71 mmol, 1.0 equiv; BB 143/Step 1) as a white solid (1.20 g, 41%). MS (ESI): m/z=325.2 [M+2H-tBu]$^+$.

Step 2: Tert-Butyl 7-[[6-(difluoromethoxy)-3-pyridyl]methyl]-2-azaspiro[3.5]nonane-2-carboxylate The title compound was obtained in analogy to BB 80/Step 3 starting from tert-butyl 7-[[6-(difluoromethoxy)-3-pyridyl]methylene]-2-azaspiro[3.5]nonane-2-carboxylate (1.30 g, 3.42 mmol, 1.0 equiv) as a white solid (1.20 g, 92%). MS (ESI): m/z=327.4 [M+2H-tBu]$^+$.

Step 3: 7-[[6-(Difluoromethoxy)-3-pyridyl]methyl]-2-azaspiro[3.5]nonane; 4-methylbenzenesulfonic Acid The title compound was obtained in analogy to BB 4/Step 2 starting from tert-butyl 7-[[6-(difluoromethoxy)-3-pyridyl]methyl]-2-azaspiro[3.5]nonane-2-carboxylate (1.20 g, 3.14 mmol, 1.0 equiv) as a white solid (1.39 g, 67%). MS (ESI): m/z=283.2 [M+H]$^+$.

BB 147

4-Methylbenzenesulfonic Acid; 7-[(4-methylsulfonylphenyl)methyl]-2,7-diazaspiro[3.5]nonane Step 1: Tert-Butyl 7-[(4-methylsulfonylphenyl)methyl]-2,7-diazaspiro[3.5]nonane-2-carboxylate The title compound was obtained in analogy to BB 81/Step 1 starting from 4-methylsulfonylbenzaldehyde (0.30 g, 1.63 mmol, 1.0 equiv; CAS RN 5398-77-6) and tert-butyl 2,7-diazaspiro[3.5]nonane-2-carboxylate (0.37 g, 1.63 mmol, 1.0 equiv; CAS RN 236406-55-6) as a colorless oil (0.59 g, 87%). MS (ESI): m/z=395.2 [M+H]$^+$.

Step 2: 4-Methylbenzenesulfonic Acid; 7-[(4-methylsulfonylphenyl)methyl]-2,7-diazaspiro[3.5]nonane The title compound was obtained in analogy to BB 4/Step 2 starting from tert-butyl 7-[(4-methylsulfonylphenyl)

BB 148

4-Methylbenzenesulfonic Acid; 7-[(3-methylsulfonylphenyl)methyl]-2,7-diazaspiro[3.5]nonane

Step 1: Tert-Butyl 7-[(3-methylsulfonylphenyl)methyl]-2,7-diazaspiro[3.5]nonane-2-carboxylate The title compound was obtained in analogy to BB 81/Step 1 starting from 3-methylsulfonylbenzaldehyde (0.30 g, 1.63 mmol, 1.0 equiv; CAS RN 43114-43-8) and tert-butyl 2,7-diazaspiro[3.5]nonane-2-carboxylate (0.37 g, 1.63 mmol, 1.0 equiv; CAS RN 236406-55-6) as a colorless oil (0.48 g, 72%). MS (ESI): m/z=395.2 [M+H]$^+$.

Step 2: 4-Methylbenzenesulfonic Acid: 7-[(3-methylsulfonylphenyl)methyl]-2,7-diazaspiro[3.5]nonane The title compound was obtained in analogy to BB 4/Step 2 starting from tert-butyl 7-[(3-methylsulfonylphenyl)methyl]-2,7-diazaspiro[3.5]nonane-2-carboxylate (0.48 g, 1.23 mmol, 1.0 equiv) as a colorless solid (0.78 g, 79%). MS (ESI): m/z=295.2 [M+H]$^+$.

BB 149

4-Methylbenzenesulfonic Acid; 7-[[4-(trifluoromethylsulfonyl)phenyl]methyl]-2,7-diazaspiro[3.5]nonane

Step 1: Tert-Butyl 7-[[4-(trifluoromethylsulfonyl)phenyl]methyl]-2,7-diazaspiro[3.5]nonane-2-carboxylate The title compound was obtained in analogy to BB 81/Step 1 starting from 4-(trifluoromethylsulfonyl)benzaldehyde (0.32 g, 1.33 mmol, 1.0 equiv; CAS RN 650-89-5) and tert-butyl 2,7-diazaspiro[3.5]nonane-2-carboxylate (0.30 g, 1.33 mmol, 1.0 equiv; CAS RN 236406-55-6) as a white solid (0.36 g, 58%). MS (ESI): m/z=449.5 [M+H]$^+$.

Step 2: 4-Methylbenzenesulfonic Acid: 7-[[4-(trifluoromethylsulfonyl phenyl]methyl]-2,7-diazaspiro[3.5]nonane The title compound was obtained in analogy to BB 4/Step 2 starting from tert-butyl 7-[[4-(trifluoromethylsulfonyl)phenyl]methyl]-2,7-diazaspiro[3.5]nonane-2-carboxylate (0.36 g, 0.80 mmol, 1.0 equiv) as a white solid (0.54 g, 92%). MS (ESI): m/z=349.1 [M+H]$^+$.

BB 150

4-Methylbenzenesulfonic Acid; 7-[[3-(trifluoromethylsulfonyl)phenyl]methyl]-2,7-diazaspiro[3.5]nonane

Step 1: Tert-Butyl 7-[[3-(trifluoromethylsulfonyl)phenyl]methyl]-2,7-diazaspiro[3.5]nonane-2-carboxylate The title compound was obtained in analogy to BB 81/Step 1 starting from 3-(trifluoromethylsulfonyl)benzaldehyde (0.53 g, 2.21 mmol, 1.0 equiv; CAS RN 1274904-33-4) and tert-butyl 2,7-diazaspiro[3.5]nonane-2-carboxylate (0.50 g, 2.21 mmol, 1.0 equiv; CAS RN 236406-55-6) as a colorless oil (0.63 g, 61%). MS (ESI): m/z=449.2 [M+H]$^+$.

Step 2: 4-Methylbenzenesulfonic acid; 7-[[3-(trifluoromethylsulfonyl)phenyl]methyl]-2,7-diazaspiro[3.5]nonane The title compound was obtained in analogy to BB 4/Step 2 starting from tert-butyl 7-[[3-(trifluoromethylsulfonyl)phenyl]methyl]-2,7-diazaspiro[3.5]nonane-2-carboxylate (0.63 g, 1.40 mmol, 1.0 equiv) as a white solid (0.87 g, 85%). MS (ESI): m/z=349.1 [M+H]$^+$.

BB 151

4-Methylbenzenesulfonic Acid; 7-[[6-(trifluoromethyl)-3-pyridyl]methyl]-2,7-diazaspiro[3.5]nonane

Step 1: Tert-Butyl 7-[[6-(trifluoromethyl)-3-pyridyl]methyl]-2,7-diazaspiro[3.5]nonane-2-carboxylate The title compound was obtained in analogy to BB 81/Step 1 starting from 6-(trifluoromethyl)pyridine-3-carbaldehyde (0.53 g, 2.21 mmol, 1.0 equiv; CAS RN 386704-12-7) and tert-butyl 2,7-diazaspiro[3.5]nonane-2-carboxylate (0.50 g, 2.21 mmol, 1.0 equiv; CAS RN 236406-55-6) as a white solid (0.57 g, 64%). MS (ESI): m/z=386.2 [M+H]$^+$.

Step 2: 4-Methylbenzenesulfonic Acid; 7-[[6-(trifluoromethyl)-3-pyridyl]methyl]-2,7-diazaspiro[3.5]nonane The title compound was obtained in analogy to BB 4/Step 2 starting from tert-butyl 7-[[6-(trifluoromethyl)-3-pyridyl]methyl]-2,7-diazaspiro[3.5]nonane-2-carboxylate (0.57 g, 1.48 mmol, 1.0 equiv) as a white solid (0.89 g, 91%). MS (ESI): m/z=286.1 [M+H]$^+$.

BB 152

4-Methylbenzenesulfonic Acid; 7-[[5-(trifluoromethyl)-2-pyridyl]methyl]-2,7-diazaspiro[3.5]nonane

Step 1: Tert-Butyl 7-[[5-(trifluoromethyl)-2-pyridyl]methyl]-2,7-diazaspiro[3.5]nonane-2-carboxylate The title compound was obtained in analogy to BB 81/Step 1 starting from 5-(trifluoromethyl)pyridine-2-carbaldehyde (0.39 g, 2.21 mmol, 1.0 equiv; CAS RN 31224-82-5) and tert-butyl 2,7-diazaspiro[3.5]nonane-2-carboxylate (0.50 g, 2.21 mmol, 1.0 equiv; CAS RN 236406-55-6) as a white solid (0.65 g, 72%). MS (ESI): m/z=386.2 [M+H]$^+$.

Step 2: 4-Methylbenzenesulfonic Acid; 7-[[5-(trifluoromethyl)-2-pyridyl]methyl]-2,7-diazaspiro[3.5]nonane The title compound was obtained in analogy to BB 4/Step 2 starting from tert-butyl 7-[[5-(trifluoromethyl)-2-pyridyl]methyl]-2,7-diazaspiro[3.5]nonane-2-carboxylate (0.64 g, 1.66 mmol, 1.0 equiv) as a white solid (1.00 g, 91%). MS (ESI): m/z=286.1 [M+H]$^+$.

methyl]-2,7-diazaspiro[3.5]nonane-2-carboxylate (0.59 g, 1.49 mmol, 1.0 equiv) as a white solid (0.74 g, 74%). MS (ESI): m/z=303.1 [M+H]$^+$.

BB 153

4-Methylbenzenesulfonic Acid; 6-[[6-(trifluoromethyl)-3-pyridyl]methyl]-2-azaspiro[3.4]octane Step 1: Tert-Butyl (6Z)-6-[(4,4,5,5-tetramethyl-1,3, 2-dioxaborolan-2-yl)methylene]-2-azaspiro[3.4]octane-2-carboxylate The title compound was obtained in analogy to BB 80/Step 1 starting from tert-butyl 6-oxo-2-azaspiro[3.4]octane-2-carboxylate (3.50 g, 15.54 mmol, 1.0 equiv; CAS RN 1363382-39-1) and 4,4,5,5-tetramethyl-2-[(4,4,5,5-tetramethyl-1,3,2-dioxaborolan-2-yl)methyl]-1,3,2-dioxaborolane (4.58 g, 17.1 mmol, 1.1 equiv; CAS RN 78782-17-9) as a colorless oil (3.59 g, 63%). MS (ESI): m/z=293.9 [M+2H-tBu]$^+$.

Step 2: Tert-Butyl (6Z)-6-[[6-(trifluoromethyl)-3-pyridyl]methylene]-2-azaspiro[3.4]octane-2-carboxylate The title compound was obtained in analogy to BB 80/Step 2 starting from 5-bromo-2-(trifluoromethyl)pyridine (0.56 g, 2.47 mmol, 1.2 equiv; CAS RN 436799-32-5) and tert-butyl (6Z)-6-[(4,4,5,5-tetramethyl-1,3,2-dioxaborolan-2-yl)methylene]-2-azaspiro[3.4]octane-2-carboxylate (0.72 g, 2.06 mmol, 1.0 equiv) as a white solid (0.59 g, 74%). MS (ESI): m/z=313.1 [M+2H-tBu]$^+$.

Step 3: tert-Butyl 6-[[6-(trifluoromethyl)-3-pyridyl]methyl]-2-azaspiro[3.4]octane-2-carboxylate The title compound was obtained in analogy to BB 80/Step 3 starting from tert-butyl (6Z)-6-[[6-(trifluoromethyl)-3-pyridyl]methylene]-2-azaspiro[3.4]octane-2-carboxylate (0.59 g, 1.60 mmol, 1.0 equiv) as an off-white solid (0.59 g, 90%). MS (ESI): m/z=315.1 [M+2H-tBu]$^+$.

Step 4: 4-Methylbenzenesulfonic Acid; 6-[[6-(trifluoromethyl)-3-pyridyl]methyl]-2-azaspiro[3.4]octane The title compound was obtained in analogy to BB 4/Step 2 starting from tert-butyl 6-[[6-(trifluoromethyl)-3-pyridyl]methyl]-2-azaspiro[3.4]octane-2-carboxylate (0.59 g, 1.59 mmol, 1.0 equiv) as an off-white solid (0.69 g, 78%). MS (ESI): m/z=271.1 [M+H]$^+$.

Example 219

A compound of formula (I) can be used in a manner known per se as the active ingredient for the production of tablets of the following composition:

|  | Per tablet |
| --- | --- |
| Active ingredient | 200 mg |
| Microcrystalline cellulose | 155 mg |
| Corn starch | 25 mg |
| Talc | 25 mg |
| Hydroxypropylmethylcellulose | 20 mg |
|  | 425 mg |

Example 220

A compound of formula (I) can be used in a manner known per se as the active ingredient for the production of capsules of the following composition:

|  | Per capsule |
| --- | --- |
| Active ingredient | 100.0 mg |
| Corn starch | 20.0 mg |
| Lactose | 95.0 mg |
| Talc | 4.5 mg |
| Magnesium stearate | 0.5 mg |
|  | 220.0 mg |

The invention claimed is:
1. A compound of formula (I):

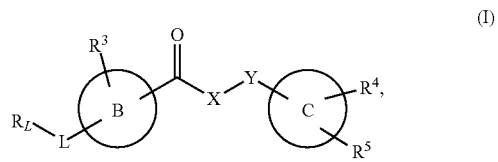

or a pharmaceutically acceptable salt thereof, wherein:
X is selected from O, NH, N($C_{1-6}$-alkyl), and $(CH_2)_m$CHR$^6$;
Y is $(CH_2)_n$CHR$^7$;
m and n are each independently an integer selected from 0 and 1;
L is selected from a covalent bond, —CHR$^8$—, —CH$_2$O—, SO$_2$, —SO$_2$NH—, —SO$_2$NH—$C_{1-6}$-alkyl-, —O—, —NH—, —CH$_2$NH—, —CH$_2$N($C_{1-6}$-alkyl)-, and —C≡C—;
L$^D$ is selected from a covalent bond, SO$_2$, —O—, —NR$^{11}$—, and —CH$_2$NH—;
B is selected from:

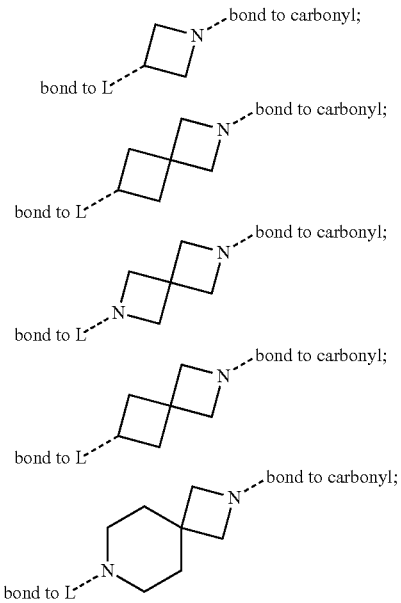

-continued
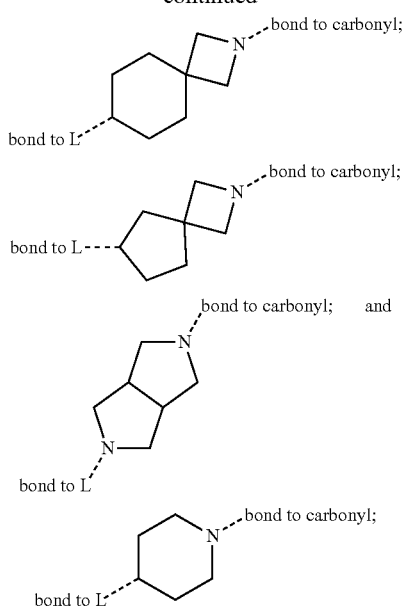
C is selected from:
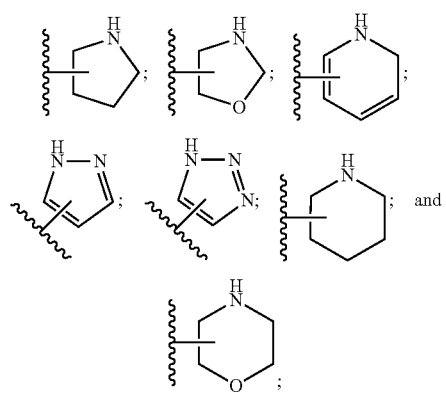
D is selected from:
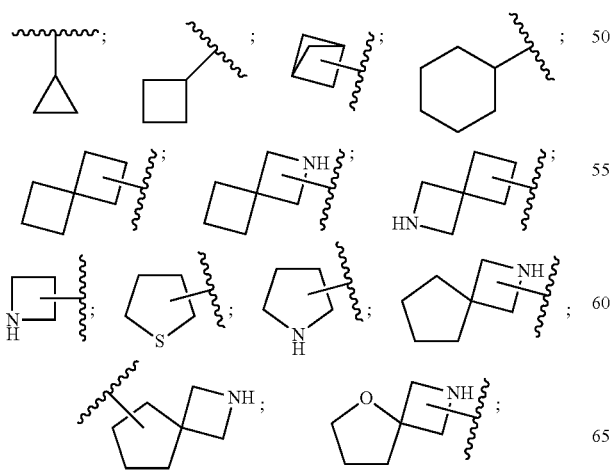
-continued
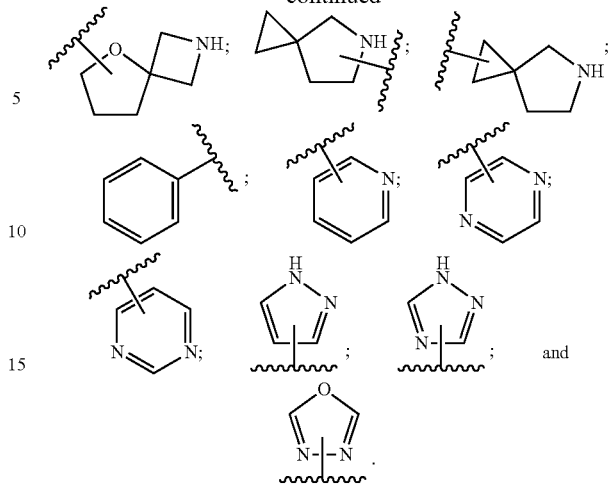
$R_L$ is selected from $C_{1-6}$-alkyl and a group
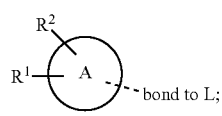
(i) A is
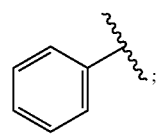 [SMILES: *c1ccccc1]
$R^1$ is selected from halogen, $SF_5$, sulfamoyl, $C_{1-6}$-alkyl, $CF_3CH_2-$, $C_{1-6}$-alkyl-$SO_2-$, halo-$C_{1-6}$-alkyl-$SO_2-$, cyano-$C_{1-6}$-alkyl-$SO_2-$, halo-$C_{1-6}$-alkoxy, and a group
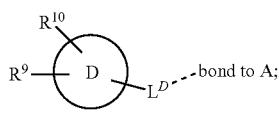
and
$R^2$ is selected from hydrogen, $C_{1-6}$-alkyl-$SO_2-$ and halogen; or
(ii) A is selected from
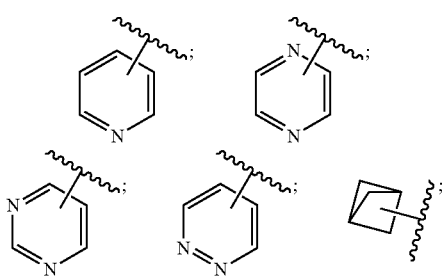

-continued

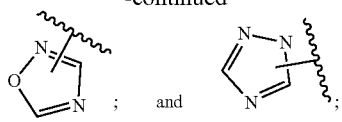 ; and $R^1$ is selected from halogen, $SF_5$, sulfamoyl, $C_{1-6}$-alkyl, halo-$C_{1-6}$-alkyl, $C_{1-6}$-alkyl-$SO_2$—, halo-$C_{1-6}$-alkyl-$SO_2$—, cyano-$C_{1-6}$-alkyl-$SO_2$—, halo-$C_{1-6}$-alkoxy, and a group

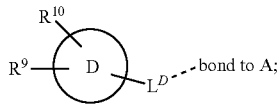

and
$R^2$ is selected from hydrogen, $C_{1-6}$-alkyl-$SO_2$— and halogen;
$R^3$ and $R^7$ are both hydrogen;
$R^4$ is hydrogen or oxo;
$R^5$ is hydrogen or $C_{1-6}$-alkyl;
$R^6$ is selected from hydrogen, halogen, hydroxy and $C_{1-6}$-alkyl;
$R^8$ is selected from hydrogen and $C_6$-$C_{14}$-aryl;
$R^9$ is selected from hydrogen, hydroxy, oxo, halogen, cyano, carbamoyl, $C_{1-6}$-alkyl, $C_3$-$C_{10}$-cycloalkyl, $C_{1-6}$-alkoxy, halo-$C_{1-6}$-alkyl, hydroxy-$C_{1-6}$-alkyl, halo-$C_{1-6}$-alkoxy, $C_{1-6}$-alkyl-$SO_2$—$C_{1-6}$-alkyl-, $C_{1-6}$-alkyl-$SO_2$—, $C_{1-6}$-alkoxy-carbonyl, wherein said $C_3$-$C_{10}$-cycloalkyl is optionally substituted with one halo-$C_1$-$C_6$-alkyl;
$R^{10}$ is selected from hydrogen, halogen, hydroxy, oxo, $C_{1-6}$-alkyl, and halo-$C_{1-6}$-alkyl; and
$R^{11}$ is selected from hydrogen, $C_{1-6}$-alkyl, $C_{1-6}$-alkoxy-$C_{1-6}$-alkyl, $C_{3-10}$-cycloalkyl-$C_{1-6}$-alkyl-, and $C_6$-$C_{14}$-aryl.

2. The compound of claim 1, or a pharmaceutically acceptable salt thereof, wherein:
X is N($C_{1-6}$-alkyl) or $(CH_2)_m CHR^6$;
m is 0; and
$R^6$ is hydrogen.

3. The compound of claim 2, or a pharmaceutically acceptable salt thereof, wherein:
X is N-methyl or $(CH_2)_m CHR^6$.

4. The compound of claim 1, or a pharmaceutically acceptable salt thereof, wherein:
A is selected from

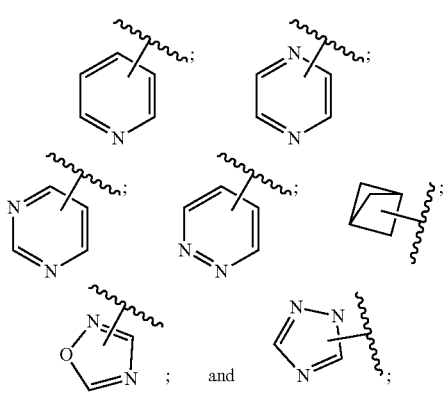

and
$R^1$ is selected from halogen, $SF_5$, sulfamoyl, $C_{1-6}$-alkyl, halo-$C_{1-6}$-alkyl, $C_{1-6}$-alkyl-$SO_2$—, halo-$C_{1-6}$-alkyl-$SO_2$—, cyano-$C_{1-6}$-alkyl-$SO_2$—, halo-$C_{1-6}$-alkoxy, and a group

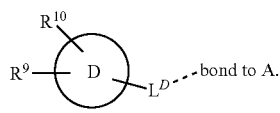

5. The compound of claim 1, or a pharmaceutically acceptable salt thereof, wherein:
$R_L$ is a group

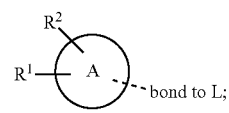

L is selected from a covalent bond, —$CHR^8$—, and —$CH_2O$—;
$L^D$ is selected from a covalent bond, —O—, and —$NR^{11}$—;
A is selected from

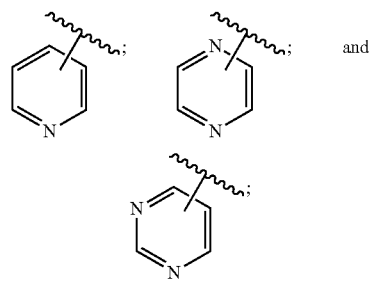

D is selected from:

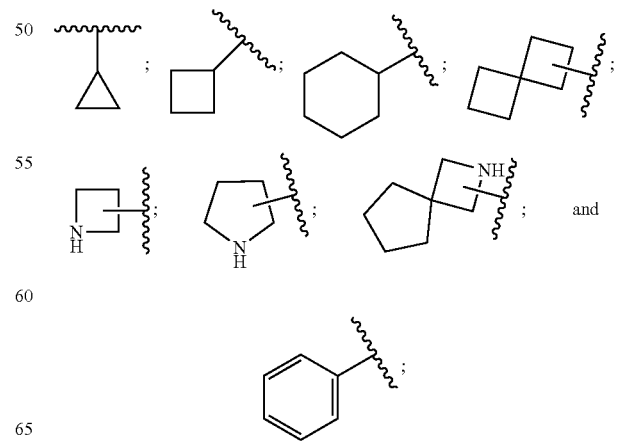

$R^1$ is halo-$C_{1-6}$-alkyl or a group

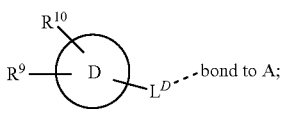

$R^2$ is hydrogen or halogen;
$R^8$ is hydrogen;
$R^9$ is selected from hydrogen, halogen, halo-$C_{1-6}$-alkyl, halo-$C_{1-6}$-alkoxy, and $C_{1-6}$-alkyl-$SO_2$—;
$R^{10}$ is selected from hydrogen, halogen, and halo-$C_{1-6}$-alkyl; and
$R^{11}$ is $C_{1-6}$-alkyl or $C_{3-10}$-cycloalkyl-$C_{1-6}$-alkyl-.

6. The compound of claim 5, or a pharmaceutically acceptable salt thereof, wherein:
$R^1$ is $CF_3$ or group

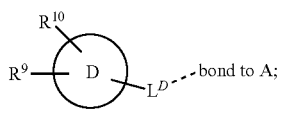

$R^2$ is hydrogen or fluoro;
$R^9$ is selected from hydrogen, fluoro, chloro, $CF_3$, 2,2,2-trifluoroethoxy, and methylsulfonyl;
$R^{10}$ is selected from hydrogen, chloro, and $CF_3$; and
$R^{11}$ is methyl or cyclopropylmethyl.

7. The compound of claim 1, or a pharmaceutically acceptable salt thereof, wherein:
B is selected from:

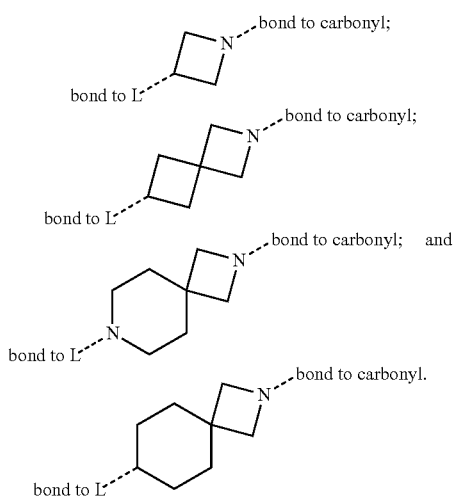

8. The compound of claim 1, or a pharmaceutically acceptable salt thereof, wherein:
C is selected from

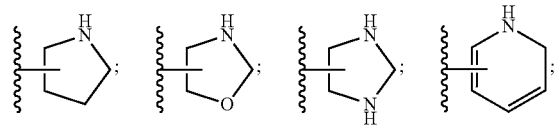

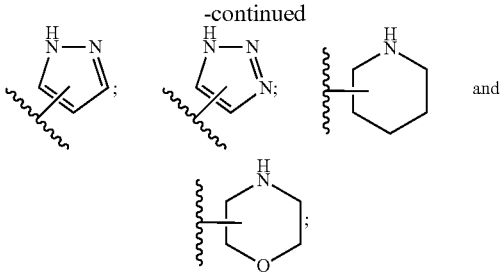

$R^4$ is hydrogen or oxo; and
$R^5$ is hydrogen or $C_{1-6}$-alkyl.

9. The compound of claim 8, or a pharmaceutically acceptable salt thereof, wherein:
C is

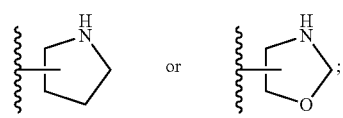

$R^4$ is oxo; and
$R^5$ is hydrogen.

10. The compound of claim 1, or a pharmaceutically acceptable salt thereof, wherein:
X is $N(C_{1-6}$-alkyl) or $(CH_2)_m CHR^6$; m is 0;
L is selected from a covalent bond, —$CHR^8$—, and —$CH_2O$—;
$L^D$ is selected from a covalent bond, —O—, and —$NR^{11}$—;
A is selected from

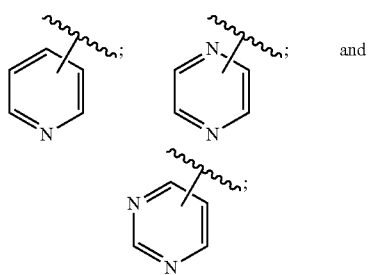

B is selected from

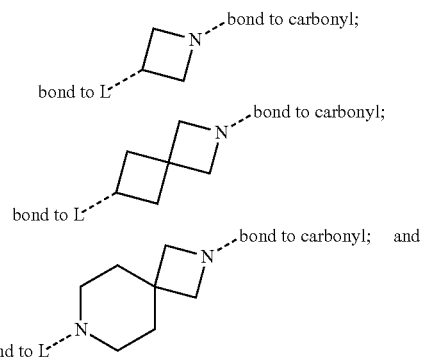

-continued

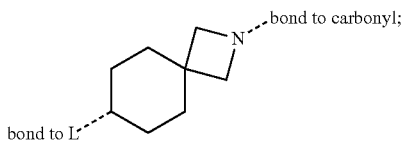

C is

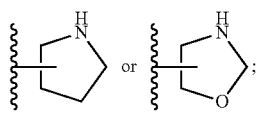

D is selected from:

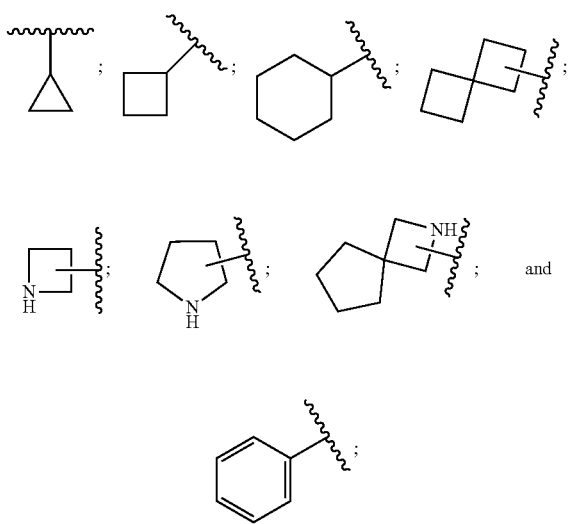

$R_L$ is a group

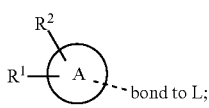

$R^1$ is halo-$C_{1-6}$-alkyl or a group

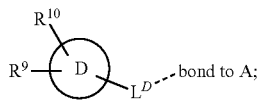

$R^2$ is hydrogen or halogen;
$R^5$, $R^6$, and $R^8$ are all hydrogen;
$R^9$ is selected from hydrogen, halogen, halo-$C_{1-6}$-alkyl, halo-$C_{1-6}$-alkoxy, and $C_{1-6}$-alkyl-$SO_2$—;
$R^{10}$ is selected from hydrogen, halogen, and halo-$C_{1-6}$-alkyl; and
$R^{11}$ is $C_{1-6}$-alkyl or $C_{3-10}$-cycloalkyl-$C_{1-6}$-alkyl-.

11. The compound of claim 10, or a pharmaceutically acceptable salt thereof, wherein:
X is N(methyl) or $(CH_2)_m CHR^6$;
$R^1$ is $CF_3$ or a group

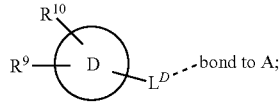

$R^2$ is hydrogen or fluoro;
$R^9$ is selected from hydrogen, fluoro, chloro, $CF_3$, 2,2,2-trifluoroethoxy, and methylsulfonyl;
$R^{10}$ is selected from hydrogen, chloro, and $CF_3$; and
$R^{11}$ is methyl or cyclopropylmethyl.

12. The compound of claim 1, selected from the group consisting of:
(−)-5-[3-[3-[[2-fluoro-4-(trifluoromethyl)phenyl]methoxy]azetidin-1-yl]-3-oxo-propyl]pyrrolidin-2-one;
(+)-5-[3-[3-[[2-fluoro-4-(trifluoromethyl)phenyl]methoxy]azetidin-1-yl]-3-oxo-propyl]pyrrolidin-2-one;
(−)-[3-[3-(4-tert-Butylphenyl)azetidin-1-yl]-3-oxo-propyl]pyrrolidin-2-one;
(+)-5-[3-[3-(4-tert-Butylphenyl)azetidin-1-yl]-3-oxo-propyl]pyrrolidin-2-one;
(−)-5-[3-Oxo-3-[3-[4-[1-(trifluoromethyl)cyclopropyl]phenyl]azetidin-1-yl]propyl]pyrrolidin-2-one;
(+)-5-[3-Oxo-3-[3-[4-[1-(trifluoromethyl)cyclopropyl]phenyl]azetidin-1-yl]propyl]pyrrolidin-2-one;
(−)- or (+)-5-[3-Oxo-3-[3-[4-(2,2,2-trifluoroethyl)phenyl]azetidin-1-yl]propyl]pyrrolidin-2-one;
(+)- or (−)-5-[3-Oxo-3-[3-[4-(2,2,2-trifluoroethyl)phenyl]azetidin-1-yl]propyl]pyrrolidin-2-one;
(−)-5-[3-[3-[4-(2,4-Difluorophenyl)phenyl]azetidin-1-yl]-3-oxo-propyl]pyrrolidin-2-one;
(+)-5-[3-[3-[4-(2,4-Difluorophenyl)phenyl]azetidin-1-yl]-3-oxo-propyl]pyrrolidin-2-one;
(−)-5-[3-Oxo-3-[rac-(3aS,6aS)-2-[[2-fluoro-4-(trifluoromethyl)phenyl]methyl]-1,3,3a,4,6,6a-hexahydropyrrolo[3,4-c]pyrrol-5-yl]propyl]pyrrolidin-2-one;
(+)-5-[3-Oxo-3-[rac-(3aS,6aS)-2-[[2-fluoro-4-(trifluoromethyl)phenyl]methyl]-1,3,3a,4,6,6a-hexahydropyrrolo[3,4-c]pyrrol-5-yl]propyl]pyrrolidin-2-one;
(−)- or (+)-5-[3-[3-[[2-Fluoro-4-(trifluoromethyl)phenyl]methoxy]azetidin-1-yl]-3-oxo-propyl]-5-methyl-pyrrolidin-2-one;
(+)- or (−)-5-[3-[3-[[2-Fluoro-4-(trifluoromethyl)phenyl]methoxy]azetidin-1-yl]-3-oxo-propyl]-5-methyl-pyrrolidin-2-one;
(−)- or (+)-5-Methyl-5-[3-oxo-3-[3-[4-[1-(trifluoromethyl)cyclopropyl]phenyl]azetidin-1-yl]propyl]pyrrolidin-2-one;
(+)- or (−)-5-Methyl-5-[3-oxo-3-[3-[4-[1-(trifluoromethyl)cyclopropyl]phenyl]azetidin-1-yl]propyl]pyrrolidin-2-one;
(−)- or (+)-5-[3-[3-[6-(3-Chlorophenoxy)-3-pyridyl]azetidin-1-yl]-3-oxo-propyl]-5-methyl-pyrrolidin-2-one;
(+)- or (−)-5-[3-[3-[6-(3-Chlorophenoxy)-3-pyridyl]azetidin-1-yl]-3-oxo-propyl]-5-methyl-pyrrolidin-2-one;
(4S)-4-[3-[3-[[2-Fluoro-4-(trifluoromethyl)phenyl]methoxy]azetidin-1-yl]-3-oxo-propyl]oxazolidin-2-one;

(4R)-4-[3-[3-[[2-Fluoro-4-(trifluoromethyl)phenyl]methoxy]azetidin-1-yl]-3-oxo-propyl]oxazolidin-2-one;
(4S)-4-[3-Oxo-3-[3-[4-[1-(trifluoromethyl)cyclopropyl]phenyl]azetidin-1-yl]propyl]oxazolidin-2-one;
(4R)-4-[3-Oxo-3-[3-[4-[1-(trifluoromethyl)cyclopropyl]phenyl]azetidin-1-yl]propyl]oxazolidin-2-one;
(4S)-4-[3-[3-[4-(2,4-Difluorophenyl)phenyl]azetidin-1-yl]-3-oxo-propyl]oxazolidin-2-one;
(4R)-4-[3-[3-[4-(2,4-Difluorophenyl)phenyl]azetidin-1-yl]-3-oxo-propyl]oxazolidin-2-one;
(4R)-4-[3-Oxo-3-[3-[4-(2,2,2-trifluoro-1,1-dimethyl-ethoxy)phenyl]azetidin-1-yl]propyl]oxazolidin-2-one;
(4R)-4-[3-[3-[[2-Fluoro-4-(pentafluoro-)$^6$-sulfanyl)phenyl]methoxy]azetidin-1-yl]-3-oxo-propyl]oxazolidin-2-one;
(4R)-4-[3-[6-[(2,4-Difluorophenyl)methyl]-2-azaspiro[3.3]heptan-2-yl]-3-oxo-propyl]oxazolidin-2-one;
(4R)-4-[3-[3-[6-(2-Chlorophenoxy)-3-pyridyl]azetidin-1-yl]-3-oxo-propyl]oxazolidin-2-one;
(4R)-4-[3-[6-(2-Chloro-4-fluoro-phenoxy)-2-azaspiro[3.3]heptan-2-yl]-3-oxo-propyl]oxazolidin-2-one;
(4R)-4-[3-[3-[4-(4-Fluorophenoxy)phenyl]azetidin-1-yl]-3-oxo-propyl]oxazolidin-2-one;
(4R)-4-[3-Oxo-3-[3-[6-[4-(trifluoromethoxy)phenoxy]-3-pyridyl]azetidin-1-yl]propyl]oxazolidin-2-one;
(4R)-4-[3-Oxo-3-[6-[6-(trifluoromethyl)pyrazin-2-yl]oxy-2-azaspiro[3.3]heptan-2-yl]propyl]oxazolidin-2-one;
(4R)-4-[3-[3-[2-(3-Chlorophenyl)ethynyl]azetidin-1-yl]-3-oxo-propyl]oxazolidin-2-one;
(4R)-4-[3-Oxo-3-[3-[6-[3-(trifluoromethyl)pyrrolidin-1-yl]-3-pyridyl]azetidin-1-yl]propyl]oxazolidin-2-one;
(4R)-4-[3-[3-[[2-Fluoro-4-(trifluoromethyl)phenyl]methoxy]azetidin-1-yl]-2-methyl-3-oxo-propyl]oxazolidin-2-one;
1-(3-((2-Fluoro-4-(trifluoromethyl)benzyl)oxy)azetidin-1-yl)-3-(1H-1,2,3-triazol-5-yl)propan-1-one;
3-(1H-1,2,3-Triazol-5-yl)-1-(3-(4-(1-(trifluoromethyl)cyclopropyl)phenyl)azetidin-1-yl)propan-1-one;
3-(1H-1,2,3-Triazol-5-yl)-1-(3-(4-((1,1,1-trifluoro-2-methylpropan-2-yl)oxy)phenyl)azetidin-1-yl)propan-1-one;
1-[3-[[2-Fluoro-4-(trifluoromethyl)phenyl]methoxy]azetidin-1-yl]-4-(1H-triazol-5-yl)butan-1-one;
4-(1H-Triazol-5-yl)-1-[3-[4-[1-(trifluoromethyl)cyclopropyl]phenyl]azetidin-1-yl]butan-1-one;
4-(1H-Triazol-5-yl)-1-[3-[4-(2,2,2-trifluoro-1,1-dimethyl-ethoxy)phenyl]azetidin-1-yl]butan-1-one;
4-(1H-Triazol-5-yl)-1-[3-[6-[4-(trifluoromethoxy)phenoxy]-3-pyridyl]azetidin-1-yl]butan-1-one;
4-(1H-Triazol-5-yl)-1-[6-[6-(trifluoromethyl)pyrazin-2-yl]oxy-2-azaspiro[3.3]heptan-2-yl]butan-1-one;
1-[3-[2-(3-Chlorophenyl)ethynyl]azetidin-1-yl]-4-(1H-triazol-5-yl)butan-1-one;
rac-4-(1H-Triazol-5-yl)-1-[3-[6-[3-(trifluoromethyl)pyrrolidin-1-yl]-3-pyridyl]azetidin-1-yl]butan-1-one;
4-(1H-Triazol-5-yl)-1-[3-[4-[3-(2,2,2-trifluoroethoxy)azetidin-1-yl]phenyl]azetidin-1-yl]butan-1-one;
1-[3-[[2-Fluoro-4-(trifluoromethyl)phenyl]methoxy]azetidin-1-yl]-3-(1H-pyrazol-5-yl)propan-1-one;
6-[3-[3-[[2-Fluoro-4-(trifluoromethyl)phenyl]methoxy]azetidin-1-yl]-3-oxo-propyl]-1H-pyridin-2-one;
6-[3-[3-[[2-Fluoro-4-(trifluoromethyl)phenyl]methoxy]azetidin-1-yl]-3-oxo-propyl]piperidin-2-one;
(−)-5-[3-[3-[[2-Fluoro-4-(trifluoromethyl)phenyl]methoxy]azetidin-1-yl]-3-oxo-propyl]morpholin-3-one;
(+)-5-[3-[3-[[2-Fluoro-4-(trifluoromethyl)phenyl]methoxy]azetidin-1-yl]-3-oxo-propyl]morpholin-3-one;
[(2S)-5-Oxopyrrolidin-2-yl]methyl 3-[[2-fluoro-4-(trifluoromethyl)phenyl]methoxy]azetidine-1-carboxylate;
[(2R)-5-Oxopyrrolidin-2-yl]methyl 3-[[2-fluoro-4-(trifluoromethyl)phenyl]methoxy]azetidine-1-carboxylate;
[(4S)-2-Oxooxazolidin-4-yl]methyl 3-[[2-fluoro-4-(trifluoromethyl)phenyl]methoxy]azetidine-1-carboxylate;
[(4R)-2-Oxooxazolidin-4-yl]methyl 3-[[2-fluoro-4-(trifluoromethyl)phenyl]methoxy]azetidine-1-carboxylate;
[(4S)-2-Oxooxazolidin-4-yl]methyl 3-[4-[1-(trifluoromethyl)cyclopropyl]phenyl]azetidine-1-carboxylate;
[(4S)-2-Oxooxazolidin-4-yl]methyl 6-[(2,4-difluorophenyl)methyl]-2-azaspiro[3.3]heptane-2-carboxylate;
[(4S)-2-Oxooxazolidin-4-yl]methyl 3-[4-(4-fluorophenoxy)phenyl]azetidine-1-carboxylate;
[(4R)-2-Oxooxazolidin-4-yl]methyl 6-[(2,4-difluorophenyl)methyl]-2-azaspiro[3.3]heptane-2-carboxylate;
[(4S)-2-Oxooxazolidin-4-yl]methyl 3-[6-(2-chlorophenoxy)-3-pyridyl]azetidine-1-carboxylate;
[(4S)-2-Oxooxazolidin-4-yl]methyl 3-[2-[2-(difluoromethyl)phenyl]ethynyl]azetidine-1-carboxylate;
[(4S)-2-Oxooxazolidin-4-yl]methyl 3-[6-[3-(trifluoromethyl)pyrrolidin-1-yl]-3-pyridyl]azetidine-1-carboxylate;
2-(1H-Triazol-5-yl)ethyl 3-[[2-fluoro-4-(trifluoromethyl)phenyl]methoxy]azetidine-1-carboxylate;
3-[[2-Fluoro-4-(trifluoromethyl)phenyl]methoxy]-N-[2-(1H-triazol-5-yl)ethyl]azetidine-1-carboxamide;
N-Methyl-N-[2-(1H-triazol-5-yl)ethyl]-3-[4-[1-(trifluoromethyl)cyclopropyl]phenyl]azetidine-1-carboxamide;
3-[[2-Fluoro-4-(trifluoromethyl)phenyl]methoxy]-N-methyl-N-[2-(1H-triazol-5-yl)ethyl]azetidine-1-carboxamide;
3-[4-(2-Chloro-4-methylsulfonyl-phenyl)phenyl]-N-methyl-N-[2-(1H-triazol-5-yl)ethyl]azetidine-1-carboxamide;
2-Methyl-4-(1H-triazol-5-yl)-1-[3-[4-[1-(trifluoromethyl)cyclopropyl]phenyl]azetidin-1-yl]butan-1-one;
3-Hydroxy-4-(1H-triazol-5-yl)-1-[3-[4-[1-(trifluoromethyl)cyclopropyl]phenyl]azetidin-1-yl]butan-1-one;
2-Fluoro-4-(1H-triazol-5-yl)-1-[3-[4-[1-(trifluoromethyl)cyclopropyl]phenyl]azetidin-1-yl]butan-1-one;
(4R)-4-[3-[3-[4-(N-Methylanilino)phenyl]azetidin-1-yl]-3-oxo-propyl]oxazolidin-2-one;
(4R)-4-[3-[3-(5-tert-Butyl-2-pyridyl)azetidin-1-yl]-3-oxo-propyl]oxazolidin-2-one;
(4R)-4-[3-[3-[4-(2-chloro-4-methylsulfonyl-phenyl)phenyl]azetidin-1-yl]-3-oxo-propyl]oxazolidin-2-one;
(4R)-4-[3-[3-[4-(Benzenesulfonyl)phenyl]azetidin-1-yl]-3-oxo-propyl]oxazolidin-2-one;
2-[4-[1-[3-[(4R)-2-Oxooxazolidin-4-yl]propanoyl]azetidin-3-yl]phenyl]sulfonylacetonitrile;
(4R)-4-[3-Oxo-3-[3-[4-(trifluoromethylsulfonyl)phenyl]azetidin-1-yl]propyl]oxazolidin-2-one;
(4R)-4-[3-[3-(4-Cyclohexylsulfonylphenyl)azetidin-1-yl]-3-oxo-propyl]oxazolidin-2-one;
1-[5-[1-[3-[(4R)-2-Oxooxazolidin-4-yl]propanoyl]azetidin-3-yl]-2-pyridyl]cyclobutanecarbonitrile;
(4R)-4-[3-[3-[4-[(2-Methyl-3-pyridyl)oxy]phenyl]azetidin-1-yl]-3-oxo-propyl]oxazolidin-2-one;

(4R)-4-[3-[3-[4-(4-Cyclopropylpyrimidin-2-yl)oxyphenyl]azetidin-1-yl]-3-oxo-propyl]oxazolidin-2-one;
(4R)-4-[3-[3-[4-[3-(2,2-Dimethylpropyl)triazol-4-yl]phenyl]azetidin-1-yl]-3-oxo-propyl]oxazolidin-2-one;
(4R)-4-[3-[3-[4-(4-Chloro-2-methylsulfonyl-phenyl)phenyl]azetidin-1-yl]-3-oxo-propyl]oxazolidin-2-one;
(+)- or (−)-(4R)-4-[3-[4-[(4-Methylsulfonylphenyl)-phenyl-methyl]-1-piperidyl]-3-oxo-propyl]oxazolidin-2-one;
(−)- or (+)-(4R)-4-[3-[4-[(4-Methylsulfonylphenyl)-phenyl-methyl]-1-piperidyl]-3-oxo-propyl]oxazolidin-2-one;
5-Chloro-2-[[5-[1-[3-[(4R)-2-oxooxazolidin-4-yl]propanoyl]azetidin-3-yl]-2-pyridyl]oxy]benzamide;
(−)- or (+)-[(4S)-2-Oxooxazolidin-4-yl]methyl 3-[6-[3-(trifluoromethyl)pyrrolidin-1-yl]-3-pyridyl]azetidine-1-carboxylate;
(+)- or (−)-[(4S)-2-Oxooxazolidin-4-yl]methyl 3-[6-[3-(trifluoromethyl)pyrrolidin-1-yl]-3-pyridyl]azetidine-1-carboxylate;
(5S)-5-[3-[3-[[2-Fluoro-4-(trifluoromethyl)phenyl]methoxy]azetidin-1-yl]-3-oxo-propyl]thiomorpholin-3-one;
(4R)-4-[3-[3-[4-[N-(Cyclopropylmethyl)anilino]phenyl]azetidin-1-yl]-3-oxo-propyl]oxazolidin-2-one;
(4R)-4-[3-Oxo-3-[3-[4-(N-phenylanilino)phenyl]azetidin-1-yl]propyl]oxazolidin-2-one;
(4R)-4-[3-[3-(6-tert-Butyl-3-pyridyl)azetidin-1-yl]-3-oxo-propyl]oxazolidin-2-one;
(4R)-4-[3-[3-[6-[(5-Methoxy-2-pyridyl)-methyl-amino]-3-pyridyl]azetidin-1-yl]-3-oxo-propyl]oxazolidin-2-one;
(4R)-4-[3-[3-[6-(N-Methylanilino)-3-pyridyl]azetidin-1-yl]-3-oxo-propyl]oxazolidin-2-one;
(4R)-4-[3-[3-[6-(4-Isopropyl-N-methyl-anilino)-3-pyridyl]azetidin-1-yl]-3-oxo-propyl]oxazolidin-2-one;
(4R)-4-[3-[3-[6-[N-(Cyclopropylmethyl)anilino]-3-pyridyl]azetidin-1-yl]-3-oxo-propyl]oxazolidin-2-one;
(4R)-4-[3-[3-[4-[2-Methoxyethyl(3-pyridyl)amino]phenyl]azetidin-1-yl]-3-oxo-propyl]oxazolidin-2-one;
(4R)-4-[3-[2-[4-Fluoro-2-(trifluoromethyl)phenyl]sulfonyl-2,6-diazaspiro[3.3]heptan-6-yl]-3-oxo-propyl]oxazolidin-2-one;
(4R)-4-[3-[2-(2,2-Dimethylpropylsulfonyl)-2,6-diazaspiro[3.3]heptan-6-yl]-3-oxo-propyl]oxazolidin-2-one;
(4R)-4-[3-Oxo-3-[3-[4-[3-(2,2,2-trifluoroethoxy)azetidin-1-yl]phenyl]azetidin-1-yl]propyl]oxazolidin-2-one;
(4R)-4-[3-Oxo-3-[3-[4-[3-(trifluoromethyl)azetidin-1-yl]phenyl]azetidin-1-yl]propyl]oxazolidin-2-one;
(4R)-4-[3-Oxo-3-[3-[2-[1-(trifluoromethyl)cyclopropyl]pyrimidin-5-yl]azetidin-1-yl]propyl]oxazolidin-2-one;
(4R)-4-[3-Oxo-3-[3-[6-[1-(trifluoromethyl)cyclopropyl]-3-pyridyl]azetidin-1-yl]propyl]oxazolidin-2-one;
(4R)-4-[3-Oxo-3-[3-[5-[3-(trifluoromethyl)pyrrolidin-1-yl]-2-pyridyl]azetidin-1-yl]propyl]oxazolidin-2-one;
(4R)-4-[3-[3-[4-[3-(Methylsulfonylmethyl)azetidin-1-yl]phenyl]azetidin-1-yl]-3-oxo-propyl]oxazolidin-2-one;
(4R)-4-[3-Oxo-3-[3-[5-[3-(trifluoromethyl)pyrrolidin-1-yl]pyrazin-2-yl]azetidin-1-yl]propyl]oxazolidin-2-one;
(4R)-4-[3-Oxo-3-[3-[5-[3-(trifluoromethyl)pyrrolidin-1-yl]pyrimidin-2-yl]azetidin-1-yl]propyl]oxazolidin-2-one;
(4R)-4-[3-Oxo-3-[3-[2-[3-(trifluoromethyl)pyrrolidin-1-yl]pyrimidin-5-yl]azetidin-1-yl]propyl]oxazolidin-2-one;
(4R)-4-[3-[3-[5-(2-Chloro-4-methylsulfonyl-phenyl)-2-pyridyl]azetidin-1-yl]-3-oxo-propyl]oxazolidin-2-one;
(4R)-4-[3-Oxo-3-[3-[1-(trifluoromethyl)cyclopropyl]phenyl]azetidin-1-yl]propyl]oxazolidin-2-one;
(4R)-4-[3-[3-[5-(2-Chloro-4-methylsulfonyl-phenyl)pyrazin-2-yl]azetidin-1-yl]-3-oxo-propyl]oxazolidin-2-one;
(4R)-4-[3-[3-(6-tert-Butylsulfonyl-3-pyridyl)azetidin-1-yl]-3-oxo-propyl]oxazolidin-2-one;
(4R)-4-[3-[3-[5-(4-Chloro-2-fluoro-phenyl)pyrimidin-2-yl]azetidin-1-yl]-3-oxo-propyl]oxazolidin-2-one;
(4R)-4-[3-[3-[5-(4-Chloro-2-fluoro-phenyl)-2-pyridyl]azetidin-1-yl]-3-oxo-propyl]oxazolidin-2-one;
(4R)-4-[3-[3-[5-(2,4-Dichlorophenyl)-2-pyridyl]azetidin-1-yl]-3-oxo-propyl]oxazolidin-2-one;
(4R)-4-[3-[3-[4-(5-Chloro-3-methylsulfonyl-2-pyridyl)phenyl]azetidin-1-yl]-3-oxo-propyl]oxazolidin-2-one;
(4R)-4-[3-[3-[6-(2-Chloro-4-methylsulfonyl-phenyl)-3-pyridyl]azetidin-1-yl]-3-oxo-propyl]oxazolidin-2-one;
(4R)-4-[3-[3-[6-(4-Chloro-2-methylsulfonyl-phenyl)-3-pyridyl]azetidin-1-yl]-3-oxo-propyl]oxazolidin-2-one;
(4R)-4-[3-[3-[4-(6-Chloro-4-methylsulfonyl-3-pyridyl)phenyl]azetidin-1-yl]-3-oxo-propyl]oxazolidin-2-one;
(4R)-4-[3-Oxo-3-[3-[4-[5-(trifluoromethyl)pyrazin-2-yl]phenyl]azetidin-1-yl]propyl]oxazolidin-2-one;
(4R)-4-[3-[3-[4-(4-Chloro-2-fluoro-phenyl)-3-methylsulfonyl-phenyl]azetidin-1-yl]-3-oxo-propyl]oxazolidin-2-one;
(4R)-4-[3-[3-[5-(4-Chloro-2-methylsulfonyl-phenyl)-2-pyridyl]azetidin-1-yl]-3-oxo-propyl]oxazolidin-2-one;
(4R)-4-[3-[3-[5-(2-Chloro-4-methylsulfonyl-phenyl)pyrimidin-2-yl]azetidin-1-yl]-3-oxo-propyl]oxazolidin-2-one;
(4R)-4-[3-[3-[2-(2-Chloro-4-methylsulfonyl-phenyl)pyrimidin-5-yl]azetidin-1-yl]-3-oxo-propyl]oxazolidin-2-one;
(4R)-4-[3-[3-[4-[2-Methylsulfonyl-5-(trifluoromethyl)-3-pyridyl]phenyl]azetidin-1-yl]-3-oxo-propyl]oxazolidin-2-one;
(4R)-4-[3-Oxo-3-[6-[[6-(trifluoromethyl)-3-pyridyl]methyl]-2-azaspiro[3.3]heptan-2-yl]propyl]oxazolidin-2-one;
(4R)-4-[3-[7-[[2-Fluoro-4-(trifluoromethyl)phenyl]methyl]-2,7-diazaspiro[3.5]nonan-2-yl]-3-oxo-propyl]oxazolidin-2-one;
(4R)-4-[3-Oxo-3-[3-[4-[4-(trifluoromethyl)pyrimidin-2-yl]oxyphenyl]azetidin-1-yl]propyl]oxazolidin-2-one;
(4R)-4-[3-[3-[4-[4-Methylsulfonyl-2-(trifluoromethyl)phenyl]phenyl]azetidin-1-yl]-3-oxo-propyl]oxazolidin-2-one;
(4R)-4-[3-[3-[3-Fluoro-4-[3-(trifluoromethyl)pyrrolidin-1-yl]phenyl]azetidin-1-yl]-3-oxo-propyl]oxazolidin-2-one;
(4R)-4-[3-[3-[4-(1,1-Dioxothiolan-3-yl)phenyl]azetidin-1-yl]-3-oxo-propyl]oxazolidin-2-one;
(4R)-4-[3-[3-[4-(2-Azaspiro[3.4]octan-2-yl)phenyl]azetidin-1-yl]-3-oxo-propyl]oxazolidin-2-one;
(4R)-4-[3-[3-[4-(6,6-Difluoro-2-azaspiro[3.3]heptan-2-yl)phenyl]azetidin-1-yl]-3-oxo-propyl]oxazolidin-2-one;
(4R)-4-[3-Oxo-3-[3-[4-[3-(trifluoromethyl)cyclobutyl]phenyl]azetidin-1-yl]propyl]oxazolidin-2-one;
(4R)-4-[3-[3-[3-Fluoro-4-[3-(trifluoromethyl)azetidin-1-yl]phenyl]azetidin-1-yl]-3-oxo-propyl]oxazolidin-2-one;
(4R)-4-[3-Oxo-3-[3-[4-[3-(trifluoromethyl)pyrrolidin-1-yl]phenyl]azetidin-1-yl]propyl]oxazolidin-2-one;

(4R)-4-[3-Oxo-3-[7-[6-(trifluoromethyl)pyridazin-3-yl]oxy-2-azaspiro[3.5]nonan-2-yl]propyl]oxazolidin-2-one;

(4R)-4-[3-[7-(4-Fluoro-2-methylsulfonyl-phenoxy)-2-azaspiro[3.5]nonan-2-yl]-3-oxo-propyl]oxazolidin-2-one;

N-[2-[3-[(4R)-2-Oxooxazolidin-4-yl]propanoyl]-2-azaspiro[3.5]nonan-7-yl]-3-(trifluoromethoxy)benzenesulfonamide;

(4R)-4-[3-[3-[5-(6,6-Difluoro-2-azaspiro[3.3]heptan-2-yl)pyrazin-2-yl]azetidin-1-yl]-3-oxo-propyl]oxazolidin-2-one;

(4R)-4-[3-[3-[5-(2-Azaspiro[3.4]octan-2-yl)pyrazin-2-yl]azetidin-1-yl]-3-oxo-propyl]oxazolidin-2-one;

(4R)-4-[3-[3-[6-(6,6-Difluoro-2-azaspiro[3.3]heptan-2-yl)-3-pyridyl]azetidin-1-yl]-3-oxo-propyl]oxazolidin-2-one;

(4R)-4-[3-[3-[6-(2-Azaspiro[3.4]octan-2-yl)-3-pyridyl]azetidin-1-yl]-3-oxo-propyl]oxazolidin-2-one;

(4R)-4-[3-[7-[2-Fluoro-4-(trifluoromethyl)phenyl]sulfonyl-2,7-diazaspiro[3.5]nonan-2-yl]-3-oxo-propyl]oxazolidin-2-one;

(4R)-4-[3-[3-[6-[3-Hydroxy-3-(trifluoromethyl)azetidin-1-yl]-3-pyridyl]azetidin-1-yl]-3-oxo-propyl]oxazolidin-2-one;

(4R)-4-[3-[3-[4-(3, 5-Dimethylpyrazol-1-yl)phenyl]azetidin-1-yl]-3-oxo-propyl]oxazolidin-2-one;

(4R)-4-[3-[3-[6-[3-Hydroxy-3-(trifluoromethyl)pyrrolidin-1-yl]-3-pyridyl]azetidin-1-yl]-3-oxo-propyl]oxazolidin-2-one;

(4R)-4-[3-Oxo-3-[2-[4-(trifluoromethyl)phenyl]sulfonyl-2,6-diazaspiro[3.3]heptan-6-yl]propyl]oxazolidin-2-one;

(4R)-4-[3-Oxo-3-[2-[2-(trifluoromethoxy)phenyl]sulfonyl-2,6-diazaspiro[3.3]heptan-6-yl]propyl]oxazolidin-2-one;

(4R)-4-[3-Oxo-3-[2-[3-(trifluoromethoxy)phenyl]sulfonyl-2,6-diazaspiro[3.3]heptan-6-yl]propyl]oxazolidin-2-one;

(4R)-4-[3-Oxo-3-[2-[4-(trifluoromethoxy)phenyl]sulfonyl-2,6-diazaspiro[3.3]heptan-6-yl]propyl]oxazolidin-2-one;

2-[[2-[3-[(4R)-2-Oxooxazolidin-4-yl]propanoyl]-2,6-diazaspiro[3.3]heptan-6-yl]methyl]benzenesulfonamide;

N-[2-[3-[(4R)-2-Oxooxazolidin-4-yl]propanoyl]-2-azaspiro[3.3]heptan-6-yl]-3-(trifluoromethyl)benzenesulfonamide;

(4R)-4-[3-Oxo-3-[3-[[4-(trifluoromethyl)phenyl]methyl-amino]azetidin-1-yl]propyl]oxazolidin-2-one;

(4R)-4-[3-[3-[[2-Fluoro-5-(trifluoromethyl)phenyl]methylamino]azetidin-1-yl]-3-oxo-propyl]oxazolidin-2-one;

(4R)-4-[3-[6-[(4-Fluoro-2-methylsulfonyl-phenyl)methyl]-2-azaspiro[3.3]heptan-2-yl]-3-oxo-propyl]oxazolidin-2-one;

N-[[1-[3-[(4R)-2-Oxooxazolidin-4-yl]propanoyl]-4-piperidyl]methyl]-4-(trifluoromethyl)benzenesulfonamide;

N-[[1-[3-[(4R)-2-Oxooxazolidin-4-yl]propanoyl]-4-piperidyl]methyl]-4-(trifluoromethoxy)benzenesulfonamide;

(4R)-4-[3-[3-[6-(3-Hydroxy-3-methyl-azetidin-1-yl)-3-pyridyl]azetidin-1-yl]-3-oxo-propyl]oxazolidin-2-one;

(4R)-4-[3-Oxo-3-[3-[6-[3-(trifluoromethyl)azetidin-1-yl]-3-pyridyl]azetidin-1-yl]propyl]oxazolidin-2-one;

(4R)-4-[3-[3-[[2-Fluoro-4-(trifluoromethyl)phenyl]methyl-methyl-amino]azetidin-1-yl]-3-oxo-propyl]oxazolidin-2-one;

(4R)-4-[3-Oxo-3-[3-(6-spiro[3.3]heptan-2-yl-3-pyridyl)azetidin-1-yl]propyl]oxazolidin-2-one;

(4R)-4-[3-Oxo-3-[3-(5-spiro[3.3]heptan-2-ylpyrazin-2-yl)azetidin-1-yl]propyl]oxazolidin-2-one;

(4R)-4-[3-[3-[3-[5-(2,2-Dimethylpropyl)-1,3,4-oxadiazol-2-yl]-1-bicyclo[1.1.1]pentanyl]azetidin-1-yl]-3-oxo-propyl]oxazolidin-2-one;

(4R)-4-[3-Oxo-3-[3-[[4-(trifluoromethylsulfonyl)phenyl]methoxy]azetidin-1-yl]propyl]oxazolidin-2-one;

(4R)-4-[3-Oxo-3-[3-[5-[6-(trifluoromethyl)-3-pyridyl]-1,2,4-oxadiazol-3-yl]azetidin-1-yl]propyl]oxazolidin-2-one;

(4R)-4-[3-Oxo-3-[3-[5-[3-(trifluoromethyl)-1-bicyclo[1.1.1]pentanyl]-1,2,4-oxadiazol-3-yl]azetidin-1-yl]propyl]oxazolidin-2-one;

(4R)-4-[3-Oxo-3-[3-[[3-(trifluoromethylsulfonyl)phenyl]methoxy]azetidin-1-yl]propyl]oxazolidin-2-one;

Methyl 5-chloro-2-[[5-[1-[3-[(4R)-2-oxooxazolidin-4-yl]propanoyl]azetidin-3-yl]-2-pyridyl]oxy]benzoate;

(4R)-4-[3-Oxo-3-[3-[[3-(trifluoromethylsulfonyl)phenyl]methoxy]azetidin-1-yl]propyl]oxazolidin-2-one;

(4R)-4-[3-[3-[6-[3-(1-Hydroxy-1-methyl-ethyl)azetidin-1-yl]-3-pyridyl]azetidin-1-yl]-3-oxo-propyl]oxazolidin-2-one;

(4R)-4-[3-[3-[4-[1-(Hydroxymethyl)cyclopropyl]phenyl]azetidin-1-yl]-3-oxo-propyl]oxazolidin-2-one;

(4R)-4-[3-[3-[6-(5-Oxa-2-azaspiro[3.4]octan-2-yl)-3-pyridyl]azetidin-1-yl]-3-oxo-propyl]oxazolidin-2-one;

(4R)-4-[3-[3-[6-(2,2-Difluoro-5-azaspiro[2.4]heptan-5-yl)-3-pyridyl]azetidin-1-yl]-3-oxo-propyl]oxazolidin-2-one;

(4R)-4-[3-Oxo-3-[3-[4-[5-(trifluoromethyl)pyrazin-2-yl]oxyphenyl]azetidin-1-yl]propyl]oxazolidin-2-one;

(4R)-4-[3-Oxo-3-[3-[5-[[1-(trifluoromethyl)cyclopropyl]methylamino]-2-pyridyl]azetidin-1-yl]propyl]oxazolidin-2-one;

(4R)-4-[3-Oxo-3-[3-[5-[[1-(trifluoromethyl)cyclopropyl]methylamino]pyrazin-2-yl]azetidin-1-yl]propyl]oxazolidin-2-one;

(4R)-4-[3-[3-[4-(3-Cyclopropyl-1H-1,2,4-triazol-5-yl)phenyl]azetidin-1-yl]-3-oxo-propyl]oxazolidin-2-one;

(4R)-4-[3-Oxo-3-[3-[4-[3-[1-(trifluoromethyl)cyclopropyl]-1H-1,2,4-triazol-5-yl]phenyl]azetidin-1-yl]propyl]oxazolidin-2-one;

(4R)-4-[3-[6-[(3-Methylsulfonylphenyl)methyl]-2-azaspiro[3.3]heptan-2-yl]-3-oxo-propyl]oxazolidin-2-one;

(4R)-4-[3-[6-[(4-Methylsulfonylphenyl)methyl]-2-azaspiro[3.3]heptan-2-yl]-3-oxo-propyl]oxazolidin-2-one;

(4R)-4-[3-Oxo-3-[6-[[6-(trifluoromethyl)pyridazin-3-yl]methyl]-2-azaspiro[3.3]heptan-2-yl]propyl]oxazolidin-2-one;

(4R)-4-[3-Oxo-3-[6-[[2-(trifluoromethyl)pyrimidin-5-yl]methyl]-2-azaspiro[3.3]heptan-2-yl]propyl]oxazolidin-2-one;

(4R)-4-[3-Oxo-3-[6-[[5-(trifluoromethyl)pyrimidin-2-yl]methyl]-2-azaspiro[3.3]heptan-2-yl]propyl]oxazolidin-2-one;

(4R)-4-[3-[6-[(3-Fluoro-5-methylsulfonyl-phenyl)methyl]-2-azaspiro[3.3]heptan-2-yl]-3-oxo-propyl]oxazolidin-2-one;

(4R)-4-[3-[6-(3-Cyclopropyl-1,2,4-triazol-1-yl)-2-azaspiro[3.3]heptan-2-yl]-3-oxo-propyl]oxazolidin-2-one;
(4R)-4-[3-Oxo-3-[6-[[3-(trifluoromethylsulfonyl)phenyl]methyl]-2-azaspiro[3.3]heptan-2-yl]propyl]oxazolidin-2-one;
(4R)-4-[3-Oxo-3-[6-[[4-(trifluoromethylsulfonyl)phenyl]methyl]-2,6-diazaspiro[3.3]heptan-2-yl]propyl]oxazolidin-2-one;
(4R)-4-[3-Oxo-3-[7-[[6-(trifluoromethyl)-3-pyridyl]methyl]-2-azaspiro[3.5]nonan-2-yl]propyl]oxazolidin-2-one;
(4R)-4-[3-Oxo-3-[7-[[5-(trifluoromethyl)-2-pyridyl]methyl]-2-azaspiro[3.5]nonan-2-yl]propyl]oxazolidin-2-one;
(4R)-4-[3-Oxo-3-[7-[[5-(trifluoromethyl)pyrazin-2-yl]methyl]-2-azaspiro[3.5]nonan-2-yl]propyl]oxazolidin-2-one;
(4R)-4-[3-[7-[[6-(Difluoromethoxy)-3-pyridyl]methyl]-2-azaspiro[3.5]nonan-2-yl]-3-oxo-propyl]oxazolidin-2-one;
(4R)-4-[3-[7-[(4-Methylsulfonylphenyl)methyl]-2,7-diazaspiro[3.5]nonan-2-yl]-3-oxo-propyl]oxazolidin-2-one;
(4R)-4-[3-[7-[(3-Methylsulfonylphenyl)methyl]-2,7-diazaspiro[3.5]nonan-2-yl]-3-oxo-propyl]oxazolidin-2-one;
(4R)-4-[3-Oxo-3-[7-[[4-(trifluoromethylsulfonyl)phenyl]methyl]-2,7-diazaspiro[3.5]nonan-2-yl]propyl]oxazolidin-2-one;
(4R)-4-[3-Oxo-3-[7-[[3-(trifluoromethylsulfonyl)phenyl]methyl]-2,7-diazaspiro[3.5]nonan-2-yl]propyl]oxazolidin-2-one;
(4R)-4-[3-Oxo-3-[7-[[6-(trifluoromethyl)-3-pyridyl]methyl]-2,7-diazaspiro[3.5]nonan-2-yl]propyl]oxazolidin-2-one;
(4R)-4-[3-Oxo-3-[7-[[5-(trifluoromethyl)-2-pyridyl]methyl]-2,7-diazaspiro[3.5]nonan-2-yl]propyl]oxazolidin-2-one;
(4R)-4-[3-Oxo-3-[6-[[6-(trifluoromethyl)-3-pyridyl]methyl]-2-azaspiro[3.4]octan-2-yl]propyl]oxazolidin-2-one;
Methyl 5-chloro-2-[[5-[1-[3-[(4R)-2-oxooxazolidin-4-yl]propanoyl]azetidin-3-yl]-2-pyridyl]oxy]benzoate;
cis-(4R)-4-[3-Oxo-3-[3-[6-[4-(trifluoromethyl)cyclohexyl]-3-pyridyl]azetidin-1-yl]propyl]oxazolidin-2-one;
trans-(4R)-4-[3-Oxo-3-[3-[6-[4-(trifluoromethyl)cyclohexyl]-3-pyridyl]azetidin-1-yl]propyl]oxazolidin-2-one;
cis-(4R)-4-[3-Oxo-3-[3-[6-[3-(trifluoromethyl)cyclobutyl]-3-pyridyl]azetidin-1-yl]propyl]oxazolidin-2-one;
trans-(4R)-4-[3-Oxo-3-[3-[6-[3-(trifluoromethyl)cyclobutyl]-3-pyridyl]azetidin-1-yl]propyl]oxazolidin-2-one;
(−)- or (+)-(4R)-4-[3-[3-[6-[3-Hydroxy-3-(trifluoromethyl)pyrrolidin-1-yl]-3-pyridyl]azetidin-1-yl]-3-oxo-propyl]oxazolidin-2-one;
(+)- or (−)-(4R)-4-[3-[3-[6-[3-Hydroxy-3-(trifluoromethyl)pyrrolidin-1-yl]-3-pyridyl]azetidin-1-yl]-3-oxo-propyl]oxazolidin-2-one;
(−)- or (+)-(4R)-4-[3-[3-[6-[3-Hydroxy-3-(trifluoromethyl)pyrrolidin-1-yl]-3-pyridyl]azetidin-1-yl]-3-oxo-propyl]oxazolidin-2-one;
(+)- or (−)-(4R)-4-[3-[3-[6-[3-Hydroxy-3-(trifluoromethyl)pyrrolidin-1-yl]-3-pyridyl]azetidin-1-yl]-3-oxo-propyl]oxazolidin-2-one;
(−)- or (+)-(4R)-4-[3-Oxo-3-[3-[2-[3-(trifluoromethyl)pyrrolidin-1-yl]pyrimidin-5-yl]azetidin-1-yl]propyl]oxazolidin-2-one;
(+)- or (−)-(4R)-4-[3-Oxo-3-[3-[2-[3-(trifluoromethyl)pyrrolidin-1-yl]pyrimidin-5-yl]azetidin-1-yl]propyl]oxazolidin-2-one;
(−)- or (+)-(4R)-4-[3-Oxo-3-[6-[[6-(trifluoromethyl)-3-pyridyl]methyl]-2-azaspiro[3.4]octan-2-yl]propyl]oxazolidin-2-one;
(+)- or (−)-(4R)-4-[3-Oxo-3-[6-[[6-(trifluoromethyl)-3-pyridyl]methyl]-2-azaspiro[3.4]octan-2-yl]propyl]oxazolidin-2-one;
3-[4-(4-Chloro-2-methylsulfonyl-phenyl)phenyl]-N-[(2-oxooxazolidin-4-yl)methyl]azetidine-1-carboxamide;
4-[3-Oxo-3-[6-[[6-(trifluoromethyl)-3-pyridyl]methyl]-2-azaspiro[3.3]heptan-2-yl]propyl]imidazolidin-2-one;
4-[3-Oxo-3-[3-[4-[1-(trifluoromethyl)cyclopropyl]phenyl]azetidin-1-yl]propyl]imidazolidin-2-one;
4-[3-[3-[[2-Fluoro-4-(trifluoromethyl)phenyl]methoxy]azetidin-1-yl]-3-oxo-propyl]imidazolidin-2-one;
4-[3-[3-[4-(4-Chloro-2-methylsulfonyl-phenyl)phenyl]azetidin-1-yl]-3-oxo-propyl]imidazolidin-2-one;
(−)- or (+)-4-[3-[3-[4-(4-Chloro-2-methylsulfonyl-phenyl)phenyl]azetidin-1-yl]-3-oxo-propyl]imidazolidin-2-one; and
(+)- or (−)-4-[3-[3-[4-(4-Chloro-2-methylsulfonyl-phenyl)phenyl]azetidin-1-yl]-3-oxo-propyl]imidazolidin-2-one,
or a pharmaceutically acceptable salt thereof.

13. The compound of claim 12, selected from the group consisting of:
(+)-5-[3-[3-[[2-fluoro-4-(trifluoromethyl)phenyl]methoxy]azetidin-1-yl]-3-oxo-propyl]pyrrolidin-2-one;
(+)-5-[3-Oxo-3-[3-[4-[1-(trifluoromethyl)cyclopropyl]phenyl]azetidin-1-yl]propyl]pyrrolidin-2-one;
(+)-5-[3-[3-[4-(2,4-Difluorophenyl)phenyl]azetidin-1-yl]-3-oxo-propyl]pyrrolidin-2-one;
(4R)-4-[3-[3-[[2-Fluoro-4-(trifluoromethyl)phenyl]methoxy]azetidin-1-yl]-3-oxo-propyl]oxazolidin-2-one;
(4R)-4-[3-Oxo-3-[3-[4-[1-(trifluoromethyl)cyclopropyl]phenyl]azetidin-1-yl]propyl]oxazolidin-2-one;
(4R)-4-[3-[3-[4-(2,4-Difluorophenyl)phenyl]azetidin-1-yl]-3-oxo-propyl]oxazolidin-2-one;
(4R)-4-[3-[3-[6-(2-Chlorophenoxy)-3-pyridyl]azetidin-1-yl]-3-oxo-propyl]oxazolidin-2-one;
(4R)-4-[3-[3-[4-(N-Methylanilino)phenyl]azetidin-1-yl]-3-oxo-propyl]oxazolidin-2-one;
(4R)-4-[3-[3-[4-(4-Chloro-2-methylsulfonyl-phenyl)phenyl]azetidin-1-yl]-3-oxo-propyl]oxazolidin-2-one;
(4R)-4-[3-[3-[4-[N-(Cyclopropylmethyl)anilino]phenyl]azetidin-1-yl]-3-oxo-propyl]oxazolidin-2-one;
(4R)-4-[3-[3-[6-[N-(Cyclopropylmethyl)anilino]-3-pyridyl]azetidin-1-yl]-3-oxo-propyl]oxazolidin-2-one;
(4R)-4-[3-Oxo-3-[3-[4-[3-(2,2,2-trifluoroethoxy)azetidin-1-yl]phenyl]azetidin-1-yl]propyl]oxazolidin-2-one;
(4R)-4-[3-Oxo-3-[3-[4-[3-(trifluoromethyl)azetidin-1-yl]phenyl]azetidin-1-yl]propyl]oxazolidin-2-one;
(4R)-4-[3-[3-[5-(4-Chloro-2-fluoro-phenyl)pyrimidin-2-yl]azetidin-1-yl]-3-oxo-propyl]oxazolidin-2-one;
(4R)-4-[3-[3-[5-(4-Chloro-2-fluoro-phenyl)-2-pyridyl]azetidin-1-yl]-3-oxo-propyl]oxazolidin-2-one;

(4R)-4-[3-[3-[5-(2,4-Dichlorophenyl)-2-pyridyl]azetidin-1-yl]-3-oxo-propyl]oxazolidin-2-one;
(4R)-4-[3-Oxo-3-[6-[[6-(trifluoromethyl)-3-pyridyl]methyl]-2-azaspiro[3.3]heptan-2-yl]propyl]oxazolidin-2-one;
(4R)-4-[3-[7-[[2-Fluoro-4-(trifluoromethyl)phenyl]methyl]-2,7-diazaspiro[3.5]nonan-2-yl]-3-oxo-propyl]oxazolidin-2-one;
(4R)-4-[3-[3-[4-[4-Methylsulfonyl-2-(trifluoromethyl)phenyl]phenyl]azetidin-1-yl]-3-oxo-propyl]oxazolidin-2-one;
(4R)-4-[3-[3-[3-Fluoro-4-[3-(trifluoromethyl)pyrrolidin-1-yl]phenyl]azetidin-1-yl]-3-oxo-propyl]oxazolidin-2-one;
(4R)-4-[3-Oxo-3-[3-[4-3-(trifluoromethyl)cyclobutyl]phenyl]azetidin-1-yl]propyl]oxazolidin-2-one;
(4R)-4-[3-[3-[6-(2-Azaspiro[3.4]octan-2-yl)-3-pyridyl]azetidin-1-yl]-3-oxo-propyl]oxazolidin-2-one;
(4R)-4-[3-[3-[3-[5-(2,2-Dimethylpropyl)-1,3,4-oxadiazol-2-yl]-1-bicyclo[1.1.1]pentanyl]azetidin-1-yl]-3-oxo-propyl]oxazolidin-2-one;
(4R)-4-[3-Oxo-3-[3-[[4-(trifluoromethylsulfonyl)phenyl]methoxy]azetidin-1-yl]propyl]oxazolidin-2-one;
(4R)-4-[3-Oxo-3-[7-[[6-(trifluoromethyl)-3-pyridyl]methyl]-2-azaspiro[3.5]nonan-2-yl]propyl]oxazolidin-2-one; and
cis-(4R)-4-[3-Oxo-3-[3-[6-[4-(trifluoromethyl)cyclohexyl]-3-pyridyl]azetidin-1-yl]propyl]oxazolidin-2-one,
or a pharmaceutically acceptable salt thereof.

14. A pharmaceutical composition, comprising a compound of claim 1, or a pharmaceutically acceptable salt thereof, and a therapeutically inert carrier.

15. A pharmaceutical composition, comprising a compound of claim 12, or a pharmaceutically acceptable salt thereof, and a therapeutically inert carrier.

16. The compound of claim 1, or a pharmaceutically acceptable salt thereof, wherein:
$R_L$ is a group

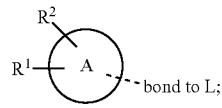

L is selected from a covalent bond, —CHR$^8$—, and —CH$_2$O—;
$L^D$ is selected from a covalent bond, —O—, and —NR$^{11}$—;
A is

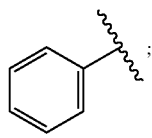 [SMILES: *c1ccccc1]

D is selected from:

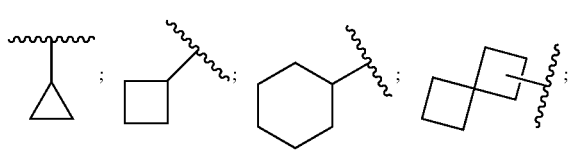

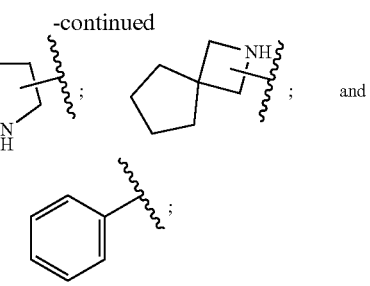

$R^1$ is CF$_3$CH$_2$— or a group

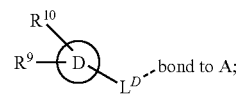

$R^2$ is hydrogen or halogen;
$R^8$ is hydrogen;
$R^9$ is selected from hydrogen, halogen, halo-C$_{1-6}$-alkyl, halo-C$_{1-6}$-alkoxy, and C$_{1-6}$-alkyl-SO$_2$—;
$R^{10}$ is selected from hydrogen, halogen, and halo-C$_{1-6}$-alkyl; and
$R^{11}$ is C$_{1-6}$-alkyl or C$_{3-10}$-cycloalkyl-C$_{1-6}$-alkyl-.

17. The compound of claim 1, or a pharmaceutically acceptable salt thereof, wherein:
X is N(C$_{1-6}$-alkyl) or (CH$_2$)$_m$CHR$^6$;
m is 0;
L is selected from a covalent bond, —CHR$^8$—, and —CH$_2$O—;
$L^D$ is selected from a covalent bond, —O—, and —NR$^{11}$—;
A is

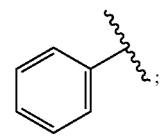 [SMILES: *c1ccccc1]

B is selected from

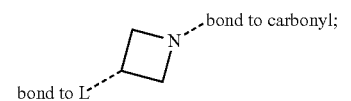

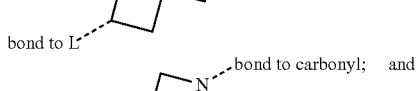

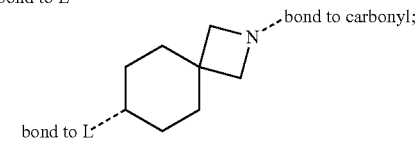

C is
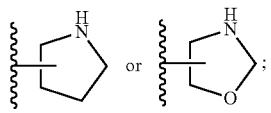
D is selected from:
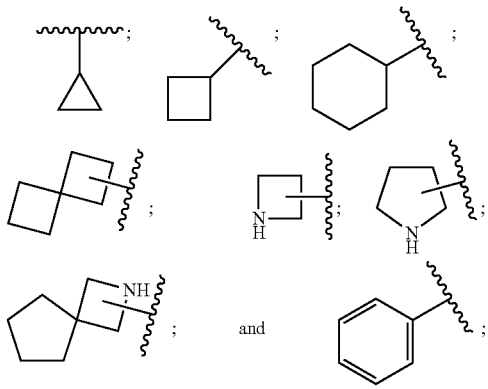
$R_L$ is a group
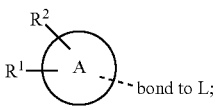
$R^1$ is $CF_3CH_2$— or a group
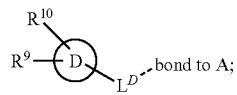
$R^2$ is hydrogen or halogen;
$R^5$, $R^6$, and $R^8$ are all hydrogen;
$R^9$ is selected from hydrogen, halogen, halo-$C_{1-6}$-alkyl, halo-$C_{1-6}$-alkoxy, and $C_{1-6}$-alkyl-$SO_2$—;
$R^{10}$ is selected from hydrogen, halogen, and halo-$C_{1-6}$-alkyl; and
$R^{11}$ is $C_{1-6}$-alkyl or $C_{3-10}$-cycloalkyl-$C_{1-6}$-alkyl-.
* * * * *